United States Patent
Anderson et al.

(10) Patent No.: US 9,174,941 B2
(45) Date of Patent: Nov. 3, 2015

(54) PYRAZOLYL AND PYRIMIDINYL TRICYCLIC ENONES AS ANTIOXIDANT INFLAMMATION MODULATORS

(71) Applicant: REATA PHARMACEUTICALS, INC., Irving, TX (US)

(72) Inventors: Eric Anderson, Southlake, TX (US); Gary L. Bolton, Ann Arbor, MI (US); Bradley Caprathe, Livonia, MI (US); Xin Jiang, Coppell, TX (US); Chitase Lee, Ann Arbor, MI (US); William H. Roark, Ann Arbor, MI (US); Melean Visnick, Irving, TX (US)

(73) Assignee: Reata Pharmaceuticals, Inc., Irving, TX (US)

( * ) Notice: Subject to any disclaimer, the term of this patent is extended or adjusted under 35 U.S.C. 154(b) by 0 days.

(21) Appl. No.: 13/939,818

(22) Filed: Jul. 11, 2013

(65) Prior Publication Data

US 2014/0051739 A1    Feb. 20, 2014

Related U.S. Application Data

(63) Continuation of application No. 13/330,378, filed on Dec. 19, 2011, now Pat. No. 8,513,436.

(60) Provisional application No. 61/424,601, filed on Dec. 17, 2010.

(51) Int. Cl.
| | |
|---|---|
| *C07D 231/54* | (2006.01) |
| *C07D 239/70* | (2006.01) |
| *C07D 401/04* | (2006.01) |
| *C07D 403/04* | (2006.01) |
| *C07D 413/04* | (2006.01) |
| *C07D 417/04* | (2006.01) |
| *C07D 487/04* | (2006.01) |

(52) U.S. Cl.
CPC ............ *C07D 231/54* (2013.01); *C07D 239/70* (2013.01); *C07D 401/04* (2013.01); *C07D 403/04* (2013.01); *C07D 413/04* (2013.01); *C07D 417/04* (2013.01); *C07D 487/04* (2013.01)

(58) Field of Classification Search
None
See application file for complete search history.

(56) References Cited

U.S. PATENT DOCUMENTS

| | | | |
|---|---|---|---|
| 2,875,201 A | 2/1959 | Johns et al. | |
| 3,071,577 A | 1/1963 | Mancera et al. | |
| 3,994,935 A | 11/1976 | Varma et al. | |
| 4,395,423 A | 7/1983 | Neumann | |
| 5,064,823 A | 11/1991 | Lee et al. | |
| 5,565,408 A | 10/1996 | Hagen et al. | |
| 6,326,507 B1 | 12/2001 | Gribble et al. | |
| 6,369,101 B1 | 4/2002 | Carlson et al. | |
| 6,552,075 B2 | 4/2003 | Gribble et al. | |
| 6,642,217 B2 | 11/2003 | Krasutsky et al. | |
| 6,649,654 B1 | 11/2003 | Karin et al. | |
| 6,890,946 B2 | 5/2005 | Nakshatri et al. | |
| 6,951,847 B2 | 10/2005 | Gibson et al. | |
| 6,974,801 B2 | 12/2005 | Honda et al. | |
| 6,991,814 B2 | 1/2006 | Ray et al. | |
| 7,053,119 B2 | 5/2006 | Karin et al. | |
| 7,144,875 B2 | 12/2006 | Gibson et al. | |
| 7,176,237 B2 | 2/2007 | Honda et al. | |
| 7,202,033 B2 | 4/2007 | Prescott et al. | |
| 7,288,568 B2 | 10/2007 | Gribble et al. | |
| 7,399,606 B2 | 7/2008 | Karin et al. | |
| 7,410,958 B2 | 8/2008 | Krasutsky et al. | |
| 7,435,755 B2 | 10/2008 | Konopleva et al. | |
| 7,678,830 B2 | 3/2010 | Honda et al. | |
| 7,714,012 B2 | 5/2010 | Honda et al. | |
| 7,795,305 B2 | 9/2010 | Konopleva et al. | |

(Continued)

FOREIGN PATENT DOCUMENTS

| | | |
|---|---|---|
| CN | 102 079 772 | 6/2011 |
| DE | 10 2005 041613 | 3/2007 |

(Continued)

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995, pp. 783-802.*

(Continued)

*Primary Examiner* — Marcos Sznaidman
*Assistant Examiner* — Rayna B Rodriguez
(74) *Attorney, Agent, or Firm* — Parker Highlander PLLC

(57) ABSTRACT

Disclosed herein are novel antioxidant inflammation modulators, including those of the formula:

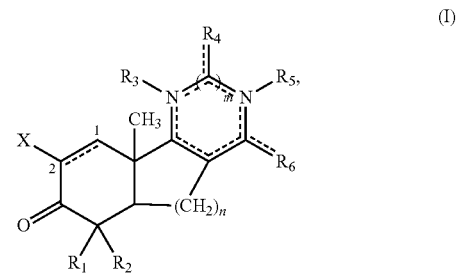

(I)

wherein the variables are defined herein. Also provided are pharmaceutical compositions, kits and articles of manufacture comprising such compounds. Methods and intermediates useful for making the compounds, and methods of using the compounds and compositions thereof are also provided.

7 Claims, No Drawings

(56) References Cited

U.S. PATENT DOCUMENTS

| | | |
|---|---|---|
| 7,863,327 B2 | 1/2011 | Gribble et al. |
| 7,915,402 B2 | 3/2011 | Anderson et al. |
| 7,943,778 B2 | 5/2011 | Jiang et al. |
| 8,034,955 B2 | 10/2011 | Gribble et al. |
| 8,067,394 B2 | 11/2011 | Honda et al. |
| 8,067,465 B2 | 11/2011 | Honda et al. |
| 8,071,632 B2 | 12/2011 | Jiang et al. |
| 8,088,824 B2 | 1/2012 | Walling et al. |
| 8,124,656 B2 | 2/2012 | Anderson et al. |
| 8,124,799 B2 | 2/2012 | Anderson et al. |
| 8,129,429 B2 | 3/2012 | Sporn et al. |
| 8,258,329 B2 | 9/2012 | Anderson et al. |
| 8,299,046 B2 | 10/2012 | Sporn et al. |
| 8,309,601 B2 | 11/2012 | Walling et al. |
| 8,314,137 B2 | 11/2012 | Honda et al. |
| 8,338,618 B2 | 12/2012 | Jiang et al. |
| 8,394,967 B2 | 3/2013 | Jiang et al. |
| 8,440,820 B2 | 5/2013 | Anderson et al. |
| 8,440,854 B2 | 5/2013 | Anderson et al. |
| 8,455,544 B2 | 6/2013 | Sporn et al. |
| 2002/0042535 A1 | 4/2002 | Gribble et al. |
| 2003/0119732 A1 | 6/2003 | Konopleva et al. |
| 2003/0232786 A1 | 12/2003 | Honda et al. |
| 2003/0236303 A1 | 12/2003 | Gribble et al. |
| 2004/0002463 A1 | 1/2004 | Honda et al. |
| 2004/0097436 A1 | 5/2004 | Krasutsky et al. |
| 2005/0208151 A1 | 9/2005 | Hurez et al. |
| 2005/0288363 A1 | 12/2005 | Gribble et al. |
| 2006/0258752 A1 | 11/2006 | Vander Jagt et al. |
| 2007/0155742 A1 | 7/2007 | Honda et al. |
| 2007/0232577 A1 | 10/2007 | Xu et al. |
| 2007/0244081 A1 | 10/2007 | Krasutsky et al. |
| 2007/0249561 A1 | 10/2007 | Taylor |
| 2007/0259839 A1 | 11/2007 | Krasutsky et al. |
| 2007/0259842 A1 | 11/2007 | Krasutsky et al. |
| 2008/0188452 A1 | 8/2008 | Altenbach et al. |
| 2008/0220057 A1 | 9/2008 | Gribble et al. |
| 2008/0233195 A1 | 9/2008 | Spoorn et al. |
| 2008/0261985 A1 | 10/2008 | Honda et al. |
| 2009/0048204 A1 | 2/2009 | Walling et al. |
| 2009/0048205 A1 | 2/2009 | Meyer et al. |
| 2009/0060873 A1 | 3/2009 | Sporn et al. |
| 2009/0093447 A1 | 4/2009 | Konopleva et al. |
| 2009/0326063 A1 | 12/2009 | Sporn et al. |
| 2010/0041904 A1 | 2/2010 | Jiang et al. |
| 2010/0048887 A1 | 2/2010 | Anderson et al. |
| 2010/0048892 A1 | 2/2010 | Anderson et al. |
| 2010/0048911 A1 | 2/2010 | Jiang et al. |
| 2010/0056777 A1 | 3/2010 | Anderson et al. |
| 2010/0261930 A1 | 10/2010 | Honda et al. |
| 2011/0009363 A1 | 1/2011 | Honda et al. |
| 2011/0196007 A1 | 8/2011 | Honda et al. |
| 2011/0245206 A1 | 10/2011 | Jiang et al. |
| 2011/0245233 A1 | 10/2011 | Anderson et al. |
| 2011/0281955 A1 | 11/2011 | Meyer et al. |
| 2012/0071684 A1 | 3/2012 | Walling et al. |
| 2012/0101149 A1 | 4/2012 | Honda et al. |
| 2012/0214814 A1 | 8/2012 | Anderson et al. |
| 2012/0220652 A1 | 8/2012 | Sporn et al. |
| 2012/0238767 A1 | 9/2012 | Jiang et al. |
| 2012/0245374 A1 | 9/2012 | Anderson et al. |
| 2012/0283450 A1 | 11/2012 | Anderson et al. |
| 2012/0302548 A1 | 11/2012 | Puschl et al. |
| 2013/0261154 A1 | 10/2013 | Hanagan et al. |

FOREIGN PATENT DOCUMENTS

| | | |
|---|---|---|
| JP | S52-65260 | 5/1977 |
| JP | 55-055153 | 4/1980 |
| JP | H08-208479 | 8/1996 |
| JP | 2001 240573 | 9/2001 |
| JP | 2005-314381 | 11/2005 |
| JP | 2008-110962 | 5/2008 |
| JP | 2008-247898 | 10/2008 |
| WO | WO 95/29912 | 11/1995 |
| WO | WO 99/65478 | 12/1999 |
| WO | WO 00/73253 | 12/2000 |
| WO | WO 01/82923 | 11/2001 |
| WO | WO 02/03996 | 1/2002 |
| WO | WO 02/26761 | 4/2002 |
| WO | WO 02/26762 | 4/2002 |
| WO | WO 02/32410 | 4/2002 |
| WO | WO 02/47611 | 6/2002 |
| WO | WO 02/092768 | 11/2002 |
| WO | WO 03/015761 | 2/2003 |
| WO | WO 03/024935 | 3/2003 |
| WO | WO 03/059339 | 7/2003 |
| WO | WO 03/062260 | 7/2003 |
| WO | WO 2004/064723 | 8/2004 |
| WO | WO 2004/089357 | 10/2004 |
| WO | WO 2004/064723 | 3/2005 |
| WO | WO 2005/042002 | 5/2005 |
| WO | WO 2005/046732 | 5/2005 |
| WO | WO 2006/029221 | 3/2006 |
| WO | WO 2006/089406 | 8/2006 |
| WO | WO 2006/102097 | 9/2006 |
| WO | WO 2007/005879 | 1/2007 |
| WO | WO 2007/112043 | 10/2007 |
| WO | WO 2007/127791 | 11/2007 |
| WO | WO 2008/000068 | 1/2008 |
| WO | WO 2008/000070 | 1/2008 |
| WO | WO 2008/016095 | 2/2008 |
| WO | WO 2008/063318 | 5/2008 |
| WO | WO 2008/064132 | 5/2008 |
| WO | WO 2008/064133 | 5/2008 |
| WO | WO 2008/097596 | 8/2008 |
| WO | WO 2008/111497 | 9/2008 |
| WO | WO 2008/136838 | 11/2008 |
| WO | WO 2009/023232 | 2/2009 |
| WO | WO 2009/023845 | 2/2009 |
| WO | WO 2009/058849 | 5/2009 |
| WO | WO 2009/089545 | 7/2009 |
| WO | WO 2009/129545 | 10/2009 |
| WO | WO 2009/129546 | 10/2009 |
| WO | WO 2009/129548 | 10/2009 |
| WO | WO 2009/146216 | 12/2009 |
| WO | WO 2009/146218 | 12/2009 |
| WO | WO 2010/011782 | 1/2010 |
| WO | WO 2010/053817 | 5/2010 |
| WO | WO 2010/093944 | 8/2010 |
| WO | WO 2011/130302 | 10/2011 |
| WO | WO 2012/083306 | 6/2012 |
| WO | WO 2012/106190 | 8/2012 |
| WO | WO 2012/125488 | 9/2012 |

OTHER PUBLICATIONS

Andresen and Margaretha, "Preparation of Dialkyl 2-Cyanocycloalk-2-en-1-ones," J. Chem. Research (S), 332, 1994.

Liu, et al., "An Efficacious Synthetic Strategy for cis-Clerodane Diterpenoids. Application to the Total Synthesis of (±)-6β-Acetoxy-2-oxokolavenool," Synlett, 11:1805-1807, 2001.

"CDDO in treating patients with metastatic or unresectable solid tumors or lymphoma," http://www.clinicaltrials.gov/ct2/show/NCT00352040?term=CDDO&rank=1, Dec. 14, 2008.

"Phase IIa trail to determine the effects of bardoxolone methyl on renal function in patients with diabetic nephropathy," http://www.clinicaltrials.gov/ct2/show/NCT00664027?term=rta&rank=10, Dec. 14, 2000.

"RTA 402 in advanced solid tumors or lymphoid malignancies," http://www.clinicaltrials.gov/ct2/show/NCT00508807?term=rta&rank=2&show_desc=Y, Dec. 14, 2008.

"RTA 402, Therapeutic Properties I", slides/handouts presented by Reata Pharmaceuticals, Inc. at private partnering meetings at BioSquare 2006 conference, Mar. 8-10, 2006, Geneva, Switzerland.

"RTA 402, Therapeutic Properties II", slides/handouts presented by Reata Pharmaceuticals, Inc. at private partnering meetings at BIO 2006 conference, Apr. 9-12, 2006, Chicago, Illinois.

"RTA 402, Therapeutic Properties III", slides presented by Reata Pharmaceuticals, Inc. as a podium presentation at BIO 2006 conference, Apr. 9-12, 2006, Chicago, Illinois.

(56) References Cited

OTHER PUBLICATIONS

"RTA 402, Therapeutic Properties IV", slides/handouts presented by Reata Pharmaceuticals, Inc. at private partnering meetings at BioPartnering Europe 2006 conference, Oct. 8-10, 2006, London, England.

"RTA 402, Therapeutic Properties IX", slides/handouts presented by Reata Pharmaceuticals, Inc. at private partnering meeting at BIO Europe 2007 conference, Nov. 12-14, 2007, Hamburg, Germany.

"RTA 402, Therapeutic Properties V", slides/handouts presented by Reata Pharmaceuticals, Inc. at private partnering meetings at BIO 2007 conference, May 6-9, 2007, Boston Massachusetts.

"RTA 402, Therapeutic Properties VI", slides/handouts presented by Reata Pharmaceuticals, Inc. at private partnering meetings at BIO 2007 conference, May 6-9, 2007, Boston, Massachusetts.

"RTA 402, Therapeutic Properties VII", slides presented by Reata Pharmaceuticals, Inc. as a podium presentation at BIO 2007 conference, May 6-9, 2007, Boston, Massachusetts.

"RTA 402, Therapeutic Properties VIII", slides/handouts presented by Reata Pharmaceuticals, Inc. at private partnering meetings at BIO Europe 2007 conference, Nov. 12-14, 2007, Hamburg, Germany.

"Study to assess the safety, tolerability, and pharmacodynamics of RTA 402 in patients with hepatic dysfunction," http://www.clinicaltrials.gov/ct2/show/NCT00550849?term=rta&rank=4, Dec. 14, 2008.

Abad et al., "Diastereoselective synthesis of antiquorin and related polyoxygenated atisene-type diterpenes," *Tetrahedron*, 63 (7): 1664-1679, 2007.

Aghoramurthy et al., "Structure of cedrelone," *J Sci. Ind. Res.*, 21B: 95-96, 1962.

Ahmad et al., "Triterpenoid CDDO-Me blocks the NF-kappaB pathway by direct inhibition of IKKbeta on Cys-179," *J. Biol. Chem.*, 281:35764-35769, 2006.

Ahmad et al., "Triterpenoid CDDO-methyl ester inhibits the Janus-activated kinase-1 (JAK1)àsignal transducer and activator of transcription-3 (STAT3) pathway by direct inhibition of JAK1 and STAT3," *Cancer Res.*, 68 (8): 2920-2926, 2008.

Akisanya et al., "West african timbers. XII. The interrelation of gedunin and khivorin," *J. Chem. Soc. Org.*, 5: 506-509, 1966.

Akiyama et al., "Cell mediators of inflammation in the Alzheimer disease brain," *Alzheimer Dis. Assoc. Disord.*, 14 (1): S47-S53, 2000.

Albini and Sporn, "Opinion: the tumour microenvironment as a target for chemoprevention," *Nature Reviews Cancer*, 7: 139-147, 2007.

Andreef et al., "PPARgamma nuclear rescector as a novel molecular target in leukemias," 2002 Keystone Symposia, Abstract 501:149, 2002.

Anjaneyulu et al., "ent-Kaurane and beyerane diterpenoids from *Excoecaria agallocha*," *J. of Natural Products*, 65 (3): 382-385, 2002.

Appendino et al., "Polycyclic diterpenoids from *Euphorbia characias*," *Fitoterapia*, 71 (2): 134-142, 2000.

Awale et al., "Four highly oxygenated isopimarene-type diterpenes of *Orthosiphon stamineus*," *Planta Medica*, 68 (3): 286-288, 2002.

Awale et al, "Inhibition of NO production by highly-oxygenated diterpenes of *Orthosiphon stamineus* and their structure-activity relationship," *Biological and Pharmaceutical Bulletin*, 26 (4): 468-473, 2003.

Awale et al., "Norstaminane- and isopimarane-type diterpenes of *Orthosiphon stamineus* from Okinawa," *Tetrahedron*, 58 (27): 5503-5512, 2002.

Baarschers et al., "The structure of some diterpenes from tambooti wood, *Spirostachys africana* sond," *J. of the Chemical Society*, 4046-4055, 1962.

Ballesta-Acosta et al., "A new 24-nor-oleanane triterpenoid from *Salvia carduacea*," *J. Nat. Prod.*, 65(10): 1513-1515, 2002.

Barrero et al., "Ring a functionalization of terpenoids by the unusual Baeyer-Villiger rearrangement of aliphatic aldehydes," *Synlett*, 6: 713, 1999.

Barton et al., "Dehydrogenation of steroidal and triterpenoid ketones using benzeneseleninic anhydride," *J. Chem. Soc. Perkin Trans. 1.*, 2209, 1980.

Berge et al., "Addition of vinylketenes to enamines. A method for the preparation of 6,6-dialkylcyclohexa-2,4-dienones and 4,4-dialkyl-2-vinylcyclobutenones," *Helvetica Chimica Acta*, 65 (7): 2230-2341, 1982.

Bore et al., "The anti-inflammatory triterpenoid methyl 2-cyano-3,12-dioxoolean 1,9(11)-dien-28-oate methanol solvate hydrate," *Acta Crystallorg C.*, 58(Pt 3):199-200, 2002.

Bowden et al, "Constituents of the fruit of *Pseudopanax arboretum* (Araliaceae)," *Australian Journal of Chemistry*, 28(1): 91-107, 1975.

Brookes et al., "The triterpenoid 2-cyano-3,12-dioxooleana-1,9-dien-28-oic acid and its derivatives elicit human lymphoid cell apoptosis through a novel pathway involving the unregulated mitochondrial permeability transition pore," *Cancer Res.*, 67:1793-1802, 2007.

Buchanan et al., "The conversion of turraeanthin and turraeanthin A into simple melaiacins by a route involving an oxidative rearrangement of probable biogenetic importance," *J Chem. Soc C*, 17:2280-2284, 1970.

Buchanan et al., "The synthesis of the simplest mealiacins (limonoids) from tetranortirucallen triterpenoids containing a beta-substituted furyl side-chain," *Chemical Communications*, 5:242-243, 1969.

Cambie et al., "Chemistry of the podocarpaceae. LXXVI. 8,13-Epoxy-3-β-hydroxylabd-14-en-2-one and 8,13-Epoxy-2-hydroxylabda-1,14-dien-3-one, new diterpenoids from *Lagarostrobus colensoi*," *Australian Journal of Chemistry*, 43 (4): 791-794, 1990.

Campbell and Cromwell, "Endocyclic α,β-Unsaturated Ketones. VI.1 Ultraviolet and Infrared Absorption Spectra and Resonance Stabilizations," *J. Am. Chem. Soc.*, 79:3456-3463, 1957.

Cao et al., "Total synthesis of (—)-elegansidiol by using an abnormal Beckmann fragmentation of Hajos ketone oxime as a key step," *Tetrahedron*, 63 (23): 5036-5041, 2007.

Caron et al., "Versatile Strategy to access tricycles related to quassinoids and triterpenes," *Org. Letters*, 12(3) 508-511, 2010.

Cassady and Suffness, In *Anticancer Agents Based on Natural Product Models*; Academic Press, NY, 254-269, 1980.

Chauhan et al., "The bortezomib/proteasome inhibitor PS-341 and triterpenoid CDDO-Im induce synergistic anti-multiple myeloma (MM) activity and overcome bortezomib resistance," *Blood*, 103:3158-3166, 2004.

Chintharlapalli et al., "2-Cyano-3,12-dioxoolean-1,9-dien-28-oic acid and related compounds inhibit growth of colon cancer cells through peroxisome proliferator-activated receptor gamma-dependent and -independent pathways," *Mol. Pharmacol.*, 68:119-128, 2005.

Chintharlapalli et al., "2-Cyano-lup-1-en-3-oxo-20-oic acid, a cyano derivative of betulinic acid, activates peroxisome proliferator-activated receptor [gamma] in colon and pancreatic cancer cells.," *Carcinogenesis*, 28 (11): 2337-2346, 2007.

Chintharlapalli et al., "Structure-dependent activity of glycyrrhetinic acid derivatives as peroxisome proliferator-activated receptor {gamma} agonists in colon cancer cells," *Molecular Cancer Therapeutics*, 6 (5): 1588-1598, 2007.

Chow and Erdtman, "The chemistry of the natural order cupressales. 43. The structure and configuration of hinokiol and hinokione," *Acta Chemica Scandinavica*, 16: 1296-1300, 1962.

ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Jul. 6, 2009.

ClinicalTrials.gov study record NCT 00508807, "RTA 402 in advanced solid tumors or lymphoid malignancies conditions: lymphoid malignancies; solid tumors," update of Oct. 5, 2010.

ClinicalTrials.gov study record NCT 00529113, "Study with gemcitabine and RTA 402 for patients with unresectable pancreatic cancer," update of Dec. 1, 2010.

ClinicalTrials.gov study record NCT 00529438, "RTA 402 in patients with advanced solid tumors or lymphoid malignancies conditions: advanced solid tumors; lymphoid malignancies," update of Dec. 21, 2008.

(56) References Cited

OTHER PUBLICATIONS

ClinicalTrials.gov study record NCT 00535314, "Study of two dose levels of RTA 402 in patients with advanced malignant melanoma condition: malignant melanoma," update of Dec. 10, 2007.
ClinicalTrials.gov study record NCT 00550849, "Study to assess the safety, tolerability, and pharmacodynamics of RTA 402 in patients with hepatic dysfunction condition: liver disease," update of Nov. 6, 2007.
ClinicalTrials.gov study record NCT 00664027, "Phase IIa trial to determine the effects of bardoxolone methyl on renal function in patients with diabetic nephropathy condition: diabetic nephropathy," update of Feb. 18, 2009.
ClinicalTrials.gov study record NCT 00811889, "Trial to determine the effects of bardoxolone methyl on eGFR in patients with type 2 diabetes and chronic kidney disease conditions: chronic kidney disease; type 2 diabetes; diabetic nephropathy," update of Jan. 6, 2011.
ClinicalTrials.gov study record NCT 01053936, "Phase II Pharmacodynamic Trial to Determine the Effects of Bardoxolone Methyl on eGFR in Patients With Type 2 Diabetes and Chronic Kidney Disease," update of Aug. 27, 2010.
Clinton et al., "Steroidal[3,2-c]pyrazoles. II. Androstanes, 19-norandrostanes and their unsaturated analogs," *J. Am Chem Soc.*, 83:1478-1491, 1961.
Cohen et al., "A general method for removal of a 4-methyl group from triterpenoids. Synthesis of 4beta-demethylglycyrrhetinic acid," *J. Chem. Soc. Perkin Trans 1*, (19): 2076-2082, 1973.
Connolly et al., "Grandiofolione: a novel tetranortriterpenoid," *Chemical Communications*, 23:867-568, 1966.
Couch et al., "2-cyano-3,12-dioxooleana-1,9(11)-diene-28-oic acid disrupts microtubule polymerization: a possible mechanism contributing to apoptosis," *Molecular Pharmacology*, 69 (4): 1158-1165, 2006.
Couch et al., "Studies on the reactivity of CDDO, a promising new chemopreventive and chemotherapeutic agent: implications for a molecular mechanism of action," *Bioorganic and Medicinal Chemistry Letters*, 15 (9): 2215-2219, 2005.
Crespi-Perellino et al., "Identification of new diterpenoids from *Euphoria calyptrata* cell cultures," *J. of Natural Products*, 59 (8): 773-776, 1996.
Cromwell et al., "Endocyclic α,β-unsaturated ketones. V.1 Synthesis and reaction of 3-bromo-1,1-dimethyl-2-keto-1,2-dihydronaphthalene with morpholine," *J. of Organic Chemistry*, 22: 520-523, 1957.
Damsté et al., "A sedimentary tetrahydrophenanthrene derivative of tetrahymanol," *Tetrahedron Letters*, 40(20: 3949-3952, 1999.
Danishefsky et al., "Diels-Alder reactions of trans-1-methoxy-3-trimethylsilyloxy-1, 3-butadiene," *J. Am. Chem. Sol.*, 101: 6996-7000, 1979.
De Mico et al., "A Versatile and Highly Selective Hypervalent Iodine (III)/2,2,6,6-Tetramethyl-1-piperidinyloxyl-Mediated Oxidation of Alcohols to Carbonyl Compounds," *J. Org. Chem.*, 62: 6974, 1997.
De Ruggieri et al., "Deidrogenazione e bromurazione di beta-chetonitrili steroidali," *Il Farmaco*, 20: 358-388, 1964. (English summary).
Dezube et al., "Interim results of a phase I trial with a novel orally administered synthetic triterpenoid RTA 402 (CDDO-ME) in patients with solid tumors and lymphoid malignancies," *J. Clin. Oncol.*, 2007 ASCO Annual Meeting Proceedings, 25(185):14101, 2007.
Dinkova-Kostova et al., "Direct evidence that sulfhydryl groups of Keap1 are the sensors regulating induction of phase 2 enzymes that protect against carcinogens and oxidants," *Proc. Natl. Acad. Sci.*, 99(18): 11908-11913, 2002.
Dinkova-Kostova et al., "Extremely potent triterpenoid inducers of the phase 2 response: correlations of protection against oxidant and inflammatory stress," *Proc. Natl. Acad. Sci.*, 102(12): 4584-4589, 2005.
Dirsch et al., "The triterpenoid quinonemethide pristimerin inhibits induction of inducible nitric oxide synthase in murine macrophages," *Eur J Pharmacol.*, 336(2-3): 211-217, 1997.

Dracinsky et al., "Preparation and Conformational Study of 19β,28-Epoxy-18α-olean-5-ene Derivatives," *Collection of Czechoslovak Chemical Communications*, 71(3): 387-410, 2006.
Dragnev et al., "Specific chemopreventive agents trigger proteasomal degradation of G1 cyclins: implications for combination therapy," *Clin. Cancer Research*, 10 (7): 2570-2577, 2004.
Duan et al., "Di- and triterpenoids from *Triptergium hypoglaucum*," *Phytochemistry*, 46(3): 535-543, 1997.
Duan et al., "Immunosuppressive terpenoids from extracts of *Tripterygium wilfordii*," *Tetrahedron*, 57 (40): 8413-8424, 2001.
Eistert et al., "Reaktionen von diazoalkanen mit α-diketonen und chinonen, XII. ringerweiterung von 1.1-dimethyl-indandion-(2.3)," *Chemische Berichte*, 102 (7): 2429-2439, 1969.
Ekong and Olagbemi, "West African timbers. Part XVII. Correlation of gedunin, methyl angolensate, and andirobin," *J. of the Chemical Society*, [Section] C: Organic, 10: 944-966, 1966.
Elliot et al., "The triterpenoid CDDO inhibits expression of matrix metalloproteinase-1, matrix metalloproteinase-13 and Bcl-3 in primary human chondrocytes," *Arthritis Res. Ther.*, 5:R285-R291, 2003.
Elsawa et al., "Preferential Inhibition of Malignant Cell Growth by CDDO in Waldenstrom Macroglobulinemia," *Blood*, 108(11):2528, 2006.
Favaloro et al., "Design and synthesis of tricyclic compounds with enone functionalities in rings A and C: a novel class of highly active inhibitors of nitric oxide production in mouse macrophages," *J. Med. Chem.*, 45:4801-4805, 2002.
Ferreira et al., "Phytochemistry of the mopane, *Colophosperum mopane*," *Phytochemistry*, 64 (1): 31-51, 2003.
Finlay et al., "Novel A-ring cleaved analogs of oleanolic and ursolic acids which affect growth regulation in NRP.152 prostate cells," *Biorg. Med. Chem. Lett.*, 7(13): 1769-1772, 1997.
Finlay et al., "The Effect of A and C Ring Modification of Oleanolic and Ursolic Acid on the Inhibition of Nitric Oxide Formation in Mouse Macrophages," 213th American Chemical Society National Meeting, Abstract: 084, 1997.
Fraga et al., "Partial synthesis of a colensenone isomer," *Anales de Quimica*, 90 (7-8): 513-516, 1994.
Gao et al., "Synthetic triterpenoids inhibit growth and induce apoptosis in human glioblastoma and neuroblastoma cells through inhibition of prosurvival Akt, NF-κb and Notch1 signaling," *J. of Neuro-oncology*, 84 (2): 147-157, 2007.
Grant and Carman, "Colensenone," *J. of the Chemical Society*, 3740-3746, 1962.
Grant et al., "Boron trifluoride catalyzed rearrangements of novel expoxide derivatives of manool and manoyl oxide," *Australian Journal of Chemistry*, 46 (8): 1125-1145, 1993.
Grieco and Speake, "Synthetic Studies on Quassinoids: Total Synthesis and Biological Evaluation of (+)-Des-D-chaparrinone," *J. Org. Chem.*, 63:5929-5936, 1998.
Hail et al., "Evidence supporting a role for calcium in apoptosis induction by the synthetic triterpenoid 2-cyano-3,12-dioxooleana-1,9-dien-28-oic acid (CDDO)," *J. Biol. Chem.*, 279:11179-11187, 2004.
Han et al., "CDDO-Imidazolide inhibits growth and survival of c-Myc-induced mouse B cell and plasma cell neoplasms," *Molecular Cancer*, 5:22, 2006.
Hanson and White, "The chemistry of the tetracyclic diterpenoids—XV : The complete structure of abbeokutone," *Tetrahedron*, 26 (20): 4839-4841, 1970.
Hatcher et al., "Curcumin: from ancient medicine to current clinical trials," *CMLS Cellular and Molecular Life Sciences*, 65 (11): 1631-1652, 2008.
Hill et al., "Synthetical approaches to the pristimerin chromophore," *J. of the Chemical Society*, 361-375, 1965.
Hirota et al., "Stereoselective total synthesis of (±)-eperuane-8b,15-diol1," *Bull. Chem. Soc. Jpn.*, 61:4023-4028, 1988.
Hirota et al., "Suppression of tumor promoter-induced inflammation of mouse ear by ursolic acid and 4,4-dimethycholestane derivatives" *Agric. Biol. Chem.*, 54:1073-1075, 1990.
Hirota et al., "Total synthesis of (±)-amarolide, a quassinoid bitter principle," *J. Org. Chem.*, 56:1119-1127, 1991.

(56) References Cited

OTHER PUBLICATIONS

Honda et al., "A novel dicyanotriterpenoid, 2-cyano-3,12-dioxooleana-1,9(11)-dien-28-onitrile, active at picomolar concentrations for inhibition of nitric oxide production," *Bioorg. Med. Chem. Lett.*, 12:1027-1030, 2002.

Honda et al., "An efficient synthesis of tricyclic compounds (+)—(4aβ, 8aβ, 10aα)—1,2,3,4,4a,6,7,8,8a,9,1-,10a-Dodecahydro-1,1,4a-Trimethy1-2-Oxophenanthrene-8a-Carboxolic acid, its methyl ester, and (+)-(4aβ,8aβ,10aα)-3,4,4a,6,7,8,8a,9,10,10a-DecahydRO-8a, hydroxymethyl-1,1,4a-trimethylphenanthren-2(1H)-one," *Org. Prep. Proced. Int.*, 37(6): 546-550, 2005.

Honda et al., "Design and synthesis of 23, 24-dinoroleanolic acid derivatives, novel triterpenoid—steroid hybrid molecules," *J. Org. Chem.*, 63:4846-4849, 1998.

Honda et al., "Design and synthesis of 2-cyano-3,12-dioxoolean-1,9-dien-28-oic acid, a novel and highly active inhibitor of nitric oxide production in mouse macrophages," *Bioorg Med Chem Lett.*, 8(19):2711-2714, 1998.

Honda et al., "Design, synthesis, and biological evaluation of biotin conjugates of 2-cyano-3,12-dioxooleana-1,9(11)-dien-28-oic acid for the isolation of the protein targets," *J. Med. Chem.*, 47 (20): 4923-4932, 2004.

Honda et al., "Efficient synthesis of (−)- and (+)-tricyclic compounds with enome functionalities in rings A and C. A novel class of orally active anti-inflammatory and cancer chemopreventive agents," *Org Biomol Chem.*, 1:4384-4391, 2003.

Honda et al., "New enone derivatives of oleanolic acid and ursolic acid as inhibitors of nitric oxide productiCon in mouse macrophages," *Bioorg. Med. Chem. Lett.*, 7:1623-1628, 1997.

Honda et al., "New synthetic oleanane and ursane triterpenoids as inhibitors of nitric oxide production in mouse macrophages," The Fifth Chemical Congress of North America, Cancun, Mexico, Abstract 552 and slides for oral presentation, Nov. 1997.

Honda et al., "Novel synthetic oleanane and ursane triterpenoids with various enone functionalities in ring A as inhibitors of nitric oxide production in mouse macrophages," *J. Med. Chem.*, 43:1866-1877, 2000.

Honda et al., "Novel synthetic oleanane triterpenoids: a series of highly active inhibitors of nitric oxide production in mouse macrophages," *Bioorg Med Chem Lett*, 9(24):3429-3434, 1999.

Honda et al., "Novel tricyclic compounds having acetylene groups at C-8a and cyano enones in rings A and C: highly potent anti-inflammatory and cytoprotective agents," *J. Med. Chem.*, 50:1731-1734, 2007.

Honda et al., "Revision and confirmation of the regiochemistry of isoxazoles derived from methyl oleanonate and lanost-8-en-3-one. Synthesis of a new lanostane triterpenoid with a cyano-enone functionality in ring A," *J. Org. Chem.*, 68:4991-4993, 2003.

Honda et al., "Synthesis of (±)-3,3-ethylenedioxy-14a-hydroxy-5-picrasene-11,16-dione, a 14aH-picrasane derivative," *Chem. Lett.*, 299-302, 1981.

Honda et al., "Synthesis of a novel dicyano abietane analogue: a potential antiinflammatory agent," *J. Org. Chem.*, 71:3314-3316, 2006.

Honda et al., "Synthetic oleanane and ursane triterpenoids with modified rings A and C: A series of highly active inhibitors of nitric oxide production in mouse macrophages," *J. Med. Chem.*, 43:4233-4246, 2000.

Hong et al., "Phase I trial of a novel oral NF-κb/pSTAT3 inhibitor RTA-402 in patients with solid tumors and lymphoid malignancies," 44th Annual Meeting of the American Society of Clinical Oncology, 2008.

Hyer et al., "Synthetic triterpenoids cooperate with tumor necrosis factor-related apoptosis-inducing ligand to induce apoptosis of breast cancer cells," *Cancer Res.*, 65:4799-4808, 2005.

Iddon et al., "Synthesis and reactions of 1,2,3,4,5,6-hexahydro-3,6-dimethyl-2,6-methano-3-benzazocin-11-one (2,5-dimethyl-9-oxo-6,7-benzomorphan); a new route to 3-benzazocines," *J. of the Chemical Society*, Perkin Transactions, 1:2583-2593, 1983.

Ikeda et al., "Induction of redox imbalance and apoptosis in multiple myeloma cells by the novel triterpenoid 2-cyano-3,12-dioxoolean-1,9-dien-28-oic acid," *Mol. Cancer Ther.*, 3:39-45, 2004.

Ikeda et al., "The novel triterpenoid CDDO and its derivatives induce apoptosis by disruption of intracellular redox balance," *Cancer Res.*, 63:5551-5558, 2003.

Ikeda et al., "Triterpenoid CDDO-Im downregulates PML/RAR αexpression in acute promyelocytic leukemia cell," *Cell Death and Differentiation*, 12 (5): 523-531, 2005.

Inoue et al., "CDDO induces apoptosis via the intrinsic pathway in lymphoid cells," *Leukemia*, 18 (5): 948-952, 2004.

International Search Report and Written Opinion issued in PCT/US2011/065897, dated Jul. 27, 2012.

Invitation to Pay Additional Fees issued in PCT/US2011/065897, dated May 7, 2012.

Ito et al., "Involvement of caspase-8 in the induction of osteosarcoma cell apoptosis by the novel triterpenoid CDDO," 47th Annual Meeting, Orthopaedic Research Society, Feb. 25-28, 2001, San Francisco, California, p. 0863, Poster Session, 2001.

Ito et al., "The novel triterpenoid 2-cyano-3, 12-dioxoolean-1,9-dien-28-oic acid induces apoptosis of human myeloid leukemia cells by a caspase-8-dependent mechanism," *Cell Growth & Differentiation*, 11(5):261-267, 2000.

Ito et al., "The novel triterpenoid CDDO induces apoptosis and differentiation of human osteosarcoma cells by a caspase-8 dependent mechanism," *Mol. Pharmacol.*, 59:1094-1099, 2001.

Jang et al., "24-nor-ursane type triterpenoids from the stems of *Rumex japonicus*," *Chem. Pharm Bull* (Tokyo), 53(12): 1594-1596, 2005.

Ji et al., "The synthetic triterpenoid CDDO-imidazolide induces monocytic differentiation by activating the Smad and ERK signaling pathways in HL60 leukemia cells," *Molecular Cancer Therapeutics*, 5 (6): 1452-1458, 2006.

Johansen et al., "Pharmacology and preclinical pharmacokinetics of the triterpenoid CDDO methyl ester," *Proc. Amer. Assoc. Cancer Res.*, 44:1728, 2003.

Kahne and Collum, "Kinetic cyanations of ketone enolates," *Tetrahedron Lett.*, 22:5011-5014, 1981.

Kamal et al., "23-oxoisopristimerin III: an new natural phenolic (9→8)-24-nor-D:A-friedo-oleanane triterpene," *Tetrahedron Letters*, 24(27):2799-2800, 1983.

Kamal et al., "Structures of two new phenolic 24-nor-D: A-friedoleananes related to zeylasterone: a partial synthesis of trimethylzeylasterone," *Tetrahetron Letters*, 24(19): 2025-2028, 1983.

Kamal et al., "The structure of zeylasterone, the first of a new series of phenolic 24-nor-D: A friedo-oleanane triterpenes," *Tetrahedron Letters*, 21(49): 4749-4752, 1980.

Kansanen et al., "Regulation of Nrf2-dependent gene expression by 15-deoxy-Delta12,14-prostaglandin J2," *Free Radic. Biol. Med.*, 47(9):1310-7, 2009.

Kerwin et al., "Quassinoid synthesis. 2. Preparation of a tetracyclic intermediate having the Bruceantin tetrahydrofuran ring," *J. Org. Chem.*, 52:1686-1695, 1987.

Khalid et al., "Isolation and characterization of pristimerin as the antiplasmodial and antileishmanial agent of *Maytenus senegalensis* (Lam.) Exell," *ARKIVOC*, 129-134, 2007.

Kim et al., "An inducible pathway for degradation of FLIP protein sensitizes tumor cells to TRAIL-induced apoptosis," *J. of Biological Chemistry*, 277 (25): 22320-22329, 2002.

Kim et al., "Capasase-3 activation is involved in apoptosis induced by a synthetic triterpenoid in Non-small cell lung cancer (NSCLC) cells," *Proc. Amer. Assoc. Cancer Res.*, 41:770, Abstract #4894, 2000.

Kim et al., "Identification of a novel synthetic triterpenoid, methyl-2-cyano-3,12-dioxooleana-1,9-dien-28-oate, that potently induces caspace-mediated apoptosis in human lung cancer cells," *Molecular Cancer Therapeutics*, 1:177-184, 2002.

Kind et al., "Pituitary gonadotropin inhibitory action of netral steroids," *Acta. Endocrinologica*, 46: 300-306, 1964.

Klyne et al., "The molecular rotations of polyclyclic compounds. III. Polyclyclic alcohols and their derivatives," *J Chem Soc.*, 1979-1988, 1954.

(56) References Cited

OTHER PUBLICATIONS

Kobayashi et al., "The antioxidant defense system Keap1-Nrf2 comprises a multiple sensing mechanism for responding to a wide range of chemical compounds," *Mol. Cell Biol.*, 29(2):493-502, 2009.

Kokpol et al., "Structure of trigonostemone, a new phenanthrenone from the thai plant *Trigonostemon reidioide*," *Journal of Natural Products*, 53 (5): 1148-1151, 1990.

Kolak et al., "Antioxidant and anticholinesterase constituents of *Salvia poculata*," *Turkish Journal of Chemistry*, 33(6): 813-823, 2009.

Konishi et al., "Anti-tumor-promoting activity of diterpenes from *Excoecaria agallocha*," *Biological and Pharmaceutical Bulletin*, 21 (9): 993-996, 1998.

Konishi et al., "Five new labdane-type diterpenes from *Excoecaria agallocha* IV," *Chemical and Pharmaceutical Bulletin*, 46 (9): 1393-1398, 1998.

Konopleva et al., "Activation of nuclear transcription factor PPARgamma by the novel triterpenoid CDDO as targeted therapy in breast cancer," 2002 Keystone Symposium, Abstract No. 539, 2002.

Konopleva et al., "Mechanisms and Activity of PPARgamma-Active Triterpenoids CDDO and CDDO-Me in Leukemias," *Blood*, 106:2460, 2005.

Konopleva et al., "Novel synthetic triterpenoid CDDO-Me: potent antiproliferative, proapoptotic and differentiating agent in AML," *Blood*, 96(11), Part 1: 121A, abstract # 522, 2000.

Konopleva et al., "Novel synthetic triterpenoid, CDDO, and its methyl ester: Potent antiproliferative, proapoptotic and differentiating agents in AML," *Blood*, 94(Suppl 1):479a, Abstract #2140, 1999.

Konopleva et al., "Novel triterpenoid CDDO-Me is a potent inducer of apoptosis and differentiation in acute myelogenous leukemia," *Blood*, 99(1):326-335, 2002.

Konopleva et al., "Peroxisome proliferator-activated receptor gamma and retinoid X receptor ligands are potent inducers of differentiation and apoptosis in leukemias," *Mol. Cancer Ther.*, 3:1249-1262, 2004.

Konopleva et al., "PPARg nuclear receptor as a novel therapeutic target in AML," *Blood*, 96(11):460a, Abstract #1982, 2000.

Konopleva et al., "PPARg nuclear receptor as a novel therapeutic target in AML," *Proc. of the AACR*, 42, Abstract #4458, 2001.

Konopleva et al., "PPARgamma Ligand CDDO Induces Apoptosis in Leukemias Via Multiple Apoptosis Pathways," Abstracts of the 44th Annual Meeting of the American Society of Hematology, Abstract No. 2209, 2002.

Konopleva et al., "PPARgamma Ligands Are Potent Inducers of Apoptosis in Leukemias and Lymphomas," American Society of Hematology 43rd Annual Meeting and Exposition, Abstract No. 501, 2001.

Konopleva et al., "PPARgamma Nuclear Receptor as a Novel Molecular Target in Leukemia Therapy," *Proc. Amer. Assoc. Cancer Res.*, 43:4730, 2002.

Konopleva et al., "Suppression of ERK Activation is Required for Triterpenoid Methyl-CDDO-Induced Apoptosis in AML," *Blood*, 102(11):1404, 2003.

Konopleva et al., "Synthetic triterpenoid 2-cyano-3,12-dioxooleana-1,9-dien-28-oic acid induces growth arrest in HER2-overexpressing breast cancer cells," *Mol. Cancer Ther.*, 5:317-328, 2006.

Konopleva et al., "Synthetic triterpenoid CDDO as a novel therapy for resistant breast cancer," *Proc. Amer. Assoc. Cancer Res.*, 44:2726, 2003.

Konopleva et al., "The novel triterpenoid CDDO-Me suppresses MAPK pathways and promotes p38 activation in acute myeloid leukemia cells," *Leukemia*, 19:1350-1354, 2005.

Konopleva et al., "The synthetic triterpenoid 2-cyano-3,12-dioxooleana-1,9-dien-28-oic acid induces caspase-dependent and -independent apoptosis in acute myelogenous leukemia," *Cancer Res.*, 64:7927-7935, 2004.

Korovin and Tkachev, "Synthesis of quinoxalines fused with triterpenes, ursolic acid and betulin derivatives," *Russian Chemical Bulletin, (Translation of Izvestiya Akademii Nauk, Seriya Khimicheskaya)*, 20 (2): 304-310, 2001.

Koschmieder et al. "CDDO induces granulocytic differentiation of myeloid leukemic blasts through translational up-regulation of p42 CCAAT enhancer-binding protein alpha," *Blood*, 110 (10): 3695-3705, 2007.

Kress et al., "Triterpenoids display single agent activity in a mouse model of CLL/SBL," *Blood*, 108(11):2530, 2006.

Kress et al., "Triterpenoids display single agent anti-tumor activity in a transgenic mouse model of chronic lymphocytic leukemia and small B cell lymphoma," *PLOS ONE*, 6(e559):1-11, 2007.

Kurinna et al., "The novel triterpenoid CDDO-Me promotes apoptosis in Gleevec-resistant chronic myeloid leukemia cells by caspase-independent mechanisms," *Proc. Amer. Assoc. Cancer Res.*, 46:2240, 2005.

Kutschabsky et al., "Natural products from Vietnamese plants. Part XV. Molecular and crystal structure of a new 24-nor triperpenoid carboxylic acid from *Acanthopanax trifoliatus*," *Croatica Chemica Acta*, 58(4): 427-434, 1986.

Laing et al., "The x-ray crystal and molecular structure of a tetracyclic diterpenoid-benzaldehyde reaction product and the long range protective influence of its benzene ring," *Tetrahedron Letters*, 32: 3043-3046, 1973.

Lapillonne et al., "Activation of peroxisome proliferator-activated receptor gamma by a novel synthetic triterpenoid 2-cyano-3,12-dioxooleana-1,9-dien-28-oic acid induces growth arrest and apoptosis in breast cancer cells," *Cancer Res.*, 63:5926-5939, 2003.

Larock et al., "Carbocycle synthesis via carbopalladation of nitriles," *J. of the American Chemical Society*, 121 (13): 3238-3239, 1999.

Lavie et al., "Studies on epoxides. IV. Rearrangements in triterpenoids," *Tetrahedron Letters*, 17: 2097-2100, 1968.

Lavie et al., "Tetranortriterpenoids from *Melia azadirachta*," *Chemical Communications*, 6:278-280, 1967.

Lawson et al., "Isolation and preliminary characterization of a monoclonal antibody that interacts preferentially with the liver isoenzyme of human alkaline phosphatase," *Clin. Chem.*, 31:381-385, 1985.

Li et al., "Terpenoids from *Tripterygium wilfordii*," *Phytochemistry*, 45(4): 791-796, 1997.

Liby et al., "A novel acetylenic tricyclic bis-(cyano enone) potently induces phase 2 cytoprotective pathways and blocks liver carcinogenesis induced by aflatoxin," *Cancer Res.*, 68:6727-6733, 2008.

Liby et al., "Novel semisynthetic analogues of betulinic acid with diverse cytoprotective, antiproliferative, and proapoptotic activities," *Mol. Cancer. Ther.*, 6(7): 2113-2119, 2007.

Liby et al., "The rexinoid LG100268 and the synthetic triterpenoid CDDO-methyl amide are more potent than erlotinib for prevention of mouse lung carcinogenesis," *Mol. Cancer Ther.*, 7:1251-1257, 2008.

Liby et al., "The synthetic triterpenoid CDDO-Imidazolide suppresses STAT phosphorylation and induces apoptosis in myeloma and lung cancer cells," *Clinical Cancer Research*, 12 (14 Part 1): 4288-4293, 2006.

Liby et al., "The synthetic triterpenoids CDDO-Methyl ester and CDDO-ethyl amide prevent lung cancer induced by vinyl carbamate in A/J mice," *Cancer Research*, 67 (6): 1-7, 2007.

Liby et al., "The synthetic triterpenoids, CDDO and CDDO-imidazolide, are potent inducers of heme oxygenase-1 and Nrf2/ARE signaling," *Cancer Res.*, 65:4789-4798, 2005.

Liby et al., "Triterpenoids and rexinoids as multifunctional agents for the prevention and treatment of cancer," *Nat. Rev. Cancer*, 7 (5): 357-369, 2007.

Ling et al., "The novel triterpenoid C-28 methyl ester of 2-cyano-3, 12-dioxoolen-1, 9-dien-28-oic acid inhibits metastatic murine breast tumor growth through inactivation of STAT3 signaling," *Cancer Res.*, 67:4210-4218, 2007.

Ling et al., "The novel triterpenoid CDDO-Me inhibits metastatic murine breast tumor through inhibition of Stat3 signaling," 2007 AACR Annual Meeting, Abstract No. 301, 2007.

Liotta et al., "A simple method for the efficient sysnthesis of unsaturated β-dicarbonyl compunds," *J. Org. Chem.*, 46:2920-2923, 1981.

Liu et al, "New lupane-type triterpenoid saponins from leaves of *Oplopanax horridus* (Devil's Club)," *Nat Prod Comm.*, 5(7): 1019-1022, 2010.

(56) References Cited

OTHER PUBLICATIONS

Liu et al., "Diels-Alder reactions of 4,4-disubstituted 2-cyano-2,5-cyclohexadienones. A facile approach to the angularly substituted cis-decalin system," *Synlett*, 8:1119-1122, 2000.
Ma et al., "Two pimarane diterpenoids from *Ephemerantha lonchophylla* and their evaluation as modulators of the multidrug resistance phenotype," *J. of Natural Products*, 61 (1): 112-115, 1998.
Mai et al., "Epigenetic multiple ligands: mixed histone/protein mathyltransferase, acetyltransferase, and class III deacetylase (sirtuin) inhibitors," *J. Med. Chem.*, 51:2279-2290, 2008.
Marples and Spilling, "Ene reactions of unsaturated acyloins," *Tetrahedron Letters*, 26 (52): 6515-6518, 1985.
Marples and Spilling, "Facile intramolecular ene reactions of steroidal unsaturated acyloins," *Tetrahedron*, 48 (19): 4017-4026, 1992.
Matsumoto et al., "Synthesis of pygmaeocine E, a linear abietane diterpene from *Pygmaeopremna herbacea* (Roxb.) moldenke," *Chemical and Pharmaceutical Bulletin*, 44 (7): 1318-1325, 1996.
Melichar et al., "Growth-inhibitory effect of a novel synthetic triterpenoid, 2-cyano-3,12-dioxoolean-1,9-dien-28-oic acid, on ovarian carcinoma cell lines not dependent on peroxisome proliferator-activated receptor-gamma expression," *Gynecologic Oncology*, 93:149-154, 2004.
Mencherini et al., "Triterpenoid constituents from the roots of the *Paeonia rockii* ssp. *rockii*," *J Nat Prod.*, 74(10): 2116-2121, 2011.
Meng et al., "A diterpenoid with a new carbon skeleton from *Pygmaeopremna herbacea*," *Phytochemistry*, 27 (4): 1151-1152, 1988.
Miller and Shi, "Formation of 2,3-dehydro-1,2-dihydro-1,1-dimethylnaphthalene, 'isoaromatic' molecule," *J. of the American Chemical Society*, 109 (2): 578-579, 1987.
Miller and Shi, "Novel rearrangement and cyclization processes resulting from bromination of 1,1-dibenzyltetralin derivatives," *Journal of Organic Chemistry*, 57 (6): 1677-1681, 1992.
Minghetti et al., "Production of diterpenoids by *Euphorbia calyptrata* cell cultures," *Phytochemistry*, 42 (6): 1587-1589, 1996.
Minns et al., "A novel triterpenoid induces transforming growth factor beta production by intraepithelial lymphocytes to prevent ileitis," *Gastroenterology*, 127:119-126, 2004.
Mix et al., "A synthetic triterpenoid selectively inhibits the induction of matrix metalloproteinases 1 and 13 by inflammmatory cytokines," *Arthritis Rheum.*, 44:1096-1104, 2001.
Mix et al., "Peroxisome proliferator-activated receptor-gamma-independent repression of collagenase gene expression by 2-cyano-3,12-dioxooleana-1,9-dien-28-oic acid and prostaglandin 15-deoxy-delta(12,14) J2: a role for Smad signaling," *Mol. Pharmacol.*, 65(2): 309-318, 2004.
Mori et al., "Further preparation of steroidal diospenols. I. Synthesis of some 4,4-dimethyl-2-hydroxy-3-oxo-1-ene steroids in androstane and pregnane series," *Chemical and Pharmaceutical Bulletin*, 16 (9): 1795-1801, 1968.
Mori et al., "Synthesis of 4,4-dimethyl-2-nitro-5α-cholest-1-en-3-one," *Chemical and Pharmaceutical Bulletin*, 30 (12): 4516-4517, 1982.
Morzycki and Wilczewska, "Reactions of 4-azacholest-5-en-3-one, 6-azacholest-4-en-7-one, and their N-methyl derivatives with electrophilic reagents," *Tetrahedron*, 52 (44): 14057-14068, 1996.
Murphy et al., "Immunomodulatory Effects of the Triterpenoid CDDO after Allogeneic Bone Marrow Transplantation in Mice: Reduction of Acute Graft-Versus-Host Disease Lethality," *Blood*, 106:1316, 2005.
Murray and Zweifel, "Preparation of Phenyl Cyanate and Its Utilization for the Synthesis of α, β-Unsaturated Nitriles," *Synthesis*, 150-151, 1980.
Muzart, "Synthesis of unsaturated carbonyl compounds via a chromium-mediated allylic oxidation by 70% tert.butylhydroperoxide," *Tetrahedron Lett.*, 28:4665-4668, 1987.
Na and Surh et al., "Transcriptional regulation via cysteine thiol modification: a novel molecular strategy for chemoprevention and cytoprotection," *Mol. Carcinog.*,45 (6): 368-380, 2006.

Nair et al., "Triterpenes. XLVII. Oxidation rates of triterpenoid secondary alcohols with chromic acid," *Collection of Czechoslovak Chemical Communications*, 41(3): 770-779, 1976.
Nanduri et al., "Biological investigation and structure-activity relationship studies on azadirone from *Azadirachta indica* A. juss," *Bioorganic and Medicinal Chemistry*, 13 (22): 4111-4115, 2003.
Nelson et al., "Oxidative demethylation at C-4 of a steroid via nitroxide photolysis," *J. of the American Chemical Society*, 97 (3): 648-649, 1975.
Niikura et al., "The effects of synthetic triterpenoids on superficial zone protein synthesis in articular chondrocytes," Abstract, *Orthopedic Research Society*, San Diego, 2007.
Niikura et al., "The effects of synthetic triterpenoids on szp synthesis in articular chondrocytes," Abstract P197, *Osteoarthritis and Cartilage*, 14(Suppl B):5112-5113, 2006.
Nishimura et al., "Activity-guided isolation of triterpenoid acyl CoA cholesteryl acyl transferase (ACAT) inhibitors from *Ilex kudincha*," *J Nat Prod.*, 62(7): 1061-1064, 1999.
Nishino et al, "Inhibition of the tumor-promoting action of 12-O tetradecanoylphorbol-13-acetate by some oleanane-type triterpenoid compounds," *Cancer Res.*, 48:5210-5215, 1988.
On et al, "Steroids. CCLXV. Studies in cyano steroids. 3. Unsaturated 2-cyano steroids," *J. Org. Chem.*, 29(11): 3300-3303, 1964.
Osburn et al., "Genetic of pharmacologic amplification of Nrf2 signaling inhibits acute inflammatory liver injury in mice," *Toxicological Sciences*, 104:218-227, 2008.
Overnell and Whitehurts, "Reactions of steroid A-ring lactones with Grignard reagents," *J. of the Chemical Society* [Section] *C: Organic*, 2: 378-384, 1971.
Pappas et al., "Photoisomerization of phenalen-1-one oxide. New course of light-induced alpha beta-epoxy ketone rearrangement," *J. of the American Chemical Society*, 92 (19): 5797-5798, 1970.
Peakmen et al, "Characterization of 24-nor-triterpenoids occurring in sediments and crude oils by comparison with synthesized standards," *Tetrahedron*, 47(23): 3779-3786, 1991.
Pedersen et al., "The triterpenoid CDDO induces apoptosis in refractory CLL B cells," *Blood*, 100:2965-2972, 2002.
Piacenza et al., "A new atisane diterpene: ent-16alpha-hydroxyatis-13-en-3-one from *Androstachys johnsonii* prain," *J. Chem. Soc. Perkin Trans.*, 703-709, 1985.
Piacenza et al., "Beyerane diterpenes: structure and reactivity of the α-ketol ent-3β- hydroxybeyer-15-ene-2,12-dione, its corresponding diosphenol, and synthesis of the isomeric β-ketol acetates," *J. of the Chemical Society*, Perkin Transactions 1, 1004-1012, 1979.
Place et al., "The novel synthetic triterpenoid, CDDO-imidazolide, inhibits inflammatory response and tumor growth in vivo," *Clin. Cancer Res.*, 9:2798-2806, 2003.
Pletnev et al., "Carbopalladation of nitriles: Synthesis of 2,3-diarylindenones and polycyclic aromatic ketones by the Pd-catalyzed annulation of alkynes and bicyclic alkenes by 2-iodoarenenitriles," *J. of Organic Chemistry*, 67 (26): 9276-9287, 2002.
Rasmusson et al., "Azasteroids: structure-activity relationships for inhibition of 5 alpha-reductase and of androgen receptor binding," *J. Med. Chem.*, 29 (11): 2298-2315, 1986.
Ray et al., "The novel triterpenoid 2-cyano-3,12-dioxooleana-1,9-dien-28-oic acid (CDDO) induces apoptosis of human diffuse large B-cell lymphoma cells through a peroxisome proliferator-activated receptor gamma-independent pathway," *Exp. Hematology*, 34:1201-1210, 2006.
Ribo et al., "Synthesis of methyl 1, 11-dioxooleanan-2, 12-dien-30-oate and its 24-nor derivative," *Afinidad*, 38(373): 197-200, 1981.
Rossi et al., "Anti-inflammatory cyclopentenone prostaglandins are direct inhibitors of IkappaB kinase," *Nature*, 403:103-108, 2000.
Rouquette et al., "A ring-D functionalized nor-triterpenoid of the lupane series as a key intermediate in the formation of widespread hydrocarbon derivatives of higher plant origin in petroleum," *Organic Geochemistry*, 36(9): 1227-1233, 2005.
Ruvolo et al., "The novel triterpenoid methyl-CDDO inhibits Bcl2 phosphorylation and potently kolls U937 cells," *Blood*, 94(10), Suppl. 1, Part 1: 280A, abstract #1251, 1999.

(56) References Cited

OTHER PUBLICATIONS

Samudio et al., "2, cyano-3,12 dioxoolean-1,9 diene-28-imidazolide induces apoptosis in pancreatic cancer via redox-dependent cytoplasmic stress," *Proc. Amer. Assoc. Cancer Res.*, 46: Abstract No. 5899, 2005.

Samudio et al., "2-Cyano-3,12-dioxooleana-1,9-dien-28-imidazolide (CDDO-Im) directly targets mitochondrial glutathione to induce apoptosis in pancreatic cancer," *J. Biol. Chem.*, 280:36273-36282, 2005.

Samudio et al., "A novel mechanism of action of methyl-2-cyano-3,12 dioxoolean-1,9 diene-28-oate (CDDO-Me): Direct permeabilization of the inner mitochondrial membrane to inhibit electron transport and induce apoptosis," *Proc. Am. Assoc. Cancer Res.*, 47, Abstract 4693, 2006.

Samudio et al., "A novel mechanism of action of methyl-2-cyano-3,12 dioxoolean-1,9 diene-28-oate: direct permeabilization of the inner mitochondrial membrane to inhibit electron transport and induce apoptosis," *Mol. Pharmacol.*, 69:1182-1193, 2006.

Samudio et al., "The novel triterpenoid CDDOme potently synergizes with inhibition of bcl-2 function to induce apoptosis in AML via disruption of intracellular redox homeostasis," *Proc. Amer. Assoc. Cancer Res.*, 46: Abstract No. 4955, 2005.

Satoh et al., "Activation of the Keap1/Nrf2 pathway for neuroprotection by electrophillic phase II inducers," *PNAS*, 103 (3): 768-773, 2006.

Scholz et al., "Sensitive and specific methods for the determination of CDDO methyl ester in mouse, rat, dog, monkey, and human plasma by LC-tandem mass spectrometry," *Proc. Amer. Assoc. Cancer Res.*, 4: Abstract No. 6321, 2003.

Sharpless et al., "Electrophilic and nucleophilic organoselenium reagents. New routes to alpha, beta-unsaturated carbonyl compounds," *J. Am. Chem. Soc.*, 95:6137, 1973.

Shin et al., "Inhibitory roles of NRF2 and an oleanolic triterpenoid on adipocyte differentiation and obesity," dissertation submitted to John Hopkins University in conformity with the requirements for the degree of Doctor of Philosophy, Mar. 2009.

Shin et al., "NRF2 modulates aryl hydrocarbon receptor signaling: influence on adipogenesis," *Molecular and Cellular Biology*, 27 (20): 7188-7197, 2007.

Shin et al., "Role of Nrf2 in prevention of high-fat diet-induced obesity by synthetic triterpenoid CDDO-imidazolidem" *Eur. J. Pharmacol.*, 620(1-3):138-144, 2009.

Shishodia et al., "A synthetic triterpenoid, CDDO-Me, inhibits IkappaBalpha kinase and enhances apoptosis induced by TNF and chemotherapeutic agents through down-regulation of expression of nuclear factor kappaB-regulated gene products in human leukemic cells," *Clin Cancer Research*, 12(6):1828-1838, 2006.

Siddiqui et al., "Kanerin and 12, 13-dihydroursolic acid, two new pentacyclic triterpenes from the leaves of *Nerium oleander*," *J Nat Prod.*, 52(1): 57-62, 1989.

Snitman et al., "Synthetic approaches to taxodione synthesis of methyl 12-oxopodocarpa-5,9(11)-diene-8b-carboxylate," *Synth. Comm.*, 8:187-194, 1978.

Sporn and Roberts, "Peptide growth factors and inflammation, tissue repair, and cancer," *J. Clin. Invest.*, 78:329-332, 1986.

Sporn et al., "Prospects for prevention and treatment of cancer with selective PPARg modulators (SPARMs)," *Trends in Molecular Medicine*, 7(9):395-400, 2001.

Stadheim et al., "The novel triterpenoid 2-cyano-3,12-dioxooleana-1,9-dien-28-oic acid (CDDO) potently enhances apoptosis induced by tumor necrosis factor in human leukemia cells," *J. Biol. Chem.*, 277:16448-16455, 2002.

Stork et al., "A stereospecific total synthesis of 18-substituted steroids. Application to the synthesis of dl-conessine," *J. of the American Chemical Society*, 84: 2018-2020, 1962.

Suginome et al., "Photoinduced molecular transformations. Part 98. The photochemistry of steroidal 6-membered cyclic α-nitro ketones," *Bulletin of the Chemical Society of Japan*, 61 (11): 4005-4014, 1988.

Suh et al., "A novel synthetic oleanane triterpenoid, 2-cyano-3,12-dioxoolean-1,9-dien-28-oic acid (CDDO), induces cell differentiation in human myeloid leukemias," Proceedings of the American Association for Cancer Research Annual Meeting, 40:300, abstract 1989, 1999.

Suh et al., "A novel synthetic oleanane triterpenoid, 2-cyano-3,12-dioxoolean-1,9-dien-28-oic acid, with potent differentiating, antiproliferative, and anti-inflammatory activity," *Cancer Res.*, 59(2):336-341, 1999.

Suh et al., "New triterpenoids as cancer preventive and anti-inflammatory agents," Proceedings of the American Association for Cancer Research, Abstract No. 1457, 38: 216, 1997.

Suh et al., "Novel triterpenoids suppress inducible nitric oxide synthase (iNOS) and inducible cyclooxygenase (COX-2) in mouse macrophages," *Cancer Res.*, 58:717-723, 1998.

Suh et al., "Novel triterpenoids suppress inducible nitric oxide synthase (iNOS) and inducible cyclooxygenase (COX-2)," Proceedings of the American Association for Cancer Research Annual Meeting, 39: Abstract No. 1821, 1998.

Suh et al., "Synthetic triterpenoids activate a pathway for apoptosis in AML cells involving downregulation of FLIP and sensitization to TRAIL," *Leukemia*, 17:2122-2129, 2003.

Suh et al., "Synthetic triterpenoids enhance transforming growth factor β/Smad signaling," *Cancer Res.*, 63:1371-1376, 2003.

Suh et al., "Triterpenoids CDDO and CDDO-Me Down-Regulate FLIP Expression and Sensitize AML Cells to Trail-Induced Apoptosis," American Society of Hematology 43rd Annual Meeting and Exposition, Abstract No. 498, 2001.

Sultana et al., "Phytochemical studies on *Alstonia scholaris*," *Zeitschrift fur Natuiforschung. B, A Journal of Chemical Sciences*, 65(2): 203-210, 2010.

Sun et al., "Structure-activity relationships of oleanan- and ursane-type triterpenoids," *Botanical Studies*, 47:339-368, 2006.

Sun et al., "The Synthetic Triterpenoid, CDDO, Suppresses Alloreactive T Cell Responses and Reduces Murine Early Acute Graft-versus-Host Disease Mortality," *Biology of Blood and Marrow Transplantation*, 13 (5): 521-529, 2007.

Tabe et al., "Chromatin-Mediated Transcriptional Activation with Novel Peroxisome Proliferator-Activated Receptor gamma(P-PARgamma) Ligand 2-cyano-1,9-dien-28-oic Acid (CDDO) in Acute Promyelocytic Leukemia Cells," Abstracts of the 44th Annual Meeting of the American Society of Hematology, Abstract 2191, 2002.

Takeda et al., "Orthosiphol D and E, minor diterpenes from *Orthosiphon stamineus*," *Phytochemistry*, 33 (2): 411-415, 1993.

Thimmulappa et al., "Nrf2 is a critical regulator of the innate immune response and survival during experimental sepsis," *J. Clinical Investigation*, 116 (4): 984-995, 2006.

Thimmulappa et al., "Nrf2-dependent protection from LPS induced inflammatory response and mortality by CDDO-imidazolide," *Biochem. Biophys. Res. Commun.*, 351:883-889, 2006.

Thimmulappa et al., "Preclinical evaluation of targeting the Nrf2 pathway by triterpenoids (CDDO-Im and CDDO-Me) for protection from LPS-induced inflammatory response and reactive oxygen species in human peripheral blood mononuclear cells and neutrophils," *Antioxidants and Redox Signalling*, 9:1-8, 2007.

Tinto et al., "Terpenoid constituents of *Oxandra asbeckii*," *Journal of Natural Products*, 55 (6): 701-706, 1992.

Tran et al., "The synthetic triterpenoid CDDO-methyl ester modulates microglial activities, inhibits TNF production, and provides dopaminergic neuroprotection," *Journal of Neuroinflammation*, 5:1-14, 2008.

Tsao et al., "DRIP205 co-activator overexpression enhances PPARgamma-mediated differentiation of leukemia cells by CDDO," *Proc. Amer. Assoc. Cancer Res.*, 46: Abstract No. 1855, 2005.

Tsao et al., "Targeted Induction of Apoptosis in Leukemias by PPARgammma Ligation," American Society of Hematology 43rd Annual Meeting and Exposition, Abstract No. 2381, 2001.

Urban et al., "Influence of esterification and modification of A-ring in a group of lupane acids on their cytotoxicity ," *Bioorganic and Medicinal Chemistry*, 13 (19): 5527-5535, 2005.

Urban et al., "Synthesis of A-seco derivatives of betulinic acid with cytotoxic activity," *J. of Natural Products*, 67 (7): 1100-1105, 2004.

(56) References Cited

OTHER PUBLICATIONS

Uskoković et al., "D-Homosteroids. I. 3β-Hydroxy-17a,17a-dimethyl-D-homoandrostane-17-one and related compounds," *J. of the American Chemical Society*, 81: 4561-4566, 1959.
Vannini et al., "The synthetic oleanane triterpenoid, CDDO-methyl ester, is a potent antiangiogenic agent," *Molecular Cancer Therapeutics*, 6 (12 Part 1), 3139-3146, 2007.
Vilayur and Harris, "Emerging therapies for chronic kidney disease: what is their role?" *Nature Reviews*, 5: 375-383, 2009.
Vincenti et al., "The synthetic triterpenoid TP-222 inhibits RANKL induction of differentiation and MMP-9 gene expression in osteoclasts," Abstract 1385, American College of Rheumatology Annual Scientific Meeting, 2006.
Wada and Tanaka, "Synthetic lanostane-type triterpenoids as inhibitors of DNA topoisomerase II," *Bioorganic and Medicinal Chemistry Letters*, 15 (12): 2966-2969, 2005.
Wang et al., "A novel synthetic triterpenoid, 2-cyano-3,12-dioxoolean-1,9-dien-28-oic acid (CDDO) induces adipocyte differentiation in 3T3-L1 cells," *Proceedings of the American Association for Cancer Research Annual Meeting*, 40:300, abstract # 1989, 1999.
Wang et al., "A synthetic triterpenoid, 2-cyano-3,12-dioxooleana-1,9-dien-28-oic acid (CDDO), is a ligand for the peroxisome proliferator-activated receptor g," *Mol. Endocrin.*, 14(10):1550-1556, 2000.
Wang et al., "Diterpenoids from roots of *Euphorbia wallichii*," *Zhongcaoyao*, 35 (6): 611-614, 2004.
Wang et al., "Synthetic triterpenoid CDDO and its derivatives increase ceramides and are cytotoxic to pediatric acute lymphoblastic leukemia cell lines," *Proc. Am. Assoc. Cancer Res.*, 47: 4643, 2006.
Wen et al., "Pentacyclic triterpenes. Part 2: Synthesis and biological evaluation of maslinic acid derivatives as glycogen phosphorylase inhibitors ," *Bioorganic and Medicinal Chemistry Letters*, 16 (3): 722-726, 2006.
Wu et al., "An improved general synthetic approach to cis-clerodane diterpenoids. A more efficient total synthesis of (±)-6β-acetoxy-2-oxokolavenool," *Tetrahedron*, 42(25): 4207-4209, 2001.
Wulff et al., "The Natural Product Avrainvillamide Binds to the Oncoprotein Nucleophosmin," *J. of the American Chemical Society*, 129 (46): 14444-14451, 2007.
Yates et al., "Pharmacodynamic characterization of chemopreventive triterpenoids as exceptionally potent inducers of Nrf2-regulated genes," *Mol. Cancer Ther.*, 6:154-162, 2007.
Yates et al., "Potent protection against aflatoxin-induced tumorigenesis through induction of Nrf2-regulated pathways by the triterpenoid 1-[2-cyano-3-,12-dioxooleana-1,9(11)-dien-28-oyl]imidazole," *Cancer Res.*, 66 (4): 2488-2494, 2007.
Yore et al., "The synthetic triterpenoid 1-[2-cyano-3,12-dioxooleana-1,9(11)-dien-28-oyl]imidazole blocks nuclear factor-kappaB activation through direct inhibition of IkappaB kinase beta," *Mol. Cancer Ther.*, 5 (12): 3232-3239, 2006.
You et al., "Synthesis and cytotoxic activity of a-ring modified betulinic acid derivatives ," *Bioorganic and Medicinal Chemistry Letters*, 13 (19): 3137-3140, 2003.
Yue et al., "Depletion of intracellular glutathione contributes to JNK-mediated death receptor 5 upregulation and apoptosis induction by the novel synthetic triterpenoid methyl-2-cyano-3, 12-dioxooleana-1, 9-dien-28-oate (CDDO-Me)," *Cancer & Biology Ther.*, 5(5):492-497, 2006.
Zapata et al., "CDDO and CDDO-Im Reduce Tumor Burden in a Transgenic Mouse Model of CLL," *Blood*, 104:3477, 2004.
Zapata et al., "Triterpenoids show activity against leukemic cells in a transgenic mouse model of CLL," *Proc. Amer. Assoc. Cancer Res.*, 46: Abstract No. 5179, 2005.
Zhang et al., "Synthetic triterpenoid CDDO as effective therapy for HER2-expressing resistant breast cancer," *Proc. Amer. Assoc. Cancer Res.*, Abstract No. 3799, 2004.
Zhang et al., "The novel synthetic oleanane triterpenoid CDDO (2-cyano-3, 12-dioxoolean-1, 9-dien-28-oic acid) induces apoptosis in Mycosis fungoides/Sézary syndrome cells," *J. Invest. Dermatol.*, 123:380-387, 2004.
Zhou et al., "A new triterpenoid from the roots of *Tripterygium wildfordii*," *Chinese Chemical Letters*, 21(5): 600-602, 2010.
Ziegler et al., "Isolation and structure of eucosterol and 16beta-hydroxyeucosterol, two novel spirocyclic nortriterpenes, and of a new 24-nor-5alpha-chola-8, 16-diene-23-oic acid from bulbs of several *Eucomis* species," *Helv Chim Acta*, 59(6):1997-2011, 1976.
Zoretic et al., "Advanced tetracycles in a stereoselective approach to d,1-spongiatriol and related metabolites: the use of radicals in the synthesis of angular electrophores," *J. of Organic Chemistry*, 63 (4): 1162-1167, 1998.
Zou et al., "c-Jun NH2-terminal kinase-mediated up-regulation of death receptor 5 contributes to induction of apoptosis by the novel synthetic triterpenoid methyl-2-cyano-3,12-dioxooleana-1, 9-dien-28-oate in human lung cancer cells," *Cancer Res.*, 64:7570-7578, 2004.
Notice of Allowance issued in U.S. Appl. No. 13/330,378, dated Apr. 19, 2013.
Office Communication issued in U.S. Appl. No. 13/330,378, dated Oct. 29, 2012.
International Preliminary Report on Patentability issued in PCT/US2011/065897, dated Jun. 27, 2013.
Pergola, et al., "Bardoxolone methyl and kidney function in CKD with type 2 diabetes," *N. Engl. J. Med.*, 365:327-336, 2011.
Saha, et al., "The triterpenoid 2-cyano-3,12-dioxo-oleano-19-dien-28-oic acid methyl ester has potent anti-diabetic effects in diet-induced diabetic mice and lepr$^{db/db}$ mice," *J. Biol. Chem.*, 285:40581-92, 2010.
Wu, et al., "Beneficial role of Nrf2 in regulating NADPH generation and consumption," *Tox. Sci.*, 123(2):590-600, 2011.
Takaishi, et al., "Triterpenoid inhibitors of interleukin-1 secretion and tumour-promotion from *Tripterygium wilfordii* var. *regelii*," *Phytochemistry*, 45(5):969-974, 1997.
Tanaka, et al., "A new triterpenoid from the leaves of *Eucommia ulmoides* Oliv .," *Chem. Pharm Bull.*, 45(8):1379-1380, 1997.
ten Haven, et al., "Early diagenetic transformation of higher-plant triterpenoids in deep-sea sediments from Baffin Bay," *Geochimica et Cosmochimica Acta*, 56:2001-2024, 1992.
Van Kiem, et al., "A new 24-nor-lupane-glycoside of *Acanthopanax trifoliatus*," *Arch. Pharm. Res.*, 26(9):706-708, 2003.
Waratchareeyakul, et al., "2,19-dihydroxyl-3-oxo-(2,4,19)-24-nor-olean-12-en-28-oic acid monohydrate," *Acta. Cryst.*, E63, o4062-o4063, 2007.
White, et al., "A novel demethylated oxygenated triterpenoid in crude oils from the Canadian Beaufort sea and northeast Alaska," *Tetrahedron Letters*, 39(19):3031-3034, 1998.
Deeb, et al., "CDDO-Me Induces Apoptosis and Inhibits Akt, mTOR and NF-κB Signaling Proteins in Prostate Cancer Cells," *Anticancer Research*, 27:3035-3044, 1007.
Alabran, et al., "Human neuroblastoma cells rapidly enter cell cycle arrest and apoptosis following exposure to C-28 derivatives of the synthetic triterpenoid CDDO," *Cancer Biology & Therapy*, 7(5):709-717, 2008.
Campaigne and Forsch, "Rearrangement of 2-cyano-3-(1-methylcyclopentyl)indenone to 4a-methyl-9-oxo-10-cyano-1,2,3,4,4a,9-hexahydrophenanthrene," *J. Org. Chem.*, 43(6):1044-1050, 1978.
Chadalapaka, et al., "Structure-dependent inhibition of bladder and pancreatic cancer cell growth by 2-substituted glycyrrhetinic and ursolic acid derivatives," *Bioorganic & Medicinal Chemistry Letters*, 18:2633-2639, 2008.
Deeb, et al., "CDDO-Me inhibits proliferation, induces apoptosis, down-regulates Akt, mTOR, NF-κB and NF-κB-regulated antiapoptotic and proangiogenic proteins in TRAMP prostate cancer cells," *J of Experimental Therapeutics and Oncology*, 7:31-39, 2008.
Heather E. Ferguson, "PPARγ ligands have potent anti-fibrotic activity: mechanism of action and implications for therapy of pulmonary fibrosis," Dissertation, University of Rochester, 2008.
Hughes, et al., "The synthetic triterpenoid CDDO-Im inhibits fatty acid synthase expression and has antiproliferative and proapoptotic effects in human liposarcoma cells," *Cancer Investigation*, 26:118-127, 2008.

(56) References Cited

OTHER PUBLICATIONS

Hyer, et al., "Apoptotic activity and mechanism of 2-cyano-3,12-dioxoolean-1,9-dien-28-oic acid and related synthetic triterpenoids in prostate cancer," *Cancer Res.*, 68:2927-2933, 2008.

Liu, et al., "Coordinate regulation of enzyme markers for inflammation and for protection against oxidants and electrophiles," *Proc. Natl. Acad. Sci.*, 105(41):15926-15931, 2008.

Andrew E. Place, "Pre-clincial evaluation of the novel synthetic triterpenoid CDDO-Imidazolide," Thesis, Dartmouth College, May 5, 2004.

Riccioni, et al., "Resistance of acute myeloid leukemic cells to the triterpenoid CDDO-Imidazolide is associated with low caspase-8 and FADD levels," *Leukemia Research*, 32:1244-1258, 2008.

Samudio, et al., "Inhibition of mitochondrial metabolism by methyl-2-cyano-3,12-dioxoolean-1,9-diene-28-oate induces apoptotic or autophagic cell death in chronic myelogenous leukemia cells," *Mol. Cancer Ther.*, 7(5):1130-1139, 2008.

Subba Rao, et al., "Chemical modifications of natural triterpenes—glycyrrhetinic and boswellic acids: evaluation of their biological activity," *Tetrahedron*, 64(51):11541-11548, 2008.

Sun, et al., "Therapeutic potential of synthetic triterpenoids in neuroblastoma," *Cancer Biology & Therapy*, 7(5):720-722, 2008.

To, et al., "The synthetic triterpenoid 2-cyano-3,12-dioxooleana-1,9-dien-28-oic acid-imidazolide alters transforming growth factor β-dependent signaling and cell migration by affecting the cytoskeleton and the polarity complex," *J. Biol. Chem.*, 283:11700-11713, 2008.

Vene, et al., "Glycogen synthase kinase 3β regulates cell death induced by synthetic triterpenoids," *Cancer Res.*, 68:6987-6996, 2008.

Wang, "Differentiating and anti-inflammatory activities of the triterpenoid, CDDO," Thesis, Dartmouth College, May 4, 2001.

Wen, et al., "Naturally occurring pentacyclic triterpenes as inhibitors of glycogen phosphorylase: synthesis, structure-activity relationships, and X-ray crystallographic studies," *J. Med. Chem.*, 51:3540-3554, 2008.

Xu, et al., "Inhibition of the signal transducer and activator of transcription-3 (STAT3) signaling pathway by 4-oxo-l-phenyl-1,4-dihydroquinoline-3-carboxylic acid esters," *J. Med. Chem.*, 51:4115-4121, 2008.

Zou, et al., "c-FLIP downregulation contributes to apoptosis induction by the novel synthetic triterpenoid methyl-2-cyano-3,12-dioxooleana-1,9-dien-28-oate (CDDO-Me) in human lung cancer cells," *Cancer Biology & Therapy*, 6(10):1614-1620, 2007.

Zou, et al., "Coupling of endoplasmic reticulum stress to CDDO-Me-induced up-regulation of death receptor 5 via a CHOP-dependent mechanism involving JNK activation," *Cancer Res.*, 68:7484-7492, 2008.

Office Action No. 15832 in Co-Pending Colombian Patent Application No. 13-167.243 issued on Dec. 31, 2014. (Spanish, English Summary).

Honda, et al., "Tricyclic Compounds Containing Nonenolizable Cyano Enones. A Novel Class of Highly Potent Anti-Inflammatory and Cytoprotective Agents[79]," *J. Med. Chem.*, 54(6):1762-1778, 2011.

Japanese Office Action issued in Co-pending Japanese Application JP 2013-544872 issued on Jul. 27, 2015.

\* cited by examiner

SEQUENCE LISTING

<160> NUMBER OF SEQ ID NOS: 1

<210> SEQ ID NO 1
<211> LENGTH: 26
<212> TYPE: DNA
<213> ORGANISM: Homo sapiens

<400> SEQUENCE: 1
cagtcacagt gactcagcag aatctg   26

PYRAZOLYL AND PYRIMIDINYL TRICYCLIC ENONES AS ANTIOXIDANT INFLAMMATION MODULATORS

The present application is a continuation application of U.S. patent application Ser. No. 13/330,378, filed Dec. 19, 2011, now U.S. Pat. No. 8,513,436, issued on Aug. 20, 2013, which claims the benefit of priority to U.S. Provisional Application No. 61/424,601, filed Dec. 17, 2010, the entire contents of which are each incorporated herein by reference.

The sequence listing that is contained in the file named "REATP0066USD1_ST25.txt", which is 1 KB (as measured in Microsoft Windows®) and was created on Jul. 10, 2013, is filed herewith by electronic submission and is incorporated by reference herein.

BACKGROUND OF THE INVENTION

I. Field of the Invention

The present invention relates generally to the fields of biology and medicine. More particularly, it concerns compounds, compositions and methods for the treatment and prevention of diseases such as those associated with oxidative stress and inflammation.

II. Description of Related Art

The anti-inflammatory and anti-proliferative activity of the naturally occurring triterpenoid, oleanolic acid, has been improved by chemical modifications. For example, 2-cyano-3,12-dioxooleana-1,9(11)-dien-28-oic acid (CDDO) and related compounds have been developed (Honda et al., 1997; Honda et al., 1998; Honda et al., 1999; Honda et al., 2000a; Honda et al., 2000b; Honda, et al., 2002; Suh et al. 1998; Suh et al., 1999; Place et al., 2003; Liby et al., 2005). The methyl ester, bardoxolone-methyl (CDDO-Me), is currently being evaluated in phase II clinical trials for the treatment of diabetic nephropathy and chronic kidney disease.

Synthetic triterpenoid analogs of oleanolic acid have also been shown to be inhibitors of cellular inflammatory processes, such as the induction by IFN-γ of inducible nitric oxide synthase (iNOS) and of COX-2 in mouse macrophages. See Honda et al. (2000a); Honda et al. (2000b), and Honda et al. (2002), which are all incorporated herein by reference. Synthetic derivatives of another triterpenoid, betulinic acid, have also been shown to inhibit cellular inflammatory processes, although these compounds have been less extensively characterized (Honda et al., 2006). The pharmacology of these synthetic triterpenoid molecules is complex. Compounds derived from oleanolic acid have been shown to affect the function of multiple protein targets and thereby modulate the activity of several important cellular signaling pathways related to oxidative stress, cell cycle control, and inflammation (e.g., Dinkova-Kostova et al., 2005; Ahmad et al., 2006; Ahmad et al., 2008; Liby et al., 2007a). Derivatives of betulinic acid, though they have shown comparable anti-inflammatory properties, also appear to have significant differences in their pharmacology compared to OA-derived compounds (Liby et al., 2007b).

In general, it is not certain that the triterpenoid starting materials employed to date have optimal properties for all applications compared to other possible starting materials.

In addition, it is often necessary to synthesize triterpenoid derivatives from natural product starting materials. The production of highly purified triterpenoid starting materials can be expensive, and the plant materials that are the ultimate sources of these compounds can vary in availability, including due to adverse weather conditions, disease, and other environmental factors. Given that the biological activity profiles of known triterpenoid derivatives vary, and in view of the wide variety of diseases that may be treated or prevented with compounds having potent antioxidant and anti-inflammatory effects, and the high degree of unmet medical need represented within this variety of diseases, it is desirable to synthesize new compounds with diverse structures that may have improved biological activity profiles for the treatment of one or more indications. Therefore, the design of potent, selective antioxidant/anti-inflammatory compounds that can be readily synthesized from simple starting materials is a desirable goal.

SUMMARY OF THE INVENTION

The present disclosure provides novel compounds, including pyrazolyl and pyrimidinyl tricyclic enones with anti-inflammatory and/or antioxidant properties, pharmaceutical compositions thereof, methods for their manufacture, and methods for their use.

In one aspect of the present disclosure there are provided compounds of the formula:

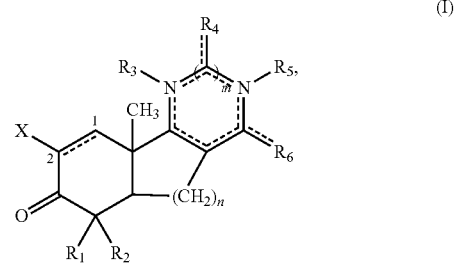

wherein:
the atoms labeled 1 and 2 are connected either by a double bond or an epoxidized double bond;
n is 1 or 2;
m is 0 or 1;
X is —CN, —CF$_3$, or —C(O)R$_a$, wherein R$_a$ is —OH, alkoxy$_{(C \leq 6)}$, alkylamino$_{(C \leq 6)}$, dialkylamino$_{(C \leq 6)}$, or —NHS(O)$_2$-alkyl$_{(C1-4)}$;
R$_1$ and R$_2$ are each independently hydrogen, hydroxy, halo, or amino; or alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, hetero-aryl$_{(C \leq 12)}$, heterocycloalkyl$_{(C \leq 12)}$, acyl$_{(C \leq 12)}$, alkoxy$_{(C \leq 12)}$, aryloxy$_{(C \leq 12)}$, aralkoxy$_{(C \leq 12)}$, heteroaryloxy$_{(C \leq 12)}$, acyloxy$_{(C \leq 12)}$, alkylamino$_{(C \leq 12)}$, dialkyl-amino$_{(C \leq 12)}$, arylamino$_{(C \leq 12)}$, aralkylamino$_{(C \leq 12)}$, heteroarylamino$_{(C \leq 12)}$, amido$_{(C \leq 12)}$, or a substituted version of any of these groups; or
R$_1$ and R$_2$ are taken together and are alkanediyl$_{(C \leq 12)}$, alkenediyl$_{(C \leq 12)}$, alkoxydiyl$_{(C \leq 12)}$, alkylaminodiyl$_{(C \leq 12)}$, or a substituted version of any of these groups;
R$_3$ is absent, hydrogen; or alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heterocycloalkyl$_{(C \leq 12)}$, or a acyl$_{(C \leq 12)}$ substituted version of any of these groups; or R$_3$ is taken together with R$_4$ as provided below; provided that R$_3$ is absent when and only when the atom to which it is bound forms part of a double bond;
R$_4$ is hydrogen, hydroxy, amino, halo, cyano, or oxo; or alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heterocycloalkyl$_{(C \leq 12)}$, acyl$_{(C \leq 12)}$, alkoxy$_{(C \leq 12)}$, aryloxy$_{(C \leq 12)}$, aralkoxy$_{(C \leq 12)}$, heteroaryloxy$_{(C \leq 12)}$, acyloxy$_{(C \leq 12)}$, alkylamino$_{(C \leq 12)}$, dialkylamino$_{(C \leq 12)}$, arylamino$_{(C \leq 12)}$, aralkyl-amino$_{(C \leq 12)}$, heteroarylamino$_{(C≤12)}$, amido$_{(C≤12)}$, or a substituted version of any of these groups; or R$_4$ is taken together with either R$_3$ or R$_5$ as provided below;

R$_5$ is absent, hydrogen; or alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$ or a substituted version of any of these groups; or R$_5$ is taken together with R$_4$ as provided below; provided that R$_5$ is absent when and only when the atom to which it is bound forms part of a double bond; and R$_6$ is hydrogen, hydroxy, amino, halo, cyano, or oxo; or alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$, alkoxy$_{(C≤12)}$, aryloxy$_{(C≤12)}$, aralkoxy$_{(C≤12)}$, heteroaryloxy$_{(C≤12)}$, acyloxy$_{(C≤12)}$, alkylamino$_{(C≤12)}$, dialkylamino$_{(C≤12)}$, arylamino$_{(C≤12)}$, aralkylamino$_{(C≤12)}$, heteroarylamino$_{(C≤12)}$, amido$_{(C≤12)}$, or a substituted version of any of these groups;

provided that when R$_3$ and R$_4$ are taken together, the compound is further defined by formula Ia:

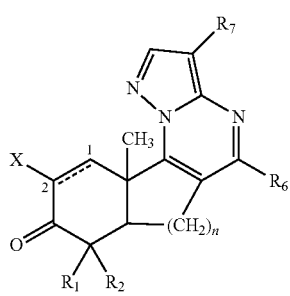

(Ia)

wherein R$_7$ is hydrogen, hydroxy, amino, halo, or cyano; or alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, hetero-cycloalkyl$_{(C≤12)}$, acyl$_{(C≤12)}$, alkoxy$_{(C≤12)}$, aryloxy$_{(C≤12)}$, aralkoxy$_{(C≤12)}$, heteroaryloxy$_{(C≤12)}$, acyloxy$_{(C≤12)}$, alkylamino$_{(C≤12)}$, dialkylamino$_{(C≤12)}$, arylamino$_{(C≤12)}$, aralkylamino$_{(C≤12)}$, heteroarylamino$_{(C≤12)}$, amido$_{(C≤12)}$, or a substituted version of any of these groups; or provided that when R$_4$ and R$_5$ are taken together, the compound is further defined by formula Ib:

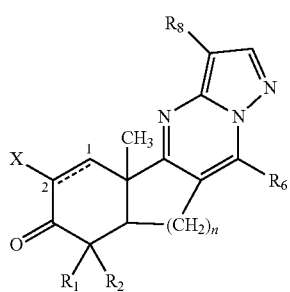

(Ib)

wherein R$_8$ is hydrogen, hydroxy, amino, halo, or cyano; or alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, hetero-cycloalkyl$_{(C≤12)}$, acyl$_{(C≤12)}$, alkoxy$_{(C≤12)}$, aryloxy$_{(C≤12)}$, aralkoxy$_{(C≤12)}$, heteroaryloxy$_{(C≤12)}$, acyloxy$_{(C≤12)}$, alkylamino$_{(C≤12)}$, dialkylamino$_{(C≤12)}$, arylamino$_{(C≤12)}$, aralkylamino$_{(C≤12)}$, heteroarylamino$_{(C≤12)}$, amido$_{(C≤12)}$, or a substituted version of any of these groups;

or a pharmaceutically acceptable salt or tautomer thereof.

In some embodiments, the compounds are further defined by the formula:

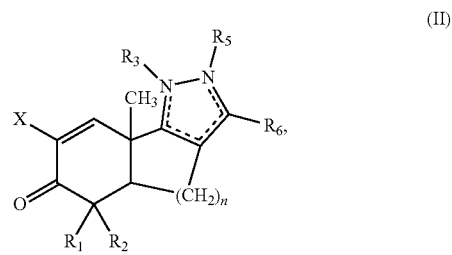

(II)

wherein:

n is 1 or 2;

X is —CN, —CF$_3$, or —C(O)R$_a$, wherein R$_a$ is —OH, alkoxy$_{(C≤6)}$, alkylamino$_{(C≤6)}$, dialkylamino$_{(C≤6)}$, or —NHS(O)$_2$-alkyl$_{(C1-4)}$;

R$_1$ and R$_2$ are each independently hydrogen, hydroxy, halo, or amino; or alkyl$_{(C≤12)}$, alkenyl$_{(C≤12)}$, alkynyl$_{(C≤12)}$, aryl$_{(C≤12)}$, aralkyl$_{(C≤12)}$, hetero-aryl$_{(C≤12)}$, heterocycloalkyl$_{(C≤12)}$, acyl$_{(C≤12)}$, alkoxy$_{(C≤12)}$, aryloxy$_{(C≤12)}$, aralkoxy$_{(C≤12)}$, heteroaryloxy$_{(C≤12)}$, acyloxy$_{(C≤12)}$, alkylamino$_{(C≤12)}$, dialkyl-amino$_{(C≤12)}$, arylamino$_{(C≤12)}$, aralkylamino$_{(C≤12)}$, heteroarylamino$_{(C≤12)}$, amido$_{(C≤12)}$, or a substituted version of any of these groups; or R$_1$ and R$_2$ are taken together and are alkanediyl$_{(C≤12)}$, alkenediyl$_{(C≤12)}$, alkoxydiyl$_{(C≤12)}$, alkylaminodiyl$_{(C≤12)}$, or a substituted version of any of these groups;

R$_3$ is absent, hydrogen; or alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$ or a substituted version of any of these groups; provided that R$_3$ is absent when and only when the atom to which it is bound forms part of a double bond;

R$_5$ is absent, hydrogen; or alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$ or a substituted version of any of these groups; provided that R$_5$ is absent when and only when the atom to which it is bound forms part of a double bond; and R$_6$ is hydrogen, hydroxy, amino, halo, or cyano; or alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$, alkoxy$_{(C≤12)}$, aryloxy$_{(C≤12)}$, aralkoxy$_{(C≤12)}$, heteroaryloxy$_{(C≤12)}$, acyloxy$_{(C≤12)}$, alkylamino$_{(C≤12)}$, dialkylamino$_{(C≤12)}$, arylamino$_{(C≤12)}$, aralkylamino$_{(C≤12)}$, heteroarylamino$_{(C≤12)}$, amido$_{(C≤12)}$, or a substituted version of any of these groups;

or a pharmaceutically acceptable salt or tautomer thereof.

In some embodiments, the compounds are further defined by the formula:

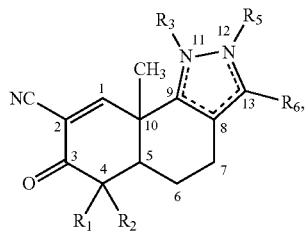

(III)

wherein:
- $R_1$ and $R_2$ are each independently hydrogen, hydroxy, halo, or amino; or alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, hetero-aryl$_{(C \leq 12)}$, heterocycloalkyl$_{(C \leq 12)}$, acyl$_{(C \leq 12)}$, alkoxy$_{(C \leq 12)}$, aryloxy$_{(C \leq 12)}$, aralkoxy$_{(C \leq 12)}$, heteroaryloxy$_{(C \leq 12)}$, acyloxy$_{(C \leq 12)}$, alkylamino$_{(C \leq 12)}$, dialkyl-amino$_{(C \leq 12)}$, arylamino$_{(C \leq 12)}$, aralkylamino$_{(C \leq 12)}$, heteroarylamino$_{(C \leq 12)}$, amido$_{(C \leq 12)}$, or a substituted version of any of these groups; or
- $R_1$ and $R_2$ are taken together and are alkanediyl$_{(C \leq 12)}$, alkenediyl$_{(C \leq 12)}$, alkoxydiyl$_{(C \leq 12)}$, alkylaminodiyl$_{(C \leq 12)}$, or a substituted version of any of these groups;
- $R_3$ is absent, hydrogen; or alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heterocycloalkyl$_{(C \leq 12)}$, acyl$_{(C \leq 12)}$ or a substituted version of any of these groups; provided that $R_3$ is absent when and only when the atom to which it is bound forms part of a double bond;
- $R_5$ is absent, hydrogen; or alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heterocycloalkyl$_{(C \leq 12)}$, acyl$_{(C \leq 12)}$ or a substituted version of any of these groups; provided that $R_5$ is absent when and only when the atom to which it is bound forms part of a double bond; and
- $R_6$ is hydrogen, hydroxy, amino, halo, or cyano; or alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heterocycloalkyl$_{(C \leq 12)}$, acyl$_{(C \leq 12)}$, alkoxy$_{(C \leq 12)}$, aryloxy$_{(C \leq 12)}$, aralkoxy$_{(C \leq 12)}$, heteroaryloxy$_{(C \leq 12)}$, acyloxy$_{(C \leq 12)}$, alkylamino$_{(C \leq 12)}$, dialkylamino$_{(C \leq 12)}$, arylamino$_{(C \leq 12)}$, aralkylamino$_{(C \leq 12)}$, heteroarylamino$_{(C \leq 12)}$, amido$_{(C \leq 12)}$, or a substituted version of any of these groups;

or a pharmaceutically acceptable salt or tautomer thereof.

In some embodiments, the compounds are further defined by the formula:

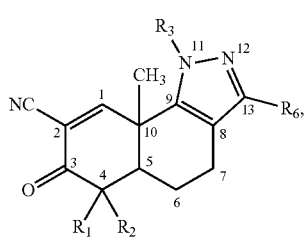

(IV)

wherein:
$R_1$ and $R_2$ are each independently hydrogen, hydroxy, halo, or amino; or alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, hetero-aryl$_{(C \leq 12)}$, heterocycloalkyl$_{(C \leq 12)}$, acyl$_{(C \leq 12)}$, alkoxy$_{(C \leq 12)}$, aryloxy$_{(C \leq 12)}$, aralkoxy$_{(C \leq 12)}$, heteroaryloxy$_{(C \leq 12)}$, acyloxy$_{(C \leq 12)}$, alkylamino$_{(C \leq 12)}$, dialkyl-amino$_{(C \leq 12)}$, arylamino$_{(C \leq 12)}$, aralkylamino$_{(C \leq 12)}$, heteroarylamino$_{(C \leq 12)}$, amido$_{(C \leq 12)}$, or a substituted version of any of these groups;

- $R_3$ is hydrogen; or alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heterocycloalkyl$_{(C \leq 12)}$, acyl$_{(C \leq 12)}$ or a substituted version of any of these groups; and
- $R_6$ is hydrogen, hydroxy, amino, halo, or cyano; or alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heterocycloalkyl$_{(C \leq 12)}$, acyl$_{(C \leq 12)}$, alkoxy$_{(C \leq 12)}$, aryloxy$_{(C \leq 12)}$, aralkoxy$_{(C \leq 12)}$, heteroaryloxy$_{(C \leq 12)}$, acyloxy$_{(C \leq 12)}$, alkylamino$_{(C \leq 12)}$, dialkylamino$_{(C \leq 12)}$, arylamino$_{(C \leq 12)}$, aralkylamino$_{(C \leq 12)}$, heteroarylamino$_{(C \leq 12)}$, amido$_{(C \leq 12)}$, or a substituted version of any of these groups;

or a pharmaceutically acceptable salt or tautomer thereof.

In some embodiments, the compounds are further defined by the formula:

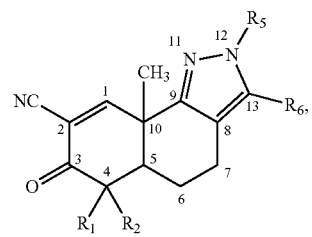

(V)

wherein:
- $R_1$ and $R_2$ are each independently hydrogen, hydroxy, halo, or amino; or alkyl$_{(C \leq 12)}$, alkynyl$_{(C \leq 12)}$, aryl$_{(C \leq 12)}$, aralkyl$_{(C \leq 12)}$, heteroalkenyl$_{(C \leq 12)}$, aryl$_{(C \leq 12)}$, heterocycloalkyl$_{(C \leq 12)}$, acyl$_{(C \leq 12)}$, alkoxy$_{(C \leq 12)}$, aryloxy$_{(C \leq 12)}$, aralkoxy$_{(C \leq 12)}$, heteroaryloxy$_{(C \leq 12)}$, acyloxy$_{(C \leq 12)}$, alkylamino$_{(C \leq 12)}$, dialkyl-amino$_{(C \leq 12)}$, amino$_{(C \leq 12)}$, aralkylamino$_{(C \leq 12)}$, heteroarylamino$_{(C \leq 12)}$, amido$_{(C \leq 12)}$, or a substituted version of any of these groups; or
- $R_1$ and $R_2$ are taken together and are alkanediyl$_{(C \leq 12)}$, alkenediyl$_{(C \leq 12)}$, alkoxydiyl$_{(C \leq 12)}$, alkylaminodiyl$_{(C \leq 12)}$, or a substituted version of any of these groups;
- $R_5$ is hydrogen; or alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heterocycloalkyl$_{(C \leq 12)}$, acyl$_{(C \leq 12)}$ or a substituted version of any of these groups; and
- $R_6$ is hydrogen, hydroxy, amino, halo, or cyano; or alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heterocycloalkyl$_{(C \leq 12)}$, acyl$_{(C \leq 12)}$, alkoxy$_{(C \leq 12)}$, aryloxy$_{(C \leq 12)}$, aralkoxy$_{(C \leq 12)}$, heteroaryloxy$_{(C \leq 12)}$, acyloxy$_{(C \leq 12)}$, alkylamino$_{(C \leq 12)}$, dialkylamino$_{(C \leq 12)}$, arylamino$_{(C \leq 12)}$, aralkylamino$_{(C \leq 12)}$, heteroarylamino$_{(C \leq 12)}$, amido$_{(C \leq 12)}$, or a substituted version of any of these groups;

or a pharmaceutically acceptable salt or tautomer thereof.

In some embodiments, the compounds are further defined by the formula:

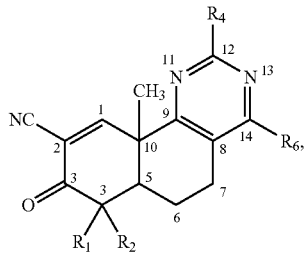

(VI)

wherein:
R$_1$ and R$_2$ are each independently hydrogen, hydroxy, halo, or amino; or alkyl$_{(C\leq12)}$, alkynyl$_{(C\leq12)}$, aryl$_{(C\leq12)}$, aralkyl$_{(C\leq12)}$, heteroalkenyl$_{(C\leq12)}$, aryl$_{(C\leq12)}$, heterocycloalkyl$_{(C\leq12)}$, acyl$_{(C\leq12)}$, alkoxy$_{(C\leq12)}$, aryloxy$_{(C\leq12)}$, aralkoxy$_{(C\leq12)}$, heteroaryloxy$_{(C\leq12)}$, acyloxy$_{(C\leq12)}$, alkylamino$_{(C\leq12)}$, dialkyl-amino$_{(C\leq12)}$, arylamino$_{(C\leq12)}$, aralkylamino$_{(C\leq12)}$, heteroarylamino$_{(C\leq12)}$, amido$_{(C\leq12)}$, or a substituted version of any of these groups;
R$_4$ is hydrogen, hydroxy, amino, halo, or cyano; or alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heterocycloalkyl$_{(C\leq12)}$, acyl$_{(C\leq12)}$, alkoxy$_{(C\leq12)}$, aryloxy$_{(C\leq12)}$, aralkoxy$_{(C\leq12)}$, heteroaryloxy$_{(C\leq12)}$, acyloxy$_{(C\leq12)}$, alkylamino$_{(C\leq12)}$, dialkylamino$_{(C\leq12)}$, arylamino$_{(C\leq12)}$, aralkylamino$_{(C\leq12)}$, heteroarylamino$_{(C\leq12)}$, amido$_{(C\leq12)}$, or a substituted version of any of these groups;
R$_6$ is hydrogen, hydroxy, amino, halo, or cyano; or alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heterocycloalkyl$_{(C\leq12)}$, acyl$_{(C\leq12)}$, alkoxy$_{(C\leq12)}$, alkoxy$_{(C\leq12)}$, aryloxy$_{(C\leq12)}$, heteroaryloxy$_{(C\leq12)}$, acyloxy$_{(C\leq12)}$, alkylamino$_{(C\leq12)}$, dialkylamino$_{(C\leq12)}$, arylamino$_{(C\leq12)}$, aralkylamino$_{(C\leq12)}$, heteroarylamino$_{(C\leq12)}$, amido$_{(C\leq12)}$, or a substituted version of any of these groups;
or a pharmaceutically acceptable salt or tautomer thereof.

In some embodiments, the atoms labeled 1 and 2 are connected by a double bond. In some embodiments, the atoms labeled 1 and 2 are connected by an epoxidized double bond. In some embodiments, n is 1. In some embodiments, n is 2. In some embodiments, m is 0. In some embodiments, m is 1. In some embodiments, X is —CN. In some embodiments, X is —CF$_3$. In some embodiments, X is hydrogen.

In some embodiments, R$_1$ or R$_2$ is alkyl$_{(C\leq8)}$ or substituted alkyl$_{(C\leq8)}$. In some embodiments, R$_1$ or R$_2$ is alkyl$_{(C\leq8)}$. In some embodiments, R$_1$ or R$_2$ is methyl. In some embodiments, R$_1$ and R$_2$ are each methyl. In some embodiments, R$_1$ is methyl and R$_2$ is hydrogen. In some embodiments, R$_1$ or R$_2$ is ethyl. In some embodiments, R$_1$ is ethyl and R$_2$ is hydrogen. In some embodiments, R$_1$ or R$_2$ is hydrogen. In some embodiments, R$_1$ and R$_2$ are each hydrogen. In some embodiments, R$_1$ and R$_2$ are taken together and are alkanediyl$_{(C\leq8)}$. In some embodiments, R$_1$ and R$_2$ are taken together and are 1,4-butanediyl. In some embodiments, R$_1$ or R$_2$ is aryl$_{(C\leq8)}$. In some embodiments, R$_1$ or R$_2$ is phenyl. In some embodiments, R$_1$ is phenyl and R$_2$ is hydrogen. In some embodiments, R$_1$ or R$_2$ is aralkyl$_{(C\leq8)}$. In some embodiments, R$_1$ or R$_2$ is benzyl. In some embodiments, R$_1$ is benzyl and R$_2$ is hydrogen. In some embodiments, R$_1$ and R$_2$ are each benzyl.

In some embodiments, R$_3$ is absent. In some embodiments, R$_3$ is hydrogen. In some embodiments, R$_3$ is alkyl$_{(C\leq8)}$, aryl$_{(C\leq8)}$, acyl$_{(C\leq8)}$, alkoxy$_{(C\leq8)}$ or a substituted version of any of these groups. In some embodiments, R$_3$ is alkyl$_{(C\leq4)}$ or substituted alkyl$_{(C\leq4)}$. In some embodiments, R$_3$ is alkyl$_{(C\leq4)}$. In some embodiments, R$_3$ is methyl. In some embodiments, R$_3$ is aryl$_{(C\leq8)}$ or substituted aryl$_{(C\leq8)}$. In some embodiments, R$_3$ is aryl$_{(C\leq8)}$. In some embodiments, R$_3$ is phenyl.

In some embodiments, R$_4$ is hydrogen. In some embodiments, R$_4$ is oxo. In some embodiments, R$_4$ is alkyl$_{(C\leq8)}$, aryl$_{(C\leq8)}$, acyl$_{(C\leq8)}$, alkoxy$_{(C\leq8)}$ or a substituted version of any of these groups. In some embodiments, R$_4$ is alkyl$_{(C\leq6)}$ or substituted alkyl$_{(C\leq6)}$. In some embodiments, R$_4$ is alkyl$_{(C\leq6)}$. In some embodiments, R$_4$ is methyl, isopropyl, t-butyl, or cyclopropyl. In some embodiments, R$_4$ is haloalkyl$_{(C\leq6)}$. In some embodiments, R$_4$ is trifluoromethyl. In some embodiments, R$_4$ is alkoxy$_{(C\leq6)}$. In some embodiments, R$_4$ is methoxy or ethoxy. In some embodiments, R$_4$ is aryl$_{(C\leq8)}$ or substituted aryl$_{(C\leq8)}$. In some embodiments, R$_4$ is phenyl, chlorophenyl, methylphenyl, or methoxyphenyl. In some embodiments, R$_4$ is heteroaryl$_{(C\leq8)}$. In some embodiments, R$_4$ is pyridinyl or pyrimidinyl. In some embodiments, R$_4$ is acyl$_{(C\leq6)}$ or substituted acyl$_{(C\leq6)}$. In some embodiments, R$_4$ is ethoxycarbonyl.

In some embodiments, R$_5$ is absent. In some embodiments, R$_5$ is hydrogen. In some embodiments, R$_5$ is alkyl$_{(C\leq8)}$, aryl$_{(C\leq8)}$, acyl$_{(C\leq8)}$, alkoxy$_{(C\leq8)}$ or a substituted version of any of these groups. In some embodiments, R$_5$ is alkyl$_{(C\leq6)}$ or substituted alkyl$_{(C\leq6)}$. In some embodiments, R$_5$ is alkyl$_{(C\leq6)}$. In some embodiments, R$_5$ is methyl, cyclohexyl, or t-butyl. In some embodiments, R$_5$ is substituted alkyl$_{(C\leq4)}$. In some embodiments, R$_5$ is 2-hydroxyethyl or 2,2,2-trifluoroethyl. In some embodiments, R$_5$ is aryl$_{(C\leq8)}$ or substituted aryl$_{(C\leq8)}$. In some embodiments, R$_5$ is aryl$_{(C\leq8)}$. In some embodiments, R$_5$ is phenyl. In some embodiments, R$_5$ is acyl$_{(C\leq8)}$ or substituted acyl$_{(C\leq8)}$. In some embodiments, R$_5$ is acetyl, methoxycarbonyl, ethoxycarbonyl, or phenylcarbonyl.

In some embodiments, R$_6$ is hydrogen. In some embodiments, R$_6$ is cyano. In some embodiments, R$_6$ is halo. In some embodiments, R$_6$ is chloro or bromo. In some embodiments, R$_6$ is alkyl$_{(C\leq6)}$ or substituted alkyl$_{(C\leq6)}$. In some embodiments, R$_6$ is alkyl$_{(C\leq6)}$. In some embodiments, R$_6$ is methyl, isopropyl or cyclohexyl. In some embodiments, R$_6$ is aryl$_{(C\leq8)}$, heteroaryl$_{(C\leq8)}$ or a substituted version of either of these groups. In some embodiments, R$_6$ is aryl$_{(C\leq10)}$. In some embodiments, R$_6$ is phenyl, methylphenyl or naphthyl. In some embodiments, R$_6$ is substituted aryl$_{(C\leq8)}$. In some embodiments, R$_6$ is chlorophenyl, fluorophenyl or methoxyphenyl. In some embodiments, R$_6$ is heteroaryl$_{(C\leq8)}$. In some embodiments, R$_6$ is pyridinyl, pyrimidinyl, methylpyrazolyl, dimethylisoxazolyl, methyltriazolyl, or methyltetrazolyl. In some embodiments, R$_6$ is aralkyl$_{(C\leq12)}$ or substituted aralkyl$_{(C\leq12)}$. In some embodiments, R$_6$ is benzyl. In some embodiments, R$_6$ is amido$_{(C\leq8)}$. In some embodiments, R$_6$ is phenylcarbonylamino. In some embodiments, R$_6$ is alkynyl$_{(C\leq8)}$. In some embodiments, R$_6$ is ethynyl. In some embodiments, R$_6$ is acyl$_{(C\leq8)}$. In some embodiments, R$_6$ is aminocarbonyl or dimethylaminocarbonyl. In some embodiments, R$_6$ is alkoxy$_{(C\leq8)}$. In some embodiments, R$_6$ is methoxy. In some embodiments, carbon atom 10 is in the R configuration. In some embodiments, carbon atom 10 is in the S configuration. In some embodiments, carbon atom 5 is in the R configuration. In some embodiments, carbon atom 5 is in the S configuration.

In some embodiments, R$_7$ or R$_8$ is hydrogen. In some embodiments, R$_7$ or R$_8$ is halo. In some embodiments, R$_7$ or R$_8$ is bromo. In some embodiments, R$_7$ or R$_8$ is aryl$_{(C\leq8)}$. In some embodiments, R$_7$ or R$_8$ is phenyl.

In some embodiments, the compounds are further defined as:
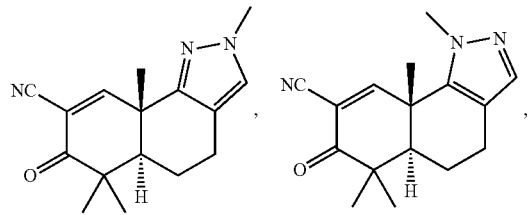
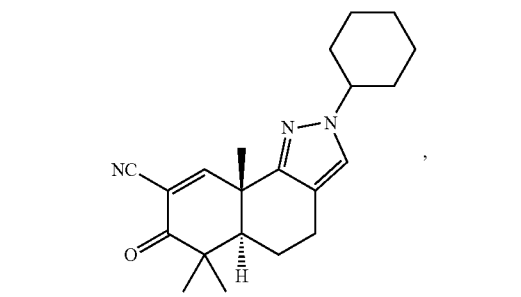
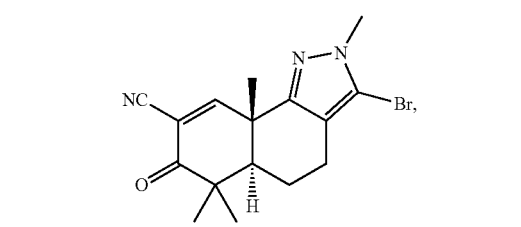
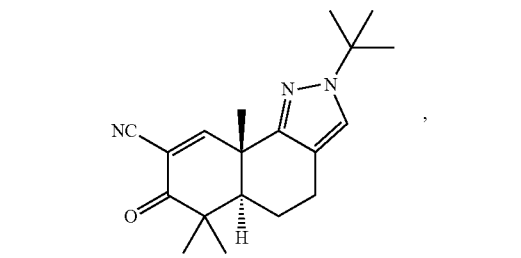
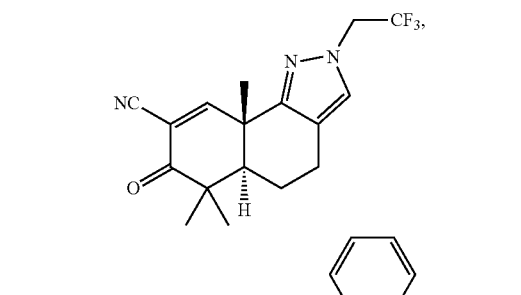
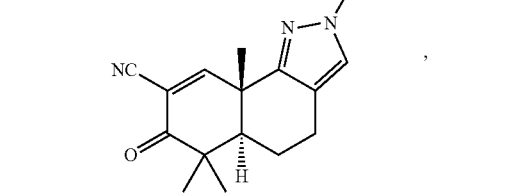
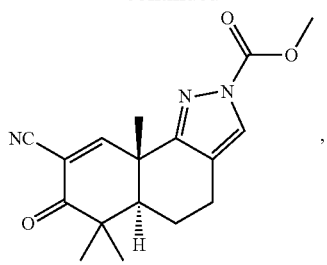
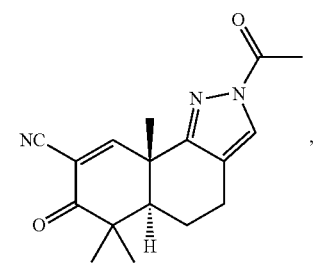
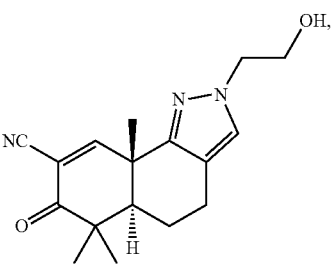
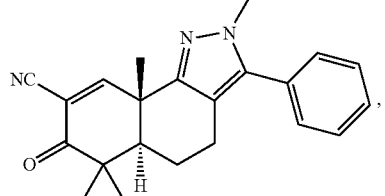
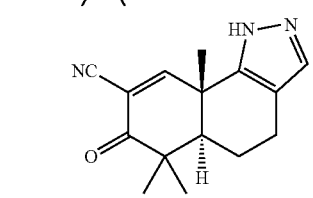
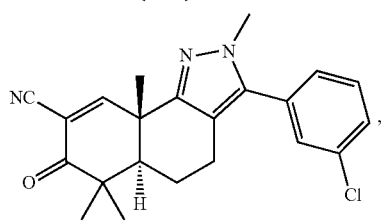
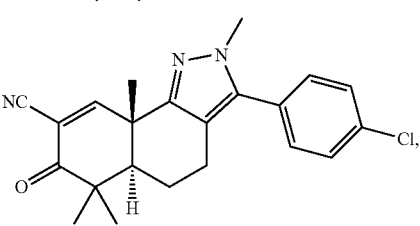

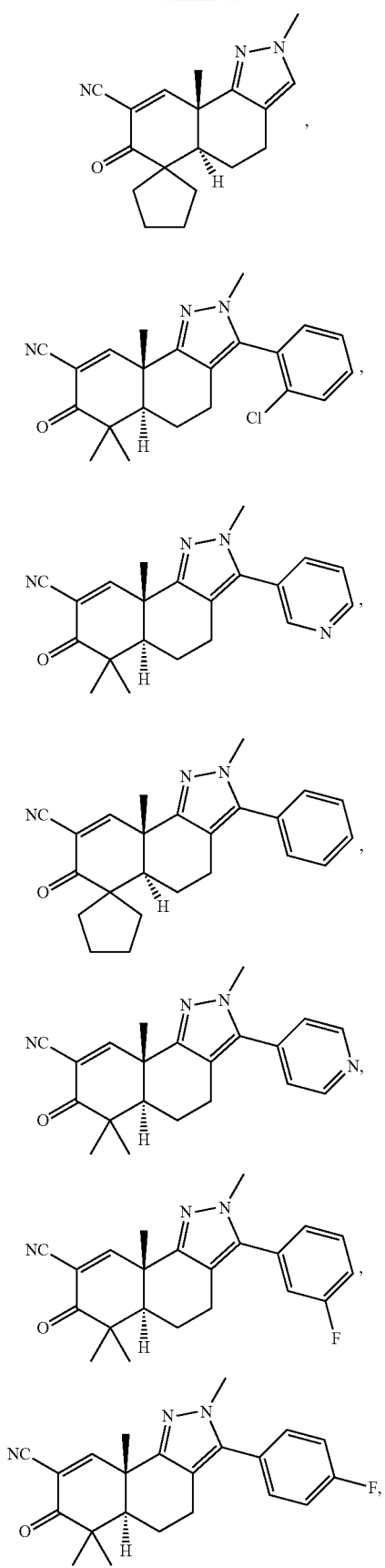
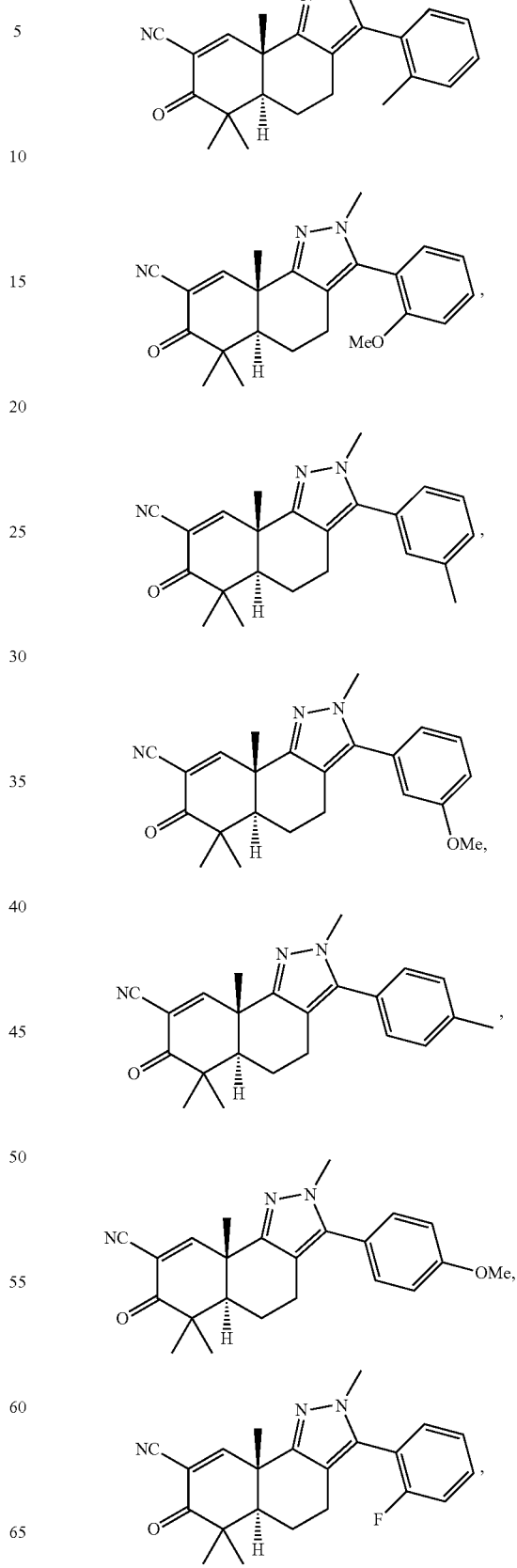

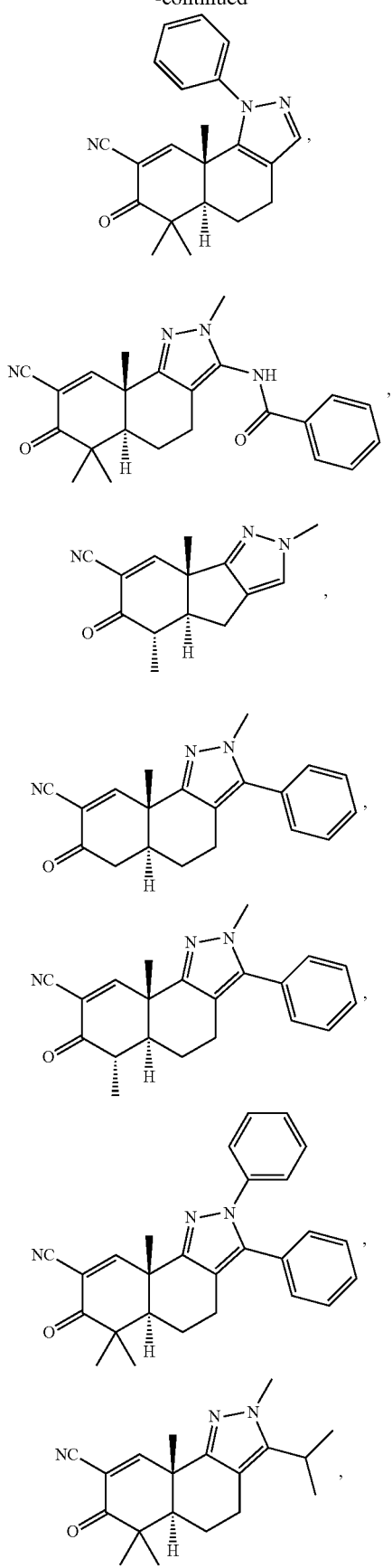
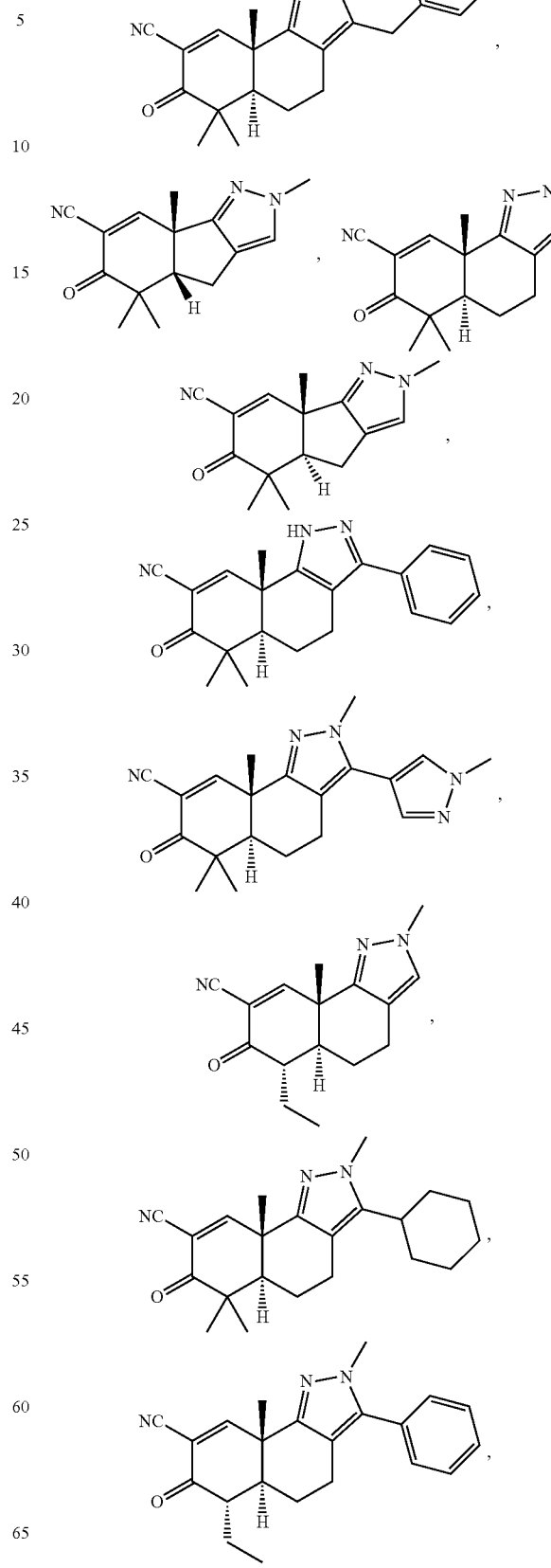

15
-continued
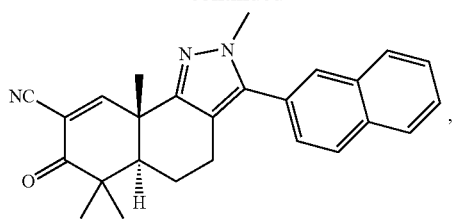
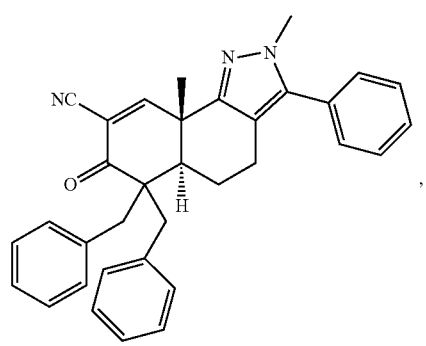
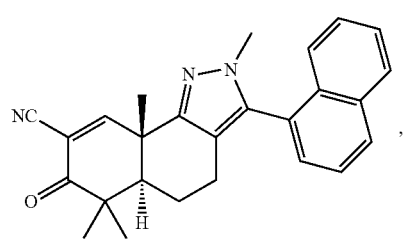
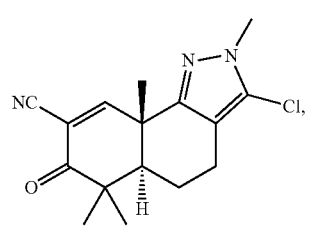
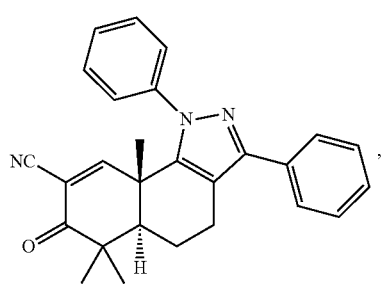
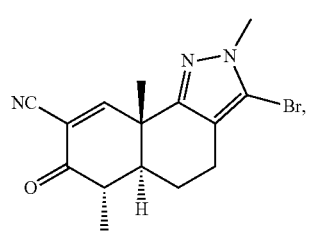
16
-continued
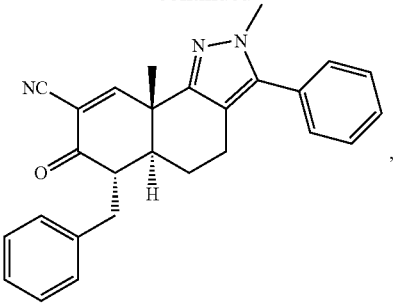
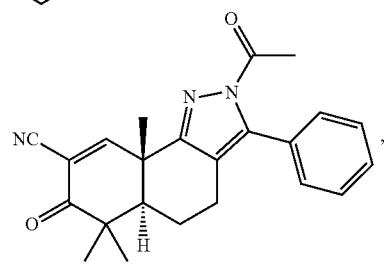
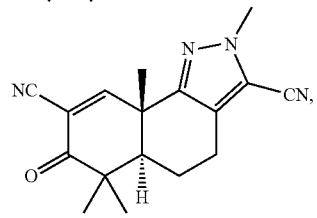
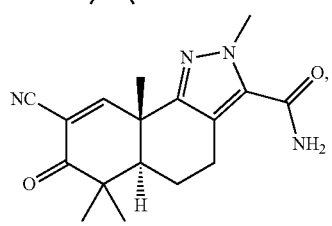
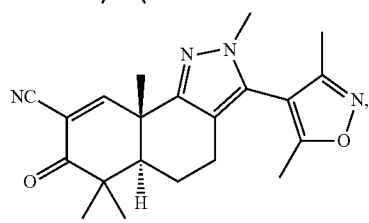
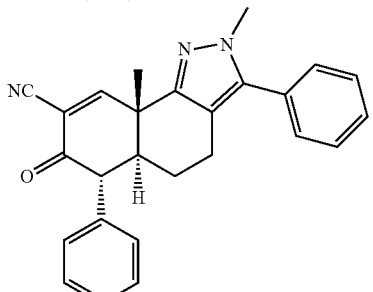
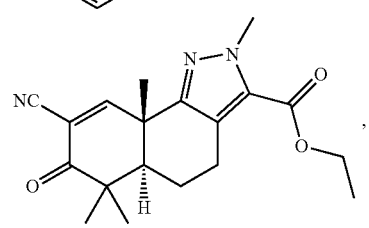

17
-continued
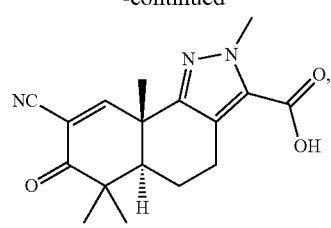
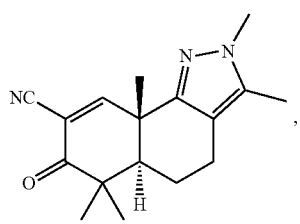
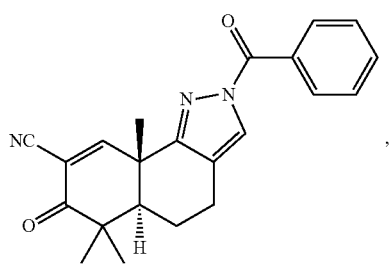
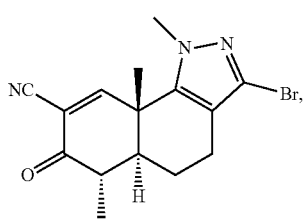
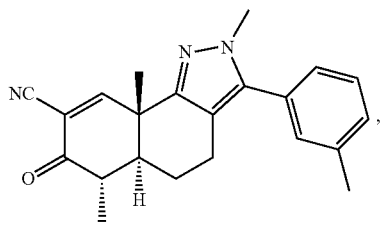
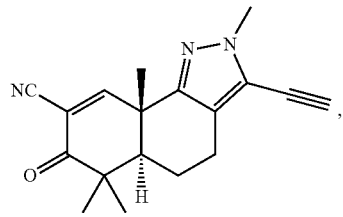
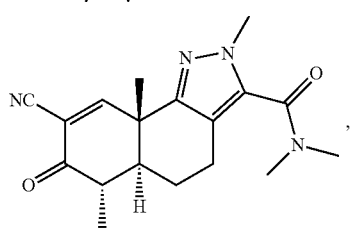
18
-continued
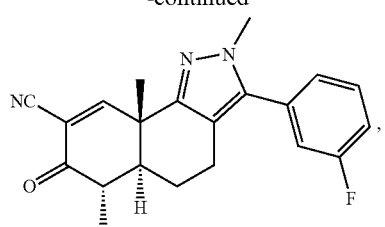
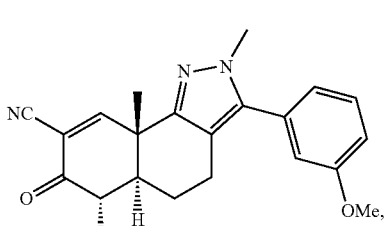
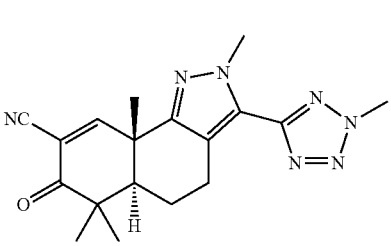
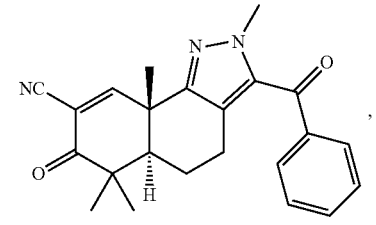
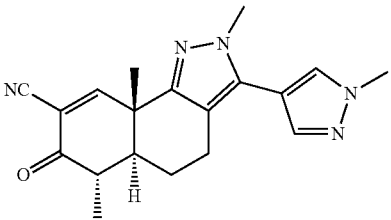
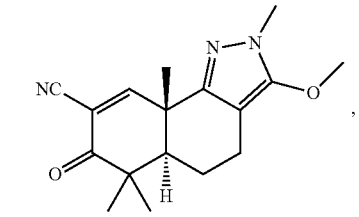
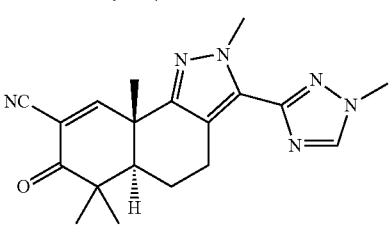

-continued
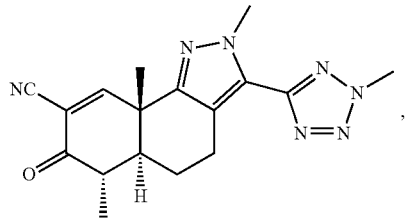,
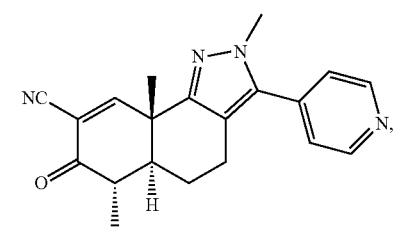,
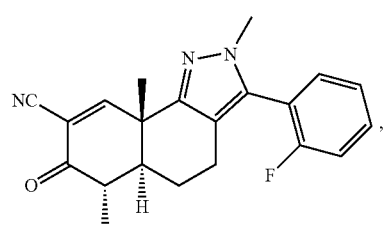,
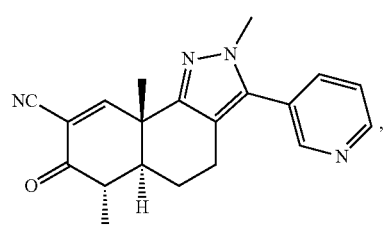,
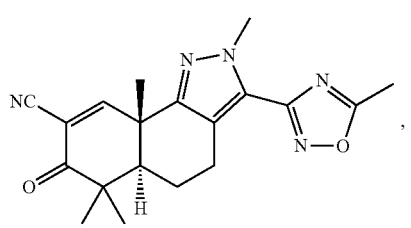,
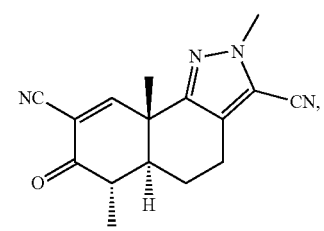,
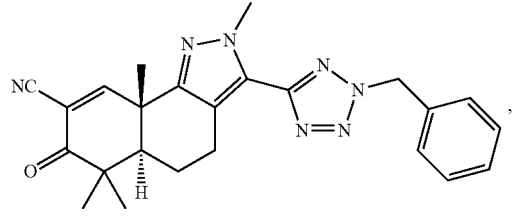,
-continued
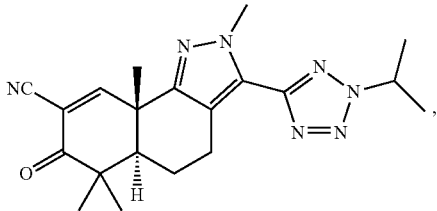,
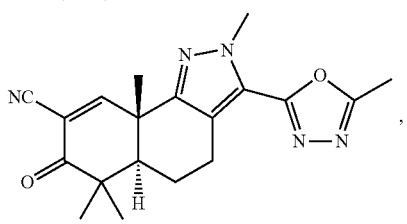,
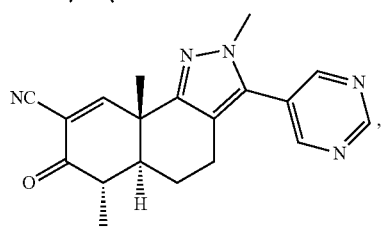,
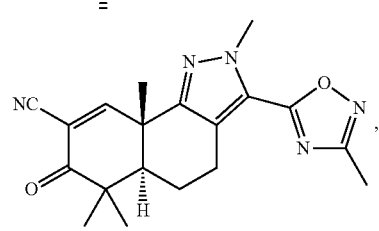,
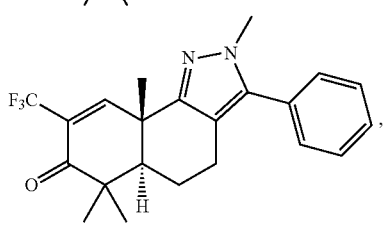,
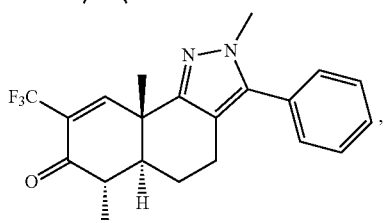,
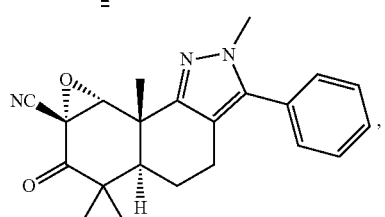,
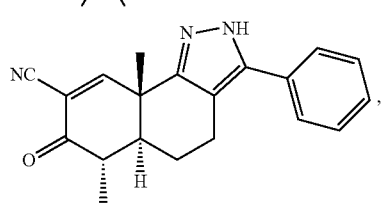,

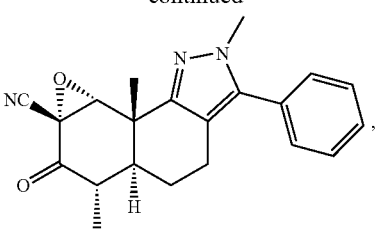,
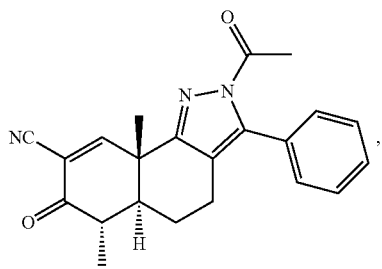,
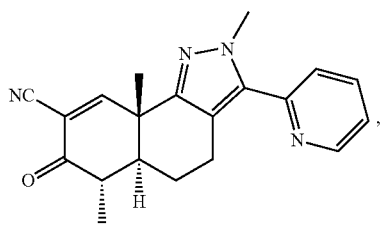,
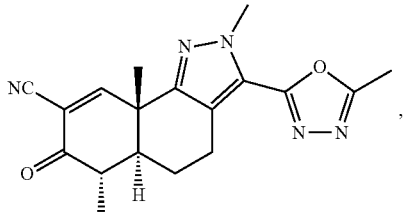,
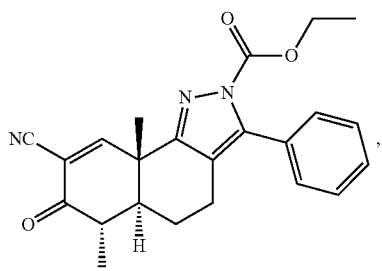,
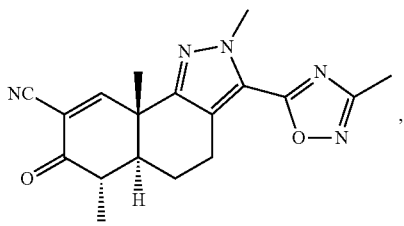,
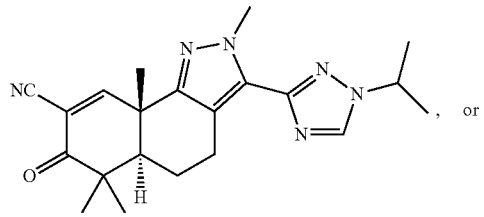, or
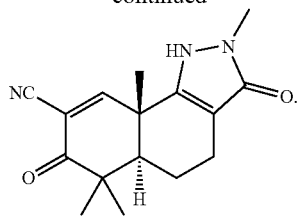.
In some embodiments, the compounds are further defined as:
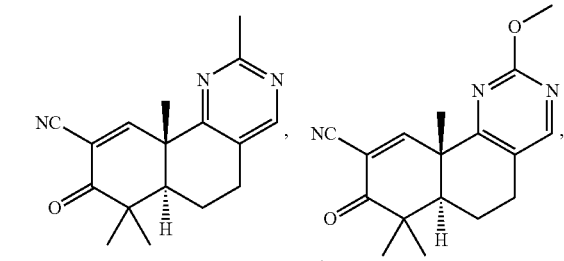,
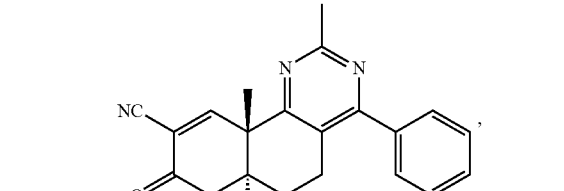,
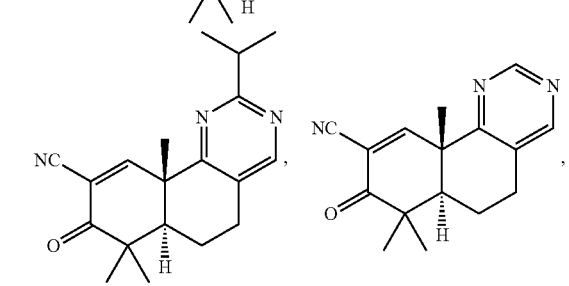,
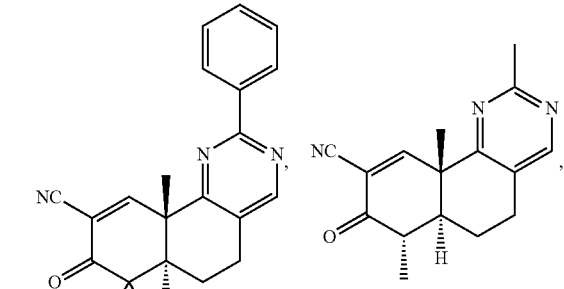,
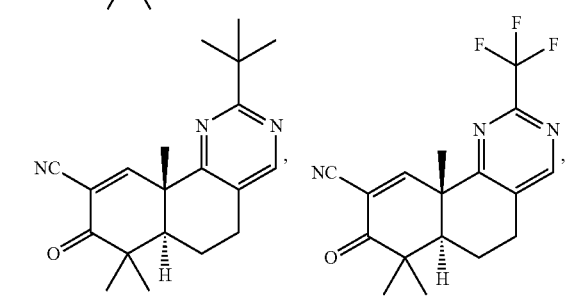, -continued
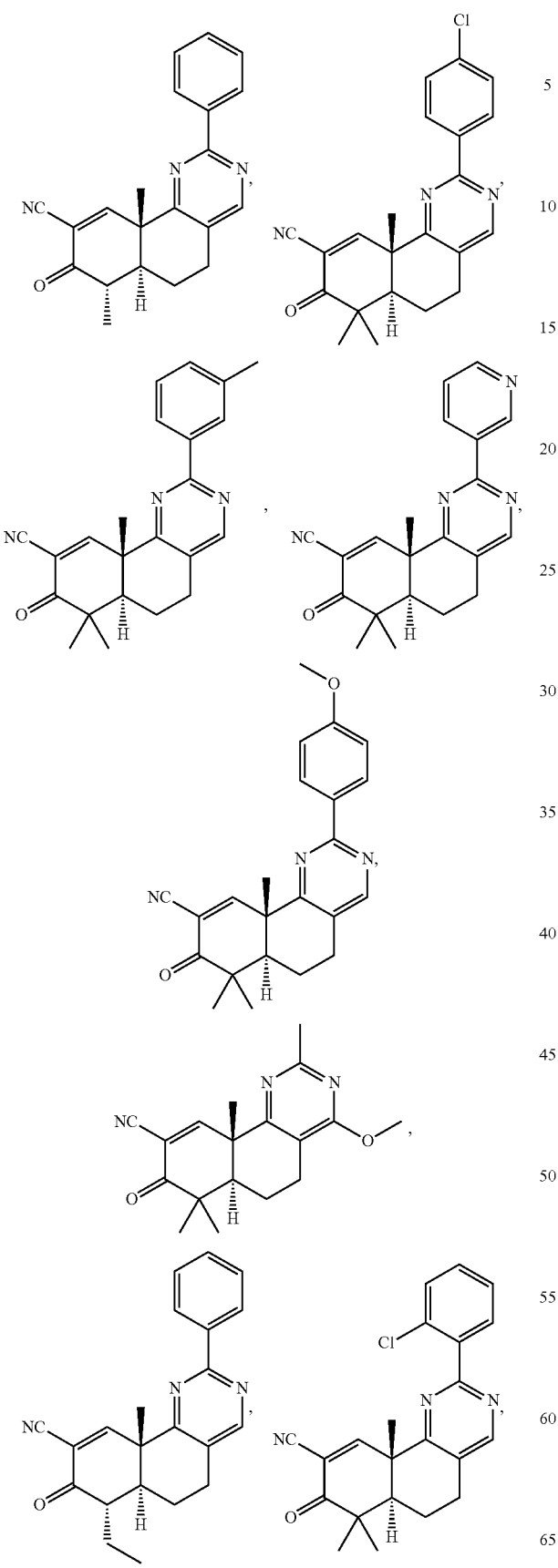
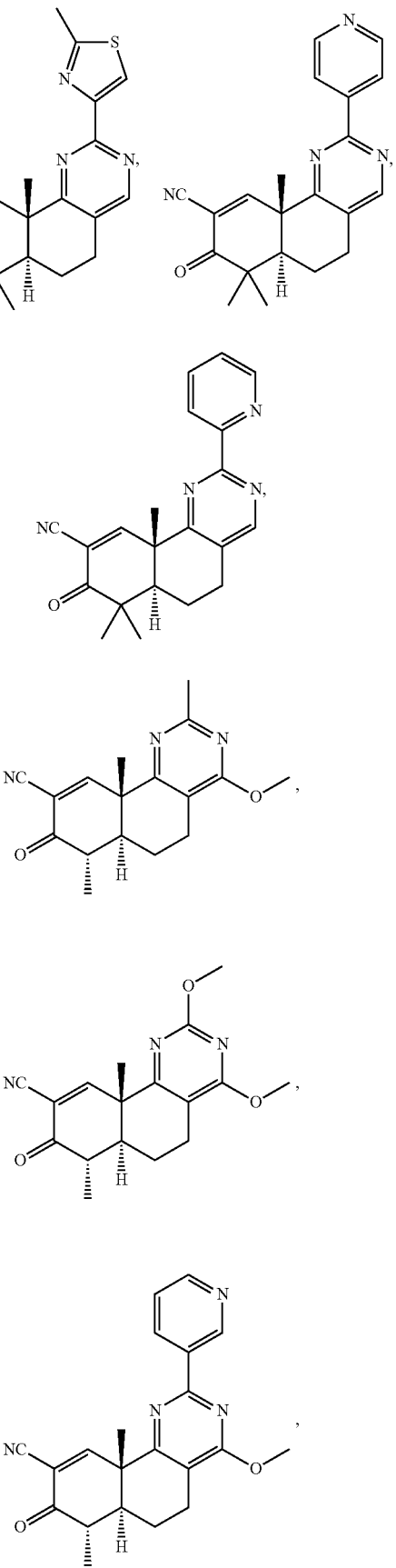

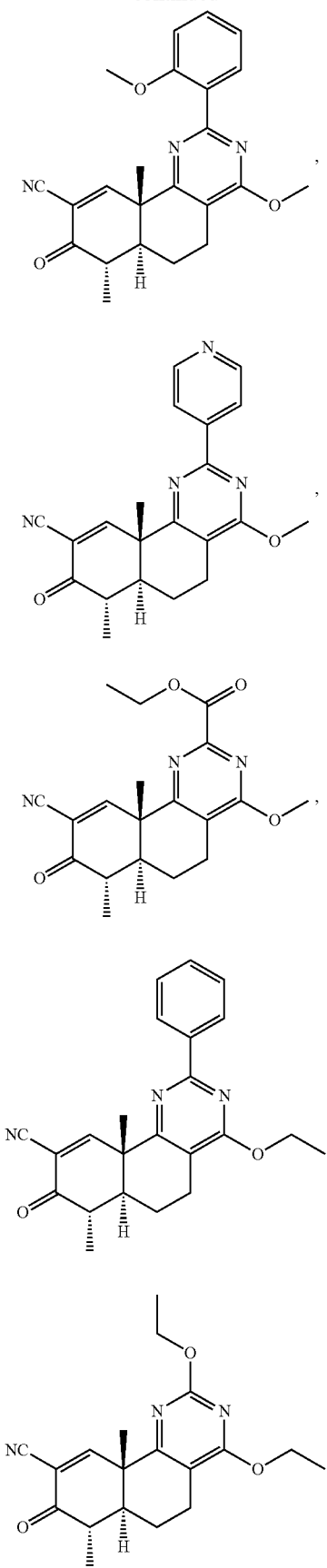
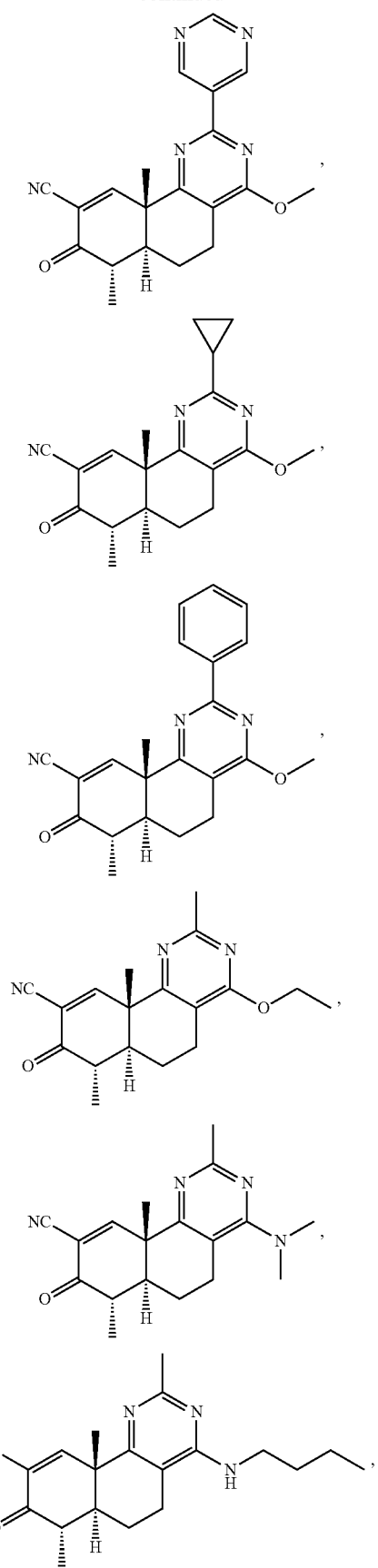

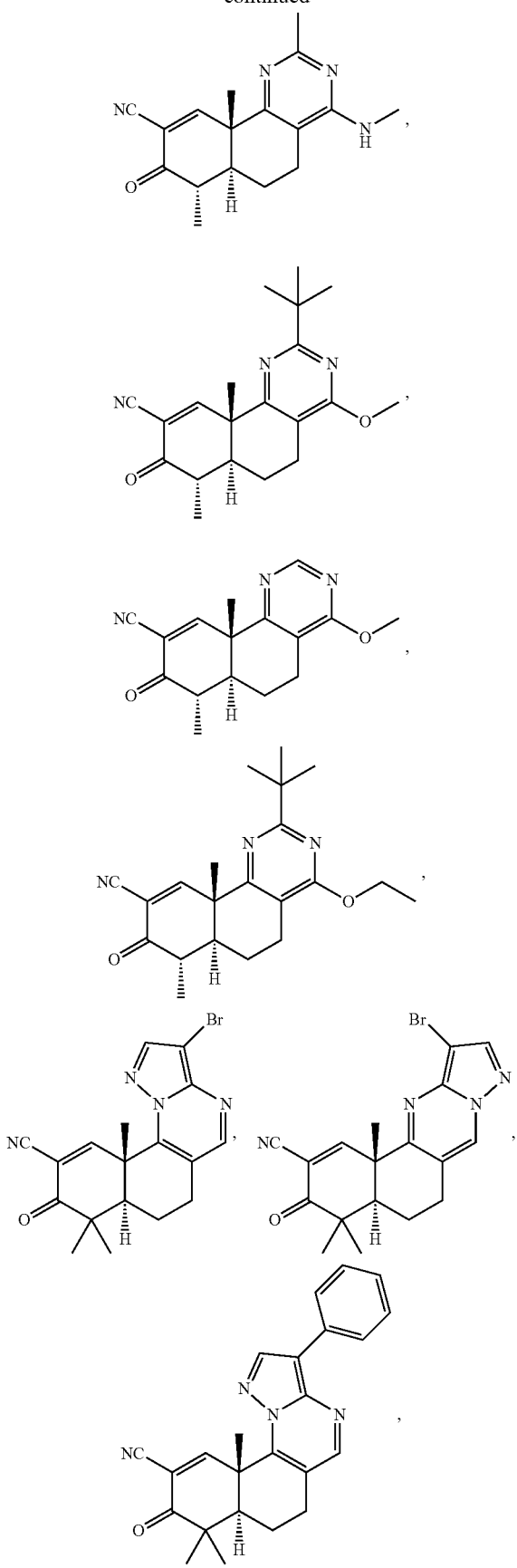
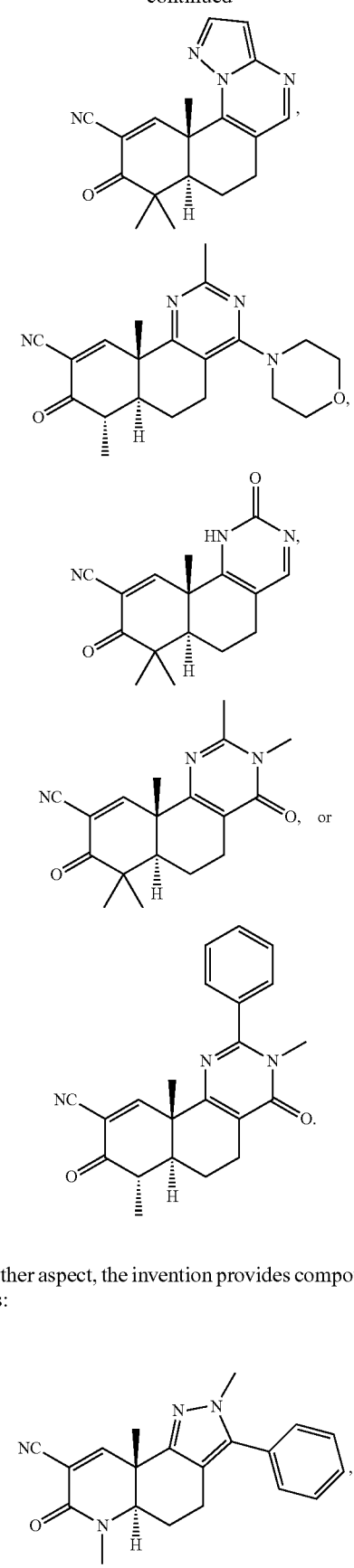
In another aspect, the invention provides compounds of the formulas:
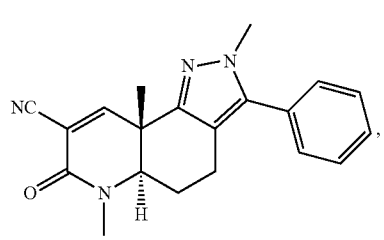

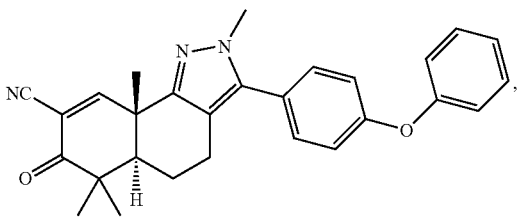

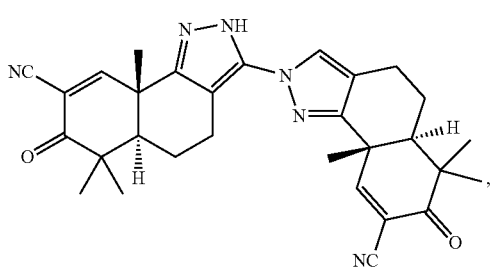

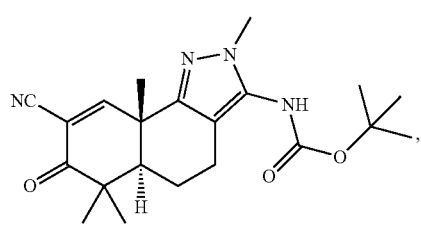

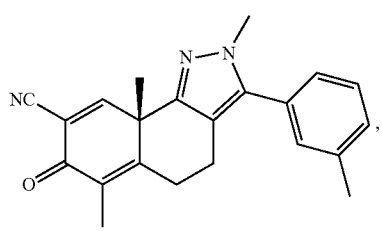

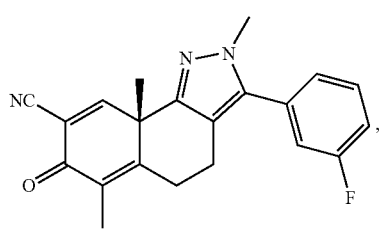

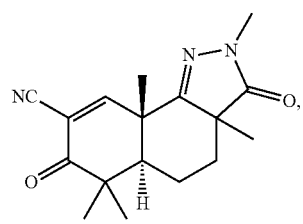

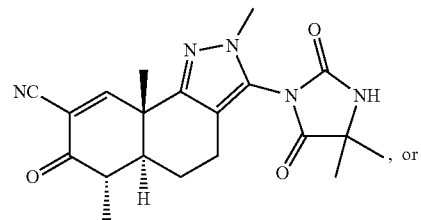

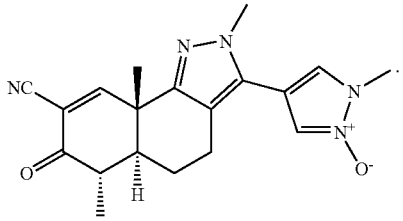 [SMILES: C[C@@H]1C(=O)C(C#N)=C[C@]2(C)c3nn(C)c(-c4cn(C)[n+]([O-])c4)c3CC[C@@H]12]

In another aspect, the invention provides compounds of the formulas:

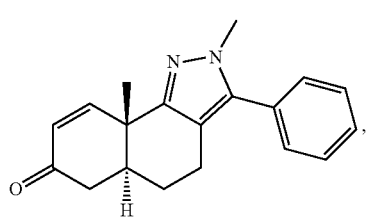

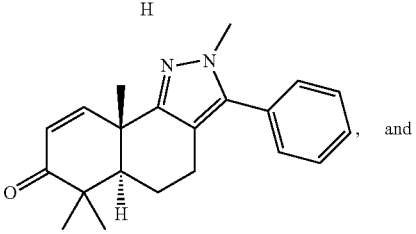
and

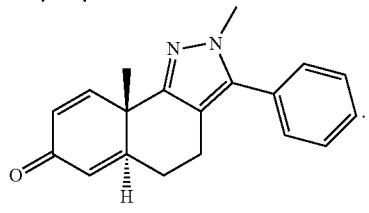

In another aspect, the invention provides compounds of the formula:

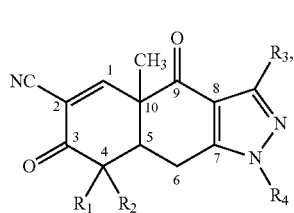

(VII)

wherein:

$R_1$ and $R_2$ are each independently:

hydrogen, hydroxy or amino; or alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, hetero-aryl$_{(C \leq 12)}$, heterocycloalkyl$_{(C \leq 12)}$, acyl$_{(C \leq 12)}$, alkoxy$_{(C \leq 12)}$, aryloxy$_{(C \leq 12)}$, aralkoxy$_{(C \leq 12)}$, heteroaryloxy$_{(C \leq 12)}$, acyloxy$_{(C \leq 12)}$, alkyl-amino$_{(C \leq 12)}$, dialkylamino$_{(C \leq 12)}$, arylamino$_{(C \leq 12)}$, aralkylamino$_{(C \leq 12)}$, heteroarylamino$_{(C \leq 12)}$, amido$_{(C \leq 12)}$, or a substituted version of any of these groups; or $R_1$ and $R_2$ are taken together and are alkanediyl$_{(C \leq 12)}$, alkenediyl$_{(C \leq 12)}$, arenediyl$_{(C \leq 12)}$, alkoxydiyl$_{(C \leq 12)}$, alkenyloxydiyl$_{(C≤12)}$, alkylamino-diyl$_{(C≤12)}$, alkenylaminodiyl$_{(C≤12)}$, or a substituted version of any of these groups;

R$_3$ is:
hydrogen, hydroxy or amino, or
alkyl$_{(C≤12)}$, alkenyl$_{(C≤12)}$, alkynyl$_{(C≤12)}$, aryl$_{(C≤12)}$, aralkyl$_{(C≤12)}$, hetero-aryl$_{(C≤12)}$, heterocycloalkyl$_{(C≤12)}$, acyl$_{(C≤12)}$, alkoxy$_{(C≤12)}$, aryloxy$_{(C≤12)}$, aralkoxy$_{(C≤12)}$, heteroaryloxy$_{(C≤12)}$, acyloxy$_{(C≤12)}$, alkylamino$_{(C≤12)}$, dialkylamino$_{(C≤12)}$, aralkylamino$_{(C≤12)}$, heteroarylamino$_{(C≤12)}$, amido$_{(C≤12)}$, or a substituted version of any of these groups; and R$_4$ is:
hydrogen; or
alkyl$_{(C≤12)}$, alkenyl$_{(C≤12)}$, alkynyl$_{(C≤12)}$, aryl$_{(C≤12)}$, aralkyl$_{(C≤12)}$, hetero-aryl$_{(C≤12)}$, acyl$_{(C≤12)}$ or a substituted version of any of these groups;

or a pharmaceutically acceptable salt or tautomer thereof.

In some embodiments, R$_1$ or R$_2$ is alkyl$_{(C≤8)}$ or substituted alkyl$_{(C≤8)}$. In some embodiments, R$_1$ and R$_2$ are alkyl$_{(C≤8)}$. In some embodiments, R$_1$ and R$_2$ are methyl. In some embodiments, R$_3$ is hydrogen. In some embodiments, R$_4$ is aryl$_{(C≤8)}$ or substituted aryl$_{(C≤8)}$. In some embodiments, R$_4$ is aryl$_{(C≤8)}$. In some embodiments, R$_4$ is phenyl. In some embodiments, R$_4$ is alkyl$_{(C≤6)}$ or substituted alkyl$_{(C≤6)}$. In some embodiments, R$_4$ is alkyl$_{(C≤6)}$. In some embodiments, R$_4$ is t-butyl. In some embodiments, carbon atom 10 is in the R configuration. In some embodiments, carbon atom 10 is in the S configuration. In some embodiments, carbon atom 5 is in the R configuration. In some embodiments, carbon atom 5 is in the S configuration.

In some embodiments, the compounds are further defined as:

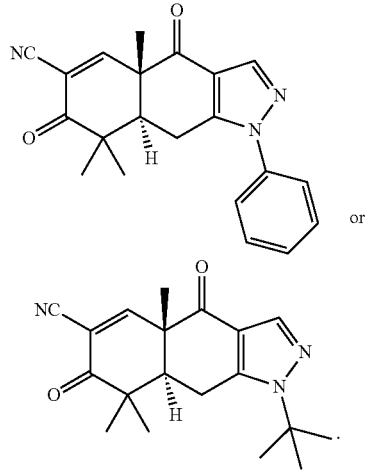

or

In another aspect, the invention provides compounds of the formula:

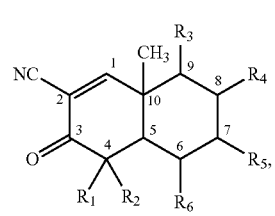

(VIII)

wherein:
R$_1$ and R$_2$ are each independently:
hydrogen, hydroxy or amino; or
alkyl$_{(C≤12)}$, alkenyl$_{(C≤12)}$, alkynyl$_{(C≤12)}$, aryl$_{(C≤12)}$, aralkyl$_{(C≤12)}$, hetero-aryl$_{(C≤12)}$, heterocycloalkyl$_{(C≤12)}$, acyl$_{(C≤12)}$, alkoxy$_{(C≤12)}$, aryloxy$_{(C≤12)}$, aralkoxy$_{(C≤12)}$, heteroaryloxy$_{(C≤12)}$, acyloxy$_{(C≤12)}$, alkyl-amino$_{(C≤12)}$, dialkylamino$_{(C≤12)}$, aralkylamino$_{(C≤12)}$, arylamino$_{(C≤12)}$, heteroarylamino$_{(C≤12)}$, amido$_{(C≤12)}$, or a substituted version of any of these groups; or R$_1$ and R$_2$ are taken together and are alkanediyl$_{(C≤12)}$, alkenediyl$_{(C≤12)}$, arenediyl$_{(C≤12)}$, alkoxydiyl$_{(C≤12)}$, alkenyloxydiyl$_{(C≤12)}$, alkylamino-diyl$_{(C≤12)}$, alkenylaminodiyl$_{(C≤12)}$, or a substituted version of any of these groups; and R$_3$, R$_4$, R$_5$ and R$_6$ are each independently:
hydrogen, hydroxy or amino, or
alkenyl$_{(C≤12)}$, alkynyl$_{(C≤12)}$, aryl$_{(C≤12)}$, aralkyl$_{(C≤12)}$, hetero-aryl$_{(C≤12)}$, heterocycloalkyl$_{(C≤12)}$, acyl$_{(C≤12)}$, alkoxy$_{(C≤12)}$, aryl-oxy$_{(C≤12)}$, heteroaryloxy$_{(C≤12)}$, acyloxy$_{(C≤12)}$, alkylamino$_{(C≤12)}$, dialkylamino$_{(C≤12)}$, arylamino$_{(C≤12)}$, aralkylamino$_{(C≤12)}$, heteroarylamino$_{(C≤12)}$, amido$_{(C≤12)}$, or a substituted version of any of these groups; and or a pharmaceutically acceptable salt or tautomer thereof.

In some embodiments, R$_1$ or R$_2$ is alkyl$_{(C≤8)}$ or substituted alkyl$_{(C≤8)}$. In some embodiments, R$_1$ and R$_2$ are alkyl$_{(C≤8)}$. In some embodiments, R$_1$ and R$_2$ are methyl. In some embodiments, R$_4$, R$_5$ and R$_6$ are hydrogen. In some embodiments, R$_3$ is hydroxy. In some embodiments, R$_4$ is alkoxy$_{(C≤6)}$ or substituted alkoxy$_{(C≤6)}$. In some embodiments, R$_4$ is substituted alkoxy$_{(C≤6)}$. In some embodiments, R$_4$ is methoxymethoxy. In some embodiments, carbon atom 10 is in the R configuration. In some embodiments, carbon atom 10 is in the S configuration. In some embodiments, carbon atom 5 is in the R configuration. In some embodiments, carbon atom 5 is in the S configuration. In some embodiments, the compounds are further defined as:

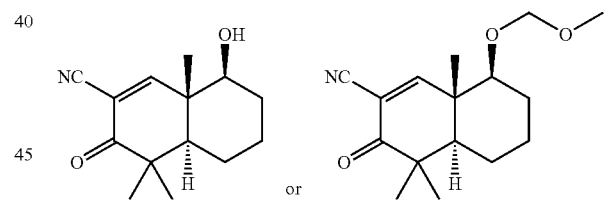

or

In another aspect, the invention provides pharmaceutical compositions comprising the compound according to any of the formulas disclosed herein and an excipient. In some embodiments, the pharmaceutical compositions are further defined as:
a) the compound according to any of the formulas disclosed herein;
b) an optical isomer of the compound, wherein the optical isomer is the enantiomer of the compound; and
c) an excipient.

In some embodiments, the ratio of the amount of compound to the amount of optical isomer is approximately 1:1. In some embodiments, the ratio of the amount of compound to the amount of optical isomer is approximately 5:1. In some embodiments, the ratio of the amount of compound to the amount of optical isomer is approximately 10:1. In some embodiments, the ratio of the amount of compound to the amount of optical isomer is approximately 20:1.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

DESCRIPTION OF ILLUSTRATIVE EMBODIMENTS

Disclosed herein are new compounds and compositions with antioxidant and/or anti-inflammatory properties, methods for their manufacture, and methods for their use, including for the treatment and/or prevention of disease.

I. DEFINITIONS

When used in the context of a chemical group, "hydrogen" means —H; "hydroxy" means —OH; "oxo" means =O; "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; "thio" means =S; "sulfonyl" means —S(O)$_2$—; and "sulfinyl" means —S(O)—.

In the context of chemical formulas, the symbol "—" means a single bond, "=" means a double bond; and "≡" means triple bond. An "epoxidized double bond" represents the group:

The symbol "----" represents an optional bond, which if present is either single or double. The symbol "≡≡≡" represents a single bond or a double bond. Thus, for example, the structure

includes the structures

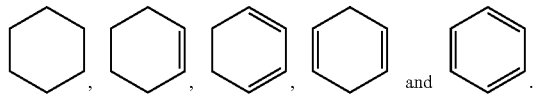

As will be understood by a person of skill in the art, no one such ring atom forms part of more than one double bond. The symbol "〰", when drawn perpendicularly across a bond indicates a point of attachment of the group. It is noted that the point of attachment is typically only identified in this manner for larger groups in order to assist the reader in rapidly and unambiguously identifying a point of attachment. The symbol "◤" means a single bond where the group attached to the thick end of the wedge is "out of the page." The symbol "⫶⫶⫶" means a single bond where the group attached to the thick end of the wedge is "into the page". The symbol "〰" means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

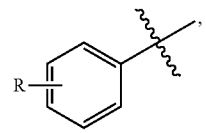

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

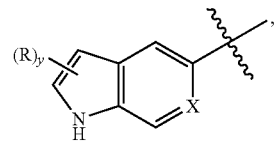

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$-(methylene), —CH$_2$CH$_2$—, —CH$_2$C(CH$_3$)$_2$CH$_2$—, —CH$_2$CH$_2$CH$_2$—, and

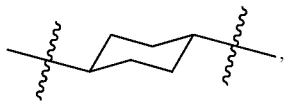 [SMILES: *C1CCC(*)CC1]

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen has been substituted with a halo group and no other atoms aside from carbon, hydrogen and halogen are present. The group, —CH$_2$Cl is a non-limiting examples of a haloalkyl. An "alkane" refers to the compound H—R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one non-aromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

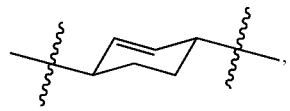 [SMILES: *C1C=CC(*)CC1]

are non-limiting examples of alkenediyl groups. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. When alkynyl is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. An "alkyne" refers to the compound H—R, wherein R is alkynyl.

The term "aryl" when used without the "substituted" modifier refers to a monovalent group with an aromatic carbon atom as the point of attachment, said carbon atom forming part of one or more six-membered aromatic ring structure(s) wherein the ring atoms are all carbon, and wherein the monovalent group consists of no atoms other than carbon and hydrogen. Non-limiting examples of aryl groups include phenyl (Ph), methylphenyl, (dimethyl)phenyl, —$C_6H_4$—$CH_2CH_3$ (ethylphenyl), —$C_6H_4$—$CH_2CH_2CH_3$ (propylphenyl), —$C_6H_4$—$CH(CH_3)_2$, —$C_6H_4$—$CH(CH_2)_2$, —$C_6H_3$(CH_3)CH_2CH_3$ (methylethylphenyl), —$C_6H_4$—CH=$CH_2$ (vinylphenyl), —$C_6H_4$—CH=$CHCH_3$, —$C_6H_4$C≡CH, —$C_6H_4$C≡$CCH_3$, naphthyl, and the monovalent group derived from biphenyl. The term "substituted aryl" refers to a monovalent group with an aromatic carbon atom as the point of attachment, said carbon atom forming part of one or more six-membered aromatic ring structure(s) wherein the ring atoms are all carbon, and wherein the monovalent group further has at least one atom independently selected from the group consisting of N, O, F, Cl, Br, I, Si, P, and S. Non-limiting examples of substituted aryl groups include the groups: —$C_6H_4F$, —$C_6H_4Cl$, —$C_6H_4Br$, —$C_6H_4I$, —$C_6H_4OH$, —$C_6H_4OCH_3$, —$C_6H_4OCH_2CH_3$, —$C_6H_4OC(O)CH_3$, —$C_6H_4NH_2$, —$C_6H_4NHCH_3$, —$C_6H_4N(CH_3)_2$, —$C_6H_4$—$CH_2OH$, —$C_6H_4$—$CH_2OC(O)CH_3$, —$C_6H_4$—$CH_2NH_2$, —$C_6H_4CF_3$, —$C_6H_4CN$, —$C_6H_4$—CHO, —$C_6H_4$—CHO, —$C_6H_4C(O)CH_3$, —$C_6H_4C(O)C_6H_5$, —$C_6H_4CO_2H$, —$C_6H_4CO_2CH_3$, —$C_6H_4CONH_2$, —$C_6H_4CONHCH_3$, and —$C_6H_4CON(CH_3)_2$. The term "arenediyl" when used without the "substituted" modifier refers to a divalent group, wherein the arenediyl group is attached with two σ-bonds, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. Non-limiting examples of arenediyl groups include:

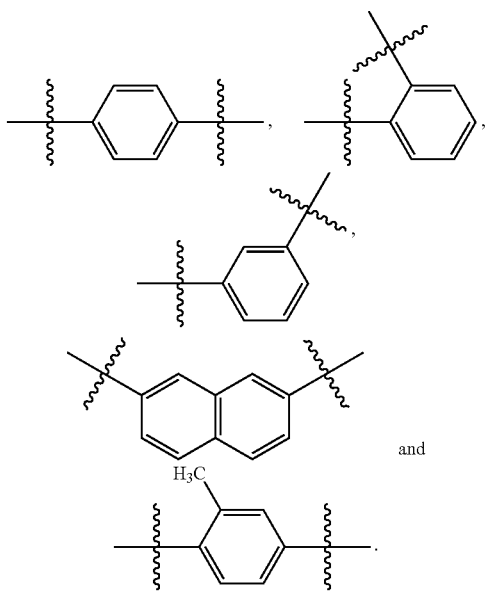

The term "substituted arenediyl" refers to a divalent group, wherein the arenediyl group is attached with two σ-bonds, with two aromatic carbon atoms as points of attachment, said carbon atoms forming part of one or more six-membered aromatic rings structure(s), wherein the ring atoms are carbon, and wherein the divalent group further has at least one atom independently selected from the group consisting of N, O, F, Cl, Br, I, Si, P, and S. The term "arene" when used without the "substituted" modifier refers to an hydrocarbon having at least one six-membered aromatic ring. One or more alkyl, alkenyl or alkynyl groups may be optionally attached to this ring. Also this ring may optionally be fused with other rings, including non-aromatic rings. Benzene, toluene, naphthalene, and biphenyl are non-limiting examples of arenes. A "substituted arene" differs from an arene in that it also comprises at least one atom independently selected from the group consisting of N, O, F, Cl, Br, I, Si, P, and S. Phenol and nitrobenzene are non-limiting examples of substituted arenes.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —$C(O)CH_3$, —$N(CH_3)_2$, —$C(O)NH_2$, —$OC(O)CH_3$, or —$S(O)_2NH_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said aromatic carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroarenediyl groups include:

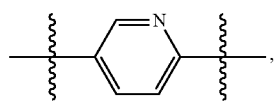

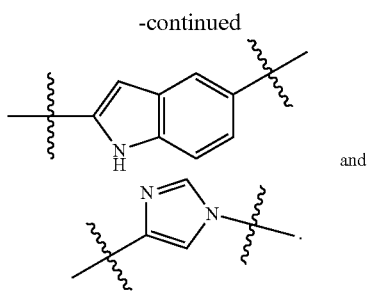

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. As used herein, the term does not preclude the presence of one or more alkyl groups (carbon number limitation permitting) attached to the ring or ring system. If more than one ring is present, the rings may be fused or unfused. Non-limiting examples of heterocycloalkyl groups include aziridinyl, pyrrolidinyl, piperidinyl, piperazinyl, morpholinyl, thiomorpholinyl, tetrahydrofuranyl, tetrahydrothiofuranyl, tetrahydropyranyl, and pyranyl. When the term "heterocycloalkyl" used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$—CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom (including the hydrogen atom directly attached the carbonyl or thiocarbonyl group) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl. The terms "alkenyloxy", "alkynyloxy", "aryloxy", "aralkoxy", "heteroaryloxy", and "acyloxy", when used without the "substituted" modifier, refers to groups, defined as —OR, in which R is alkenyl, alkynyl, aryl, aralkyl, heteroaryl, and acyl, respectively. The term "alkoxydiyl" refers to the divalent group —O-alkanediyl-, —O-alkanediyl-O—, or -alkanediyl-O-alkanediyl-. The term "alkylthio" when used without the "substituted" modifier refers to the group —SR, in which R is an alkyl, as that term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", and "alkylsulfonylamino" when used without the "substituted" modifier, refers to groups, defined as —NHR, in which R is alkoxy, alkenyl, alkynyl, aryl, aralkyl, heteroaryl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynylsulfonyl", "arylsulfonyl", "aralkylsulfonyl", and "heteroarylsulfonyl", are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

As used herein, a "chiral auxiliary" refers to a removable chiral group that is capable of influencing the stereoselectivity of a reaction. Persons of skill in the art are familiar with such compounds, and many are commercially available.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylenebis-β-hydroxynaphthoate, gentisates, isethionates, di-p-toluoyltartrates, methane-sulfonates, ethanesulfonates, benzenesulfonates, p-toluenesulfonates, cyclohexyl-sulfamates, quinates, esters of amino acids, and the like. Similarly, a compound comprising an amine group may be administered as an amide that is converted by hydrolysis in vivo to the amine compound.

The term "saturated" when referring to an atom means that the atom is connected to other atoms only by means of single bonds.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diasteromers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Effective amount," "Therapeutically effective amount" or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

Other abbreviations used herein are as follows: DMSO, dimethyl sulfoxide; NO, nitric oxide; iNOS, inducible nitric oxide synthase; COX-2, cyclooxygenase-2; FBS, fetal bovine serum; IFNγ or IFN-γ, interferon-γ; TNFα or TNF-α, tumor necrosis factor-α; IL-1β, interleukin-1β; HO-1, inducible heme oxygenase.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

II. COMPOUNDS AND SYNTHETIC METHODS

The compounds provided by the present disclosure are shown above in the summary of the invention section and in the claims below. They may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Compounds employed in methods of the invention may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration, as defined by the IUPAC 1974 Recommendations. For example, mixtures of stereoisomers may be separated using the techniques taught in the Examples section below, as well as modifications thereof.

Atoms making up the compounds of the present invention are intended to include all isotopic forms of such atoms. Compounds of the present invention include those with one or more atoms that have been isotopically modified or enriched, in particular those with pharmaceutically acceptable isotopes or those useful for pharmaceutically research. Isotopes, as used herein, include those atoms having the same atomic number but different mass numbers. By way of general example and without limitation, isotopes of hydrogen include deuterium and tritium, and isotopes of carbon include $^{13}$C and $^{14}$C. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It should be further recognized that the compounds of the present invention include those that have been further modified to comprise substituents that are convertible to hydrogen in vivo. This includes those groups that may be convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydropyranyl, diphenylphosphinyl, and the like. Examples of acyl groups include formyl, acetyl, trifluoroacetyl, and the like. Examples of groups having an oxycarbonyl group include ethoxycarbonyl, tert-butoxycarbonyl (—C(O)OC(CH$_3$)$_3$), benzyloxycarbonyl, p-methoxybenzyloxycarbonyl, vinyloxycarbonyl, β-(p-toluenesulfonyl)ethoxycarbonyl, and the like. Suitable amino acid residues include, but are not limited to, residues of Gly (glycine), Ala (alanine), Arg (arginine), Asn (asparagine), Asp (aspartic acid), Cys (cysteine), Glu (glutamic acid), His (histidine), Ile (isoleucine), Leu (leucine), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable amino acid residues also include amino acid residues that are protected with a protecting group. Examples of suitable protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$), and the like. Suitable peptide residues include peptide residues comprising two to five amino acid residues. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$), and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxy-benzyloxycarbonyl); and haloethoxycarbonyl groups (such as β,β,β-trichloroethoxycarbonyl and β-iodoethoxycarbonyl).

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

III. BIOLOGICAL ACTIVITY

Assay results for the suppression of IFNγ-induced NO production are shown for several of the compounds of the present invention in Table 1 below. In the right-hand column of this table under the RAW264.7 heading, the results are compared to those of bardoxolone methyl (RTA 402). NQO1-ARE Luciferase Reporter Assay results are shown in the last column. Details regarding both assays are provided in the Examples section below. Except for those formulas labeled "chiral," each compound depicted in Table 1 is racemic. For the racemic compounds, the molecular structure shown is the formula of one of the two enantiomers. For those formulas labeled "chiral," the molecular formula shows the predominant stereoisomer present.

TABLE 1

| | Suppression of IFNγ-Induced NO Production. | | | | |
|---|---|---|---|---|---|
| | | | | RAW264.7 | NQO1-ARE assay |
| Compound No. | Molecular Structure | | MW | NO IC$_{50}$ (nM) | Relative NO IC$_{50}$ | Fold induction at 62.5 nM |
| TX63341 | 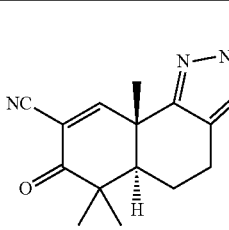 chiral | | 269.34 | 70 | — | 1.7 |
| TX63342 | 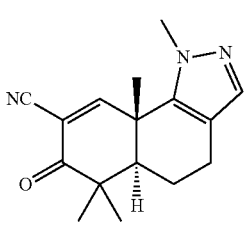 chiral | | 269.34 | 180 | 40 | |
| TX63363 | 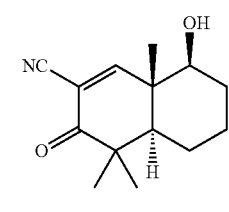 chiral | | 233.31 | >200 | — | |

TABLE 1-continued

Suppression of IFNγ-Induced NO Production.

| Compound No. | Molecular Structure | MW | RAW264.7 NO IC$_{50}$ (nM) | RAW264.7 Relative NO IC$_{50}$ | NQO1-ARE assay Fold induction at 62.5 nM |
|---|---|---|---|---|---|
| TX63364 | 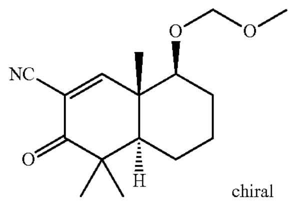 [SMILES: COCO[C@H]1CCC[C@H]2C(C)(C)C(=O)C(C#N)=C[C@]12C] | 277.36 | >200 | — | |
| TX63432 | 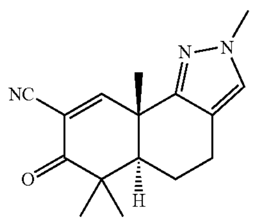 [SMILES: Cn1cc2c(n1)[C@@]1(C)C=C(C#N)C(=O)C(C)(C)[C@@H]1CC2] | 269.34 | 166 | 68 | |
| TX63436 | 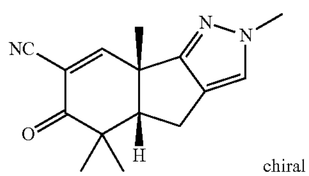 [SMILES: Cn1cc2c(n1)[C@@]1(C)C=C(C#N)C(=O)C(C)(C)[C@H]1C2] | 255.31 | >200 | — | |
| TX63444 | 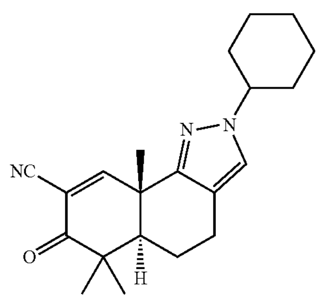 [SMILES: CC1(C)C(=O)C(C#N)=C[C@]2(C)c3nn(C4CCCCC4)cc3CC[C@@H]12] | 337.46 | 140 | 108 | |
| TX63445 | 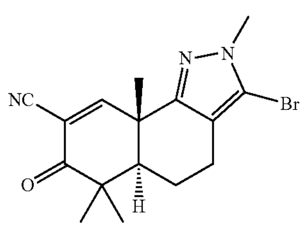 [SMILES: Cn1nc2c(c1Br)CC[C@H]1C(C)(C)C(=O)C(C#N)=C[C@]21C] | 348.24 | 37.9 | 23 | |
| TX63450 | 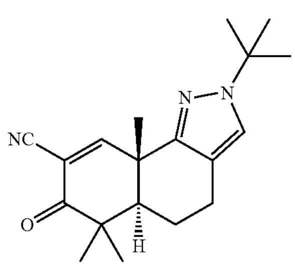 [SMILES: CC1(C)C(=O)C(C#N)=C[C@]2(C)c3nn(C(C)(C)C)cc3CC[C@@H]12] | 311.42 | 148 | 49 | |

TABLE 1-continued

Suppression of IFNγ-Induced NO Production.

| Compound No. | Molecular Structure | MW | RAW264.7 NO IC$_{50}$ (nM) | Relative NO IC$_{50}$ | NQO1-ARE assay Fold induction at 62.5 nM |
|---|---|---|---|---|---|
| TX63451 | 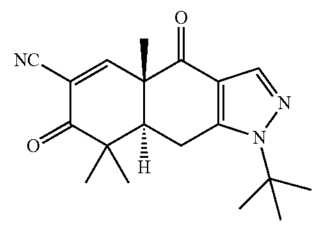 [SMILES: CC1(C)C(=O)C(C#N)=C[C@]2(C)C(=O)c3cnn(C(C)(C)C)c3C[C@@H]12] | 325.40 | 137 | 45 | |
| TX63454 | 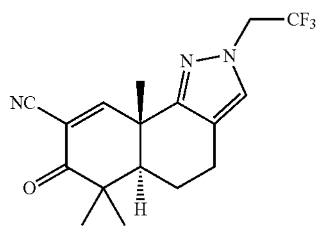 [SMILES: CC1(C)C(=O)C(C#N)=C[C@]2(C)c3nn(CC(F)(F)F)cc3CC[C@@H]12] | 337.30 | 134 | 44 | |
| TX63455 | 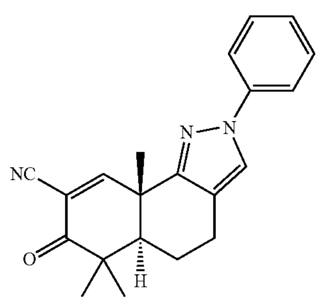 [SMILES: CC1(C)C(=O)C(C#N)=C[C@]2(C)c3nn(-c4ccccc4)cc3CC[C@@H]12] | 331.40 | 109 | 62 | |
| TX63456 | 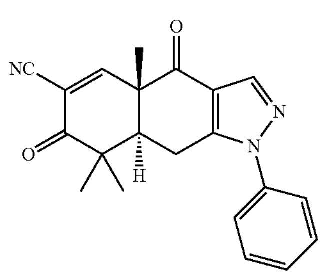 [SMILES: CC1(C)C(=O)C(C#N)=C[C@]2(C)C(=O)c3cnn(-c4ccccc4)c3C[C@@H]12] | 345.40 | >200 | — | |
| TX63462 | 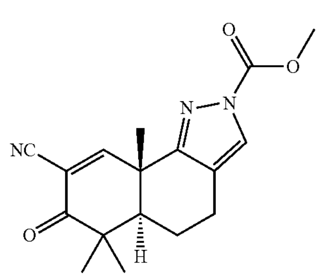 [SMILES: COC(=O)n1cc2c(n1)[C@@]1(C)C=C(C#N)C(=O)C(C)(C)[C@@H]1CC2] | 313.35 | 147 | 77 | |

TABLE 1-continued

Suppression of IFNγ-Induced NO Production.

| Compound No. | Molecular Structure | MW | RAW264.7 NO IC$_{50}$ (nM) | Relative NO IC$_{50}$ | NQO1-ARE assay Fold induction at 62.5 nM |
|---|---|---|---|---|---|
| TX63463 | 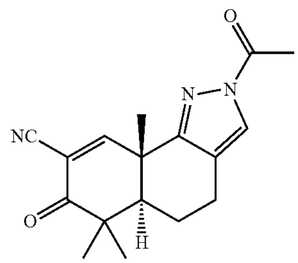 [SMILES: CC(=O)n1cc2c(n1)[C@@]1(C)C=C(C#N)C(=O)C(C)(C)[C@@H]1CC2] | 297.35 | 205 | 108 | |
| TX63464 | 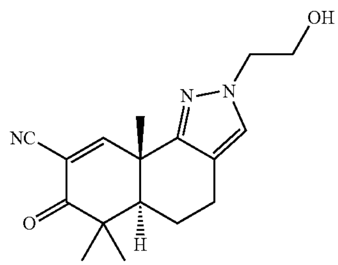 [SMILES: CC1(C)C(=O)C(C#N)=C[C@]2(C)c3nn(CCO)cc3CC[C@@H]12] | 299.37 | >200 | — | |
| TX63465 | 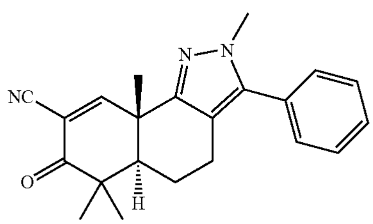 [SMILES: Cn1nc2c(c1-c1ccccc1)CC[C@H]1C(C)(C)C(=O)C(C#N)=C[C@]21C] | 345.44 | 18.3 | 11 | 4.8 |
| TX63466 | 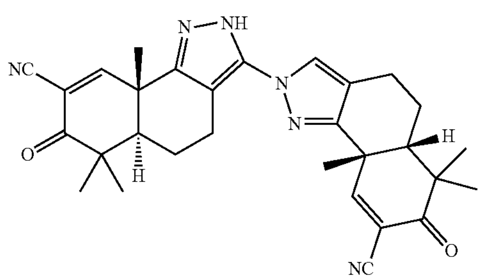 [SMILES: CC1(C)C(=O)C(C#N)=C[C@]2(C)c3nn(-c4[nH]nc5c4CC[C@H]4C(C)(C)C(=O)C(C#N)=C[C@]54C)cc3CC[C@H]12] | 508.61 | 10.4 | 4.5 | |
| TX63467 | 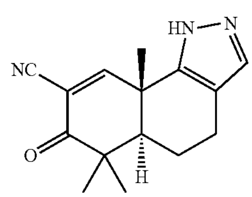 [SMILES: CC1(C)C(=O)C(C#N)=C[C@]2(C)c3[nH]ncc3CC[C@@H]12] | 255.31 | >200 | — | |
| TX63468 | 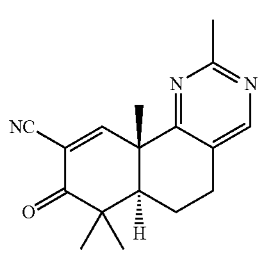 [SMILES: Cc1ncc2c(n1)[C@@]1(C)C=C(C#N)C(=O)C(C)(C)[C@@H]1CC2] | 281.35 | 64 | 33.7 | 2.0 |

TABLE 1-continued

Suppression of IFNγ-Induced NO Production.

| Compound No. | Molecular Structure | MW | RAW264.7 NO IC$_{50}$ (nM) | Relative NO IC$_{50}$ | NQO1-ARE assay Fold induction at 62.5 nM |
|---|---|---|---|---|---|
| TX63485 | | 379.88 | 34 | 24.3 | |
| TX63486 | | 379.88 | 48 | 34.3 | |
| TX63487 | | 295.38 | 85 | 60.7 | |
| TX63491 | | 379.90 | 35 | 15.2 | |
| TX63503 | | 346.43 | 17 | 7.4 | 5.5 |
| TX63504 | | 371.47 | 20 | 8.9 | |

TABLE 1-continued

Suppression of IFNγ-Induced NO Production.

| Compound No. | Molecular Structure | MW | RAW264.7 NO IC$_{50}$ (nM) | Relative NO IC$_{50}$ | NQO1-ARE assay Fold induction at 62.5 nM |
|---|---|---|---|---|---|
| TX63505 | 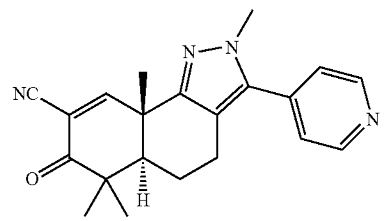 [SMILES: Cn1nc2c(c1-c1ccncc1)CC[C@H]1C(C)(C)C(=O)C(C#N)=C[C@]21C] | 346.43 | 16 | 6.9 | 6.8 |
| TX63506 | 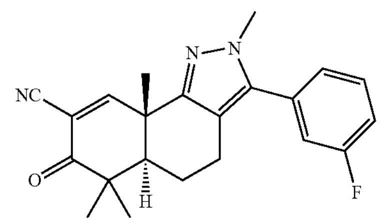 [SMILES: Cn1nc2c(c1-c1cccc(F)c1)CC[C@H]1C(C)(C)C(=O)C(C#N)=C[C@]21C] | 363.43 | 25 | 15.6 | 3.2 |
| TX63507 | 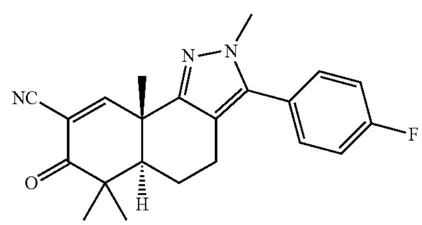 [SMILES: Cn1nc2c(c1-c1ccc(F)cc1)CC[C@H]1C(C)(C)C(=O)C(C#N)=C[C@]21C] | 363.43 | 39 | 24.4 | |
| TX63508 | 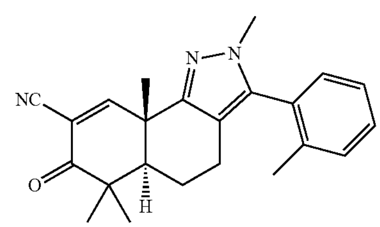 | 359.48 | 33 | 20.6 | |
| TX63509 | 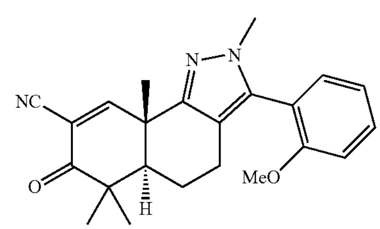 [SMILES: COc1ccccc1-c1c2c(nn1C)[C@@]1(C)C=C(C#N)C(=O)C(C)(C)[C@@H]1CC2] | 375.47 | 38 | 23.8 | |
| TX63512 | 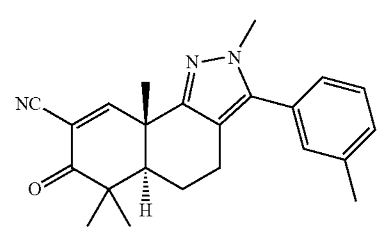 [SMILES: Cc1cccc(-c2c3c(nn2C)[C@@]2(C)C=C(C#N)C(=O)C(C)(C)[C@@H]2CC3)c1] | 359.47 | 25 | 20.8 | 1.4 |

TABLE 1-continued

Suppression of IFNγ-Induced NO Production.

| Compound No. | Molecular Structure | MW | RAW264.7 NO IC$_{50}$ (nM) | Relative NO IC$_{50}$ | NQO1-ARE assay Fold induction at 62.5 nM |
|---|---|---|---|---|---|
| TX63513 | 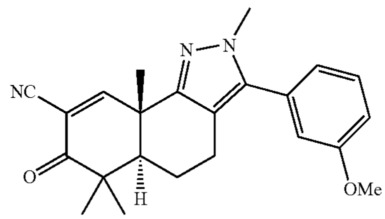 [SMILES: COc1cccc(-c2c3c(nn2C)[C@@]2(C)C=C(C#N)C(=O)C(C)(C)[C@@H]2CC3)c1] | 375.47 | 25 | 20.8 | 2.9 |
| TX63514 | 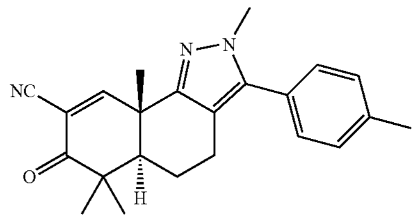 [SMILES: Cc1ccc(-c2c3c(nn2C)[C@@]2(C)C=C(C#N)C(=O)C(C)(C)[C@@H]2CC3)cc1] | 359.47 | 37 | 30.8 | |
| TX63515 | 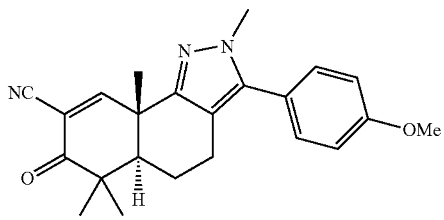 [SMILES: COc1ccc(-c2c3c(nn2C)[C@@]2(C)C=C(C#N)C(=O)C(C)(C)[C@@H]2CC3)cc1] | 375.47 | 35 | 29.2 | |
| TX63519 | 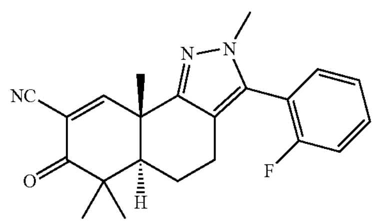 | 363.43 | 21 | 14 | 2.5 |
| TX63524 | 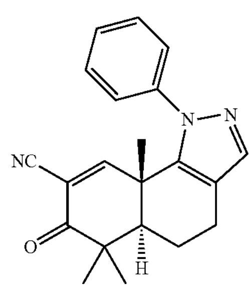 [SMILES: CC1(C)C(=O)C(C#N)=C[C@]2(C)c3c(cnn3-c3ccccc3)CC[C@@H]12] | 331.41 | 68 | 48.6 | |
| TX63528 | 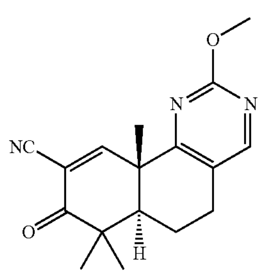 [SMILES: COc1ncc2c(n1)[C@@]1(C)C=C(C#N)C(=O)C(C)(C)[C@@H]1CC2] | 297.36 | 85 | 56.7 | |

TABLE 1-continued

Suppression of IFNγ-Induced NO Production.

| Compound No. | Molecular Structure | MW | RAW264.7 NO IC$_{50}$ (nM) | RAW264.7 Relative NO IC$_{50}$ | NQO1-ARE assay Fold induction at 62.5 nM |
|---|---|---|---|---|---|
| TX63529 | | 357.45 | 46 | 30.7 | |
| TX63531 | | 388.47 | >200 | — | 1.1 |
| TX63533 | | 241.29 | >200 | — | |
| TX63534 | | 309.41 | 49 | 23.3 | |
| TX63540 | | 317.39 | 66.8 | 45.0 | 1.6 |
| TX63541 | | 331.41 | 6 | 3.7 | 4.4 |

TABLE 1-continued

Suppression of IFNγ-Induced NO Production.

| Compound No. | Molecular Structure | MW | RAW264.7 NO IC$_{50}$ (nM) | Relative NO IC$_{50}$ | NQO1-ARE assay Fold induction at 62.5 nM |
|---|---|---|---|---|---|
| TX63542 | 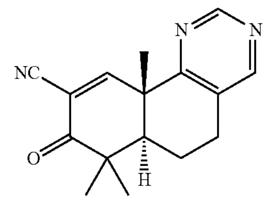 [SMILES: CC1(C)C(=O)C(C#N)=C[C@]2(C)c3ncncc3CC[C@@H]12] | 267.33 | 55 | 36.7 | |
| TX63544 | 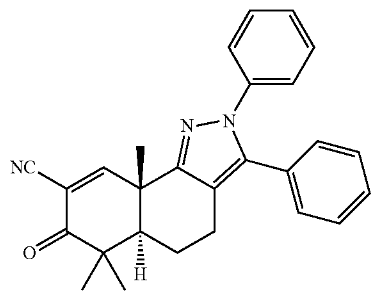 [SMILES: CC1(C)C(=O)C(C#N)=C[C@]2(C)c3nn(-c4ccccc4)c(-c4ccccc4)c3CC[C@@H]12] | 407.51 | 39 | 17 | |
| TX63547 | 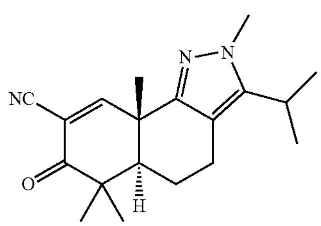 [SMILES: CC(C)c1c2c(nn1C)[C@@]1(C)C=C(C#N)C(=O)C(C)(C)[C@@H]1CC2] | 311.43 | 87 | 32 | 3.1 |
| TX63550 | 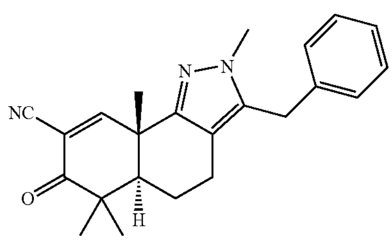 [SMILES: Cn1nc2c(c1Cc1ccccc1)CC[C@H]1C(C)(C)C(=O)C(C#N)=C[C@]21C] | 359.47 | 54 | 20 | 1.8 |
| TX63551 | 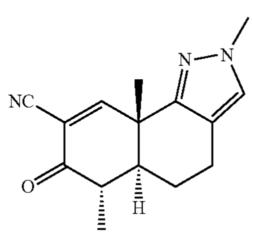 [SMILES: C[C@@H]1C(=O)C(C#N)=C[C@]2(C)c3nn(C)cc3CC[C@@H]12] | 255.32 | 49 | 18.1 | |

TABLE 1-continued

Suppression of IFNγ-Induced NO Production.

| Compound No. | Molecular Structure | MW | RAW264.7 NO IC$_{50}$ (nM) | Relative NO IC$_{50}$ | NQO1-ARE assay Fold induction at 62.5 nM |
|---|---|---|---|---|---|
| TX63552 | | 343.43 | 24 | 8.9 | 1.9 |
| TX63553 | | 283.33 | >200 | — | |
| TX63554 | | 267.33 | 42 | 15.6 | 1.9 |
| TX63559 | | 255.31 | >200 | — | |
| TX63561 | | 323.44 | 44 | 15.7 | 2.4 |

TABLE 1-continued

Suppression of IFNγ-Induced NO Production.

| Compound No. | Molecular Structure | MW | RAW264.7 NO IC$_{50}$ (nM) | Relative NO IC$_{50}$ | NQO1-ARE assay Fold induction at 62.5 nM |
|---|---|---|---|---|---|
| TX63567 | | 335.33 | 43 | 18.9 | |
| TX63568 | | 332.41 | >200 | — | 1.3 |
| TX63569 | | 329.40 | 9.8 | 4.3 | 2.0 |
| TX63570 | | 292.38 | >200 | — | |
| TX63578 | | 290.36 | >200 | — | |
| TX63579 | | 331.41 | 22 | 10.8 | |

TABLE 1-continued

Suppression of IFNγ-Induced NO Production.

| Compound No. | Molecular Structure | MW | RAW264.7 NO IC$_{50}$ (nM) | Relative NO IC$_{50}$ | NQO1-ARE assay Fold induction at 62.5 nM |
|---|---|---|---|---|---|
| TX63582 | | 377.88 | 33 | 13 | |
| TX63583 | | 357.46 | 33 | 13 | |
| TX63584 | | 311.39 | >200 | — | 3.1 |
| TX63586 | | 344.42 | 22 | 11 | 2.9 |

TABLE 1-continued

Suppression of IFNγ-Induced NO Production.

| Compound No. | Molecular Structure | MW | RAW264.7 NO IC$_{50}$ (nM) | Relative NO IC$_{50}$ | NQO1-ARE assay Fold induction at 62.5 nM |
|---|---|---|---|---|---|
| TX63587 | 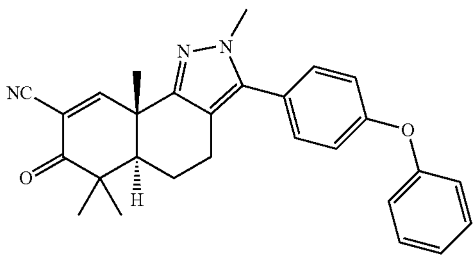 [SMILES: Cn1nc2c(c1-c1ccc(Oc3ccccc3)cc1)CC[C@H]1C(C)(C)C(=O)C(C#N)=C[C@]21C] | 437.53 | 40 | 20 | |
| TX63588 | 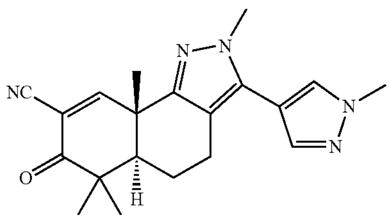 [SMILES: Cn1cc(-c2c3c(nn2C)[C@@]2(C)C=C(C#N)C(=O)C(C)(C)[C@@H]2CC3)cn1] | 349.43 | 33 | 17 | 5.2 |
| TX63589 | 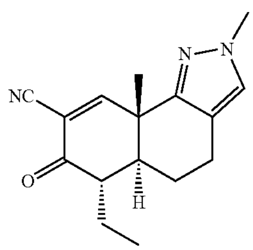 [SMILES: CC[C@@H]1C(=O)C(C#N)=C[C@]2(C)c3nn(C)cc3CC[C@@H]12] | 269.35 | 44 | 22 | |
| TX63590 | 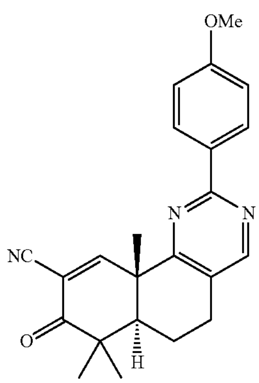 [SMILES: COc1ccc(-c2ncc3c(n2)[C@@]2(C)C=C(C#N)C(=O)C(C)(C)[C@@H]2CC3)cc1] | 373.46 | 31 | 12.5 | |
| TX63591 | 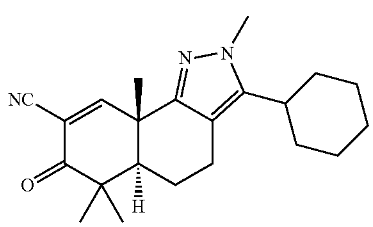 [SMILES: Cn1nc2c(c1C1CCCCC1)CC[C@H]1C(C)(C)C(=O)C(C#N)=C[C@]21C] | 351.49 | 74 | 37 | |

TABLE 1-continued

Suppression of IFNγ-Induced NO Production.

| Compound No. | Molecular Structure | MW | RAW264.7 NO IC$_{50}$ (nM) | RAW264.7 Relative NO IC$_{50}$ | NQO1-ARE assay Fold induction at 62.5 nM |
|---|---|---|---|---|---|
| TX63594 | | 384.47 | >200 | — | |
| TX63595 | | 311.39 | 20 | 8.0 | |
| TX63598 | | 343.43 | 12 | 4.8 | 1.9 |
| TX63599 | | 345.45 | 14 | 5.8 | 3.2 |
| TX63600 | | 395.50 | 59 | 25 | |

TABLE 1-continued

Suppression of IFNγ-Induced NO Production.

| Compound No. | Molecular Structure | MW | RAW264.7 NO IC$_{50}$ (nM) | RAW264.7 Relative NO IC$_{50}$ | NQO1-ARE assay Fold induction at 62.5 nM |
|---|---|---|---|---|---|
| TX63601 | 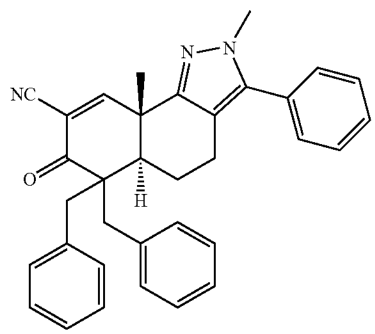 [SMILES: Cn1nc2c(c1-c1ccccc1)CC[C@H]1C(Cc3ccccc3)(Cc3ccccc3)C(=O)C(C#N)=C[C@]21C] | 497.63 | 150 | 63 | |
| TX63603 | 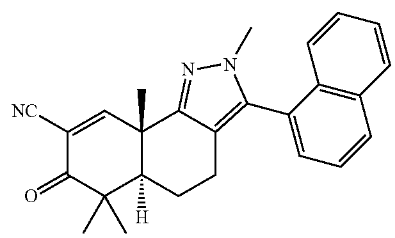 [SMILES: Cn1nc2c(c1-c1cccc3ccccc13)CC[C@H]1C(C)(C)C(=O)C(C#N)=C[C@]21C] | 395.50 | 61 | 25 | |
| TX63604 | 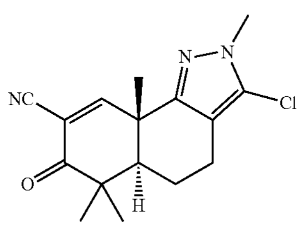 [SMILES: Cn1nc2c(c1Cl)CC[C@H]1C(C)(C)C(=O)C(C#N)=C[C@]21C] | 303.79 | 49 | 20 | 3.4 |
| TX63605 | 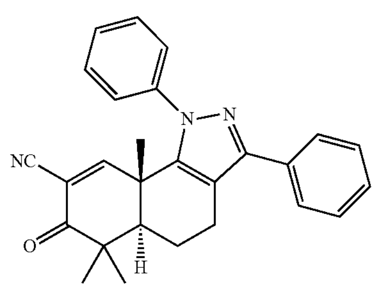 [SMILES: CC1(C)C(=O)C(C#N)=C[C@]2(C)c3c(c(-c4ccccc4)nn3-c3ccccc3)CC[C@@H]12] | 407.51 | 37 | 14.8 | 2.8 |
| TX63606 | 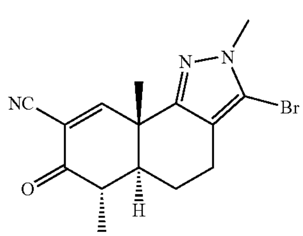 [SMILES: C[C@@H]1C(=O)C(C#N)=C[C@]2(C)c3nn(C)c(Br)c3CC[C@@H]12] | 334.22 | 11 | 4.6 | |

TABLE 1-continued

Suppression of IFNγ-Induced NO Production.

| Compound No. | Molecular Structure | MW | RAW264.7 NO IC$_{50}$ (nM) | Relative NO IC$_{50}$ | NQO1-ARE assay Fold induction at 62.5 nM |
|---|---|---|---|---|---|
| TX63607 | | 407.51 | >200 | — | 1.0 |
| TX63611 | | 373.45 | 22 | 11 | |
| TX63612 | | 377.88 | 43 | 22 | |
| TX63613 | | 294.35 | 101 | 50 | |
| TX63615 | | 385.26 | 52 | 18 | |

TABLE 1-continued

Suppression of IFNγ-Induced NO Production.

| Compound No. | Molecular Structure | MW | RAW264.7 NO IC$_{50}$ (nM) | Relative NO IC$_{50}$ | NQO1-ARE assay Fold induction at 62.5 nM |
|---|---|---|---|---|---|
| TX63617 | | 385.26 | 33 | 11 | |
| TX63619 | | 312.37 | >200 | — | |
| TX63625 | | 364.44 | 77 | 59 | |
| TX63626 | | 382.46 | 38 | 29 | |
| TX63627 | | 306.36 | 38 | 29 | |

TABLE 1-continued

Suppression of IFNγ-Induced NO Production.

| Compound No. | Molecular Structure | MW | RAW264.7 NO IC$_{50}$ (nM) | Relative NO IC$_{50}$ | NQO1-ARE assay Fold induction at 62.5 nM |
|---|---|---|---|---|---|
| TX63628 | | 364.47 | 62 | 44 | |
| TX63629 | | 393.48 | 137 | 98 | |
| TX63630 | | 341.40 | 38 | 27 | |
| TX63631 | | 313.35 | >200 | — | |
| TX63636 | | 344.42 | 27 | 14 | |

TABLE 1-continued

Suppression of IFNγ-Induced NO Production.

| Compound No. | Molecular Structure | MW | RAW264.7 NO IC$_{50}$ (nM) | Relative NO IC$_{50}$ | NQO1-ARE assay Fold induction at 62.5 nM |
|---|---|---|---|---|---|
| TX63637 | | 283.37 | 45 | 35 | |
| TX63641 | | 344.42 | 43 | 23 | |
| TX63642 | | 359.42 | 147 | 77 | |
| TX63646 | | 297.35 | 8.5 | 5.0 | |
| TX63649 | | 334.21 | 21 | 16 | |

TABLE 1-continued

Suppression of IFNγ-Induced NO Production.

| Compound No. | Molecular Structure | MW | RAW264.7 NO IC$_{50}$ (nM) | Relative NO IC$_{50}$ | NQO1-ARE assay Fold induction at 62.5 nM |
|---|---|---|---|---|---|
| TX63650 | 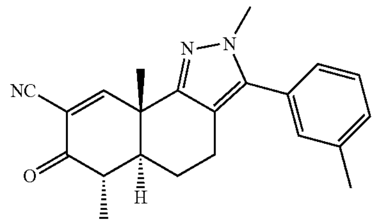 [SMILES: Cc1cccc(-c2c3c(nn2C)[C@@]2(C)C=C(C#N)C(=O)[C@@H](C)[C@@H]2CC3)c1] | 345.44 | 6.1 | 4.7 | |
| TX63651 | 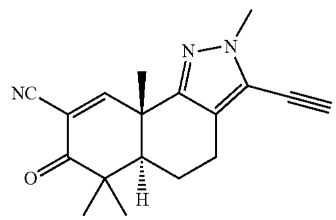 [SMILES: C#Cc1c2c(nn1C)[C@@]1(C)C=C(C#N)C(=O)C(C)(C)[C@@H]1CC2] | 293.36 | 23 | 18 | |
| TX63655 | 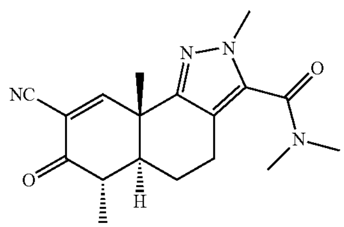 [SMILES: C[C@@H]1C(=O)C(C#N)=C[C@]2(C)c3nn(C)c(C(=O)N(C)C)c3CC[C@@H]12] | 326.39 | >200 | — | |
| TX63656 | 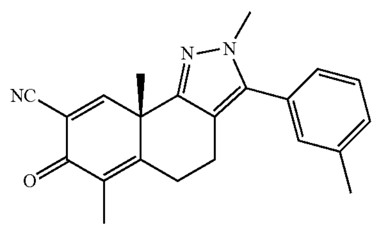 [SMILES: CC1=C2CCc3c(nn(C)c3-c3cccc(C)c3)[C@@]2(C)C=C(C#N)C1=O] | 343.42 | >200 | — | |
| TX63659 | 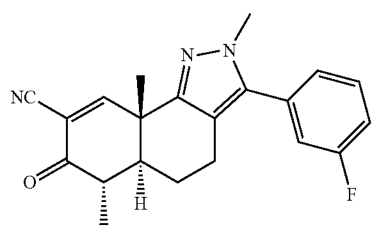 [SMILES: C[C@@H]1C(=O)C(C#N)=C[C@]2(C)c3nn(C)c(-c4cccc(F)c4)c3CC[C@@H]12] | 349.41 | 8.1 | 6.2 | |
| TX63663 | 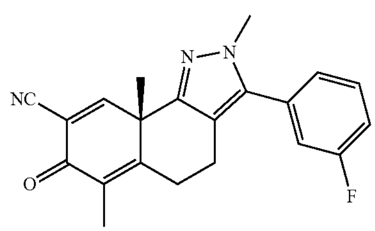 [SMILES: CC1=C2CCc3c(nn(C)c3-c3cccc(F)c3)[C@@]2(C)C=C(C#N)C1=O] | 347.39 | 108 | 63.5 | |

TABLE 1-continued

Suppression of IFNγ-Induced NO Production.

| Compound No. | Molecular Structure | MW | RAW264.7 NO IC$_{50}$ (nM) | Relative NO IC$_{50}$ | NQO1-ARE assay Fold induction at 62.5 nM |
|---|---|---|---|---|---|
| TX63664 | | 361.44 | 8 | 4.0 | |
| TX63665 | | 351.41 | 14 | 7.0 | |
| TX63666 | | 359.42 | 25 | 12.5 | |
| TX63667 | | 373.45 | 155 | 91 | |
| TX63676 | | 285.34 | >200 | — | |
| TX63690 | | 335.41 | 11 | 6.5 | |

TABLE 1-continued

Suppression of IFNγ-Induced NO Production.

| Compound No. | Molecular Structure | MW | RAW264.7 NO IC$_{50}$ (nM) | Relative NO IC$_{50}$ | NQO1-ARE assay Fold induction at 62.5 nM |
|---|---|---|---|---|---|
| TX93691 | 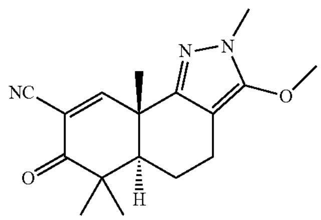 [SMILES: COc1c2c(nn1C)[C@@]1(C)C=C(C#N)C(=O)C(C)(C)[C@@H]1CC2] | 299.37 | 62 | 36.5 | |
| TX63692 | 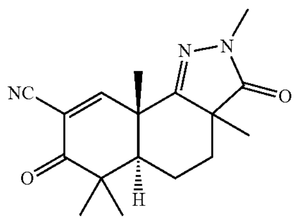 [SMILES: CN1N=C2C(C)(CC[C@H]3C(C)(C)C(=O)C(C#N)=C[C@]23C)C1=O] | 299.37 | >200 | — | |
| TX63714 | 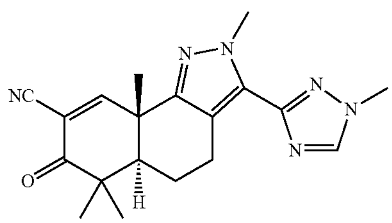 [SMILES: Cn1cnc(-c2c3c(nn2C)[C@@]2(C)C=C(C#N)C(=O)C(C)(C)[C@@H]2CC3)n1] | 350.42 | >200 | — | |
| TX63718 | 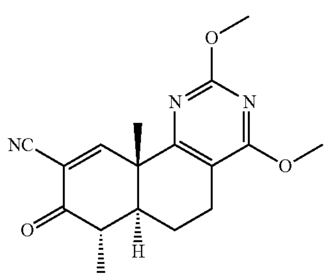 [SMILES: COc1nc(OC)c2c(n1)[C@@]1(C)C=C(C#N)C(=O)[C@@H](C)[C@@H]1CC2] | 313.35 | 6 | 4.3 | |
| TX63719 | 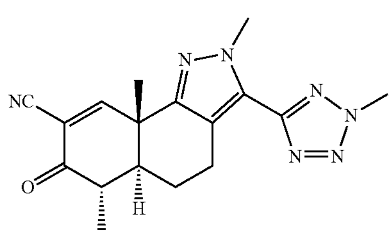 [SMILES: C[C@@H]1C(=O)C(C#N)=C[C@]2(C)c3nn(C)c(-c4nnn(C)n4)c3CC[C@@H]12] | 337.38 | 5.9 | 3.9 | |
| TX63720 | 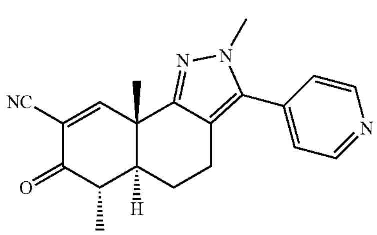 [SMILES: C[C@@H]1C(=O)C(C#N)=C[C@]2(C)c3nn(C)c(-c4ccncc4)c3CC[C@@H]12] | 332.40 | 4.9 | 3.1 | |

TABLE 1-continued
Suppression of IFNγ-Induced NO Production.
| Compound No. | Molecular Structure | MW | RAW264.7 NO IC$_{50}$ (nM) | Relative NO IC$_{50}$ | NQO1-ARE assay Fold induction at 62.5 nM |
|---|---|---|---|---|---|
| TX63721 | 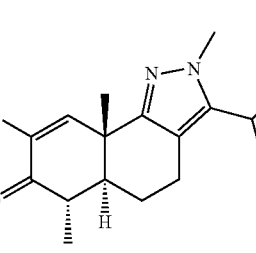 | 349.40 | 7.8 | 4.9 | |
| TX63722 | 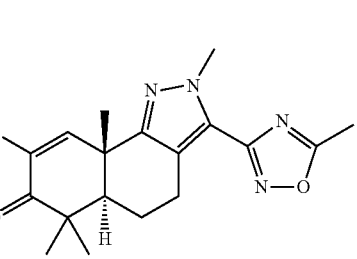 | 332.40 | 8.3 | 5.2 | |
| TX63723 | 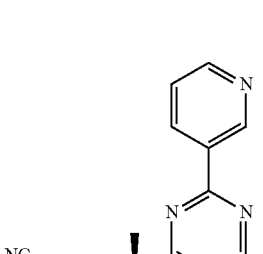 | 351.40 | 35 | 23.3 | |
| TX63724 | 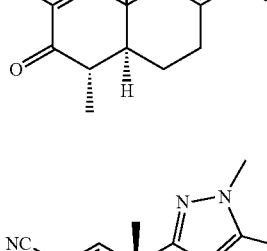 | 360.41 | 3.1 | 2.1 | 4.9 |
| TX63725 | 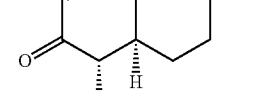 | 280.32 | 24 | 16 | |

TABLE 1-continued

Suppression of IFNγ-Induced NO Production.

| Compound No. | Molecular Structure | MW | RAW264.7 NO IC$_{50}$ (nM) | Relative NO IC$_{50}$ | NQO1-ARE assay Fold induction at 62.5 nM |
|---|---|---|---|---|---|
| TX63727 | | 389.45 | 11.5 | 4.6 | |
| TX63728 | | 360.41 | 6.7 | 2.7 | |
| TX63729 | | 427.50 | 29 | 11.5 | |
| TX63730 | | 355.39 | 16 | 6.4 | |
| TX63731 | | 373.45 | 32 | 12.9 | |

TABLE 1-continued

Suppression of IFNγ-Induced NO Production.

| Compound No. | Molecular Structure | MW | RAW264.7 NO IC$_{50}$ (nM) | Relative NO IC$_{50}$ | NQO1-ARE assay Fold induction at 62.5 nM |
|---|---|---|---|---|---|
| TX63734 | 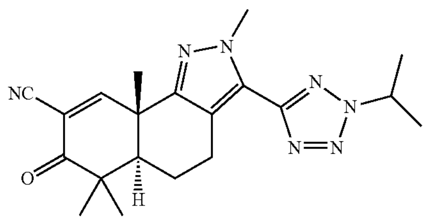 [SMILES: CC(C)n1nnc(-c2c3c(nn2C)[C@@]2(C)C=C(C#N)C(=O)C(C)(C)[C@@H]2CC3)n1] | 379.46 | 43 | 37 | |
| TX63735 | 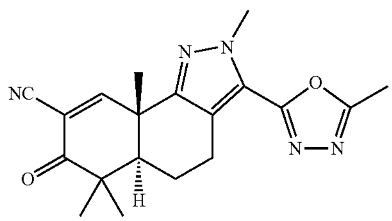 [SMILES: Cc1nnc(-c2c3c(nn2C)[C@@]2(C)C=C(C#N)C(=O)C(C)(C)[C@@H]2CC3)o1] | 351.40 | 15.6 | 13 | |
| TX63736 | 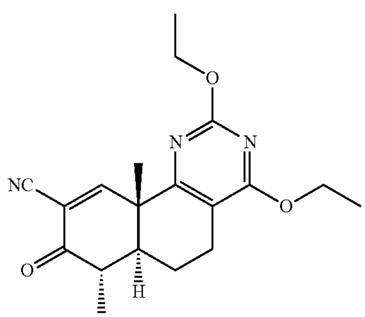 [SMILES: CCOc1nc(OCC)c2c(n1)[C@@]1(C)C=C(C#N)C(=O)[C@@H](C)[C@@H]1CC2] | 341.40 | 9.8 | 5.3 | |
| TX63748 | 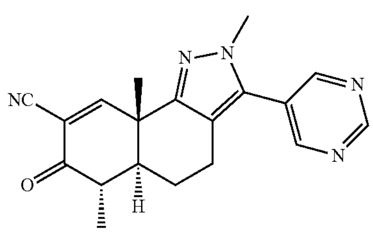 [SMILES: C[C@@H]1C(=O)C(C#N)=C[C@]2(C)c3nn(C)c(-c4cncnc4)c3CC[C@@H]12] | 333.39 | 23 | 16.5 | |
| TX63757 | 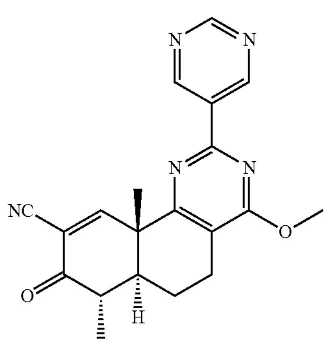 [SMILES: COc1nc(-c2cncnc2)nc2c1CC[C@H]1[C@H](C)C(=O)C(C#N)=C[C@]21C] | 361.40 | 4.3 | 3.4 | |

TABLE 1-continued

Suppression of IFNγ-Induced NO Production.

| Compound No. | Molecular Structure | MW | RAW264.7 NO IC$_{50}$ (nM) | Relative NO IC$_{50}$ | NQO1-ARE assay Fold induction at 62.5 nM |
|---|---|---|---|---|---|
| TX63758 | | 352.44 | 55 | 44 | |
| TX63760 | | 351.40 | 6.2 | 4.8 | |
| TX63761 | | 323.39 | 8.9 | 7.2 | |
| TX63769 | | 359.42 | 9.4 | 7.6 | |
| TX63773 | | 311.38 | 6 | 4.9 | |

TABLE 1-continued

Suppression of IFNγ-Induced NO Production.

| Compound No. | Molecular Structure | MW | RAW264.7 NO IC$_{50}$ (nM) | Relative NO IC$_{50}$ | NQO1-ARE assay Fold induction at 62.5 nM |
|---|---|---|---|---|---|
| TX63774 | 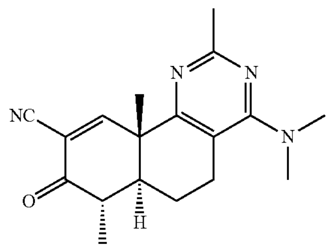 [SMILES: Cc1nc(N(C)C)c2c(n1)[C@@]1(C)C=C(C#N)C(=O)[C@@H](C)[C@@H]1CC2] | 310.40 | 26.7 | 21.5 | |
| TX63776 | 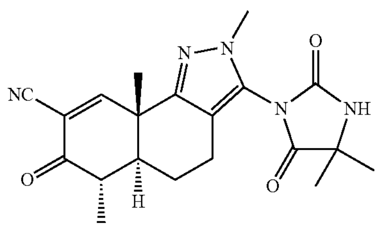 [SMILES: C[C@@H]1C(=O)C(C#N)=C[C@]2(C)c3nn(C)c(N4C(=O)NC(C)(C)C4=O)c3CC[C@@H]12] | 381.43 | >200 | — | |
| TX63791 | 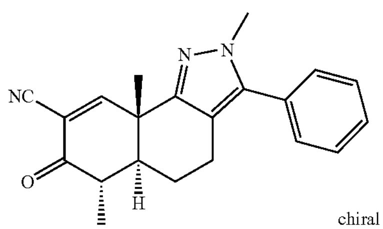 [SMILES: C[C@@H]1C(=O)C(C#N)=C[C@]2(C)c3nn(C)c(-c4ccccc4)c3CC[C@@H]12] | 331.41 | 2.3 | 1.4 | |
| TX63792 | 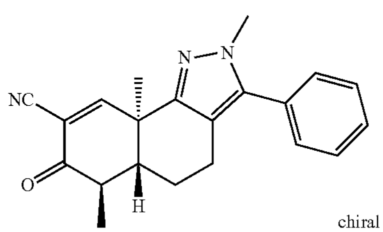 [SMILES: C[C@H]1C(=O)C(C#N)=C[C@@]2(C)c3nn(C)c(-c4ccccc4)c3CC[C@H]12] | 331.41 | 147 | 95 | |
| TX63793 | 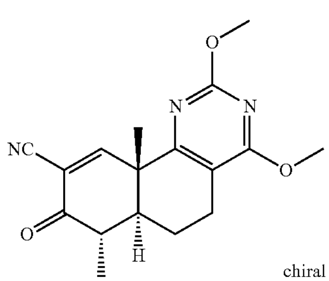 [SMILES: COc1nc(OC)c2c(n1)[C@@]1(C)C=C(C#N)C(=O)[C@@H](C)[C@@H]1CC2] | 313.35 | 2.5 | 2.0 | |

TABLE 1-continued

Suppression of IFNγ-Induced NO Production.

| Compound No. | Molecular Structure | MW | RAW264.7 NO IC$_{50}$ (nM) | Relative NO IC$_{50}$ | NQO1-ARE assay Fold induction at 62.5 nM |
|---|---|---|---|---|---|
| TX63794 | | 313.35 | 88.5 | 69 | |
| TX63803 | | 388.43 | 50 | 43 | |
| TX63804 | | 334.41 | >200 | — | |
| TX63827 | | 338.45 | 59 | 47 | |
| TX63829 | | 374.40 | 22 | 18 | |
| TX63834 | | 361.44 | 105 | 83 | |

TABLE 1-continued

Suppression of IFNγ-Induced NO Production.

| Compound No. | Molecular Structure | MW | RAW264.7 NO IC$_{50}$ (nM) | Relative NO IC$_{50}$ | NQO1-ARE assay Fold induction at 62.5 nM |
|---|---|---|---|---|---|
| TX63836 | 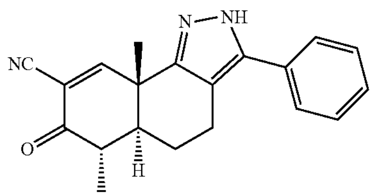 [SMILES: C[C@@H]1C(=O)C(C#N)=C[C@]2(C)c3n[nH]c(-c4ccccc4)c3CC[C@@H]12] | 317.39 | 6.1 | 4.8 | |
| TX63848 | 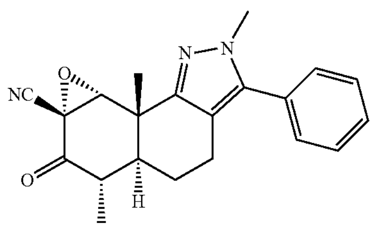 [SMILES: C[C@@H]1C(=O)[C@]2(C#N)O[C@@H]2[C@]2(C)c3nn(C)c(-c4ccccc4)c3CC[C@@H]12] | 347.41 | 9.5 | 5.7 | |
| TX63849 | 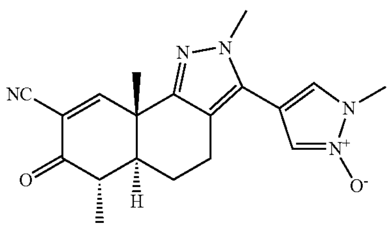 [SMILES: C[C@@H]1C(=O)C(C#N)=C[C@]2(C)c3nn(C)c(-c4cn(C)[n+]([O-])c4)c3CC[C@@H]12] | 351.41 | >200 | — | |
| TX63850 | 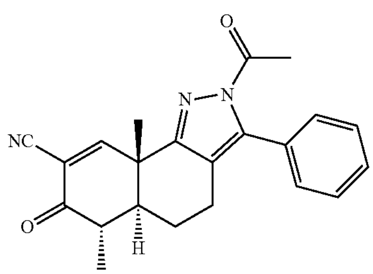 [SMILES: CC(=O)n1nc2c(c1-c1ccccc1)CC[C@H]1[C@H](C)C(=O)C(C#N)=C[C@]21C] | 359.42 | 8.9 | 5.3 | |
| TX63851 | 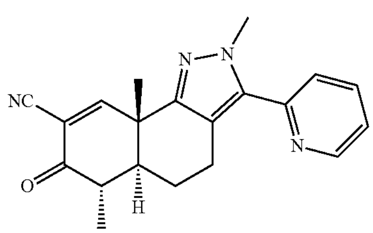 [SMILES: C[C@@H]1C(=O)C(C#N)=C[C@]2(C)c3nn(C)c(-c4ccccn4)c3CC[C@@H]12] | 332.40 | 5.1 | 3.0 | |
| TX63852 | 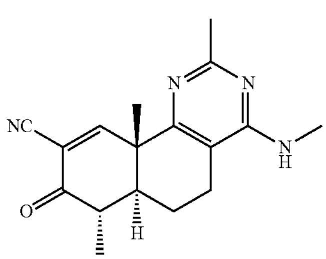 [SMILES: CNc1nc(C)nc2c1CC[C@H]1[C@H](C)C(=O)C(C#N)=C[C@]21C] | 296.37 | 30 | 18 | |

TABLE 1-continued

Suppression of IFNγ-Induced NO Production.

| Compound No. | Molecular Structure | MW | RAW264.7 NO IC$_{50}$ (nM) | Relative NO IC$_{50}$ | NQO1-ARE assay Fold induction at 62.5 nM |
|---|---|---|---|---|---|
| TX63853 | | 339.44 | 31 | 18.6 | |
| TX63857 | | 337.38 | 6.3 | 5.1 | |
| TX63871 | | 389.45 | 7.5 | 4.5 | |
| TX63872 | | 337.38 | 4.6 | 2.8 | |
| TX63874 | | 283.33 | 5.5 | 4.8 | |

TABLE 1-continued

Suppression of IFNγ-Induced NO Production.

| | | | RAW264.7 | | NQO1-ARE assay |
| --- | --- | --- | --- | --- | --- |
| Compound No. | Molecular Structure | MW | NO IC$_{50}$ (nM) | Relative NO IC$_{50}$ | Fold induction at 62.5 nM |
| TX63900 | | 353.47 | 40 | | 26 |
| TX63905 | | 378.47 | 129 | | 85 |

IV. DISEASES ASSOCIATED WITH INFLAMMATION AND/OR OXIDATIVE STRESS

Inflammation is a biological process that provides resistance to infectious or parasitic organisms and the repair of damaged tissue. Inflammation is commonly characterized by localized vasodilation, redness, swelling, and pain, the recruitment of leukocytes to the site of infection or injury, production of inflammatory cytokines such as TNF-α and IL-1, and production of reactive oxygen or nitrogen species such as hydrogen peroxide, superoxide and peroxynitrite. In later stages of inflammation, tissue remodeling, angiogenesis, and scar formation (fibrosis) may occur as part of the wound healing process. Under normal circumstances, the inflammatory response is regulated and temporary and is resolved in an orchestrated fashion once the infection or injury has been dealt with adequately. However, acute inflammation can become excessive and life-threatening if regulatory mechanisms fail. Alternatively, inflammation can become chronic and cause cumulative tissue damage or systemic complications. Based at least on the evidence presented above, the compounds of this invention may be used in the treatment or prevention of inflammation or diseases associated with inflammation.

Many serious and intractable human diseases involve dysregulation of inflammatory processes, including diseases such as cancer, atherosclerosis, and diabetes, which were not traditionally viewed as inflammatory conditions. In the case of cancer, the inflammatory processes are associated with tumor formation, progression, metastasis, and resistance to therapy. Atherosclerosis, long viewed as a disorder of lipid metabolism, is now understood to be primarily an inflammatory condition, with activated macrophages playing an important role in the formation and eventual rupture of atherosclerotic plaques. Activation of inflammatory signaling pathways has also been shown to play a role in the development of insulin resistance, as well as in the peripheral tissue damage associated with diabetic hyperglycemia. Excessive production of reactive oxygen species and reactive nitrogen species such as superoxide, hydrogen peroxide, nitric oxide, and peroxynitrite is a hallmark of inflammatory conditions. Evidence of dysregulated peroxynitrite production has been reported in a wide variety of diseases (Szabo et al., 2007; Schulz et al., 2008; Forstermann, 2006; Pall, 2007).

Autoimmune diseases such as rheumatoid arthritis, lupus, psoriasis, and multiple sclerosis involve inappropriate and chronic activation of inflammatory processes in affected tissues, arising from dysfunction of self vs. non-self recognition and response mechanisms in the immune system. In neurodegenerative diseases such as Alzheimer's and Parkinson's diseases, neural damage is correlated with activation of microglia and elevated levels of pro-inflammatory proteins such as inducible nitric oxide synthase (iNOS). Chronic organ failure such as renal failure, heart failure, liver failure, and chronic obstructive pulmonary disease is closely associated with the presence of chronic oxidative stress and inflammation, leading to the development of fibrosis and eventual loss of organ function. Oxidative stress in vascular endothelial cells, which line major and minor blood vessels, can lead to endothelial dysfunction and is believed to be an important contributing factor in the development of systemic cardiovascular disease, complications of diabetes, chronic kidney disease and other forms of organ failure, and a number of other aging-related diseases including degenerative diseases of the central nervous system and the retina.

Many other disorders involve oxidative stress and inflammation in affected tissues, including inflammatory bowel disease; inflammatory skin diseases; mucositis related to radiation therapy and chemotherapy; eye diseases such as uveitis, glaucoma, macular degeneration, and various forms of retinopathy; transplant failure and rejection; ischemia-reperfusion injury; chronic pain; degenerative conditions of the bones and joints including osteoarthritis and osteoporosis; asthma and cystic fibrosis; seizure disorders; and neuropsychiatric conditions including schizophrenia, depression, bipolar disorder, post-traumatic stress disorder, attention deficit disorders, autism-spectrum disorders, and eating disorders such as anorexia nervosa. Dysregulation of inflammatory signaling pathways is believed to be a major factor in the pathology of muscle wasting diseases including muscular dystrophy and various forms of cachexia.

A variety of life-threatening acute disorders also involve dysregulated inflammatory signaling, including acute organ failure involving the pancreas, kidneys, liver, or lungs, myocardial infarction or acute coronary syndrome, stroke, septic shock, trauma, severe burns, and anaphylaxis.

Many complications of infectious diseases also involve dysregulation of inflammatory responses. Although an inflammatory response can kill invading pathogens, an excessive inflammatory response can also be quite destructive and in some cases can be a primary source of damage in infected tissues. Furthermore, an excessive inflammatory response can also lead to systemic complications due to overproduction of inflammatory cytokines such as TNF-α and IL-1. This is believed to be a factor in mortality arising from severe influenza, severe acute respiratory syndrome, and sepsis.

The aberrant or excessive expression of either iNOS or cyclooxygenase-2 (COX-2) has been implicated in the pathogenesis of many disease processes. For example, it is clear that NO is a potent mutagen (Tamir and Tannebaum, 1996), and that nitric oxide can also activate COX-2 (Salvemini et al., 1994). Furthermore, there is a marked increase in iNOS in rat colon tumors induced by the carcinogen, azoxymethane (Takahashi et al., 1997). A series of synthetic triterpenoid analogs of oleanolic acid have been shown to be powerful inhibitors of cellular inflammatory processes, such as the induction by IFN-γ of inducible nitric oxide synthase (iNOS) and of COX-2 in mouse macrophages. See Honda et al. (2000a); Honda et al. (2000b), and Honda et al. (2002), which are all incorporated herein by reference.

In one aspect, compounds disclosed herein are characterized by their ability to inhibit the production of nitric oxide in macrophage-derived RAW 264.7 cells induced by exposure to γ-interferon. They are further characterized by their ability to induce the expression of antioxidant proteins such as NQO1 and reduce the expression of pro-inflammatory proteins such as COX-2 and inducible nitric oxide synthase (iNOS). These properties are relevant to the treatment of a wide array of diseases and disorders involving oxidative stress and dysregulation of inflammatory processes including cancer, complications from localized or total-body exposure to ionizing radiation, mucositis resulting from radiation therapy or chemotherapy, autoimmune diseases, cardiovascular diseases including atherosclerosis, ischemia-reperfusion injury, acute and chronic organ failure including renal failure and heart failure, respiratory diseases, diabetes and complications of diabetes, severe allergies, transplant rejection, graft-versus-host disease, neurodegenerative diseases, diseases of the eye and retina, acute and chronic pain, degenerative bone diseases including osteoarthritis and osteoporosis, inflammatory bowel diseases, dermatitis and other skin diseases, sepsis, burns, seizure disorders, and neuropsychiatric disorders.

Without being bound by theory, the activation of the anti-oxidant/anti-inflammatory Keap1/Nrf2/ARE pathway is believed to be implicated in both the anti-inflammatory and anti-carcinogenic properties of the compounds disclosed herein.

In another aspect, compounds disclosed herein may be used for treating a subject having a condition caused by elevated levels of oxidative stress in one or more tissues. Oxidative stress results from abnormally high or prolonged levels of reactive oxygen species such as superoxide, hydrogen peroxide, nitric oxide, and peroxynitrite (formed by the reaction of nitric oxide and superoxide). The oxidative stress may be accompanied by either acute or chronic inflammation. The oxidative stress may be caused by mitochondrial dysfunction, by activation of immune cells such as macrophages and neutrophils, by acute exposure to an external agent such as ionizing radiation or a cytotoxic chemotherapy agent (e.g., doxorubicin), by trauma or other acute tissue injury, by ischemia/reperfusion, by poor circulation or anemia, by localized or systemic hypoxia or hyperoxia, by elevated levels of inflammatory cytokines and other inflammation-related proteins, and/or by other abnormal physiological states such as hyperglycemia or hypoglycemia.

In animal models of many such conditions, stimulating expression of inducible heme oxygenase (HO-1), a target gene of the Nrf2 pathway, has been shown to have a significant therapeutic effect including models of myocardial infarction, renal failure, transplant failure and rejection, stroke, cardiovascular disease, and autoimmune disease (e.g., Sacerdoti et al., 2005; Abraham & Kappas, 2005; Bach, 2006; Araujo et al., 2003; Liu et al., 2006; Ishikawa et al., 2001; Kruger et al., 2006; Satoh et al., 2006; Zhou et al., 2005; Morse and Choi, 2005; Morse and Choi, 2002). This enzyme breaks free heme down into iron, carbon monoxide (CO), and biliverdin (which is subsequently converted to the potent antioxidant molecule, bilirubin).

In another aspect, compounds of this invention may be used in preventing or treating tissue damage or organ failure, acute and chronic, resulting from oxidative stress exacerbated by inflammation. Examples of diseases that fall in this category include: heart failure, liver failure, transplant failure and rejection, renal failure, pancreatitis, fibrotic lung diseases (cystic fibrosis and COPD, among others), diabetes (including complications), atherosclerosis, ischemia-reperfusion injury, glaucoma, stroke, autoimmune disease, autism, macular degeneration, and muscular dystrophy. For example, in the case of autism, studies suggest that increased oxidative stress in the central nervous system may contribute to the development of the disease (Chauhan and Chauhan, 2006).

Evidence also links oxidative stress and inflammation to the development and pathology of many other disorders of the central nervous system, including psychiatric disorders such as psychosis, major depression, and bipolar disorder; seizure disorders such as epilepsy; pain and sensory syndromes such as migraine, neuropathic pain or tinnitus; and behavioral syndromes such as the attention deficit disorders. See, e.g., Dickerson et al., 2007; Hanson et al., 2005; Kendall-Tackett, 2007; Lencz et al., 2007; Dudhgaonkar et al., 2006; Lee et al., 2007; Morris et al., 2002; Ruster et al., 2005; McIver et al., 2005; Sarchielli et al., 2006; Kawakami et al., 2006; Ross et al., 2003, which are all incorporated by reference herein. For example, elevated levels of inflammatory cytokines, including TNF, interferon-γ, and IL-6, are associated with major mental illness (Dickerson et al., 2007). Microglial activation has also been linked to major mental illness. Therefore, downregulating inflammatory cytokines and inhibiting excessive activation of microglia could be beneficial in patients with schizophrenia, major depression, bipolar disorder, autism-spectrum disorders, and other neuropsychiatric disorders.

Accordingly, in pathologies involving oxidative stress alone or oxidative stress exacerbated by inflammation, treatment may comprise administering to a subject a therapeutically effective amount of a compound of this invention, such as those described above or throughout this specification.

Treatment may be administered preventively, in advance of a predictable state of oxidative stress (e.g., organ transplantation or the administration of radiation therapy to a cancer patient), or it may be administered therapeutically in settings involving established oxidative stress and inflammation.

The compounds disclosed herein may be generally applied to the treatment of inflammatory conditions, such as sepsis, dermatitis, autoimmune disease and osteoarthritis. In one aspect, the compounds of this invention may be used to treat inflammatory pain and/or neuropathic pain, for example, by inducing Nrf2 and/or inhibiting NF-κB.

In some embodiments, the compounds disclosed herein may be used in the treatment and prevention of diseases such as cancer, inflammation, Alzheimer's disease, Parkinson's disease, multiple sclerosis, autism, amyotrophic lateral sclerosis, Huntington's disease, autoimmune diseases such as rheumatoid arthritis, lupus, Crohn's disease and psoriasis, inflammatory bowel disease, all other diseases whose pathogenesis is believed to involve excessive production of either nitric oxide or prostaglandins, and pathologies involving oxidative stress alone or oxidative stress exacerbated by inflammation.

Another aspect of inflammation is the production of inflammatory prostaglandins such as prostaglandin E. These molecules promote vasodilation, plasma extravasation, localized pain, elevated temperature, and other symptoms of inflammation. The inducible form of the enzyme COX-2 is associated with their production, and high levels of COX-2 are found in inflamed tissues. Consequently, inhibition of COX-2 may relieve many symptoms of inflammation and a number of important anti-inflammatory drugs (e.g., ibuprofen and celecoxib) act by inhibiting COX-2 activity. Recent research, however, has demonstrated that a class of cyclopentenone prostaglandins (cyPGs) (e.g., 15-deoxy prostaglandin J2, a.k.a. PGD2) plays a role in stimulating the orchestrated resolution of inflammation (e.g., Rajakariar et al., 2007). COX-2 is also associated with the production of cyclopentenone prostaglandins. Consequently, inhibition of COX-2 may interfere with the full resolution of inflammation, potentially promoting the persistence of activated immune cells in tissues and leading to chronic, "smoldering" inflammation. This effect may be responsible for the increased incidence of cardiovascular disease in patients using selective COX-2 inhibitors for long periods of time.

In one aspect, the compounds disclosed herein may be used to control the production of pro-inflammatory cytokines within the cell by selectively activating regulatory cysteine residues (RCRs) on proteins that regulate the activity of redox-sensitive transcription factors. Activation of RCRs by cyPGs has been shown to initiate a pro-resolution program in which the activity of the antioxidant and cytoprotective transcription factor Nrf2 is potently induced and the activities of the pro-oxidant and pro-inflammatory transcription factors NF-κB and the STATs are suppressed. In some embodiments, this increases the production of antioxidant and reductive molecules (NQO1, HO-1, SOD1, γ-GCS) and decreases oxidative stress and the production of pro-oxidant and pro-inflammatory molecules (iNOS, COX-2, TNF-α). In some embodiments, the compounds of this invention may cause the cells that host the inflammatory event to revert to a non-inflammatory state by promoting the resolution of inflammation and limiting excessive tissue damage to the host.

V. PHARMACEUTICAL FORMULATIONS AND ROUTES OF ADMINISTRATION

The compounds of the present disclosure may be administered by a variety of methods, e.g., orally or by injection (e.g. subcutaneous, intravenous, intraperitoneal, etc.). Depending on the route of administration, the active compounds may be coated in a material to protect the compound from the action of acids and other natural conditions which may inactivate the compound. They may also be administered by continuous perfusion/infusion of a disease or wound site.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. See for example U.S. patent application by J. Zhang, entitled "Amorphous Solid Dispersions of CDDO-Me for Delayed Release Oral Dosage Compositions," filed Feb. 13, 2009, which is incorporated herein by reference. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier.

The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

Active compounds are administered at a therapeutically effective dosage sufficient to treat a condition associated with a condition in a patient. For example, the efficacy of a compound can be evaluated in an animal model system that may be predictive of efficacy in treating the disease in humans, such as the model systems shown in the examples and drawings.

The actual dosage amount of a compound of the present disclosure or composition comprising a compound of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day. For example, regarding treatment of diabetic patients, the unit dosage may be an amount that reduces blood glucose by at least 40% as compared to an untreated subject. In another embodiment, the unit dosage is an amount that reduces blood glucose to a level that is ±10% of the blood glucose level of a non-diabetic subject.

In other non-limiting examples, a dose may also comprise from about 1 micro-gram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milli-gram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present disclosure may comprise, for example, at least about 0.1% of a compound of the present disclosure. In other embodiments, the compound of the present disclosure may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may taken orally and that the timing of which is or is not dependent upon food intake. Thus, for example, the agent can be taken every morning and/or every evening, regardless of when the subject has eaten or will eat.

VI. COMBINATION THERAPY

In addition to being used as a monotherapy, the compounds of the present invention may also find use in combination therapies. Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

Non-limiting examples of such combination therapy include combination of one or more compounds of the invention with another anti-inflammatory agent, a chemotherapeutic agent, radiation therapy, an antidepressant, an antipsychotic agent, an anticonvulsant, a mood stabilizer, an anti-infective agent, an antihypertensive agent, a cholesterol-lowering agent or other modulator of blood lipids, an agent for promoting weight loss, an antithrombotic agent, an agent for treating or preventing cardiovascular events such as myocardial infarction or stroke, an antidiabetic agent, an agent for reducing transplant rejection or graft-versus-host disease, an anti-arthritic agent, an analgesic agent, an anti-asthmatic agent or other treatment for respiratory diseases, or an agent for treatment or prevention of skin disorders. Compounds of the invention may be combined with agents designed to improve a patient's immune response to cancer, including (but not limited to) cancer vaccines. See Lu et al. (2011), which is incorporated herein by reference.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Methods and Materials

Nitric Oxide Production and Cell Viability.

RAW264.7 mouse macrophages were plated in 96-well plates at 30,000 cells/well in triplicate in RPMI1640+0.5% FBS and incubated at 37° C. with 5% $CO_2$. On the next day, cells were pre-treated with DMSO or drug (0-200 nM dose range) for 2 hours, and then treated with recombinant mouse IFNγ (R&D Systems) for 24 hours. Nitric Oxide concentration in media was determined using the Griess reagent system (Promega). Cell viability was determined using WST-1 reagent (Roche). $IC_{50}$ values were determined based on the suppression of IFNγ induced Nitric Oxide production normalized to cell viability.

NQO1-ARE Luciferase Reporter Assay.

This assay allows for quantitative assessment of the endogenous activity of the Nrf2 transcription factor in cultured mammalian cells. Expression of Firefly luciferase from NQO1-ARE luciferase reporter plasmid is controlled by binding of Nrf2 to a specific enhancer sequence corresponding to the antioxidant response element (ARE) that was identified in the promoter region of the human NADPH:quinone oxidoreductase 1 (NQO1) gene (Xie et al., 1995). The plasmid was constructed by inserting a sequence:

```
                                (SEQ ID NO: 1)
   5'-CAGTCACAGTGACTCAGCAGAATCTG-3'
``` encompassing the human NQO1-ARE into the pLuc-MCS vector using HindIII/XhoI cloning sites (GenScript Corp., Piscataway, N.J.). The assay is performed in HuH7 cells maintained in DMEM (Invitrogen) supplemented with 10% FBS and 100 U/ml (each) of penicillin and streptomycin. For the assay, cells are plated in 96-well plates at 17,000 cells per well. Twenty four hours later, the cells are co-transfected with 50 ng each of NQO1-ARE reporter plasmid and pRL-TK plasmid using Lipofectamine 2000 transfection reagent (Invitrogen). pRL-TK plasmid constitutively expresses *Renilla* luciferase and is used as an internal control for normalization of transfection levels. Thirty hours after transfection, the cells are treated with compounds (at concentrations ranging from 0 to 1 μM) for eighteen hours. Firefly and *Renilla* luciferase activity is assayed by Dual-Glo Luciferase Assay (Promega Corp., Madison, Wis.), the luminescence signal is measured on an L-Max II luminometer (Molecular Devices). Firefly luciferase activity is normalized to the *Renilla* activity, and fold induction over a vehicle control (DMSO) of normalized Firefly activity is calculated. The fold induction at 62.5 nM concentration is used for comparing relative potencies of compounds to induce Nrf2 transcriptional activity. See Xie T, Belinsky M, Xu Y, Jaiswal A K. ARE- and TRE-mediated regulation of gene expression. Response to xenobiotics and antioxidants. *J Biol. Chem.* (1995) 270(12):6894-6900, which is incorporated herein by reference.

Syntheses of Certain Synthetic AIM Compounds of the Present Disclosure

Scheme 1(a):

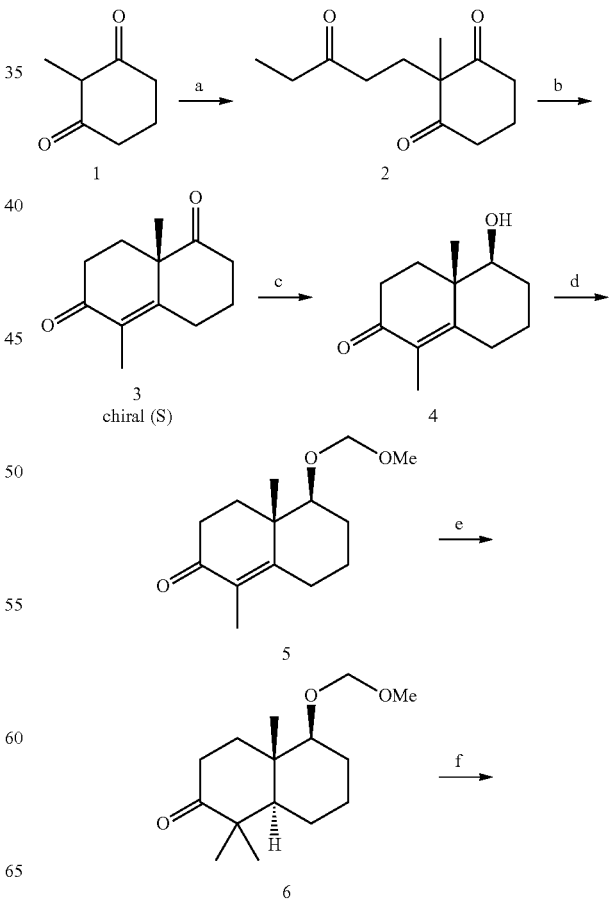

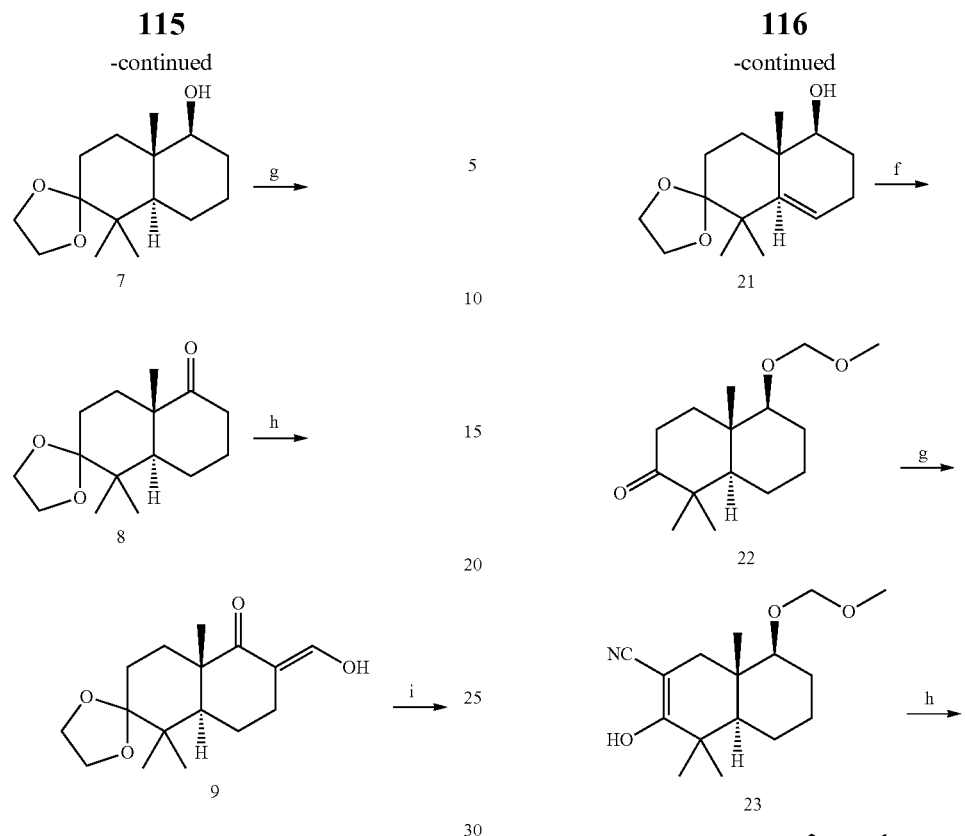
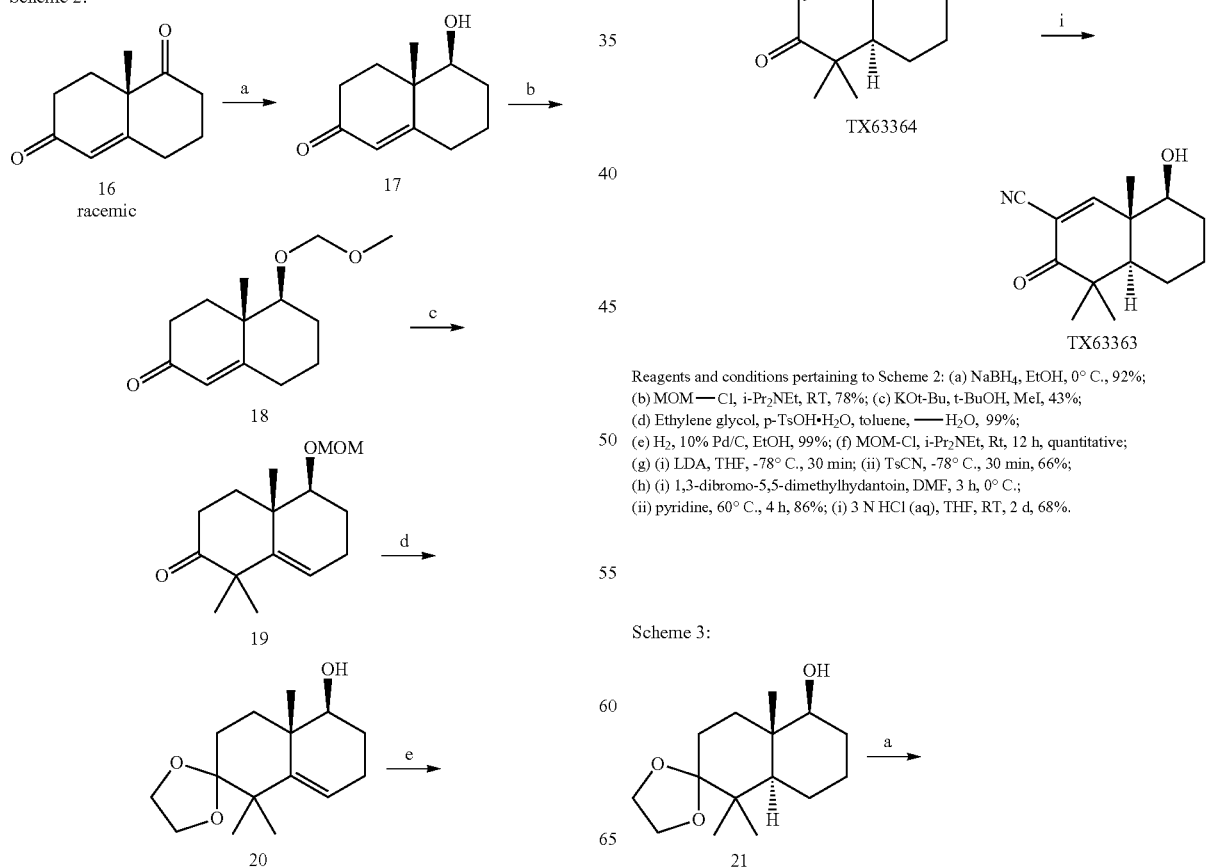
Reagents and conditions pertaining to Scheme 2: (a) NaBH₄, EtOH, 0° C., 92%;
(b) MOM—Cl, i-Pr₂NEt, RT, 78%; (c) KOt-Bu, t-BuOH, MeI, 43%;
(d) Ethylene glycol, p-TsOH·H₂O, toluene, —H₂O, 99%;
(e) H₂, 10% Pd/C, EtOH, 99%; (f) MOM-Cl, i-Pr₂NEt, Rt, 12 h, quantitative;
(g) (i) LDA, THF, -78° C., 30 min; (ii) TsCN, -78° C., 30 min, 66%;
(h) (i) 1,3-dibromo-5,5-dimethylhydantoin, DMF, 3 h, 0° C.;
(ii) pyridine, 60° C., 4 h, 86%; (i) 3 N HCl (aq), THF, RT, 2 d, 68%.
Scheme 3:

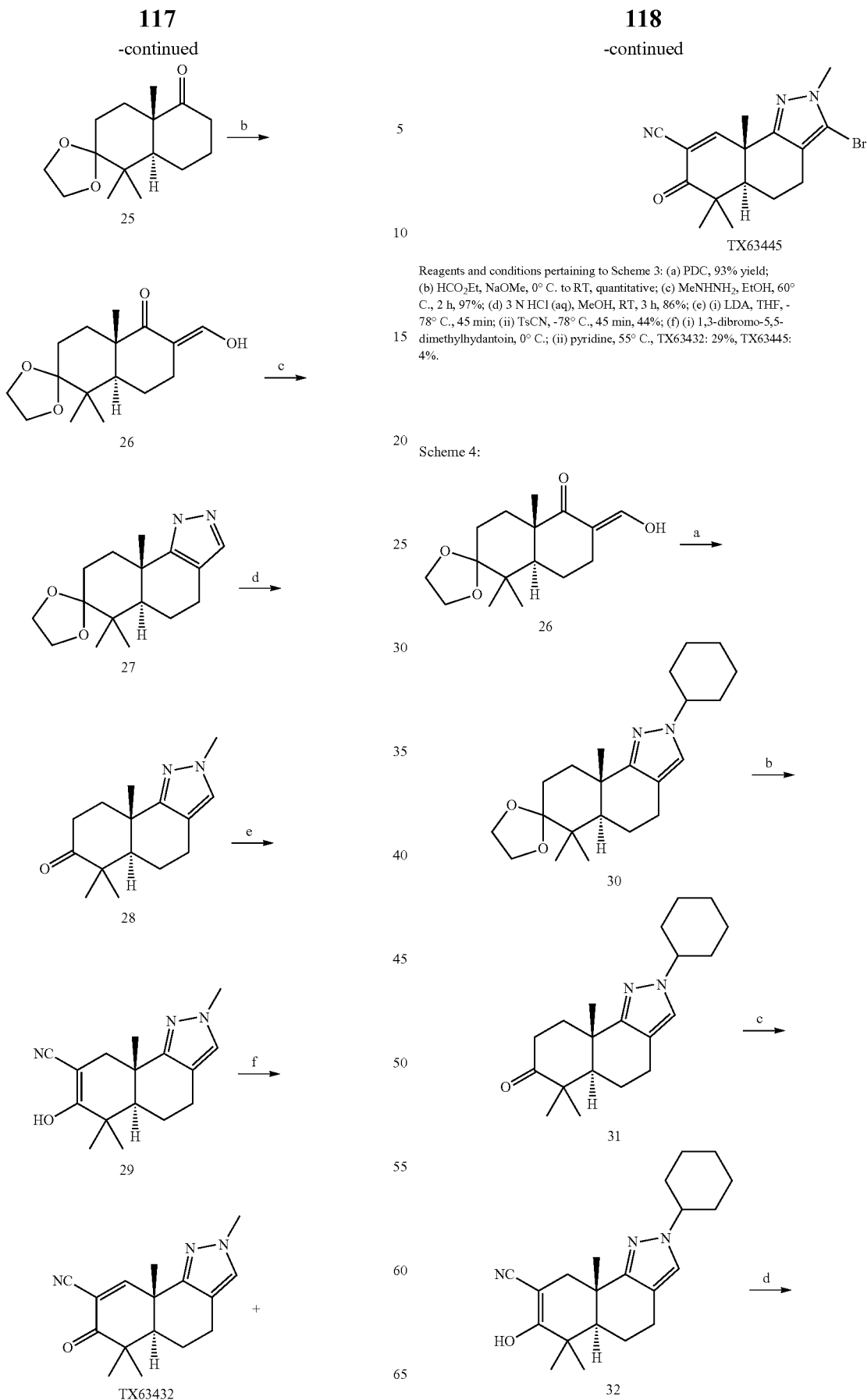
Reagents and conditions pertaining to Scheme 3: (a) PDC, 93% yield; (b) HCO$_2$Et, NaOMe, 0° C. to RT, quantitative; (c) MeNHNH$_2$, EtOH, 60° C., 2 h, 97%; (d) 3 N HCl (aq), MeOH, RT, 3 h, 86%; (e) (i) LDA, THF, -78° C., 45 min; (ii) TsCN, -78° C., 45 min, 44%; (f) (i) 1,3-dibromo-5,5-dimethylhydantoin, 0° C.; (ii) pyridine, 55° C., TX63432: 29%, TX63445: 4%.
Scheme 4:

119
-continued

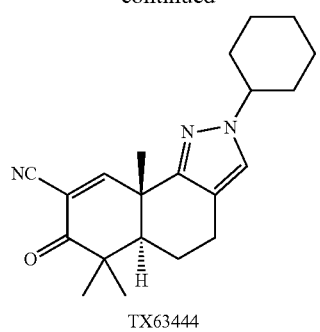

TX63444

Reagents and conditions pertaining to Scheme 4: (a) Cyclohexylhydrazine-HCl, Et₃N, EtOH, 15 min, 36%; (b) 3 N HCl (aq), MeOH, rt. 3 h, 98% yield; (c) LDA, TsCN, THF, -78° C., 1.5 h, 46% yield; (d) (i) 1,3-dibromo-5,5-dimethylhydantoin, DMF, 0° C., 2 h; (ii) pyridine, 55° C., 16 h, 59% yield.

Scheme 5:

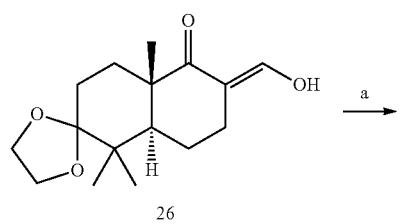

26

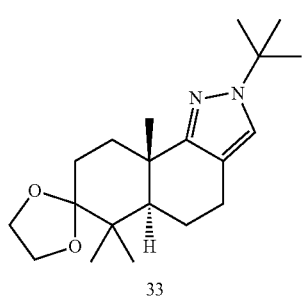

33

+

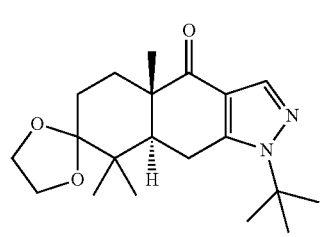

34

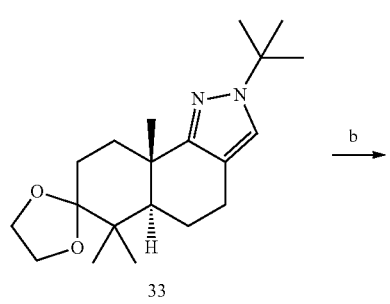

33

120
-continued

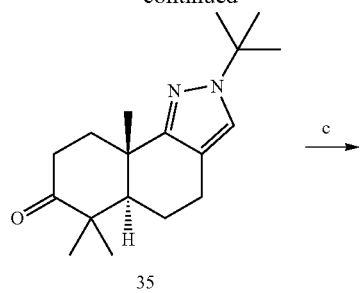

35

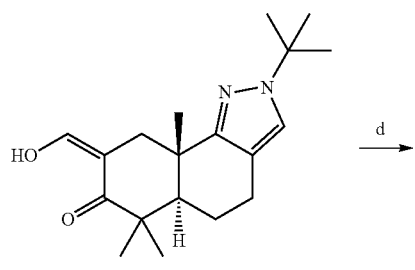

36

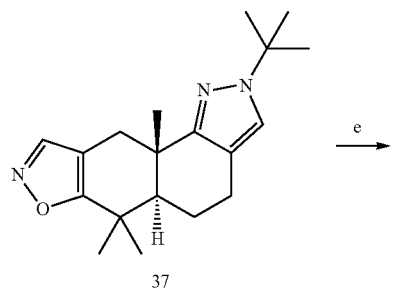

37

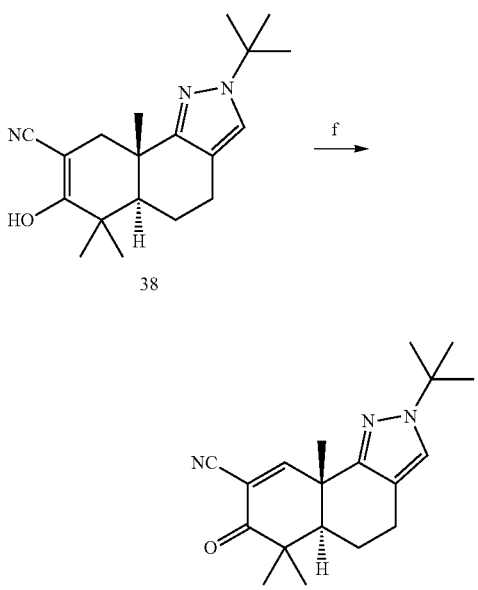

38

TX63450

Reagents and conditions pertaining to Scheme 5: (a) tBuNHNH₂—HCl, Et₃N, EtOH, reflux, 5 h; RT, 12 h, 35% compound 36; 36% compound 37; (b) 1N HCl (aq), MeOH, RT, 12 h, quantitative; (c) HCO₂Et, NaOMe, RT, 12 h, 90%; (d) NH₂OH—HCl, 50° C., 12 h, quantitative; (e) NaOMe, 55° C., 5.5 h; RT, 12 h, 59%; (f) (i) 1,3-dibromo-5-5,-dimethylhydantoin, DMF, 0° C., time; (ii) pyridine, 50° C., 12 h, 56%.

Scheme 6:
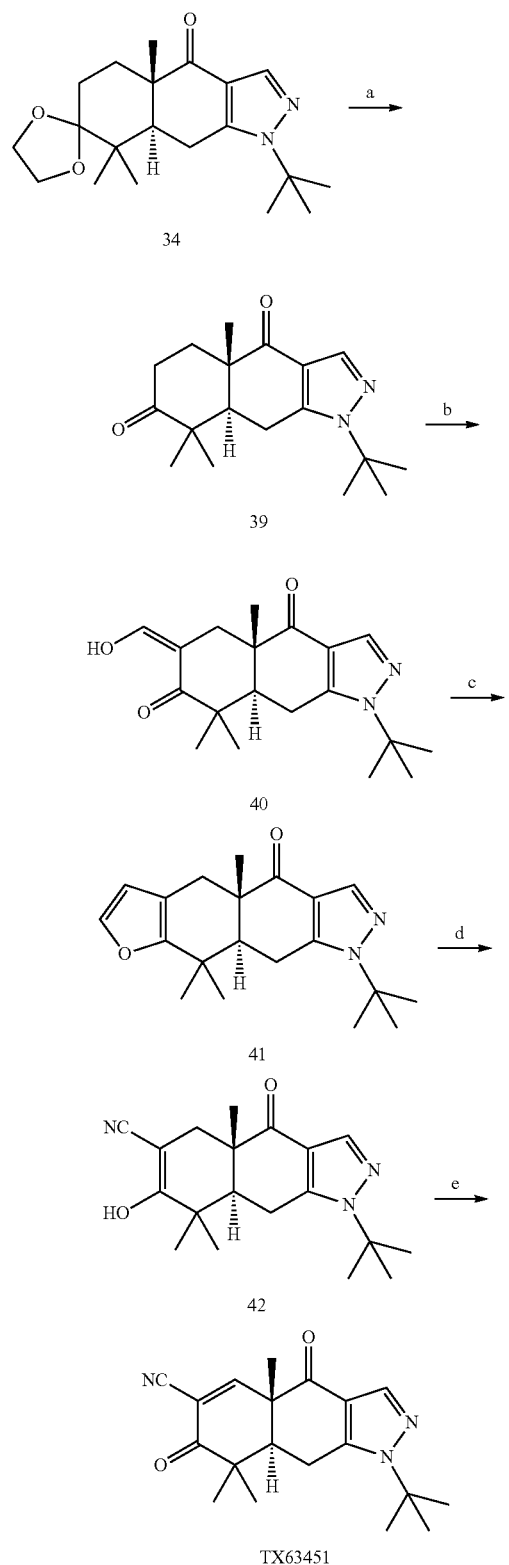
TX63451
Reagents and conditions pertaining to Scheme 6: (a) 1 N HCl (aq), MeOH, RT, 12 h, 86%; (b) HCO₂Et, NaOMe, RT, 12 h, 83%; (c) NH₂OH—HCl, 50° C., 12 h, quantitative; (d) NaOMe, 55° C., 5.5 h; RT, 12 h, 80%; (e) (i) 1,3-dibromo-5,5-dimethylhydantoin, DMF, 0° C., time; (ii) pyridine, 50° C., 12 h, 67%.
Scheme 7:
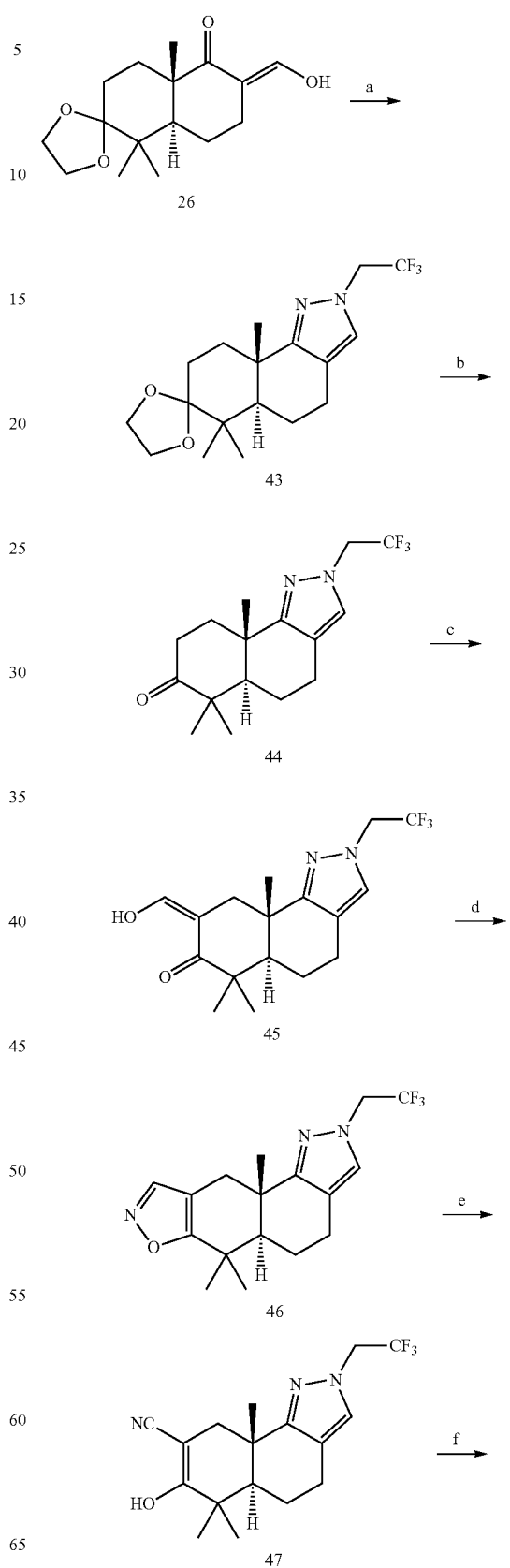

123
-continued
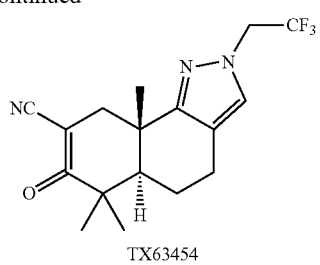
TX63454
Reagents and conditions pertaining to Scheme 7: (a) (2,2,2-trifluoroethyl) hydrazine, EtOH, 60° C., 2 h, 70% (b) 3 N HCl (aq), MeOH, RT, 12 h, quantitative; (c) HCO₂Et, NaOMe, RT, 12 h, 96%; (d) NH₂OH—HCl, 50° C., 12 h, 93%; (e) NaOMe, 50° C., 6 h, 52% (f) (i) 1,3-dibromo-5,5-dimethylhydantoin, DMF, 0° C., 2 h; (ii) pyridine, 50° C., 12 h, 54%.
Scheme 8:
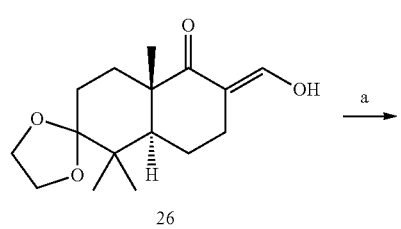
26
a →
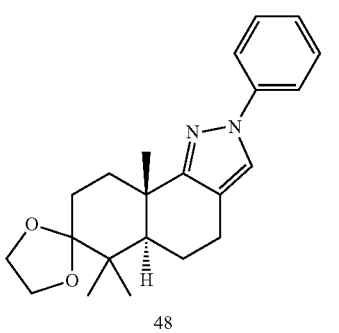
48
+
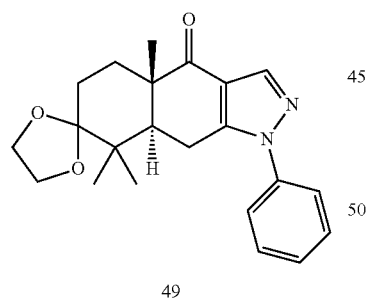
49
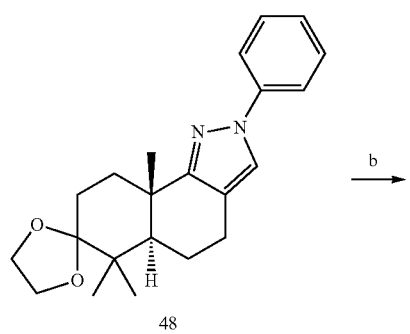
48
b →
124
-continued
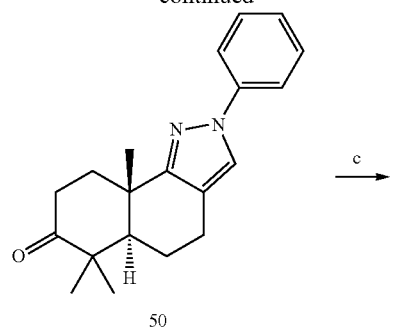
50
c →
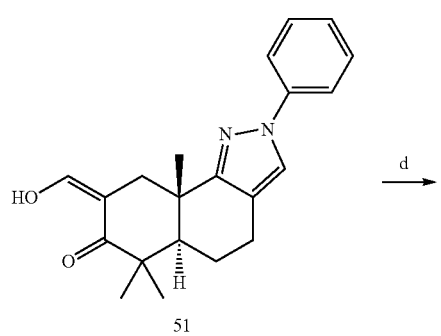
51
d →
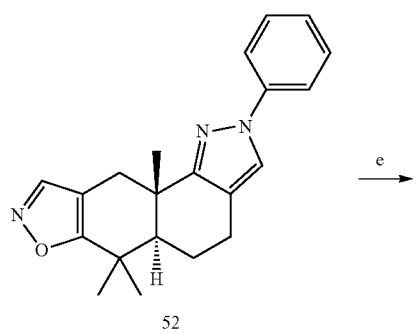
52
e →
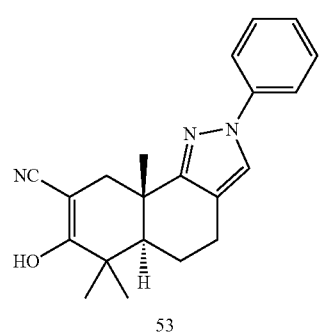
53
f →
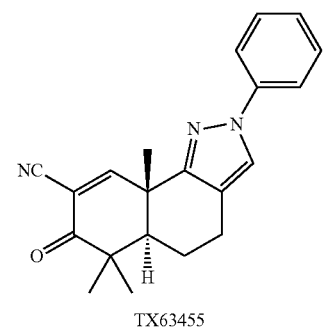
TX63455

-continued

Reagents and conditions pertaining to Scheme 8: (a) Phenylhydrazine-HCl, NaOAc—3H₂O, EtOH, 70° C., 12 h, 35% compound 51; 51% compound 52; (b) 1N HCl (aq), MeOH, RT, 12 h, 92%; (c) HCO₂Et, NaOMe, RT, 12 h, 97%; (d) NH₂OH—HCl, 50° C., 12 h, 91%; (e) NaOMe, 55° C., 5.5 h; RT, 12 h, 80%; (f) (i) 1,3-dibromo-5-5,-dimethylhydantoin, DMF, 0° C., time; (ii) pyridine, 50° C., 12 h, 3%.

Scheme 9:

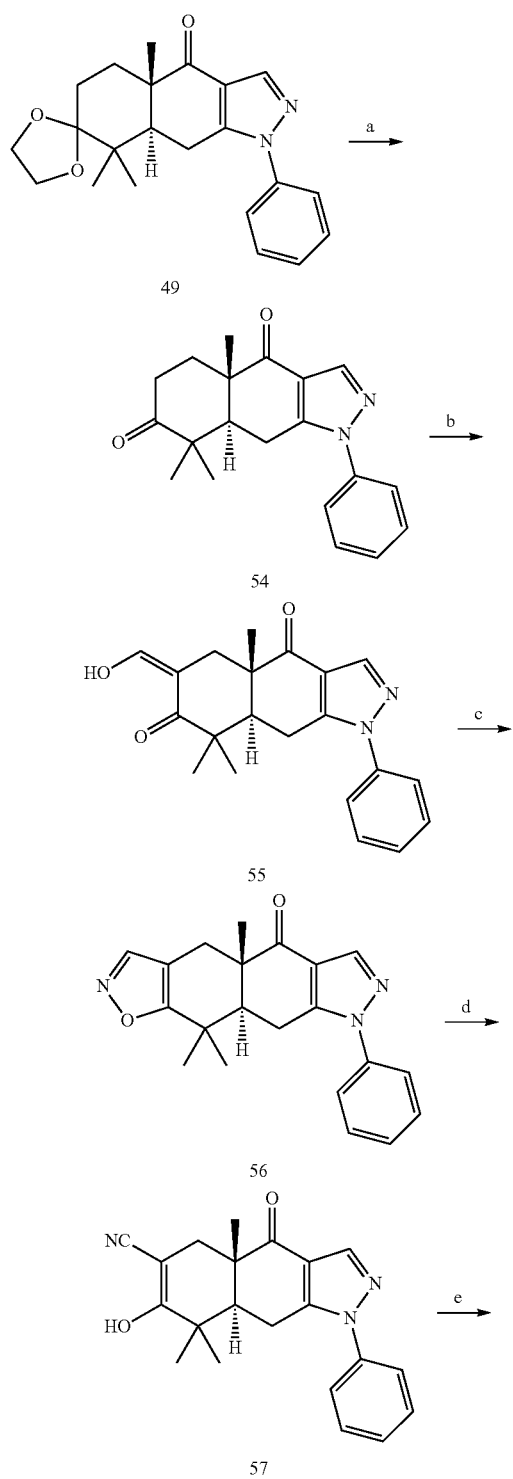

-continued

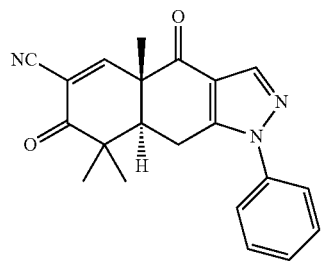

TX63456

Reagents and conditions pertaining to Scheme 9: (a) 1 N HCl (aq), MeOH, RT, 12 h, 92%; (b) HCO₂Et, NaOMe, RT, 12 h, 95%; (c) NH₂OH—HCl, 50° C., 12 h, 76% (d) NaOMe, 55° C., 5.5 h; RT, 12 h, 79%, (e) (i) 1,3-dibromo-5,5-dimethylhydantoin, DMF, 0° C., time; (ii) pyridine, 50° C., 12 h, 24%.

Scheme 10:

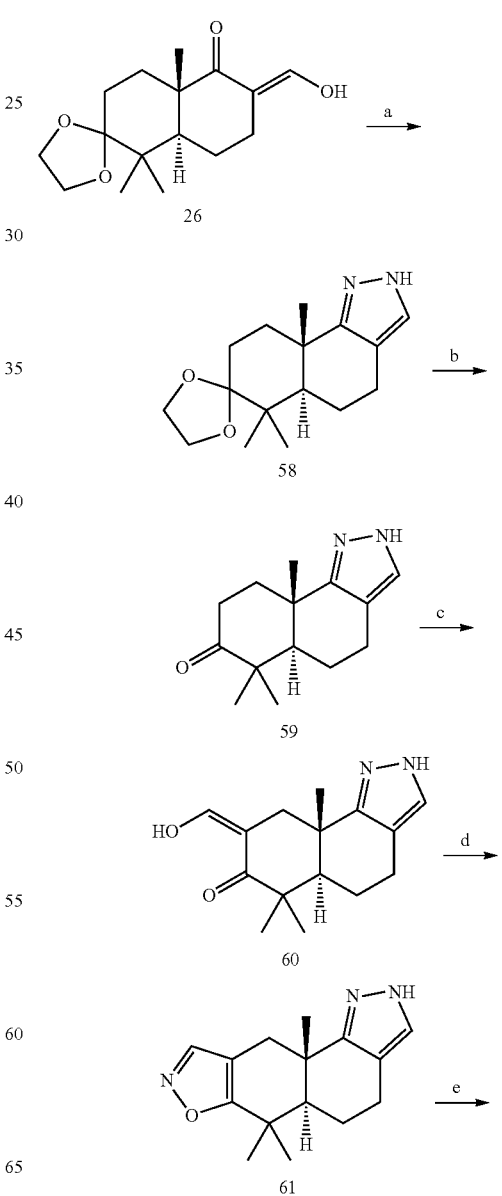

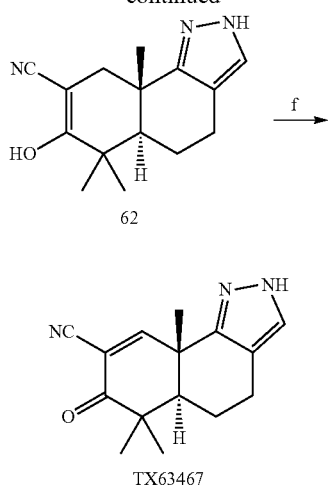
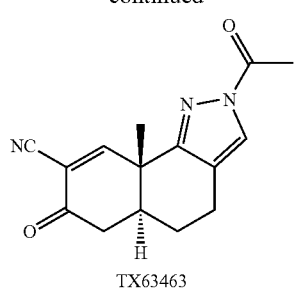
TX63463
Reagents and conditions pertaining to Scheme 12: (a) AcCl, NaHCO₃ (aq), THF, 0° C., 1 h, 24%.
Scheme 13:
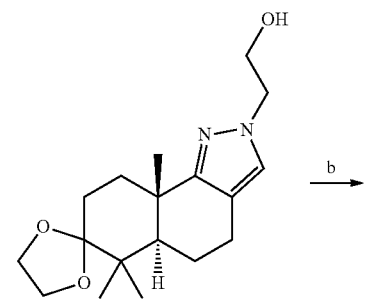
Reagents and conditions pertaining to Scheme 10:
(a) hydrazine, EtOH, r.t, 1 h; 60° C., 1 h, 82%;
(b) 1 N HCl (aq), MeOH, RT, 12 h, quantitative;
(c) HCO₂Et, NaOMe, RT, 12 h, 99%;
(d) NH₂OH—HCl, 50° C., 12 h, 97%
(e) NaOMe, 55° C., 5.5 h; RT, 12 h, 83%;
(f) (i) DDQ, benzene, reflux, 4.5 h, 43%
Scheme 11:
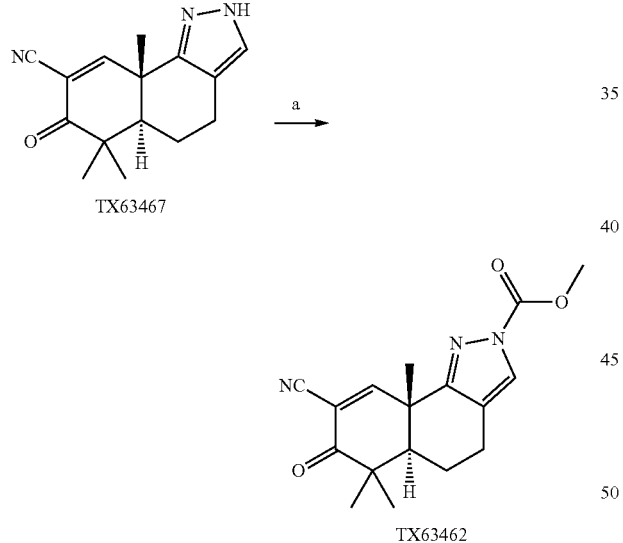
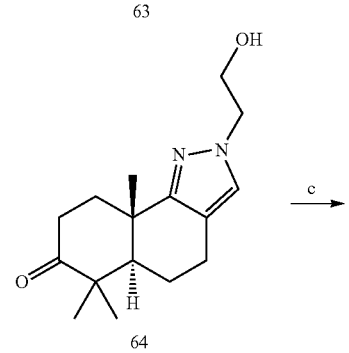
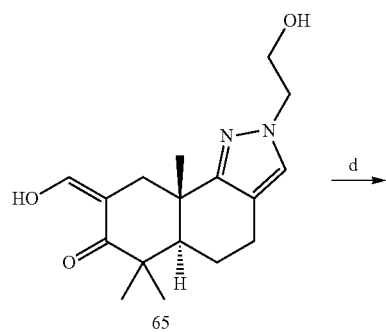
Reagents and conditions pertaining to Scheme 11: (a) AcCl, NaHCO₃ (aq), THF, 0° C., 1 h, 16%.
Scheme 12:
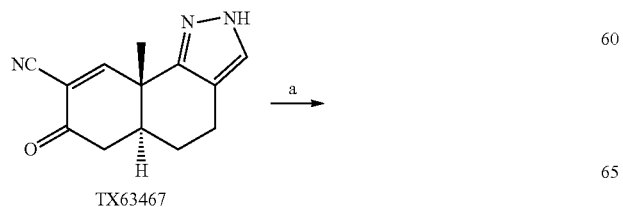

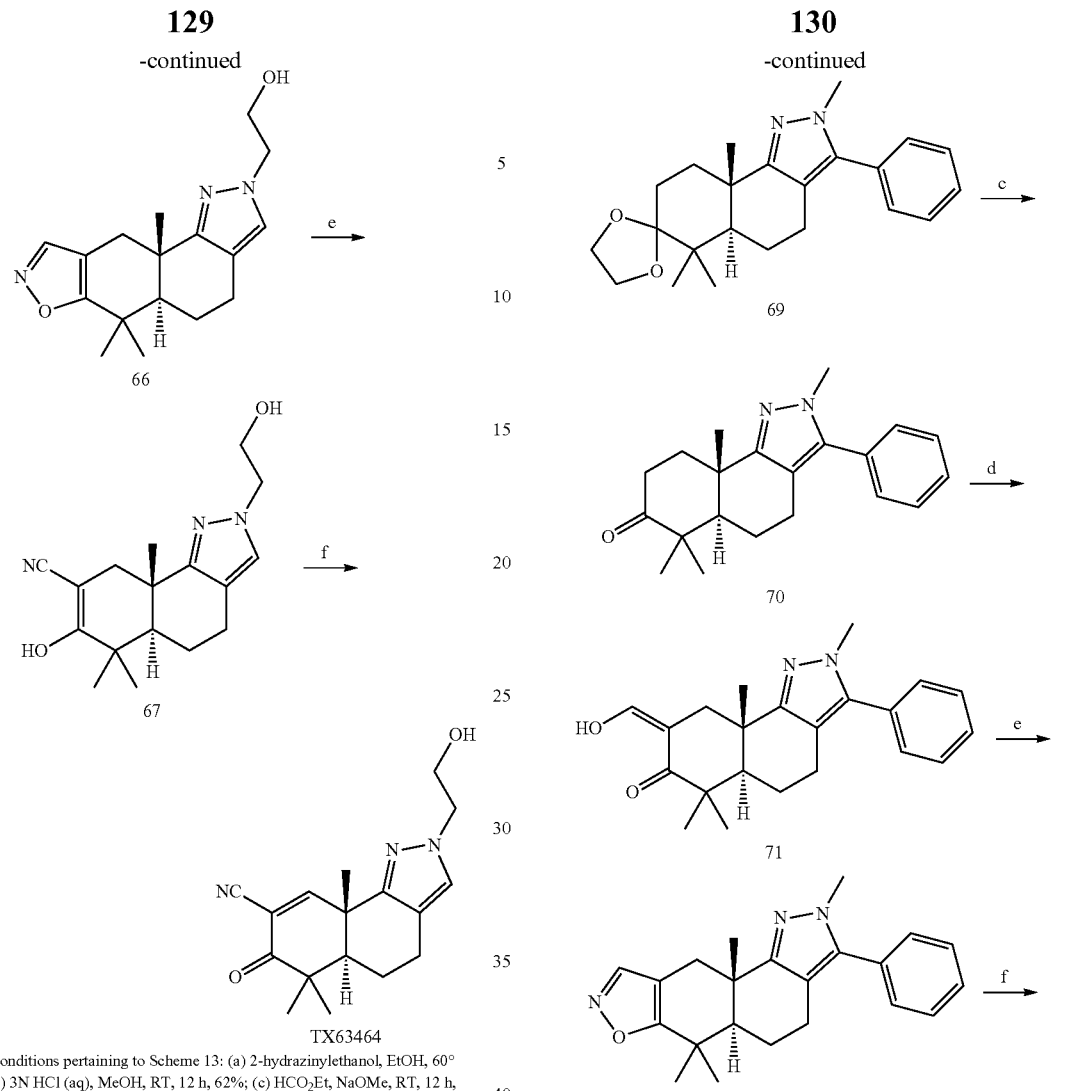

TX63464

Reagents and conditions pertaining to Scheme 13: (a) 2-hydrazinylethanol, EtOH, 60° C., 2 h, 93% (b) 3N HCl (aq), MeOH, RT, 12 h, 62%; (c) HCO$_2$Et, NaOMe, RT, 12 h, 91%; (d) NH$_2$OH—HCl, 50° C., 12 h, quantitative; (e) NaOMe, 50° C., 6 h, quantitative; (f) (i) pyridinium bromide perbromide, dioxane, RT, 2 h; (ii) pyridine, 50° C., 12 h, 5%.

Scheme 14:

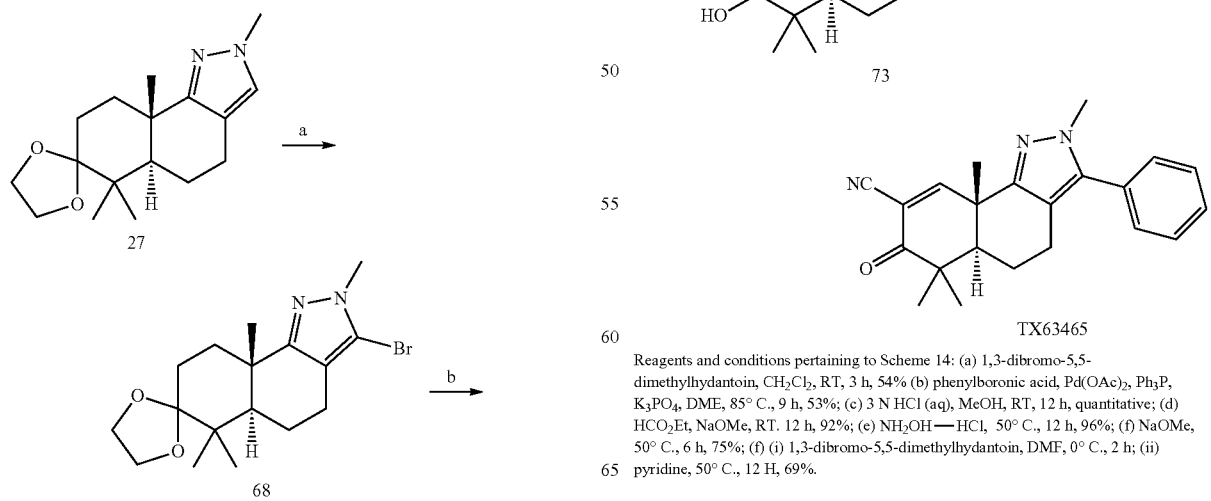

TX63465

Reagents and conditions pertaining to Scheme 14: (a) 1,3-dibromo-5,5-dimethylhydantoin, CH$_2$Cl$_2$, RT, 3 h, 54% (b) phenylboronic acid, Pd(OAc)$_2$, Ph$_3$P, K$_3$PO$_4$, DME, 85° C., 9 h, 53%; (c) 3 N HCl (aq), MeOH, RT, 12 h, quantitative; (d) HCO$_2$Et, NaOMe, RT. 12 h, 92%; (e) NH$_2$OH—HCl, 50° C., 12 h, 96%; (f) NaOMe, 50° C., 6 h, 75%; (i) 1,3-dibromo-5,5-dimethylhydantoin, DMF, 0° C., 2 h; (ii) pyridine, 50° C., 12 H, 69%.

Scheme 15:

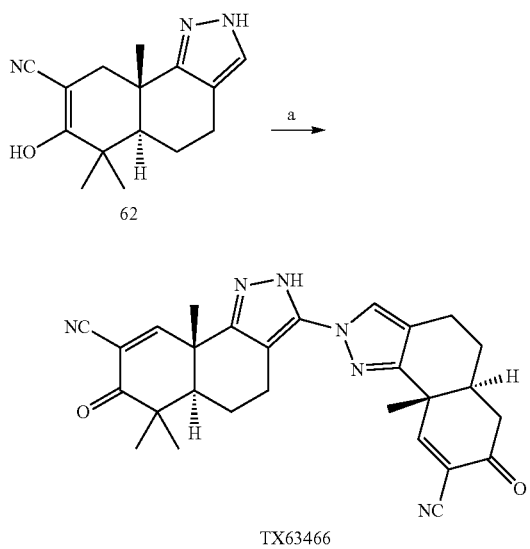

Reagents and conditions pertaining to Scheme 15 (a) (i) 1,3-dibromo-5,5-dimethylhydantoin, DMF, 0° C., 2 h; (ii) pyridine, 50° C., 12 h, 6%.

Scheme 16:

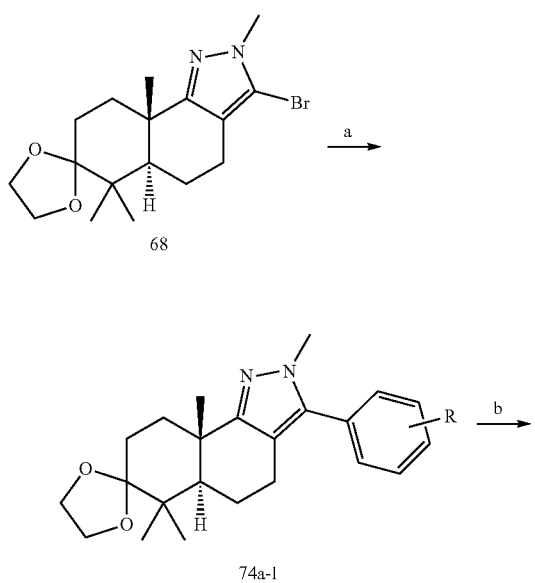

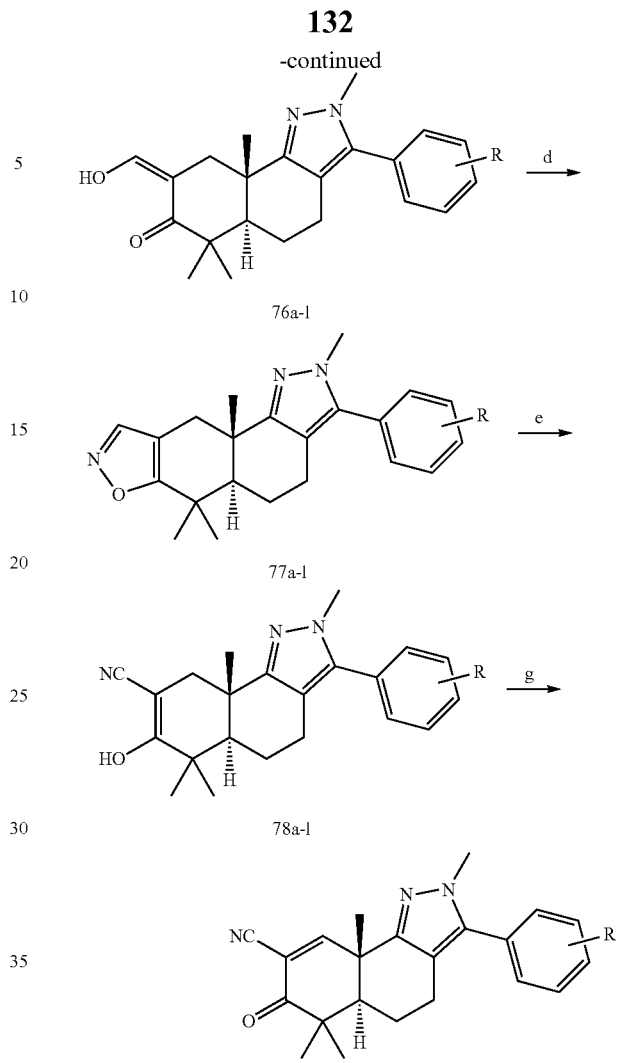

a: TX63485 R = 3-Cl
b: TX63486 R = 4-Cl
c. TX63491 R = 2-Cl
d. TX63506 R = 3-F
e. TX63507 R = 4-F
f: TX63508 R = 2-Me
g: TX63509 R = 2-OMe
h: TX63512 R = 3-Me
i: TX63513 R = 3-OMe
j: TX63514 R = 4-Me
k: TX63515 R = 4-OMe
l: TX63519 R = 2-F

Reagents and conditions pertaining to Scheme 16: (a) arylboronic acid, Pd(OAc)$_2$, Ph$_3$P, K$_3$PO$_4$, DME, 85° C., 9 h, yields; (b) N HCl (aq), MeOH, RT, 12 h, yields; (c) HCO$_2$Et, NaOMe, RT, 12 h, yields; (d) NH$_2$OH—HCl, 50° C., 12 h, yields; (e) NaOMe, 50° C., 6 h, yields; (f) (i) 1,3-dibromo-5,5-dimethylhydantoin, DMF, 0° C., 2 h; (ii) pyridine, 50° C., 12 h, yields.

Scheme 17:

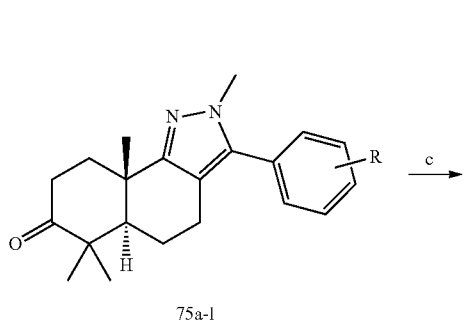

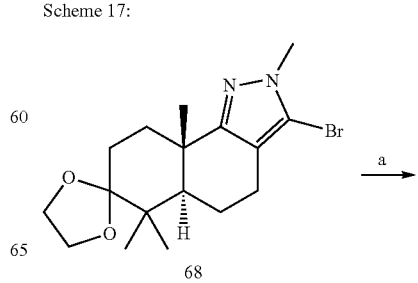

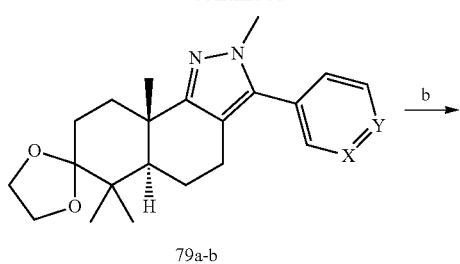
79a-b
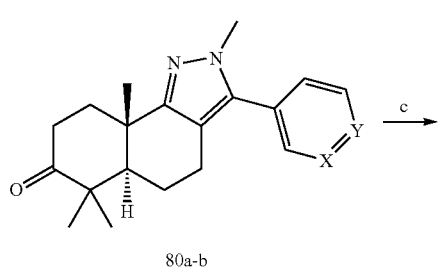
80a-b
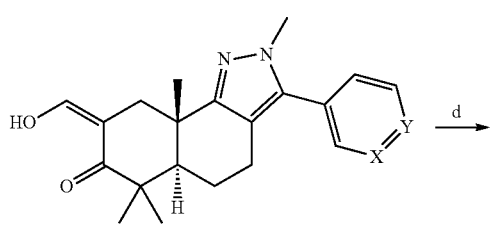
81a-b
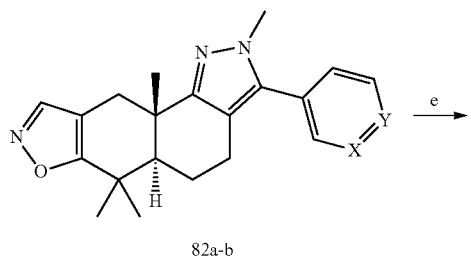
82a-b
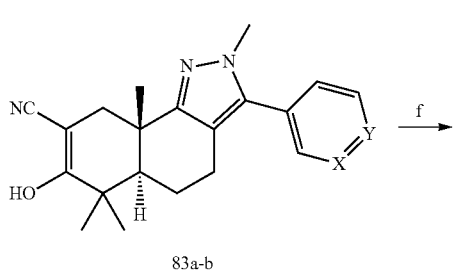
83a-b
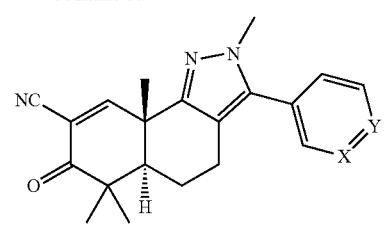
a: TX63503 X = N, Y = CH
b: TX63505 X = CH, Y = N
Reagents and conditions pertaining to Scheme 17:
(a) 3- or 4-pyridinylboronic acid, Pd(OAc)₂, Ph₃P, K₃PO₄, DME, 85° C., 9 h, 83a: 26%, 83b: 49%;
(b) 3 N HCl (aq), MeOH, RT, 12 h, 84a: 97%, 84b: quantitative;
(c) HCO₂Et, NaOMe, RT, 12 h, 85a: quantitative, 85b: quantitative;
(d) NH₂OH—HCl, 50° C., 12 h, 86a: quantitative, 86b: quantitative;
(e) NaOMe, 50° C., 6 h, 87a: quantitative, 87b: quantitative;
(f) (i) Br₂, DMF, 0° C., 2 h; (ii) pyridine, 50° C., 12 h, TX63503: 31%, TX63505: 27%.
Scheme 18(a):
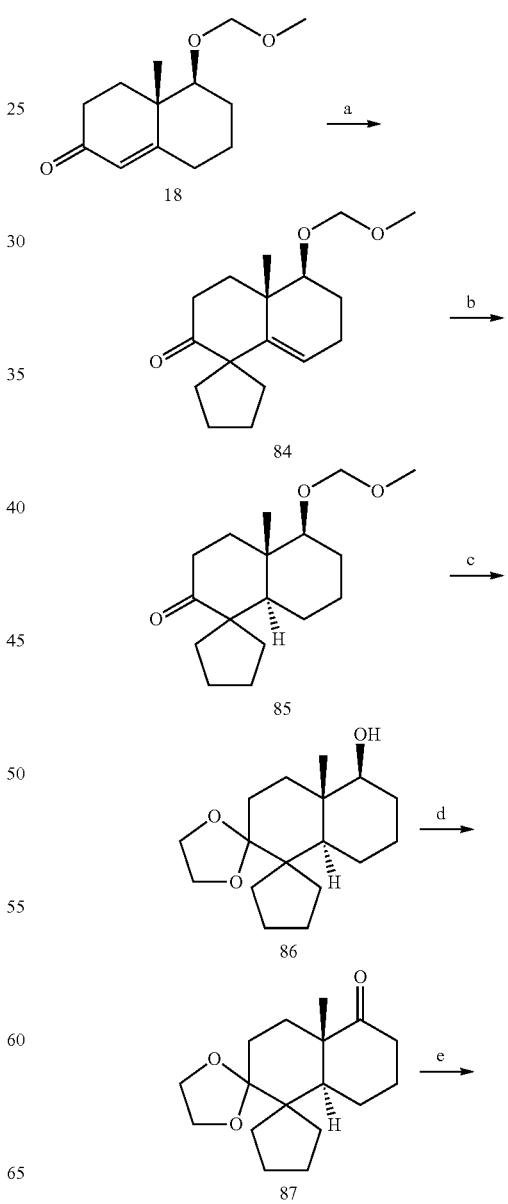

135
-continued

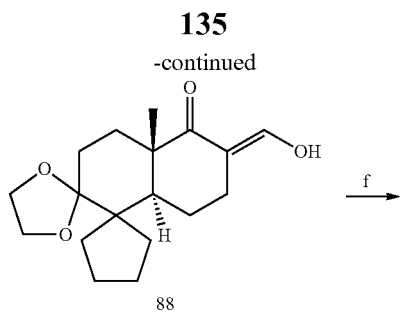
88

Scheme 18(b):

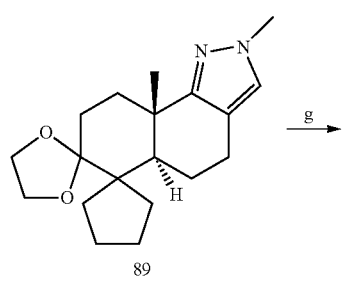
89

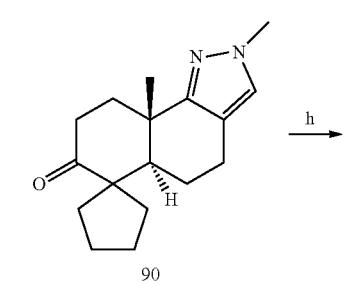
90

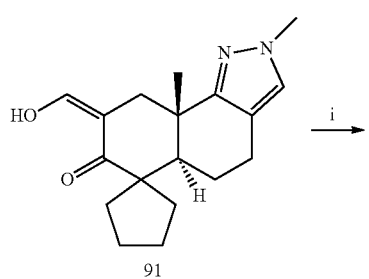
91

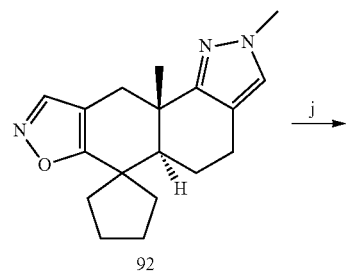
92

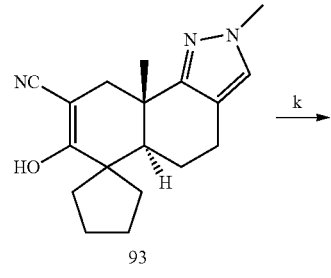
93

136
-continued

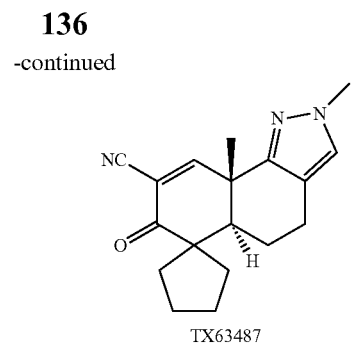
TX63487

Reagents and conditions pertaining to Schemes 18(a) & (b): (a) KOt-Bu, t-BuOH, 1,4-dibromobutane, 45° C., 78%; (b) H₂, 20% Pd(OH)₂, EtOH, 31%; (c) Ethylene glycol, p-TsOH•H₂O, toluene, —H₂O, quantitative; (d) PDC, 45° C., 73%; (e) HCO₂Et, NaOMe, RT, 12 h, 99%; (f) MeNHNH₂, EtOH, RT → 60° C., 75%; (g) 1 N HCl (aq), MeOH, RT, 12 h, quantitative; (h) HCO₂Et, NaOMe, RT, 12 h quantitative; (i) NH₂OH—HCl, 50° C., 12 h, 96%; (j) NaOMe, 50° C., 6 h, quantitative; (k) (i) 1,3-dibromo-5,5-dimethylhydantoin, DMF, 0° C., 2 h; (ii) pyridine, 50° C., 12 h, 38%.

Scheme 19:

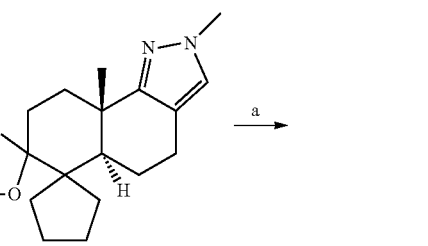
89

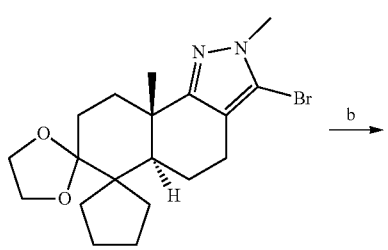
94

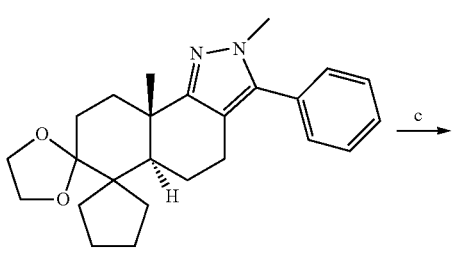
95

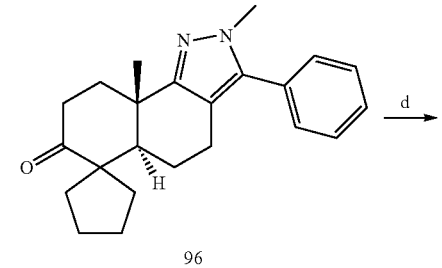
96

137
-continued
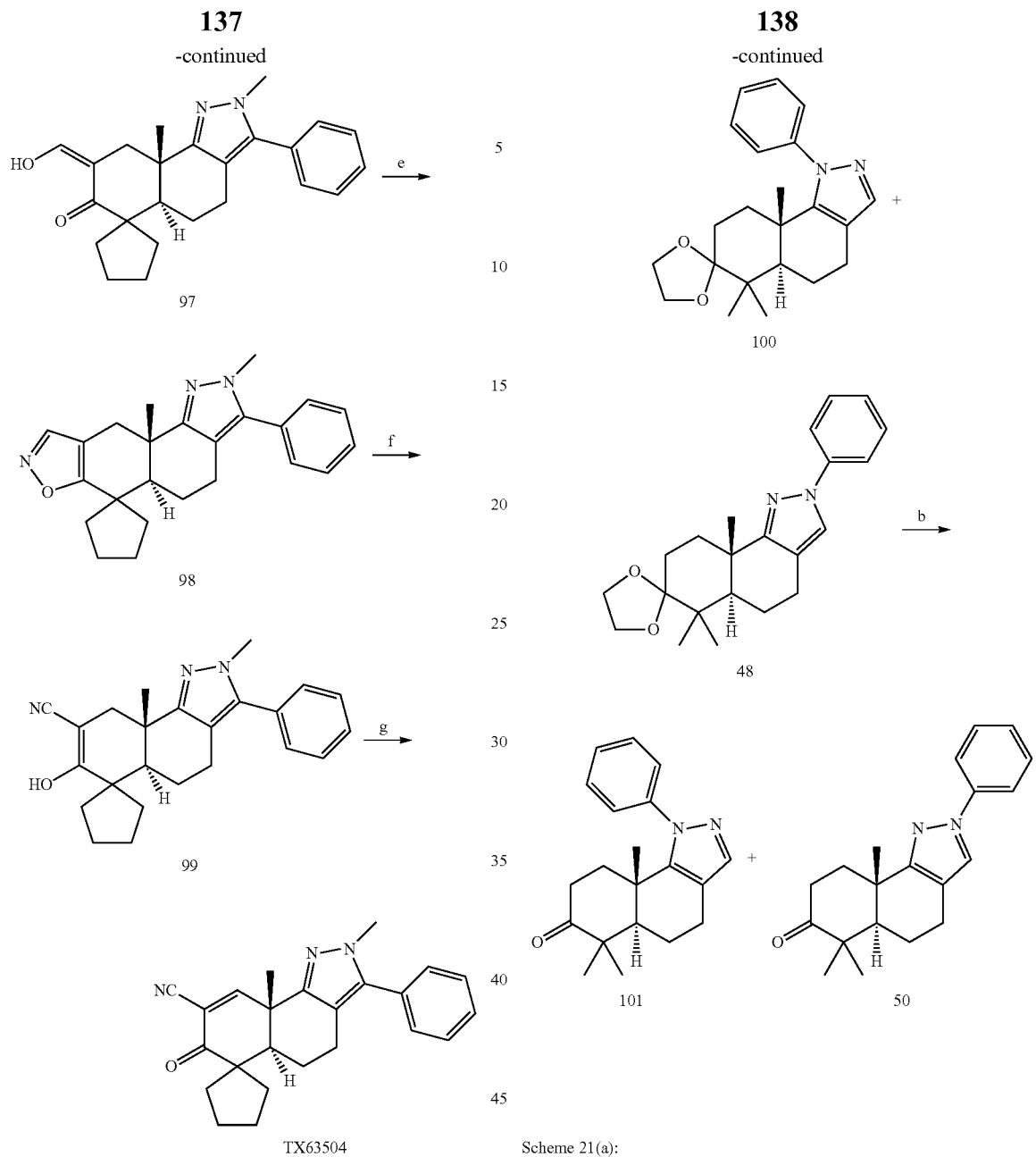
TX63504
Reagents and conditions pertaining to Scheme 19: (a) 1,3-dibromo-5,5-dimethylhydantoin, CH₂Cl₂, RT, 2 h, 62%; (b) phenylboronic acid, Pd(OAc)₂, Ph₃P, K₃PO₄, DME, 85° C., 12 h, 73%; (c) 1 N HCl (aq), MeOH, RT, 12 h, quantitative; (d) HCO₂Et, NaOMe, RT, 12 h, 47%; (e) NH₂OH—HCl, 50° C., 12 h, quantitative; (f) NaOMe, 50° C., 6 h, quantitative; (g) (i) 1,3-dibromo-5,5-dimethylhydantoin, DMF, 0° C.; (ii) pyridine, 50° C., 12 h, 37%.
Scheme 20(a):
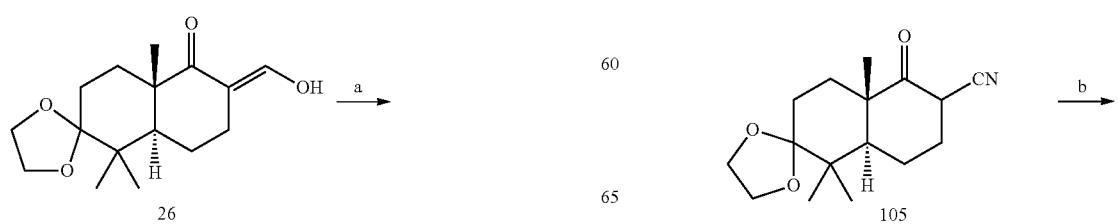
Scheme 21(a):
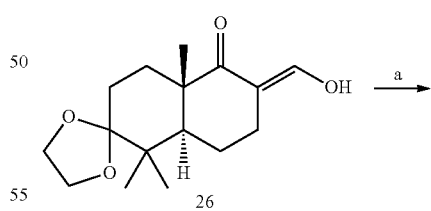

139
-continued
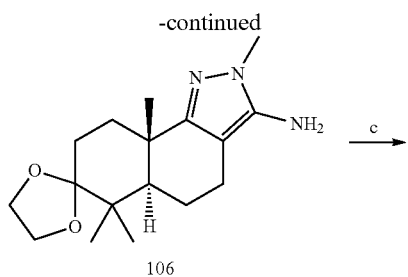
106
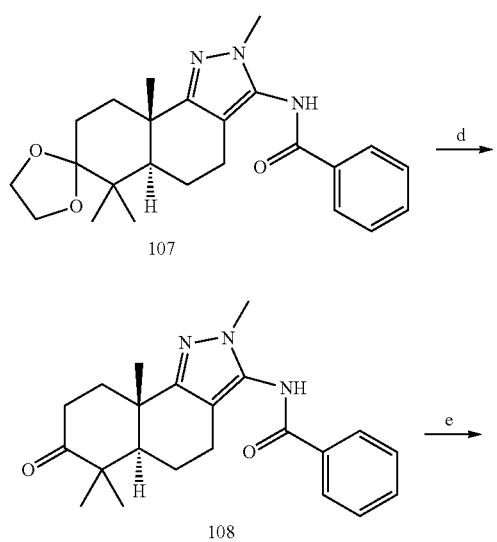
107
108
Scheme 21(b):
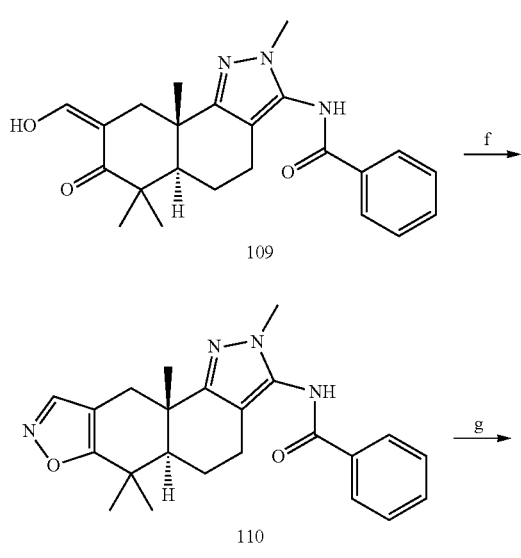
109
110
111
140
-continued
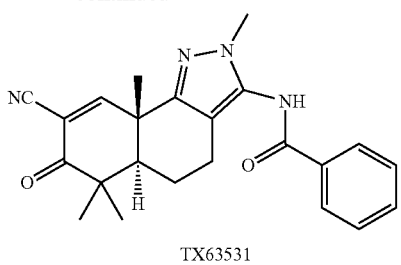
TX63531
Reagents and conditions pertaining to Schemes 21(a) and (b): (a) (i) NH₂OH—HCl, TEA, EtOH, H₂O, RT, 16 h; (ii) NaOMe, MeOH, THF, RT; (b) MeNHNH₂, EtOH,, reflux, 16 hr; (c) PhCOCl, TEA, EtOAc; (d) 3 N HCl (aq), THF, RT; (e) HCO₂Et, NaOMe, RT, 16 hr; (f) NH₂OH—HCl, 50° C., 12 h; (g) NaOMe, 50° C., 6 h, (h) (i) 1,3-dibromo-5,5-dimethylhydantoin, DMF, 0° C., 2 h; (ii) pyridine, 50° C., 12h.
Scheme 22(a):
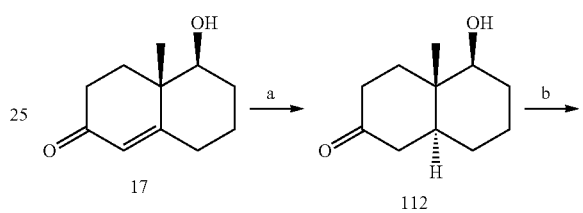
17          112
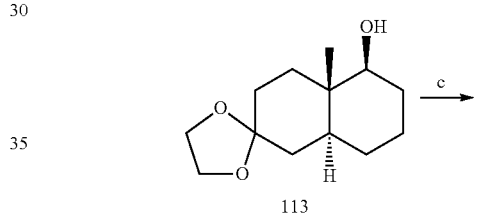
113
114
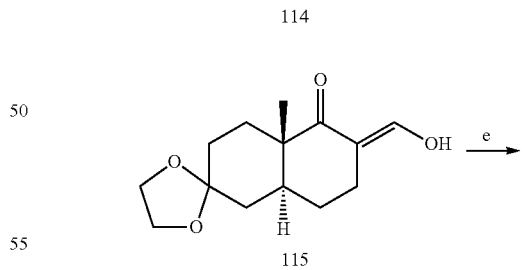
115
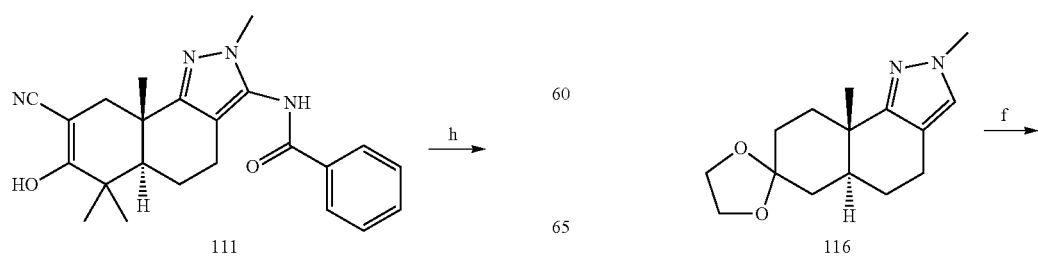
116

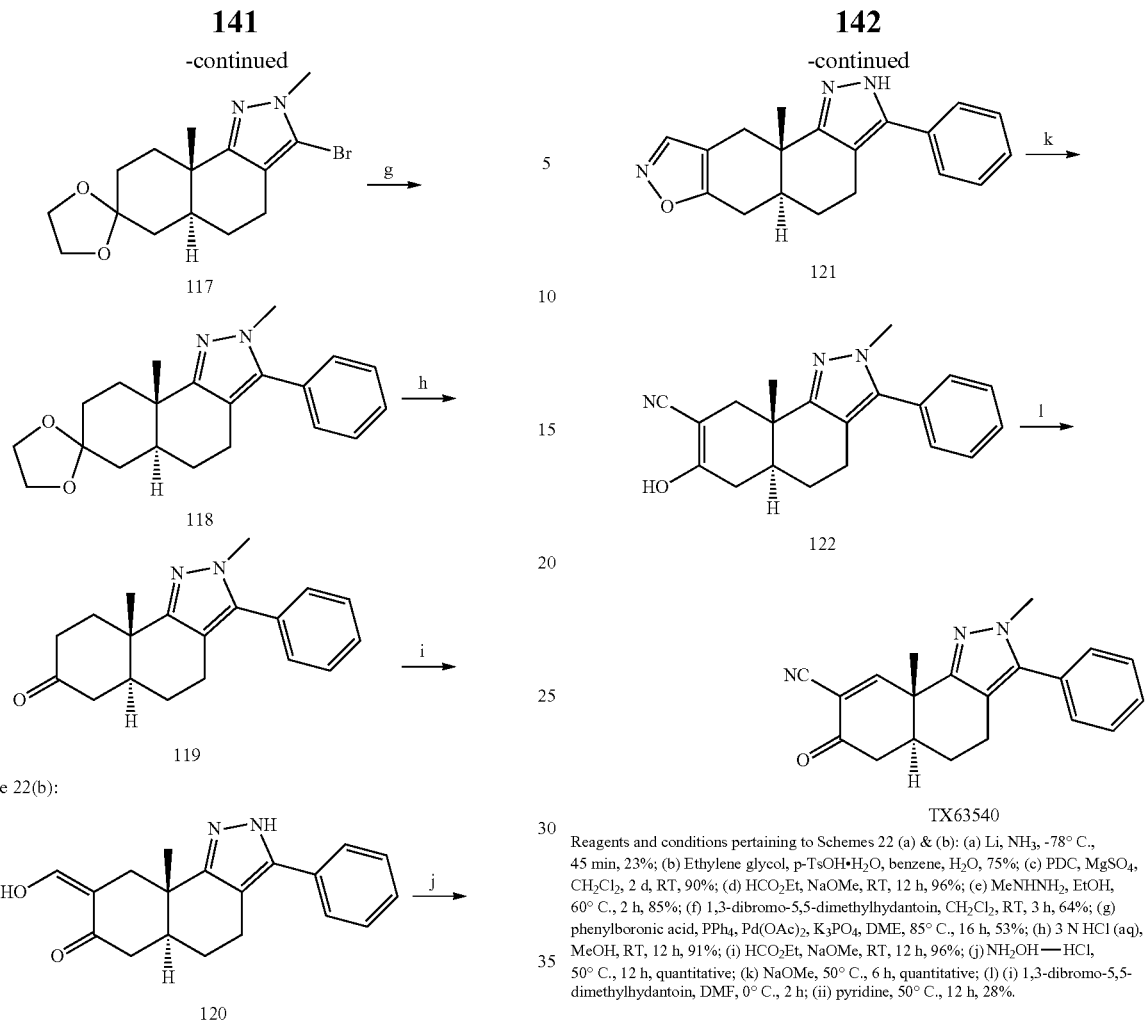

Scheme 22(b):

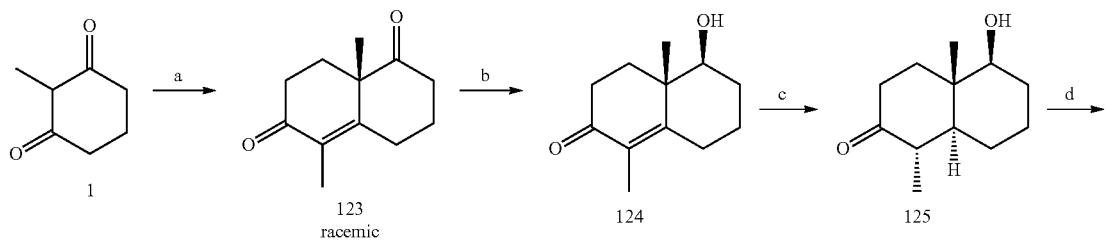

Reagents and conditions pertaining to Schemes 22 (a) & (b): (a) Li, NH₃, -78° C., 45 min, 23%; (b) Ethylene glycol, p-TsOH•H₂O, benzene, H₂O, 75%; (c) PDC, MgSO₄, CH₂Cl₂, 2 d, RT, 90%; (d) HCO₂Et, NaOMe, RT, 12 h, 96%; (e) MeNHNH₂, EtOH, 60° C., 2 h, 85%; (f) 1,3-dibromo-5,5-dimethylhydantoin, CH₂Cl₂, RT, 3 h, 64%; (g) phenylboronic acid, PPh₄, Pd(OAc)₂, K₃PO₄, DME, 85° C., 16 h, 53%; (h) 3 N HCl (aq), MeOH, RT, 12 h, 91%; (i) HCO₂Et, NaOMe, RT, 12 h, 96%; (j) NH₂OH—HCl, 50° C., 12 h, quantitative; (k) NaOMe, 50° C., 6 h, quantitative; (l) (i) 1,3-dibromo-5,5-dimethylhydantoin, DMF, 0° C., 2 h; (ii) pyridine, 50° C., 12 h, 28%.

Scheme 23(a):

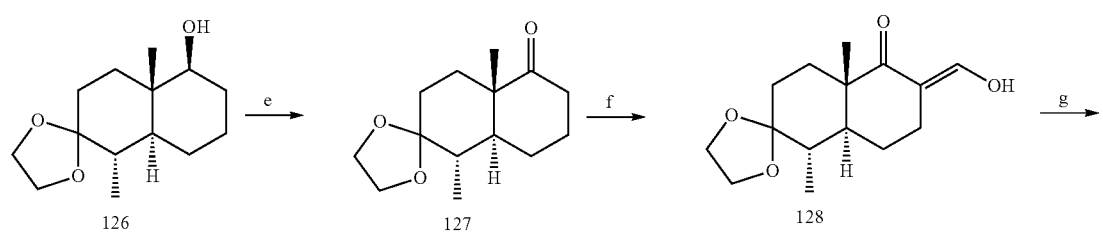

143

-continued

144

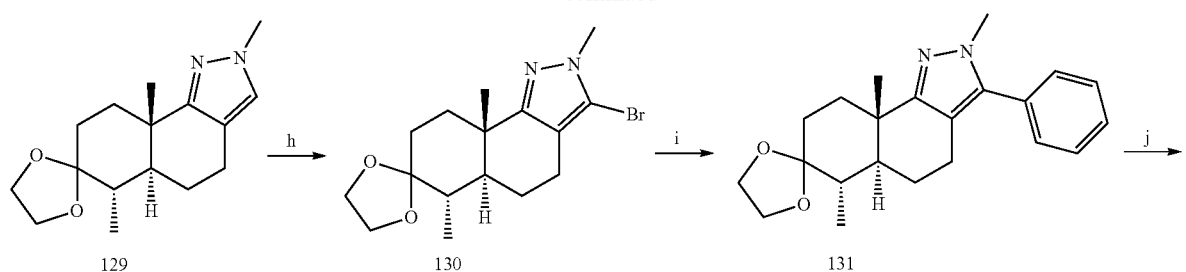

Scheme 23(b):

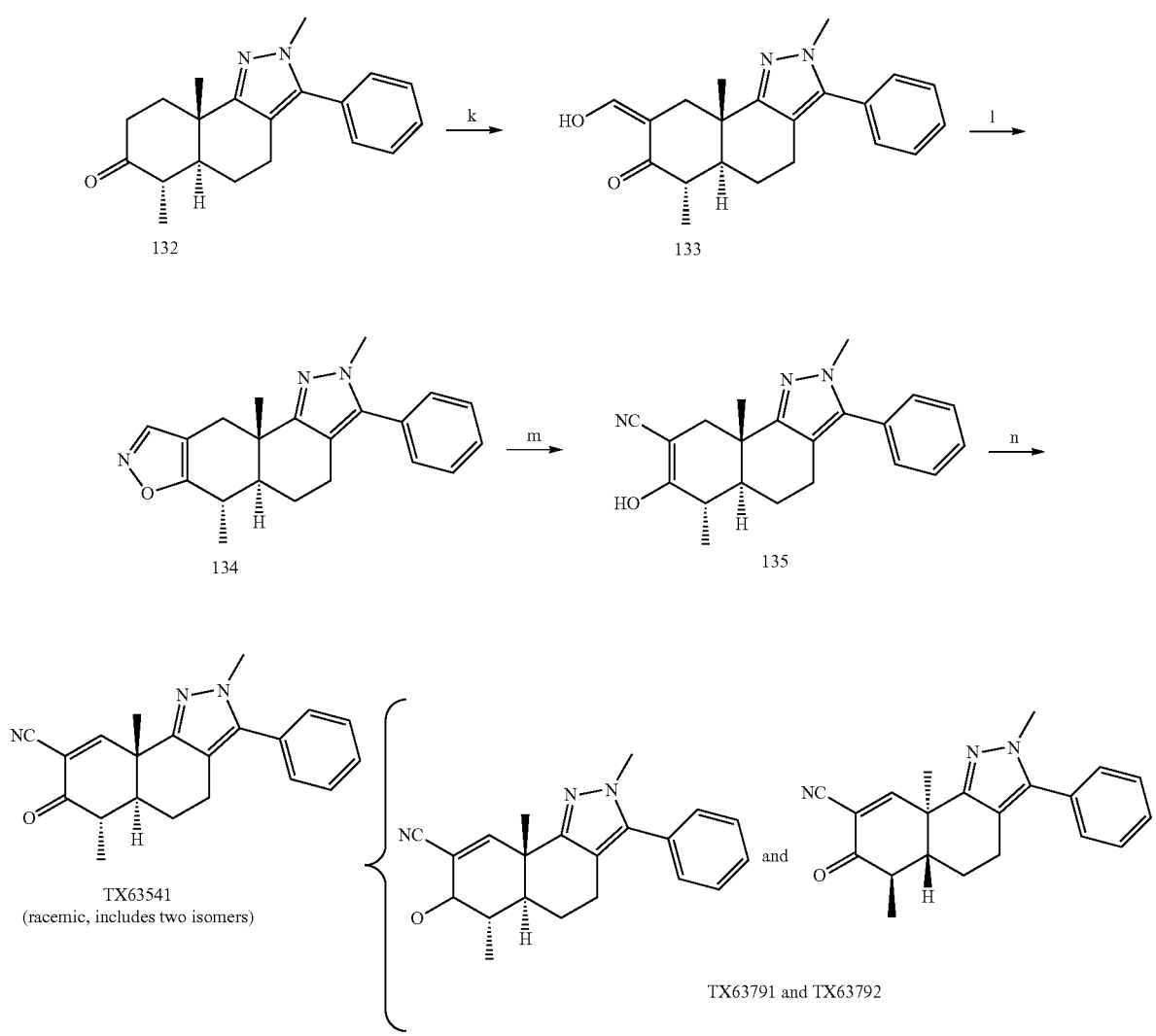

Reagents and conditions pertaining to Scheme 23(a) and (b): (a) (i) Ethyl vinyl ketone, Et$_3$N, MeCN, RT, 12 h; (ii) pyrrolidine, benzene, —H$_2$O, 48 h, 41%; (b) NaBH$_4$, EtOH, 0° C., 45 min, 56%; (c) Li, NH$_3$, -78° C., 45 min, 28%; (d) ethylene glycol, p-TsOH•H$_2$O, benzene, —H$_2$O, 62%; (e) PDC, MgSO$_4$, CH$_2$Cl$_2$, 2 d, RT, 92%; (f) HCO$_2$Et, NaOMe, RT, 12 h, quantitative; (g) MeNHNH$_2$, EtOH, 60° C., 2 h, 79%; (h) 1,3-dibromo-5,5-dimethylhydantoin, CH$_2$Cl$_2$, RT, 3 h, 74%; (i) phenylboronic acid, PPh$_4$, Pd(OAc)$_2$, K$_3$PO$_4$, DME, 85° C., 16 h, 63%; (j) 3 N HCl (aq), MeOH, RT, 12 h, quantitative; (k) HCO$_2$Et, NaOMe, RT, 12 h, 95%; (l) NHOH—HCl, 50° C., 12 h, quantitative; (m) NaOMe, 50° C., 6 h, quantitative; (n) (i) 1,3-dibromo-5,5-dimethylhydantoin, DMF, 0° C., 2 h; (ii) pyridine, 50° C., 12 h, 33%.

Scheme 24:
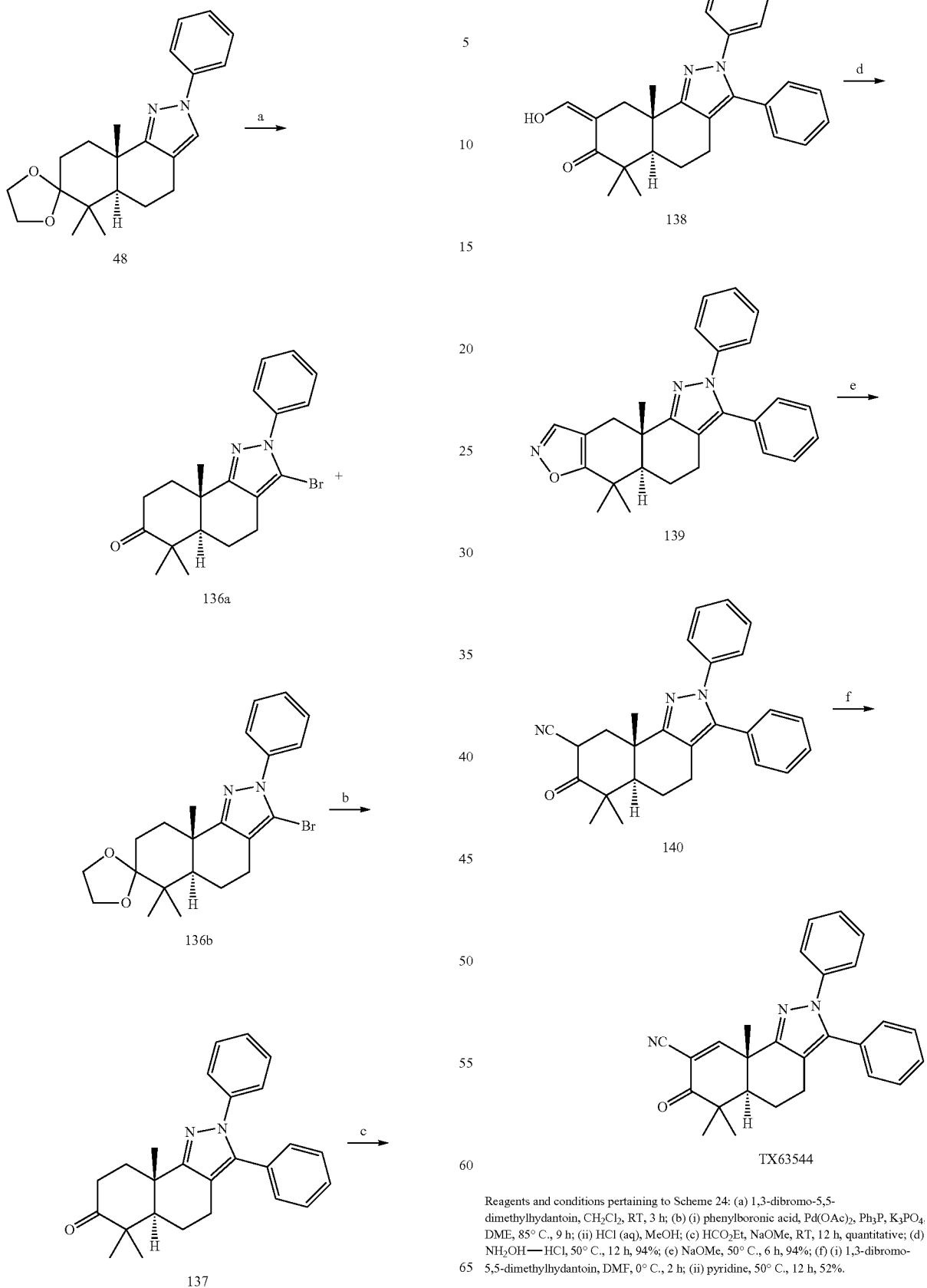
Reagents and conditions pertaining to Scheme 24: (a) 1,3-dibromo-5,5-dimethylhydantoin, $CH_2Cl_2$, RT, 3 h; (b) (i) phenylboronic acid, $Pd(OAc)_2$, $Ph_3P$, $K_3PO_4$, DME, 85° C., 9 h; (ii) HCl (aq), MeOH; (c) $HCO_2Et$, NaOMe, RT, 12 h, quantitative; (d) $NH_2OH$—HCl, 50° C., 12 h, 94%; (e) NaOMe, 50° C., 6 h, 94%; (f) (i) 1,3-dibromo-5,5-dimethylhydantoin, DMF, 0° C., 2 h; (ii) pyridine, 50° C., 12 h, 52%.

Scheme 25:
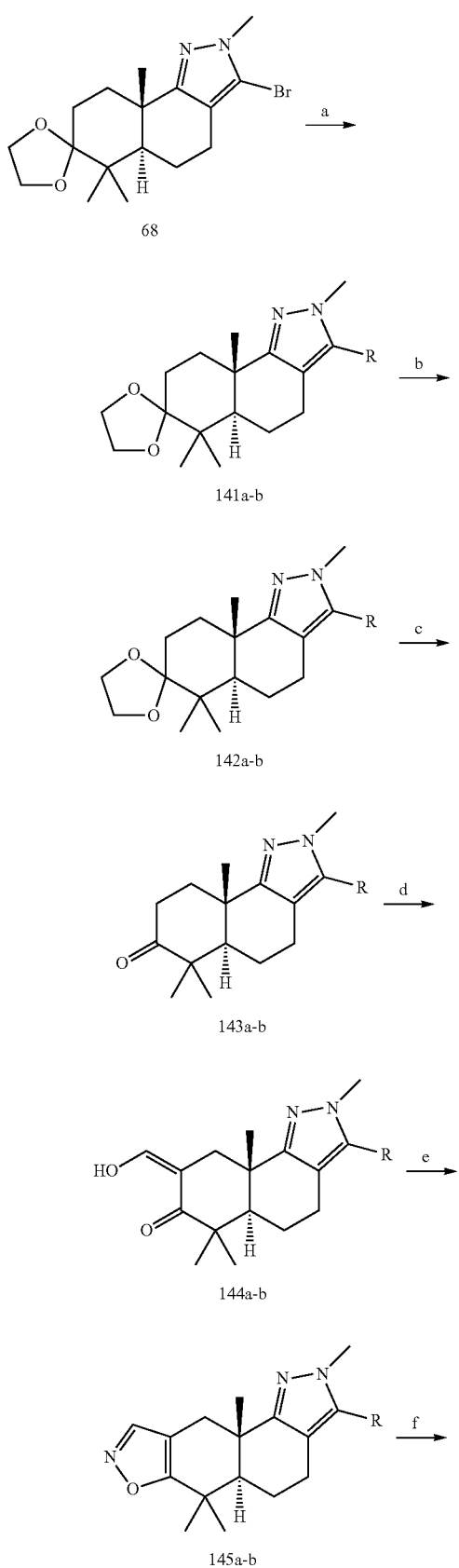
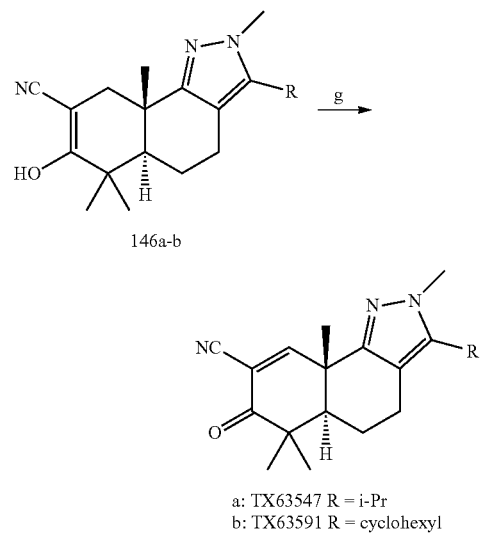
a: TX63547 R = i-Pr
b: TX63591 R = cyclohexyl
Reagents and conditions pertaining to Scheme 25: (a) isopropenyl pinacol boronate, Pd(II), 16 h, 141a: 41%, 141b: 40%; (b) H$_2$, 10% Pd/C, 142a: 99%, 141b: 93%; (c) 3 N HCl (aq), MeOH, RT, 12 h, 142a: 99%, 141b: 93%; (d) HCO$_2$Et, NaOMe, RT, 12 h, 144a: quantitative, 144b: quantitative; (e) NH$_2$OH—HCl, 50° C., 12 h, 145a: quantitative, 145b: 87%; (f) NaOMe, 50° C., 6 h, 146a: 99% 141b: 97%; (g) (i) 1,3-dibromo-5,5-dimethylhydantoin, DMF, 0° C., 2 h; (ii) pyridine, 50° C., 12 h, TX63547: 15% TX63591: 13%.
Scheme 26:
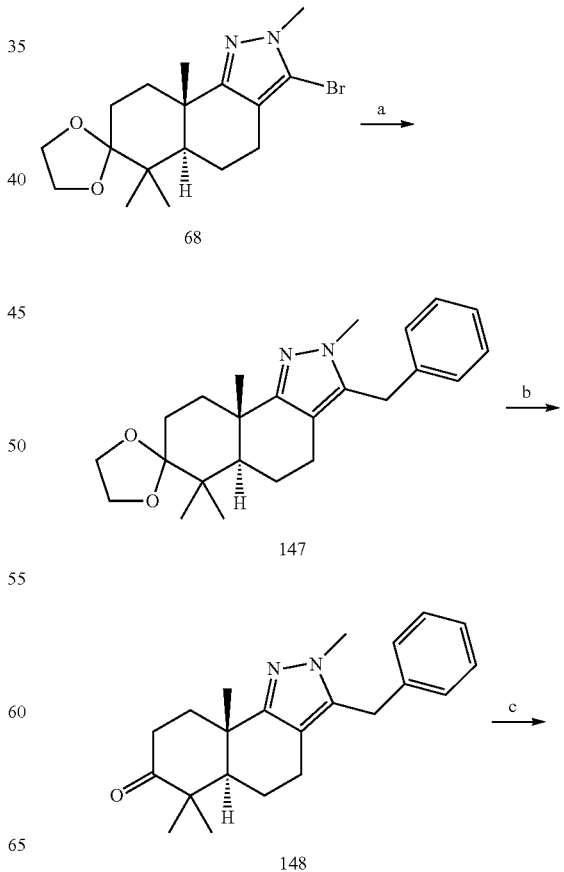

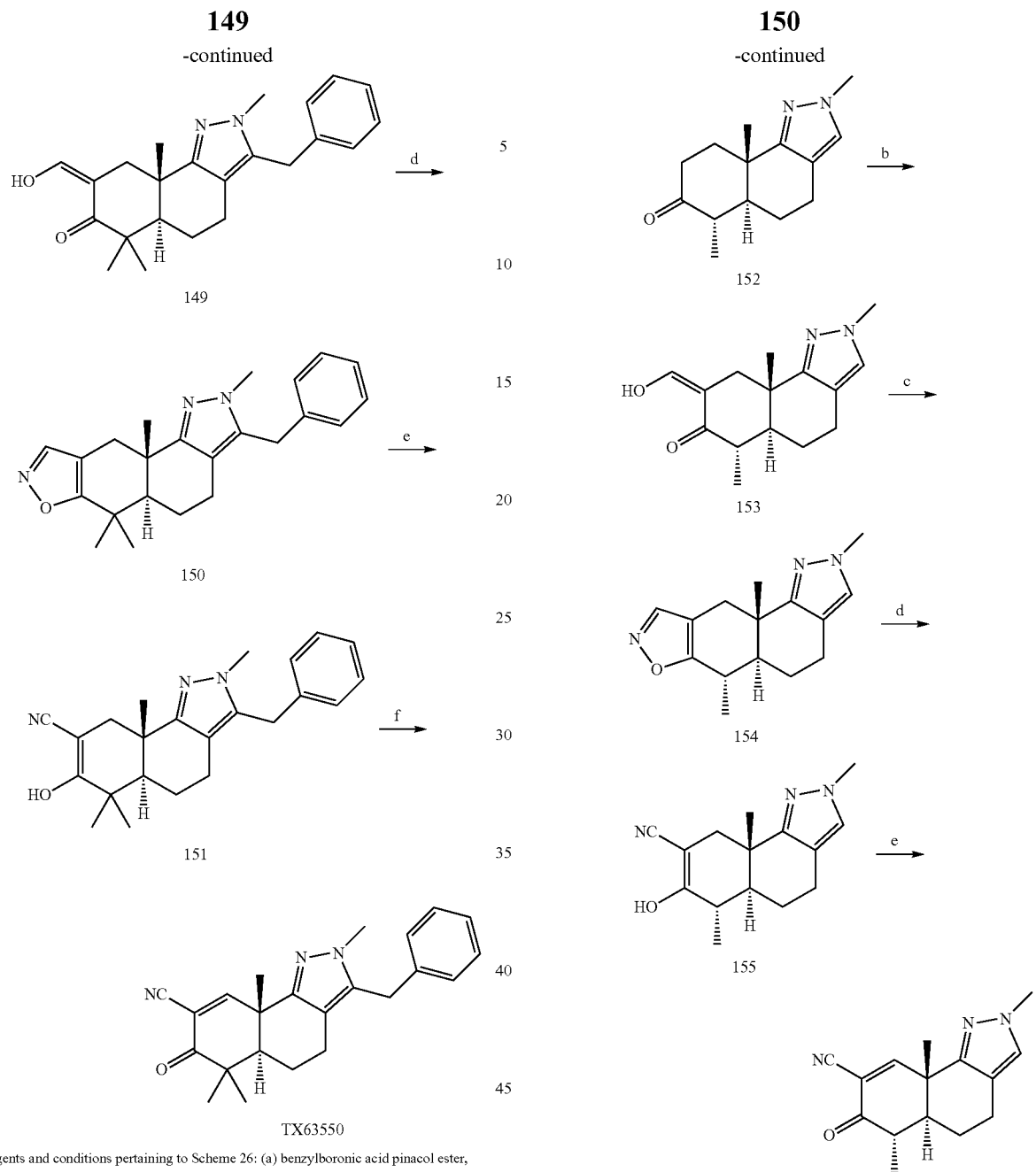
Scheme 27:
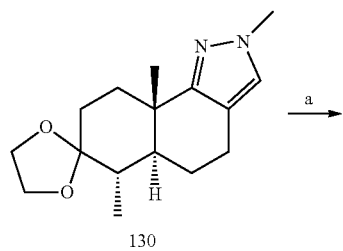
Scheme 28(a):
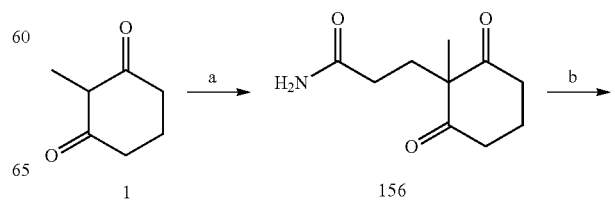

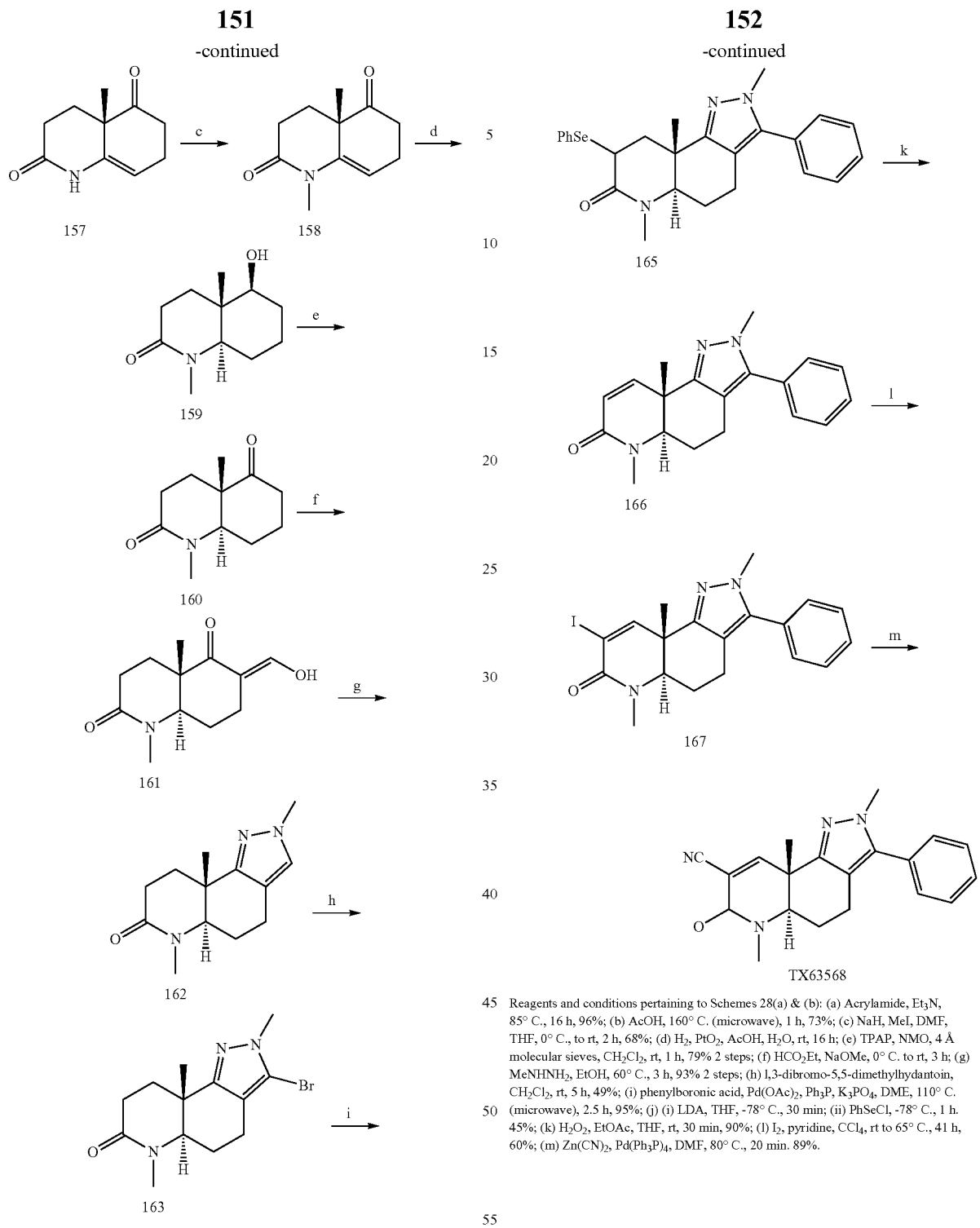

153
-continued
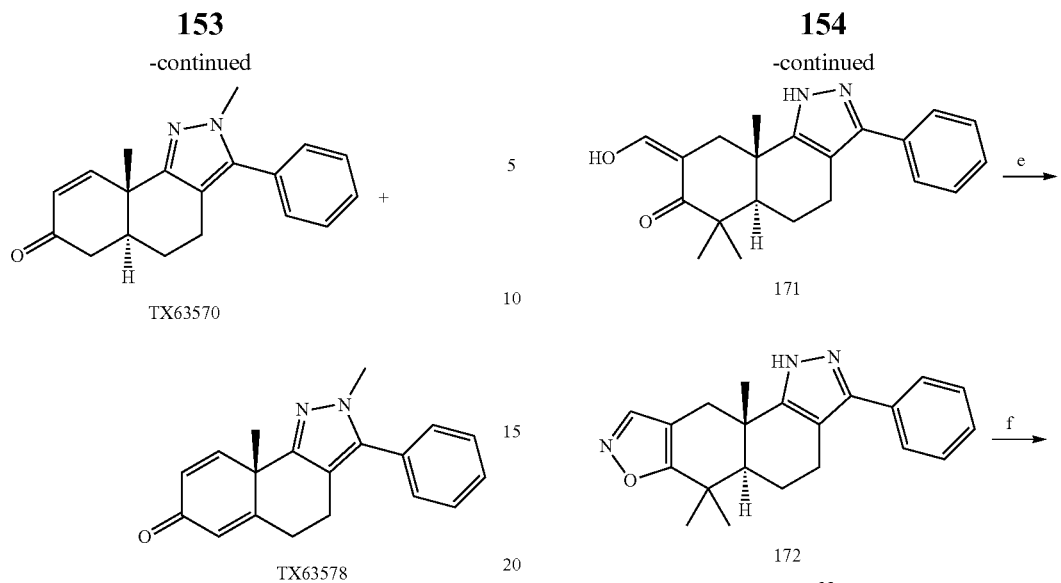
TX63570
TX63578
Reagents and conditions pertaining to Scheme 29: (a) IBX.
Scheme 30:
154
-continued
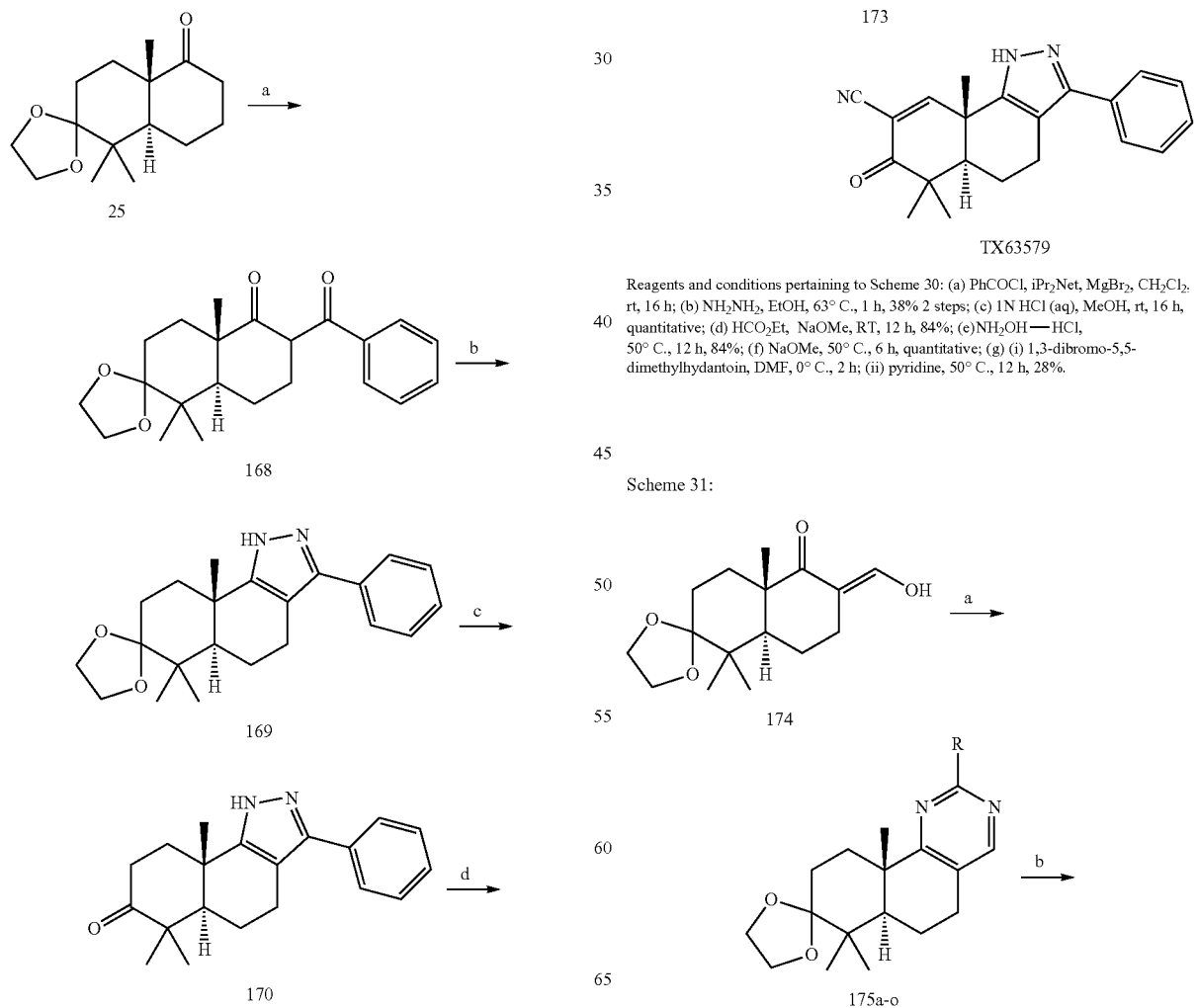
171
172
173
TX63579
Reagents and conditions pertaining to Scheme 30: (a) PhCOCl, iPr$_2$Net, MgBr$_2$, CH$_2$Cl$_2$, rt, 16 h; (b) NH$_2$NH$_2$, EtOH, 63° C., 1 h, 38% 2 steps; (c) 1N HCl (aq), MeOH, rt, 16 h, quantitative; (d) HCO$_2$Et, NaOMe, RT, 12 h, 84%; (e)NH$_2$OH—HCl, 50° C., 12 h, 84%; (f) NaOMe, 50° C., 6 h, quantitative; (g) (i) 1,3-dibromo-5,5-dimethylhydantoin, DMF, 0° C., 2 h; (ii) pyridine, 50° C., 12 h, 28%.
Scheme 31:
168
169
170
174
175a-o

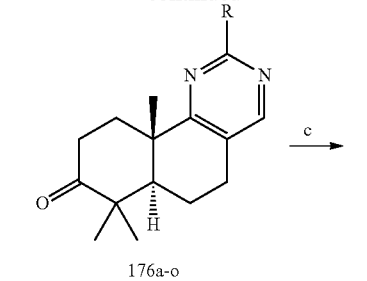
176a-o

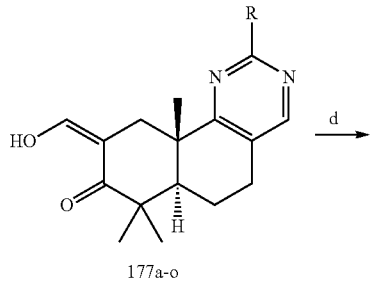
177a-o

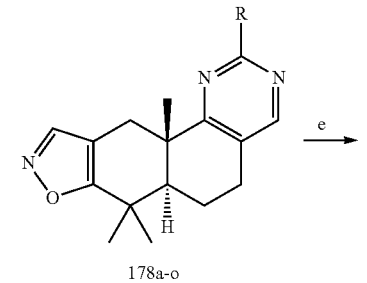
178a-o

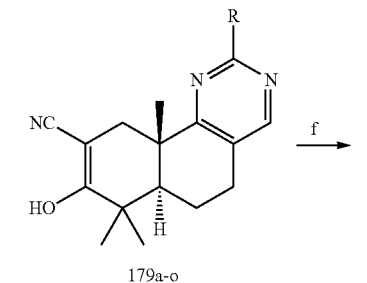
179a-o

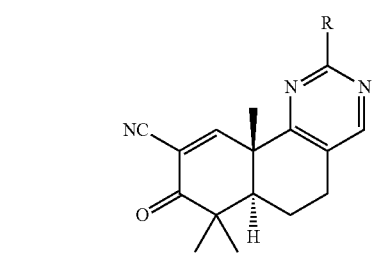

a: TX63528 R = OMe   i: TX63612 R = Ph(2-Cl)
b: TX63468 R = Me    j: TX63583 R = Ph(3-Me)
c: TX63534 R = i-Pr  k: TX63590 R = Ph(4-Me)
d: TX63542 R = H     l: TX63628 R = 4-thiazole(2-Me)
e: TX63552 R = Ph    m: TX63586 R = 3-pyridyl
f: TX63561 R = t-Bu  n: TX63636 R = 4-pyridyl
g: TX63567 R = CF₃   o: TX63641 R = 2-pyridyl
h: TX63582 R = Ph(4-Cl)

Reagents and conditions pertaining to Schemes 31: (a) substituted amidine, piperidine, iPrOH, 85° C., sealed tube, 2 d; (b) 3N HCl (aq); (b) HCO₂Et, NaOMe, RT, 16 h; (c) NH₂OH—HCl;  50° C., 16 h; (d) NaOMe, 50° C., 6 h; (e) (i) 1,3-dibromo-5,5-dimethylhydantoin, DMF, 0° C., 2 h; (ii) pyridine, 50° C., 16 h.

Scheme 32(a):

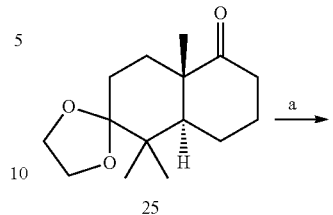
25

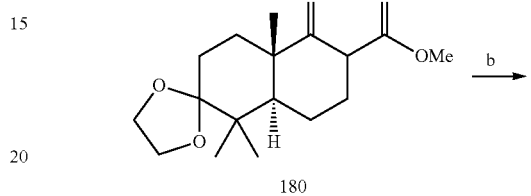
180

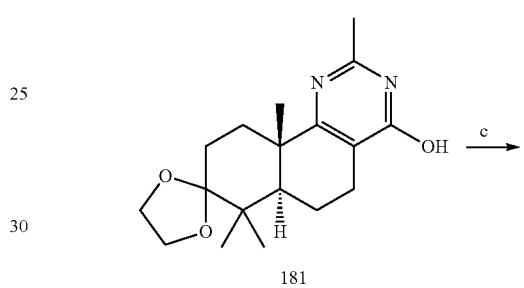
181

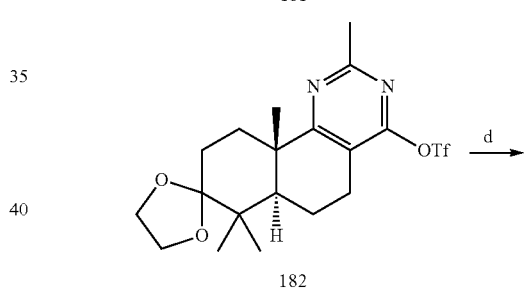
182

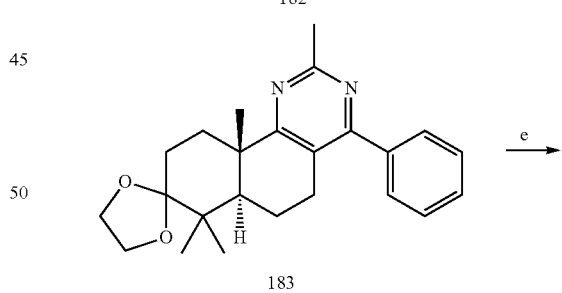
183

Scheme 32(b):

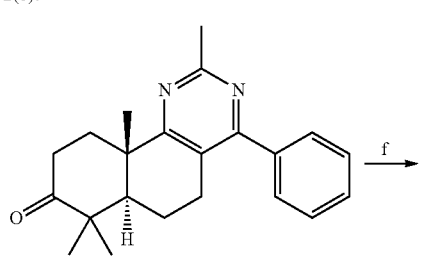
184

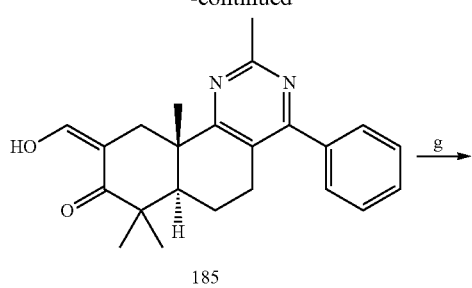

185

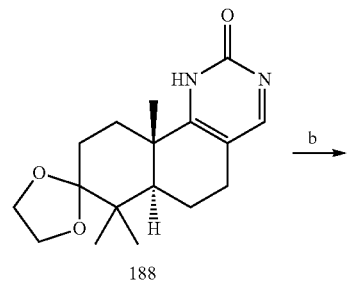

188

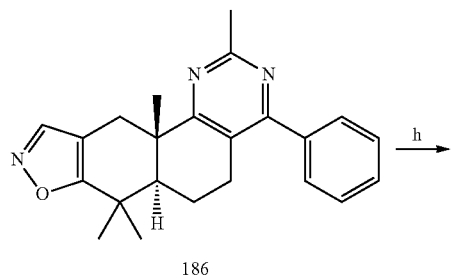

186

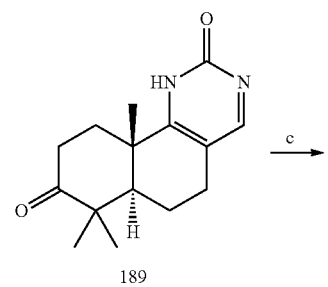

189

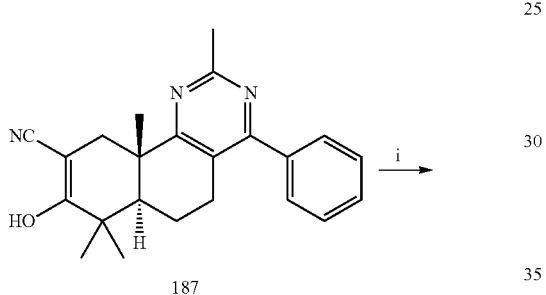

187

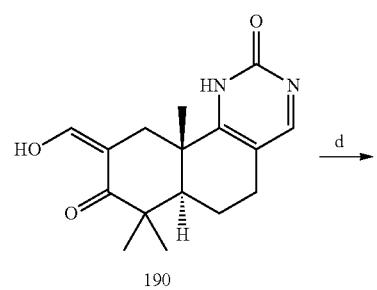

190

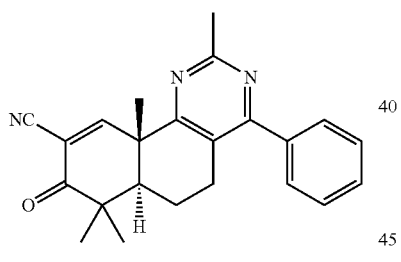

TX63529

Reagents and conditions pertaining to Scheme 32: (a) (MeO)$_2$CO, NaH, THF, reflux, 3 h, 87%; (b) acetamidine·HCl, piperidine, i-PrOH, reflux, 2 d, 62%; (c) Tf$_2$O, Et$_3$N, CHCl$_3$, 0° C., 2 h, 83%; (d) phenylboronic acid, PPh$_4$, Pd(OAc)$_2$, K$_3$PO$_4$, DME. 85° C., 16 h, 83%; (e) 3N HCl (aq), MeOH, RT, 12 h, quantitative; (f) HCO$_2$Et, NaOMe, RT, 12 h, quantitative; (g) NH$_2$OH—HCl, 50° C., 12 h, quantitative; (h) NaOMe, 50° C., 6 h, quantitative; (i) (i) 1,3-dibromo-5,5-dimethylhydantoin, DMF, 0° C., 2h; (ii) pyridine, 50° C., 12 h, 67%.

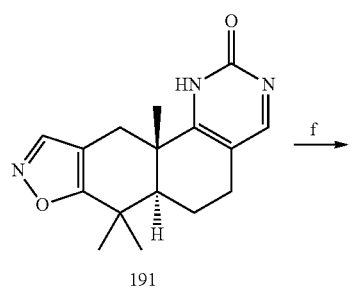

191

Scheme 33:

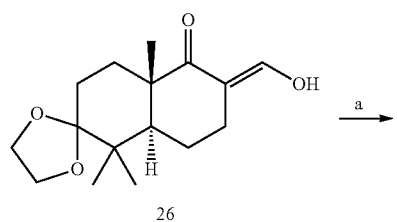

26

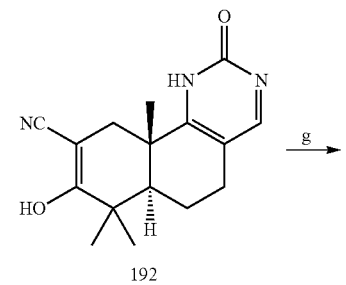

192

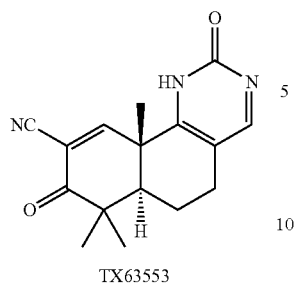

TX63553

Reagents and conditions pertaining to Scheme 33: (a) (i) urea, dioxane, reflux, 3 d; (ii) MeOH, NaOMe, reflux, 3 d; (b) 1N HCl (aq), MeOH, RT, 12 h, 71% 2 steps; (c) HCO₂Et, NaOMe, RT to 50° C., 49%; (c) NH₂OH—HCl, 50° C., 12 h; (d) NaOMe, 50° C., 6 h, 15% 2 steps; (e) (i) 1,3-dibromo-5,5-dimethylhydantoin, DMF, 0° C., 2 h; (ii) pyridine, 50° C., 12 h, 31%.

Scheme 34:

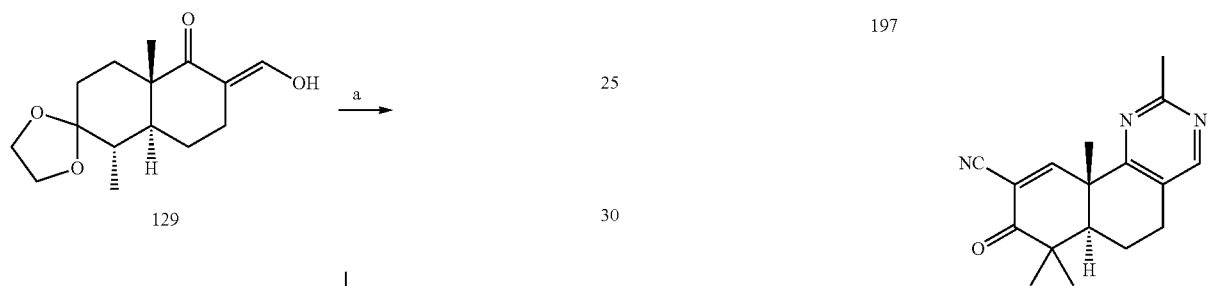

Reagents and conditions pertaining to Scheme 35: (a) acetamidine-HCl, piperidine, i-PrOH, reflux, 2 d, 48%; (b) 3N HCl (aq), MeOH, RT, 16 h, 94%, (c) HCO₂Et, NaOMe, RT, 16 h, 90%; (d) NH₂OH—HCl, 50° C., 16 h, 98%; (e) NaOME, RT, 48 h, 80%; (f) (i) 1,3-dibromo-5,5-dimethylhydantoin, DMF, 0° C., 1 h; (ii) pyridine, 50° C., 16 h, 51%.

Scheme 35:

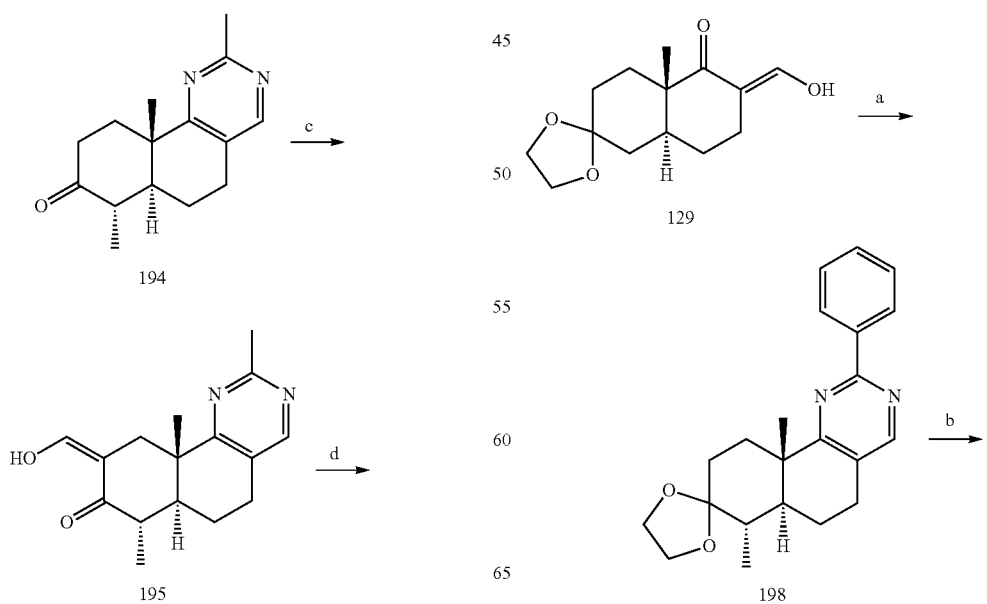

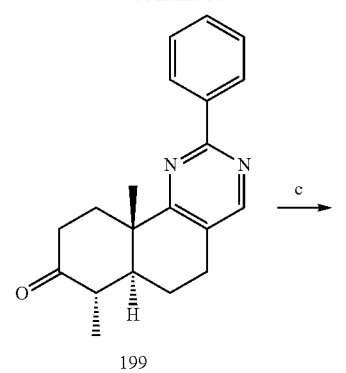
199
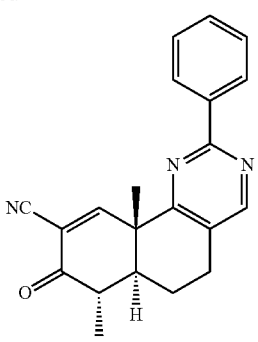
TX63569
Reagents and conditions pertaining to Schemes 35: (a) acetamidine-HCl, piperidine, i-PrOH, 85° C., 4 d, 60%; (b) 3N HCl (aq), MeOH, RT, 16 h, 95%; (c) HCO₂Et, NaOMe, RT, 16 h, 91%; (d) NH₂OH—HCl, 50° C., 16 h, 89%; (e) NaOMe, RT, 16 h, quantitative; (f) (i) 1,3-dibromo-5-5,-dimethylhydantoin, DMF, 0° C., 1 h; (ii) pyridine, 50° C., 16 h, 36%.
Scheme 36:
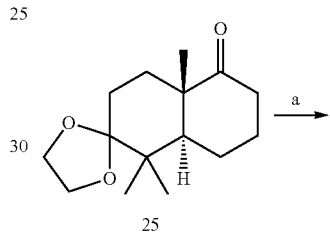
25
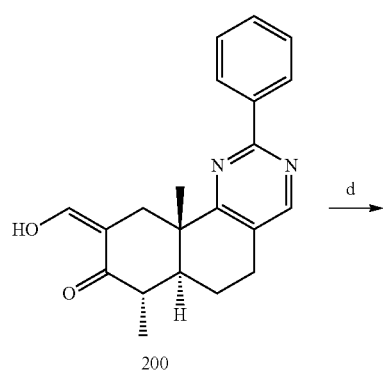
200
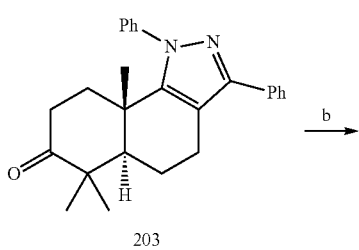
203
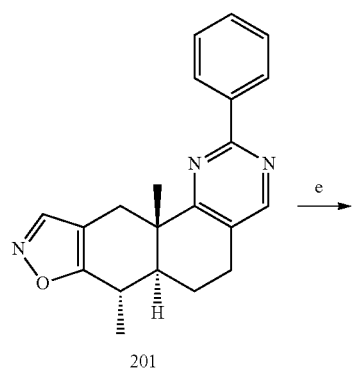
201
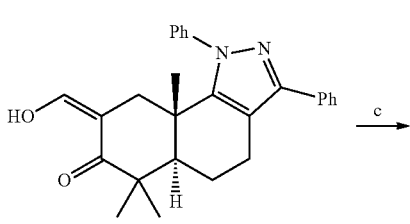
204
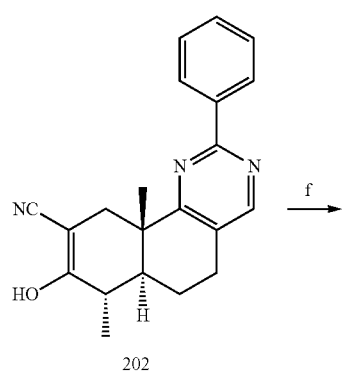
202
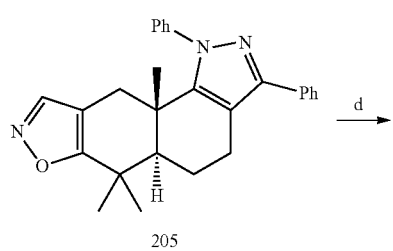
205

163
-continued

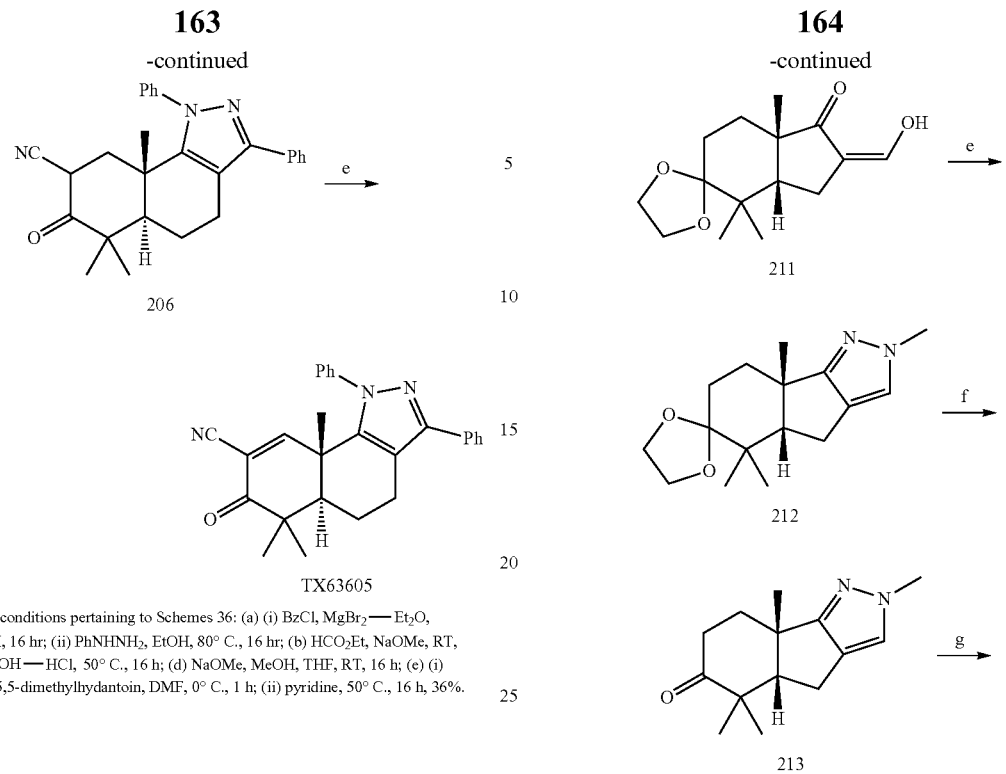

Reagents and conditions pertaining to Schemes 36: (a) (i) BzCl, MgBr₂—Et₂O, DIPEA, DCM, 16 hr; (ii) PhNHNH₂, EtOH, 80° C., 16 hr; (b) HCO₂Et, NaOMe, RT, 16 h; (c) NH₂OH—HCl, 50° C., 16 h; (d) NaOMe, MeOH, THF, RT, 16 h; (e) (i) 1,3-dibromo-5,5-dimethylhydantoin, DMF, 0° C., 1 h; (ii) pyridine, 50° C., 16 h, 36%.

Scheme 37:

164
-continued

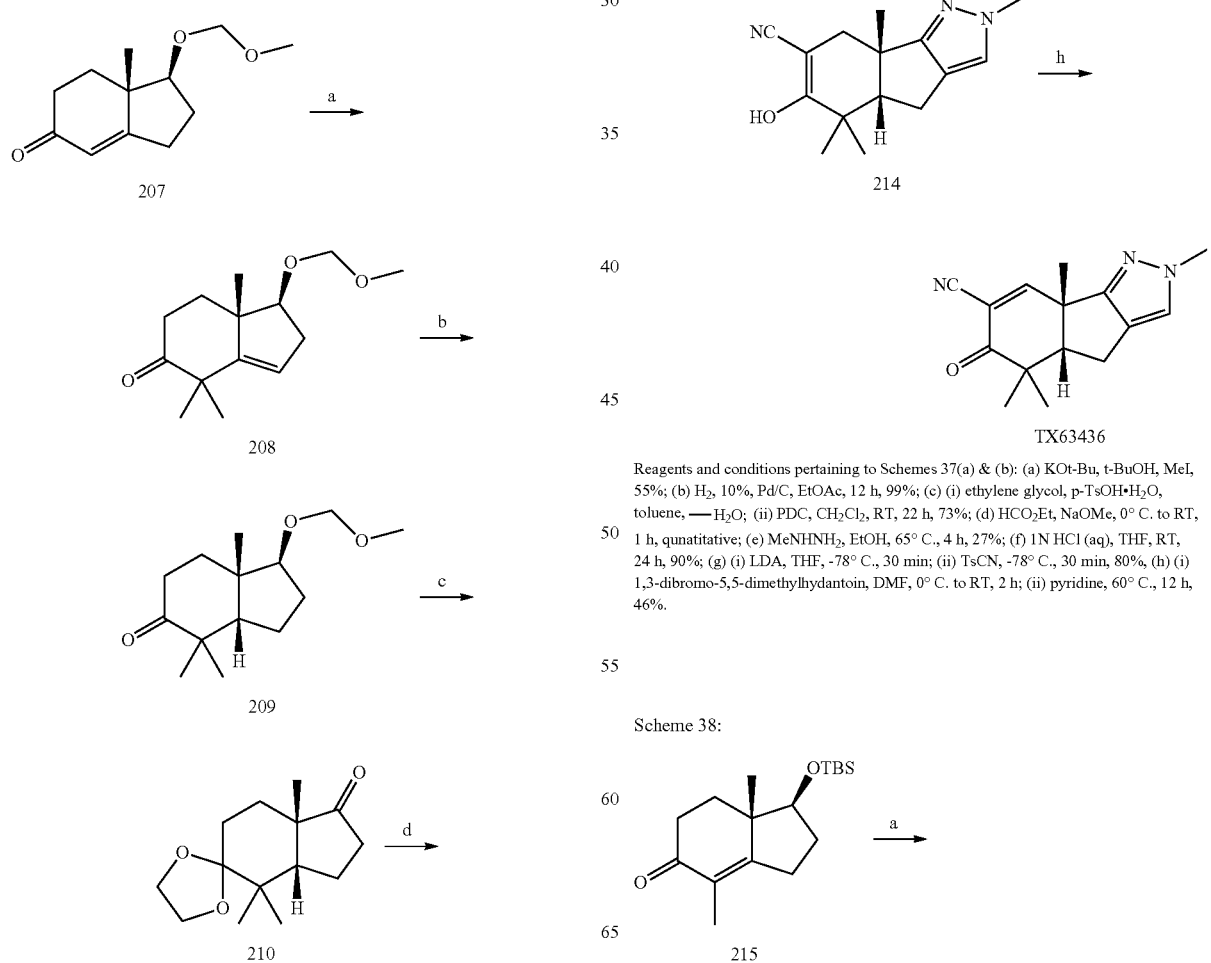

Reagents and conditions pertaining to Schemes 37(a) & (b): (a) KOt-Bu, t-BuOH, MeI, 55%; (b) H₂, 10%, Pd/C, EtOAc, 12 h, 99%; (c) (i) ethylene glycol, p-TsOH•H₂O, toluene, —H₂O; (ii) PDC, CH₂Cl₂, RT, 22 h, 73%; (d) HCO₂Et, NaOMe, 0° C. to RT, 1 h, qunatitative; (e) MeNHNH₂, EtOH, 65° C., 4 h, 27%; (f) 1N HCl (aq), THF, RT, 24 h, 90%; (g) (i) LDA, THF, -78° C., 30 min; (ii) TsCN, -78° C., 30 min, 80%, (h) (i) 1,3-dibromo-5,5-dimethylhydantoin, DMF, 0° C. to RT, 2 h; (ii) pyridine, 60° C., 12 h, 46%.

Scheme 38:

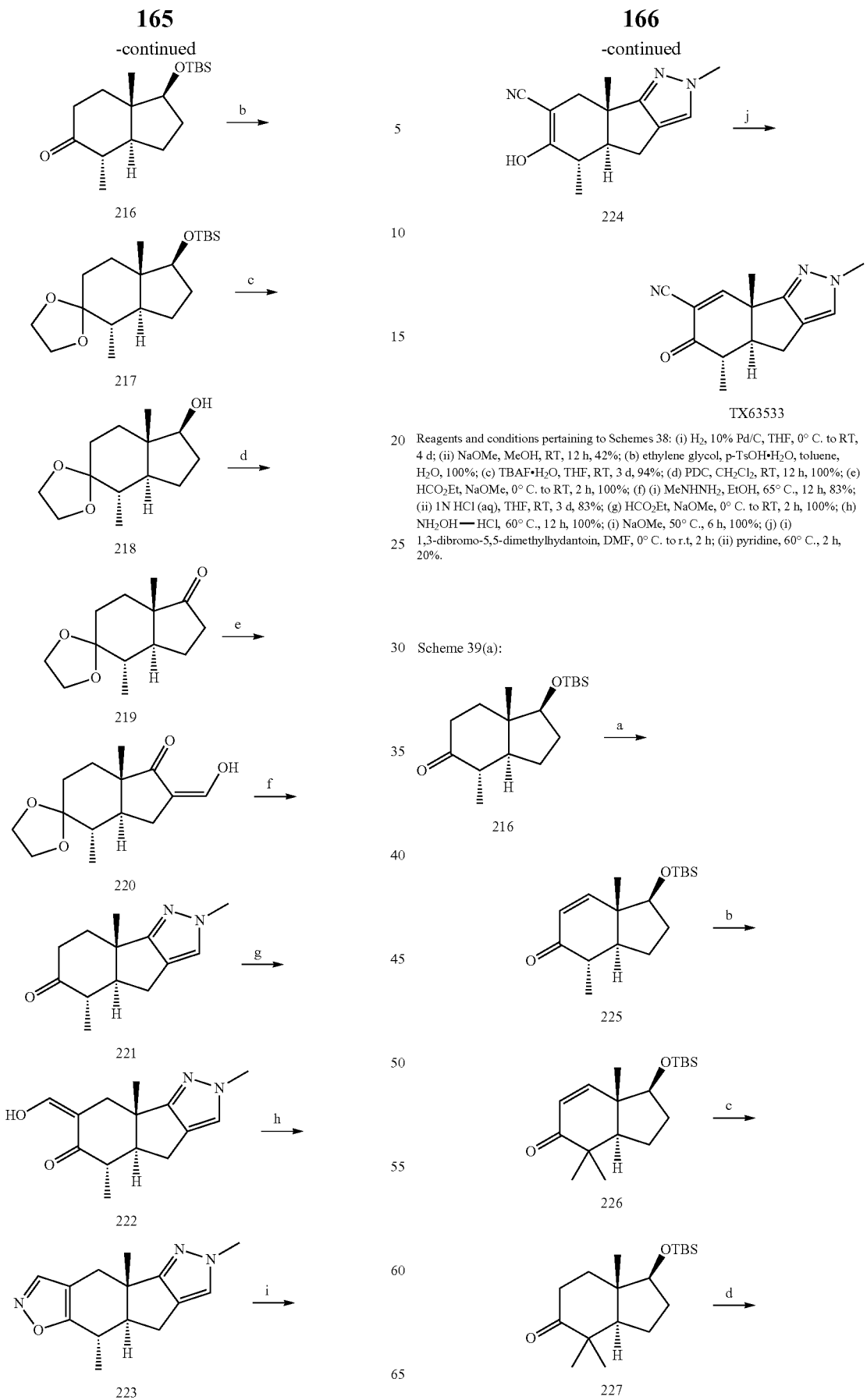

167
-continued

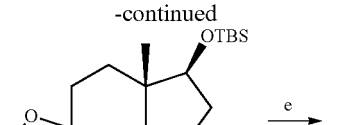
228

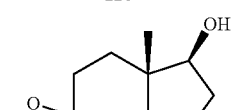
229

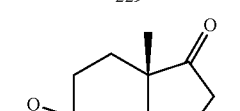
230

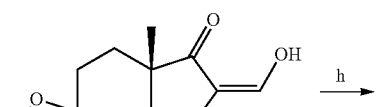
231

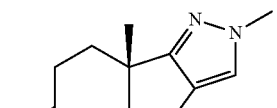
232

Scheme 39(b):

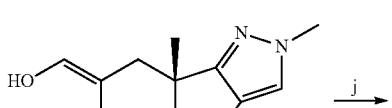
233

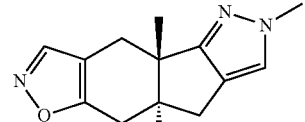
234

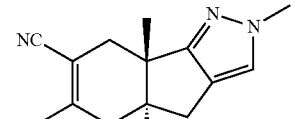
235

168
-continued

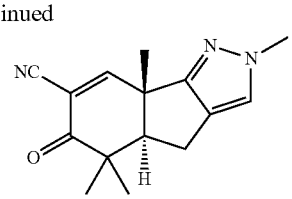
TX63559

Reagents and conditions pertaining to Schemes 39(a) & (b): (a) (i) hexamethyldisilazane, NaI, TMSCl, MeCN, RT, 12 h; (ii) Pd(OAc)$_2$, MeCN, RT, 12 h, 79%; (b) (i) KHMDS, THF, 0° C., 30 min; (ii) MeI, 0° C., 30 min, 81%; (c) H$_2$, 10% Pd/C, THF, RT, 3 h, 99% (d) methylethyldioxolane, ethylene glycol, p-TsOH, CH$_2$Cl$_2$, RT, 2 d, 99%; (e) TBAF, THF, RT, 4 d, 89%; (f) PDC, CH$_2$Cl$_2$, RT, 12 h, 90%; (g) HCO$_2$Et, NaOMe, 0° C. to RT, 2 h, quantitative; (h) (i) MeNHNH$_2$, EtOH, 65° C., 12 h; (ii) 1N HCl (aq), THF, RT, 2 d, 76%; (i) HCO$_2$Et, NaOMe, 0° C to RT, 2 h, 96%, (j) NH$_2$OH—HCl, 60° C., 12 h, 91%; (k) NaOMe, 50° C., 6 h, 71%; (l) (i) 1,3-dibromo-5,5-dimethylhydantoin, DMF, 0° C. to RT, 2 h; (ii) pyridine, 60° C., 5 h, 71%.

Scheme 40:

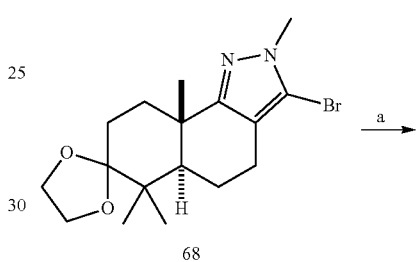
68

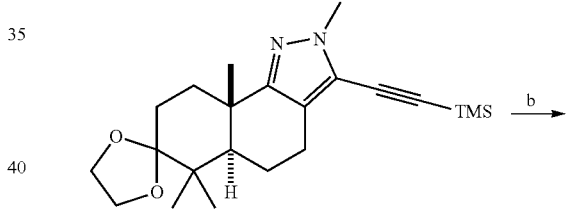
236

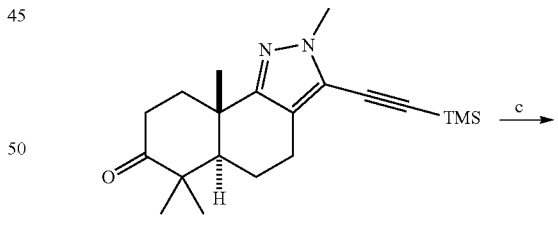
237

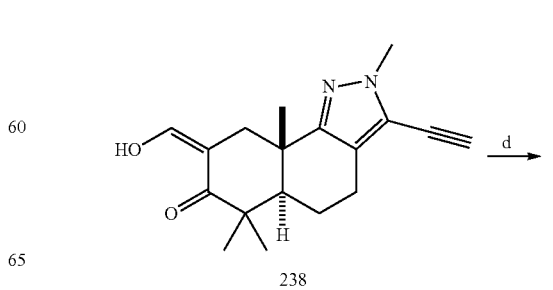
238

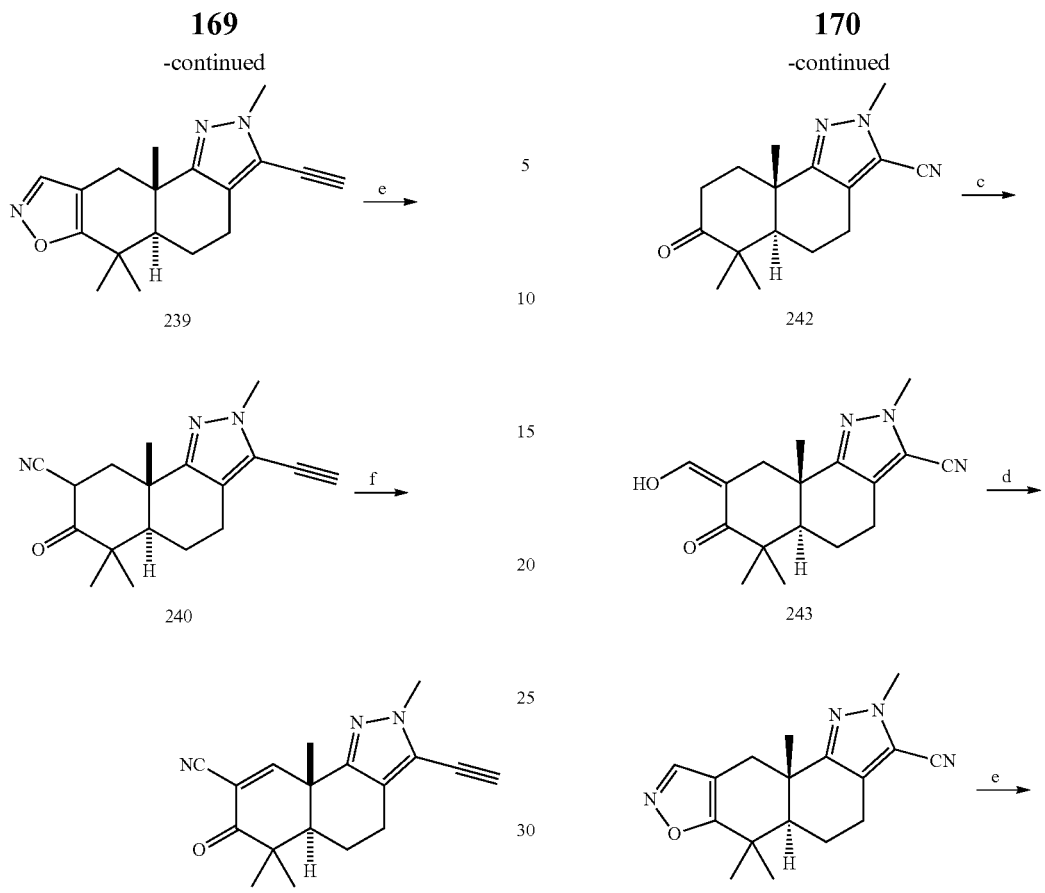
Reagents and conditions pertaining to Schemes 40: (a) TMS-acetylene, CuI, TEA, dioxane, 80° C., 16 hr, 3%; (b) HCl (aq), THF, 3 day, 98%; (c) HCO$_2$Et, NaOMe, 0° C. to RT, 2 h, quantitative; (d) NH$_2$OH—HCl, 60° C., 12 h, quantitative; (e) NaOMe, 50° C., 6 h, 50%; (f) (i) 1,3-dibromo-5,5-dimethylhydantoin, DMF, 0° C. to RT, 2 h; (ii) pyridine, 60° C., 5 h, 55%.
Scheme 41:
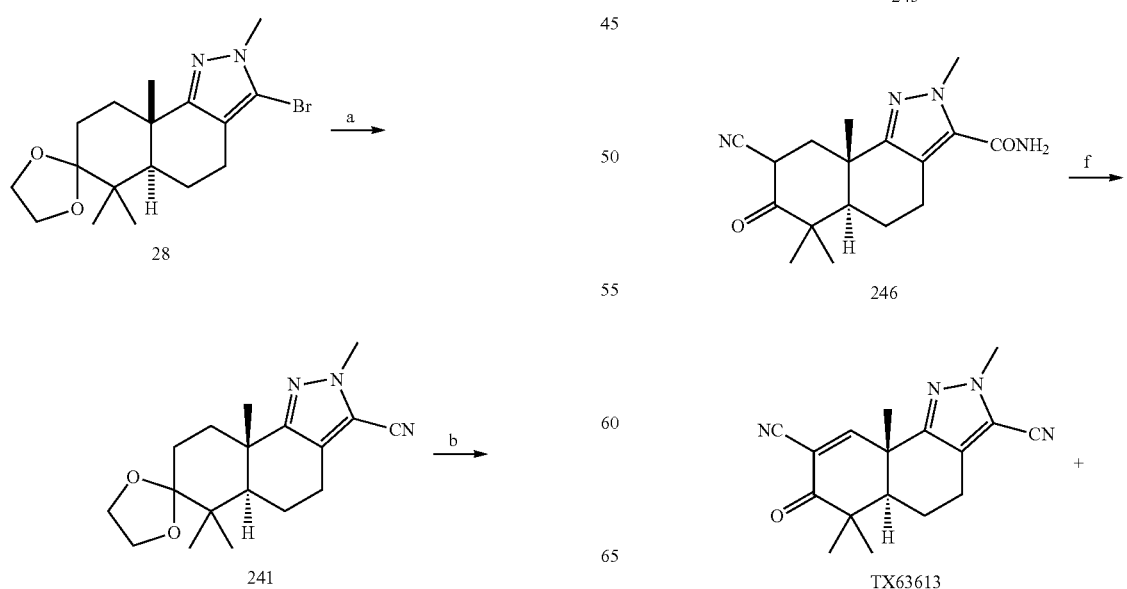

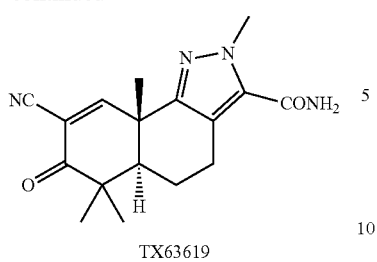

TX63619

Reagents and conditions pertaining to Schemes 41: (a) Zn(CN)$_2$, dppf, NaCO$_3$, Pb(OAc)$_2$, DMAc, 120° C., 16 hr, 80%; (b) HCl (aq), MeOH, 16 hr, 96%; (c) HCO$_2$Et, NaOMe, 0° C. to RT, 16 h, quantitative; (d) NH$_2$OH—HCl, 50° C., 16 h, quantitative; (e) NaOMe, THF, MeOH, 50° C., 6 h, 100% as mixture; (f) (i) 1,3-dibromo-5,5-dimethylhydantoin, DMF, 0° C to RT, 2 h, (ii) pyridine, 50° C., 16 h, TX63613: 39%, TX63619: 8%.

Scheme 42:

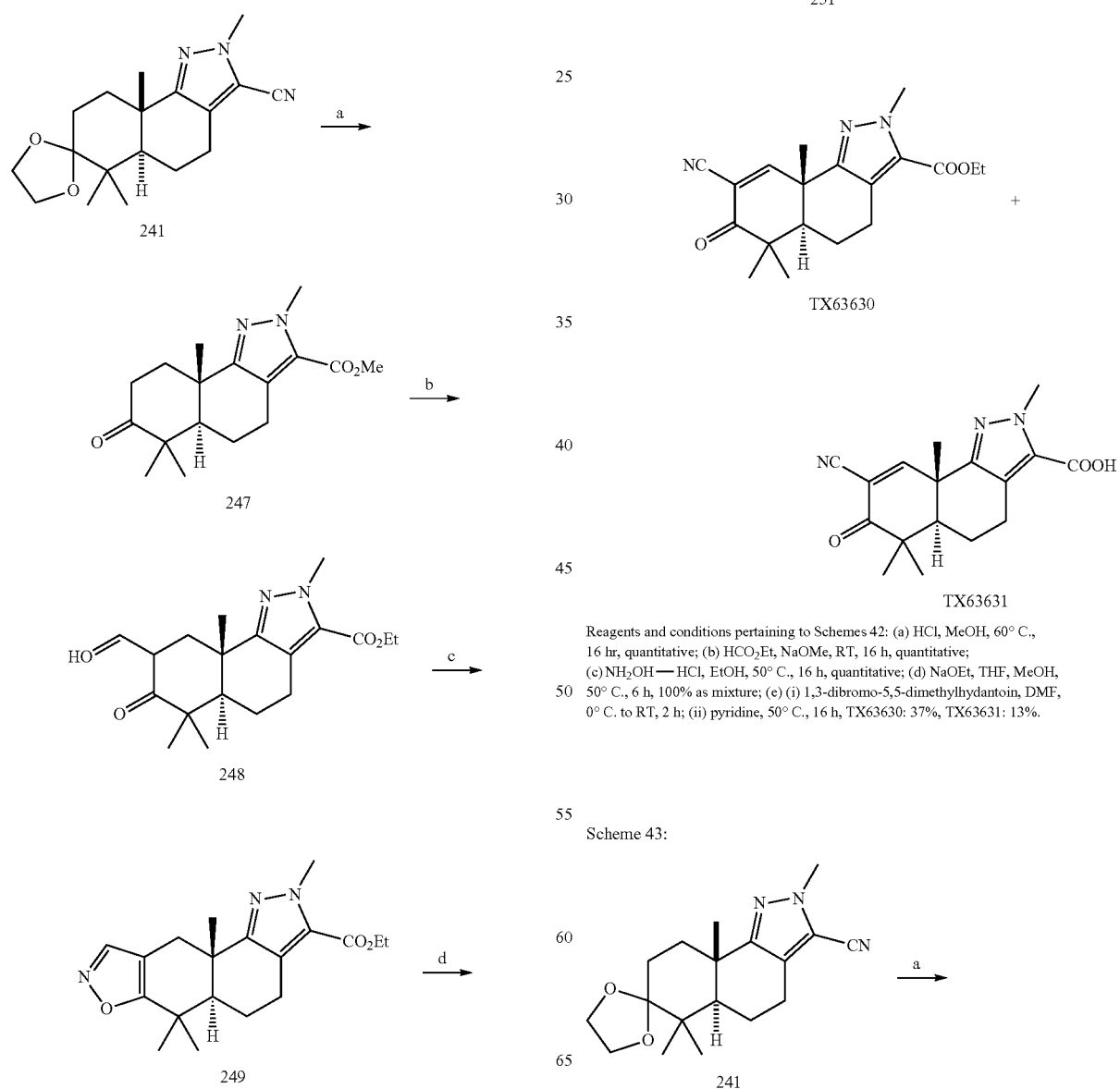

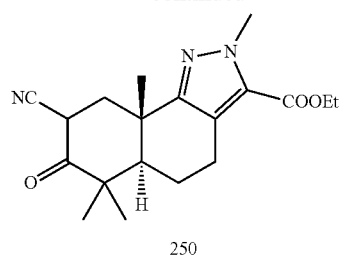

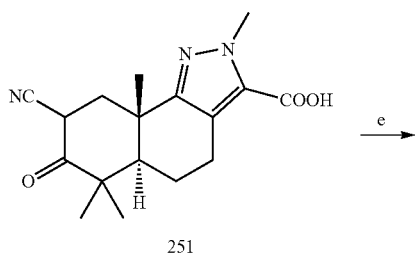

TX63631

Reagents and conditions pertaining to Schemes 42: (a) HCl, MeOH, 60° C., 16 hr, quantitative; (b) HCO$_2$Et, NaOMe, RT, 16 h, quantitative; (c) NH$_2$OH—HCl, EtOH, 50° C., 16 h, quantitative; (d) NaOEt, THF, MeOH, 50° C., 6 h, 100% as mixture; (e) (i) 1,3-dibromo-5,5-dimethylhydantoin, DMF, 0° C. to RT, 2 h; (ii) pyridine, 50° C., 16 h, TX63630: 37%, TX63631: 13%.

Scheme 43:

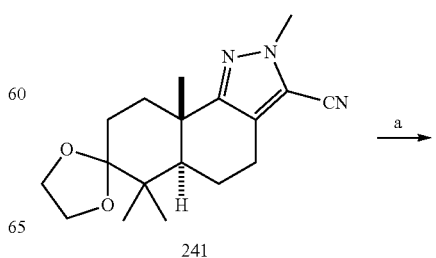

241

-continued
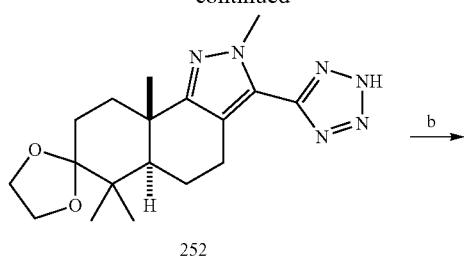
252
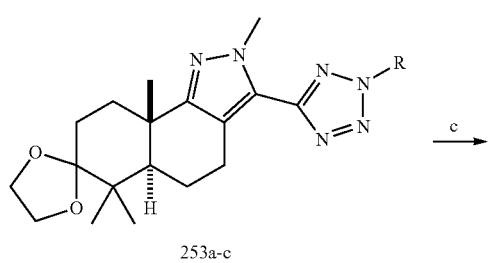
253a-c
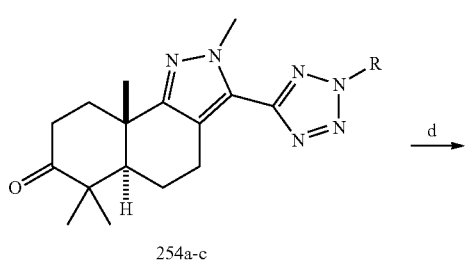
254a-c
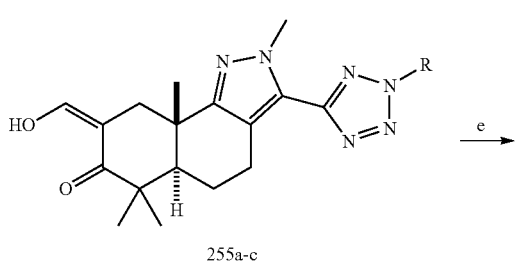
255a-c
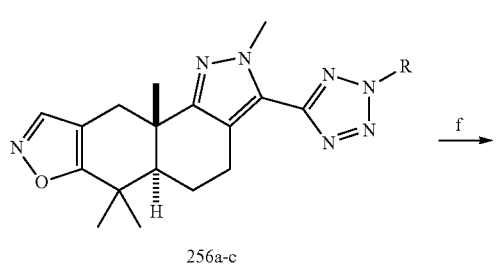
256a-c
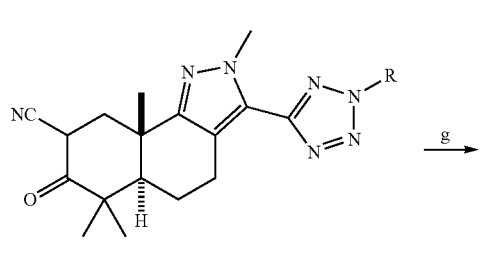
257a-c
-continued
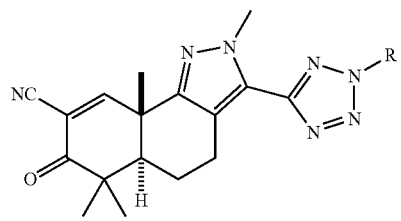
a: TX63665 R = Me
b: TX63729 R = Bn
c: TX63734 R = iPr
Reagents and conditions pertaining to Schemes 43: (a) TMSN$_3$, Bu$_3$SnO, Toluene, 110° C.; (b) RX, K$_2$CO$_3$, DMF; (c) HCl, THF; (d) HCO$_2$Et, NaOMe, RT, 16 h; (e) NH$_2$OH—HCl, EtOH, THF, H$_2$O, 50° C.; (f) NaOMe, THF, MeOH, 50° C.; (g) (i) 1,3-dibromo-5,5-dimethylhydantoin, DMF, 0° to RT, 2 h; (ii) pyridine, 60° C., 16 hr.
Scheme 44:
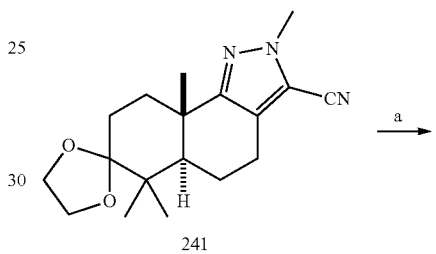
241
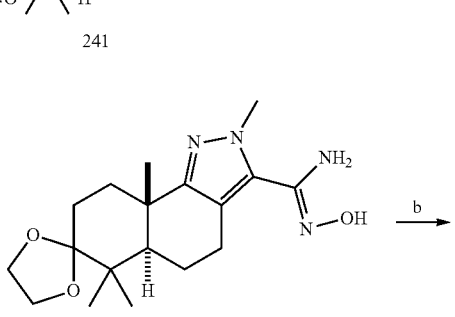
258
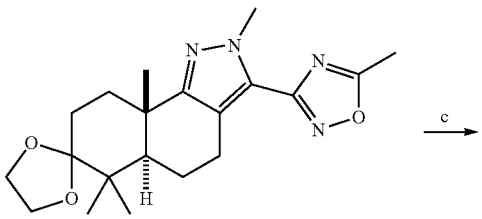
259
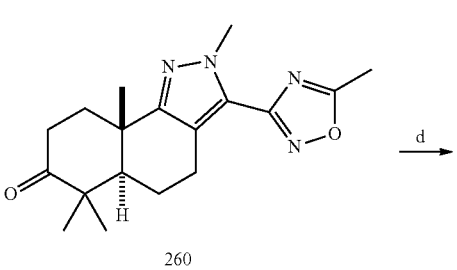
260

175
-continued

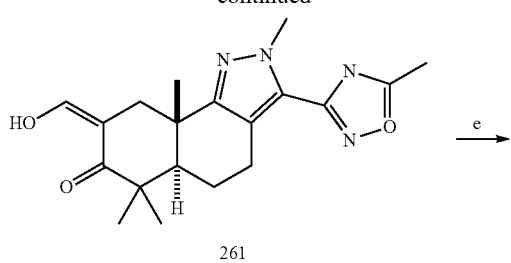
261

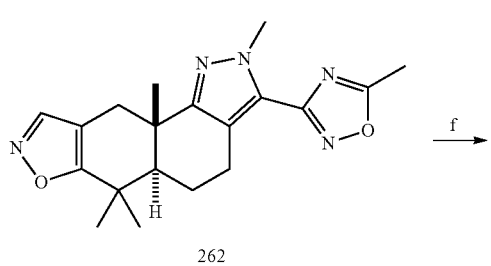
262

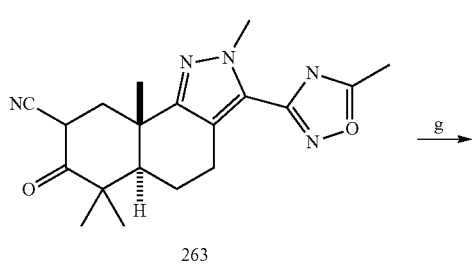
263

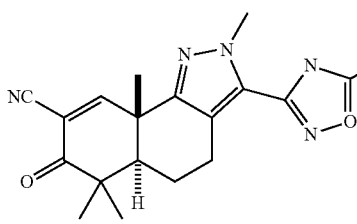
TX63723

Reagents and conditions pertaining to Schemes 44: (a) NH$_2$OH, EtOH, 50° C., 16 hr; (b) Dimethylacetamide dimethylacetal, dioxane, 60° C., 2 h, 96%; (c) HCl, THF, 2 day, quantitative; (d) HCO$_2$Et, NaOMe, RT, 16 h, quantitative; (e) NH$_2$OH—HCl, EtOH, THF, H$_2$O, 50° C., 16 h, 77%; (f) NaOMe, THF, MeOH, 50° C., 3 Hr, 98%; (g) (i) 1,3-dibromo-5,5-dimethylhydantoin, DMF, 0° to RT, 2 h; (ii) pyridine, 60° C., 4 hr, 78%.

Scheme 45:

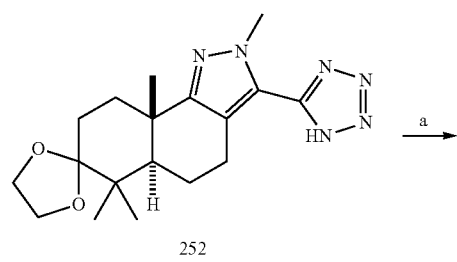
252

176
-continued

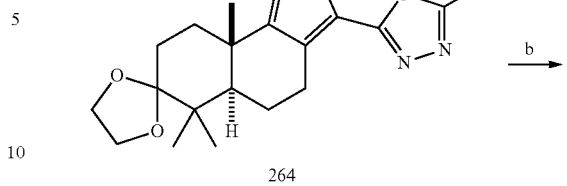
264

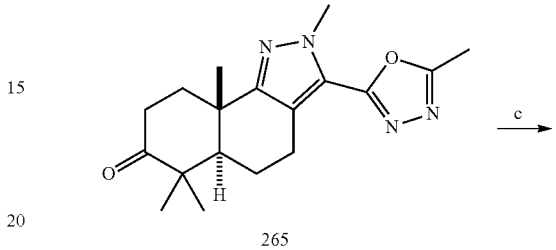
265

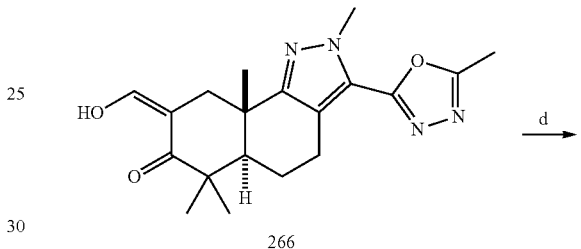
266

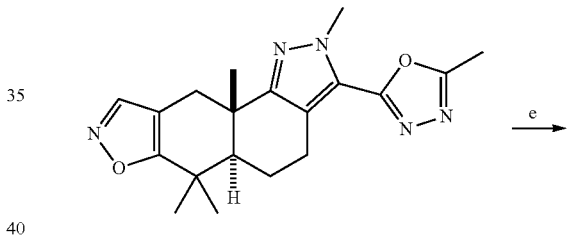
267

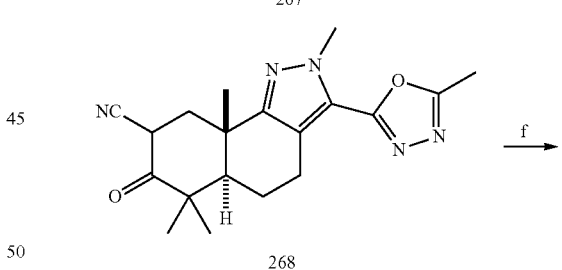
268

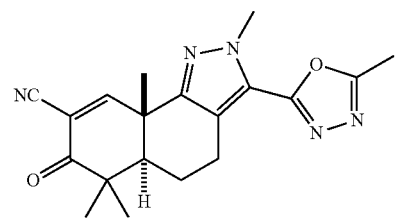
TX63735

Reagents and conditions pertaining to Schemes 45: (a) Ac$_2$O, Pyridine, 110° C., 3 hr; (b) HCl(aq), THF, 2 day, 34%; (c) HCO$_2$Et, NaOMe, RT 16 h, 99%; (d) NH$_2$OH—HCl, EtOH, THF, H$_2$O, 50° C., 16 h. 28%; (e) NaOME, THF, MeOH, 50° C., 3 Hr, 100%; (f) (i) 1,3-dibromo-5,5-dimethylhydantoin, DMF, 0° to RT, 2 h; (ii) pyridine, 60° C., 4 hr, 60%.

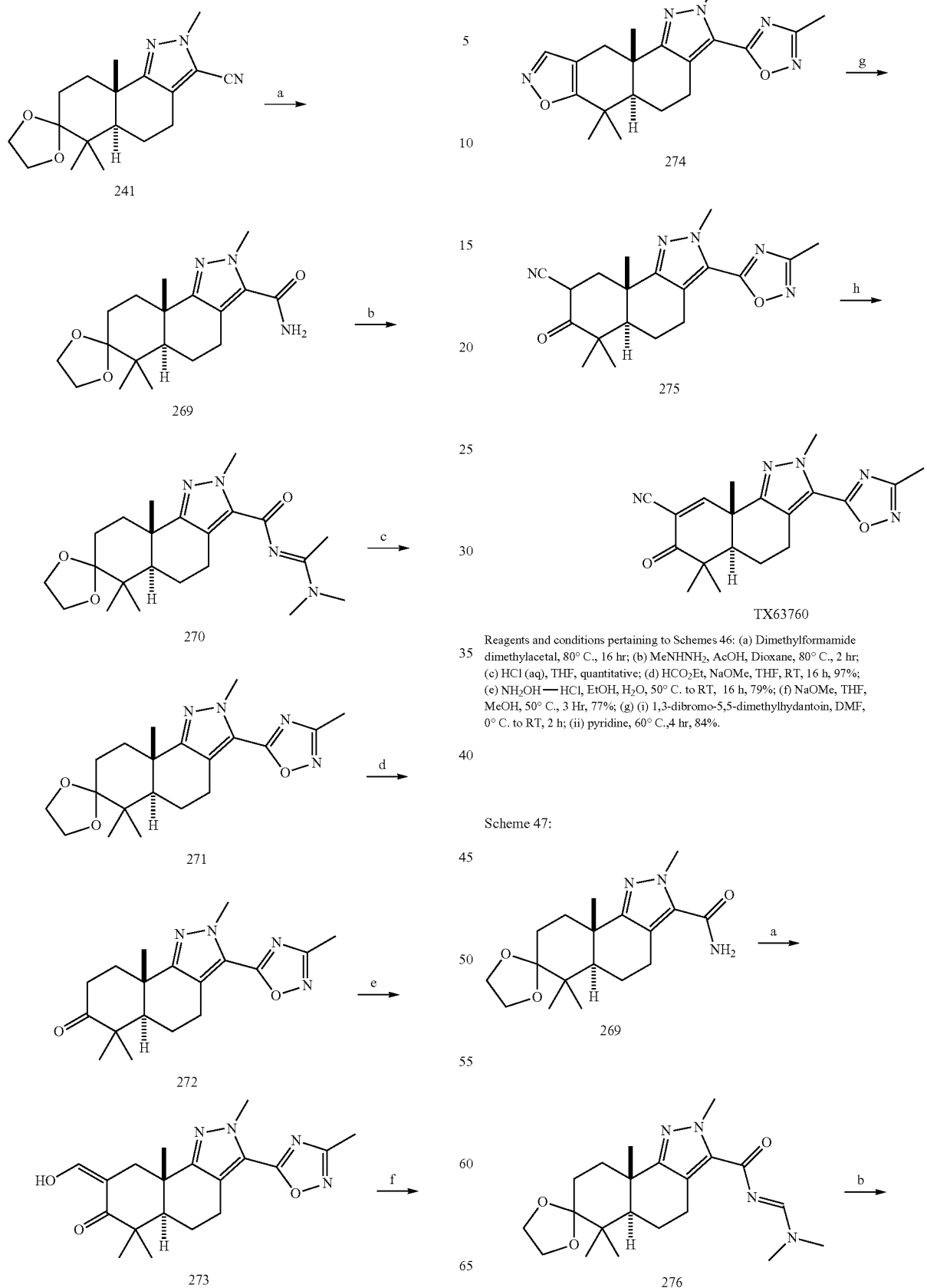

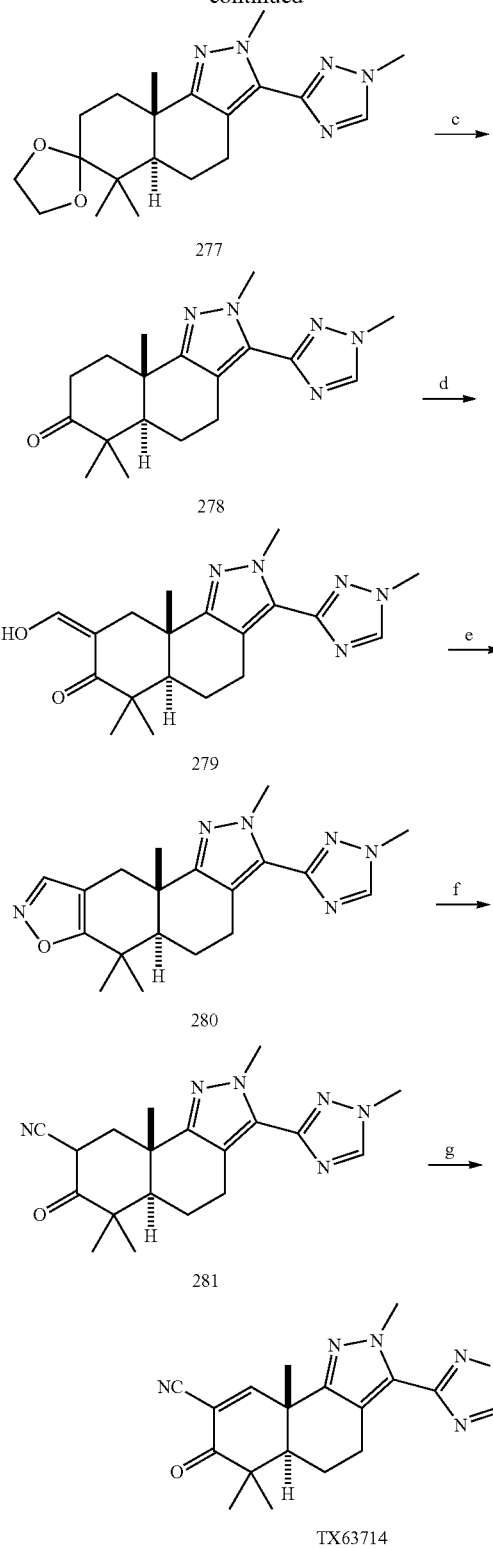
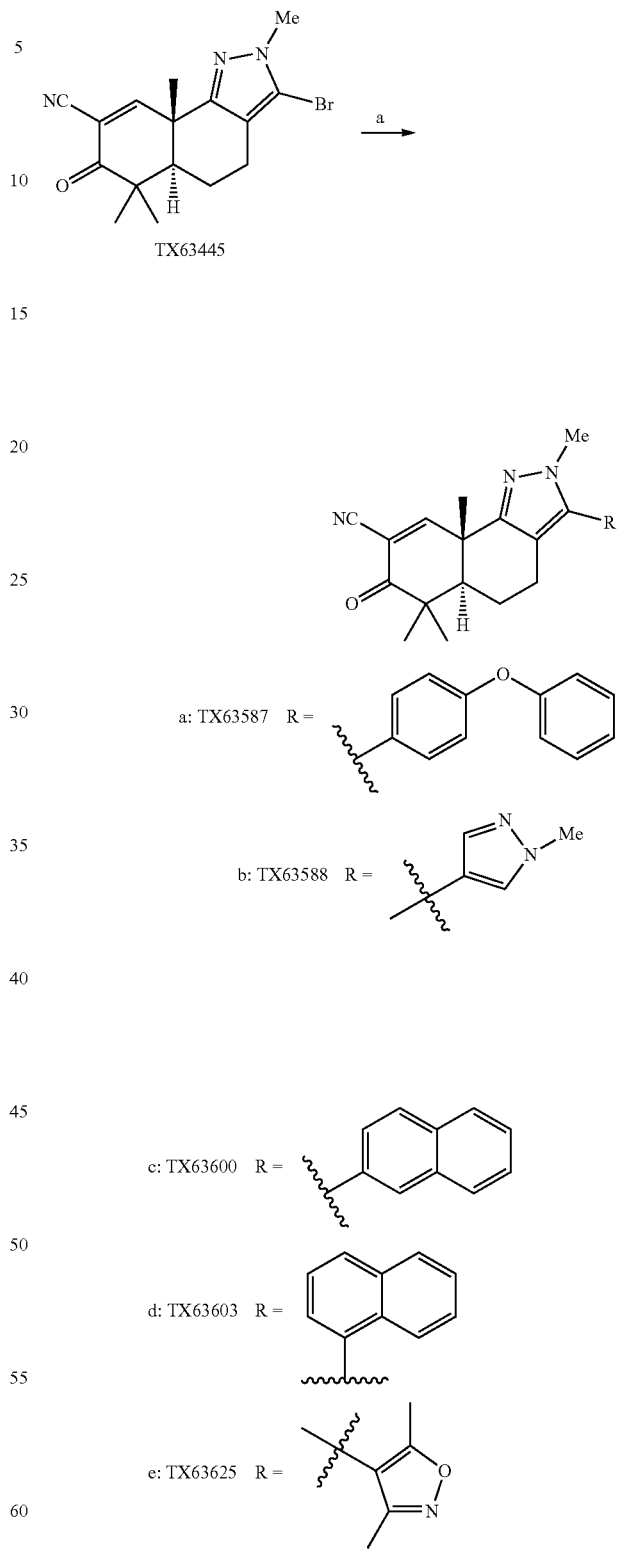

Scheme 48:

a: TX63587  R = 4-phenoxyphenyl
b: TX63588  R = 1-methylpyrazol-4-yl
c: TX63600  R = naphthalen-2-yl
d: TX63603  R = naphthalen-1-yl
e: TX63625  R = 3,5-dimethylisoxazol-4-yl
f: TX63637  R = Me Reagents and conditions pertaining to Schemes 47: (a) KOH, EtOH, H$_2$O, 3 days, quantitative; (b) Dimethylacetamide dimethylacetal, dioxane, 80° C., 2 h; (c) NH$_2$OH—HCl, TEA, AcOH, Dioxane, 80° C., 3 hr, 50%; (d) HCl (aq), THF, quantitative; (e) HCO$_2$Et, NaOMe, THF, RT, 16 h, 97%; (f) NH$_2$OH—HCl, EtOH, THF, H$_2$O, 50° C., 16 h, 94%; (g) NaOMe, THF, MeOH, 50° C., 3 Hr, 79%; (h) (i) 1,3-dibromo-5,5-dimethylhydantoin, DMF, 0° C. to RT, 2 h; (ii) pyridine, 60° C., 6 hr, 71%

Reagents and conditions pertaining to Schemes 48: (a) R—B(OH)$_2$, K$_3$PO$_4$, Pd(PPh$_3$)$_4$, dimethoxyethane, 80° C., 16 hr.

Scheme 49:
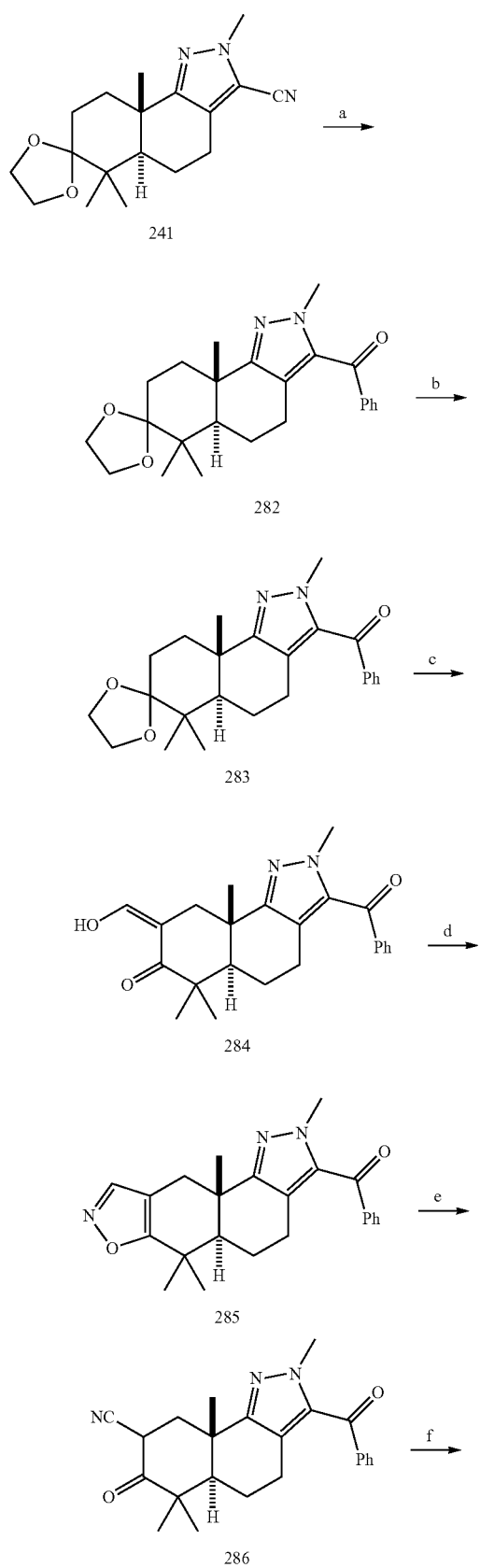
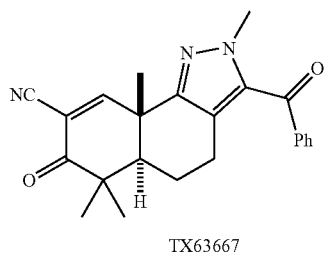
TX63667
Reagents and conditions pertaining to Schemes 49: (a) PhMgBr, THF, 0° C. to RT, 16 hr; (b) HCl (aq), THF, RT, 16 hr then 60° C., 4 Hr, 93%; (c) HCO₂Et, NaOMe, RT, 16 h, 97% (d) NH₂OH—HCl, TEA, AcOH, Dioxane, 50° C., 4 hr, 98%; (e) NaOMe, THF, MeOH, 50° C., 16 Hr. 83%; (f) (i) 1,3-dibromo-5,5-dimethylhydantoin, DMF, 0° C. to RT, 2 h; (ii) pyridine, 55° C., 5 hr, 90%
Scheme 50:
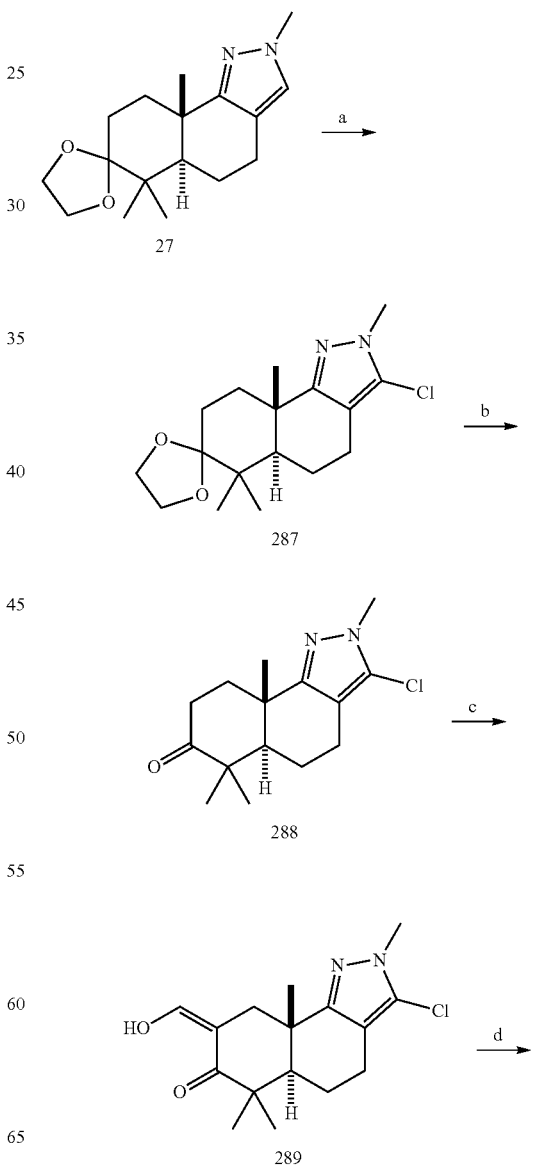

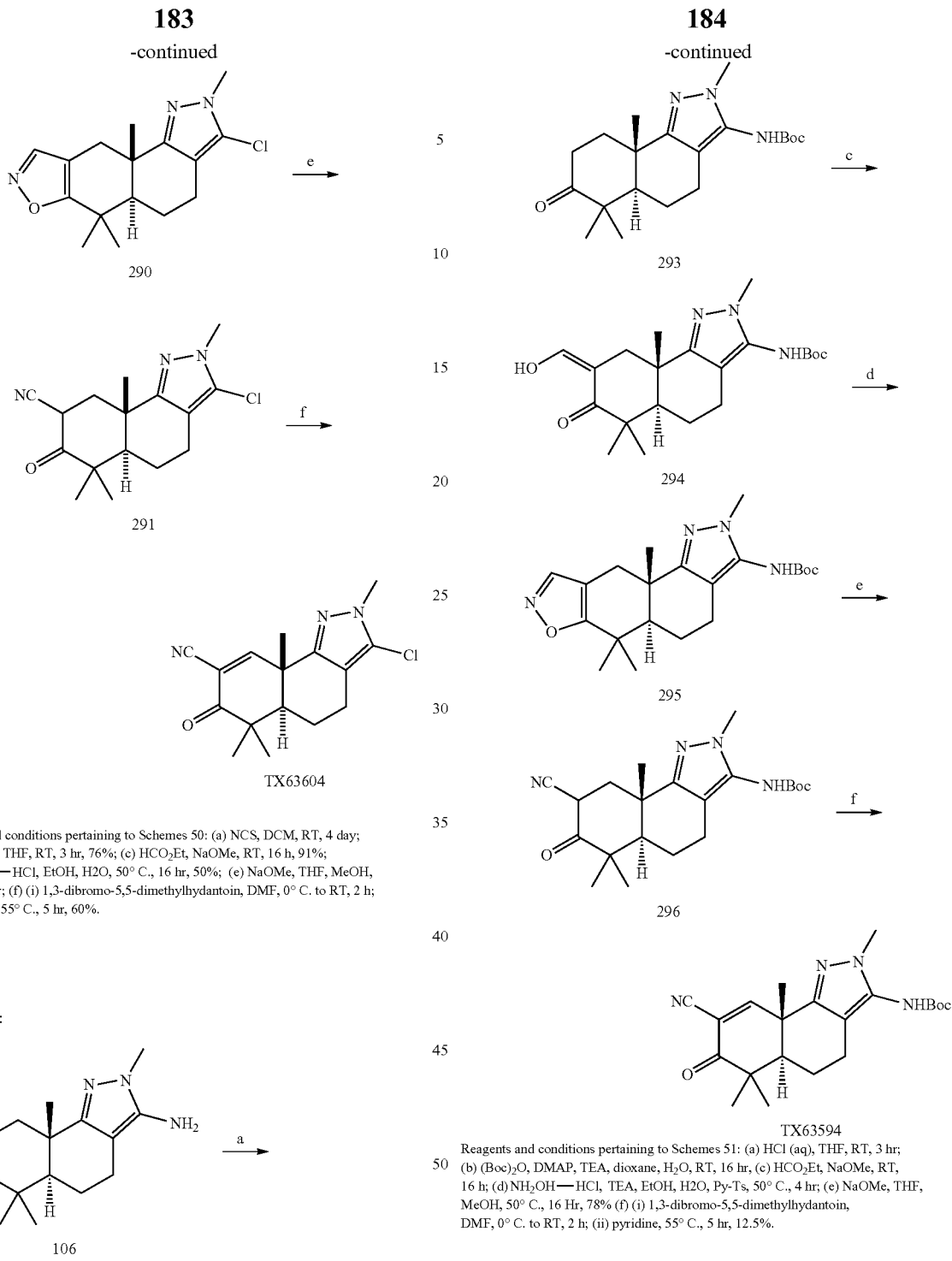

Reagents and conditions pertaining to Schemes 50: (a) NCS, DCM, RT, 4 day; (b) HCl (aq), THF, RT, 3 hr, 76%; (c) HCO₂Et, NaOMe, RT, 16 h, 91%; (d) NH₂OH—HCl, EtOH, H2O, 50° C., 16 hr, 50%; (e) NaOMe, THF, MeOH, 50° C., 16 Hr; (f) (i) 1,3-dibromo-5,5-dimethylhydantoin, DMF, 0° C. to RT, 2 h; (ii) pyridine, 55° C., 5 hr, 60%.

Scheme 51:

Reagents and conditions pertaining to Schemes 51: (a) HCl (aq), THF, RT, 3 hr; (b) (Boc)₂O, DMAP, TEA, dioxane, H₂O, RT, 16 hr, (c) HCO₂Et, NaOMe, RT, 16 h; (d) NH₂OH—HCl, TEA, EtOH, H2O, Py-Ts, 50° C., 4 hr; (e) NaOMe, THF, MeOH, 50° C., 16 Hr, 78% (f) (i) 1,3-dibromo-5,5-dimethylhydantoin, DMF, 0° C. to RT, 2 h; (ii) pyridine, 55° C., 5 hr, 12.5%.

Scheme 52:

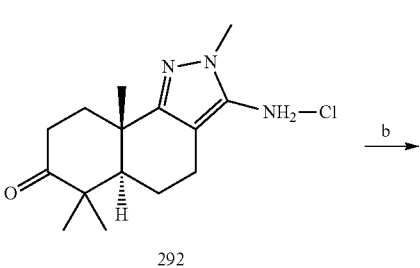

185
-continued

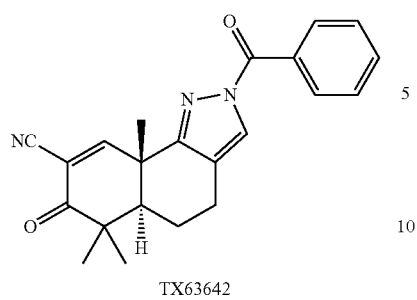

TX63642

Reagents and conditions pertaining to Scheme 52: (a) BzCl, NaHCO₃ (aq), THF, 0° C., 47%.

Scheme 53:

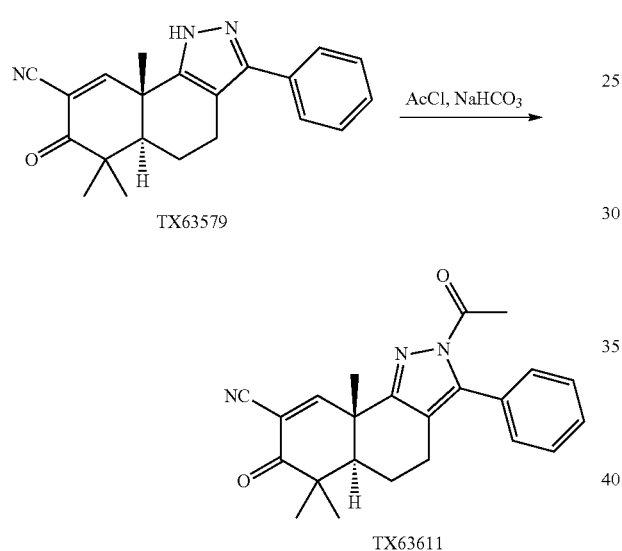

TX63579

AcCl, NaHCO₃ →

TX63611

Reagents and conditions pertaining to Scheme 53: (a) BzCl, NaHCO₃ (aq), THF, 0° C., 47%.

Scheme 54:

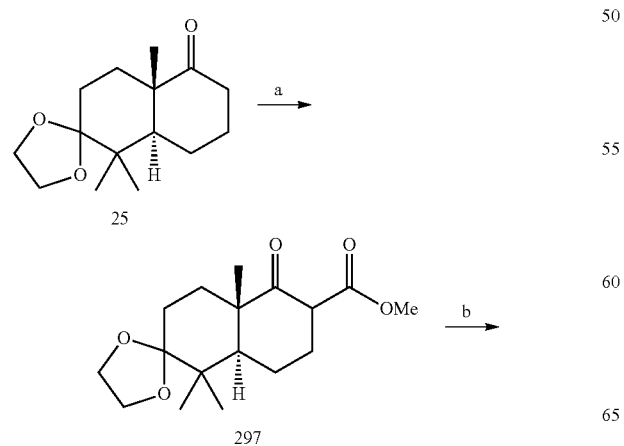

25

297

186
-continued

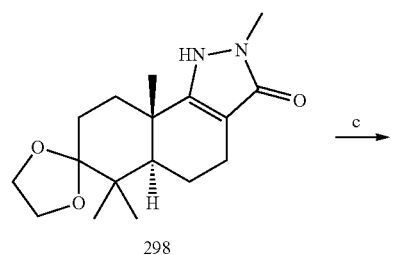

298

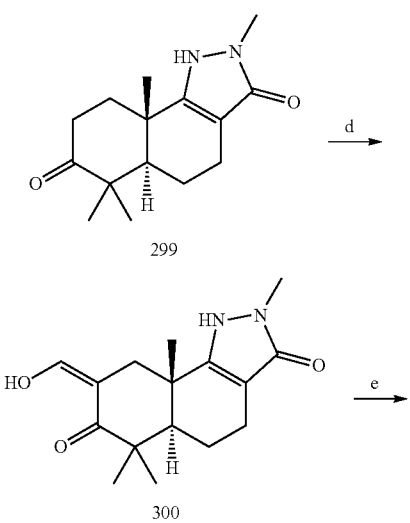

299

300

301

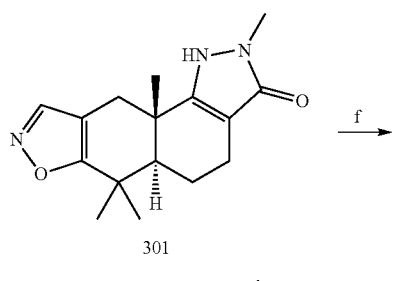

302

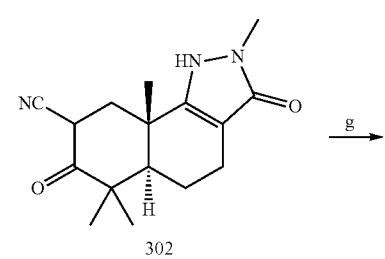

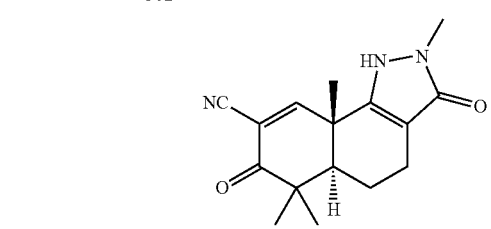

TX63676

Reagents and conditions pertaining to Schemes 54: (a) (MeO)₂CO, NaH, THF, reflux, 3 hr, 87%; (b) MeNHNH₂, EtOH, 60° C., 16 hr, (c) HCl (aq), MeOH, 16 hr, 100%; (d) HCO₂Et, NaOMe, RT, 16 h, 100°; (e) NH₂OH—HCl, EtOH, 50° C., 16 hr, 100%; (f) NaOMe, MeOH, 50° C., 9 Hr, 99%; (g) (i) 1,3-dibromo-5,5-dimethylhydantoin, DMF, 0° C. to RT, 2 h; (ii) pyridine, 55° C., 5 hr, 9%.

Scheme 55a:
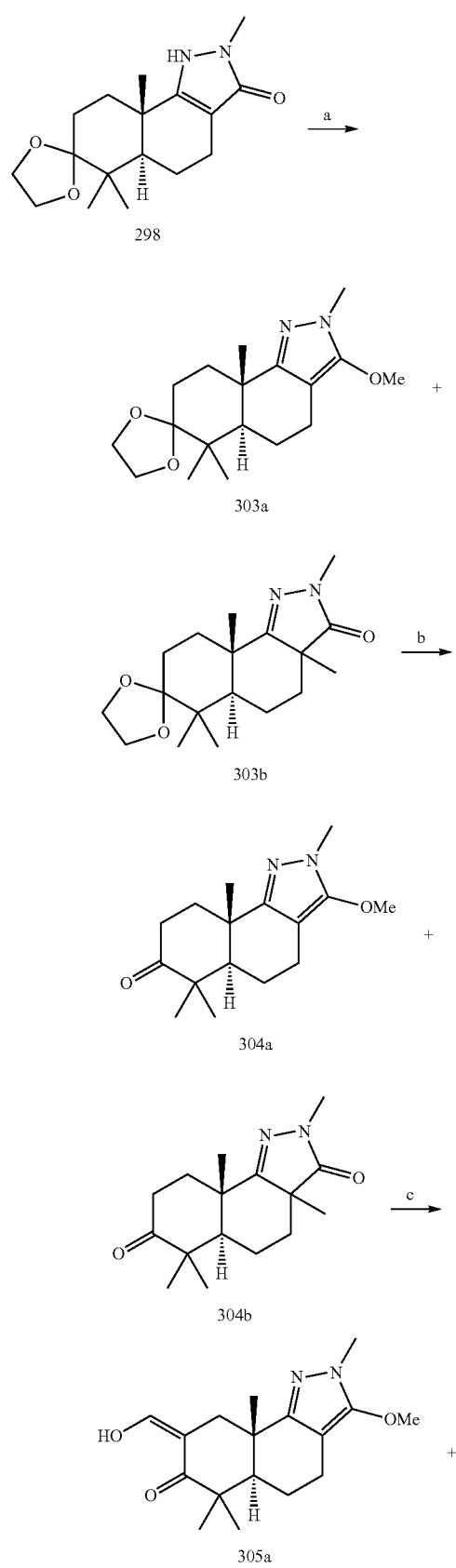
298
303a
303b
304a
304b
305a
Scheme 55b:
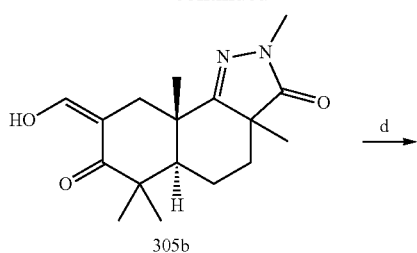
305b
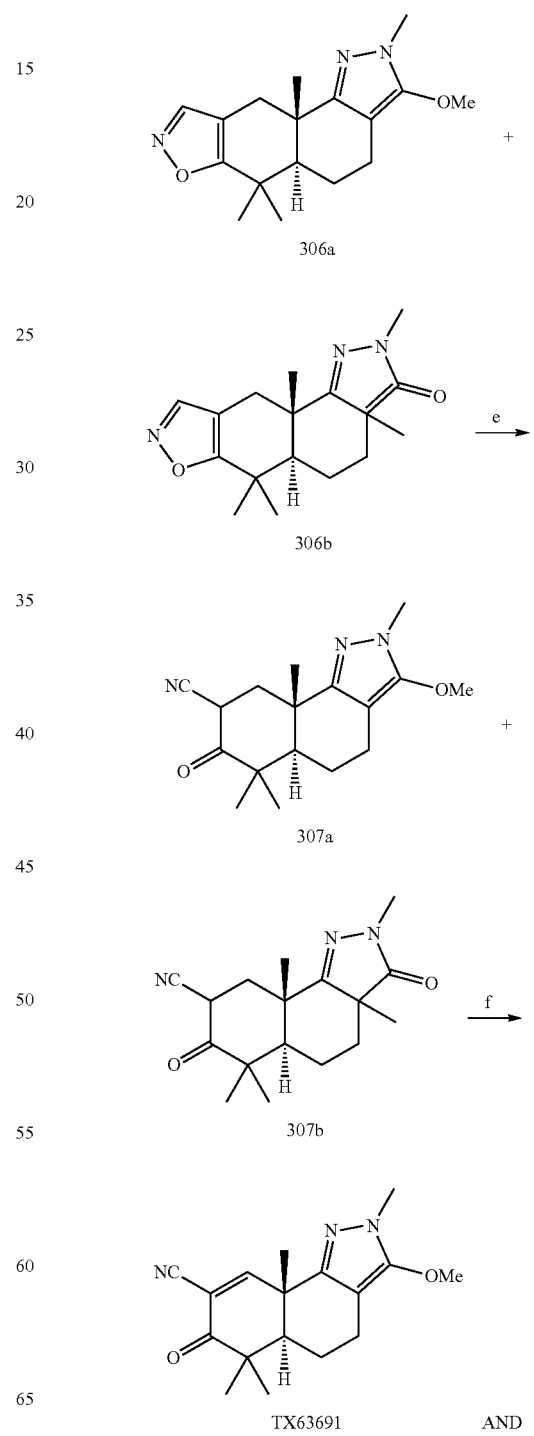
306a
306b
307a
307b
TX63691     AND 189
-continued

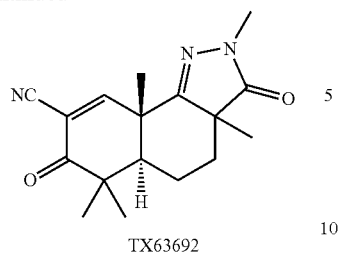
TX63692

Reagents and conditions pertaining to Schemes 55(a) and (b): (a) MeI, K₂CO₃, DMF. 16 hr, 64%; (b) HCl (aq), MeOH, 16 hr, 100%; (c) HCO₂Et, NaOMe, RT, 16 h, 100%; (d) NH₂OH—HCl, EtOH, 50° C., 16 hr, 100%; (e) NaOMe, THF/MeOH, 50° C., 6 Hr, 100%; (f) (i) 1,3-dibromo-5,5-dimethylhydantoin, DMF, 0° C. to RT, 2 h; (ii) pyridine, 55° C., 5 hr, 15%.

Scheme 56:

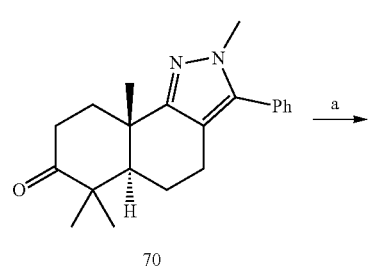
70

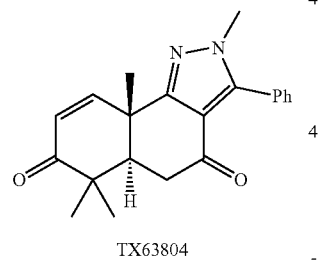
308

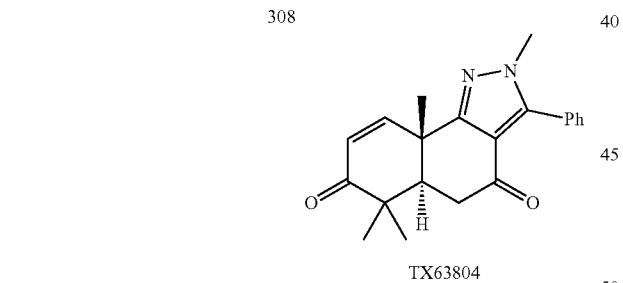
TX63804

Reagents and conditions pertaining to Scheme 56: (a) IBX, DMF, 65° C., 6 hr, 308: 60%, TX63804: 3%.

Scheme 57:

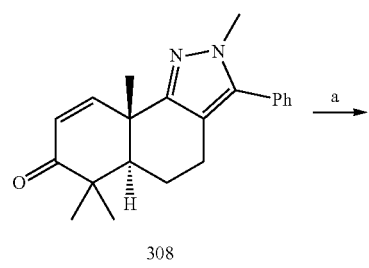
308

190
-continued

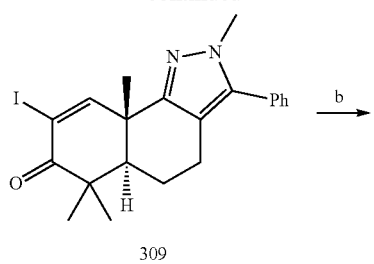
309

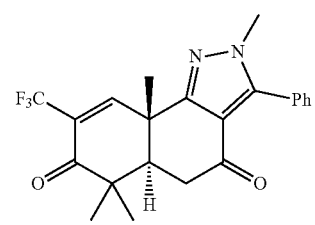
TX63803

Reagents and conditions pertaining to Scheme 57: (a) I₂, THF, Pyridine, 60° C., 16 hr, 100%; (b) FSO₂CF₂CO₂Me, CuI, HMPA, DMF, 70° C., 6 hr, 63%.

Scheme 58(a):

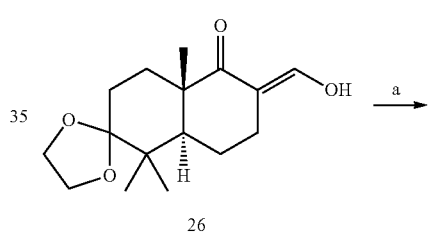
26

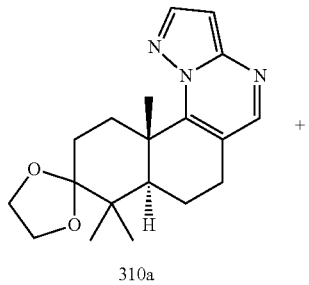
310a

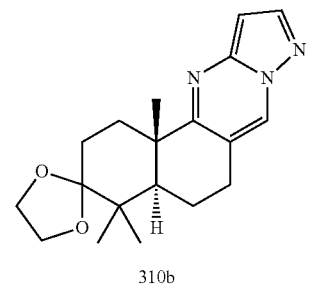
310b

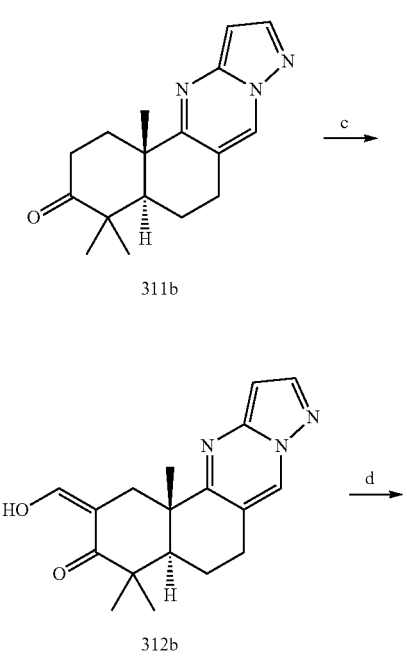
Scheme 59:
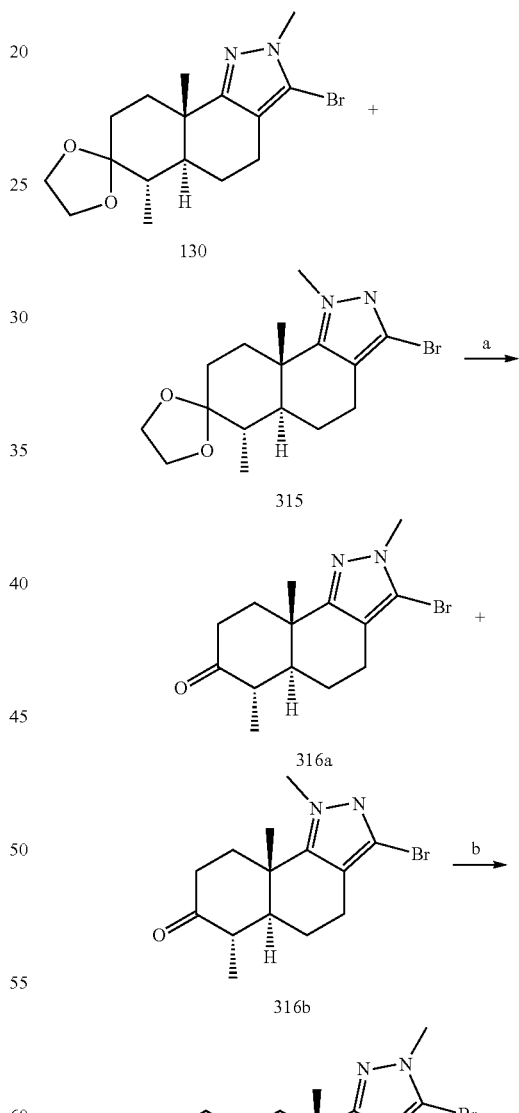

193
-continued
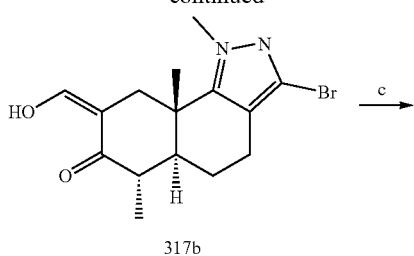
317b
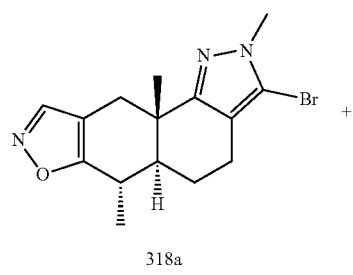
318a
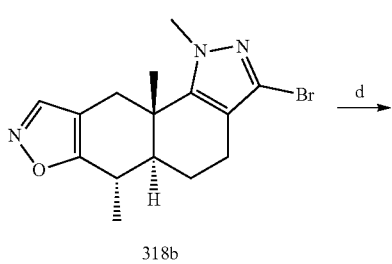
318b
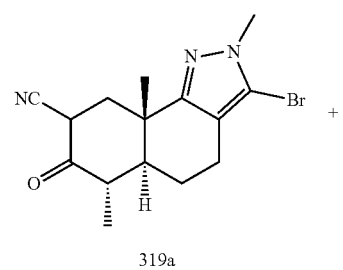
319a
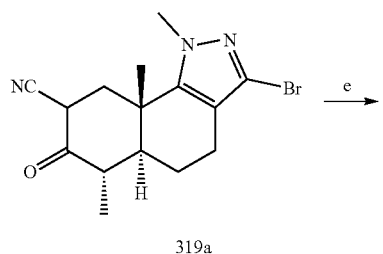
319a
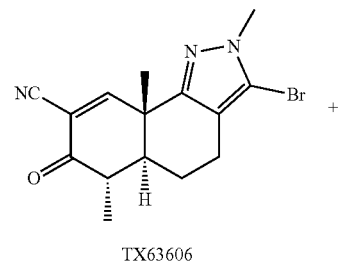
TX63606
194
-continued
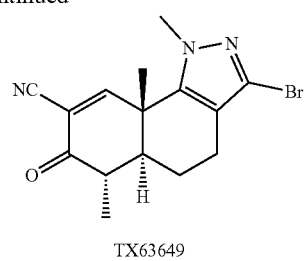
TX63649
Reagents and conditions pertaining to Schemes 59: (a) HCl (aq), MeOH; (b) HCO₂Et, NaOMe, RT; (c) NH₂OH—HCl, EtOH, 50° C.; (d) NaOMe, THF/MeOH, 50° C.; (e) (i) 1,3-dibromo-5,5-dimethylhydantoin, DMF, 0° C. to RT, 2 h; (ii) pyridine, 55° C., 5 hr, TX63606: 69%, TX63649: 2%.
Scheme 60:
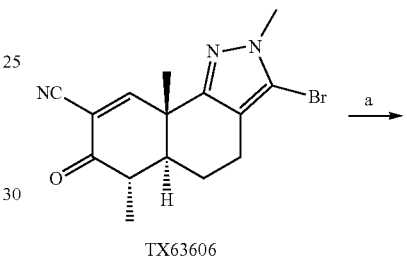
TX63606
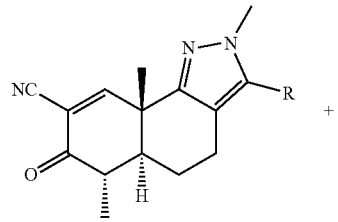
a: TX63650 R = Ph (3-Me)
b: TX63659 R = Ph (3-F)
c: TX63664 R = Ph (3-OMe)
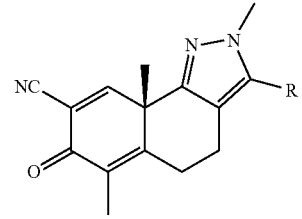
a: TX63656 R = Ph (3-Me)
b: TX63663 R = Ph (3-F)
Reagents and conditions pertaining to Scheme 60: (a) R—B(OH)₂, K₃PO₄, Pd(PPh₃)₄, DEM, 80° C., 16 hr.

Scheme 61:

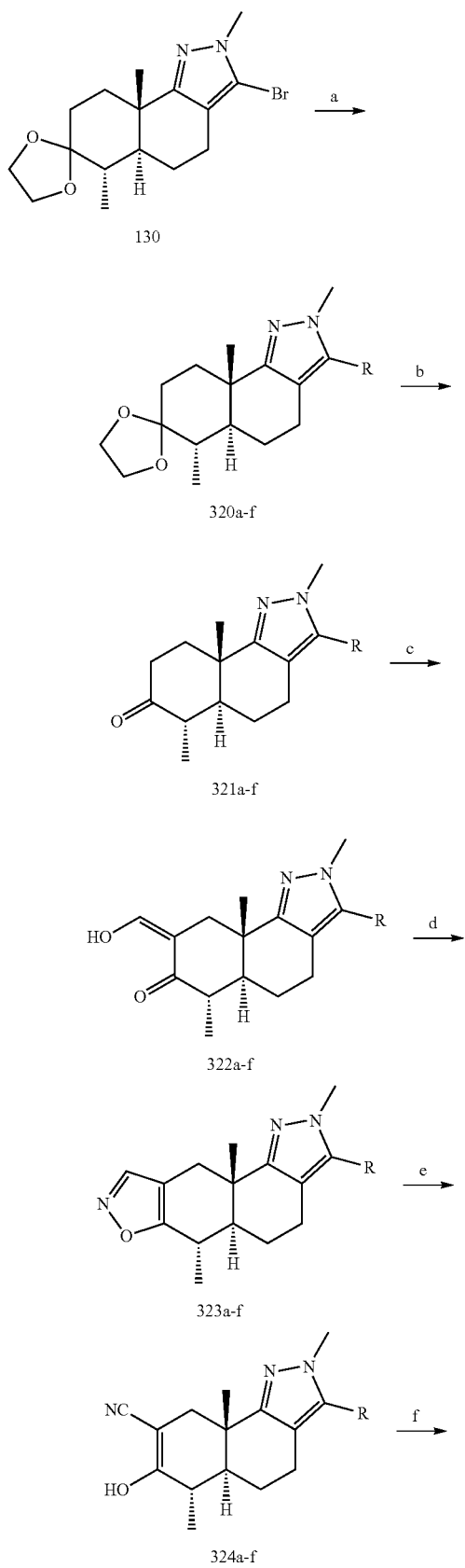

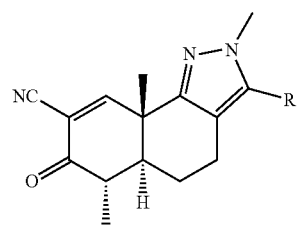

a: TX63690 R = 4-pyrazole (1-Me)
b: TX63721 R = Ph (2-F)
c: TX63720 R = 4-pyridyl
d: TX63722 R = 3-pyridyl
e: TX63748 R = 5-pyrimidinyl Reagents and conditions pertaining to Schemes 61: (a) R—B(OH)$_2$, K$_3$PO$_4$, PPh$_3$, Pd(OAc)$_2$ or Pd(PPh$_3$)$_4$, DME, 80° C., 16 hr; (b) HCl (aq), MeOH; (c) HCO$_2$Et, NaOMe, RT; (d) NH$_2$OH—HCl, EtOH, 50° C., (e) NaOMe, THF/MeOH, 50° C.; (f) (i) 1,3-dibromo-5,5-dimethylhydantoin, DMF, 0° C. to RT, 2 h; (ii) pyridine, 55° C., 5 hr.

Scheme 62:

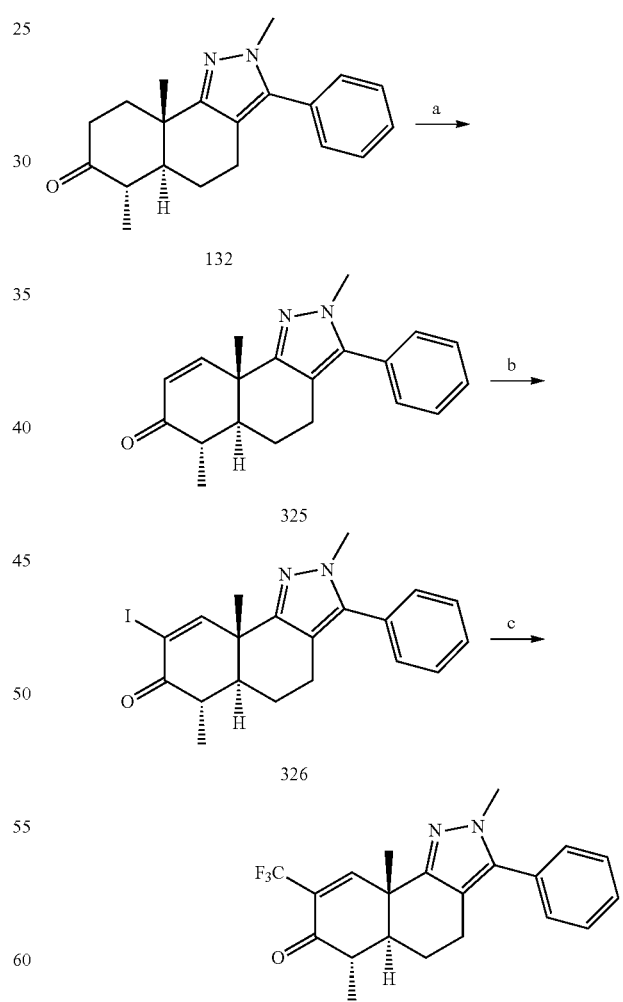

Reagents and conditions pertaining to Schemes 62: (a) IBX, DMSO, 65° C., 7 hr, 43%; (b) I$_2$, Pyridine, THF, 60° C., 30 hr, 100%; (c) FSO$_2$CF$_2$CO$_2$Me, CuI, HMPA, DMF, 70° C., 6 hr, 42%.

Scheme 63:
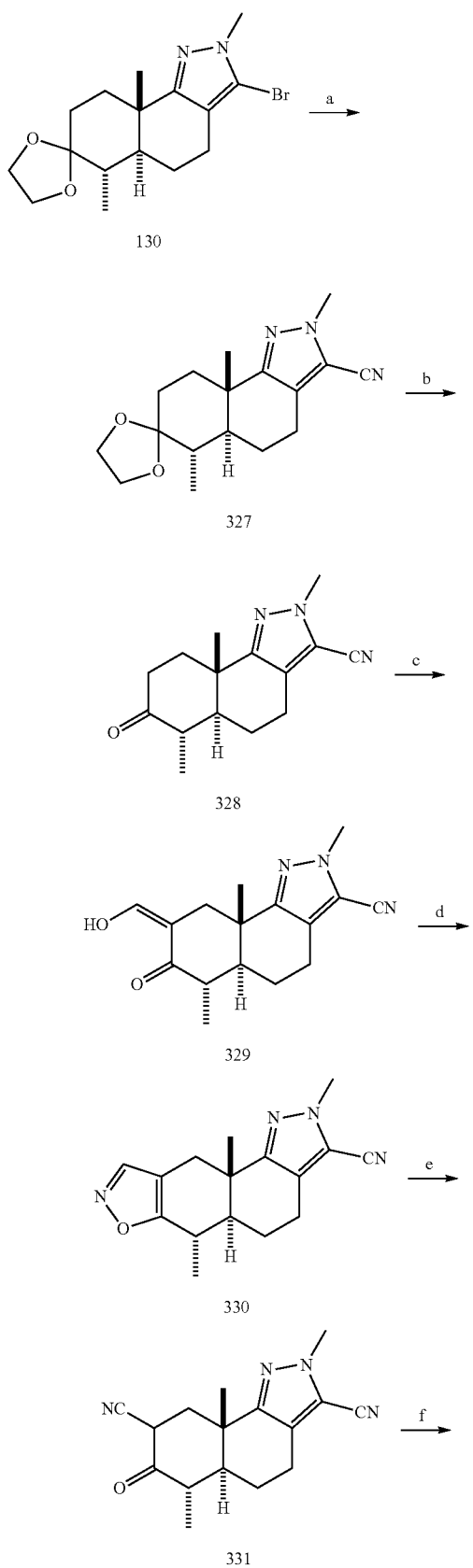
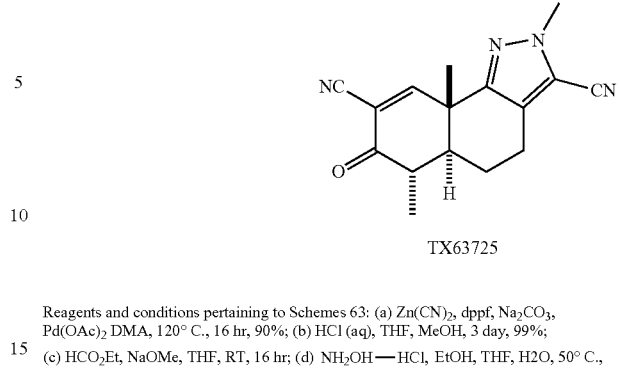
Reagents and conditions pertaining to Schemes 63: (a) Zn(CN)$_2$, dppf, Na$_2$CO$_3$, Pd(OAc)$_2$ DMA, 120° C., 16 hr, 90%; (b) HCl (aq), THF, MeOH, 3 day, 99%; (c) HCO$_2$Et, NaOMe, THF, RT, 16 hr; (d) NH$_2$OH—HCl, EtOH, THF, H2O, 50° C., 16 hr, 100%; (e) NaOMe, THF/MeOH, 50° C., 4 hr, 72%; (f) (i) 1,3-dibromo-5,5-dimethylhydantoin, DMF, 0° C. to RT, 2 h; (ii) pyridine, 55° C., 5 hr, 74%.
Scheme 64:
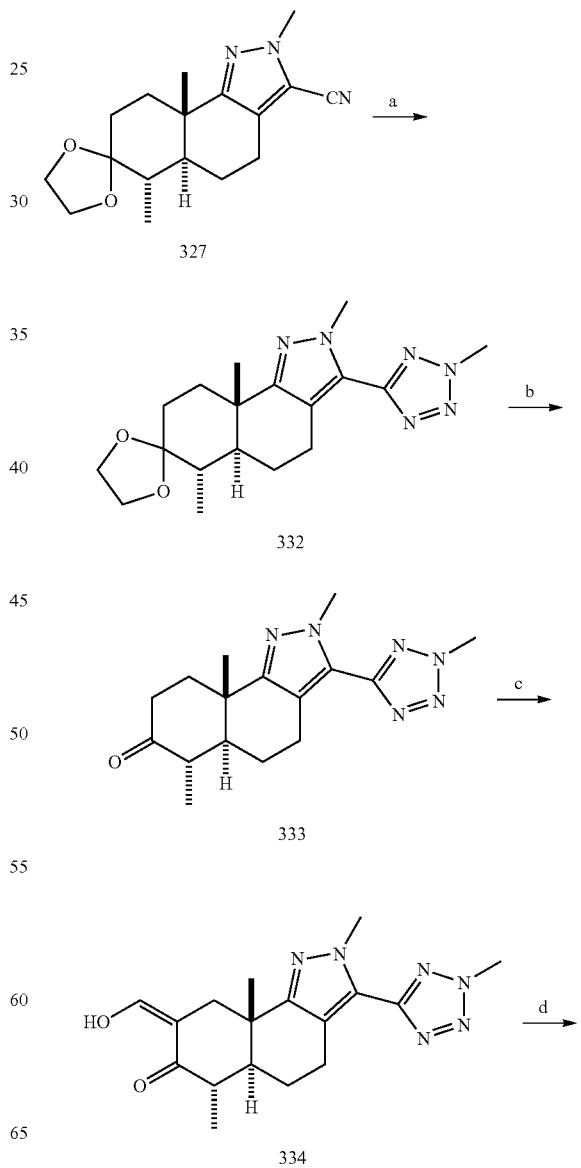

199
-continued

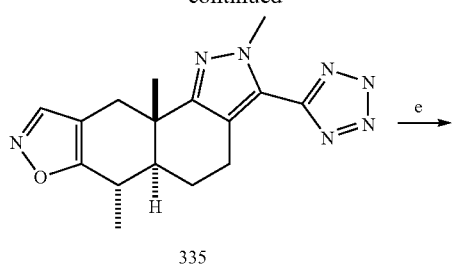
335

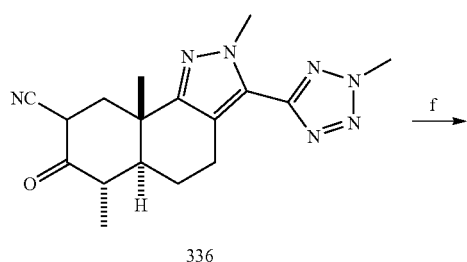
336

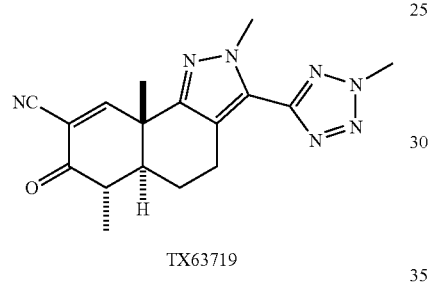
TX63719

Reagents and conditions pertaining to Schemes 64: (a) TMSN₃, Bu₂SnO, toluene, 130° C., 16 hr, 43%; (b) HCl (aq), THF, 16 hr, 97%; (c) HCO₂Et, NaOMe, THF, RT, 16 hr, 100%; (d) NH₂OH—HCl, EtOH, THF, 50° C., 16 hr, 90%; (e) NaOMe, THF/MeOH, 50° C., 4 hr, 86%; (f) (i) 1,3-dibromo-5,5-dimethylhydantoin, DMF, 0° C. to RT, 2 h; (ii) pyridine, 55° C., 5 hr, 70%.

Scheme 65:

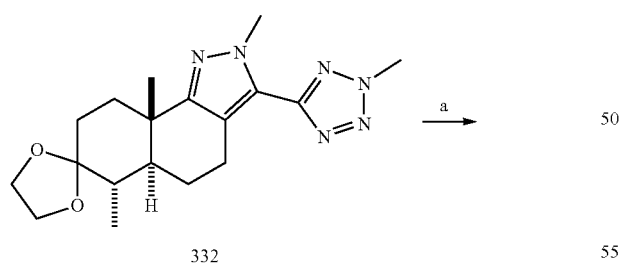
332

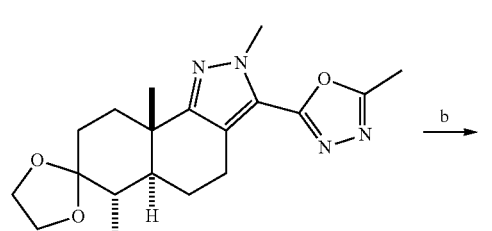
337

200
-continued

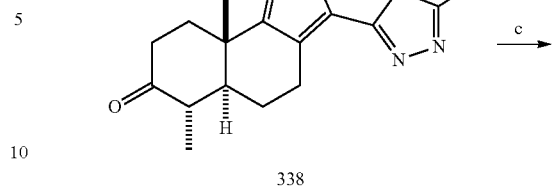
338

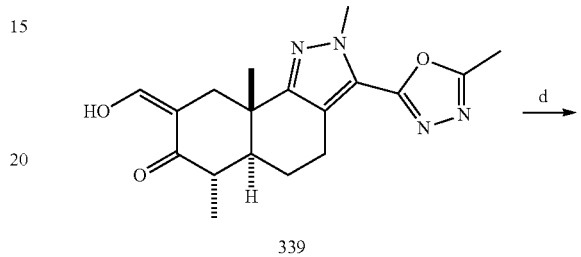
339

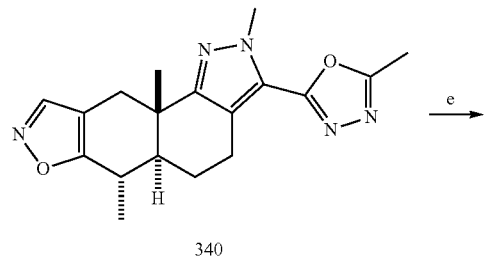
340

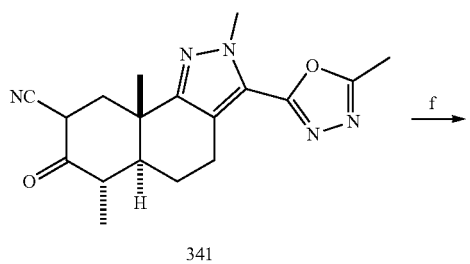
341

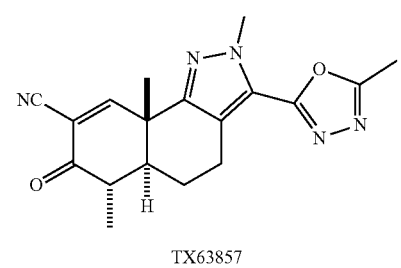
TX63857

Reagents and conditions pertaining to Schemes 65: (a) Ac₂O, Pyridine, 110° C., 3 hr; (b) HCl (aq), THF, 3 day, 20%; (c) HCO₂Et, NaOMe, THF, RT, 16 hr, 100%; (d) NH₂OH—HCl, EtOH, 50° C., 4 hr, then TsOH, benzene, reflux, 7 hr, 47%; (e) NaOMe, THF/EtOH, 50° C., 4 hr, 100%; (f) (i) 1,3-dibromo-5,5-dimethylhydantoin, DMF, 0° C. to RT, 2 h: (ii) pyridine, 55° C., 5 hr, 46%.

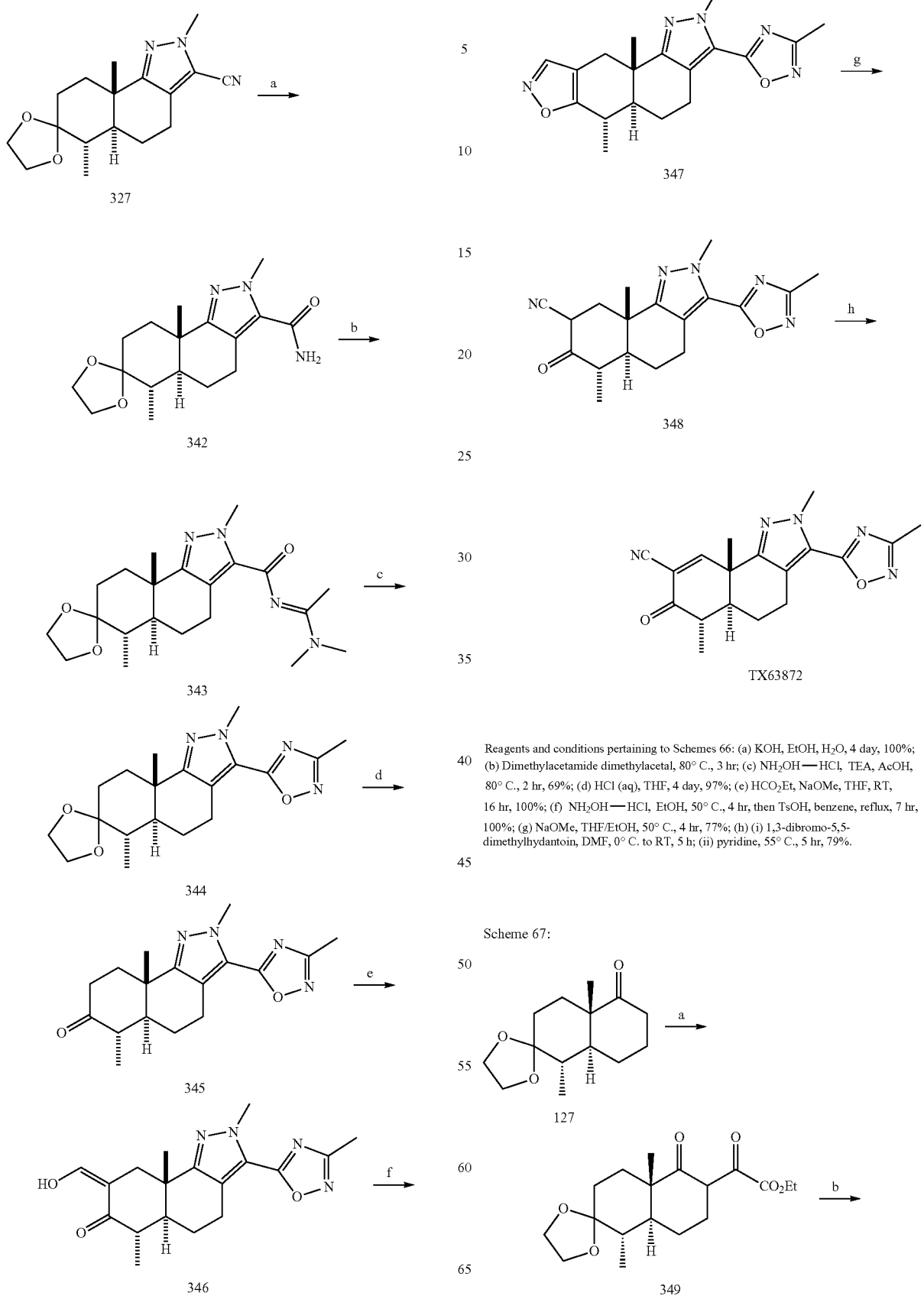

203
-continued
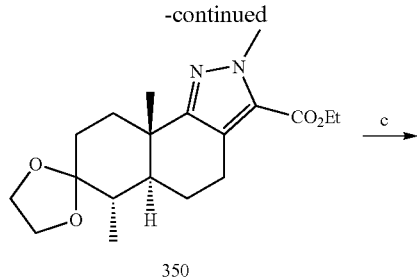
350
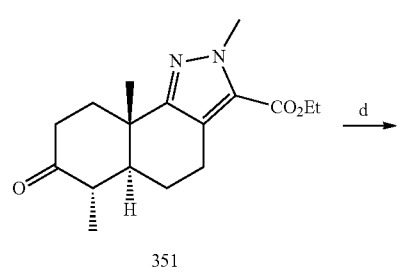
351
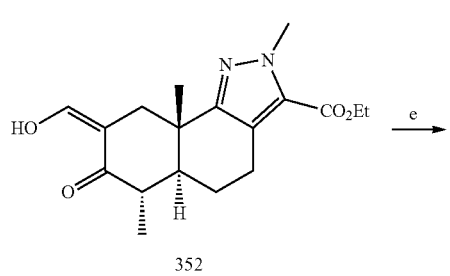
352
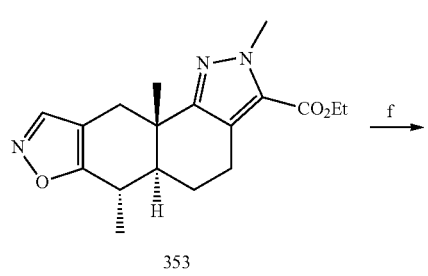
353
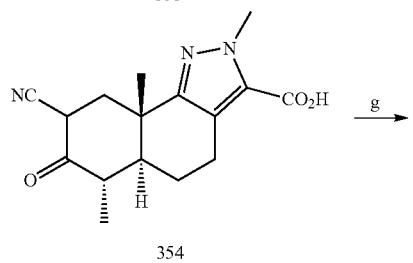
354
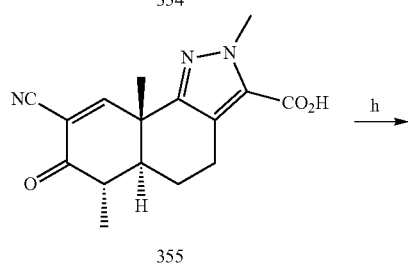
355
204
-continued
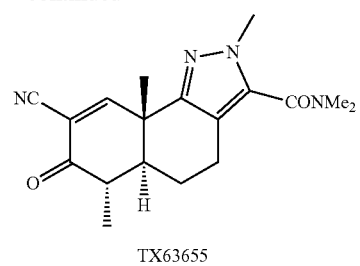
TX63655
Reagents and conditions pertaining to Schemes 67: (a) Diethyl oxalate, NaH, THF, reflux, 16 hr, 100%; (b) MeNHNH$_2$, EtOH, 60° C., 16 hr, 19%; (c) HCl (aq), THF, 16 hr, 73%; (d) HCO$_2$Et, NaOMe, THF, RT, 16 hr, 100%; (e) NH$_2$OH—HCl, EtOH, 50° C., 16 hr, 100%; (f) NaOMe, THF/MeOH, 50° C., 6 hr, 100%; (g) (i) 1,3-dibromo-5,5-dimethylhydantoin, DMF, 0° C. to RT, 2 h; (ii) pyridine, 55° C., 5 hr, 80%; (h) (COCl)$_2$, THF, RT, 3 hr, 35%.
Scheme 68:
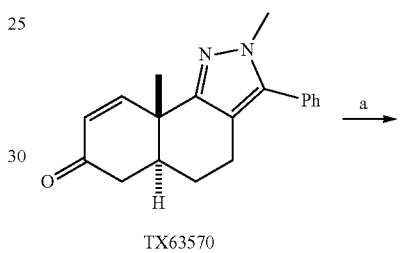
TX63570
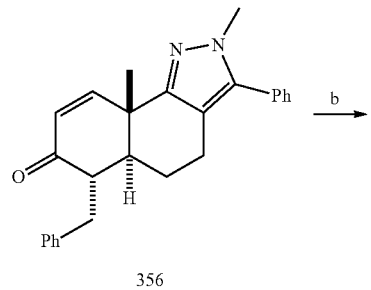
356
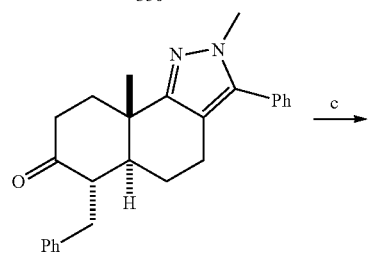
357
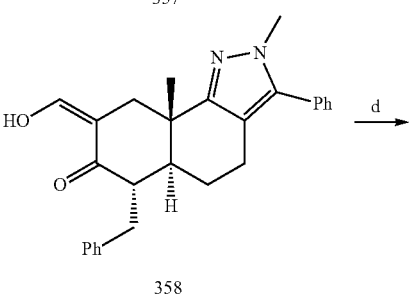
358

205
-continued

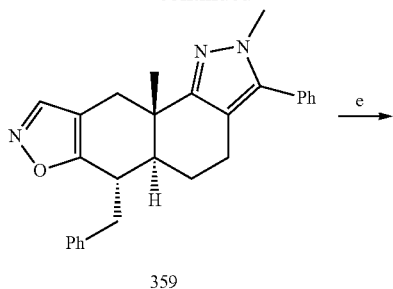

359

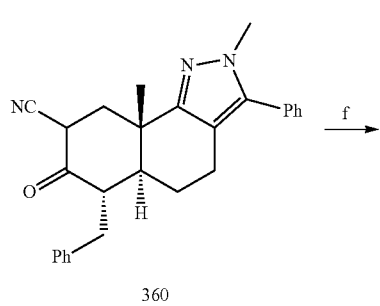

360

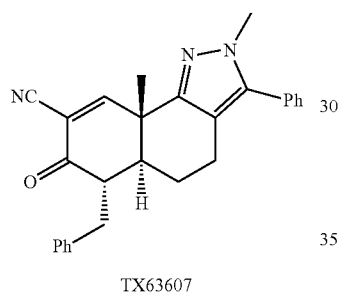

TX63607

Reagents and conditions pertaining to Schemes 68: (a) n-BuLi, DIPA, BnBr, THF, -78° C. to RT, 45%; (b) H₂, Pd/C, THF, 48 hr; (c) HCO₂Et, NaOMe, THF, RT, 16 hr, 98%; (d) NH₂OH—HCl, EtOH, 50° C., 16 hr, 100%; (e) NaOMe, THF/MeOH, 50° C., 9 hr, 100%; (f) (i) 1,3-dibromo-5,5-dimethylhydantoin, DMF, 0° C. to RT, 2 h; (ii) pyridine, 50° C., 16 hr, 39%.

Scheme 69:

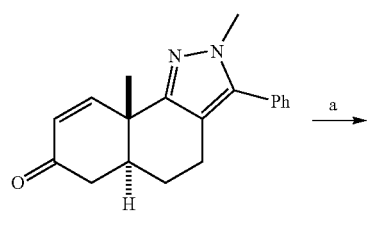

TX63570

361

206
-continued

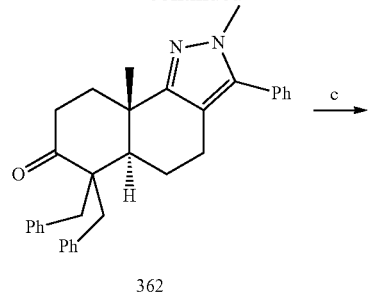

362

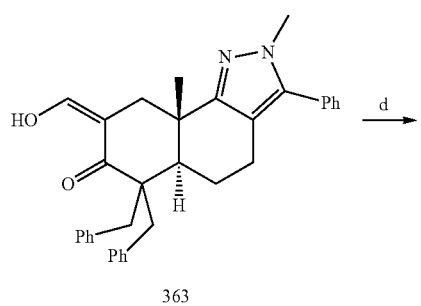

363

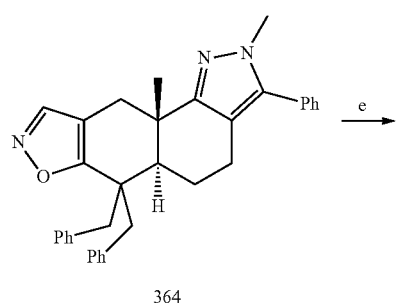

364

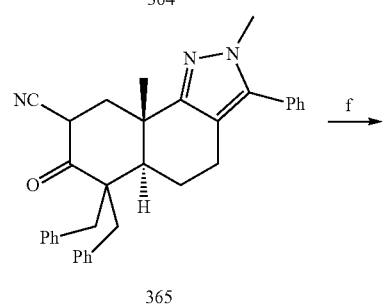

365

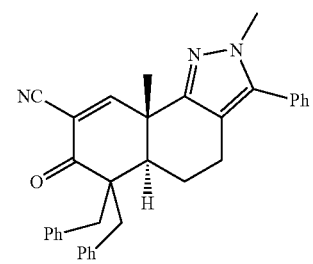

TX63601

Reagents and conditions pertaining to Schemes 69: (a) KHMDS, THF, BnBr, -60° C. to RT, 15%; (b) H₂, Pd/C, THF, 48 hr; (c) HCO₂Et, NaOMe, THF, RT, 16 hr, 95%; (d) NH₂OH—HCl, EtOH, 50° C., 16 hr, 100%; (e) NaOMe, THF/MeOH, 50° C., 9 hr, 98%; (f) (i) 1,3-dibromo-5,5-dimethylhydantoin, DMF, 0° C. to RT, 2 h; (ii) pyridine, 50° C., 16 hr, 28%.

Scheme 70:
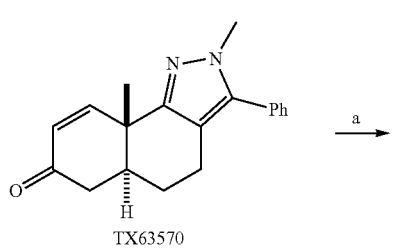
TX63570
a →
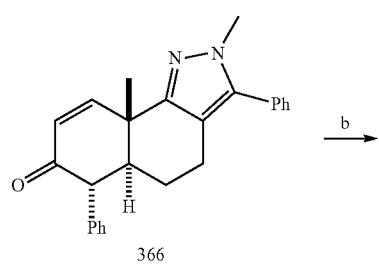
366
b →
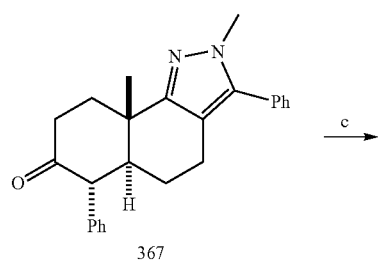
367
c →
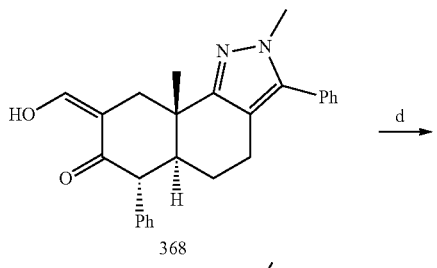
368
d →
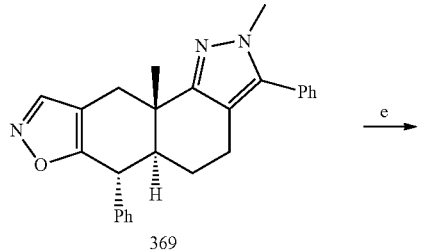
369
e →
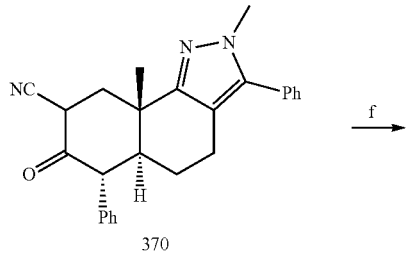
370
f →
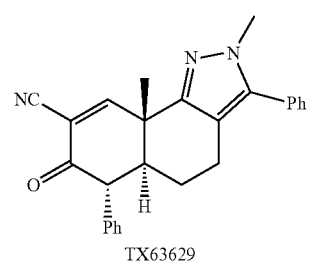
TX63629
Reagents and conditions pertaining to Schemes 70: (a) DIPA, n-BuLi, THF, Ph₂ICl, -78° C. to RT, 31%; (b) H₂, Pd/C, THF, 48 hr; (c) HCO₂OEt, NaOMe, THF, RT, 16 hr; (d) NH₂OH—HCl, EtOH, 50° C., 16 hr; (e) NaOMe, THF/MeOH, 50° C., 9 hr, 91%; (f) (i) 1,3-dibromo-5,5-dimethylhydantoin, DMF, 0° C. to RT, 2 h; (ii) pyridine, 60° C., 4 hr, 79%.
Scheme 71:
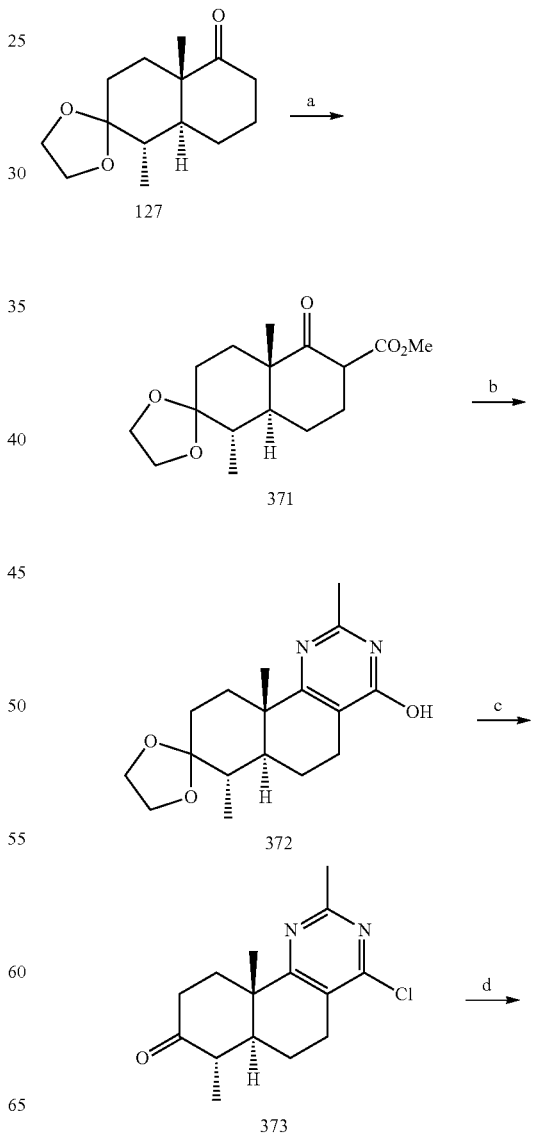

209
-continued
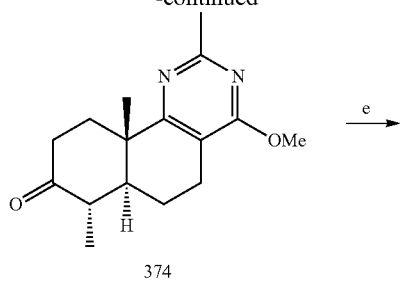
374
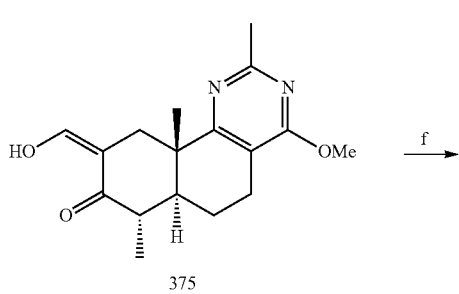
375
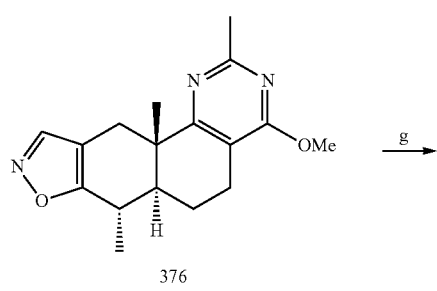
376
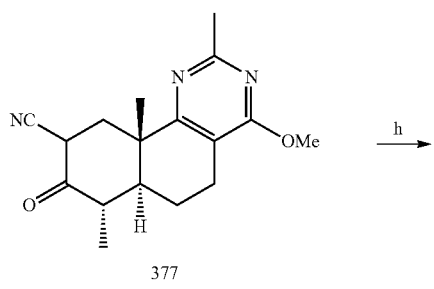
377
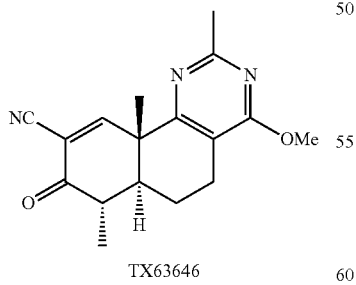
TX63646
Reagents and conditions pertaining to Schemes 71: (a) Dimethyl carbonate, NaH, THF, reflux, 16 hr; (b) Acetimidamide hydrochloride, piperidine, iPrOH, reflux, 48 hr, 42%; (c) POCl$_3$, DMF, 140° C., 3 hr, 100%; (d) NaOMe, MeOH, 50° C., 3 hr, 44%; (e) HCO$_2$Et, NaOMe, THF, RT, 16 hr, 100%; (f) NH$_2$OH—HCl, EtOH, 50° C., 16 hr, 100%; (g) NaOMe, THF/MeOH, 50° C., 9 hr, 100%; (h) (i) 1,3-dibromo-5,5-dimethyl-hydantoin, DMF, 0° C., to RT, 2 h; (ii) pyridine, 50° C., 16 hr, 30%.
210
Scheme 72:
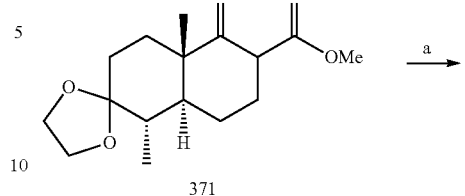
371
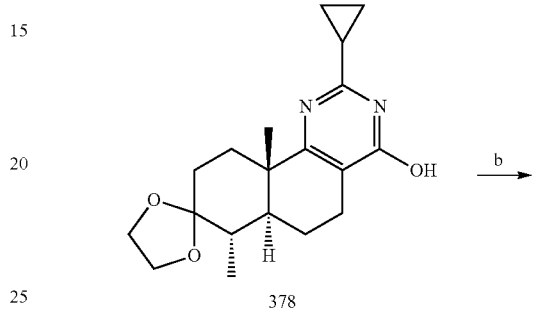
378
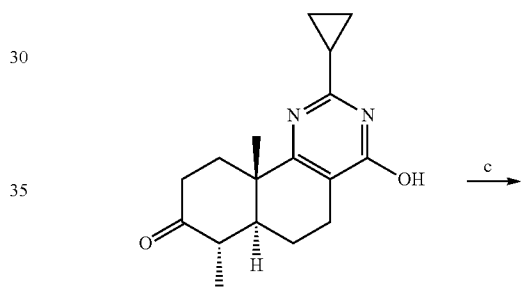
379
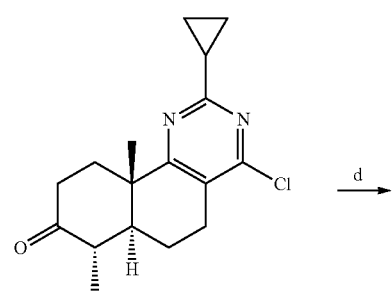
380
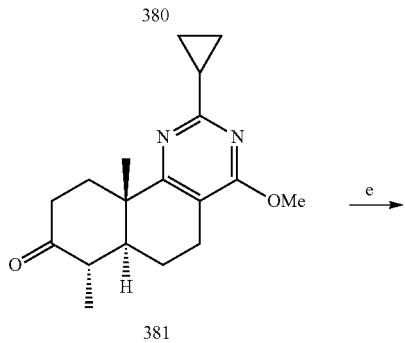
381

211
-continued
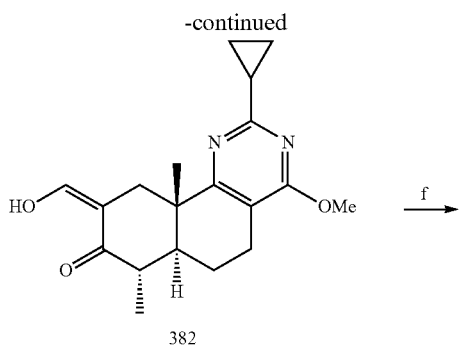
382
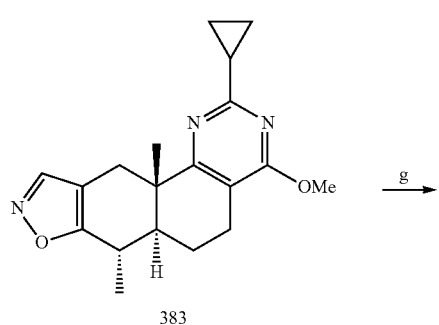
383
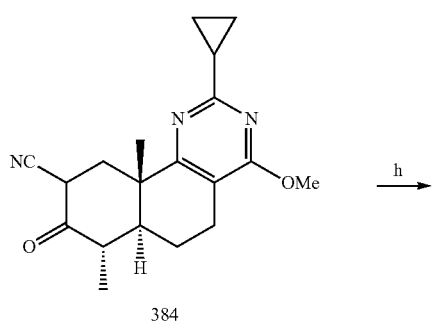
384
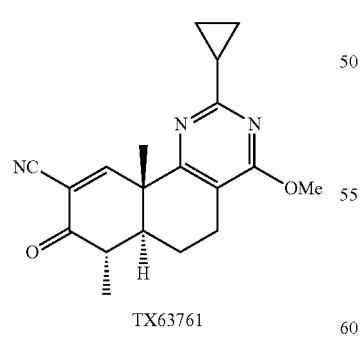
TX63761
Reagents and conditions pertaining to Schemes 72: (a) Cyclopropanecarboximidamide hydrochloride, piperidine, iPrOH, 90° C., 72 hr, 77%; (b) HCl (aq), MeOH, iPrOH, RT, 16 hr, 94%; (c) POCl₃, DIPEA, benzene, 80° C., 16 hr, 94%; (d) NaOMe, MeOH, 50° C., 2 hr, 100%; (e) HCO₂Et, NaOMe, THF, RT, 16 hr, 100%; (f) NH₂OH—HCl, EtOH, 50° C., 2 hr, then RT, 16 hr, 90%; (g) NaOMe, MeOH, RT, 16 hr, 41%; (h) (i) 1,3-dibromo-5,5-dimethylhydantoin, DMF, 0° C., to RT, 2 h; (ii) pyridine, 50° C., 3 hr, 23%.
212
Scheme 73:
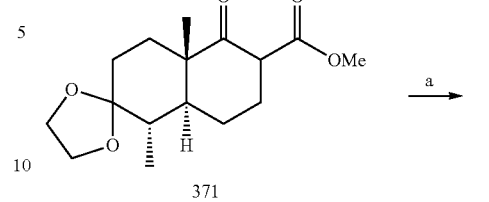
371
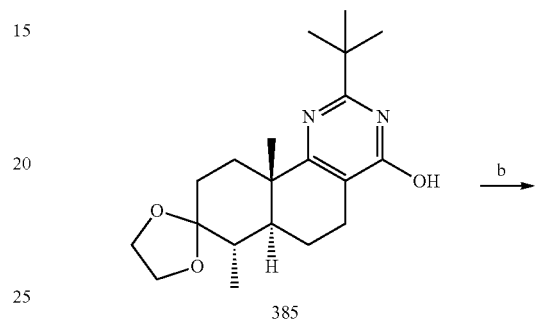
385
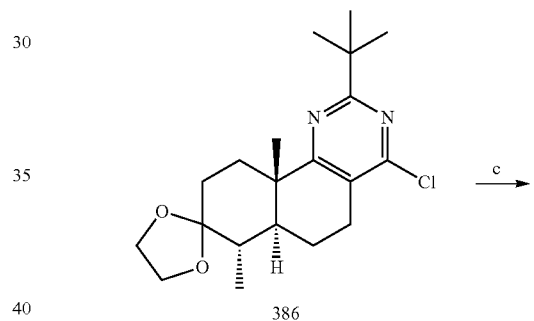
386
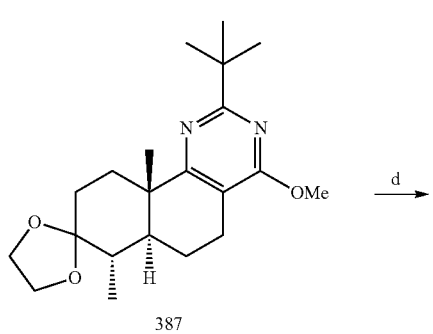
387
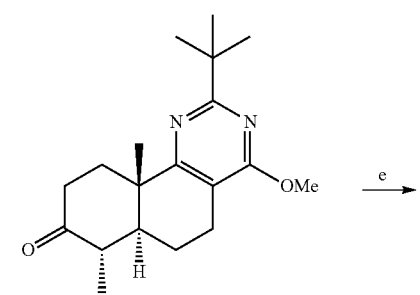
388

213
-continued
214
Scheme 74:
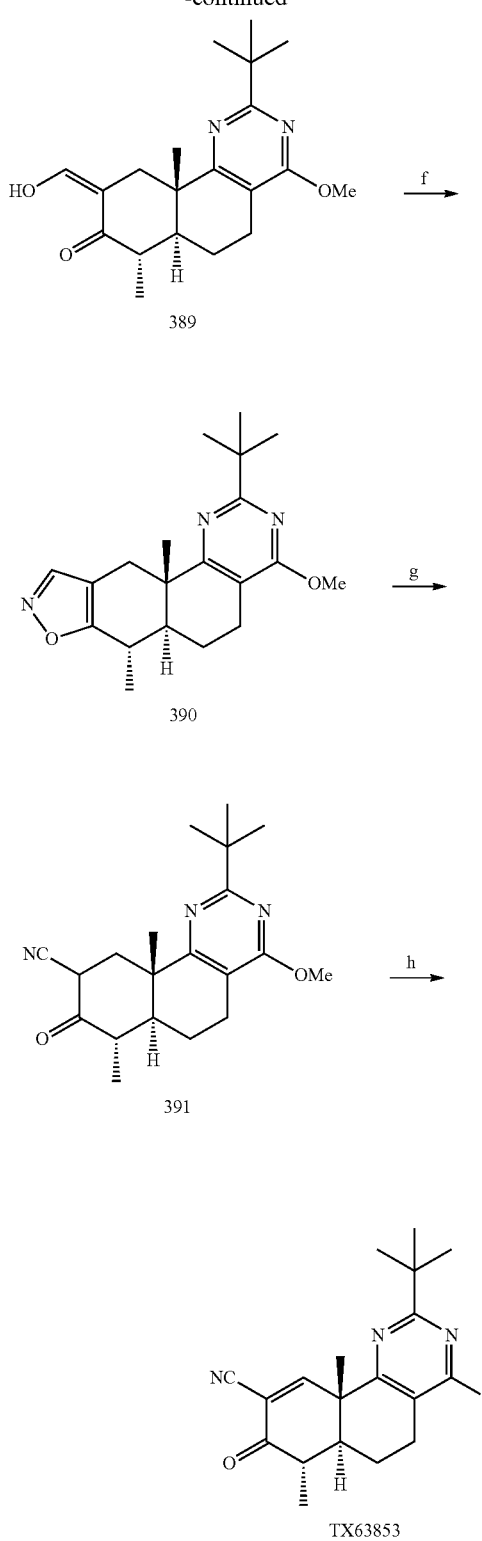
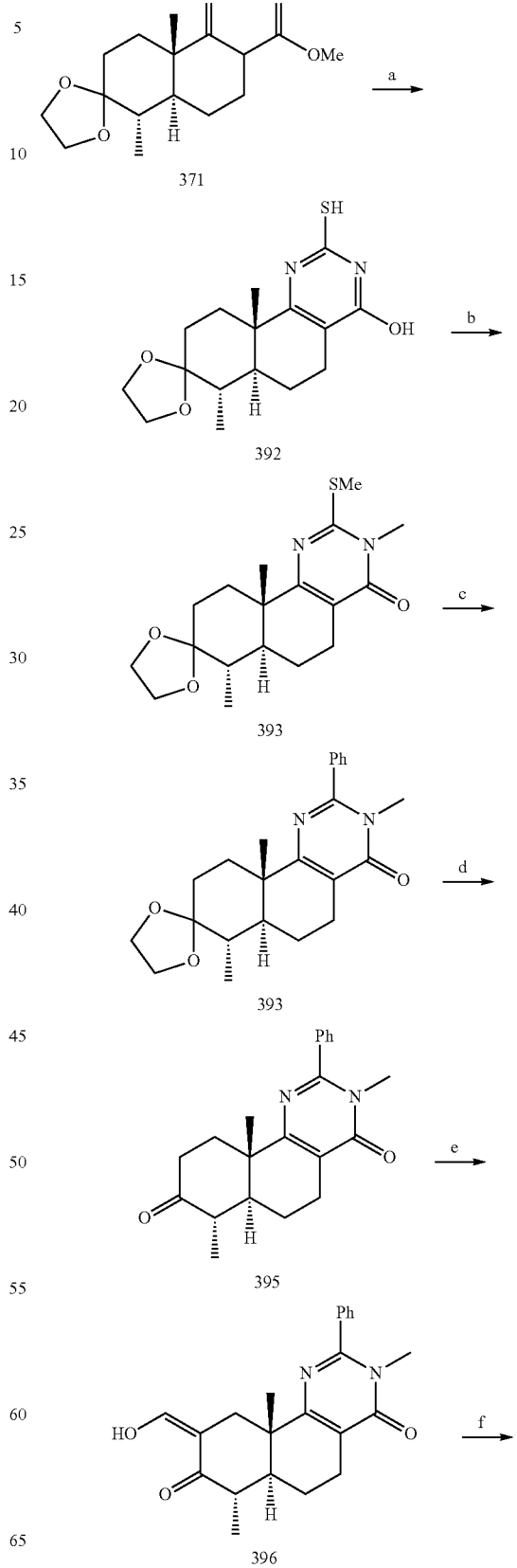
Reagents and conditions pertaining to Schemes 73: (a) 2,2-dimethylpropionamidine hydrochloride, piperidine, nBuOH, 100° C., 72 hr, 60%; (b) POCl$_3$, DIPEA, benzene, 90° C., 2 hr then RT, 16 hr, 93%: (c) NaOMe, MeOH, 50° C., 2 hr, 100%; (d) HCl (aq), MeOH, iPrOH, RT, 16 hr, 92% (e) HCO$_2$Et, NaOMe, MeOH, RT, 16 hr, 97%; (f) NH$_2$OH—HCl, EtOH, 50° C., 2 hr, then RT, 16 hr, 100%; (g) NaOMe, MeOH, RT, 16 hr, 50%; (h) (i) 1,3-dibromo-5,5-dimethylhydantoin, DMF, 0° C., to RT, 2 h; (ii) pyridine, 50° C., 2 hr, 38%.

215
-continued
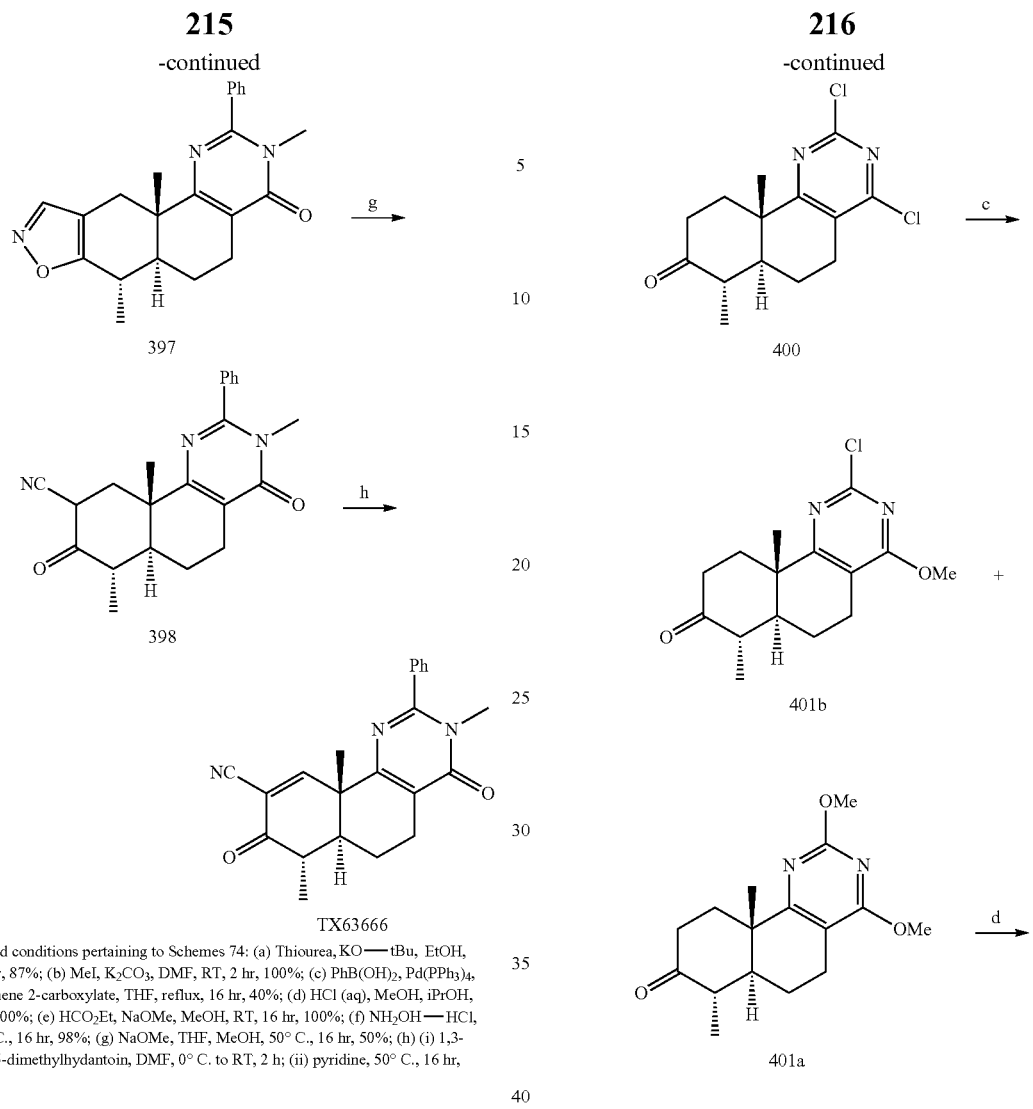
Reagents and conditions pertaining to Schemes 74: (a) Thiourea, KO—tBu, EtOH, reflux, 16 hr, 87%; (b) MeI, K$_2$CO$_3$, DMF, RT, 2 hr, 100%; (c) PhB(OH)$_2$, Pd(PPh$_3$)$_4$, Cu(I) thiophene 2-carboxylate, THF, reflux, 16 hr, 40%; (d) HCl (aq), MeOH, iPrOH, RT, 16 hr, 100%; (e) HCO$_2$Et, NaOMe, MeOH, RT, 16 hr, 100%; (f) NH$_2$OH—HCl, EtOH, 50° C., 16 hr, 98%; (g) NaOMe, THF, MeOH, 50° C., 16 hr, 50%; (h) (i) 1,3-dibromo-5,5-dimethylhydantoin, DMF, 0° C. to RT, 2 hr; (ii) pyridine, 50° C., 16 hr, 62%.
Scheme 75 (a):
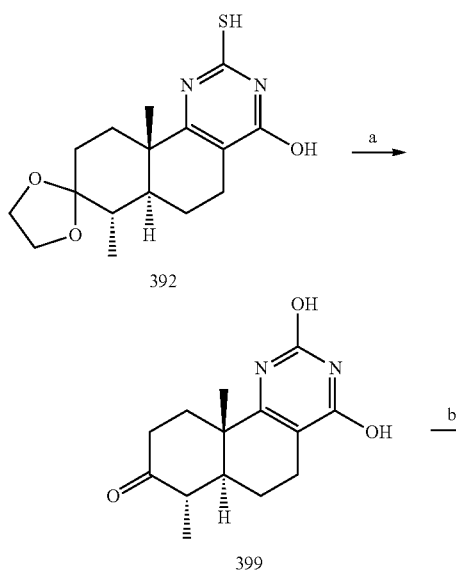
Scheme 75 (b):
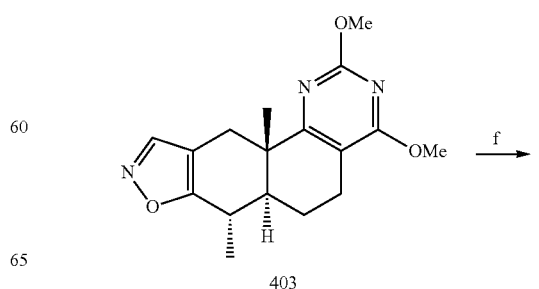

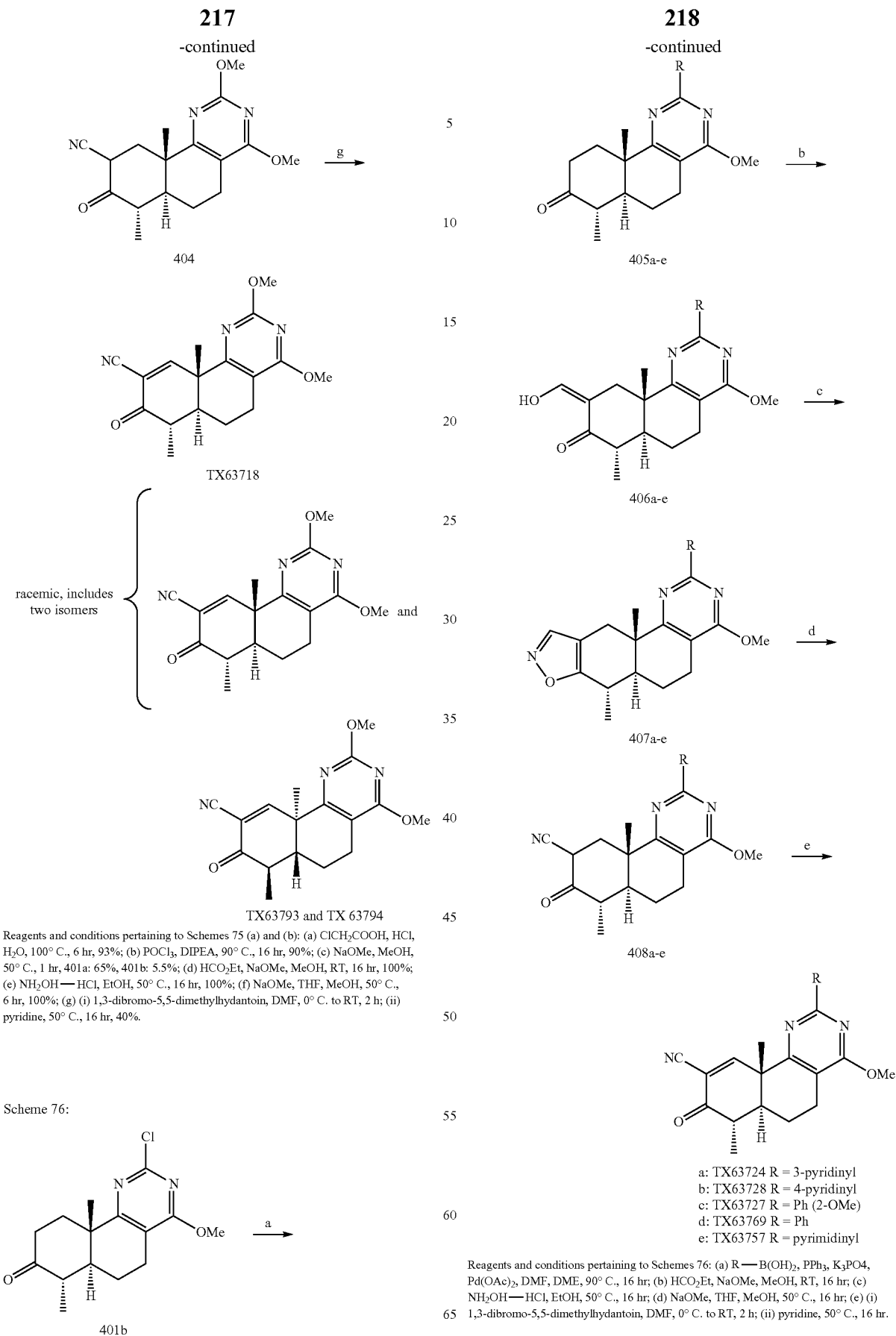

Scheme 77:
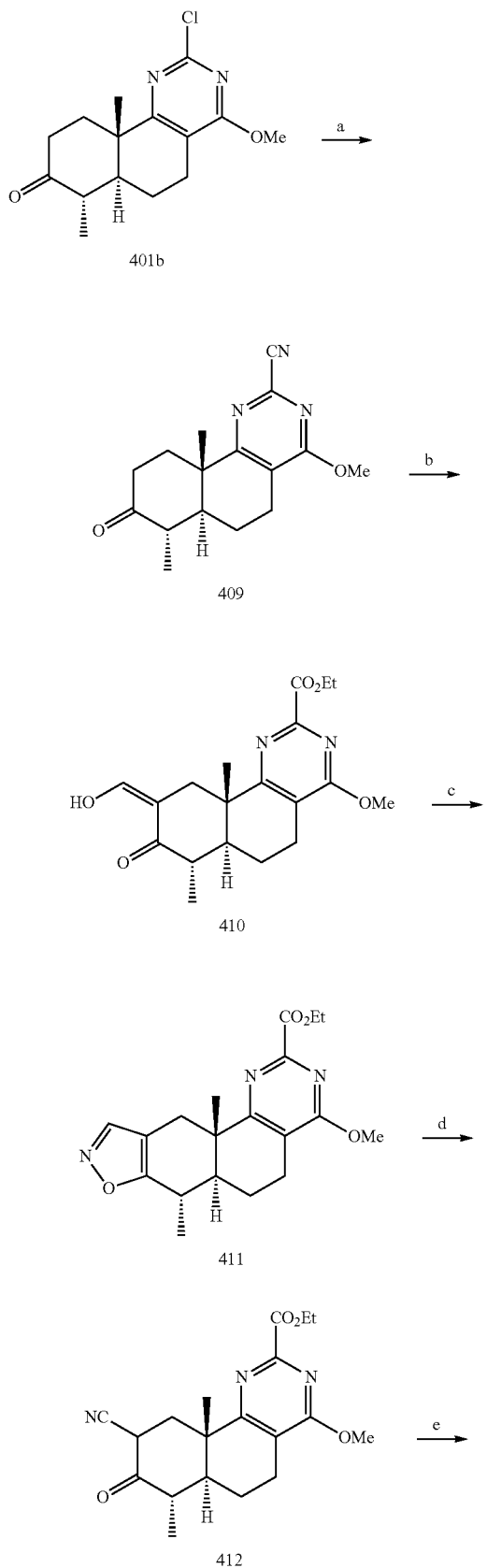
Reagents and conditions pertaining to Schemes 77: (a) Zn(CN)$_2$, dppf, Na$_2$CO$_3$, DMAc, 120° C., 16 hr, 40%; (b) HCO$_2$Et, NaOMe, MeOH, RT, 16 hr; (c) NH$_2$OH—HCl, EtOH, 50° C., 16 hr, 30%; (d) TEA, MeCN, 85° C., 16 hr; (e) (i) 1,3-dibromo-5,5-dimethylhydantoin, DMF, 0° C. to RT, 2 h; (ii) pyridine, 50° C., 16 hr, 41%.
Scheme 78:
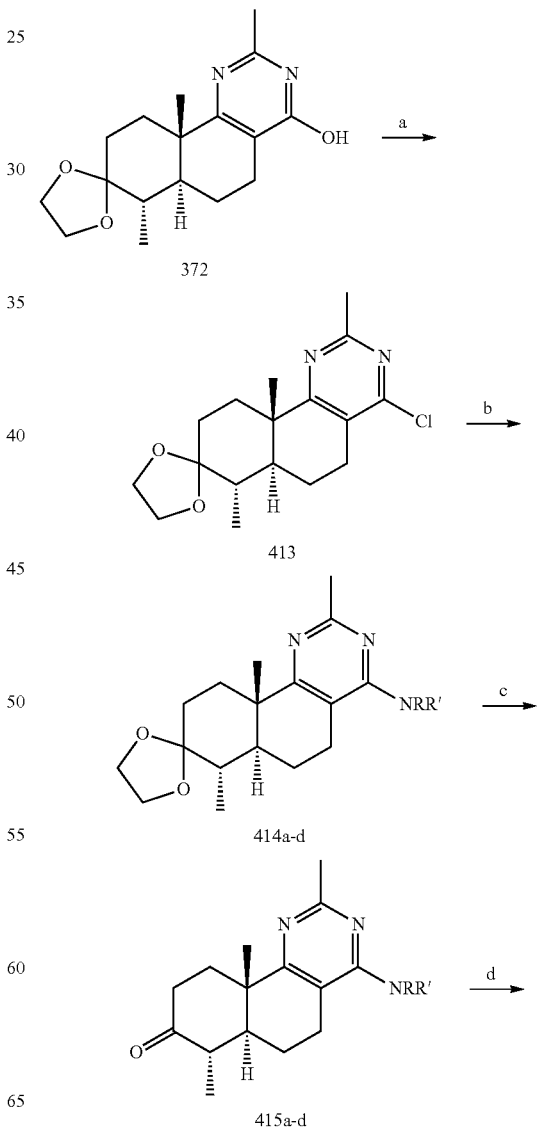

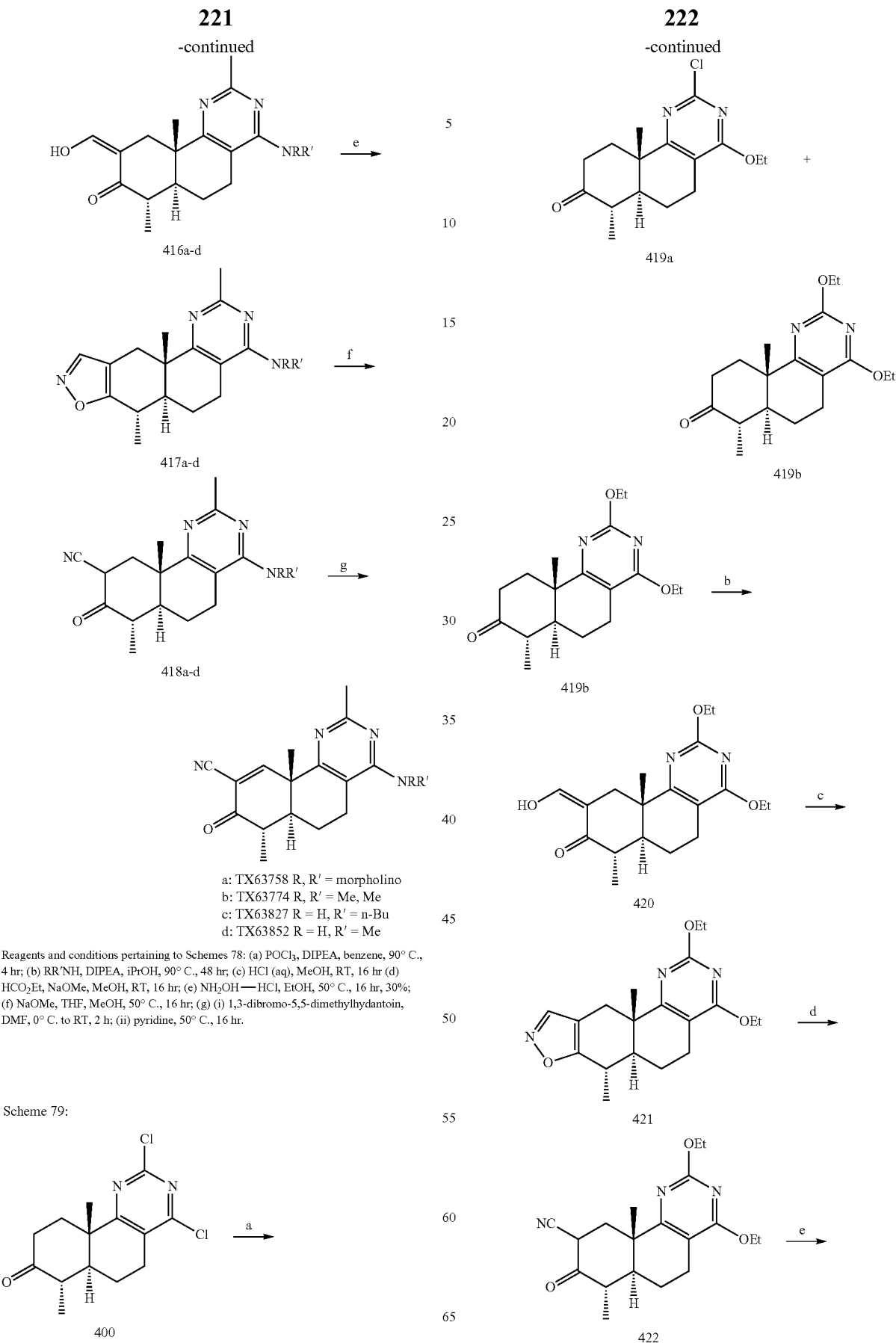
a: TX63758 R, R' = morpholino
b: TX63774 R, R' = Me, Me
c: TX63827 R = H, R' = n-Bu
d: TX63852 R = H, R' = Me
Reagents and conditions pertaining to Schemes 78: (a) POCl₃, DIPEA, benzene, 90° C., 4 hr; (b) RR'NH, DIPEA, iPrOH, 90° C., 48 hr; (c) HCl (aq), MeOH, RT, 16 hr (d) HCO₂Et, NaOMe, MeOH, RT, 16 hr; (e) NH₂OH—HCl, EtOH, 50° C., 16 hr, 30%; (f) NaOMe, THF, MeOH, 50° C., 16 hr; (g) (i) 1,3-dibromo-5,5-dimethylhydantoin, DMF, 0° C. to RT, 2 h; (ii) pyridine, 50° C., 16 hr.
Scheme 79:

223
-continued

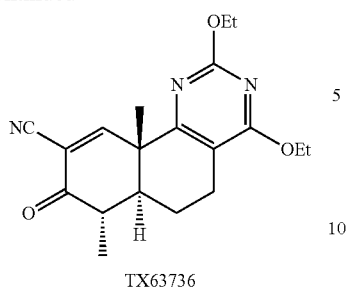

TX63736

Reagents and conditions pertaining to Schemes 79: (a) Na, EtOH, 50° C., 3 hr, 35%; (b) HCO₂Et, Na, EtOH, RT, 16 hr, 92%; (c) NH₂OH—HCl, EtOH, 50° C., 16 hr, 30%; (d) NaOMe, THF, MeOH, 50° C., 16 hr; (e) (i) 1,3-dibromo-5,5-dimethylhydantoin, DMF, 0° C. to RT, 2 h; (ii) pyridine, 50° C., 16 hr, 12%.

Scheme 80:

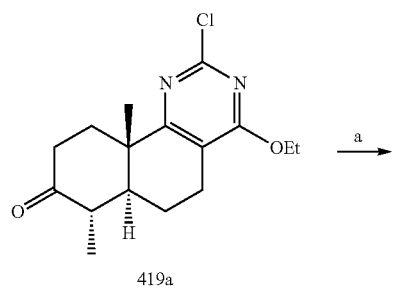

419a

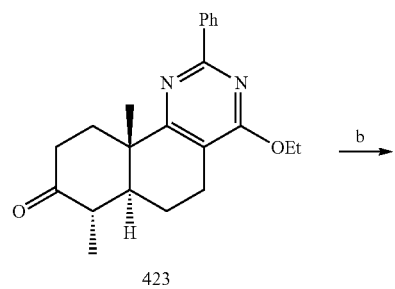

423

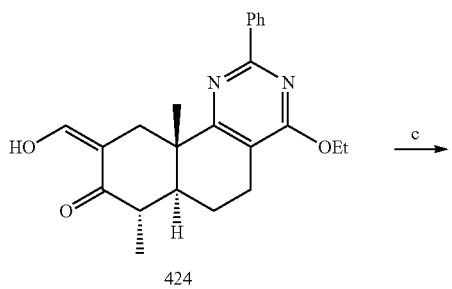

424

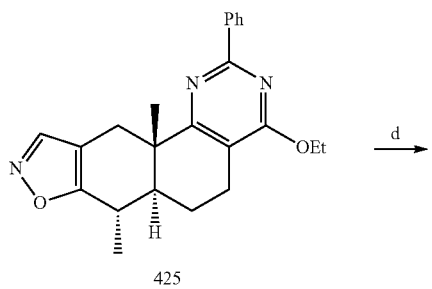

425

224
-continued

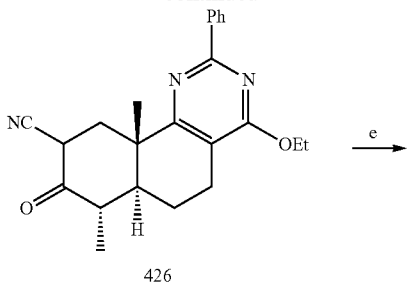

426

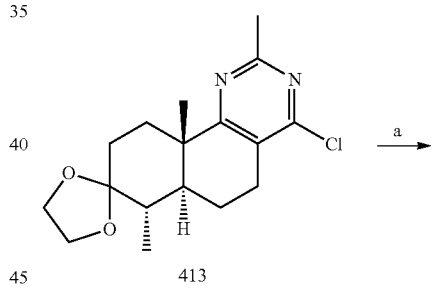

TX63731

Reagents and conditions pertaining to Schemes 80: (a) PhB(OH)₂, PPh₃, K₃PO₄, Pd(OAc)₂, DMF, DME, 90° C., 16 hr, 67%; (b) HCO₂Et, NaOMe, MeOH, RT, 16 hr; (c) NH₂OH—HCl, EtOH, 50° C., 16 hr; (d) NaOMe, THF, MeOH, 50° C., 16 hr; (e) (i) 1,3-dibromo-5,5-dimethylhydantoin, DMF, 0° C. to RT, 2 h; (ii) pyridine, 50° C., 16 hr, 69%.

Scheme 81:

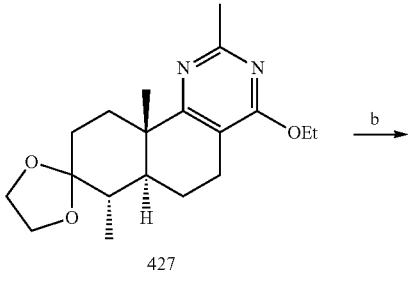

413

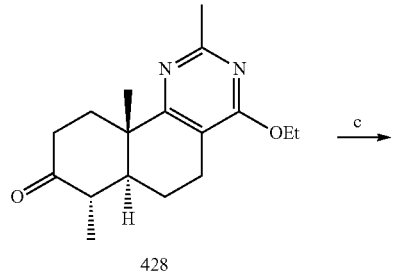

427

428

225
-continued

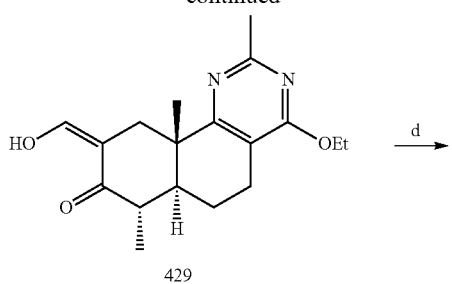
429

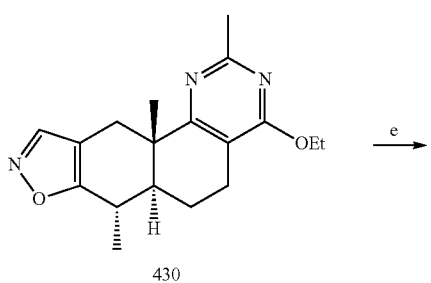
430

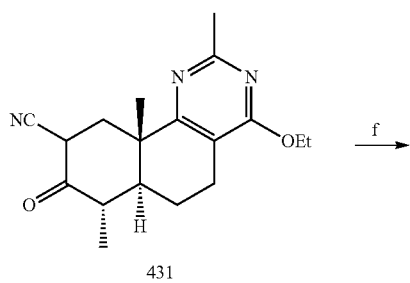
431

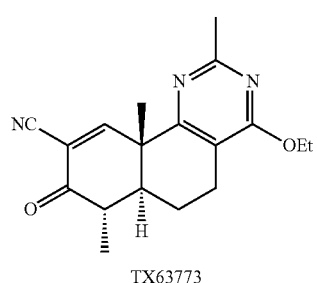
TX63773

Reagents and conditions pertaining to Schemes 81: (a) EtONa, EtOH, RT, 16 hr; (b) HCl (aq), MeOH, RT, 16 hr, 84%; (c) HCO₂Et, NaOEt, EtOH, Benzene, RT, 16 hr, 96%; (d) NH₂OH—HCl, EtOH, 50° C., 2 hr then RT, 16 hr; (e) NaOEt, EtOH, MeOH, RT, 16 hr; (f) (i) 1,3-dibromo-5,5-dimethylhydantoin, DMF, 0° C. to RT, 1 h; (ii) pyridine, 50° C., 2 hr, 48%.

Scheme 82:

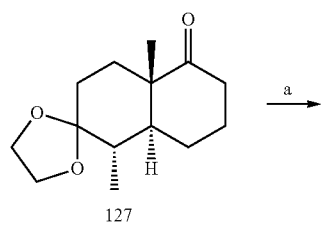
127

226
-continued

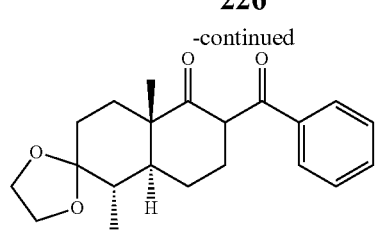

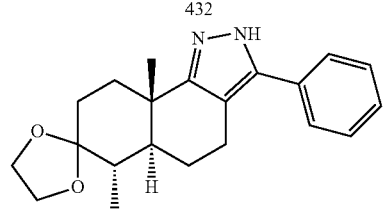
432

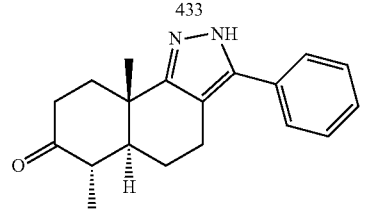
433

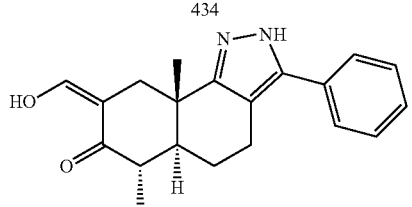
434

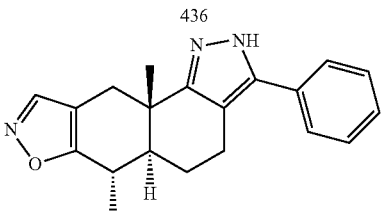
436

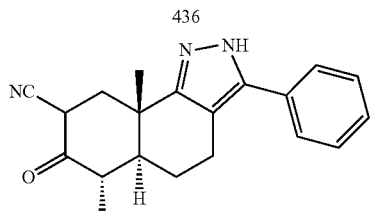
436

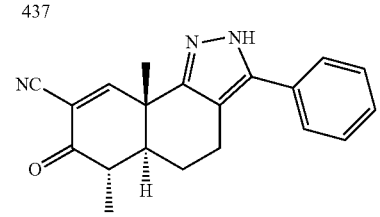
437

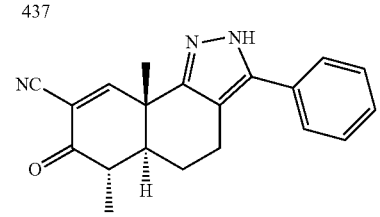
TX63836

Reagents and conditions pertaining to Schemes 82: (a) MgBr₂—Et₂O, DIPEA, DCM, then BzCl, RT, 16 hr, 27%; (b) NHNH₂—H₂O, EtOH, 65° C., 1 hr then RT 5 day; (c) HCl (aq), MeOH, RT, 16 hr; (d) HCO₂Et, NaOMe, MeOH, RT, 16 hr; (e) NH₂OH—HCl, EtOH, H₂O, RT, 16 hr, 34%; (f) NaOMe, MeOH, THF, RT, 16 hr; (g) (i) 1,3-dibromo-5,5-dimethylhydantoin, DMF, 0° C. to RT, 2 h; (ii) pyridine, 60° C., 3 hr, 43%.

227
Scheme 83:
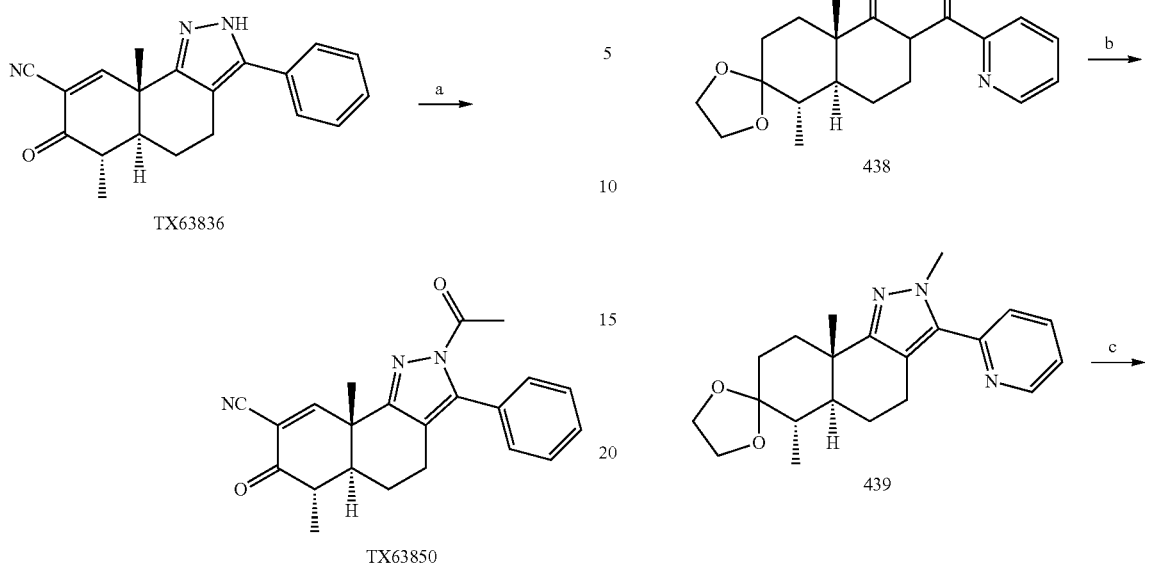
Reagents and conditions pertaining to Schemes 83: (a) Ac₂O, NaOAc, RT, 3 days, 31%.
Scheme 84:
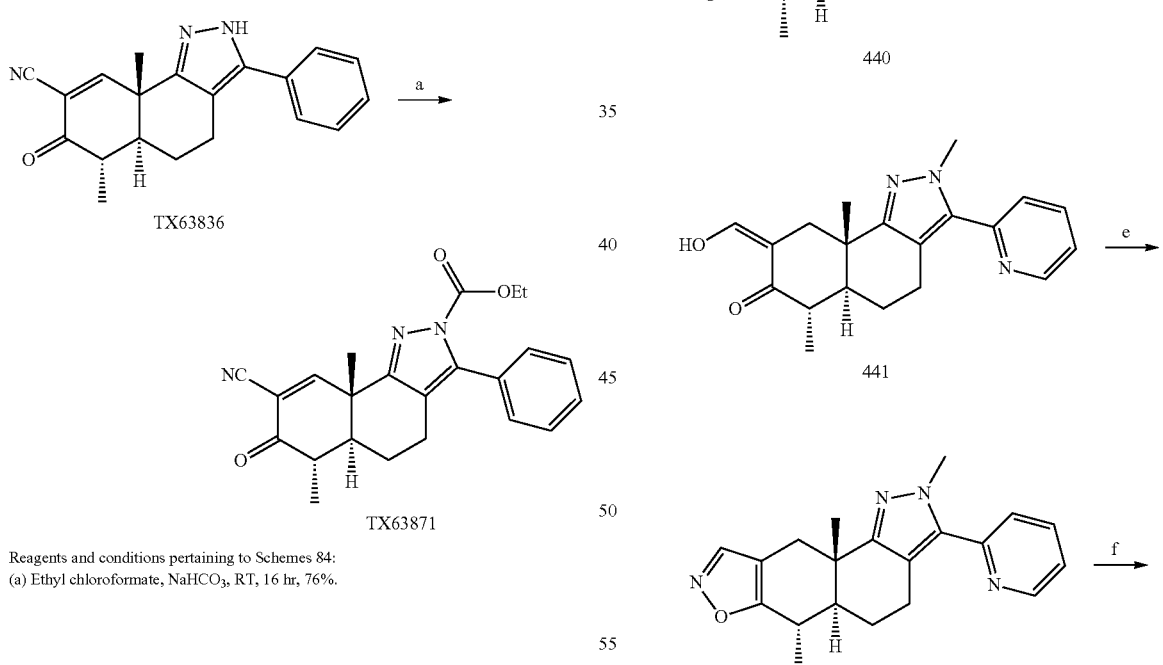
Reagents and conditions pertaining to Schemes 84:
(a) Ethyl chloroformate, NaHCO₃, RT, 16 hr, 76%.
Scheme 85:
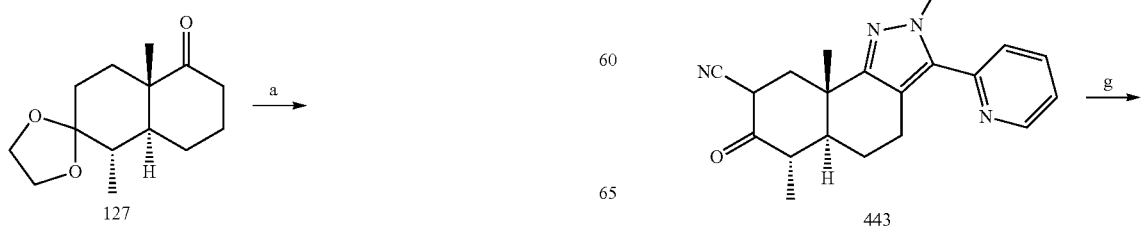

229
-continued

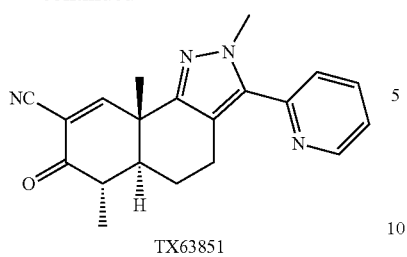

TX63851

Reagents and conditions pertaining to Schemes 85: (a) MgBr₂—Et₂O, DIPEA, DCM, then 2-pyridine carboxylic acid, chloride hydrochloride, RT, 16 hr; (b) NHNH₂—H₂O, EtOH, RT, 16 hr then 70° C., 1 hr; (c) HCl (aq), MeOH, RT, 16 hr, 94%; (d) HCO₂Et, NaOMe, MeOH, RT, 16 hr, 96%; (e) NH₂OH—HCl, EtOH, H₂O, RT, 16 hr, 85%; (f) NaOMe, MeOH, THF, RT, 16 hr, 99%; (g) (i) 1,3-dibromo-5,5-dimethylhydantoin, DMF, 0 °C. to RT, 2 h; (ii) pyridine, 60 ° C., 3 hr, 16%.

Scheme 86:

TX63690

TX63849

Reagents and conditions pertaining to Schemes 86:
(a) Accufluor, MeCN, 80° C., 2 hr then RT, 3 day, 14%.

Scheme 87:

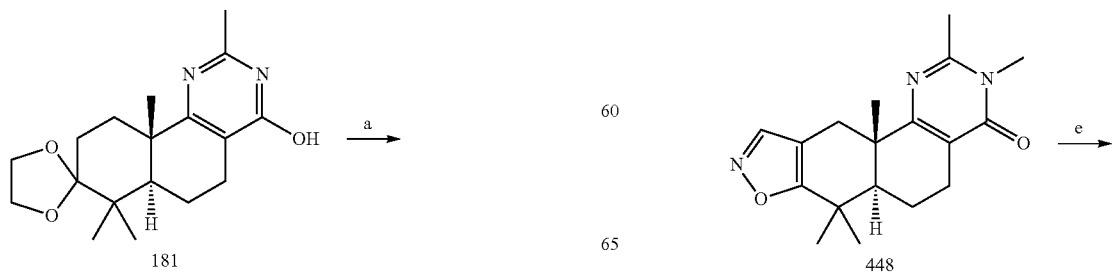

181

230
-continued

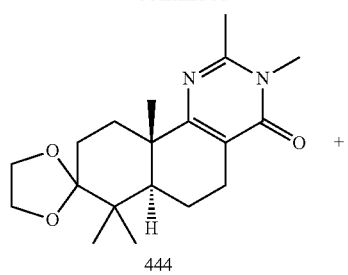

444

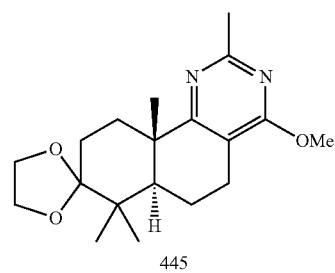

445

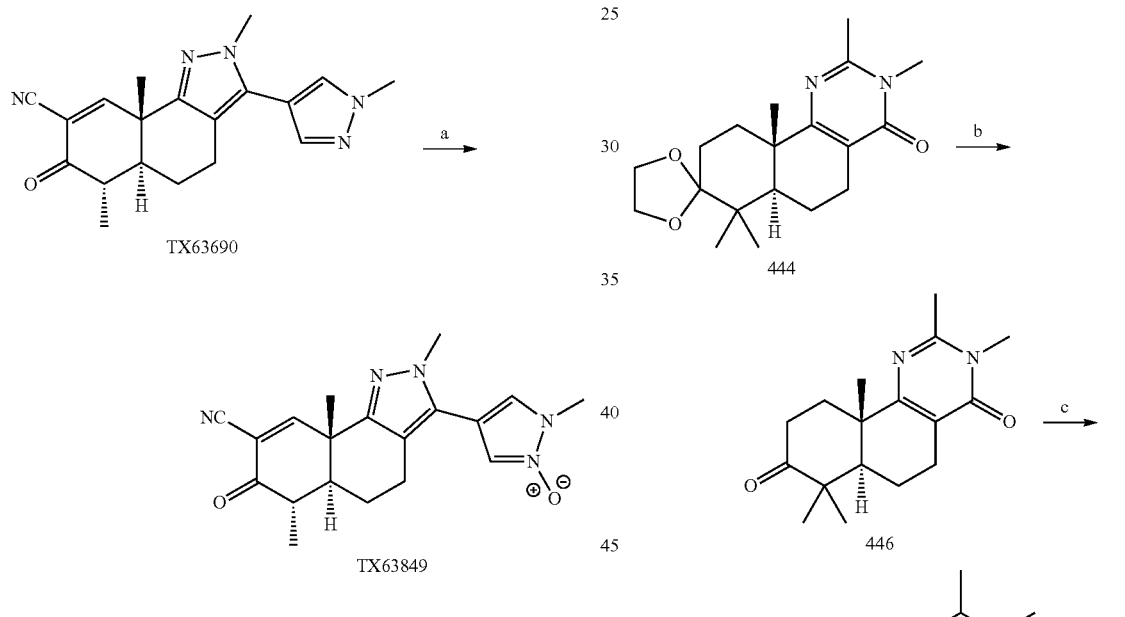

444

446

447

448

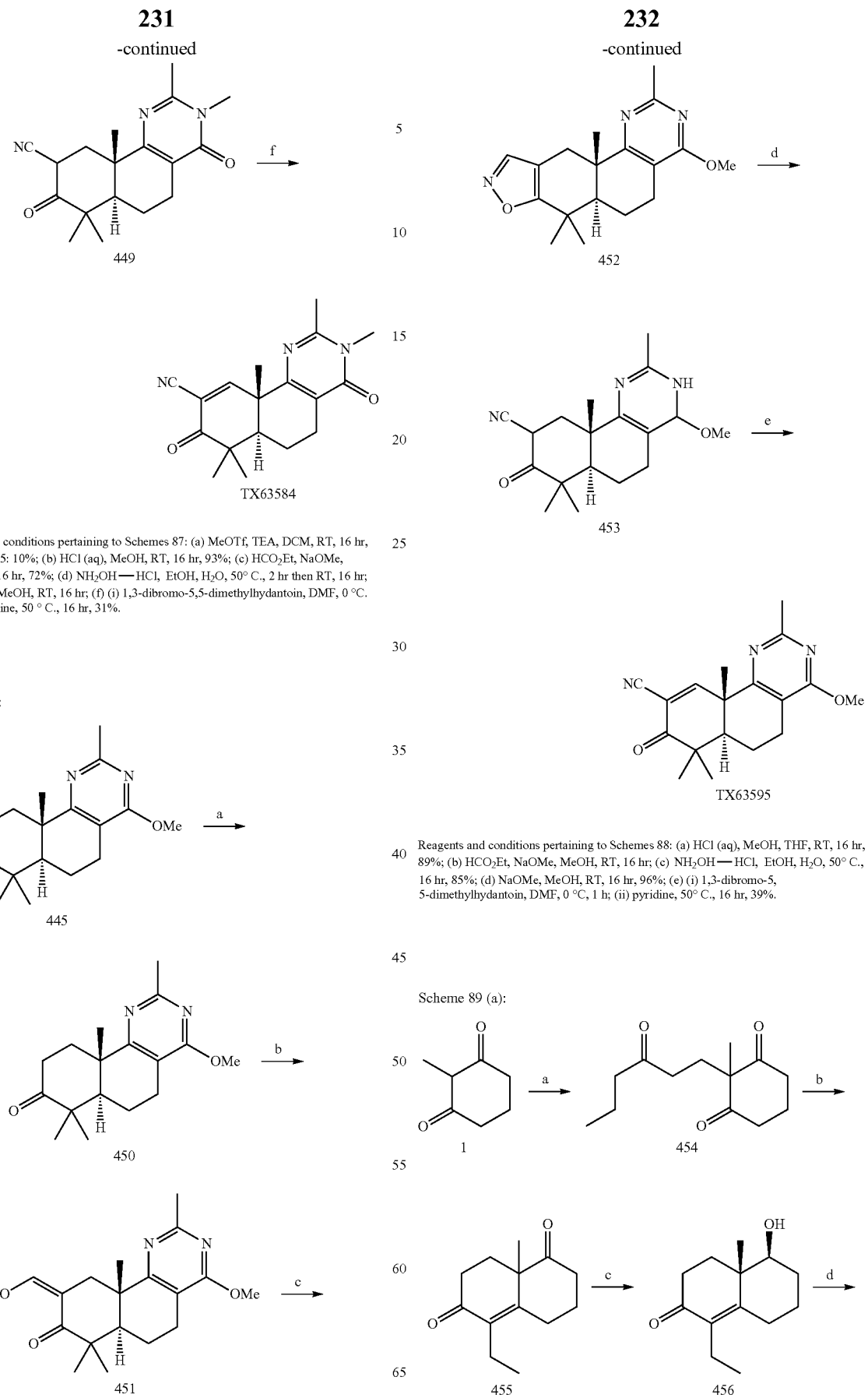

Reagents and conditions pertaining to Schemes 87: (a) MeOTf, TEA, DCM, RT, 16 hr, 444: 33%, 445: 10%; (b) HCl (aq), MeOH, RT, 16 hr, 93%; (c) HCO$_2$Et, NaOMe, MeOH, RT, 16 hr, 72%; (d) NH$_2$OH—HCl, EtOH, H$_2$O, 50° C., 2 hr then RT, 16 hr; (e) NaOMe, MeOH, RT, 16 hr; (f) (i) 1,3-dibromo-5,5-dimethylhydantoin, DMF, 0 °C. 1 h; (ii) pyridine, 50 ° C., 16 hr, 31%.

Scheme 88:

Reagents and conditions pertaining to Schemes 88: (a) HCl (aq), MeOH, THF, RT, 16 hr, 89%; (b) HCO$_2$Et, NaOMe, MeOH, RT, 16 hr; (c) NH$_2$OH—HCl, EtOH, H$_2$O, 50° C., 16 hr, 85%; (d) NaOMe, MeOH, RT, 16 hr, 96%; (e) (i) 1,3-dibromo-5, 5-dimethylhydantoin, DMF, 0 °C, 1 h; (ii) pyridine, 50° C., 16 hr, 39%.

Scheme 89 (a):

233
-continued
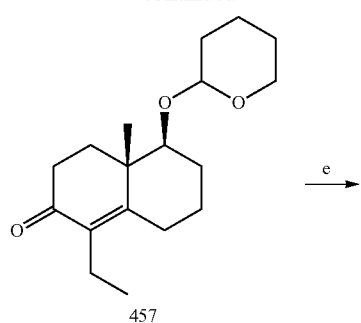
457
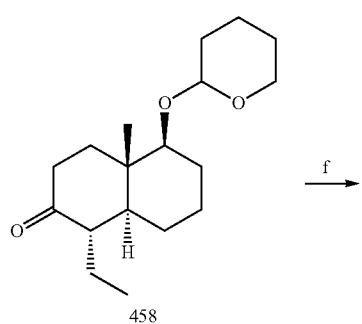
458
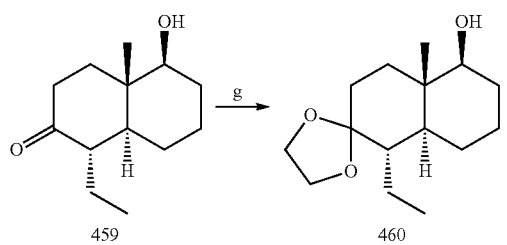
459    460
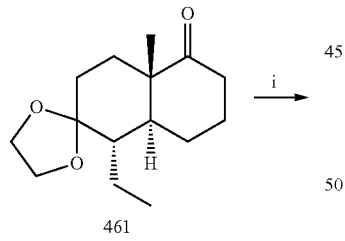
461
Scheme 90:
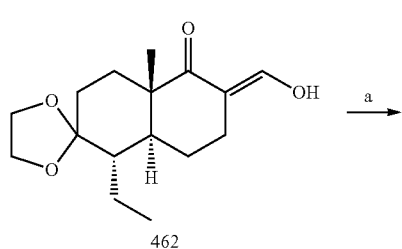
462
234
-continued
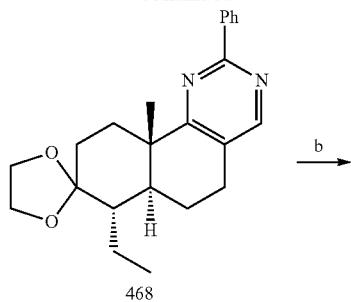
468
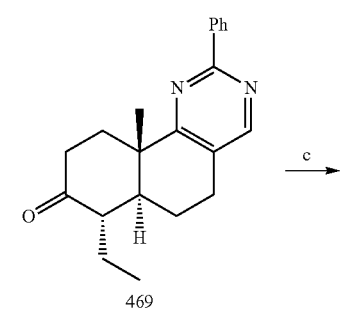
469
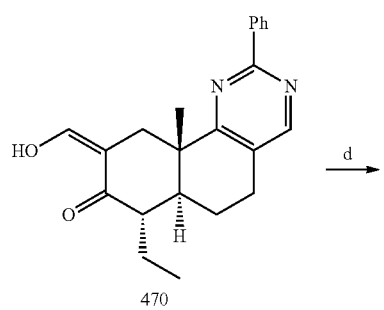
470
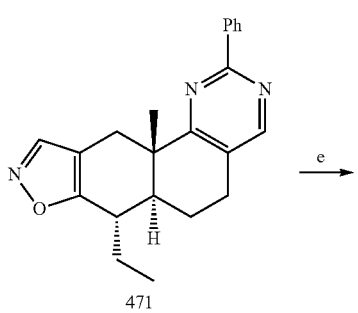
471
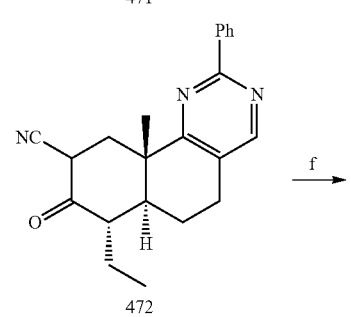
472

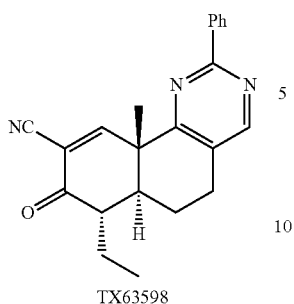

TX63598

Reagents and conditions pertaining to Schemes 90:
(a) Benzamidine hydroxhloride, piperidine, iPrOH, 85° C., 96 hr;
(b) HCl (aq), MeOH, THF, RT, 16 hr;
(c) HCO$_2$Et, Benzene, then NaOMe, MeOH, RT, 16 hr;
(d) NH$_2$OH—HCl, EtOH, H$_2$O, 50° C., 16 hr;
(e) NaOMe, MeOH, RT, 16 hr, 52%;
(f) (i) 1,3-dibromo-5,5-dimethylhydantoin, DMF, 0 °C, 1 h;
(ii) pyridine, 50° C., 16 hr, 79%.

Scheme 91:

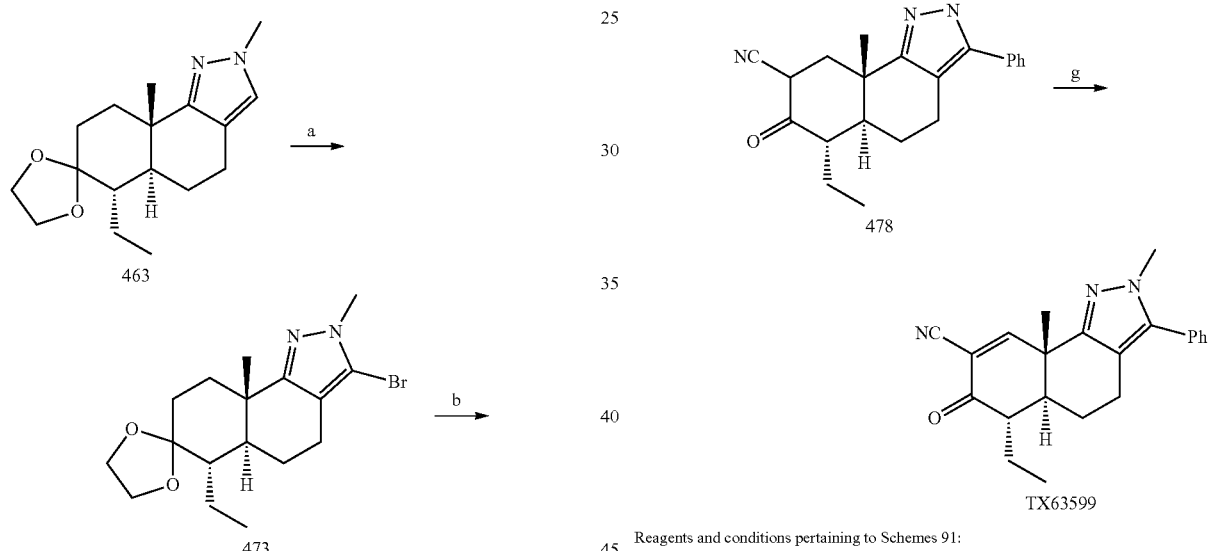

463, 473, 474, 475

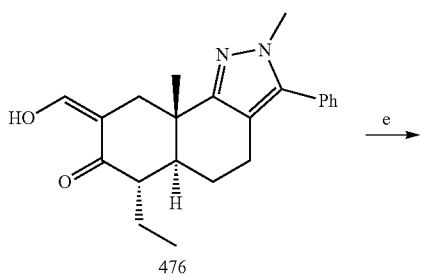

476, 477, 478

TX63599

Reagents and conditions pertaining to Schemes 91:
(a) 1,3-dibromo-5,5-dimethylhydantoin, DCM, RT, 30 min, 58%;
(b) phenylboronic acid, Pd(PPh$_3$)$_4$, K$_3$PO$_4$, DME, 80°C., 16 hr, 41%;
(c) HCl (aq), MeOH, THF, RT, 16 hr, 92%;
(d) HCO$_2$Et, Benzene, then NaOMe, MeOH, RT, 16 hr;
(e) NH$_2$OH—HCl, EtOH, H$_2$O, 50° C., 16 hr;
(f) NaOMe, MeOH, RT, 16 hr;
(g) (i) 1,3-dibromo-5,5-dimethylhydantoin, DMF, 0° C., 1 h
(ii) pyridine, 50° C., 16 hr, 30%.

Scheme 92:

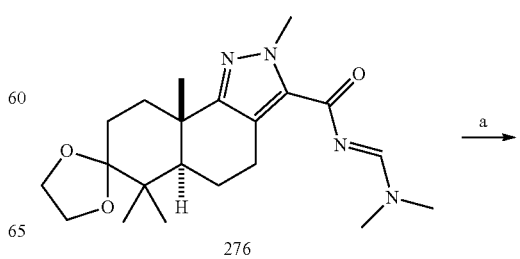

276

237
-continued

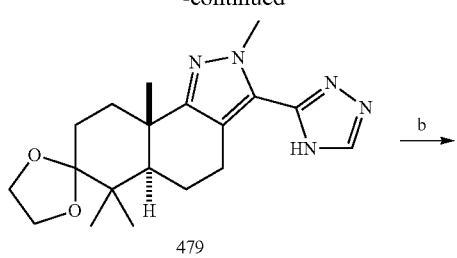
479

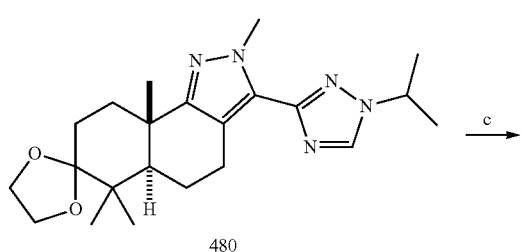
480

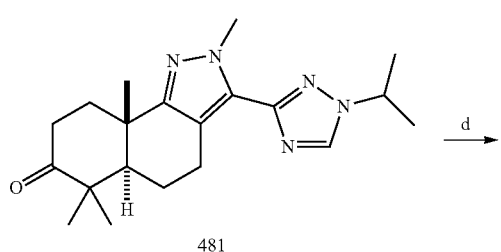
481

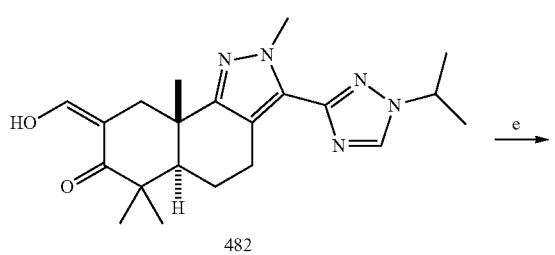
482

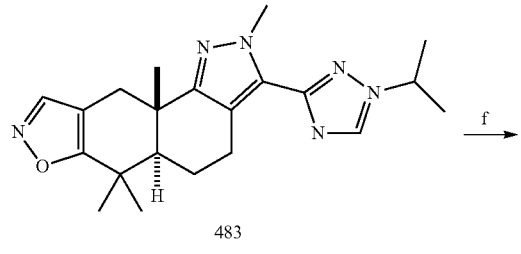
483

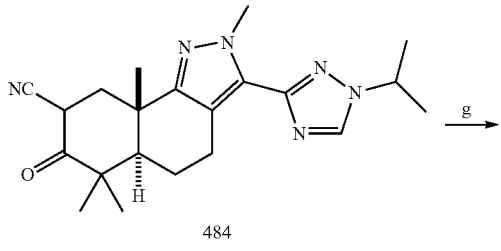
484

238
-continued

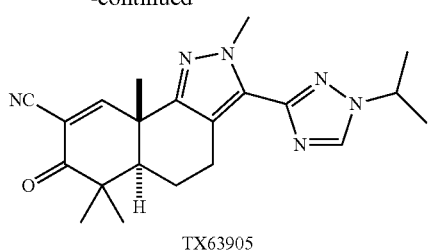
TX63905

Reagents and conditions pertaining to Schemes 92:
(a) N$_2$H$_4$—HCl, TEA, AcOH, dioxane, then 276, 70° C., 3 hr, 96%;
(b) NaH, DMF, then iPrI, 16 hr, 79%;
(c) HCl (aq), THF, RT, 48 hr, 97%;
(d) HCO$_2$Et, THF then NaOMe, MeOH, RT, 16 hr, 98%;
(e) NH$_2$OH—HCl, EtOH, H$_2$O, 50° C., 3 hr, 100%;
(f) NaOMe, MeOH, THF, 50°C., 3 hr, 72%;
(g) (i) 1,3-dibromo-5,5-dimethylhydantoin, DMF, 0° C., 1.5 h
(ii) pyridine, 60° C., 4 hr, 69%.

Scheme 93:

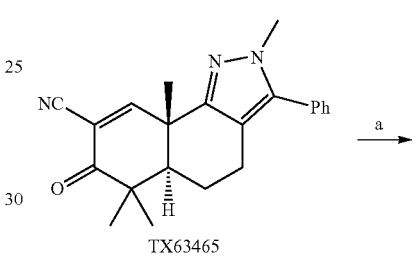
TX63465

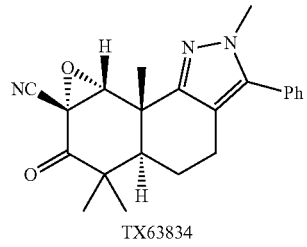
TX63834

Reagents and conditions pertaining to Scheme 93: (a) H$_2$O$_2$ (aq), CH$_3$CN, RT, 16 hr, 85%.

Scheme 94:

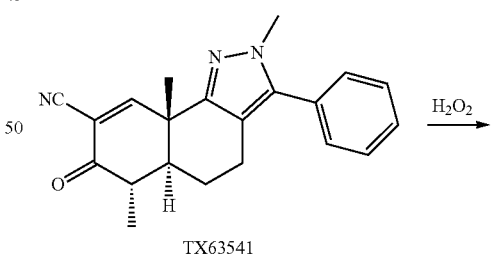
TX63541

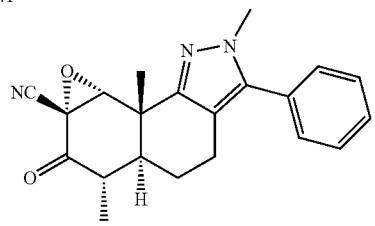
TX63848

Reagents and conditions pertaining to Schemes 94: (a) H$_2$O$_2$, MeCN, RT, 16 hr, 10%.

Scheme 95:
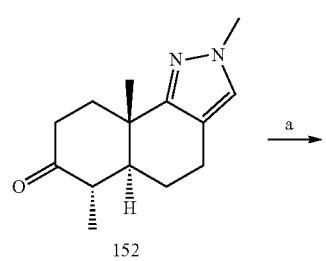
152
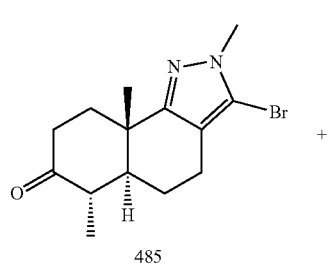
485
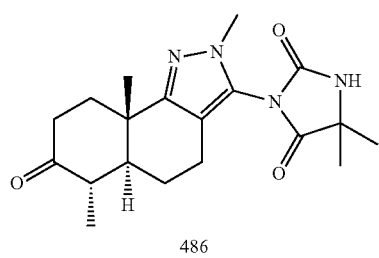
486
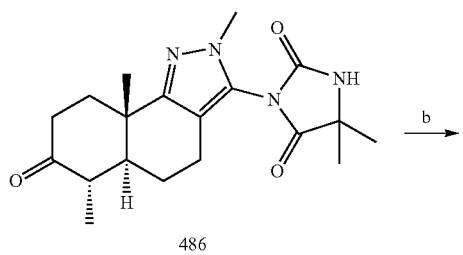
486
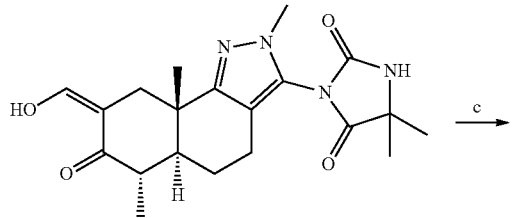
487
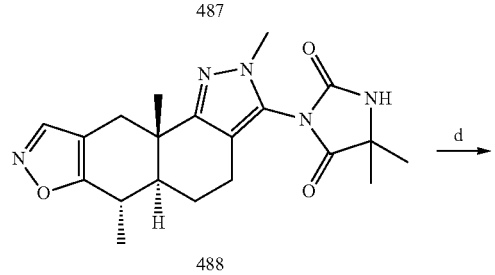
488
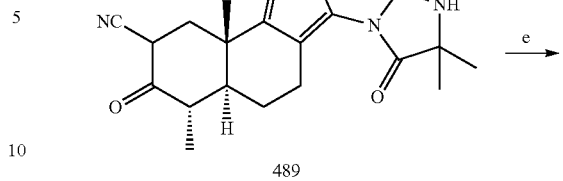
489
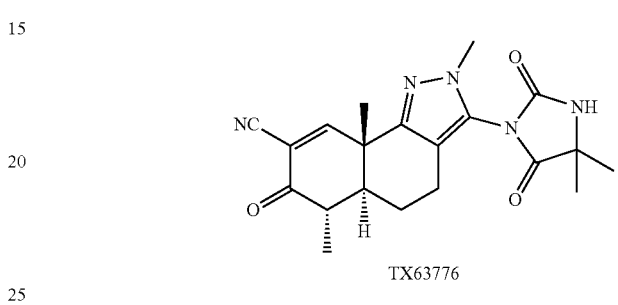
TX63776
Reagents and conditions pertaining to Schemes 95:
(a) 1,3-dibromo-5,5-dimethylhydantoin, DMF, 0° C., 0.5 h, 485: 55%, 486: 14%;
(b) HCO₂Et, benzene then NaOMe, MeOH, RT, 16 hr, 78%;
(c) NH₂OH—HCl, EtOH, H₂O, 50° C., 2 hr then RT 16 hr;
(d) NaOMe, MeOH, THF, RT, 16 hr; 81%;
(e) (i) 1,3-dibromo-5,5-dimethylhydantoin, DMF, 0° C., 1.0 h;
(ii) pyridine, 50° C., 2 hr, 27%.
Scheme 96:
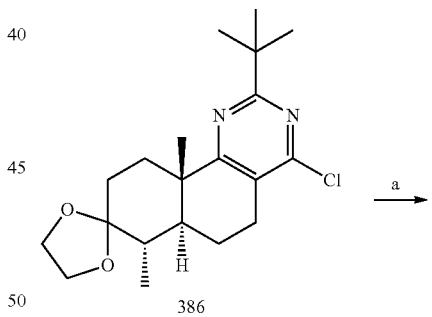
386
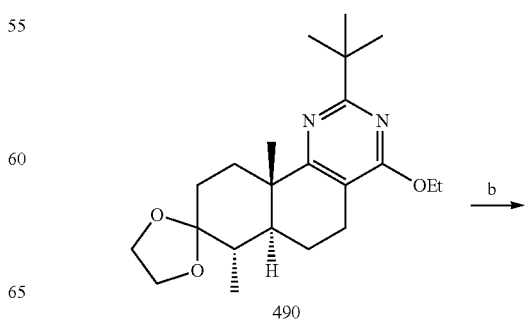
490

241
-continued
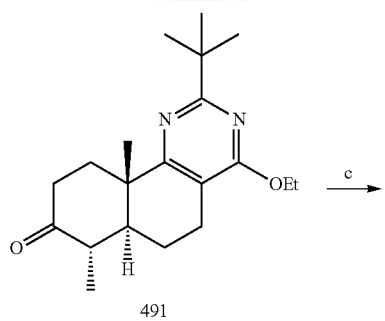
491
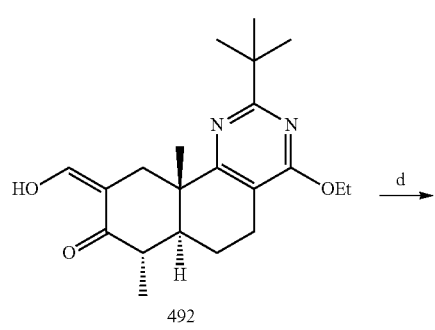
492
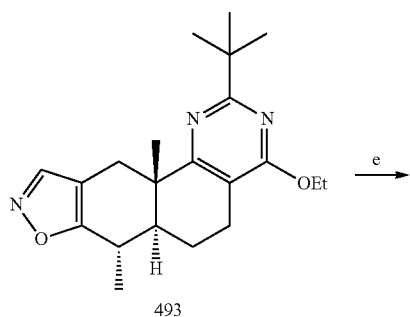
493
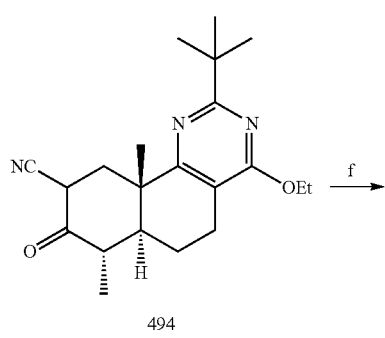
494
242
-continued
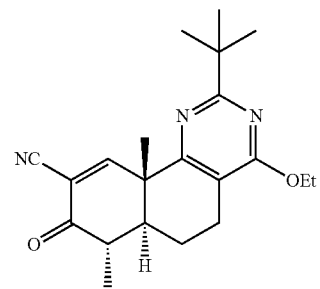
TX63900
Reagents and conditions pertaining to Schemes 96:
(a) NaOEt, EtOH, 80° C., 48 hr, 92%;
(b) HCl (aq), EtOH, RT, 16 hr, 99%;
(c) HCO$_2$Et, benzene, then NaOEt, EtOH, RT, 16 hr;
(d) NH$_2$OH—HCl, EtOH, 50° C., 2 hr, then RT, 16 hr, 88%;
(e) NaOEt, EtOH, RT, 72 hr, 96%;
(f) (i) 1,3-dibromo-5,5-dimethylhydantoin, DMF, 0° C. to RT, 1 h;
(ii) pyridine, 50° C., 2 hr, 31%.
Scheme 97:
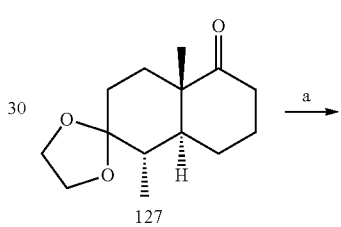
127
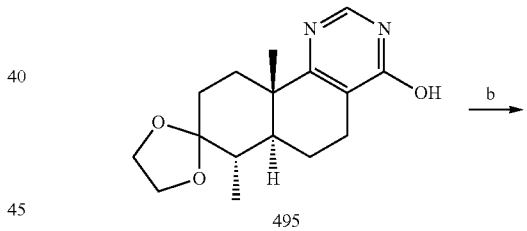
495
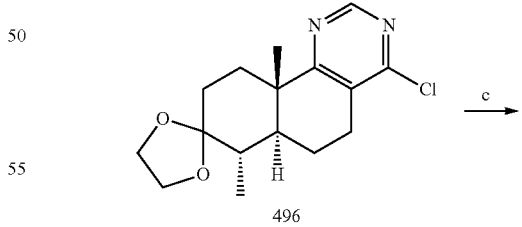
496
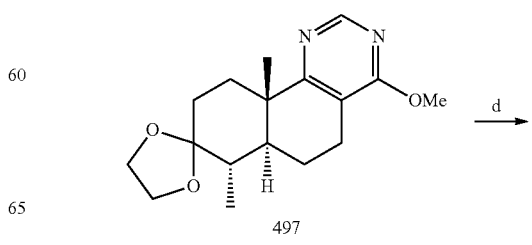
497

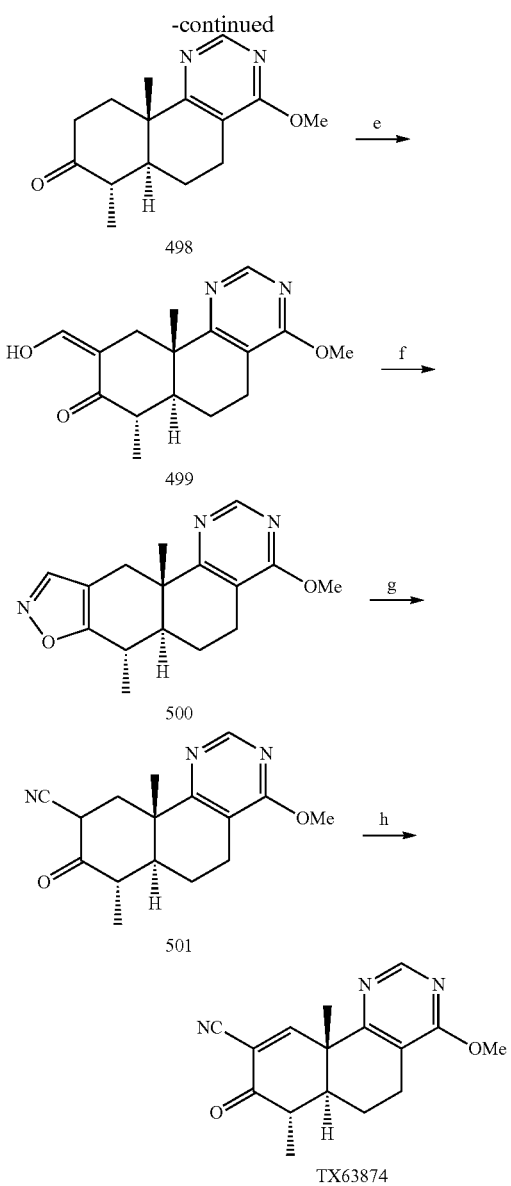

Reagents and conditions pertaining to Schemes 97:
(a) (i) Dimethyl carbonate, NaH, THF, 80° C., 16 hr; (ii) Formamidine acetate, piperidine, iPrOH, 80° C., 48 hr., 16%;
(b) POCl₃, DMF, DIPEA, 90° C., 2 hr, 86%;
(c) NaOMe, MeOH, 60° C., 16 hr, 88%;
(d) HCl, MeOH, RT, 16 hr, 99%;
(e) HCO₂Et, NaOMe, benzene MeOH, RT, 48 hr, 82%;
(f) NH₂OH—HCl, EtOH, 50° C., 16 hr, 95%;
(g) NaOMe, MeOH, RT, 16 hr, 88%;
(h) (i) 1,3-dibromo-5,5-dimethylhydantoin, DMF, 0° C. to RT, 2 h; (ii) pyridine, 50° C., 2 hr, 30%.

Synthesis and Characterization of Synthetic AIM Derivatives

Compound 2: Ethyl vinyl ketone (8.0 g, 95 mmol) was taken up in THF (75 mL) and compound 1 (10 g, 79 mmol) and triethylamine (8.37 g, 82 mmol) were added. The reaction was heated at reflux for 3 h. The reaction mixture was cooled to room temperature and concentrated. The crude residue was purified by column chromatography (silica gel, 10 to 20% EtOAc in Hexanes) to give compound 2 (13.5 g, 81%) as an oil. m/z 211 [M+H]⁺.

Compound 3: Compound 2 (13.5 g, 64.2 mmol) was taken up in DMF (600 mL), the (S)-phenylalanine (10.63 g, 64 mmol) and D-camphorsulfonic acid (735 g, 32 mmol) were added. The reaction mixture was stirred at room temperature for 4 d, then heated to 70° C. for 1 d. The reaction mixture was cooled to room temperature, diluted with saturated NaHCO₃ (aq), and extracted with ether, then dried with Na₂SO₄ and concentrated. The crude residue was purified by column chromatography (silica gel, 25% EtOAc in Hexanes) to give compound 3 (5.51 g, 45%) as an oil. m/z 193 [M+H]⁺.

Compound 4: A solution of NaBH₄ (0.296 g, 7.8 mmol) in ethanol (40 mL) was added to a 0° C. solution of compound 3 (5.51 g, 28.6 mmol) in ethanol (100 mL). The reaction was stirred at 0° C. for 1 h and quenched with acetic acid (2.9 mL). The reaction mixture was warmed to room temperature and stirred for 5 min, then concentrated. The crude residue was purified by column chromatography (silica gel, 20% EtOAc in Hexanes) to give compound 4 (5.0 g, 90%) as an oil. m/z 195 [M+H]⁺.

Compound 5: Compound 4 (3.05 g, 15.6 mmol) was taken up in CH₂Cl₂, then i-Pr₂EtN and MOMCl were added. The mixture was stirred at room temperature for 3 days. The reaction mixture was concentrated. The residue was diluted with EtOAc, washed with 0.1 N HCl and brine, then dried with Na₂SO₄, and concentrated. The crude residue was purified by column chromatography (silica gel, 25% EtOAc in Hexanes) to give compound 5 (3.35 g, 90%) as a pale yellow liquid: m/z 239 [M+H]⁺.

Compound 6: A solution of compound 5 (3.0 g, 12.6 mmol) and t-BuOH (965 mg, 13 mmol) in THF (10 mL) was added to a −78° C. solution of lithium wire (0.44 g, 64 mmol) in liq. NH₃ (50 mL). The mixture was stirred at reflux for 2 h and cooled to −78° C. A solution of methyl iodide (9.5 g, 67 mmol) in THF (25 mL) was added. The reaction mixture was stirred at −78° C. for 2 h and quenched with water (2 mL), then slowly warmed to room temperature. The mixture was extracted was extracted with ether, then washed with water and brine, dried with MgSO₄ and concentrated. The crude residue was purified by column chromatography (silica gel, 5 to 15% EtOAc in Hexanes) to give compound 6 (0.90 g, 28%) as an oil. m/z 255 [M+H]⁺.

Compound 7: A mixture of Compound 6 (0.90 g, 3.5 mmol), ethylene glycol, and camphorsulfonic acid in cyclohexane was heated to reflux for 16 h with azeotropic removal of water. The reaction mixture was cooled to room temperature, washed with saturated NaHCO₃ and concentrated. The crude residue was purified by column chromatography (silica gel, 5 to 20% EtOAc in Hexanes) to give compound 7 (0.59 g, 66%) as an oil. m/z 255 [M+H]⁺.

Compound 8: Compound 7 (190 mg, 0.75 mmol) was taken up in CH₂Cl₂ and pyridinium dichromate and MgSO₄ were added. The reaction mixture was stirred overnight at room temperature. The reaction mixture was filtered through Celite, eluted with EtOAc/CH₂Cl₂ (1/3), and concentrated to give compound 8 (180 mg, 95%) as a solid. m/z 253 [M+H]⁺.

Compound 9: Compound 8 (120 mg, 0.48 mmol) was taken up in ethyl formate and cooled to 0° C., then 30% sodium methoxide (30 wt % solution in MeOH) was added and the reaction warmed to room temperature. The reaction mixture was stirred at room temperature for 1 h, diluted with t-BuOMe and 1 N HCl, and extracted with EtOAc, then washed with water, dried with MgSO₄, and concentrated to give compound 9 (120 mg, 90%) as a solid. m/z 281 [M+H]⁺.

Compounds 10 and 11: A mixture of 9 (120 mg, 0.43 mmol) and methyl hydrazine (35 mg, 0.7 mmol) in ethanol (15 mL) was heated to 60° C. for 2 h. The reaction mixture was concentrated. The crude residue was filtered through a short plug of silica (eluted with EtOAc) and concentrated to give 10 and 11 (125 mg, quantitative) as an oil. m/z 291 [M+H]$^+$.

Compounds 12 and 13: The mixture of compounds 10 and 11 (0.40 g, 1.4 mmol) was taken up in methanol, and 3 N HCl (aq) was added. The mixture was stirred for 3 h at room temperature. The reaction mixture was quenched with saturated NaHCO$_3$ and extracted with ether, then dried with MgSO$_4$ and concentrated. The crude residue was purified by column chromatography (silica gel, 15% EtOAc in Hexanes) to give compounds 12 and 13 (0.20 g, 59%) as a solid. m/z 247 [M+H]$^+$.

Compounds 14 and 15: A solution of compounds 12 and 13 (0.20 g, 0.81 mmol) in THF was added to a −78° C. solution of LDA (2.0 equiv.) in THF. The reaction was stirred at −78° C. for 45 min, then a solution of TsCN (1.5 equiv.) in THF was added. The reaction was stirred at −78° C. for an additional 45 min, then quenched with 1 N HCl (aq) and warmed to room temperature. The reaction mixture was extracted with ether, then washed with water and brine, dried with MgSO$_4$, and concentrated. The crude residue was purified by column chromatography (silica gel, 5 to 25% EtOAc in Hexanes) to give compounds 14 and 15 (170 mg, 77%) as a solid. m/z 272 [M+H]$^+$.

Compounds TX63341 and TX63342: The mixture of compounds 14 and 15 (170 mg, 0.63 mmol) was dissolved in dry DMF, and the solution was cooled to 0° C. 1,3-Dibromo-5,5-dimethylhydantoin was added, and the reaction stirred at 0° C. until the starting material was consumed (approximately 2 h), as reported by thin layer chromatography. Then, pyridine was added, and the reaction was allowed to warm to room temperature. The reaction mixture was then stirred at 55° C. overnight. The reaction mixture was diluted with t-BuOMe and washed with water, then dried with MgSO$_4$ and concentrated. The crude residue was purified by column chromatography (silica gel, 5 to 25% EtOAc in Hexanes) to give compound TX63342 (39 mg, 23%) as a solid. $^1$H NMR (400 MHz, d6-DMSO) δ 8.44 (s, 1H), 7.39 (s, 1H), 3.78 (s, 3H), 2.69 (dd, 1H, J=5.6, 15.7 Hz), 2.46 (ddd, 1H, J=6.9, 11.6, 15.9 Hz), 2.16 (d, 1H, J=11.6 Hz), 1.82 (m, 2H), 1.40 (s, 3H), 1.21 (s, 3H), 1.13 (s, 3H); m/z 270 [M+H]$^+$, and TX63341 (15 mg, 9%) as a solid. $^1$H NMR (500 MHz, CDCl$_3$) δ 8.30 (s, 1H), 7.31 (s, 1H), 4.06 (s, 3H), 2.75 (dd, 1H, J=4.8, 15.7 Hz), 2.53 (ddd, 1H, J=6.0, 12.3, 15.6 Hz), 2.27 (d, 1H, J=11.9 Hz), 1.95 (dd, 1H, J=5.6, 13.3 Hz), 1.77 (m, 1H), 1.53 (s, 3H), 1.31 (s, 6H); m/z 270 [M+H]$^+$.

Compound 17: Compound 16 (10 g, 56 mmol) was taken up in ethanol, cooled to 0° C., and a solution of NaBH$_4$ in ethanol added. The mixture was stirred at 0° C. for 2 h, and quenched with acetic acid. The reaction mixture was concentrated. The crude residue was filtered through a short plug of silica (eluted with 30% EtOAc in Hexanes) and concentrated to give 17 (9.3 g, 92%) as a viscous liquid.

Compound 18: Compound 17 (9.3 g, 52 mmol) was taken up in CH$_2$Cl$_2$, then i-Pr$_2$EtN and MOMCl were added. The mixture was stirred at room temperature for 3 days. The reaction mixture was concentrated. The residue was diluted with EtOAc, washed with 0.1 N HCl and brine, then dried with Na$_2$SO$_4$ and concentrated. The crude residue was purified by column chromatography (silica gel, 30% EtOAc in Hexanes) to give compound 18 (9.0 g, 78%) as a pale yellow liquid: m/z 225 [M+H]$^+$.

Compound 19: Compound 18 (3.5 g, 16 mmol) was taken up in t-BuOH, and a solution of KOt-Bu in THF was added. The mixture was stirred at room temperature for 10 min, cooled to 10° C., and iodomethane was added. The reaction mixture was warmed to room temperature over 30 min and quenched with water. The mixture was extracted with EtOAc and washed with brine, then dried with Na$_2$SO$_4$ and concentrated. The crude residue was purified by column chromatography (silica gel, 10% EtOAc in Hexanes) to give compound 19 (1.7 g, 43%) as a pale yellow liquid: m/z 253 [M+H]$^+$.

Compound 20: A mixture of Compound 19 (4.31 g, 17.1 mmol), ethylene glycol, and p-toluenesulfonic acid hydrate in toluene was heated to reflux overnight with azeotropic removal of water. The reaction mixture was cooled to room temperature, diluted with EtOAc, washed with saturated NaHCO$_3$ and brine, then dried with MgSO$_4$ and concentrated to give 20 (4.26 g, 99%) as a solid. m/z 253 [M+H]$^+$.

Compound 21: Compound 20 (4.65 g, 18.4 mmol) was taken up in EtOH under N$_2$ and 10% Pd/C added. The flask was rigorously purged with H$_2$ and stirred for 4 d at room temperature adding an additional portion of 10% Pd/C after 3 d. The reaction mixture was filtered through Celite, eluted with methanol, and concentrated to give compound 21 (4.63 g, 99%) as a solid. m/z 255 [M+H]$^+$.

Compound 22: Compound 21 (58 mg, 0.28 mmol) was taken up in CH$_2$Cl$_2$, then i-Pr$_2$EtN and MOMCl were added. The mixture was stirred overnight at room temperature. The reaction mixture was concentrated. The reaction mixture was diluted with EtOAc, washed with saturated NaHCO$_3$ and brine, then dried with MgSO$_4$ and concentrated to give compound 22 (72 mg, quantitative) as a solid. m/z 255 [M+H]$^+$.

Compound 23: A solution of 22 (70 mg, 0.28 mmol) in THF was added to a −78° C. solution of LDA (3.5 equiv.) in THF. The reaction was stirred at −78° C. for 30 min, then a solution of TsCN (1.3 equiv.) in THF was added. The reaction was stirred at −78° C. for an additional 30 min, then quenched with sat. NH$_4$Cl (aq) and warmed to room temperature. The reaction mixture was extracted with EtOAc and washed with brine, then dried with MgSO$_4$ and concentrated. The crude residue was purified by column chromatography (silica gel, 15% EtOAc in Hexanes) to give compound 23 (51 mg, 66%) as a white solid. m/z 280 [M+H]$^+$.

Compound TX63364: Compound 23 (48 mg, 0.17 mmol) was dissolved in dry DMF, and the solution was cooled to 0° C. 1,3-Dibromo-5,5-dimethylhydantoin (0.6 equiv.) was added, and the reaction stirred at 0° C. for 3 h adding an additional portion of 1,3-dibromo-5,5-dimethylhydantoin (0.1 equiv.) after 2 h. Then, pyridine was added, and the reaction was allowed to warm to room temperature. The reaction mixture was stirred at 60° C. for 4 h, then stirred at room temperature overnight. The mixture was diluted with EtOAc, washed with 1N HCl (aq), saturated NaHCO$_3$ and brine, then dried with MgSO$_4$ and concentrated. The crude residue was purified by column chromatography (silica gel, 15% EtOAc in Hexanes) to give compound TX63364 (41 mg, 86%) as a white solid. $^1$H NMR (500 MHz, CDCl$_3$) δ 7.94 (s, 1H), 4.78 (d, 1H, J=6.8 Hz), 4.65 (d, 1H, J=6.8 Hz), 3.44 (s, 3H), 3.28 (dd, 1H, J=4.3, 11.4 Hz), 2.00 (m, 1H), 1.92 (m, 1H), 1.59 (m, 3H), 1.49 (m, 1H), 1.36 (m, 1H), 1.24 (s, 3H), 1.22 (s, 3H), 1.13 (s, 3H); m/z 278 [M+H]$^+$.

Compound TX63363: Compound TX63364 (28 mg, 0.10 mmol) was taken up in THF, and 3 N HCl (aq) was added. The mixture was stirred 2 d at room temperature, and quenched with saturated NaHCO$_3$. The mixture was extracted with EtOAc and washed with brine, then dried with MgSO$_4$ and concentrated. The crude residue was purified by column chromatography (silica gel, 25% EtOAc in Hexanes) to give compound TX63363 (16 mg, 68%) as a white solid. $^1$H NMR (500 MHz, CDCl$_3$) δ 8.06 (s, 1H), 8.52 (s, 1H), 3.45 (dd, 1H, J=4.3, 11.6 Hz), 1.92 (m, 1H), 1.86 (m, 1H), 1.61 (m, 3H), 1.44 (m, 2H), 1.23 (s, 3H), 1.22 (s, 3H), 1.14 (s, 3H); m/z 234 [M+H]$^+$.

Compound 25: Compound 21 (2.56 g, 10.1 mmol) was taken up in $CH_2Cl_2$ and pyridinium dichromate was added over 10 min. The reaction mixture was stirred overnight at room temperature, then heated to 45° C. until the starting material was consumed, as reported by thin layer chromatography. The reaction mixture was filtered through Celite, eluted with $CH_2Cl_2$, and concentrated. The crude residue was purified by column chromatography (silica gel, 25% EtOAc in Hexanes) to give compound 25 (2.36 g, 93%) as a solid. m/z 253 $[M+H]^+$.

Compound 26: Compound 25 (2.95 g, 11.7 mmol) was taken up in ethyl formate and cooled to 0° C., then sodium methoxide (30 wt % solution in MeOH) was added and the reaction warmed to room temperature. The mixture was stirred overnight at room temperature. The reaction mixture was diluted with water and the pH adjusted to 7 with acetic acid. The mixture was extracted with ethyl acetate and washed with brine (aq), then dried with $MgSO_4$ and concentrated to give compound 26 (3.27 g, quantitative) as a solid. m/z 281 $[M+H]^+$.

Compound 27: A mixture of 26 (1.50 g, 5.35 mmol) and methyl hydrazine (0.37 g, 8.03 mmol) in ethanol (100 mL) was heated to 60° C. for 2 h. The reaction mixture was concentrated. The crude residue was purified by column chromatography (silica gel, EtOAc) to give 27 (1.50 g, 97%) as an oil. m/z 291 $[M+H]^+$.

Compound 28: Compound 27 (1.50 g, 5.17 mmol) was taken up in methanol, and 3 N HCl (aq) was added. The mixture was stirred for 3 h at room temperature. The reaction mixture was quenched with saturated $NaHCO_3$ and extracted with ether, then dried with $MgSO_4$ and concentrated to give compound 28 (1.10 g, 86%) as a solid. m/z 247 $[M+H]^+$.

Compound 29: A solution of 28 (1.10 g, 4.47 mmol) in THF was added to a −78° C. solution of LDA (1.6 equiv.) in THF. The reaction was stirred at −78° C. for 45 min, then a solution of TsCN (1.2 equiv.) in THF was added. The reaction was stirred at −78° C. for an additional 45 min, then quenched with 1 N HCl (aq) and warmed to room temperature. The reaction mixture was extracted with ether, dried with $MgSO_4$ and concentrated. The crude residue was purified by column chromatography (silica gel, 5 to 35% EtOAc in Hexanes) to give compound 29 (0.53 g, 44%) as a solid. m/z 272 $[M+H]^+$.

Compounds TX63432 and TX63445: Compound 29 (530 mg, 1.95 mmol) was dissolved in dry DMF, and the solution was cooled to 0° C. 1,3-Dibromo-5,5-dimethylhydantoin was added, and the reaction stirred at 0° C. until the starting material was consumed (approximately 1 h), as reported by thin layer chromatography. Then, pyridine was added, and the reaction was allowed to warm to room temperature. The reaction mixture was then stirred at 50° C. overnight. The reaction mixture was concentrated, diluted with water, extracted with EtOAc, then dried with $MgSO_4$ and concentrated. The crude residue was purified by column chromatography (silica gel, 5 to 30% EtOAc in Hexanes) to give compound TX63432 (155 mg, 29%) as a solid. $^1$H NMR (400 MHz, d6-DMSO) δ 8.44 (s, 1H), 7.39 (s, 1H), 3.78 (s, 3H), 2.69 (dd, 1H, J=5.6, 15.7 Hz), 2.46 (ddd, 1H, J=6.9, 11.6, 15.9 Hz), 2.16 (d, 1H, J=11.6 Hz), 1.82 (m, 2H), 1.40 (s, 3H), 1.21 (s, 3H), 1.13 (s, 3H); m/z 270 $[M+H]^+$, and TX63445 (28 mg, 4%) as a solid. $^1$H NMR (400 MHz, $CDCl_3$) δ 8.43 (s, 1H), 3.85 (s, 3H), 2.65 (d, 1H, J=6.2, 16.1 Hz), 2.44 (ddd, 1H, J=7.0, 11.8, 16.3 Hz), 2.15 (dd, 1H, J=1.6, 12.1 Hz), 1.98 (dd, 1H, J=7.1, 13.5 Hz), 1.87 (dq, 1H, J=6.2, 12.0 Hz), 1.49 (s, 3H), 1.30 (s, 3H), 1.24 (s, 3H); m/z 348, 350 (1:1) $[M+H]^+$.

Compound 30: A solution of cyclohexylhydrazine hydrochloride (0.245 g, 1.5 eq) and triethyl amine (165 mg, 1.5 eq) in EtOH (5 mL) was stirred at room temperature for 15 min. A solution of compound 26 (0.3 g, 1.07 mmol) in EtOH (5 mL) was added slowly, and the mixture was stirred at room temperature for 30 min. The reaction mixture was then heated at 60° C. 16 h and then concentrated. The crude residue was purified by column chromatography (5% to 35% EtOAc in Hexanes) to give compound 30 (0.14 g, 36%) as a gummy solid; m/z 359 $[M+H]^+$.

Compound 31: A solution of compound 30 (0.14 g, 0.39 mmol) in MeOH was treated with 3 N HCl (aq) and stirred at room temperature for 3 h. The reaction mixture was quenched by ether and saturated $NaHCO_3$ (aq). The organic layer was separated and dried with $MgSO_4$, then filtered through a short column (silica gel, 15% EtOAc in Hexanes) to give compound 31 (0.12 g, 98%) as a solid. m/z 315 $[M+H]^+$.

Compound 32: A solution of lithium diisopropylamide (LDA) was prepared by addition of n-BuLi (1.6 M in hexane) to diisopropylamine in THF at 0° C., stifling for 30 min, and then cooling the reaction to −78° C. A solution of compound 31 (0.12 g, 0.39 mmol) in THF was added dropwise to the LDA solution. The reaction was stirred at −78° C. for 45 min, and then a solution of p-toulenesulfonyl cyanide in THF was added. After stifling 45 min, 1 N HCl (aq) was added. The reaction mixture was extracted with ether, and the combined organics were washed with water and brine, dried over $MgSO_4$, filtered, and evaporated. The crude residue was purified by column chromatography (silica gel, 5% to 25% EtOAc in Hexanes) to give compound 32 (60 mg, 46%) as a solid; m/z 340 $[M+H]^+$.

Compound TX63444: 1,3-Dibromo-5,5-dimethylhydantoin was added to a solution of compound 32 (60 mg, 0.17 mmol) in DMF at 0° C. After stifling for 2 h, pyridine was added, and the reaction mixture was heated to 55° C. for 16 h. After cooling to room temperature, MTBE was added, and the mixture was washed with water, then dried with $MgSO_4$ and concentrated. The crude residue was purified by column chromatography (silica gel, 5% to 25% EtOAc in Hexanes) to give TX63444 (35 mg, 59%) as a solid. $^1$H NMR (400 MHz, $CDCl_3$) δ 8.53 (s, 1H), 7.13 (s, 1H), 4.04 (tt, 1H, J=3.6, 11.7 Hz), 2.79 (dd, 1H, J=5.2, 16.2 Hz), 2.56 (ddd, 1H, J=6.9, 11.8, 15.9 Hz), 2.21 (dd, 1H, J=2.4, 11.5 Hz), 2.15 (m, 2H), 1.88 (m, 4H), 1.76 (m, 1H), 1.66 (m, 2H), 1.50 (s, 3H), 1.44 (m, 2H), 1.29 (s, 3H), 1.28 (m, 1H), 1.24 (s, 3H); m/z 338 $[M+H]^+$.

Compounds 33 and 34: tert-Butylhydrazine hydrochloride (0.125 g, 1.0 mmol) was taken up in ethanol (25 mL). Triethylamine (0.18 mL, 1.3 mmol) was added, and the mixture was stirred at room temperature for approximately 30 min. Compound 26 (0.203 g, 0.72 mmol) was added, and the reaction mixture was heated to reflux for 5 h and then stirred overnight at room temperature. The reaction mixture was concentrated. The residue was extracted with ethyl acetate (50 mL) and washed with water (20 mL) and brine (10 mL), then dried with $MgSO_4$ and concentrated. The crude residue was purified by column chromatography (silica gel, 25% EtOAc in Hexanes) to give two products, compound 33 (81 mg, 35%, less polar) and compound 34 (91 mg, 36%, more polar) as solids. Compound 33: m/z 333 $[M+H]^+$. Compound 34: m/z 347 $[M+H]^+$.

Compound 35: Compound 33 (81 mg, 0.24 mmol) was taken up in methanol, and 1 N HCl (aq) was added. The mixture was stirred overnight at room temperature. The reaction mixture was then concentrated. The residue was extracted with ethyl acetate (50 mL) and washed with saturated $NaHCO_3$ (aq), then dried with $MgSO_4$ and concentrated to give compound 35 (70 mg, quantitative) as a solid. m/z 289 $[M+H]^+$.

Compound 36: Compound 35 (70 mg, 0.24 mmol) was taken up in ethyl formate, and sodium methoxide (30 wt % solution in MeOH) was added. The mixture was stirred overnight at room temperature. The reaction mixture was extracted with ethyl acetate and washed with $KH_2PO_4$ (aq), then dried with $MgSO_4$ and concentrated to give compound 36 (69 mg, 90%) as a solid. m/z 317 [M+H]$^+$.

Compound 37: A solution of 0.1 N hydroxylamine hydrochloride (aq) was added to compound 36 (69 mg, 0.218 mmol). A 9/1 mixture of ethanol/water was added, and the reaction mixture was stirred overnight at 50° C. After cooling to room temperature, the reaction mixture was concentrated. The residue was taken up in ethyl acetate, then dried with $MgSO_4$ and concentrated to give compound 37 (70 mg, quantitative) as a solid. m/z 314 [M+H]$^+$.

Compound 38: Compound 37 (70 mg, 0.224 mmol) was dissolved in a 3/1 methanol/THF mixture, and sodium methoxide (30 wt % solution in MeOH) was added, and the reaction mixture was stirred at 55° C. for 5 h and then stirred at room temperature overnight. The reaction was quenched by addition of saturated $KH_2PO_4$ (aq), and the reaction mixture was concentrated. The residue was extracted with ethyl acetate and washed with brine, then dried with $MgSO_4$ and concentrated. The crude residue was purified by column chromatography (silica gel, 50% EtOAc in Hexanes) to give compound 38 (41 mg, 59%) as a solid. m/z 314 [M+H]$^+$.

Compound TX63450: Compound 38 (41 mg, 0.13 mmol) was dissolved in dry DMF, and the solution was cooled to 0° C. Dibromodimethylhydantoin was added, and the reaction stirred at 0° C. until the starting material was consumed (approximately 30 min), as reported by thin layer chromatography. Then, pyridine was added, and the reaction was allowed to warm to room temperature. The reaction mixture was then stirred at 50° C. overnight. After cooling to room temperature, the reaction mixture was extracted with ethyl acetate and washed with brine, then dried with $MgSO_4$ and concentrated. The crude residue was purified by column chromatography (silica gel, 25% EtOAc in Hexanes) to give compound TX63450 (23 mg, 56%) as a solid. $^1$H NMR (400 MHz, $CDCl_3$) δ 8.58 (s, 1H), 7.21 (s, 1H), 2.79 (dd, 1H, J=5.7, 15.7 Hz), 2.56 (ddd, 1H, J=7.3, 11.5, 15.8 Hz), 2.21 (dd, 1H, J=2.6, 11.4 Hz), 1.87 (m, 2H), 1.56 (s, 9H), 1.49 (s, 3H), 1.29 (s, 3H), 1.24 (s, 3H); m/z 312 [M+H]$^+$.

Compound 39: Compound 34 (91 mg, 0.26 mmol) was taken up in methanol, and 1 N HCl (aq) was added. The mixture was stirred overnight at room temperature. The reaction mixture was then concentrated. Reaction mixture was extracted with ethyl acetate (50 mL) and washed saturated $NaHCO_3$, then dried with $MgSO_4$ and concentrated to give compound 39 (68 mg, 86%) as a solid. m/z 303 [M+H]$^+$.

Compound 40: Compound 39 (68 mg, 0.22 mmol) was taken up in ethyl formate, and sodium methoxide (30 wt % solution in MeOH) was added. The mixture was stirred overnight at room temperature. The reaction mixture was extracted with ethyl acetate and washed with $KH_2PO_4$ (aq), then dried with $MgSO_4$ and concentrated to give compound 40 (62 mg, 83%) as a solid. m/z 331 [M+H]$^+$.

Compound 41: A solution of 0.1 N hydroxylamine hydrochloride (aq) was added to compound 40 (62 mg, 0.19 mmol). A 9/1 mixture of ethanol/water was added, and the reaction mixture was stirred overnight at 50° C. After cooling to room temperature, the reaction mixture was concentrated. The residue was taken up in ethyl acetate, then dried with $MgSO_4$ and concentrated to give compound 41 (66 mg, quantitative) as a solid. m/z 328 [M+H]$^+$.

Compound 42: Compound 41 was dissolved in a 3/1 methanol/THF mixture, and sodium methoxide (30 wt % solution in MeOH) was added, and the reaction mixture was stirred at 55° C. for 5 h and then stirred at room temperature overnight. The reaction was quenched by addition of saturated $KH_2PO_4$, and the reaction mixture was concentrated. The residue was extracted with ethyl acetate and washed with brine, then dried with $MgSO_4$ and concentrated. The crude residue was purified by column chromatography (silica gel, 50% EtOAc in Hexanes) to give compound 42 (49 mg, 80%) as a solid. m/z 328 [M+H]$^+$.

Compound TX63451: Compound 42 was dissolved in dry DMF, and the solution was cooled to 0° C. 1,3-Dibromo-5,5-dimethylhydantoin was added, and the reaction stirred at 0° C. until the starting material was consumed (approximately 30 min), as reported by thin layer chromatography. Then, pyridine was added, and the reaction was allowed to warm to room temperature. The reaction mixture was then stirred at 50° C. overnight. After cooling to room temperature, the reaction mixture was extracted with ethyl acetate and washed with brine, then dried with $MgSO_4$ and concentrated. The crude residue was purified by column chromatography (silica gel, 25% EtOAc in Hexanes) to give compound TX63451 (33 mg, 68%) as a solid. $^1$H NMR (400 MHz, $CDCl_3$) δ 8.39 (s, 1H), 7.89 (s, 1H), 3.28 (dd, 1H, J=3.8, 16.6 Hz), 3.06 (dd, 1H, J=12.2, 16.5 Hz), 2.58 (dd, 1H, J=3.7, 12.1 Hz), 1.71 (s, 9H), 1.44 (s, 3H), 1.36 (s, 3H), 1.32 (s, 3H); m/z 326 [M+H]$^+$.

Compound 43: A mixture of 26 (300 mg, 1.07 mmol) and (2,2,2-trifluoroethyl)hydrazine (70% pure, 270 mg, 2.4 mmol) in ethanol (25 mL) was heated to 60° C. for 2 h. The reaction mixture was concentrated. The crude residue was purified by column chromatography (silica gel, 5 to 45% EtOAc in Hexanes) to give 43 (270 mg, 70%) as a solid. m/z 359 [M+H]$^+$.

Compound 44: Compound 43 (0.27 g, 0.75 mmol) was taken up in methanol, and 3 N HCl (aq) was added. The mixture was stirred overnight at room temperature. The reaction mixture was then concentrated. Reaction mixture was extracted with ethyl acetate (2×25 mL) and washed saturated $NaHCO_3$, then dried with $MgSO_4$ and concentrated to give compound 44 (0.24 g, quantitative) as a solid. m/z 315 [M+H]$^+$.

Compound 45: Compound 44 (0.24 g, 0.75 mmol) was taken up in ethyl formate, and sodium methoxide (30 wt % solution in MeOH) was added. The mixture was stirred overnight at room temperature. The reaction mixture was extracted with ethyl acetate and washed with $KH_2PO_4$ (aq), then dried with $MgSO_4$ and concentrated to give compound 45 (0.25 g, 96%) as a solid. m/z 343 [M+H]$^+$.

Compound 46: A mixture of hydroxylamine hydrochloride and 45 (0.25 g, 0.73 mmol) in ethanol was stirred overnight at 50° C. After cooling to room temperature, the reaction mixture was concentrated. The residue was diluted with water and extracted with ethyl acetate, then dried with $MgSO_4$ and concentrated to give compound 46 (0.23 g, 93%) as a solid. m/z 340 [M+H]$^+$.

Compound 47: Compound 46 (0.23 g, 0.68 mmol) was dissolved in a 1/1 methanol/THF mixture, and sodium methoxide (30 wt % solution in MeOH) was added, and the reaction mixture was stirred at 50° C. for 6 h. The reaction mixture was concentrated and quenched by addition of saturated $KH_2PO_4$. The mixture was extracted with ethyl acetate and washed with brine, then dried with $MgSO_4$ and concentrated to give compound 47 (0.12 g, 52%) as a solid. m/z 340 [M+H]$^+$.

Compound TX63454: Compound 47 (0.12 g, 0.35 mmol) was dissolved in dry DMF, and the solution was cooled to 0° C. 1,3-Dibromo-5,5-dimethylhydantoin was added, and the reaction stirred at 0° C. until the starting material was consumed (approximately 2 h), as reported by thin layer chromatography. Then, pyridine was added, and the reaction was allowed to warm to room temperature. The reaction mixture was then stirred at 50° C. overnight. The reaction mixture was concentrated. The crude residue was purified by column chromatography (silica gel, 5 to 30% EtOAc in Hexanes) to give compound TX63454 (65 mg, 54%) as a solid. $^1$H NMR (400 MHz, CDCl$_3$) δ 8.47 (s, 1H), 7.22 (s, 1H), 4.65 (m, 2H), 2.84 (dd, 1H, J=5.7, 16.2 Hz), 2.59 (ddd, 1H, J=7.0, 11.9, 16.1 Hz), 2.21 (dd, 1H, J=2.1, 11.9 Hz), 1.90 (m, 2H), 1.51 (s, 3H), 1.31 (s, 3H), 1.25 (s, 3H); m/z 338 [M+H]$^+$.

Compounds 48 and 49: Ethanol was added to a mixture of 26 (204 mg, 0.73 mmol), phenylhydrazine hydrochloride (132 mg, 0.92 mmol), and sodium acetate trihydrate (140 mg, 1.08 mmol) was gradually heated to 65° C. The reaction mixture was then stirred at 70° C. overnight. The reaction mixture was concentrated. The reaction mixture was extracted with ethyl acetate and washed with saturated NaHCO$_3$, then dried with MgSO$_4$ and concentrated. The crude residue was purified by column chromatography (silica gel, 25% EtOAc in Hexanes) to give 48 (91 mg, 35%, less polar) and 49 (135 mg, 51%, more polar) as solids. Compound 48: $^1$H NMR (400 MHz, CDCl$_3$) 7.62 (d, 2H, J=8.5 Hz), 7.53 (s, 1H), 7.41 (t, 2H, J=7.6 Hz), 7.22 (t, 1H, J=7.5 Hz), 3.98 (m, 4H), 2.80 (dd, 1H, J=5.7, 15.9 Hz), 2.59 (ddd, 1H, J=6.5, 11.6, 15.8 Hz), 2.36 (m, 1H), 1.99 (m, 2H), 1.77 (m, 4H), 1.37 (s, 3H), 1.09 (3H), 0.98 (s, 3H); m/z 353 [M+H]$^+$. Compound 49: $^1$H NMR (400 MHz, CDCl$_3$) δ 8.06 (s, 1H), 7.56 (m, 4H), 7.46 (m, 1H), 3.93 (m, 4H), 2.98 (dd, 1H, J=12.2, 16.7 Hz), 2.86 (dd, 1H, J=4.0, 16.7 Hz), 2.32 (dd, 1H, J=4.0, 12.2 Hz), 2.01 (m, 1H), 1.91 (m, 2H), 1.68 (m, 1H), 1.28 (s, 3H), 1.21 (s, 3H), 0.90 (s, 3H); m/z 367 [M+H]$^+$.

Compound 50: Compound 48 (86 mg, 0.24 mmol) was taken up in methanol, and 1 N HCl (aq) was added. The mixture was stirred overnight at room temperature. The reaction mixture was then concentrated. Reaction mixture was extracted with ethyl acetate (50 mL) and washed saturated NaHCO$_3$, then dried with MgSO$_4$ and concentrated to give compound 50 (69 mg, 92%) as a solid. m/z 309 [M+H]$^+$.

Compound 51: Compound 50 (69 mg, 0.22 mmol) was taken up in ethyl formate, and sodium methoxide (30 wt % solution in MeOH) was added. The mixture was stirred overnight at room temperature. The reaction mixture was extracted with ethyl acetate and washed with KH$_2$PO$_4$ (aq), then dried with MgSO$_4$ and concentrated to give compound 51 (73 mg, 97%) as a solid. m/z 337 [M+H]$^+$.

Compound 52: A solution of 0.1 N hydroxylamine hydrochloride (aq) was added to compound 51 (73 mg, 0.22 mmol). A 9/1 mixture of ethanol/water was added, and the reaction mixture was stirred overnight at 50° C. After cooling to room temperature, the reaction mixture was concentrated. The residue was taken up in ethyl acetate, then dried with MgSO$_4$ and concentrated to give compound 52 (66 mg, 91%) as a solid. m/z 334 [M+H]$^+$.

Compound 53: Compound 52 (66 mg, 0.20 mmol) was dissolved in a 3/1 methanol/THF mixture, and sodium methoxide (30 wt % solution in MeOH) was added, and the reaction mixture was stirred at 55° C. for 5 h and then stirred at room temperature overnight. The reaction was quenched by addition of saturated KH$_2$PO$_4$, and the reaction mixture was concentrated. The residue was extracted with ethyl acetate and washed with brine, then dried with MgSO$_4$ and concentrated. The crude residue was purified by column chromatography (silica gel, 50% EtOAc in Hexanes) to give compound 53 (53 mg, 80%) as a solid. m/z 334 [M+H]$^+$.

Compound TX63455: Compound 53 (53 mg, 0.16 mmol) was dissolved in dry DMF, and the solution was cooled to 0° C. 1,3-Dibromo-5,5-dimethylhydantoin was added, and the reaction stirred at 0° C. until the starting material was consumed (approximately 30 min), as reported by thin layer chromatography. Then, pyridine was added, and the reaction was allowed to warm to room temperature. The reaction mixture was then stirred at 50° C. overnight. After cooling to room temperature, the reaction mixture was extracted with ethyl acetate and washed with brine, then dried with MgSO$_4$ and concentrated. The crude residue was purified by repeated column chromatography (silica gel, 25% EtOAc in Hexanes) to give compound TX63455 (1.8 mg, 3%) as a solid. $^1$H NMR (400 MHz, CDCl$_3$) δ 8.63 (s, 1H), 7.66 (m, 3H), 7.48 (m, 3H), 2.92 (dd, 1H, J=4.8, 15.8 Hz), 2.67 (ddd, 1H, J=6.5, 11.8, 15.8 Hz), 2.26 (dd, 1H, J=2.4, 11.4 Hz), 1.97 (m, 2H), 1.58 (s, 3H), 1.33 (s, 3H), 1.28 (s, 3H); m/z 332 [M+H]$^+$.

Compound 54: Compound 49 (0.120 g, 0.33 mmol) was taken up in methanol (20 mL), and 1N HCl (aq, 2 mL) was added. The mixture was stirred overnight at room temperature. The reaction mixture was concentrated. The residue was taken up in ethyl acetate (50 mL) and washed with saturated NaHCO$_3$ (aq, 15 mL), then dried with MgSO$_4$ and concentrated to give compound 54 (97.3 mg, 92%) as a solid.

Compound 55: Compound 54 (0.0973 g, 0.30 mmol) was taken up in ethyl formate (5 mL), and sodium methoxide (30 wt % solution in MeOH, 0.4 mL, 7.1 mmol) was added. The mixture was stirred overnight at room temperature. The reaction mixture was extracted with ethyl acetate and washed with KH$_2$PO$_4$ (aq), then dried with MgSO$_4$ and concentrated to give compound 55 (100.7 mg, 95%) as a solid. m/z 351 [M+H]$^+$.

Compound 56: A solution of 0.1 N hydroxylamine hydrochloride (aq, 3.2 mL, 0.32 mL) was added to compound 55 (100.7 mg, 0.29 mmol). A 9/1 mixture of ethanol/water (2 mL) was added, and the reaction mixture was stirred overnight at 50° C. After cooling to room temperature, the reaction mixture was concentrated. The residue was taken up in ethyl acetate, then dried with MgSO$_4$ and concentrated to give compound 56 (75.4 mg, 76%) as a solid. m/z 348 [M+H]$^+$.

Compound 57: Compound 56 (75.4 mg, 0.22 mmol) was dissolved in a 3/1 methanol/THF mixture (6 mL), and sodium methoxide (30 wt % solution in MeOH, 0.24 mL, 4.3 mL) was added, and the reaction mixture was stirred at 55° C. for approximately 5.5 h and then stirred at room temperature overnight. The reaction was quenched by addition of saturated KH$_2$PO$_4$, and the reaction mixture was concentrated. The residue was extracted with ethyl acetate (50 mL) and washed with brine (10 mL), then dried with MgSO$_4$ and concentrated. The crude residue was purified by column chromatography (silica gel, 50% EtOAc in Hexanes) to give compound 57 (59.5 mg, 79%) as a solid. m/z 348 [M+H]$^+$.

Compound TX63456: Compound 57 (59.5 mg, 0.17 mmol) was dissolved in dry DMF (1 mL), and the solution was cooled to 0° C. Dibromodimethylhydantoin (31 mg, 0.109 mmol) was added, and the reaction stirred at 0° C. until the starting material was consumed, as reported by thin layer chromatography. Then, pyridine (0.13 mL, 1.6 mmol) was added, and the reaction was allowed to warm to room temperature. The reaction mixture was then stirred at 50° C. overnight. After cooling to room temperature, the reaction mixture was extracted with ethyl acetate (60 mL) and washed with brine (10 mL), then dried with MgSO$_4$ and concentrated. The crude residue was purified by column chromatography (silica gel, 25% EtOAc in Hexanes) to give a solid (29.9 mg). The purified residue was purified again by column chromatography (silica gel, 25% EtOAc in Hexanes) to a solid. The solid was triturated with Et$_2$O/EtOAc to give compound TX63456 (14.3 mg, 24%) as a solid. $^1$H NMR (400 MHz, CDCl$_3$) δ 8.44 (s, 1H), 8.15 (s, 1H), 7.48-7.68 (m, 5H), 3.18 (dd, 1H, J=8.0, 16.0 Hz), 3.02 (dd, 1H, J=4.0, 16.0 Hz), 2.62 (dd, 1H, J=4.0, 12.0 Hz), 1.56 (s, 3H), 1.34 (s, 3H), 1.27 (s, 3H); m/z 346 [M+H]$^+$.

Compound 58: Compound 26 (1.200 g, 4.28 mmol) was taken up in ethanol (100 mL). Anhydrous hydrazine (0.36 mL, 11.5 mmol) in ethanol (5 mL) was added, and the mixture was stirred at room temperature for 2 h and then 60° C. for 1 h. The reaction mixture was concentrated. The residue was triturated with ether/ethyl acetate to give compound 58 (0.965 g, 82%) as a solid. m/z 277 [M+H]$^+$.

Compound 59: Compound 58 (280 mg, 1.01 mmol) was taken up in methanol, and 1 N HCl (aq) was added. The mixture was stirred overnight at room temperature. The reaction mixture was then concentrated. The residue was extracted with ethyl acetate and washed with saturated NaHCO$_3$ (aq), then dried with MgSO$_4$ and concentrated to give compound 59 (245.2 mg, quantitative) as a solid. m/z 233 [M+H]$^+$.

Compound 60: Compound 59 (239 mg, 1.03 mmol) was taken up in ethyl formate, and sodium methoxide (30 wt % solution in MeOH) was added. The mixture was stirred overnight at room temperature. The reaction mixture was extracted with ethyl acetate and washed with KH$_2$PO$_4$ (aq), then dried with MgSO$_4$ and concentrated to give compound 63 (264 mg, 99%): m/z 261 [M+H]$^+$.

Compound 61: A solution of 0.1 N hydroxylamine hydrochloride (aq) was added to compound 60 (260 mg, 1.00 mmol). A 9/1 mixture of ethanol/water was added, and the reaction mixture was stirred overnight at 50° C. After cooling to room temperature, the reaction mixture was concentrated. The residue was taken up in ethyl acetate, then dried with MgSO$_4$ and concentrated to give compound 61 (248.9 mg, 97%): m/z 258 [M+H]$^+$.

Compound 62: Compound 61 (245 mg, 0.95 mmol) was dissolved in a 3/1 methanol/THF mixture, and sodium methoxide (30 wt % solution in MeOH) was added, and the reaction mixture was stirred at 55° C. for 5 h and then stirred at room temperature overnight. The reaction was quenched by addition of saturated KH$_2$PO$_4$, and the reaction mixture was concentrated. The residue was extracted with ethyl acetate and washed with brine, then dried with MgSO$_4$ and concentrated. The crude residue was purified by column chromatography (silica gel, 50% EtOAc in Hexanes) to give compound 62 (204 mg, 83%) as a solid. m/z 258 [M+H]$^+$.

Compound TX63467: A mixture of compound 62 (51 mg, 0.198 mmol) and DDQ (59 mg, 0.26 mmol) were taken up in benzene (11 mL). The mixture was stirred at reflux for 4.5 h. After cooling to room temperature, the reaction mixture was concentrated. The crude residue was purified by column chromatography three times (silica gel, 1.5% MeOH in CH$_2$Cl$_2$, 2% MeOH in CH$_2$Cl$_2$ and EtOAc, respectively) to give a solid. The purified residue was taken up in ethyl acetate (40 mL) and washed with saturated NaHCO$_3$ (aq), then dried with MgSO$_4$ and concentrated to give compound TX63467 (22 mg, 43%) as a solid. $^1$H NMR (400 MHz, CD$_3$OD) δ 12.59 (s, 1H), 8.51 (s, 1H), 7.44 (s, 1H), 2.68-2.77 (m, 1H), 2.45-2.58 (m, 1H), 2.15-2.22 (m, 1H), 1.78-1.92 (m, 2H), 1.41 (s, 3H), 1.21 (s, 3H), 1.13 (s, 3H); m/z 256 [M+H]$^+$.

Compound TX63462: TX63467 (12 mg, 0.047 mmol) was taken up in a mixture of saturated NaHCO$_3$ (aq, 0.5 mL) and THF (1.5 mL), and the mixture was cooled to 0° C. Methyl chloroformate (1 drop, excess) was added and the reaction mixture was stirred 40 min at 0° C. and then more methyl chloroformate (2 drops, excess) was added and the reaction mixture was stirred 20 minutes. The reaction mixture was extracted with ethyl acetate (40 mL) and washed with NaCl (aq, 10 mL), then dried with MgSO$_4$ and concentrated. The crude residue was purified by column chromatography (silica gel, 25% EtOAc in Hexanes) to give TX63462 (2.3 mg, 16%) as a solid. $^1$H NMR (400 MHz, CDCl$_3$) δ 8.57 (s, 1H), 7.89 (s, 1H), 4.10 (s, 3H), 2.90 (dd, 1H, J=8.0, 16.0 Hz), 2.58-2.68 (m, 1H), 2.19 (dd, 1H, J=4.0, 12.0 Hz), 1.85-2.02 (m, 2H), 1.56 (s, 3H), 1.32 (s, 3H), 1.26 (s, 3H); m/z 314 [M+H]$^+$.

Compound TX63463: TX63467 (12 mg, 0.047 mmol) was taken up in a mixture of saturated NaHCO$_3$ (aq, 0.5 mL) and THF (1.5 mL), and the mixture was cooled to 0° C. Acetyl chloride (1 drop, excess) was added, and the reaction mixture was stirred 40 min at 0° C. Then more acetyl chloride (2 drops, excess) was added, and the reaction mixture was stirred an additional 20 minutes. The reaction mixture was extracted with ethyl acetate (40 mL) and washed with NaCl (aq, 10 mL), then dried with MgSO$_4$ and concentrated. The crude residue was purified by column chromatography (silica gel, 25% EtOAc in Hexanes) to give TX63463 (3.3 mg, 24%) as a solid. $^1$H NMR (400 MHz, CDCl$_3$) δ 8.49 (s, 1H), 7.97 (s, 1H), 2.90 (dd, 1H, J=4.0, 12.0 Hz), 2.69 (s, 3H), 2.57-2.68 (m, 1H), 2.19 (dd, 1H, J=4.0, 12.0 Hz), 1.85-2.02 (m, 2H), 1.54 (s, 3H), 1.32 (s, 3H), 1.26 (s, 3H); m/z 298 [M+H]$^+$.

Compound 63: A mixture of 26 (300 mg, 1.07 mmol) and 2-hydrazinylethanol (130 mg, 1.7 mmol) in ethanol (5 mL) was heated to 60° C. for 2 h. The reaction mixture was concentrated. The crude residue was purified by column chromatography (silica gel, 1% MeOH in EtOAc) to give 63 (320 mg, 93%) as an oil. m/z 321 [M+H]$^+$.

Compound 64: Compound 63 (0.32 g, 1.0 mmol) was taken up in methanol, and 3 N HCl (aq) was added. The mixture was stirred overnight at room temperature. The reaction mixture was then concentrated. Reaction mixture was extracted with ethyl acetate (2×25 mL) and washed saturated NaHCO$_3$, then dried with MgSO$_4$ and concentrated to give compound 64 (0.17 g, 62%) as a solid. m/z 277 [M+H]$^+$.

Compound 65: Compound 64 (0.17 g, 0.62 mmol) was taken up in ethyl formate, and 30% sodium methoxide (30 wt % solution in MeOH) was added. The mixture was stirred overnight at room temperature. The reaction mixture was diluted with KH$_2$PO$_4$ (aq), extracted with ethyl acetate (2×25 mL) and washed with brine, then dried with MgSO$_4$ and concentrated to give compound 65 (0.17 g, 91%) as a solid. m/z 305 [M+H]$^+$.

Compound 66: A mixture of hydroxylamine hydrochloride and 65 (0.17 g, 0.56 mmol) in ethanol was stirred overnight at 50° C. After cooling to room temperature, the reaction mixture was concentrated. The residue was diluted with water, extracted with ethyl acetate (2×25 mL) and washed with brine, dried with MgSO$_4$ and concentrated to give compound 66 (0.18 g, quantitative) as a solid. m/z 302 [M+H]$^+$.

Compound 67: Compound 66 (0.18 g, 0.56 mmol) was dissolved in a 1/1 methanol/THF mixture, and 30% sodium methoxide (30 wt % solution in MeOH) was added, and the reaction mixture was stirred at 50° C. for 6 h. The reaction mixture was concentrated and quenched by addition of saturated KH$_2$PO$_4$. The mixture was extracted with ethyl acetate (2×25 mL) and washed with brine, then dried with MgSO$_4$ and concentrated to give compound 67 (0.18 g, quantitative) as a solid. m/z 302 [M+H]$^+$.

Compound TX63464: Compound 67 (0.18 g, 0.56 mmol) was dissolved in dioxane. Pyridinium bromide perbromide was added, and the reaction stirred at room temperature for 2 h. Pyridine was added, and the reaction mixture was then stirred at 50° C. overnight. The reaction mixture was concentrated. The crude residue was purified by column chromatography (silica gel, 0 to 2% MeOH in EtOAc) to give compound TX63464 (10 mg, 5%) as an off-white solid. $^1$H NMR (400

MHz, CDCl$_3$) δ 8.45 (s, 1H), 7.17 (s, 1H), 4.21 (m, 2H), 4.01 (d, 1H, J=5.1 Hz), 4.00 (d, 1H, J=4.6 Hz), 2.81 (dd, 1H, J=5.5, 16.1 Hz), 2.57 (ddd, 1H, J=7.0, 11.8, 16.0 Hz), 2.21 (dd, 1H, J=2.1, 11.7 Hz), 1.91 (m, 2H), 1.51 (s, 3H), 1.31 (s, 3H), 1.24 (s, 3H); m/z 300 [M+H]$^+$.

Compound 68: Compound 27 (2.6 g, 9.0 mmol) was taken up in CH$_2$Cl$_2$, and 1,3-dibromo-5,5-dimethylhydantoin (1.7 g, 5.9 mmol) was added. The mixture was stirred for 3 h at room temperature. The reaction mixture was washed with 1N Na$_2$CO$_3$, then dried with MgSO$_4$ and concentrated. The crude residue was purified by column chromatography (silica gel, 5 to 35% EtOAc in Hexanes) to give compound 68 (1.8 g, 54%) as a gummy solid. m/z 369, 371 (1:1) [M+H]$^+$.

Compound 69: A mixture of Compound 68 (1.3 g, 3.5 mmol), phenylboronic acid (645 mg, 5.3 mmol), Ph$_3$P (190 mg, 0.73 mmol), K$_3$PO$_4$ (2.24 g, 10.6 mmol) and DME (15 mL) was sparged with N$_2$ for 10 min. Pd(OAc)$_2$ (80 mg, 0.35 mmol) was added and sparging with N$_2$ was continued for 10 min. The reaction was heated to 85° C. for 9 h. The reaction mixture was filtered and concentrated. The crude residue was purified by column chromatography (silica gel, 5 to 30% EtOAc in Hexanes) to give compound 69 (0.69 g, 53%) as an off-white solid. m/z 367 [M+H]$^+$.

Compound 70: Compound 69 (0.69 g, 1.9 mmol) was taken up in methanol, and 3 N HCl (aq) was added. The mixture was stirred overnight at room temperature. The reaction mixture was then concentrated. Reaction mixture was extracted with ethyl acetate (2×25 mL) and washed saturated NaHCO$_3$, then dried with MgSO$_4$ and concentrated to give compound 70 (0.64 g, quantitative) as a solid. m/z 323 [M+H]$^+$.

Compound 71: Compound 70 (0.64 g, 1.9 mmol) was taken up in ethyl formate, and 30% sodium methoxide (30 wt % solution in MeOH) was added. The mixture was stirred overnight at room temperature. The reaction mixture was diluted with KH$_2$PO$_4$ (aq), extracted with ethyl acetate (2×25 mL) and washed with brine, then dried with MgSO$_4$ and concentrated to give compound 71 (0.61 g, 92%) as a solid. m/z 351 [M+H]$^+$.

Compound 72: A mixture of hydroxylamine hydrochloride and 71 (0.61 g, 1.7 mmol) in ethanol was stirred overnight at 50° C. After cooling to room temperature, the reaction mixture was concentrated. The residue was diluted with water and extracted with ethyl acetate, then dried with MgSO$_4$ and concentrated to give compound 72 (0.58 g, 96%) as a solid. m/z 348 [M+H]$^+$.

Compound 73: Compound 72 (0.58 g, 1.7 mmol) was dissolved in a 1/1 methanol/THF mixture, and 30% sodium methoxide (30 wt % solution in MeOH) was added, and the reaction mixture was stirred at 50° C. for 6 h. The reaction mixture was concentrated and quenched by addition of saturated KH$_2$PO$_4$. The mixture was extracted with ethyl acetate and washed with brine, then dried with MgSO$_4$ and concentrated to give compound 73 (435 mg, 75%) as a solid. m/z 348 [M+H]$^+$.

Compound TX63465: Compound 73 (435 mg, 1.25 mmol) was dissolved in dry DMF, and the solution was cooled to 0° C. 1,3-Dibromo-5,5-dimethylhydantoin was added, and the reaction stirred at 0° C. until the starting material was consumed (approximately 2 h), as reported by thin layer chromatography. Then, pyridine was added, and the reaction was allowed to warm to room temperature. The reaction mixture was then stirred at 50° C. overnight. The reaction mixture was concentrated. The crude residue was purified by column chromatography (silica gel, 5 to 30% EtOAc in Hexanes) to give compound TX63465 (0.3 g, 69%) as a solid. $^1$H NMR (400 MHz, d$_6$-DMSO) δ 8.51 (s, 1H), 7.51 (m, 2H), 7.44 (s, 3H), 3.76 (s, 3H), 2.55 (m 2H), 2.23 (d, 1H, J=11.9 Hz), 1.89 (dd, 1H, J=5.0, 12.6 Hz), 1.82 (m, 1H), 1.46 (s, 3H), 1.22 (s, 3H), 1.14 (s, 3H); m/z 346 [M+H]$^+$.

TABLE 2

Compounds 74a-74l (Scheme 16).

| Compound Name | R | Aryl boronic acid (1.5 eq) | Pd(OAc)$_2$ | DME (mL) | Yield (%) |
|---|---|---|---|---|---|
| 74a | 3-Cl | 1.1 mmol | 0.1 eq. | 3.1 | 78 |
| 74b | 4-Cl | 1.1 mmol | 0.1 eq. | 3.1 | 68 |
| 74c | 2-Cl | 1.1 mmol | 0.1 eq. | 3.1 | 78 |
| 74d | 3-F | 0.57 mmol | 0.3 eq | 6 | 74 |
| 74e | 4-F | 0.58 mmol | 0.3 eq | 6 | 70 |
| 74f | 2-Me | 0.8 mmol | 0.1 eq. | 2.3 | 64 |
| 74g | 2-OMe | 1.1 mmol | 0.1 eq. | 3.1 | 69 |
| 74h | 3-Me | 0.60 mmol | 0.3 eq | 6 | 67 |
| 74i | 3-OMe | 0.61 mmol | 0.3 eq | 6 | 58 |
| 74j | 4-Me | 0.73 mmol | 0.1 eq. | 2.1 | 70 |
| 74k | 4-OMe | 1.1 mmol | 0.1 eq. | 3.1 | 48 |
| 74l | 2-F | 0.93 mmol | 0.1 eq. | 2.6 | 71 |

General method A: Compound 68 (1.0 eq.) was taken up in DME (See Table 2 for the amount). PhB(OH)$_2$ (See Table 2 for the amount), Ph$_3$P (0.2 eq.) and K$_3$PO$_4$ (3.0 eq.) were added, and the mixture was bubbled with N$_2$ for 10 min. Pd(OAc)$_2$ (See Table 2 for the amount) was added and the mixture was bubbled with N$_2$ for 10 min. Then the mixture was stirred at 85° C. for 9 h. The reaction mixture was filtered, concentrated. The crude residue was purified by column chromatography to give the corresponding derivatives:

Compound 74a: 0.23 g, 78%: m/z 401, 403 (3:1) [M+H]$^+$.
Compound 74b: 0.2 g, 68%: m/z 401, 403 (3:1) [M+H]$^+$.
Compound 74c: 0.23 g, 78%: m/z 401, 403 (3:1) [M+H]$^+$.
Compound 74d: 0.1051 g, 74%: m/z 385 [M+H]$^+$.
Compound 74e: 0.0992 g, 70%: m/z 385 [M+H]$^+$.
Compound 74f: 0.13 g, 64%: m/z 381 [M+H]$^+$.
Compound 74g: 0.2 g, 69%: m/z 397 [M+H]$^+$.
Compound 74h: 0.097 g, 67%: m/z 381 [M+H]$^+$.
Compound 74i: 0.0872 g, 58%: m/z 397 [M+H]$^+$.
Compound 74j: 0.13 g, 70%: m/z 381 [M+H]$^+$.
Compound 74k: 0.14 g, 48%: m/z 397 [M+H]$^+$.
Compound 74l: 0.17 g, 71%: m/z 385 [M+H]$^+$.

TABLE 3

Compounds 75a-75l (Scheme 16).

| Compound Name | R | 74 (mmol) (starting materials) | HCl | MeOH (mL) | Yield (%) |
|---|---|---|---|---|---|
| 75a | 3-Cl | 0.57 | 3N, 0.9 mL | 1.5 | quantitative |
| 75b | 4-Cl | 0.5 | 3N, 0.4 mL | 1.35 | quantitative |
| 75c | 2-Cl | 0.50 | 3N, 0.4 mL | 1.35 | quantitative |
| 75d | 3-F | 0.27 | 1N, 1.6 mL | 16.2 | 87 |
| 75e | 4-F | 0.26 | 1N, 1.6 mL | 15.6 | 83 |
| 75f | 2-Me | 0.34 | 3N, 0.27 mL | 0.92 | quantitative |
| 75g | 2-OMe | 0.50 | 3N, 0.4 mL | 1.35 | quantitative |
| 75h | 3-Me | 0.255 | 1N, 1.5 mL | 15.3 | 96 |
| 75i | 3-OMe | 0.22 | 1N, 1.3 mL | 13.2 | 92 |
| 75j | 4-Me | 0.34 | 3N, 0.27 mL | 0.92 | quantitative |
| 75k | 4-OMe | 0.35 | 3N, 0.28 mL | 0.95 | 97 |
| 75l | 2-F | 0.44 | 3N, 0.35 mL | 1.2 | quantitative |

General method B: Compound 74 (See Table 3 for the amount) was taken up in methanol (See Table 3 for the amount), and HCl (aq, See Table 3 for the amount) was added. The mixture was stirred overnight at room temperature. The reaction mixture was then concentrated. The residue was extracted with ethyl acetate and washed with saturated NaHCO$_3$ (aq), then dried with MgSO$_4$ and concentrated to give the corresponding derivatives:

Compound 75a: 210 mg, quantitative: m/z 357, 359 (3:1) [M+H]$^+$.
Compound 75b: 180 mg, quantitative: m/z 357, 359 (3:1) [M+H]$^+$.
Compound 75c: 180 mg, quantitative: m/z 357, 359 (3:1) [M+H]$^+$.
Compound 75d: 80.3 mg, 87%: m/z 341 [M+H]$^+$.
Compound 75e: 79.7 mg, 83%: m/z 341 [M+H]$^+$.
Compound 75f: 120 mg, quantitative: m/z 337 [M+H]$^+$.
Compound 75g: 180 mg, quantitative: m/z 353 [M+H]$^+$.
Compound 75h: 82.4 mg, 96%: m/z 337 [M+H]$^+$.
Compound 75i: 71.5 mg, 92%: m/z 353 [M+H]$^+$.
Compound 75j: 120 mg, quantitative: m/z 337 [M+H]$^+$.
Compound 75k: 120 mg, 97%: m/z 353 [M+H]$^+$.
Compound 75l: 150 mg, quantitative: m/z 341 [M+H]$^+$.

TABLE 4

Compounds 76a-76l (Scheme 16).

| Compound Name | R | 75 (mmol) (starting materials) | HCO$_2$Et (mL) | MeONa (23%$_{w/w}$, eq) | Yield (%) |
|---|---|---|---|---|---|
| 76a | 3-Cl | 0.588 | 4.7 | 10 | 97 |
| 76b | 4-Cl | 0.5 | 4 | 10 | 94 |
| 76c | 2-Cl | 0.5 | 4 | 10 | 94 |
| 76d | 3-F | 0.236 | 3.9 | 23.7 | quantitative |
| 76e | 4-F | 0.234 | 3.9 | 23.7 | 91 |
| 76f | 2-Me | 0.356 | 2.8 | 10 | 96 |
| 76g | 2-OMe | 0.51 | 4.1 | 10 | 93 |
| 76h | 3-Me | 0.245 | 4.1 | 23.7 | quantitative |
| 76i | 3-OMe | 0.20 | 3.3 | 23.7 | quantitative |
| 76j | 4-Me | 0.356 | 2.8 | 10 | 92 |
| 76k | 4-OMe | 0.34 | 2.7 | 10 | 97 |
| 76l | 2-F | 0.44 | 3.5 | 10 | 92 |

General method C: Compound 75 (See Table 4 for the amount) was taken up in ethyl formate (See Table 4 for the amount), and 30% NaOMe in methanol (See Table 4 for the amount) was added. The mixture was stirred overnight at room temperature. The reaction mixture was extracted with ethyl acetate and washed with KH$_2$PO$_4$ (aq), then dried with MgSO$_4$ and concentrated to give the corresponding derivatives:

Compound 76a: 220 mg, 97%: m/z 385, 387 (3:1) [M+H]$^+$.
Compound 76b: 180 mg, 94%: m/z 385, 387 (3:1) [M+H]$^+$.
Compound 76c: 180 mg, 94%: m/z 385, 387 (3:1) [M+H]$^+$.
Compound 76d: 93 mg, quantitative: m/z 369 [M+H]$^+$.
Compound 76e: 77.8 mg, 91%: m/z 369 [M+H]$^+$.
Compound 76f: 125 mg, 96%: m/z 365 [M+H]$^+$.
Compound 76g: 180 mg, 93%: m/z 381 [M+H]$^+$.
Compound 76h: 90.2 mg, quantitative: m/z 365 [M+H]$^+$.
Compound 76i: 75.8 mg, 99.6%: m/z 381 [M+H]$^+$.
Compound 76j: 120 mg, 92%: m/z 365 [M+H]$^+$.
Compound 76k: 125 mg, 97%: m/z 381 [M+H]$^+$.
Compound 76l: 150 mg, 92%: m/z 369 [M+H]$^+$.

TABLE 5

Compounds 77a-77l (Scheme 16).

| Compound Name | R | 76 (mmol) (starting materials) | NH$_2$OH•HCl (eq) | Yield (%) |
|---|---|---|---|---|
| 77a | 3-Cl | 0.57 | 2 | quantitative |
| 77b | 4-Cl | 0.47 | 2 | quantitative |
| 77c | 2-Cl | 0.47 | 2 | quantitative |
| 77d | 3-F | 0.29 | 1.1 | 92 |
| 77e | 4-F | 0.21 | 1.1 | 94 |
| 77f | 2-Me | 0.34 | 2 | quantitative |
| 77g | 2-OMe | 0.47 | 2 | 95 |
| 77h | 3-Me | 0.25 | 1.1 | 94 |
| 77i | 3-OMe | 0.20 | 1.1 | 87 |
| 77j | 4-Me | 0.33 | 2 | quantitative |
| 77k | 4-OMe | 0.33 | 2 | quantitative |
| 77l | 2-F | 0.41 | 2 | quantitative |

General method D: A solution of 0.1 N hydroxylamine hydrochloride (aq, See Table 5 for the amount) was added to compound 76 (See Table 5 for the amount). A 9/1 mixture of ethanol/water was added, and the reaction mixture was stirred overnight at 50° C. After cooling to room temperature, the reaction mixture was concentrated. The residue was taken up in ethyl acetate, then dried with MgSO$_4$ and concentrated to give the corresponding derivatives:

Compound 77a: 220 mg, quantitative: m/z 382, 384 (3:1) [M+H]$^+$.
Compound 77b: 180 mg, quantitative: m/z 382, 384 (3:1) [M+H]$^+$.
Compound 77c: 180 mg, quantitative: m/z 382, 384 (3:1) [M+H]$^+$.
Compound 77d: 84 mg, 92%: m/z 366 [M+H]$^+$.
Compound 77e: 72.1 mg, 94%: m/z 366 [M+H]$^+$.
Compound 77f: 125 mg, quantitative: m/z 362 [M+H]$^+$.
Compound 77g: 170 mg, 95%: m/z 378 [M+H]$^+$.
Compound 77h: 84.0 mg, 94%: m/z 362 [M+H]$^+$.
Compound 77i: 66.0 mg, 87%: m/z 378 [M+H]$^+$.
Compound 77j: 125 mg, quantitative: m/z 362 [M+H]$^+$.
Compound 77k: 130 mg, quantitative: m/z 378 [M+H]$^+$.
Compound 77l: 150 mg, quantitative: m/z 366 [M+H]$^+$.

TABLE 6

Compounds 78a-78l (Scheme 16).

| Compound Name | R | 81 (mmol) (starting materials) | MeONa (30%$_{w/w}$, eq) | Yield (%) |
|---|---|---|---|---|
| 78a | 3-Cl | 0.58 | 8 | quantitative |
| 78b | 4-Cl | 0.47 | 8 | 95 |
| 78c | 2-Cl | 0.47 | 8 | quantitative |
| 78d | 3-F | 0.23 | 20 | quantitative |
| 78e | 4-F | 0.20 | 20 | quantitative |
| 78f | 2-Me | 0.35 | 8 | 96 |
| 78g | 2-OMe | 0.45 | 8 | quantitative |
| 78h | 3-Me | 0.23 | 20 | 86 |
| 78i | 3-OMe | 0.17 | 20 | quantitative |
| 78j | 4-Me | 0.35 | 8 | 88 |
| 78k | 4-OMe | 0.34 | 8 | quantitative |
| 78l | 2-F | 0.41 | 8 | quantitative |

General method E: Compound 77 (See Table 6 for the amount) was dissolved in a 3/1 methanol/THF mixture, and 30% Sodium methoxide (See Table 6 for the amount) was added, and the reaction mixture was stirred at 55° C. for 5 h and then stirred at room temperature overnight. The reaction was quenched by addition of saturated KH$_2$PO$_4$, and the reaction mixture was concentrated. The residue was extracted with ethyl acetate and washed with brine, then dried with MgSO$_4$ and concentrated. The crude residue was purified by column chromatography (silica gel, 50% EtOAc in Hexanes) to give the corresponding derivatives:

Compound 78a: 220 mg, quantitative: m/z 382, 384 (3:1) [M+H]$^+$.
Compound 78b: 170 mg, 95%: m/z 382, 384 (3:1) [M+H]$^+$.
Compound 78c: 180 mg, quantitative: m/z 382, 384 (3:1) [M+H]$^+$.
Compound 78d: 88 mg, quantitative: m/z 366 [M+H]$^+$.
Compound 78e: 93.4 mg, quantitative: m/z 366 [M+H]$^+$.
Compound 78f: 120 mg, 96%: m/z 362 [M+H]$^+$.
Compound 78g: 170 mg, quantitative: m/z 378 [M+H]$^+$.
Compound 78h: 71.5 mg, 86%: m/z 362 [M+H]$^+$.
Compound 78i: 72.0 mg, quantitative: m/z 378 [M+H]$^+$.
Compound 78j: 110 mg, 88%: m/z 362 [M+H]$^+$.
Compound 78k: 130 mg, quantitative: m/z 378 [M+H]$^+$.
Compound 78l: 150 mg, quantitative: m/z 366 [M+H]$^+$.

TABLE 7

Compounds of Scheme 16.

| Compound Name | R | 82 (mmol) (starting materials) | DBDMH (eq) | Pyridine (eq) | Yield (%) |
|---|---|---|---|---|---|
| TX63485 | 3-Cl | 0.58 | 0.55 | 10 | 57 |
| TX63486 | 4-Cl | 0.45 | 0.55 | 10 | 53 |
| TX63491 | 2-Cl | 0.47 | 0.55 | 10 | 67 |
| TX63506 | 3-F | 0.24 | 0.64 | 9.4 | 26 |
| TX63507 | 4-F | 0.20 | 0.64 | 9.4 | 37 |
| TX63508 | 2-Me | 0.33 | 0.55 | 10 | 34 |
| TX63509 | 2-OMe | 0.45 | 0.55 | 10 | 21 |
| TX63512 | 3-Me | 0.20 | 0.64 | 9.4 | 31 |
| TX63513 | 3-OMe | 0.19 | 0.64 | 9.4 | 24 |
| TX63514 | 4-Me | 0.30 | 0.55 | 10 | 55 |
| TX63515 | 4-OMe | 0.34 | 0.55 | 10 | 39 |
| TX63519 | 2-F | 0.41 | 0.55 | 10 | 50 |

General method F: Compound 78 (See Table 7 for the amount) was dissolved in dry DMF, and the solution was cooled to 0° C. Dibromodimethylhydantoin (See Table 7 for the amount) was added, and the reaction stirred at 0° C. until the starting material was consumed (approximately 30 min), as reported by thin layer chromatography. Then, pyridine (See Table 7 for the amount) was added, and the reaction was allowed to warm to room temperature. The reaction mixture was then stirred at 50° C. overnight. After cooling to room temperature, the reaction mixture was extracted with ethyl acetate and washed with brine, then dried with MgSO$_4$ and concentrated. The crude residue was purified by column chromatography (silica gel, 25% EtOAc in Hexanes) to give the corresponding derivatives:

TX63485: 125 mg, 57%: $^1$H NMR (400 MHz, CDCl$_3$) δ 8.53 (s, 1H), 7.20-7.48 (m, 4H), 3.81 (s, 3H), 2.68 (dd, 1H, J=12.0, 4.0 Hz), 2.51-2.61 (m, 1H), 2.24 (d, 1H, J=8.0 Hz), 1.82-1.99 (m, 2H), 1.55 (s, 3H), 1.31 (s, 3H), 1.26 (s, 3H); m/z 380, 382 (3:1) [M+H]$^+$.

TX63486: 89 mg, 53%: $^1$H NMR (400 MHz, CDCl$_3$) δ 8.53 (s, 1H), 7.48 (d, 2H, J=8.0 Hz), 7.28 (d, 2H, J=8.0 Hz), 3.80 (s, 3H), 2.66 (dd, 1H, J=12.0, 4.0 Hz), 2.50-2.60 (m, 1H), 2.24 (dd, 1H, J=12.0, 2.0 Hz), 1.82-1.99 (m, 2H), 1.55 (s, 3H), 1.31 (s, 3H), 1.25 (s, 3H); m/z 380, 382 (3:1) [M+H]$^+$.

TX63491: 120 mg, 67%: $^1$H NMR (500 MHz, CDCl$_3$) δ 8.56 (s, 1H), 7.55 (m, 1H), 7.45 (m, 1H), 7.45-7.25 (m, 2H), 3.67 (s, 3H), 2.60-2.39 (m, 2H), 2.29-2.20 (m, 1H), 1.91-1.85 (m, 2H), 1.60 (s, 3H), 1.35 (s, 3H), 1.31 (s, 3H); m/z 380, 382 (3:1) [M+H]$^+$.

TX63506: 22.5 mg, 26%: $^1$H NMR (400 MHz, CDCl$_3$) δ 8.54 (s, 1H), 7.45-7.52 (m, 1H), 7.10-7.18 (m, 2H), 7.04-7.08 (m, 1H), 3.83 (s, 3H), 2.69 (dd, 1H, J=12.0, 4.0 Hz), 2.52-2.62 (m, 1H), 2.24 (d, 1H, J=8.0 Hz), 1.83-1.98 (m, 2H), 1.55 (s, 3H), 1.31 (s, 3H), 1.26 (s, 3H); m/z 364 [M+H]$^+$.

TX63507: 26.9 mg, 37%: $^1$H NMR (400 MHz, CDCl$_3$) δ 8.54 (s, 1H), 7.16-7.28 (m, 2H), 7.28-7.30 (m, 2H), 3.79 (s, 3H), 2.66 (dd, 1H, J=12.0, 4.0 Hz), 2.49-2.58 (m, 1H), 2.24 (dd, 1H, J=8.0, 2.0 Hz), 1.82-1.97 (m, 2H), 1.55 (s, 3H), 1.31 (s, 3H), 1.26 (s, 3H); m/z 364 [M+H]$^+$.

TX63508: 40 mg, 34%: $^1$H NMR (400 MHz, DMSO) δ 8.52 (s, 1H), 7.16-7.45 (m, 4H), 7.06 (d, 2H, J=8.0 Hz), 3.82 (s, 3H), 3.74 (s, 3H), 2.45-2.60 (m, 2H), 2.22 (d, 1H, J=8.0 Hz), 1.75-1.93 (m, 2H), 1.45 (s, 3H), 1.22 (s, 3H), 1.14 (s, 3H); m/z 360 [M+H]$^+$.

TX63509: 35 mg, 21%: $^1$H NMR (500 MHz, CDCl$_3$) δ 8.57 (s, 1H), 7.45 (m, 1H), 7.23-7.18 (m, 1H), 7.08-7.03 (m, 2H), 3.85 (br s, 3H), 3.69 (s, 3H), 2.58-2.52 (m, 1H), 2.27 (m, 1H), 1.89 (m, 2H), 1.57 (s, 3H), 1.30 (s, 3H), 1.25 (s, 3H); m/z 376 [M+H]$^+$.

TX63512: 22.2 mg, 31%: $^1$H NMR (400 MHz, CDCl$_3$) δ 8.55 (s, 1H), 7.38 (t, 1H, J=4.0 Hz), 7.10-7.31 (m, 3H), 3.81 (s, 3H), 2.68 (dd, 1H, J=12.0, 4.0 Hz), 2.53-2.62 (m, 1H), 2.44 (s, 3H), 2.25 (dd, 1H, J=8.0, 2.0 Hz), 1.82-1.96 (m, 2H), 1.55 (s, 3H), 1.31 (s, 3H), 1.26 (s, 3H); m/z 360 [M+H]$^+$.

TX63513: 17.1 mg, 24%: $^1$H NMR (400 MHz, CDCl$_3$) δ 8.55 (s, 1H), 7.43 (t, 1H, J=12.0 Hz), 6.85-7.01 (m, 3H), 3.87 (s, 3H), 3.82 (s, 3H), 2.70 (dd, 1H, J=12.0, 4.0 Hz), 2.52-2.62 (m, 1H), 2.25 (dd, 1H, J=12.0, 2.0 Hz), 1.82-1.98 (m, 2H), 1.56 (s, 3H), 1.31 (s, 3H), 1.26 (s, 3H); m/z 376 [M+H]$^+$.

TX63514: 60 mg, 55%: $^1$H NMR (400 MHz, DMSO) δ 8.50 (s, 1H), 7.29-7.38 (m, 4H), 3.75 (s, 3H), 2.47-2.62 (m, 2H), 2.37 (s, 3H), 2.23 (d, 1H, J=12.0 Hz), 1.76-1.93 (m, 2H), 1.45 (s, 3H), 1.22 (s, 3H), 1.14 (s, 3H); m/z 381 [M+H]$^+$.

TX63515: 50 mg, 39%: $^1$H NMR (400 MHz, DMSO) δ 8.50 (s, 1H), 7.38 (d, 2H, J=8.0 Hz), 7.06 (d, 2H, J=8.0 Hz), 3.82 (s, 3H), 3.74 (s, 3H), 2.45-2.60 (m, 2H), 2.22 (d, 1H, J=8.0 Hz), 1.75-1.93 (m, 2H), 1.45 (s, 3H), 1.22 (s, 3H), 1.14 (s, 3H); m/z 376 [M+H]$^+$.

TX63519: 75 mg, 50%: $^1$H NMR (500 MHz, d$_6$-DMSO) δ 8.51 (s, 1H), 7.56 (m, 1H), 7.49 (m, 1H), 7.43-7.34 (m, 2H), 3.68 (s, 3H), 2.45 (m, 1H), 2.23 (m, 1H), 1.84 (m, 2H), 1.47 (s, 3H), 1.25 (s, 3H), 1.14 (s, 3H); m/z 364 [M+H]$^+$.

Compound 79a: A mixture of Compound 68 (270 mg, 0.73 mmol), 3-pyridinylboronic acid (1.5 equiv.), Ph$_3$P (0.2 equiv.), K$_3$PO$_4$ (3.0 equiv.) and DME was sparged with N$_2$ for 10 min. Pd(OAc)$_2$ (0.1 equiv.) was added and sparging with N$_2$ was continued for 10 min. The reaction was heated to 85° C. for 9 h. The reaction mixture was filtered and concentrated. The crude residue was purified by column chromatography (silica gel, 5 to 30% EtOAc in Hexanes) to give compound 79a (70 mg, 26%) as a solid. m/z 368 [M+H]$^+$.

Compound 79b: Compound 68 (290 mg, 0.79 mmol) was reacted with 4-pyridinylboronic acid employing the same procedure used to produce 79a to give 79b (140 mg, 49%) as a solid. m/z 368 [M+H]$^+$.

Compound 80a: Compound 79a (70 mg, 0.19 mmol) was taken up in methanol, and 3 N HCl (aq) was added. The mixture was stirred overnight at room temperature. The reaction mixture and was then concentrated. The reaction mixture was extracted with ethyl acetate (2×25 mL) and washed saturated NaHCO$_3$, then dried with MgSO$_4$ and concentrated to give compound 80a (60 mg, 97%) as a solid. m/z 324 [M+H]$^+$.

Compound 80b: Compound 79b (140 mg, 0.38 mmol) was subjected to the same procedure used to prepare 80a to give 80b (130 mg, quantitative) as a solid. m/z 324 [M+H]$^+$.

Compound 81a: Compound 80a (60 mg, 0.19 mmol) was taken up in ethyl formate, and 30% sodium methoxide (30 wt % solution in MeOH) was added. The mixture was stirred overnight at room temperature. The reaction mixture was diluted with KH₂PO₄ (aq), extracted with ethyl acetate (2×25 mL) and washed with brine, then dried with MgSO₄ and concentrated to give compound 81a (70 mg, quantitative) as a solid. m/z 352 [M+H]⁺.

Compound 81b: Compound 80b (130 mg, 0.38 mmol) was subjected to the same procedure used to prepare 81a to give 81b (135 mg, quantitative) as a solid. m/z 352 [M+H]⁺.

Compound 82a: A mixture of hydroxylamine hydrochloride and 81a (70 mg, 0.19 mmol) in ethanol was stirred overnight at 50° C. After cooling to room temperature, the reaction mixture was concentrated. The residue was diluted with water and extracted with ethyl acetate, then dried with MgSO₄ and concentrated to give compound 82a (70 mg, quantitative) as a solid. m/z 349 [M+H]⁺.

Compound 82b: Compound 81b (135 mg, 0.38 mmol) was subjected to the same procedure used to prepare 82a to give 82b (135 mg, quantitative) as a solid. m/z 349 [M+H]⁺.

Compound 83a: Compound 82a (70 mg, 0.19 mmol) was dissolved in a 1/1 methanol/THF mixture, and 30% sodium methoxide (30 wt % solution in MeOH) was added, and the reaction mixture was stirred at 50° C. for 6 h. The reaction mixture was concentrated and quenched by addition of saturated KH₂PO₄. The mixture was extracted with ethyl acetate and washed with brine, then dried with MgSO₄ and concentrated to give compound 83a (70 mg, quantitative) as a solid. m/z 349 [M+H]⁺.

Compound 83b: Compound 82b (135 mg, 0.38 mmol) was subjected to the same procedure used to prepare 83a to give 83b (135 mg, quantitative) as a solid. m/z 349 [M+H]⁺.

Compound TX63503: Compound 83a (65 mg, 0.19 mmol) was dissolved in dry DMF, and the solution was cooled to 0° C. Br₂ was added, and the reaction stirred at 0° C. until the starting material was consumed (approximately 2 h), as reported by thin layer chromatography. Then, pyridine was added, and the reaction was allowed to warm to room temperature. The reaction mixture was then stirred at 50° C. overnight. The reaction mixture was concentrated. The crude residue was purified by column chromatography (silica gel, 5 to 35% EtOAc in Hexanes with 0.5% Et₃N) to give compound TX63503 (20 mg, 31%) as an off-white solid. ¹H NMR (400 MHz, CDCl₃) δ 8.69 (dd, 1H, J=1.5, 4.8 Hz), 8.64 (d, 1H, J=1.4 Hz), 8.53 (s, 1H), 7.69 (td, 1H, J=1.8, 7.9 Hz), 7.46 (dd, 1H, J=4.9, 7.3 Hz), 3.83 (s, 3H), 2.70 (dd, 1H, J=4.8, 16.0 Hz), 2.58 (ddd, 1H, J=6.8, 11.6, 15.9 Hz), 2.25 (dd, 1H, J=1.9, 11.9 Hz), 1.92 (m, 2H), 1.56 (s, 3H), 1.31 (s 3H), 1.26 (s, 3H); m/z 347 [M+H]⁺.

Compound TX63505: Compound 83b (135 mg, 0.38 mmol) was subjected to the same procedure used to prepare TX63503 to give TX63505 (35 mg, 27%) as a solid. ¹H NMR (400 MHz, d6-DMSO) δ 8.71 (d, 2H, J=4.6 Hz), 8.51 (s, 1H), 7.51 (d, 2H, J=4.5 Hz), 3.85 (s, 3H), 2.63 (m, 2H), 2.24 (d, J=12.0 Hz, 1H), 1.86 (m, 2H), 1.46 (s, 3H), 1.23 (s, 3H), 1.14 (s, 3H); m/z 347 [M+H]⁺.

Compound 84: Compound 18 (1.04 g, 4.64 mmol) was taken up in t-BuOH and added to a solution of KOt-Bu in t-BuOH. The reaction was stirred for 5 min at room temperature and 1,4-dibromobutane was added. The reaction was stirred at room temperature for 80 min, then warmed to 45° C. until the starting material was consumed, as reported by thin layer chromatography. The reaction mixture was concentrated, diluted with water, and extracted with EtOAc, then washed with brine, dried with MgSO₄, and concentrated. The crude residue was purified by column chromatography (silica gel, 10% EtOAc in Hexanes) to give compound 84 (1.006 g, 78%) as an oil. m/z 279 [M+H]⁺.

Compound 85: Compound 84 (1.561 g, 5.61 mmol) was taken up in EtOH under N₂ and 20% Pd(OH)₂ added. The Parr shaker bottle was rigorously purged with H₂ and charged at 54 psi. The flask was shaken overnight at room temperature. The reaction mixture was filtered and concentrated. The crude residue was purified by column chromatography (silica gel 6 to 50% EtOAc in Hexanes) to give compound 85 (0.493 g, 31%) as an oil. ¹H NMR (400 MHz, CDCl₃) δ 4.72 (d, 1H, J=6.8 Hz), 4.59 (d, 1H, J=6.8 Hz), 3.38 (s, 3H), 3.11 (dd, 1H, J=4.2, 11.6 Hz), 2.76 (dt, 1H, J=5.9, 15.0 Hz), 2.44 (td, 1H, J=7.5, 13.0 Hz), 2.32 (td, 1H, J=3.4, 15.0 Hz), 2.22 (ddd, 1H, J=2.9, 5.8, 13.8 Hz), 1.87 (m, 2H), 1.79 (m, 1H), 1.69 (m, 1H), 1.50 (m, 8H), 1.30 (m, 3H), 1.12 (s, 3H).

Compound 86: A mixture of Compound 85 (460 mg, 1.64 mmol), ethylene glycol, and p-toluenesulfonic acid hydrate in toluene was heated to reflux overnight with azeotropic removal of water. The reaction mixture was cooled to room temperature, diluted with EtOAc, washed with saturated NaHCO₃ and brined, then dried with MgSO₄ and concentrated to give compound 86 (497 mg, quantitative) as a solid. m/z 263 (M−H₂O+1).

Compound 87: Compound 86 (497 mg, 1.64 mmol) was taken up in CH₂Cl₂ and pyridinium dichromate was added over 10 min. The reaction mixture was stirred overnight at room temperature, then heated to 45° C. until the starting material was consumed, as reported by thin layer chromatography. The reaction mixture was filtered through Celite, eluted with CH₂Cl₂, and concentrated. The crude residue was purified by column chromatography (silica gel, 25% EtOAc in Hexanes) to give Compound 87 (359 mg, 73%) as a solid. m/z 279 [M+H]⁺.

Compound 88: Compound 87 (352 mg, 1.26 mmol) was taken up in ethyl formate and cooled to 0° C., then 30% sodium methoxide (30 wt % solution in MeOH) was added and the reaction warmed to room temperature. The mixture was stirred overnight at room temperature. The reaction mixture was diluted with water and the pH adjusted to 7 with acetic acid. The mixture was extracted with EtOAc and washed with brine, then dried with MgSO₄ and concentrated to give compound 88 (384 mg, 99%) as a solid. m/z 307 [M+H]⁺.

Compound 89: A mixture of 88 (227 mg, 0.74 mmol) and methyl hydrazine (2.7 equiv.) in ethanol (100 mL) was stirred at room temperature for 2 h, then heated to 60° C. for 1 h. The reaction mixture was concentrated. The crude residue was triturated with ether/EtOAc to give 89 (176 mg, 75%) as a solid. m/z 317 [M+H]⁺.

Compound 90: Compound 89 (93 mg, 0.29 mmol) was taken up in methanol, and 1 N HCl (aq) was added. The mixture was stirred overnight at room temperature. The reaction mixture was concentrated, extracted with EtOAc and washed with saturated NaHCO₃ (aq), then dried with MgSO₄ and concentrated to give compound 90 (83 mg, quantitative) as a solid. m/z 273 [M+H]⁺.

Compound 91: Compound 90 (80 mg, 0.29 mmol) was taken up in ethyl formate and cooled to 0° C., then 30% sodium methoxide (30 wt % solution in MeOH) was added and the reaction warmed to room temperature. The mixture was stirred overnight at room temperature. The reaction mixture was diluted with KH₂PO₄ (aq), extracted with EtOAc, then dried with MgSO₄ and concentrated to give 91 (89 mg, quantitative) as a solid. m/z 301 [M+H]⁺.

Compound 92: A solution of 0.1 N hydroxylamine hydrochloride (aq) was added to compound 91 (87 mg, 0.29 mmol). A 9/1 mixture of ethanol/water was added, and the reaction mixture was stirred overnight at 50° C. After cooling to room temperature, the reaction mixture was concentrated. The residue was taken up in EtOAc, then dried with MgSO$_4$ and concentrated to give compound 92 (83 mg, 96%) as a solid. m/z 298 [M+H]$^+$.

Compound 93: Compound 92 (77 mg, 0.26 mmol) was dissolved in a 3/1 methanol/THF mixture, and 30% sodium methoxide (30 wt % solution in MeOH) was added, and the reaction mixture was stirred at 55° C. for 6 h and then stirred at room temperature overnight. The reaction was quenched by addition of saturated KH$_2$PO$_4$ (aq), and the reaction mixture was concentrated. The residue was extracted with EtOAc and washed with brine, then dried with MgSO$_4$ and concentrated. The crude residue was purified by column chromatography (silica gel, 50% EtOAc in Hexanes) to give compound 93 (81 mg, quantitative) as a solid. m/z 298 [M+H]$^+$.

Compound TX63487: Compound 93 (81 mg, 0.26 mmol) was dissolved in dry DMF, and the solution was cooled to 0° C. 1,3-Dibromo-5,5-dimethylhydantoin was added, and the reaction stirred at 0° C. until the starting material was consumed, as reported by thin layer chromatography. Then, pyridine was added, and the reaction was allowed to warm to room temperature. The reaction mixture was then stirred at 50° C. overnight. After cooling to room temperature, the reaction mixture was extracted with EtOAc and washed with brine, then dried with MgSO$_4$ and concentrated. The crude residue was purified by column chromatography (silica gel, 25% EtOAc in Hexanes) to give compound TX63487 (29 mg, 38%) as a solid. $^1$H NMR (400 MHz, CDCl$_3$) δ 8.45 (s, 1H), 7.07 (s, 1H), 3.87 (s, 3H), 2.78 (dd, 1H, J=4.8, 14.9 Hz), 2.55 (ddd, 1H, J=7.5, 11.6, 15.3 Hz), 2.33 (dd, 1H, J=2.8, 10.9 Hz), 2.27 (m, 1H), 1.83 (m, 5H), 1.63 (m, 3H), 1.44 (s, 3H), 1.27 (m, 1H); m/z 296 [M+H]$^+$.

Compound 94: Compound 89 (159 mg, 0.50 mmol) was taken up in CH$_2$Cl$_2$, and 1,3-dibromo-5,5-dimethylhydantoin was added. The mixture was stirred for 2 h at room temperature. The reaction mixture was concentrated, diluted with EtOAc, washed with saturated NaHCO$_3$ (aq) and brine, then dried over MgSO$_4$ and concentrated. The crude residue was purified by column chromatography (silica gel, 25% EtOAc in Hexanes) to give compound 94 (123 mg, 62%) as a solid. m/z 395, 397 (1:1) [M+H]$^+$.

Compound 95: A mixture of Compound 94 (121 mg, 0.31 mmol), phenylboronic acid (56 mg, 0.46 mmol), Ph$_3$P (18 mg, 0.07 mmol), K$_3$PO$_4$ (210 mg, 0.99 mmol) and DME (10 mL) was sparged with N$_2$ for 10 min. Pd(OAc)$_2$ (16 mg, 0.07 mmol) was added and sparging with N$_2$ was continued for 10 min. The reaction was heated to 85° C. for 12 h. The reaction mixture was filtered through MgSO$_4$ and concentrated. The crude residue was purified by column chromatography (silica gel, 25% EtOAc in Hexanes) to give compound 95 (88 mg, 73%) as a white solid. m/z 393 [M+H]$^+$.

Compound 96: Compound 95 (84 mg, 0.21 mmol) was taken up in methanol, and 1 N HCl (aq) was added. The mixture was stirred overnight at room temperature. The reaction mixture was then concentrated. Reaction mixture was extracted with ethyl acetate and washed saturated NaHCO$_3$, then dried with MgSO$_4$ and concentrated to give compound 96 (79 mg, quantitative) as a solid. m/z 349 [M+H]$^+$.

Compound 97: Compound 96 (75 mg, 0.21 mmol) was taken up in ethyl formate, and 30% sodium methoxide (30 wt % solution in MeOH) was added. The mixture was stirred overnight at room temperature. The reaction mixture was extracted with ethyl acetate and washed with KH$_2$PO$_4$ (aq), then dried with MgSO$_4$ and concentrated to give compound 97 (38 mg, 47%) as a solid. m/z 377 [M+H]$^+$.

Compound 98: A solution of 0.1 N hydroxylamine hydrochloride (aq) was added to compound 97 (38 mg, 0.10 mmol). A 9/1 mixture of ethanol/water was added, and the reaction mixture was stirred overnight at 50° C. After cooling to room temperature, the reaction mixture was concentrated. The residue was taken up in ethyl acetate, then dried with MgSO$_4$ and concentrated to give compound 98 (38 mg, quantitative) as a solid. m/z 374 [M+H]$^+$.

Compound 99: Compound 98 (38 mg, 0.10 mmol) was dissolved in a 3/1 methanol/THF mixture, and 30% sodium methoxide (30 wt % solution in MeOH) was added, and the reaction mixture was stirred at 55° C. for 6 h and then stirred at room temperature overnight. The reaction was quenched by addition of saturated KH$_2$PO$_4$, and the reaction mixture was concentrated. The residue was extracted with ethyl acetate and washed with brine, then dried with MgSO$_4$ and concentrated. The crude residue was purified by column chromatography (silica gel, 50% EtOAc in Hexanes) to give compound 99 (40 mg, quantitative) as a solid. m/z 374 [M+H]$^+$.

Compound TX63504: Compound 99 (40 mg, 0.10 mmol) was dissolved in dry DMF, and the solution was cooled to 0° C. 1,3-Dibromo-5,5-dimethylhydantoin was added, and the reaction stirred at 0° C. until the starting material was consumed, as reported by thin layer chromatography. Then, pyridine was added, and the reaction was allowed to warm to room temperature. The reaction mixture was then stirred at 50° C. overnight. After cooling to room temperature, the reaction mixture was extracted with ethyl acetate and washed with brine, then dried with MgSO$_4$ and concentrated. The crude residue was purified by column chromatography (silica gel, 25% EtOAc in Hexanes) to give compound TX63504 (14 mg, 37%) as a solid. $^1$H NMR (400 MHz, CDCl$_3$) δ 8.52 (s, 1H), 7.50 (t, 2H, J=7.0 Hz), 7.44 (t, 1H, J=6.7 Hz), 7.34 (d, 2H, J=7.0 Hz), 3.82 (s, 3H), 2.67 (d, 1H, J=6.2 Hz), 2.56 (m, 1H), 2.40 (d, 1H, J=10.4 Hz), 2.28 (m, 1H), 1.84 (m, 5H), 1.65 (m, 3H), 1.50 (s, 3H), 1.28 (m, 1H); m/z 372 [M+H]$^+$.

Compound 48 and 100: Compound 26 (100 mg, 0.36 mmol) was taken up in toluene (10 ml), sparged with N$_2$ for 5 min, and phenylhydrazine (38 l, 0.38 mmol) was added. The vial was sealed and the reaction stirred at 75° C. overnight. The reaction mixture was cooled to room temperature and concentrated. The residue was taken up in toluene (10 mL) and p-toluenesulfonic acid hydrate (12 mg, 0.06 mmol) was added, then the mixture was sparged with N$_2$ for 3 min. The reaction was stirred at 80° C. overnight, then at room temperature for 3 d. The reaction mixture was concentrated to give a mixture of compounds 48 and 100: m/z 353 [M+H]$^+$.

Compounds 50 and 101: The mixture of compounds 48 and 100 was taken up in methanol, and 1 N HCl (aq) was added. The mixture was stirred overnight at room temperature. The reaction mixture was then concentrated. The reaction mixture was extracted with EtOAc (50 mL) and washed with saturated NaHCO$_3$, then dried with MgSO$_4$ and concentrated. The crude residue was purified by column chromatography (silica gel, 10 to 25% EtOAc in Hexanes) to give compound 50 (19 mg, 17%) and compound 101 (57.1 mg, 52%) as solids: m/z 309 [M+H]$^+$.

Compound 102: Compound 101 (50.4 mg, 0.16 mmol) was taken up in ethyl formate, and 30% sodium methoxide (30 wt % solution in MeOH) was added. The mixture was stirred overnight at room temperature. The reaction mixture was diluted with KH$_2$PO$_4$ (aq) and extracted with EtOAc, then dried with MgSO$_4$ and concentrated to give compound 102 (61.4 mg, quantitative) as a solid. m/z 337 [M+H]$^+$.

Compound 103: A solution of 0.1 N hydroxylamine hydrochloride (aq) was added to compound 102 (61.4 mg, 0.16 mmol). A 9/1 mixture of ethanol/water was added, and the reaction mixture was stirred overnight at 50° C. After cooling to room temperature, the reaction mixture was concentrated.

The residue was taken up in EtOAc, then dried with MgSO$_4$ and concentrated to give compound 103 (48.5 mg, 89%) as a solid. m/z 334 [M+H]$^+$.

Compound 104: Compound 103 (47.5 mg, 0.14 mmol) was dissolved in a 3/1 methanol/THF mixture, and 30% sodium methoxide (30 wt % solution in MeOH) was added. The reaction mixture was stirred at 55° C. for 6 h and then stirred at room temperature overnight. The reaction was quenched by addition of saturated KH$_2$PO$_4$, and the reaction mixture was concentrated. The residue was extracted with EtOAc and washed with brine, then dried with MgSO$_4$ and concentrated. The crude residue was purified by column chromatography (silica gel, 50% EtOAc in Hexanes) to give compound 104 (42.5 mg, 89%) as a solid. m/z 334 [M+H]$^+$.

Compound TX63524: Compound 104 (42.5 mg, 0.13 mmol) was dissolved in dry DMF, and the solution was cooled to 0° C. 1,3-Dibromo-5,5-dimethylhydantoin was added, and the reaction stirred at 0° C. until the starting material was consumed (approximately 30 min), as reported by thin layer chromatography. Then, pyridine was added, and the reaction was allowed to warm to room temperature. The reaction mixture was then stirred at 50° C. overnight. After cooling to room temperature, the reaction mixture was extracted with EtOAc and washed with brine, then dried with MgSO$_4$ and concentrated. The crude residue was purified by column chromatography (silica gel, 25% EtOAc/Hexanes) to give compound TX63524 (11.8 mg, 28%) as a solid. $^1$H NMR (500 MHz, CDCl$_3$) δ 7.60 (m, 3H), 7.57 (s, 1H), 7.46 (s, 1H), 7.45 (m, 2H), 2.86 (ddd, 1H, J=1.1, 5.7, 15.9 Hz), 2.65 (ddd, 1H, J=6.7, 12.0, 16.1 Hz), 2.32 (dd, 1H, J=1.9, 11.9 Hz), 1.95 (m, 2H), 1.60 (s, 3H), 1.30 (s, 3H), 1.24 (s, 3H); m/z 332 [M+H]$^+$.

Compound 105: Compound 26 (0.282 g, 1.0 mmol) was taken up in 0.1 M hydroxylamine hydrochloride in 9:1 EtOH/H$_2$O (11 mL, 1.1 mmol) and triethylamine (0.15 mL, 1.1 mmol) was added. The mixture was stirred at room temperature for 15 minutes. The reaction mixture was briefly warmed to 45° C. and was stirred overnight at room temperature. The mixture was heated to 60° C. briefly to ensure cyclization and was then concentrated, diluted with EtOAc, dried over MgSO$_4$, filtered and concentrated to a glass. m/z [M+H]$^+$ 278.1

To a solution of the above intermediate (305 mg, 1.1 mmol) in THF and MeOH (2:1), 30% NaOMe (8 eq) was added, and the solution was heated at 50° C. for 6 hours. After concentration in vacuo, the residue was mixed with KH$_2$PO$_4$ (sat.) and extracted with EtOAc. The combined organic extracts were washed with brine, dried with MgSO$_4$, and concentrated in vacuo to give 105 (0.297 g). m/z [M+H]$^+$ 278.1. This material was used directly in the next step.

Compound 106: Compound 105 (0.297 g, 1.1 mmol) was taken up in EtOH (20 mL) and methylhydrazine (0.15 g, 3.26 mmol) was added as a solution in EtOH (1 mL) dropwise at room temperature. The reaction was heated overnight and six additional hours at reflux. The reaction mixture was cooled and concentrated. The residue was chromatographed on silica gel (230-400 mesh, 18 g) using 3:1, then 1:1, Hexanes/EtOAc as eluant. Compound 106 (62 mg, 18%) was obtained as a glass. m/z [M+H]$^+$ 306.2.

Compound 107: Compound 106 (0.062 g, 0.20 mmol) was dissolved in EtOAc (7 mL). Triethylamine (0.06 mL, 0.4 mmol) was added followed by addition of benzoyl chloride (0.069 g, 0.49 mmol) and the mixture was stirred at room temperature for 3 days. The reaction mixture was diluted with EtOAc (50 mL), washed with saturated aqueous NaHCO$_3$ solution (10 mL), dried over MgSO$_4$, filtered and concentrated to a dark oil to afford 107 (0.1145 g) which was used without further purification. m/z [M+H]$^+$ 410.3.

Compound 108: A solution of 107 (114.5 mg, 0.28 mmol) in MeOH (5 mL) was treated with 3N HCl (aq), stirred at room temperature overnight. The reaction mixture was concentrated, extracted with EtOAc (2×25 mL) and sat'd NaHCO$_3$ (aq). The organic layer was dried with MgSO$_4$, concentrated to give 108 (57 mg, 57%). m/z [M+H]$^+$ 366.2.

Compound 109: To a solution of 108 (57 mg, 0.16 mmol) in 2 mL of HCOOEt at RT, 30% NaOMe in MeOH (6 eq) was added dropwise. The reaction mixture was stirred at RT overnight, poured into water and acidified with sat. KH$_2$PO$_4$ solution. The mixture was extracted with EtOAc (2×25 mL). The combined organic extracts were washed with brine, dried with MgSO$_4$, and concentrated in vacuo to give 109 (63 mg) which was used without further purification. m/z [M+H]$^+$ 394.2.

Compound 110: To a solution of 109 (0.063 g, 0.16 mmol) in 2 mL of EtOH, NH$_2$OH HCl salt (2 eq) was added, and the mixture was heated at 50° C. overnight. After concentration in vacuo, the residue was mixed with water and extracted with EtOAc. The combined organic extracts were washed with brine, dried with MgSO$_4$, and concentrated in vacuo to give 110 (0.0613 g) which was used without further purification. m/z [M+H]$^+$ 391.2.

Compound 111: To a solution of Compound 110 (0.0613 g, 0.16 mmol) in THF and MeOH (2:1), 30% NaOMe (8 eq) was added, and the solution was heated at 50° C. for 6 hours. After concentration in vacuo, the residue was mixed with KH$_2$PO$_4$ (sat.) and extracted with EtOAc. The combined organic extracts were washed with brine, dried with MgSO$_4$, and concentrated in vacuo to give 111 (0.0493 g) which was used without further purification. m/z [M+H]$^+$ 391.2.

Compound TX63531: To a solution of 111 (0.0493 g, 0.13 mmol) in 1 mL of DMF at 0° C., 1,3-Dibromo-5,5-dimethylhydantoin (0.55 eq) was added, and the solution was stirred for 2 hours. Pyridine (30 eq) was added, and the solution was heated at 50° C. overnight. After concentration in vacuo, the residue was purified on a silica gel column, eluted with 2:1 DCM/EtOAc to give TX63531 (5.8 mg, 11%). $^1$H NMR (500 MHz, CDCl$_3$) δ 8.44 (s, 1H), 7.88 (d, 2H, J=4.3 Hz), 7.60 (t, 1H, J=5.6 Hz), 7.54 (br s, 1H), 7.51 (m, 2H), 3.73 (s, 3H), 2.60 (m, 1H), 2.44 (m, 1H), 2.14 (d, 1H, J=8.8 Hz), 1.79-1.66 (m, 2H), 1.49 (s, 3H), 1.36 (s, 3H), 1.07 (s, 3H); m/z [M+H]$^+$ 389.2.

Compound TX63524: Compound 104 (42.5 mg, 0.13 mmol) was dissolved in dry DMF, and the solution was cooled to 0° C. 1,3-Dibromo-5,5-dimethylhydantoin was added, and the reaction stirred at 0° C. until the starting material was consumed (approximately 30 min), as reported by thin layer chromatography. Then, pyridine was added, and the reaction was allowed to warm to room temperature. The reaction mixture was then stirred at 50° C. overnight. After cooling to room temperature, the reaction mixture was extracted with EtOAc and washed with brine, then dried with MgSO$_4$ and concentrated. The crude residue was purified by column chromatography (silica gel, 25% EtOAc in Hexanes) to give compound TX63524 (11.8 mg, 28%) as a solid. $^1$H NMR (500 MHz, CDCl$_3$) δ 7.60 (m, 3H), 7.57 (s, 1H), 7.46 (s, 1H), 7.45 (m, 2H), 2.86 (ddd, 1H, J=1.1, 5.7, 15.9 Hz), 2.65 (ddd, 1H, J=6.7, 12.0, 16.1 Hz), 2.32 (dd, 1H, J=1.9, 11.9 Hz), 1.95 (m, 2H), 1.60 (s, 3H), 1.30 (s, 3H), 1.24 (s, 3H). m/z 332 [M+H]$^+$.

Compound 112: A solution of 17 (6.4 g, 36 mmol) in THF (25 mL) was added to a −78° C. solution of lithium (2 equiv.) in liq. NH$_3$ (10 mL). The reaction was stirred at −78° C. for 45 min, quenched with NH$_4$Cl (10 g), and warmed to room temperature. The mixture was diluted with water, extracted with EtOAc, and concentrated. The crude residue was purified by column chromatography (silica gel, 25% EtOAc in Hexanes) to give 112 (1.5 g, 23%) as an oil. m/z 183 [M+H]$^+$.

Compound 113: A mixture of Compound 112 (1.5 g, 8.2 mmol), ethylene glycol, and p-toluenesulfonic acid hydrate in benzene was heated to reflux for 4 h with azeotropic removal of water. The reaction mixture was cooled to room temperature, washed with water, and concentrated. The crude residue was purified by column chromatography (silica gel, 25% EtOAc in Hexanes) to give 113 (1.4 g, 75%) as an oil. m/z 227 [M+H]$^+$.

Compound 114: Compound 113 (1.4 g, 6.2 mmol) was taken up in $CH_2Cl_2$ (100 mL), then $MgSO_4$ (150 mg) and PDC (2 equiv.) were added. The reaction was stirred at room temperature for 2 d. The reaction mixture was filtered through a pad of silica (eluted with $CH_2Cl_2$) and concentrated. The crude residue was purified by column chromatography (silica gel, 25% EtOAc in Hexanes) to give 114 (1.25 g, 90%) as a white solid. m/z 225 [M+H]$^+$.

Compound 115: Compound 114 (1.25 g, 5.57 mmol) was taken up in ethyl formate, and 30% sodium methoxide (30 wt % solution in MeOH) was added. The mixture was stirred overnight at room temperature. The reaction mixture was quenched $KH_2PO_4$ (aq) and extracted with EtOAc, then washed with water, dried with $MgSO_4$ and concentrated to give compound 115 (1.35 g, 96%) as a solid. m/z 253 [M+H]$^+$.

Compound 116: A mixture of compound 115 (1.35 g, 5.35 mmol) and methyl hydrazine (1.6 equiv.) in ethanol was heated to 60° C. for 2 h. The reaction mixture was concentrated. The crude residue was purified by column chromatography (silica gel, EtOAc) to give 116 (1.2 g, 85%) as a solid. m/z 263 [M+H]$^+$.

Compound 117: Compound 116 (1.2 g, 4.6 mmol) was taken up in $CH_2Cl_2$ and 1,3-dibromo-5,5-dimethylhydantoin (0.55 equiv.) was added. The reaction was stirred at room temperature for 3 h. The reaction mixture was washed with 1 N $Na_2CO_3$ and concentrated. The crude residue was purified by column chromatography (silica gel, 10 to 30% EtOAc in Hexanes) to give 117 (1.0 g, 64%) as a solid. m/z 341, 343 (1:1) [M+H]$^+$.

Compound 118: A mixture of Compound 117 (1.0 g, 2.9 mmol), phenylboronic acid (1.25 equiv.), $Ph_3P$ (0.3 equiv.), $K_3PO_4$ (3 equiv.) and DME was sparged with $N_2$ for 10 min. $Pd(OAc)_2$ (0.15 equiv.) was added and sparging with $N_2$ was continued for 10 min. The reaction was heated to 85° C. for 16 h. The reaction mixture was filtered and concentrated. The crude residue was purified by column chromatography (silica gel, 10 to 30% EtOAc in Hexanes) to give compound 118 (0.53 g, 53%) as an oil. m/z 339 [M+H]$^+$.

Compound 119: Compound 118 (0.53 g, 1.6 mmol) was taken up in methanol, and 3 N HCl (aq) was added. The mixture was stirred overnight at room temperature. The reaction mixture was then concentrated. The reaction mixture was diluted with saturated $NaHCO_3$ and extracted with EtOAc (2×25 mL), then dried with $MgSO_4$ and concentrated to give compound 119 (0.42 g, 91%) as a solid. m/z 295 [M+H]$^+$.

Compound 120: Compound 119 (0.42 g, 1.4 mmol) was taken up in ethyl formate, and 30% sodium methoxide (30 wt % solution in MeOH) was added. The mixture was stirred overnight at room temperature. The reaction mixture was quenched $KH_2PO_4$ (aq) and extracted with EtOAc, then washed with brine, dried with $MgSO_4$ and concentrated to give compound 120 (0.44 g, 96%) as a solid. m/z 323 [M+H]$^+$.

Compound 121: A mixture of hydroxylamine hydrochloride and 120 (0.44 g, 1.4 mmol) in ethanol was stirred overnight at 50° C. After cooling to room temperature, the reaction mixture was concentrated. The residue was diluted with water and extracted with EtOAc, then washed with brine, dried with $MgSO_4$, and concentrated to give compound 121 (445 mg, quantitative) as a solid. m/z 320 [M+H]$^+$.

Compound 122: Compound 121 (445 mg, 1.4 mmol) was dissolved in a 1/1 methanol/THF mixture, and 30% sodium methoxide (30 wt % solution in MeOH) was added, and the reaction mixture was stirred at 50° C. for 6 h. The reaction mixture was concentrated and quenched by addition of saturated $KH_2PO_4$. The mixture was extracted with EtOAc and washed with brine, then dried with $MgSO_4$ and concentrated to give compound 122 (440 mg, quantitative) as a solid. m/z 320 [M+H]$^+$.

Compound TX63540: Compound 122 (440 mg, 1.4 mmol) was dissolved in dry DMF, and the solution was cooled to 0° C. 1,3-Dibromo-5,5-dimethylhydantoin was added, and the reaction stirred at 0° C. until the starting material was consumed (approximately 2 h), as reported by thin layer chromatography. Then, pyridine was added, and the reaction was allowed to warm to room temperature. The reaction mixture was then stirred at 50° C. overnight. The reaction mixture was concentrated. The crude residue was purified by column chromatography (silica gel, 15 to 35% EtOAc in Hexanes) to give compound TX63540 (120 mg, 28%) as a solid. $^1$H NMR (400 MHz, $CDCl_3$) δ 8.55 (s, 1H), 7.50 (t, 2H, J=8.1 Hz), 7.45 (m, 1H), 7.35 (d, 2H, J=8.0 Hz), 3.83 (s, 3H), 2.64 (m, 4H), 2.51 (ddt, 1H, J=1.7, 5.7, 12.3 Hz), 1.89 (m, 1H), 1.77 (m, 1H), 1.48 (s, 3H); m/z 318 [M+H]$^+$.

Compound 123: Compound 1 (30.0 g, 238 mmol) was suspended in acetonitrile and the mixture cooled to 0° C. Ethyl vinyl ketone (25 g, 297 mmol) and triethyl amine (53 ml, 380 mmol) were added and the reaction was warmed to room temperature and stirred overnight. The reaction mixture was concentrated. The residue was taken up in EtOAc and washed with $KH_2PO_4$ (aq) and brine, then dried with $MgSO_4$ and concentrated. The residue was taken up in benzene (250 mL), pyrrolidine (5.0 ml, 60 mmol) was added, and the reaction was heated to reflux for 48 h with azeotropic removal of water. The reaction mixture was cooled to room temperature and concentrated. The residue was taken up in EtOAc, washed with saturated $NaHCO_3$ and brine, then dried with $MgSO_4$ and concentrated. The crude residue was purified by column chromatography (silica gel, 20% EtOAc in hexanes) to give a yellow oil. The oil was crystallized from cold t-BuOMe (50 mL) to give 123 (18.59 g, 41%) as a white solid.

Compound 124: A solution of $NaBH_4$ (0.64 g, 17 mmol) in ethanol (100 mL) was added to a 0° C. solution of compound 123 (12.97 g, 67.5 mmol) in ethanol (100 mL). The reaction was stirred at 0° C. for 45 and quenched with acetic acid (7.7 mL, 135 mmol). The reaction mixture was warmed to room temperature and stirred for 1 h, then concentrated. The residue was diluted with 10% $NH_4OH$ (aq) and extracted with EtOAc, then dried with $MgSO_4$ and concentrated. The crude residue was purified by column chromatography (silica gel, 50% EtOAc in Hexanes) to give 124 (7.28 g, 56%) as a light yellow solid. m/z 195 [M+H]$^+$.

Compound 125: A solution of 124 (6.1 g, 31 mmol) in THF (25 mL) was added to a −78° C. solution of lithium (2 equiv.) in liq. $NH_3$ (10 mL). The reaction was stirred at −78° C. for 45 min, quenched with $NH_4Cl$ (10 g), and warmed to room temperature. The mixture was diluted with water, extracted with EtOAc, and concentrated. The crude residue was purified by column chromatography (silica gel, 25% EtOAc in Hexanes) to give 125 (1.7 g, 28%) as an oil. m/z 197 [M+H]$^+$.

Compound 126: A mixture of compound 125 (1.7 g, 8.7 mmol), ethylene glycol, and p-toluenesulfonic acid hydrate in benzene was heated to reflux for 4 h with azeotropic removal of water. The reaction mixture was cooled to room temperature, washed with water, and concentrated. The crude residue was purified by column chromatography (silica gel, 25% EtOAc in Hexanes) to give 126 (1.3 g, 62%) as an oil. m/z 241 [M+H]$^+$.

Compound 127: Compound 126 (1.3 g, 6.2 mmol) was taken up in $CH_2Cl_2$ (100 mL), then $MgSO_4$ (150 mg) and PDC (2 equiv.) were added. The reaction was stirred at room temperature for 2 d. The reaction mixture was filtered through a pad of silica (eluted with $CH_2Cl_2$) and concentrated. The crude residue was purified by column chromatography (silica gel, 25% EtOAc in Hexanes) to give 127 (1.18 g, 92%) as a white solid. m/z 239 [M+H]$^+$.

Compound 128: Compound 127 (0.67 g, 2.8 mmol) was taken up in ethyl formate, and 30% sodium methoxide (30 wt % solution in MeOH) was added. The mixture was stirred overnight at room temperature. The reaction mixture was quenched $KH_2PO_4$ (aq) and extracted with EtOAc, then washed with water, dried with $MgSO_4$ and concentrated to give compound 128 (0.75 g, quantitative) as a solid. m/z 267 [M+H]$^+$.

Compound 129: A mixture of compound 128 (0.75 g, 2.8 mmol) and methyl hydrazine (1.6 equiv.) in ethanol was heated to 60° C. for 2 h. The reaction mixture was concentrated. The crude residue was purified by column chromatography (silica gel, EtOAc) to give 129 (613 mg, 79%) as a solid. m/z 277 [M+H]$^+$.

Compound 130: Compound 129 (0.61 g, 2.2 mmol) was taken up in $CH_2Cl_2$ and 1,3-dibromo-5,5-dimethylhydantoin (0.55 equiv.) was added. The reaction was stirred at room temperature for 3 h. The reaction mixture was washed with 1 N $Na_2CO_3$ and concentrated. The crude residue was purified by column chromatography (silica gel, 10 to 30% EtOAc in Hexanes) to give 130 (580 mg, 74%) as a solid. m/z 355, 357 (1:1) [M+H]$^+$.

Compound 131: A mixture of Compound 130 (0.58 g, 1.6 mmol), phenylboronic acid (1.25 equiv.), $Ph_3P$ (0.3 equiv.), $K_3PO_4$ (3 equiv.) and DME was sparged with $N_2$ for 10 min. $Pd(OAc)_2$ (0.15 equiv.) was added and sparging with $N_2$ was continued for 10 min. The reaction was heated to 85° C. for 16 h. The reaction mixture was filtered and concentrated. The crude residue was purified by column chromatography (silica gel, 10 to 30% EtOAc in Hexanes) to give compound 131 (360 mg, 63%) as an off-white solid. m/z 353 [M+H]$^+$.

Compound 132: Compound 131 (0.33 g, 0.94 mmol) was taken up in methanol, and 3 N HCl (aq) was added. The mixture was stirred overnight at room temperature. The reaction mixture was then concentrated. The reaction mixture was diluted with saturated $NaHCO_3$ and extracted with EtOAc (2×25 mL), then dried with $MgSO_4$ and concentrated to give compound 132 (300 mg, quantitative) as a solid. m/z 309 [M+H]$^+$.

Compound 133: Compound 132 (0.30 g, 0.94 mmol) was taken up in ethyl formate, and 30% sodium methoxide (30 wt % solution in MeOH) was added. The mixture was stirred overnight at room temperature. The reaction mixture was quenched $KH_2PO_4$ (aq) and extracted with EtOAc, then washed with brine, dried with $MgSO_4$ and concentrated to give compound 133 (300 mg, 95%) as a solid. m/z 337 [M+H]$^+$.

Compound 134: A mixture of hydroxylamine hydrochloride and 133 (0.30 g, 0.89 mmol) in ethanol was stirred overnight at 50° C. After cooling to room temperature, the reaction mixture was concentrated. The residue was diluted with water and extracted with EtOAc, then washed with brine, dried with $MgSO_4$, and concentrated to give compound 134 (300 mg, quantitative) as a solid. m/z 334 [M+H]$^+$.

Compound 135: Compound 134 (0.30 g, 0.89 mmol) was dissolved in a 1/1 methanol/THF mixture, and 30% sodium methoxide (30 wt % solution in MeOH) was added, and the reaction mixture was stirred at 50° C. for 6 h. The reaction mixture was concentrated and quenched by addition of saturated $KH_2PO_4$. The mixture was extracted with EtOAc and washed with brine, then dried with $MgSO_4$ and concentrated to give compound 135 (300 mg, quantitative) as a solid. m/z 334 [M+H]$^+$.

Compound TX63541: Compound 135 (0.30 g, 0.89 mmol) was dissolved in dry DMF, and the solution was cooled to 0° C. 1,3-Dibromo-5,5-dimethylhydantoin was added, and the reaction stirred at 0° C. until the starting material was consumed (approximately 2 h), as reported by thin layer chromatography. Then, pyridine was added, and the reaction was allowed to warm to room temperature. The reaction mixture was then stirred at 50° C. overnight. The reaction mixture was concentrated. The crude residue was purified by column chromatography (silica gel, 15 to 35% EtOAc in Hexanes) to give compound TX63541 (97 mg, 33%) as a solid. $^1$H NMR (400 MHz, $CDCl_3$) δ 8.53 (s, 1H), 7.51 (m, 2H), 7.45 (tt, 1H, J=2.1, 7.3 Hz), 7.35 (m, 2H), 3.83 (s, 3H), 2.61 (m, 3H), 2.15 (dt, 1H, J=2.1, 12.7 Hz), 2.04 (m, 1H), 1.75 (qd, 1H, J=6.6, 12.7 Hz), 1.50 (s, 3H), 1.33 (s, 3H); m/z 332 [M+H]$^+$.

Compounds TX63791 and TX63792: The enantiomers of compound TX63541 (488.9 mg) were separated using chiral HPLC (CHIRALPAK IA, 5μ, 30×250 mm, 2:50:50 EtOH/EtOAc/Hexane) to afford two well resolved peaks. One is at 3.98 min, which gave TX63791 (206.2 mg, 99.6% ee). $^1$H NMR (400 MHz, $CDCl_3$) δ 8.50 (s, 1H), 7.48 (m, 2H), 7.42 (m, 1H), 7.32 (m, 2H), 3.80 (s, 3H), 2.59 (m, 3H), 2.12 (t, 1H, J=12.6 Hz), 2.01 (m, 1H), 1.73 (m, 1H), 1.47 (s, 3H), 1.30 (d, 3H, J=6.0 Hz). And another on is at 5.04 min, which gave TX63792 (220.7 mg, 99.8% ee). $^1$H NMR (400 MHz, $CDCl_3$) δ 8.50 (s, 1H), 7.48 (m, 2H), 7.42 (m, 1H), 7.32 (m, 2H), 3.80 (s, 3H), 2.59 (m, 3H), 2.12 (t, 1H, J=12.6 Hz), 2.01 (m, 1H), 1.73 (m, 1H), 1.47 (s, 3H), 1.30 (d, 3H, J=6.0 Hz).

Compound 136a-b: Compound 48 (0.360 g, 1.02 mmol) was taken up in DCM (30 mL) at room temperature. N,N'-Dibromodimethylhydantoin (0.169 g, 0.59 mmol) was added and the mixture was stirred overnight at room temperature. The reaction mixture was concentrated to dryness and the residue chromatographed on silica gel (230-400 mesh, 24 g) using 10% EtOAc/Hexanes to give 136b (0.1057 g), m/z 433.0, [M+H]$^+$; and 136a (0.1141 g). m/z 389.0, [M+H]$^+$.

Compound 137: The mixture of 136a (105.7 mg) and 136b (114.1 mg) was taken up in DME. $PhB(OH)_2$ (1.5 eq), $Ph_3P$ (0.2 eq.) and $K_3PO_4$ (3.0 eq.) were added, and the mixture was bubbled with $N_2$ for 10 min. $Pd(OAc)_2$ (0.1 eq) was added and the mixture was bubbled with $N_2$ for 10 min. Then the mixture was stirred at 85° C. for 9 h. The reaction mixture was filtered, concentrated. The crude residue was purified by column chromatography to give corresponding cross coupled products as a mixture (a: 81.6 mg, b: 37.4 mg), which was taken up in MeOH and HCl (aq, 3N) was added. The mixture was stirred overnight at room temperature. The reaction mixture was then concentrated. The residue was extracted with EtOAc and washed with saturated $NaHCO_3$ (aq), then dried with $MgSO_4$ and concentrated to give 137 (108.9 mg). m/z [M+H]$^+$ 385.1.

Compound 138: Compound 137 (0.116 g, 0.30 mmol) was taken up in ethyl formate, and 30% sodium methoxide (30 wt % solution in MeOH) was added. The mixture was stirred overnight at room temperature. The reaction mixture was diluted with $KH_2PO_4$ (aq), extracted with EtOAc (2×25 mL)

and washed with brine, then dried with MgSO$_4$ and concentrated to give compound 138 (134.2 mg, 100%). m/z [M+H]$^+$ 413.1.

Compound 139: A mixture of hydroxylamine hydrochloride and 117 (0.134 g, 0.33 mmol) in EtOH was stirred overnight at 50° C. After cooling to room temperature, the reaction mixture was concentrated. The residue was diluted with water and extracted with EtOAc, then dried with MgSO$_4$ and concentrated to give compound 139 (124.9 mg, 94%), m/z [M+H]$^+$ 410.2.

Compound 140: Compound 139 (0.1249 g, 0.31 mmol) was dissolved in a 1/1 MeOH/THF mixture, and 30% sodium methoxide (30 wt % solution in MeOH) was added, and the reaction mixture was stirred at 50° C. for 6 h. The reaction mixture was concentrated and quenched by addition of saturated KH$_2$PO$_4$. The mixture was extracted with EtOAc and washed with brine, then dried with MgSO$_4$ and concentrated to give compound 140 (119.5 mg, 94%), m/z [M+H]$^+$ 410.2.

Compound TX63544: Compound 140 (0.1195 g, 0.29 mmol) was dissolved in dry DMF, and the solution was cooled to 0° C. 1,3-Dibromo-5,5-dimethylhydantoin was added, and the reaction stirred at 0° C. until the starting material was consumed (approximately 2 h), as reported by thin layer chromatography. Then, pyridine was added, and the reaction was allowed to warm to room temperature. The reaction mixture was then stirred at 50° C. overnight. The reaction mixture was concentrated. The crude residue was purified by column chromatography (silica gel, 5-30% EtOAc/Hexanes) to give compound TX63544 (60.9 mg, 52%). $^1$H NMR (500 MHz, CDCl$_3$) δ 8.60 (s, 1H), 7.31-7.28 (m, 5H), 7.26-7.21 (m, 3H), 7.15-7.13 (m, 2H), 2.80 (dd, 1H, J=5.1, 16.4 Hz), 2.67-2.60 (m, 1H), 2.28 (dd, 1H, J=2.1, 11.6 Hz), 1.98-1.86 (m, 2H), 1.60 (s, 3H), 1.29 (s, 3H), 1.24 (s, 3H); m/z [M+H]$^+$ 408.2.

Compound 141a: A mixture of Compound 68 (0.23 g, 0.62 mmol), isopropenyl pinacol boronate (1.25 equiv.), Ph$_3$P (0.3 equiv.), K$_3$PO$_4$ (3 equiv.) and DME was sparged with N$_2$ for 10 min. Pd(OAc)$_2$ (0.15 equiv.) was added and sparging with N$_2$ was continued for 10 min. The reaction was heated to 85° C. for 16 h. The reaction mixture was filtered and concentrated. The crude residue was purified by column chromatography (silica gel, 10 to 30% EtOAc in Hexanes) to give compound 141a (85 mg, 41%) as a solid. m/z 331 [M+H]$^+$.

Compound 142a: Compound 141a (85 mg, 0.26 mmol) was taken up in THF under N$_2$ and 10% Pd/C added. The flask was rigorously purged with H$_2$ and stirred for 2 d at room temperature. The reaction mixture was filtered and concentrated to give compound 142a (85 mg, 99%) as a solid. m/z 333 [M+H]$^+$.

Compound 143a: Compound 142a (85 mg, 0.26 mmol) was taken up in methanol, and 3 N HCl (aq) was added. The mixture was stirred overnight at room temperature. The reaction mixture was then concentrated. The reaction mixture was diluted with saturated NaHCO$_3$ and extracted with EtOAc (2×25 mL), then dried with MgSO$_4$ and concentrated to give compound 143a (70 mg, 95%) as a solid. m/z 289 [M+H]$^+$.

Compound 144a: Compound 143a (70 mg, 0.24 mmol) was taken up in ethyl formate, and 30% sodium methoxide (30 wt % solution in MeOH) was added. The mixture was stirred overnight at room temperature. The reaction mixture was quenched KH$_2$PO$_4$ (aq) and extracted with EtOAc, then washed with brine, dried with MgSO$_4$ and concentrated to give compound 144a (80 mg, quantitative) as a solid. m/z 317 [M+H]$^+$.

Compound 145a: A mixture of hydroxylamine hydrochloride and 144a (80 mg, 0.24 mmol) in ethanol was stirred overnight at 50° C. After cooling to room temperature, the reaction mixture was concentrated. The residue was diluted with water and extracted with EtOAc, then washed with brine, dried with MgSO$_4$, and concentrated to give compound 145a (80 mg, quantitative) as a solid. m/z 314 [M+H]$^+$.

Compound 146a: Compound 145a (80 mg, 0.24 mmol) was dissolved in a 1/1 methanol/THF mixture, and 30% sodium methoxide (30 wt % solution in MeOH) was added, and the reaction mixture was stirred at 50° C. for 6 h. The reaction mixture was concentrated and quenched by addition of saturated KH$_2$PO$_4$. The mixture was extracted with EtOAc and washed with brine, then dried with MgSO$_4$ and concentrated to give compound 146a (75 mg, 99%) as a solid. m/z 314 [M+H]$^+$.

Compound TX63547: Compound 146a (75 mg, 0.24 mmol) was dissolved in dry DMF, and the solution was cooled to 0° C. 1,3-Dibromo-5,5-dimethylhydantoin was added, and the reaction stirred at 0° C. until the starting material was consumed (approximately 2 h), as reported by thin layer chromatography. Then, pyridine was added, and the reaction was allowed to warm to room temperature. The reaction mixture was then stirred at 50° C. overnight. The reaction mixture was concentrated. The crude residue was purified by column chromatography (silica gel, 15 to 35% EtOAc in Hexanes) to give compound TX63547 (11 mg, 15%) as a solid. $^1$H NMR (500 MHz, CDCl$_3$) δ 8.50 (s, 1H), 3.80 (s, 3H), 3.05 (septet, 1H, J=7.0 Hz), 2.84 (ddd, 1H, J=7.0, 11.7, 15.7 Hz), 2.58 (ddd, 1H, J=7.0, 11.7, 15.7 Hz), 2.16 (dd, 1H, J=2.1, 11.9 Hz), 1.88 (m, 2H), 1.50 (s, 3H), 1.32 (d, 3H, J=7.1 Hz), 1.29 (s, 3H), 1.29 (d, 3H, J=7.1 Hz), 1.24 (s, 3H); m/z 312 [M+H]$^+$.

Compound 141b: Compound 68 (0.371 g, 1.00 mmol), K$_2$CO$_3$ (0.417 g, 3.02 mmol), 1-cyclohexenylboronic acid pinacol ester (0.269 g, 0.23 mmol) and dioxane (15 mL) were mixed and the reaction was sparged with N$_2$ for 2-3 minutes. Pd(dppf)Cl$_2$ (0.079 g, 0.097 mmol) was added and the reaction was sparged with N$_2$ for about 5 minutes. The vial was tightly sealed and heated at 100° C. overnight with stifling. The reaction was cooled and concentrated to dryness. The residue was partitioned between EtOAc (100 mL) and saturated aqueous NaHCO$_3$ solution (30 mL), the layers were separated, and the organic layer dried over MgSO$_4$, filtered and concentrated to an oil. The oil was chromatographed on silica gel (230-400 mesh, 19 g) using 20% EtOAc/Hexane to give 141b (151 mg, 40%) as a glass/white solid. m/z [M+H]$^+$ 371.2.

Compound 142b: Compound 141b (0.147 g, 0.40 mmol) was taken up in EtOH (20 mL), and the flask was flushed with nitrogen gas. 10% Pd/C (0.035 g) was added and the flask was evacuated and flushed with H$_2$ three times and was stirred overnight plus 6 hours under a balloon of H$_2$ at room temperature. The catalyst was filtered off and the filtrate concentrated give 142b (139 mg, 93%) as a clear foam/glass, m/z [M+H]$^+$ 373.1.

Compound 143b: Compound 142b (0.139 g, 0.37 mmol) was treated according to the procedure for 37a to give 143b (110.6 mg, 92%) as a glass/solid. m/z [M+H]$^+$329.1.

Compound 144b: Compound 143b (0.1106 g, 0.34 mmol) was treated according to the procedure for 143a to give 144a (128 mg, quantitative). m/z [M+H]$^+$ 357.1.

Compound 145b: Compound 144b (0.128 g, 0.36 mmol) was treated according to the procedure for 144a to give 145a (111.4 mg, 89%) as a foam. m/z [M+H]$^+$ 354.1.

Compound 146b: Compound 145b (0.1114 g, 0.32 mmol) was treated according to the procedure for 145a to give 146a (111.7 mg, 97%) as an off-white foam. m/z [M+H]$^+$ 354.0.

Compound TX63591: Compound 146b (0.111 g, 0.31 mmol) was treated according to the procedure for 146a to give TX63547 and chromatographed on silica gel (230-400 mesh, 12 g) using 3:1 Hexanes/EtOAc and was chromatographed a second time on silica gel (230-400 mesh, 8 g) using 5% methyl tert-butylether in DCM to give TX63591 (14 mg, 12%). $^1$H NMR (500 MHz, CDCl$_3$) δ 8.45 (s, 1H), 3.75 (s, 3H), 2.82 (dd, 1H, J=15, 5 Hz), 2.51-2.62 (m, 2H), 2.12 (dd, 1H, J=10, 2.5 Hz), 1.74-1.89 (m, 7H), 1.50-1.58 (m, 3H), 1.46 (s, 3H), 1.29-1.37 (m, 2H), 1.25 (s, 3H), 1.23 (s, 3H).

Compound 147: Compound 68 (0.151 g, 0.41 mmol), K$_2$CO$_3$ (0.176 g, 1.29 mmol), benzylboronic acid pinacol ester (0.176 g, 0.8 mmol), Pd(dppf)Cl$_2$ (0.038 g, 0.0046 mmol) and dioxane (8 mL) were reacted under nitrogen at 90° C. for 1.5 hours and then overnight at 100° C. More Pd(dppf)Cl$_2$ (0.041 g, 0.005 mmol) was added and the reaction mixture was heated at 120° C. overnight and purified by chromatography on silica gel (230-400 mesh, 9.9 g) eluting with 5:1 Hexanes/EtOAc, then 3:1 Hexanes/EtOAc to give 147 as a mixture with dehalogenated starting bromopyrazole as an oil, (0.0736 g), m/z [M+H]$^+$ 381.1.

Compound 148: Compound 147 (73.6 mg, 0.19 mmol) was taken up in MeOH, and 3 N HCl (aq) was added. The mixture was stirred overnight at room temperature. The reaction mixture and was then concentrated. The reaction mixture was extracted with EtOAc (2×25 mL) and washed saturated NaHCO$_3$, then dried with MgSO$_4$ and concentrated to give compound 148 (58.8 mg) as a solid. m/z 337.1 [M+H]$^+$.

Compound 149: Compound 148 (58.8 mg, 0.18 mmol) was taken up in ethyl formate, and 30% sodium methoxide (30 wt % solution in MeOH) was added. The mixture was stirred overnight at room temperature. The reaction mixture was diluted with KH$_2$PO$_4$ (aq), extracted with EtOAc (2×25 mL) and washed with brine, then dried with MgSO$_4$ and concentrated to give compound 149 (74 mg) as a solid This was used directly in the next step.

Compound 150: A mixture of hydroxylamine hydrochloride and 149 (74 mg, 0.2 mmol) in EtOH was stirred overnight at 50° C. After cooling to room temperature, the reaction mixture was concentrated. The residue was diluted with water and extracted with EtOAc, then dried with MgSO$_4$ and concentrated to give compound 150 (71 mg) as a solid. m/z 362.1 [M+H]$^+$.

Compound 151: Compound 150 (71 mg, 0.2 mmol) was dissolved in a 1/1 MeOH/THF mixture, and 30% sodium methoxide (30 wt % solution in MeOH) was added, and the reaction mixture was stirred at 50° C. for 6 h. The reaction mixture was concentrated and quenched by addition of saturated KH$_2$PO$_4$. The mixture was extracted with EtOAc and washed with brine, then dried with MgSO$_4$ and concentrated. The residue was chromatographed on silica gel (230-400 mesh, 11 g) using 50% Hexanes/EtOAc to give 151 (23 mg) as a solid. m/z [M+H]$^+$ 362.1.

Compound TX63550: Compound 151 (23 mg, 0.063 mmol) was dissolved in dry DMF, and the solution was cooled to 0° C. Br$_2$ was added, and the reaction stirred at 0° C. until the starting material was consumed (approximately 2 h), as reported by thin layer chromatography. Then, pyridine was added, and the reaction was allowed to warm to room temperature. The reaction mixture was then stirred at 50° C. overnight. The reaction mixture was concentrated. The crude residue was purified by column chromatography (230-400 mesh, 7 g) using 50% Hexanes/EtOAc to give TX63550 (8.3 mg). $^1$H NMR (500 MHz, CDCl$_3$) δ 8.45 (s, 1H), 7.28 (dd, 2H, J=7.3, 7.5 Hz), 7.21 (t, 1H, J=7.3 Hz), 7.04 (d, 2H, J=7.4 Hz), 3.90 (s, 2H), 3.65 (s, 3H), 2.57 (dd, 1H, J=5.9, 15.8 Hz), 2.35 (m, 1H), 2.14 (dd, 1H, J=1.9, 11.8 Hz), 1.90-1.77 (m, 2H), 1.47 (s, 3H), 1.25 (s, 3H), 1.20 (s, 3H); m/z [M+H]$^+$ 360.1.

Compound 152: Compound 130 (355 mg, 1.28 mmol) was taken up in methanol, and 3 N HCl (aq) was added. The mixture was stirred overnight at room temperature. The reaction mixture was then concentrated. The reaction mixture was diluted with saturated NaHCO$_3$ and extracted with EtOAc (2×25 mL), then dried with MgSO$_4$ and concentrated to give compound 152 (305 mg, quantitative) as a solid. m/z 233 [M+H]$^+$.

Compound 153: Compound 152 (305 mg, 1.28 mmol) was taken up in ethyl formate, and 30% sodium methoxide (30 wt % solution in MeOH) was added. The mixture was stirred overnight at room temperature. The reaction mixture was quenched KH$_2$PO$_4$ (aq) and extracted with EtOAc, then washed with brine, dried with MgSO$_4$ and concentrated to give compound 153 (330 mg, 99%) as a solid. m/z 261 [M+H]$^+$.

Compound 154: A mixture of hydroxylamine hydrochloride and 153 (330 mg, 1.27 mmol) in ethanol was stirred overnight at 50° C. After cooling to room temperature, the reaction mixture was concentrated. The residue was diluted with water and extracted with EtOAc, then washed with brine, dried with MgSO$_4$, and concentrated to give compound 154 (320 mg, 98%) as a solid. m/z 258 [M+H]$^+$.

Compound 155: Compound 154 (320 mg, 1.24 mmol) was dissolved in a 1/1 methanol/THF mixture, and 30% sodium methoxide (30 wt % solution in MeOH) was added, and the reaction mixture was stirred at 50° C. for 6 h. The reaction mixture was concentrated and quenched by addition of saturated KH$_2$PO$_4$. The mixture was extracted with EtOAc and washed with brine, then dried with MgSO$_4$ and concentrated to give compound 155 (320 mg, quantitative) as a solid. m/z 258 [M+H]$^+$.

Compound TX63551: Compound 155 (320 mg, 1.24 mmol) was dissolved in dry DMF, and the solution was cooled to 0° C. 1,3-Dibromo-5,5-dimethylhydantoin was added, and the reaction stirred at 0° C. until the starting material was consumed (approximately 2 h), as reported by thin layer chromatography. Then, pyridine was added, and the reaction was allowed to warm to room temperature. The reaction mixture was then stirred at 50° C. overnight. The reaction mixture was concentrated. The crude residue was purified by column chromatography (silica gel, 15 to 35% EtOAc in Hexanes) to give compound TX63551 (120 mg, 38%) as a solid. $^1$H NMR (500 MHz, CDCl$_3$) δ 8.46 (s, 1H), 7.08 (s, 1H), 3.87 (s, 3H), 2.75 (dd, 1H, J=6.3, 16.0 Hz), 2.57 (m, 2H), 2.09 (dt, 1H, J=1.8, 12.4 Hz), 2.02 (dd, 1H, J=7.1, 13.7 Hz), 1.74 (m, 1H), 1.44 (s, 3H), 1.31 (d, 3H, J=6.7 Hz); m/z 256 [M+H]$^+$.

Compound 156: A solution of compound 1 (2.50 g, 19.8 mmol) and acrylamide (2.15 g, 30.2 mmol) in Et$_3$N (50 mL) was heated at 85° C. for 16 h. The reaction mixture was cooled to room temperature and the brown solid isolated by filtration. The crude solid was triturated with EtOAc to give 156 (3.77 g, 96%) as a light brown solid. m/z 198 [M+H]$^+$.

Compound 157: Compound 156 (3.75 g, 19.0 mmol) was taken up in HOAc (37.5 mL), divided into 3 equal portions and sealed in microwave vials. Each vial was heated to 160° C. for 1 h in the microwave. The reaction mixtures were combined, diluted with EtOH (20 mL), and heated to reflux for 20 min, then cooled to room temperature. The mixture was filtered and the filtrate washed with EtOAc to give 157 (2.48 g, 73%) as a light brown solid. m/z 180 [M+H]$^+$.

Compound 158: NaH (1.0 equiv.) was added to a 0° C. solution of 157 (1.5 g, 8.4 mmol) in DMF/THF (2.3/1, 30 mL) and the mixture stirred for 45 min. MeI (1.5 equiv.) was added and the reaction warmed to room temperature. After 1.5 h at room temperature the reaction was quenched with saturated NH₄Cl and extracted with CH₂Cl₂, then washed with water, dried with MgSO₄ and concentrated. The crude residue was purified by column chromatography (silica gel, 0 to 100% EtOAc in Hexanes) to give 158 (1.1 g, 68%) as a light yellow solid. m/z 194 [M+H]⁺.

Compound 159: Compound 158 (600 mg, 3.1 mmol) was taken up in AcOH/water (19/1, 12 mL) under N₂ and PtO₂ (120 mg) added. The flask was rigorously purged with H₂ and stirred for 16 h at room temperature. The reaction mixture was filtered through Celite, eluted with EtOAc, and concentrated. The crude residue was taken up in CH₂Cl₂, dried with MgSO₄, and concentrated to give compound 159 (864 mg, quantitative) as a viscous oil. m/z 198 [M+H]⁺.

Compound 160: TPAP (107 mg, 0.30 mmol) was added to a room temperature mixture of compound 159 (864 mg, 3.1 mmol), NMO (770 mg, 6.6 mmol), and 4 Å molecular sieves (2 g) in CH₂Cl₂ (40 mL). The reaction mixture was stirred at room temperature for 1 h. The mixture was filtered through a pad of silica, eluted with acetone/CH₂Cl₂ (1/1, 100 mL) and concentrated. The residue was taken up in CH₂Cl₂, washed with 1 N HCl (aq) and water, then dried with MgSO₄ and concentrated. The crude residue was purified by column chromatography (silica gel, 0 to 50% Acetone in Hexanes) to give 160 (480 mg, 79%) as a white solid. m/z 196 [M+H]⁺.

Compound 161: Compound 160 (120 mg, 0.61 mmol) was taken up in ethyl formate, cooled to 0° C., and 25% sodium methoxide (25 wt % solution in MeOH) was added. The mixture was stirred for 1 h at 0° C., then warmed to room temperature and stirred for 2 h. The reaction mixture was quenched with 12 N HCl (0.55 mL) and extracted with CH₂Cl₂, then dried with MgSO₄ and concentrated to give crude compound 161: m/z 224 [M+H]⁺.

Compound 162: A mixture of crude compound 161 and methyl hydrazine (52 L, 0.98 mmol) in ethanol (6.1 mL) was heated to 60° C. for 3 h. The reaction mixture was concentrated. The crude residue was purified by column chromatography (silica gel, 0 to 10% MeOH in CH₂Cl₂) to give 162 (134 mg, 93%) as an oil. m/z 234 [M+H]⁺.

Compound 163: A solution of 1,3-dibromo-5,5-dimethylhydantoin (107 mg, 0.37 mmol) in CH₂Cl₂ (3 mL) was added to a room temperature solution of compound 162 (134 mg, 0.57 mmol) in CH₂Cl₂ (3 mL). The reaction was stirred for 5 h at room temperature. The reaction mixture was directly purified by successive column chromatography, first directly loaded (silica gel, 0 to 70% Acetone in Hexanes), then (silica gel, 0 to 5% MeOH in CH₂Cl₂) to give 163 (87 mg, 49%) as an oil. m/z 312, 314 (1:1), [M+H]⁺.

Compound 164: A mixture of Compound 163 (87 mg, 0.28 mmol), 3-phenylboronic acid (1.5 equiv.), Ph₃P (0.2 equiv.), K₃PO₄ (3.0 equiv.) and DME was sparged with N₂ for 10 min. Pd(OAc)₂ (0.1 equiv.) was added and sparging with N₂ was continued for 10 min. The reaction vial was sealed and heated to 110° C. for 2.5 h in the microwave. The reaction mixture was filtered and concentrated. The crude residue was purified by column chromatography (silica gel, 0 to 65% Acetone in Hexanes) to give compound 164 (82 mg, 95%) as a white solid. m/z 310 [M+H]⁺.

Compound 165: A solution of LDA (2.0 equiv.) in THF was added to a −78° C. solution of 164 (40 mg, 0.13 mmol) in THF (1.3 mL). The reaction was stirred at −78° C. for 30 min, then a solution of PhSeCl (3 equiv.) in THF (0.4 mL) was added. The reaction was stirred at −78° C. for an additional 1 h, then quenched with saturated NH₄Cl (aq) and warmed to room temperature. The reaction mixture was extracted with EtOAc, then washed with water, dried with MgSO₄ and concentrated. The crude residue was purified by column chromatography (silica gel, 0 to 100% EtOAc in Hexanes) to give compound 165 (27 mg, 45%) as a yellow solid. m/z 466 [M+H]⁺.

Compound 166: Compound 165 (27 mg, 0.058 mmol) was taken up in EtOAc/THF (3/1, 1.2 mL), and H₂O₂ (30%, 5 equiv.) was added. The reaction mixture was stirred at room temperature for 30 min. The reaction mixture was diluted EtOAc, washed with saturated Na₂SO₃ (aq) and water, then dried with MgSO₄ and concentrated. The crude residue was purified by column chromatography (silica gel, 0 to 100% EtOAc in Hexanes) to give compound 166 (16 mg, 90%) as a white solid. m/z 308 [M+H]⁺.

Compound 167: Iodine (2 equiv.) was added to a room temperature solution of compound 166 (14.2 mg, 0.046 mmol) in pyridine/CCl₄ (1/2, 0.69 mL). The reaction mixture was stirred for 5 h at room temperature, then for 16 h at 50° C., and finally for 20 h at 65° C. The reaction was cooled to room temperature and diluted with EtOAc. The mixture was washed with saturated Na₂SO₃ (aq), water, and brine, then dried with MgSO₄ and concentrated. The crude residue was purified by column chromatography (silica gel, 0 to 100% EtOAc in Hexanes) to give compound 167 (12 mg, 60%) as a yellow solid. m/z 434 [M+H]⁺.

Compound TX63568: Compound 167 (11 mg, 0.036 mmol), Zn(CN)₂ (3 equiv.) and Pd(PPh₃)₄ (0.2 equiv.) were taken up in degassed DMF (0.5 mL). The vial was purged with N₂, sealed and the reaction stirred for 20 min at 80° C. The reaction mixture was diluted with EtOAc and washed with water, then dried with MgSO₄ and concentrated. The crude residue was purified by column chromatography (silica gel, 0 to 50% EtOAc in Hexanes) to give compound TX63568 (7.5 mg, 89%) as a light yellow solid. NMR (400 MHz, CDCl₃) δ 8.08 (s, 1H), 7.49 (t, 2H, J=7.0 Hz), 7.43 (t, 1H, J=7.2 Hz), 7.32 (d, 2H, J=6.9 Hz), 3.88 (dd, 1H, J=2.8, 13.2 Hz), 3.80 (s, 3H), 3.12 (s, 3H), 2.72 (ddd, 1H, J=1.3, 6.6, 16.4 Hz), 2.63 (ddd, 1H, J=6.6, 11.4, 16.3 Hz), 2.30 (m, 1H), 2.00 (m, 1H), 1.35 (s, 3H); m/z 333 [M+H]⁺.

Compound 169: Compound 25 (0.294 g, 1.17 mmol) was taken up in DCM (50 mL). MgBr-Et₂O (0.777 g, 3.0 mmol) and iPr₂EtN (0.4 mL, 2.3 mmol) were added sequentially and the reaction mixture was stirred at room temperature for about 15 minutes, gradually turning orange. Benzoyl chloride (0.342 g, 2.43 mmol) in DCM (2 mL) was added dropwise and the mixture was stirred overnight at room temperature. The reaction was quenched by adding saturated aqueous NaHCO₃ solution, the layers were separated, and the organic layer was dried over MgSO₄, filtered and concentrated to an oil to afford crude 168. The residue was taken up in EtOH (25 mL) and treated with hydrazine monohydrate (0.63 g, 12.6 mmol) in EtOH and the mixture was heated at 63° C. for about 1 hour and was then concentrated to a yellow oil. The oil was chromatographed on silica gel (230-400 mesh, 15 g) using 50% EtOAc/Hexane to yield 169 (158 mg, 38%) as an almost clear oil. m/z [M+H]⁺ 353.1.

Compound 170: Compound 169 (0.158 g, 0.45 mmol) was taken up in MeOH, and 1 N HCl (aq) was added. The mixture was stirred overnight at room temperature. The reaction mixture was then concentrated. The residue was extracted with EtOAc and washed with saturated NaHCO₃ (aq), then dried with MgSO₄ and concentrated to give compound 170 (174 mg, quantitative) as an oil. m/z [M+H]⁺ 309.0.

Compound 171: Compound 170 (0.169 g, 0.55 mmol) was taken up in ethyl formate, and sodium methoxide (30 wt % solution in MeOH) was added. The mixture was stirred overnight at room temperature. The reaction mixture was extracted with EtOAc and washed with KH₂PO₄ (aq), then dried with MgSO₄ and concentrated to give compound 171 (154.8 mg, 84%). m/z [M+H]⁺ 337.0.

Compound 172: A solution of 0.1 N hydroxylamine hydrochloride (aq) was added to compound 171 (0.1548 g, 0.46 mmol). A 9:1 mixture of EtOH/water was added, and the reaction mixture was stirred overnight at 50° C. After cooling to room temperature, the reaction mixture was concentrated. The residue was taken up in EtOAc, then dried with MgSO$_4$ and concentrated to give compound 172 (128 mg, 83%) as a light yellow solid. m/z [M+H]$^+$ 334.0.

Compound 173: Compound 172 (0.128 g, 0.38 mmol) was dissolved in a 3:1 MeOH/THF mixture, and sodium methoxide (30 wt % solution in MeOH) was added, and the reaction mixture was stirred at 55° C. for 5 h and then stirred at room temperature overnight. The reaction was quenched by addition of saturated KH$_2$PO$_4$, and the reaction mixture was concentrated. The residue was extracted with EtOAc and washed with brine, then dried with MgSO$_4$ and concentrated. The crude residue was purified by column chromatography (silica gel, 50% EtOAc/Hexanes) to give compound 173 (129 mg, quantitative) as a yellow glass/solid. m/z [M+H]$^+$ 334.0.

Compound TX63579: A mixture of compound 173 (0.129 g, 0.39 mmol) and DDQ (1.3 eq) were taken up in benzene. The mixture was stirred at reflux for 4.5 h. After cooling to room temperature, the reaction mixture was concentrated. The crude residue was chromatographed on silica gel (230-400 mesh, 11 g) using 3:1 Hexanes/EtOAc to give TX63579 (35.47 mg, 27%). $^1$H NMR (500 MHz, d$_6$-DMSO) δ 13.05 (s, 1H), 8.55 (s, 1H), 7.61 (d, 2H), 7.47 (dd, 2H, J=7.4, 7.5 Hz), 7.35 (t, 1H, J=7.4 Hz), 2.87 (dd, 1H, J=5.5, 15.8 Hz), 2.76-2.69 (m, 1H), 2.26 (d, 1H), 1.98-1.86 (m, 2H), 1.45 (s, 3H), 1.24 (s, 3H), 1.15 (s, 3H); m/z [M+H]$^+$ 332.0.

Compound 174: A solution of acetamide hydrochloride (0.68 g, 7.2 mmol) and piperidine (0.60 g, 7.0 mmol) in i-PrOH (10 mL) was stirred at room temperature for 15 min, then compound 26 (0.20 g, 0.71 mmol) was added. The reaction mixture was heated at reflux for 3 d, then concentrated. The crude residue was purified by column chromatography (silica gel, 5 to 25% EtOAc in Hexanes) to give 174 (0.12 g, 56%) as a solid. m/z 303 [M+H]$^+$.

Compound 175a: O-Methylisourea hemisulfate (0.946 g, 7.7 mmol) and piperidine (0.58 g, 6.8 mmol) were taken up in iPrOH (15 mL), and the mixture was stirred at room temperature for approximately 15 min. Compound 174 (0.212 g, 0.76 mmol) was added, and the reaction mixture was stirred at room temperature for 30 min and then heated to reflux for 4 d. The iPrOH was replaced with n-BuOH and more O-methylisourea hemisulfate (0.432 g, 3.5 mmol) was added. The reaction mixture was heated to reflux overnight. After cooling to room temperature, the reaction mixture was concentrated. The residue was extracted with EtOAc (80 mL) and washed with saturated aq. NaHCO$_3$ (15 mL), and brine (15 mL), then dried with MgSO$_4$ and concentrated. The crude residue was purified by column chromatography (silica gel, 20% EtOAc/Hexanes) to give a mixture of three components (364 mg): m/z 319.2 [M+H]$^+$.

TABLE 8

Compounds 175b-175o (Scheme 31).

| Compound Name | R | 9 (mmol) | Amidine (mmol) | Piperidine (mmol) | Yield (%) |
|---|---|---|---|---|---|
| 175b | Me | 0.71 | 7.2 | 7.0 | 56 |
| 175c | i-Pr | 1.091 | 10.93 | 6.60 | 63 |
| 175d | H | 1.081 | 10.85 | 6.46 | 75 |
| 175e | Ph | 1.091 | 11.24 | 6.77 | 75 |
| 175f | t-Bu | 1.07 | 7.3 | 5.35 | 52 |
| 175g | CF$_3$ | 1.07 | 10.7 | 5.35 | 88 |
| 175h | 4-Cl—Ph | 1.242 | 5.23 | 3.13 | 40 |
| 175i | 2-Cl—Ph | 1.25 | 5.58 | 3.23 | Quant. |
| 175j | 3-Me—Ph | 1.118 | 5.86 | 3.53 | 39 |
| 175k | 4-MeO—Ph | 1.258 | 5.4 | 3.23 | 32 |
| 175l | Me-thiazole | 1.19 | 5.75 | 3.43 | Quant. |
| 175m | 3-pyridyl | 1.079 | 6.34 | 3.84 | 44 |
| 175n | 4-pyridyl | 1.28 | 12.82 | 7.68 | Quant. |
| 175o | 2-pyridyl | 1.09 | 6.34 | 3.84 | 95 |

General method F: Compound 174 (See Table 8 for the amount), substituted amidine (See Table 8 for the amount) and piperidine (See Table 8 for the amount) were taken up in i-PrOH (10 mL), and the mixture was stirred at 85° C. for 48 h in a sealed tube. After cooling to room temperature, the reaction mixture was concentrated. The residue was extracted with CHCl$_3$ and washed with NH$_4$Cl (aq, 10%), brine, then dried with MgSO$_4$ and concentrated. The crude residue was purified by column chromatography (silica gel, EtOAc/Hexanes or MeOH/CHCl$_3$) to give the corresponding derivatives:

Compound 175b: 0.12 g, 56%: m/z 303 [M+H]$^+$.
Compound 175c: 0.2282 g, 63%: m/z 331 [M+H]$^+$.
Compound 175d: 0.233 g, 75%: m/z 289 [M+H]$^+$.
Compound 175e: 0.307 g, 75%: m/z 365 [M+H]$^+$.
Compound 175f: 0.190 g, 52%: m/z 345 [M+H]$^+$.
Compound 175g: 0.337 g, 88%: m/z 357 [M+H]$^+$.
Compound 175h: 0.2 g, 40%: m/z 399, 401 (3:1) [M+H]$^+$.
Compound 175i: 1.38 g, >100%: m/z 399/401 (39/14%) [M+H]$^+$, 155/157 (100/36%).
Compound 175j: 0.164 g, 39%: m/z 379 [M+H]$^+$.
Compound 175k: 0.161 g, 32%: m/z 395 [M+H]$^+$.
Compound 175l: 0.92 g, >100%: m/z 386 (93%) [M+H]$^+$, 143 (64%) and 126 (100%).
Compound 175m: 0.172 g, 44%: m/z 366 [M+H]$^+$.
Compound 175n: 1.05 g, >100%: m/z 366 (83%) [M+H]$^+$ and 190 (100%).
Compound 175o: 0.38 g, 95%: m/z 366 (100%) [M+H]$^+$.

Compound 176a: Compound 175a (0.364 g) was taken up in MeOH, and HCl (aq, 1 N) was added. The mixture was stirred overnight at room temperature. The reaction mixture was then concentrated. The residue was extracted with EtOAc and washed with saturated NaHCO$_3$ (aq), then dried with MgSO$_4$ and concentrated to give a mixture (0.336 g): m/z 275 [M+H]$^+$.

TABLE 9

Compounds 176b-176o (Scheme 31).

| Compound Name | R | 175b-o (mmol) | 3N HCl (mL) | Solvent | Yield (%) |
|---|---|---|---|---|---|
| 176b | Me | 0.50 | Not given | MeOH | quantitative |
| 176c | i-Pr | 0.69 | 2 | MeOH (10 mL) | 89 |
| 176d | H | 0.809 | 2 | MeOH (10 mL) | 93 |
| 176e | Ph | 0.844 | 2 | MeOH:THF (1:1) (20 mL) | quantitative |
| 176f | t-Bu | 0.552 | 2 | MeOH (10 mL) | 84 |
| 176g | CF$_3$ | 0.944 | 2 | MeOH (10 mL) | 65 |
| 176h | 4-Cl—Ph | 0.502 | 4 | MeOH:THF (1:1) (20 mL) | 87 |
| 176i | 2-Cl—Ph | 1.25 | 5 | MeOH (25 mL) | 73 |

TABLE 9-continued

Compounds 176b-176o (Scheme 31).

| Compound Name | R | 175b-o (mmol) | 3N HCl (mL) | Solvent | Yield (%) |
|---|---|---|---|---|---|
| 176j | 3-Me—Ph | 0.433 | 4 | MeOH:THF (1:1) (20 mL) | 96 |
| 176k | 4-MeO—Ph | 0.409 | 4 | MeOH:THF (1:1) (20 mL) | 88 |
| 176l | Me-thiazole | 1.19 | 5 mL (6N) | MeOH (20 mL) | 92 |

TABLE 9-continued

Compounds 176b-176o (Scheme 31).

| Compound Name | R | 175b-o (mmol) | 3N HCl (mL) | Solvent | Yield (%) |
|---|---|---|---|---|---|
| 176m | 3-pyridyl | 0.471 | 4 | MeOH:THF (1:1) (20 mL) | quantitative |
| 176n | 4-pyridyl | 1.28 | 5 mL (6N) | MeOH (25 mL) | 66 |
| 176o | 2-pyridyl | 1.06 | 5 mL (6N) | MeOH (20 mL) | 72 |

General method G: Compound 175b-o (see Table 9 for the amount) was taken up in solvent (see Table 9 for the amount), and HCl (aq) (see Table 9 for the amount) was added. The mixture was stirred under $N_2$ at room temperature for 16 h. The reaction mixture was then concentrated. The residue was basified with $NH_4OH$ (aq., 10%) to pH~9-10, extracted with $CHCl_3$ and washed with saturated NaCl (aq), then dried with $MgSO_4$ and concentrated to give the corresponding derivatives:

Compound 176b: 0.14 g, quantitative: m/z 259 $[M+H]^+$.
Compound 176c: 0.176 g, 89%: m/z 287 $[M+H]^+$.
Compound 176d: 0.184 g, 93%: m/z 245 $[M+H]^+$.
Compound 176e: 0.287 g, quantitative: m/z 321 $[M+H]^+$.
Compound 176f: 0.139 g, 84%: m/z 301 $[M+H]^+$.
Compound 176g: 0.191 g, 65%: m/z 313 $[M+H]^+$.
Compound 176h: 0.155 g, 87%: m/z 355, 357 (3:1) $[M+H]^+$.
Compound 176i: 0.32 g, 73%: m/z 355/357 (100/74%) $[M+H]^+$.
Compound 176j: 0.139 g, 96%: m/z 335 $[M+H]^+$.
Compound 176k: 0.127 g, 88%: m/z 351 $[M+H]^+$.
Compound 176l: 0.37 g, 92%: m/z 342 (100%), $[M+H]^+$.
Compound 176m: 0.174 g, 100%: m/z 322 $[M+H]^+$.
Compound 176n: 0.27 g, 66%: m/z 322 (100%), $[M+H]^+$.
Compound 176o: 0.24 g, 72%: m/z 322 (100%), $[M+H]^+$.

Compound 177a: Compound 176a (0.336 g, 1.2 mmol) was taken up in ethyl formate (20 mL), and 30% NaOMe in MeOH (1.56 mL, 28.4 mmol) was added. The mixture was stirred overnight at room temperature. The reaction mixture was extracted with EtOAc and washed with $KH_2PO_4$ (aq), then dried with $MgSO_4$ and concentrated to give the compound 177a (0.152 g, 66% over 3 steps): m/z 303 $[M+H]^+$.

TABLE 10

Compounds 177b-o (Scheme 31).

| Compound Name | R | 176b-o (mmol) | $EtO_2CH$ (mL) | MeONa in MeOH (30% w/w, mL) | Benzene (mL) | Yield (%) |
|---|---|---|---|---|---|---|
| 177b | Me | 0.500 | Not given | Not given | Not given | 92 |
| 177c | i-Pr | 0.616 | 0.50 | 0.60 | 20 | quantitative |
| 177d | H | 0.752 | 0.61 | 0.71 | 20 | 95 |
| 177e | Ph | 0.844 | 0.68 | 0.80 | 20 | 84 |
| 177f | t-Bu | 0.464 | 0.37 | 0.44 | 10 | quantitative |
| 177g | $CF_3$ | 0.613 | 0.50 | 0.57 | 10 | quantitative |
| 177h | 4-Cl—Ph | 0.437 | 0.35 | 0.41 | 10 | 99 |
| 177i | 2-Cl—Ph | 0.910 | 0.73 | 0.85 | 20 | 91 |
| 177j | 3-Me—Ph | 0.417 | 0.34 | 0.39 | 10 | 89 |
| 177k | 4-MeO—Ph | 0.362 | 0.30 | 0.34 | 10 | quantitative |
| 177l | Me-thiazole | 1.10 | 0.89 | 1.0 | 25 | 94 |
| 177m | 3-pyridyl | 0.471 | 0.38 | 0.44 | 10 | 83 |
| 177n | 4-pyridyl | 0.850 | 0.68 | 0.80 | 20 | quantitative |
| 177o | 2-pyridyl | 0.76 | 0.62 | 0.72 | 20 | 82 |

General method H: Compound 176b-o (see Table 10 for the amount) and ethyl formate (see Table 10 for the amount) were taken up in benzene (see Table 10 for the amount), and 30% NaOMe in MeOH (see Table 10 for the amount) was added. The mixture was stirred under $N_2$ at room temperature for 16 h. The reaction mixture was then concentrated. The residue was extracted with EtOAc and washed with saturated $KH_2PO_4$ (aq), saturated NaCl (aq), then dried with $MgSO_4$ and concentrated to give the corresponding derivatives:

Compound 177b: 0.13 g, 92%: m/z 287 $[M+H]^+$.
Compound 177c: 0.206 g, quantitative: m/z 315 $[M+H]^+$.
Compound 177d: 0.194 g, 95%: m/z 273 $[M+H]^+$.
Compound 177e: 0.248 g, 84%: m/z 349 $[M+H]^+$.
Compound 177f: 0.162 g, quantitative: m/z 329 $[M+H]^+$.
Compound 177g: 0.228 g, quantitative: m/z 329 $[M+H]^+$.
Compound 177h: 0.166 g, 99%: m/z 397, 399 (3:1) $[M+H]^+$.
Compound 177i: 0.32 g, 91%: m/z 383/385 (100/42%), $[M+H]^+$.
Compound 177j: 0.134 g, 89%: m/z 363 $[M+H]^+$.
Compound 177k: 0.156 g, quantitative: m/z 379 $[M+H]^+$.
Compound 177l: 0.38 g, 94%: m/z 392 (13%) $[M+Na]^+$ and 370 (100%) $[M+H]^+$.
Compound 177m: 0.137 g, 83%: m/z 350 $[M+H]^+$.
Compound 177n: 0.35 g, >100%: m/z 350 (100%) $[M+H]^+$.
Compound 177o: 0.22 g, 82%: m/z 350 (100%) $[M+H]^+$.

Compound 178a: A solution of 0.1 N hydroxylamine hydrochloride (5.5 mL, 0.55 mmol) was added to compound 177a (0.152 g, 0.5 mmol). A 9/1 mixture of ethanol/water was added, and the reaction mixture was stirred overnight at 50°

C. After cooling to room temperature, the reaction mixture was concentrated. The residue was taken up in EtOAc, then dried with MgSO$_4$ and concentrated. The crude residue was purified by column chromatography (silica gel, 25% EtOAc/Hexanes) to give the compound 178a (18 mg, 12%): m/z 300 [M+H]$^+$.

TABLE 11

Compound 178b-178o (Scheme 31).

| Compound Name | R | 177b-o (mmol) | NH$_2$OH•HCl (mmol) | Ethanol (mL) | Yield (%) |
|---|---|---|---|---|---|
| 178b | Me | 0.45 | Not given | Not given | quantitative |
| 178c | i-Pr | 0.616 | 0.921 | 10 | 96 |
| 178d | H | 0.712 | 1.065 | 10 | 88 |
| 178e | Ph | 0.711 | 1.065 | 10 | quantitative |
| 178f | t-Bu | 0.464 | 0.69 | 10 | quantitative |
| 178g | CF$_3$ | 0.613 | 0.92 | 10 | 85 |
| 178h | 4-Cl—Ph | 0.434 | 0.65 | 20 | 90 |
| 178i | 2-Cl—Ph | 0.82 | 1.24 | 20 | quantitative |
| 178j | 3-Me—Ph | 0.369 | 0.55 | 10 | quantitative |
| 178k | 4-MeO—Ph | 0.362 | 0.55 | 10 | quantitative |
| 178l | Me-thiazole | 1.02 | 1.58 | 20 | quantitative |
| 178m | 3-pyridyl | 0.391 | 0.59 | 10 | 82 |
| 178n | 4-pyridyl | 0.85 | 1.29 | 50 | 83 |
| 178o | 2-pyridyl | 0.63 | 0.94 | 25 | 45 |

General method I: Compound 177b-o (see Table 11 for the amount) was taken up in EtOH (see Table 11 for the amount), and hydroxylamine hydrochloride (see Table 11 for the amount) was added. The mixture was stirred overnight at 50° C. under N$_2$. After cooling to room temperature, the reaction mixture was concentrated. The residue was taken up in EtOAc and washed with saturated NaHCO$_3$ (aq), saturated NaCl (aq), then dried with MgSO$_4$ and concentrated to give the corresponding derivatives:

Compound 178b: 0.13 g, quantitative: m/z 284 [M+H]$^+$.

Compound 178c: 0.183 g, 96%: m/z 312 [M+H]$^+$.

Compound 178d: 0.168 g, 88%: m/z 270 [M+H]$^+$.

Compound 178e: 0.247 g, quantitative: m/z 346 [M+H]$^+$.

Compound 178f: 0.167 g, quantitative: m/z 326 [M+H]$^+$.

Compound 178g: 0.175 g, 85%: m/z 338 [M+H]$^+$.

Compound 178h: 0.149 g, 90%: m/z 380, 382 (3:1) [M+H]$^+$.

Compound 178i: 0.31 g, ~100%: m/z 380/382 (100/63%) [M+H]$^+$.

Compound 178j: 0.152 g, quantitative: m/z 360 [M+H]$^+$.

Compound 178k: 0.146 g, quantitative: m/z 376 [M+H]$^+$.

Compound 178l: 0.37 g, ~100%: m/z 367 (100%), [M+H]$^+$.

Compound 178m: 0.111 g, 82%: m/z 347 [M+H]$^+$.

Compound 178n: 0.24 g, 83%: m/z 347 (100%), [M+H]$^+$.

Compound 178o: 0.097 g, 45%: m/z 347 (100%), [M+H]$^+$.

Compound 179a: Compound 178a (18 mg, 0.06 mmol) was dissolved in a 3:1 MeOH/THF mixture (1.6 mL), and 30% sodium methoxide (0.066 mL, 1.18 mmol) was added. The reaction mixture was stirred at 55° C. for 5.5 h and then stirred at room temperature overnight. The reaction was quenched by addition of saturated KH$_2$PO$_4$, and the reaction mixture was concentrated. The residue was extracted with EtOAc and washed with brine, then dried with MgSO$_4$ and concentrated to give the compound 179a (13.3 mg, 74%).

TABLE 12

Compounds 179b-179o (Scheme 31).

| Compound Name | R | 178b-o mmol | MeONa in MeOH (30% w/w, mL) | MeOH (mL) | Yield (%) |
|---|---|---|---|---|---|
| 179b | Me | 0.45 | Not given | Not given | Quantitative |
| 179c | i-Pr | 0.588 | 0.55 | 20 | 77 |
| 179d | H | 0.625 | 0.60 | 20 | 76 |
| 179e | Ph | 0.711 | 0.67 | 10 | 92 |
| 179f | t-Bu | 0.464 | 0.44 | 10 | 81 |
| 179g | CF$_3$ | 0.518 | 0.49 | 10 | 80 |
| 179h | 4-Cl—Ph | 0.392 | 0.37 | 10 | 92 |
| 179i | 2-Cl—Ph | 0.82 | 0.77 | 20 | 68 |
| 179j | 3-Me—Ph | 0.369 | 0.35 | 10 | 90 |
| 179k | 4-MeO—Ph | 0.362 | 0.34 | 10 | 91 |
| 179l | Me-thiazole | 1.02 | 0.96 | 20 | 82 |
| 179m | 3-pyridyl | 0.320 | 0.30 | 10 | 72 |
| 179n | 4-pyridyl | 0.71 | 0.66 | 20 | Quantitative |
| 179o | 2-pyridyl | 0.28 | 0.27 | 25 | 65 |

General method J: Compound 178b-o (see Table 12 for the amount) was taken up in MeOH (see Table 12 for the amount), and 30% NaOMe in MeOH (see Table 12 for the amount) was added. The mixture was stirred under N$_2$ at 50° C. for 2 h, then at room temperature overnight. The reaction mixture was concentrated. The residue was taken up in EtOAc and washed with saturated NaHCO$_3$ (aq), saturated NaCl (aq), then dried with MgSO$_4$ and concentrated to give the corresponding derivatives:

Compound 179b: 0.13 g, quantitative: m/z 284 [M+H]$^+$.

Compound 179c: 0.141 g, 77%: m/z 312 [M+H]$^+$.

Compound 179d: 0.128 g, 76%: m/z 270 [M+H]$^+$.

Compound 179e: 0.225 g, 92%: m/z 346 [M+H]$^+$.

Compound 179f: 0.123 g, 81%: m/z 326 [M+H]$^+$.

Compound 179g: 0.140 g, 80%: m/z 338 [M+H]$^+$.

Compound 179h: 0.137 g, 92%: m/z 380, 382 (3:1) [M+H]$^+$.

Compound 179i: 0.21 g, 68%: m/z 380/382 (100/52%) [M+H]$^+$.

Compound 179j: 0.119 g, 90%: m/z 360 [M+H]$^+$.

Compound 179k: 0.123 g, 91%: m/z 376 [M+H]$^+$.

Compound 179l: 0.31 g, 82%: m/z 367 (100%) [M+H]$^+$.

Compound 179m: 0.080 g, 72%: m/z 347 [M+H]$^+$.

Compound 179n: 0.25 g, >100%: m/z 347 (100%) [M+H]$^+$.

Compound 179o: 0.063 g, 65%: m/z 347 (100%) [M+H]$^+$.

Compound TX63528: Compound 179a (13.3 mg, 0.044 mmol) was dissolved in dry DMF (0.26 mL), and the solution was cooled to 0° C. Dibromodimethylhydantoin (8.0 mg, 0.028 mmol) was added, and the reaction stirred at 0° C. until the starting material was consumed as reported by thin layer chromatography. Then, pyridine (0.034 mL, 0.416 mmol) was added, and the reaction was allowed to warm to room temperature. The reaction mixture was then stirred at 50° C. overnight. After cooling to room temperature, the reaction mixture was extracted with EtOAc and washed with brine, then dried with MgSO$_4$ and concentrated. The crude residue was purified by column chromatography (silica gel, 25% EtOAc/Hexanes) to give compound TX63528 (6.5 mg, 50%). m/z 298 [M+H]$^+$.

TABLE 13

Compounds of Scheme 31.

| Compound Name | R | 179b-o (mmol) | DBDMH (mmol) | Pyridine (mL) | Yield (%) |
|---|---|---|---|---|---|
| TX63468 | Me | 0.45 | Not given | Not given | 51 |
| TX63534 | i-Pr | 0.454 | 0.273 | 0.37 | 38 |
| TX63542 | H | 0.478 | 0.29 | 0.37 | 54 |
| TX63552 | Ph | 0.652 | 0.392 | 0.53 | 51 |
| TX63561 | t-Bu | 0.377 | 0.227 | 0.30 | 44 |
| TX63567 | $CF_3$ | 0.415 | 0.248 | 0.34 | 38 |
| TX63582 | 4-Cl—Ph | 0.361 | 0.217 | 0.30 | 35 |
| TX63612 | 2-Cl—Ph | 0.56 | 0.28 | 0.45 | 67 |
| TX63583 | 3-Me—Ph | 0.330 | 0.199 | 0.27 | 35 |
| TX63590 | 4-MeO—Ph | 0.328 | 0.196 | 0.27 | 38 |
| TX63628 | Me-thiazole | 0.84 | 0.42 | 0.70 | 23 |
| TX63586 | 3-pyridyl | 0.232 | 0.140 | 0.20 | 26 |
| TX63636 | 4-pyridyl | 0.71 | 0.35 | 0.60 | 51 |
| TX63641 | 2-pyridyl | 0.18 | 0.091 | 0.15 | 25 |

General method K: Compound 179b-o (see Table 13 for the amount) was dissolved in dry DMF (10 mL), and the solution was cooled to 0° C. under $N_2$. Dibromodimethylhydantoin (DBDMH) (see Table 13 for the amount) was added, and the reaction stirred at 0° C. for 2 h. Pyridine (see Table 13 for the amount) was added, and the reaction was allowed to warm to room temperature. The reaction mixture was stirred at 50° C. for 16 h. After cooling to room temperature, the reaction mixture was concentrated. The residue was extracted with EtOAc and washed with saturated $NaHCO_3$ (aq), saturated $KH_2PO_4$ (aq), saturated NaCl (aq), then dried with $MgSO_4$ and concentrated to give the corresponding derivatives:

Compound TX63468: 65 mg g, 51%: $^1$H NMR (400 MHz, $CDCl_3$) δ 8.88 (s, 1H), 8.44 (s, 1H), 3.00 (dd, 1H, J=6.3, 17.2 Hz), 2.85 (ddd, 1H, J=7.6, 11.4, 17.2 Hz), 2.73 (s, 3H), 2.21 (dd, 1H, J=2.2, 12.5 Hz), 2.06 (m, 1H), 1.96 (m, 1H), 1.48 (s, 3H), 1.33 (s, 3H), 1.27 (s, 3H); m/z 282 [M+H]$^+$.

Compound TX63534: 53 mg, 38%: $^1$H NMR (500 MHz, $CDCl_3$) δ 8.88 (s, 1H), 8.48 (s, 1H), 3.18-3.27 (m, 1H), 3.00 (dd, 1H, J=15.0, 10.0 Hz), 2.81-2.91 (m, 1H), 2.24 (dd, 1H, J=10.0, 5.0 Hz), 2.03-2.09 (m, 1H), 1.90-2.01 (m, 1H), 1.48 (s, 3H), 1.38 (s, 3H), 1.37 (s, 3H), 1.33 (s, 3H), 1.28 (s, 3H); m/z 310 [M+H]$^+$.

Compound TX63542: 56.8 mg, 54%: $^1$H NMR (500 MHz, $CDCl_3$) δ 9.04 (br s, 1H), 8.79 (s, 1H), 8.55 (br s, 1H), 3.02 (dd, 1H, J=6.1, 17.5 Hz), 2.92-2.84 (m, 1H), 2.20 (dd, 1H, J=1.8, 12.6 Hz), 2.06-2.02 (m, 1H), 1.93 (dddd, 1H, J=6.5, 12.0, 12.3, 12.6 Hz), 1.45 (s, 3H), 1.29 (s, 3H), 1.23 (s, 3H); m/z 268 [M+H]$^+$.

Compound TX63552: 114 mg, 51%: $^1$H NMR (500 MHz, $CDCl_3$) δ 8.95 (s, 1H), 8.57 (s, 1H), 8.43 (m, 2H), 7.50 (m, 3H), 3.03 (dd, 1H, J=6.1, 17.5 Hz), 2.92-2.85 (m, 1H), 2.25 (d, 1H, J=12.4 Hz), 2.08-2.01 (m, 1H), 1.99-1.92 (m, 1H), 1.51 (s, 3H), 1.31 (s, 3H), 1.25 (s, 3H); m/z 344 [M+H]$^+$.

Compound TX63561: 54 mg, 44%: $^1$H NMR (500 MHz, $CDCl_3$) δ 8.81 (s, 1H), 8.44 (s, 1H), 2.95 (dd, 1H, J=6.0, 17.3 Hz), 2.80 (dddd, 1H, J=7.3, 8.8, 8.9, 11.4 Hz), 2.20 (dd, 1H, J=1.9, 12.5 Hz), 2.03-1.99 (m, 1H), 1.91 (dddd, 1H, J=6.4, 12.3, 12.5, 12.6 Hz), 1.43 (s, 3H), 1.39 (s, 9H), 1.28 (s, 3H), 1.23 (s, 3H); m/z 324 [M+H]$^+$.

Compound TX63567: 52 mg, 38%: $^1$H NMR (500 MHz, $CDCl_3$) δ 8.70 (s, 1H), 8.67 (s, 1H), 3.12 (dd, 1H, J=6.1, 18.1 Hz), 2.96 (dddd, 1H, J=7.5, 9.1, 9.3, 10.9 Hz), 2.23 (dd, 1H, J=2.1, 12.8 Hz), 2.12-2.08 (m, 1H), 1.98 (dddd, 1H, J=6.6, 12.6, 13.0, 13.3 Hz), 1.49 (s, 3H), 1.30 (s, 3H), 1.25 (s, 3H); m/z 336 [M+H]$^+$.

Compound TX63582: 47 mg, 35%: $^1$H NMR (500 MHz, $CDCl_3$) δ 8.90 (s, 1H), 8.57 (s, 1H), 8.39 (d, 2H, J=8.5 Hz), 7.46 (d, 2H, J=8.5 Hz), 3.04 (dd, 1H, J=5.8, 17.4 Hz), 2.92-2.85 (m, 1H), 2.24 (dd, 1H, J=1.8, 12.5 Hz), 2.08-2.04 (m, 1H), 2.01-1.93 (m, 1H), 1.51 (s, 3H), 1.31 (s, 3H), 1.25 (s, 3H); m/z 378, 380 (100%:38%) [M+H]$^+$.

Compound TX63612: 140 mg, 67%: $^1$H NMR (500 MHz, $CDCl_3$) δ 8.88 (s, 1H), 8.66 (s, 1H), 7.79-7.81 (m, 1H), 7.51-7.54 (m, 1H), 7.39-7.42 (m, 2H), 3.08 (dd, 1H, J=20, 5 Hz), 2.90-2.97 (m, 1H), 2.28 (dd, 1H, J=15, 2.5 Hz), 1.95-2.11 (m, 2H), 1.53 (s, 3H), 1.32 (s, 3H), 1.26 (s, 3H); m/z 378/380 (100/39%) [M+H]$^+$.

Compound TX63583: 30 mg, 35%: $^1$H NMR (500 MHz, $CDCl_3$) δ 8.95 (s, 1H), 8.56 (s, 1H), 8.23 (br s, 2H), 7.44-7.30 (m, 2H), 3.04-3.01 (m, 1H), 2.91-2.84 (m, 1H), 2.47 (s, 3H), 2.25 (d, 1H, J=12.1 Hz), 2.07-1.95 (m, 2H), 1.51 (s, 3H), 1.31 (s, 3H), 1.25 (s, 3H); m/z 358 [M+H]$^+$.

Compound TX63590: 47 mg, 38%: $^1$H NMR (400 MHz, $CDCl_3$) δ 8.98 (s, 1H), 8.55 (s, 1H), 8.43 (d, 2H, J=10.0 Hz), 7.05 (d, 2H, J=5.0 Hz), 3.92 (s, 3H), 3.05 (dd, 1H, J=20.0, 5.0 Hz), 2.85-2.95 (m, 1H), 2.28 (dd, 1H, J=10.0, 5.0 Hz), 1.94-2.13 (m, 2H), 1.54 (s, 3H), 1.35 (s, 3H), 1.29 (s, 3H); m/z 374 [M+H]$^+$.

Compound TX63628: 70 mg. 23%: $^1$H NMR (500 MHz, $CDCl_3$) δ 8.93 (s, 1H), 8.65 (s, 1H), 8.22 (s, 1H), 3.09 (dd, 1H, J=6.2, 6.1 Hz), 2.93 (m, 1H), 2.86 (s, 3H), 2.28 (dd, 1H, J=1.8, 1.8 Hz), 2.03 (m, 2H), 1.55 (s, 3H), 1.35 (s, 3H), 1.29 (s, 3H); m/z 365 (100%) [M+H]$^+$.

Compound TX63586: 21 mg, 26%: $^1$H NMR (500 MHz, $CDCl_3$) δ 9.69 (s, 1H), 8.91 (dt, 1H, J=1.5, 8.0 Hz), 8.86 (s, 1H), 8.75 (dd, 1H, J=1.0, 4.8 Hz), 8.63 (s, 1H), 7.62 (dd, 1H, J=5.0, 7.9 Hz), 3.08 (dd, 1H, J=6.0, 17.9 Hz), 2.93 (dddd, 1H, J=7.3, 9.0, 9.0, 11.0 Hz), 2.25 (dd, 1H, J=2.3, 12.6 Hz), 2.11-2.06 (m, 1H), 2.02-1.94 (dddd, 1H, J=6.5, 12.5, 12.9, 13.5 Hz), 1.52 (s, 3H), 1.31 (s, 3H), 1.26 (s, 3H); m/z 345 [M+H]$^+$.

Compound TX63636: 120 mg, 51%: $^1$H NMR (500 MHz, $CDCl_3$) δ 8.94 (s, 1H), 8.83 (d, 2H, J=5.14), 8.68 (s, 1H), 8.32 (d, 2H, J=5.45), 3.12 (dd, 1H, J=6.17, 11.64, 6.04 Hz), 3.02-2.92 (m, 1H), 2.30 (dd, 1H, J=1.93, 10.6, 2.03), 2.17-1.97 (m, 2H), 1.57 (s, 3H), 1.37 (s, 3H), 1.31 (s, 3H); m/z 345 (100%) [M+H]$^+$.

Compound TX63641: 15 mg, 25%: $^1$H NMR (500 MHz, $CDCl_3$) δ 8.98 (s, 1H), 8.87 (s, 1H), 8.76 (s, 1H), 8.55 (d, 1H, J=7.7), 7.92 (t, 1H, 7.2, 7.2), 7.49 (t, 1H, J=5.25, 5.7), 3.14 (dd, 1H, J=5.99, 12.01, 5.25 Hz), 3.04-2.91 (m, 1H), 2.31 (d, 1H, J=11.88), 2.18-1.94 (m, 2H), 1.57 (s, 3H), 1.35 (s, 3H), 1.31 (s, 3H); m/z 345 (100%), [M+H]$^+$.

Compound 180: A solution of 25 (1.4 g, 5.5 mmol) in THF (10 mL) was added to a refluxing mixture of dimethyl carbonate (6 equiv.) and NaH (excess) in THF (10 mL). The reaction was stirred at reflux for 3 h. The reaction mixture was cooled to room temperature, quenched $KH_2PO_4$ (aq) and extracted with EtOAc, then washed with brine, dried with $MgSO_4$ and concentrated to give compound 180 (1.5 g, 87%) as a solid. m/z 311 [M+H]$^+$.

Compound 181: A solution of acetamide hydrochloride (5.3 g, 55 mmol) and piperidine (2.4 g, 28 mmol) in i-PrOH (20 mL) was stirred at room temperature for 15 min, then compound 184 (1.5 g, 4.8 mmol) was added. The reaction mixture was heated at reflux for 2 d, then concentrated. The crude residue was purified by column chromatography (silica gel, 15 to 65% EtOAc in Hexanes) to give 181 (0.95 g, 62%) as a solid. m/z 319 [M+H]$^+$.

Compound 182: Compound 185 (468 mg, 1.47 mmol) was taken up in $CHCl_3$ (15 mL) and the solution cooled to 0° C. Triethylamine (1.5 equiv.) and $Tf_2O$ (1.1 equiv.) were added, and the reaction was stirred at 0° C. for 2 h. The reaction mixture was washed with water, dried with MgSO$_4$, and concentrated. The crude residue was purified by column chromatography (silica gel, 5 to 15% EtOAc in Hexanes) to give 182 (548 mg, 83%) as a solid. m/z 451 [M+H]$^+$.

Compound 183: A mixture of compound 182 (548 mg, 1.22 mmol), phenylboronic acid (1.2 equiv.), Ph$_3$P (0.36 equiv.), K$_3$PO$_4$ (3 equiv.) and DME was sparged with N$_2$ for 10 min. Pd(OAc)$_2$ (0.18 equiv.) was added and sparging with N$_2$ was continued for 10 min. The reaction was heated to 85° C. for 16 h. The reaction mixture was filtered and concentrated. The crude residue was purified by column chromatography (silica gel, 5 to 35% EtOAc in Hexanes) to give compound 183 (380 mg, 83%) as an off-white sold: m/z 379 [M+H]$^+$.

Compound 184: Compound 183 (0.38 g, 1.0 mmol) was taken up in methanol, and 3 N HCl (aq) was added. The mixture was stirred overnight at room temperature. The reaction mixture was then concentrated. The reaction mixture was diluted with saturated NaHCO$_3$ and extracted with EtOAc (2×25 mL), then dried with MgSO$_4$ and concentrated to give compound 184 (0.36 g, quantitative) as a solid. m/z 335 [M+H]$^+$.

Compound 185: Compound 184 (0.36 g, 1.0 mmol) was taken up in ethyl formate, and 30% sodium methoxide (30 wt % solution in MeOH) was added. The mixture was stirred overnight at room temperature. The reaction mixture was quenched KH$_2$PO$_4$ (aq) and extracted with EtOAc, then washed with brine, dried with MgSO$_4$ and concentrated to give compound 184 (0.37 g, quantitative) as a solid. m/z 363 [M+H]$^+$.

Compound 186: A mixture of hydroxylamine hydrochloride and 185 (0.37 g, 1.0 mmol) in ethanol was stirred overnight at 50° C. After cooling to room temperature, the reaction mixture was concentrated. The residue was diluted with water and extracted with EtOAc, then washed with brine, dried with MgSO$_4$, and concentrated to give compound 186 (0.37 g, quantitative) as a solid. m/z 360 [M+H]$^+$.

Compound 187: Compound 186 (0.37 g, 1.0 mmol) was dissolved in a 2/1 THF/methanol mixture, and 30% sodium methoxide (30 wt % solution in MeOH) was added, and the reaction mixture was stirred at 50° C. for 6 h. The reaction mixture was concentrated and quenched by addition of saturated KH$_2$PO$_4$. The mixture was extracted with EtOAc and washed with brine, then dried with MgSO$_4$ and concentrated to give compound 187 (0.37 g, quantitative) as a solid. m/z 360 [M+H]$^+$.

Compound TX63529: Compound 187 (0.37 g, 1.0 mmol) was dissolved in dry DMF, and the solution was cooled to 0° C. 1,3-Dibromo-5,5-dimethylhydantoin was added, and the reaction stirred at 0° C. until the starting material was consumed (approximately 2 h), as reported by thin layer chromatography. Then, pyridine was added, and the reaction was allowed to warm to room temperature. The reaction mixture was then stirred at 50° C. overnight. The reaction mixture was concentrated. The crude residue was purified by column chromatography (silica gel, 5 to 25% EtOAc in Hexanes) to give compound TX63529 (0.24 g, 67%) as a white solid. $^1$H NMR (500 MHz, CDCl$_3$) δ 8.86 (s, 1H), 7.55 (m, 2H), 7.50 (s, 3H), 2.88 (m, 1H), 2.76 (dd, 1H, J=5.8, 17.0 Hz, 1H), 2.67 (s, 3H), 2.36 (dd, 1H, J=2.0, 12.4 Hz), 1.92 (m, 1H), 1.83 (m, 1H), 1.47 (s, 3H), 1.21 (s, 3H), 1.14 (s, 3H); m/z 358 [M+H]$^+$.

Compound 188: A mixture of compound 26 (148 mg, 0.53 mmol) and urea (2 equiv.) in dioxane was stirred at reflux for 3 d. The reaction mixture was concentrated. The residue was taken up in MeOH, and 30% sodium methoxide (30 wt % solution in MeOH) was added. The reaction mixture was stirred at reflux for 3 d, then cooled to room temperature, diluted with acetic acid (0.2 mL) and water (2 mL), and concentrated. The residue was diluted with 1 N HCl (aq) and extracted with EtOAc, then dried with MgSO$_4$ and concentrated to give 188 as a brown oil. m/z 305 [M+H]$^+$.

Compound 189: Compound 188 was taken up in MeOH, and 3 N HCl (aq) was added. The mixture was stirred overnight at room temperature. The reaction mixture was then concentrated, extracted with EtOAc (50 mL), and washed with saturated NaHCO$_3$, then dried with MgSO$_4$ and concentrated to give compound 189 (98 mg, 71%) as a solid. m/z 261 [M+H]$^+$.

Compound 190: Compound 189 (98 mg, 0.38 mmol) was taken up in ethyl formate, and 30% sodium methoxide (30 wt % solution in MeOH) was added. The mixture was stirred overnight at room temperature, then additional ethyl formate (5 mL) was added and the reaction was heated to 50° C. for 2 h. The reaction mixture was extracted with EtOAc and washed with KH$_2$PO$_4$ (aq), then dried with MgSO$_4$ and concentrated. The crude residue was purified by column chromatography (silica gel, 25-100% EtOAc/Hexanes) to give compound 190 (52.7 mg, 49%) as a solid. m/z 289 [M+H]$^+$.

Compound 191: A solution of 0.1 N hydroxylamine hydrochloride (aq.) was added to compound 190 (52.7 mg, 0.18 mmol). A 9:1 mixture of ethanol/water was added, and the reaction mixture was stirred overnight at 50° C. After cooling to room temperature, the reaction mixture was concentrated. The residue was taken up in EtOAc, then dried with MgSO$_4$ and concentrated to give compound 191 as a solid. m/z 286 [M+H]$^+$.

Compound 192: Compound 191 was dissolved in a 3:1 MeOH/THF mixture, and 30% sodium methoxide (30 wt % solution in MeOH) was added, and the reaction mixture was stirred at 55° C. for 6 h and then stirred at room temperature overnight. The reaction was quenched by addition of HOAc and concentrated. The crude residue was purified by column chromatography (silica gel, 10% MeOH/CH$_2$Cl$_2$) to give compound 192 (7.8 mg, 15%) as a solid. m/z 286 [M+H]$^+$.

Compound TX63553: Compound 192 (7.8 mg, 0.027 mmol) was dissolved in dry DMF, and the solution was cooled to 0° C. 1,3-Dibromo-5,5-dimethylhydantoin was added, and the reaction stirred at 0° C. until the starting material was consumed (approximately 30 min), as reported by thin layer chromatography. Pyridine was added, and the reaction was allowed to warm to room temperature. The reaction mixture was then stirred at 50° C. overnight. After cooling to room temperature, the reaction mixture was extracted with EtOAc and washed with brine, then dried with MgSO$_4$ and concentrated. The crude residue was purified by column chromatography (silica gel, 8% MeOH/CH$_2$Cl$_2$), then preparative thin layer chromatography (silica gel, EtOAc) to give compound TX63553 (2.4 mg, 31%) as a solid. $^1$H NMR (500 MHz, CDCl$_3$) δ 8.74 (s, 1H), 7.63 (s, 1H), 7.23 (br s, 1H), 2.84 (dd, 1H, J=6.5, 16.6 Hz), 2.71-2.64 (m, 1H), 2.14 (dd, 1H, J=2.0, 12.5 Hz), 1.94-1.85 (m, 2H), 1.47 (s, 3H), 1.26 (s, 3H), 1.19 (s, 3H); m/z 284 [M+H]$^+$.

Compound 193: A solution of compound 129 (898 mg, 3.37 mmol), acetamide hydrochloride (3.2 g, 34 mmol), and piperidine (2.0 ml, 20 mmol) in i-PrOH (15 mL) was heated at reflux for 2 d, then concentrated. The residue was taken up in CHCl$_3$, washed with 10% NH$_4$OH (aq) and brine, then dried with MgSO$_4$ and concentrated. The crude residue was purified by column chromatography (silica gel, 50% EtOAc in Hexanes) to give 193 (464 mg, 48%) as a solid. m/z 289 [M+H]$^+$.

Compound 194: Compound 193 (464 mg, 1.61 mmol) was taken up in methanol, and 3 N HCl (aq) was added. The mixture was stirred 16 h at room temperature. The reaction mixture was concentrated, diluted with 10% NH$_4$OH (aq), and extracted with CHCl$_3$, then washed with brine, dried with MgSO$_4$, and concentrated to give compound 193 (371 mg, 94%) as a solid. m/z 245 [M+H]$^+$.

Compound 195: Compound 194 (371 mg, 1.52 mmol) was taken up in benzene (20 mL), then ethyl formate (1.25 mL) and 30% sodium methoxide (30 wt % solution in MeOH) were added. The mixture was stirred 16 h at room temperature, then concentrated. The mixture was diluted with KH$_2$PO$_4$ (aq) and extracted with EtOAc, then washed with brine, dried with MgSO$_4$, and concentrated to give compound 194 (371 mg, 90%) as a solid. m/z 273 [M+H]$^+$.

Compound 196: A mixture of hydroxylamine hydrochloride and 195 (371 mg, 1.36 mmol) in ethanol was stirred for 16 h at 50° C. After cooling to room temperature, the reaction mixture was concentrated. The residue was diluted with saturated NaHCO$_3$ (aq) and extracted with EtOAc, then washed with brine, dried with MgSO$_4$, and concentrated to give compound 196 (361 mg, 98%) as a solid. m/z 270 [M+H]$^+$.

Compound 197: Compound 196 (361 mg, 1.34 mmol) was dissolved in methanol, and 30% sodium methoxide (30 wt % solution in MeOH) was added. The reaction mixture was stirred at room temperature for 48 h. The reaction mixture was concentrated and diluted with EtOAc, then washed with saturated KH$_2$PO$_4$ and brine, dried with MgSO$_4$, and concentrated to give compound 197 (287 mg, 80%) as a solid. m/z 270 [M+H]$^+$.

Compound TX63554: Compound 197 (287 mg, 0.80 mmol) was dissolved in dry DMF, and the solution was cooled to 0° C. 1,3-Dibromo-5,5-dimethylhydantoin was added, and the reaction stirred at 0° C. until the starting material was consumed (approximately 1 h), as reported by thin layer chromatography. Then, pyridine was added, and the reaction was allowed to warm to room temperature. The reaction mixture was then stirred at 50° C. for 16 h. The reaction mixture was concentrated and diluted with EtOAc, then washed with saturated KH$_2$PO$_4$ and brine, dried with MgSO$_4$, and concentrated. The crude residue was purified by column chromatography (silica gel, 50% EtOAc in Hexanes) to give compound TX63554 (145 mg, 51%) as a solid. $^1$H NMR (500 MHz, CDCl$_3$) δ 8.89 (s, 1H), 8.44 (s, 1H), 2.96 (dd, 1H, J=6.8, 17.5 Hz), 2.86 (ddd, 1H, J=7.0, 10.9, 17.1 Hz), 2.74 (s, 3H), 2.60 (qd, 1H, J=6.7, 13.1 Hz), 2.15 (m, 2H), 1.82 (m, 1H), 1.43 (s, 3H), 1.33 (d, 3H, J=6.7 Hz); m/z 268 [M+H]$^+$.

Compound 198: A solution of compound 129 (330 mg, 1.24 mmol), acetamide hydrochloride (1.94 g, 12.4 mmol), and piperidine (0.74 ml, 7.5 mmol) in i-PrOH (10 mL) was heated at 85° C. for 4 d, then concentrated. The residue was taken up in CHCl$_3$, washed with 10% NH$_4$OH (aq) and brine, then dried with MgSO$_4$ and concentrated. The crude residue was purified by column chromatography (silica gel, 20% EtOAc in Hexanes) to give 198 (260 mg, 60%) as a solid. m/z 351 [M+H]$^+$.

Compound 199: Compound 198 (260 mg, 0.74 mmol) was taken up in methanol, and 3 N HCl (aq) was added. The mixture was stirred 16 h at room temperature. The reaction mixture was concentrated, diluted with 10% NH$_4$OH (aq), and extracted with CHCl$_3$, then washed with brine, dried with MgSO$_4$, and concentrated to give compound 199 (217 mg, 95%) as a white solid. m/z 307 [M+H]$^+$.

Compound 200: Compound 199 (217 mg, 0.71 mmol) was taken up in benzene (20 mL), then ethyl formate (1.25 mL) and 30% sodium methoxide (30 wt % solution in MeOH) were added. The mixture was stirred 16 h at room temperature, then concentrated. The mixture was diluted with KH$_2$PO$_4$ (aq) and extracted with EtOAc, then washed with brine, dried with MgSO$_4$, and concentrated to give compound 200 (216 mg, 91%) as a solid. m/z 335 [M+H]$^+$.

Compound 201: A mixture of hydroxylamine hydrochloride and 200 (216 mg, 0.65 mmol) in ethanol was stirred for 4 h at 50° C. After cooling to room temperature, the reaction mixture was concentrated. The residue was diluted EtOAc, washed with saturated NaHCO$_3$ (aq) and brine, dried with MgSO$_4$, and concentrated to give compound 200 (190 mg, 89%) as a solid. m/z 332 [M+H]$^+$.

Compound 202: Compound 201 (190 mg, 0.57 mmol) was dissolved in methanol, and 30% sodium methoxide (30 wt % solution in MeOH) was added. The reaction mixture was stirred at room temperature for 16 h. The reaction mixture was concentrated and diluted with EtOAc, then washed with saturated KH$_2$PO$_4$ and brine, dried with MgSO$_4$, and concentrated to give compound 201 (228 mg, quantitative) as a solid. m/z 332 [M+H]$^+$.

Compound TX63569: Compound 202 (228 mg, 0.57 mmol) was dissolved in dry DMF, and the solution was cooled to 0° C. 1,3-Dibromo-5,5-dimethylhydantoin was added, and the reaction stirred at 0° C. until the starting material was consumed (approximately 1 h), as reported by thin layer chromatography. Then, pyridine was added, and the reaction was allowed to warm to room temperature. The reaction mixture was then stirred at 50° C. for 16 h. The reaction mixture was concentrated and diluted with EtOAc, then washed with saturated KH$_2$PO$_4$ and brine, dried with MgSO$_4$, and concentrated. The crude residue was purified by column chromatography (silica gel, 50% EtOAc in Hexanes) to give compound TX63569 (68 mg, 36%) as a solid. $^1$H NMR (500 MHz, CDCl$_3$) δ 9.01 (s, 1H), 8.62 (s, 1H), 8.49 (m, 2H), 7.55 (m, 3H), 3.04 (dd, 1H, J=6.5, 17.8 Hz), 2.94 (ddd, 1H, J=7.3, 11.3, 17.8 Hz), 2.64 (qd, 1H, J=6.7, 12.7 Hz), 2.22 (m, 2H), 1.88 (m, 1H), 1.51 (s, 3H), 1.37 (d, 3H, J=6.7 Hz); m/z 330 [M+H]$^+$.

Compound 203: Compound 25 (0.297 g, 1.18 mmol) was taken up in DCM (50 mL) and MgBr-Et$_2$O (0.776 g, 3.0 mmol) was added followed by i-Pr$_2$NEt (0.42 mL, 2.3 mmol). The reaction mixture was stirred at room temperature for about 40 minutes, during which time the reaction gradually turned orange. Benzoyl chloride (0.347 g, 2.44 mmol) in DCM (3 mL) was added dropwise and the mixture was stirred overnight at room temperature. The reaction was quenched with saturated aqueous NaHCO$_3$ solution (10 mL), the layers were separated, and the organic layer was dried over MgSO$_4$, filtered and concentrated to a reddish oil. The product was present by mass spectral analysis, MS: m/z [M+H]$^+$ 357.0. This crude material was used directly in the next step. The residue was taken up in EtOH (16 mL), and nitrogen gas was bubbled through the solution for 5 minutes. Phenylhydrazine (0.5 mL, 5.08 mmol) was added by syringe and the tightly sealed vial was heated overnight to 80° C. with stirring. After cooling to room temperature the reaction mixture was concentrated to dryness, taken up in EtOAc (80 mL), washed with saturated aqueous KH$_2$PO$_4$ (15 mL) and saturated aqueous NaHCO$_3$ solution (15 mL), dried over MgSO$_4$, filtered and concentrated to a red oil. The product was present by mass spec, MS: m/z [M+H]$^+$ 429.1. This material was used directly in the next step. The crude ketal mixture was taken up in MeOH (20 mL) and 1N HCl (4 mL) was added. The reaction was stirred overnight at room temperature, then concentrated and the residue was partitioned between EtOAc and saturated aqueous NaHCO$_3$ (20 mL). The organic layer was dried over MgSO$_4$, filtered and concentrated to a red oil/solid. The oil/solid was chromatographed 3 successive times on silica gel (230-400 mesh, 26 g) using 20% Hexanes/EtOAc to afford the more polar isomer (203, 94.4 mg) with a minor less polar impurity. MS: m/z [M+H]+ 385.1.

Compound 204: Compound 203 (91 mg, 0.237 mmol) was taken up in ethyl formate, and 30% sodium methoxide (30 wt % solution in MeOH) was added. The mixture was stirred overnight at room temperature. The reaction mixture was diluted with $KH_2PO_4$ (aq) and extracted with EtOAc, then dried with $MgSO_4$ and concentrated to give compound 204 (90 mg). m/z [M+H]+ 413.1.

Compound 205: A solution of 0.1 N hydroxylamine hydrochloride (aq) was added to compound 203 (90 mg, 0.22 mmol). A 9:1 mixture of $EtOH/H_2O$ was added, and the reaction mixture was stirred overnight at 50° C. After cooling to room temperature, the reaction mixture was concentrated. The residue was taken up in EtOAc, then dried with $MgSO_4$ and concentrated. The residue was chromatographed on silica gel (230-400 mesh, 10 g) using 20% Hexanes/EtOAc as a faintly yellow glass to give compound 205 (22.8 mg). m/z [M+H]+ 410.1.

Compound 206: Compound 205 (22.8 mg, 0.054 mmol) was dissolved in a 3:1 MeOH/THF mixture, and 30% sodium methoxide (30 wt % solution in MeOH) was added. The reaction mixture was stirred at 55° C. for 6 h and then stirred at room temperature overnight. The reaction was quenched by addition of saturated $KH_2PO_4$, and the reaction mixture was concentrated. The residue was extracted with EtOAc and washed with brine, then dried with $MgSO_4$ and concentrated. The crude residue was purified by column chromatography (silica gel, 50% EtOAc/Hexanes) to give compound 206 (22 mg) as an off-white foam. This material was used directly in the next step.

Compound TX63605: Compound 206 (22 mg, 0.038 mmol) was dissolved in dry DMF, and the solution was cooled to 0° C. 1,3-Dibromo-5,5-dimethylhydantoin was added, and the reaction stirred at 0° C. until the starting material was consumed (approximately 30 min), as reported by thin layer chromatography. Then, pyridine was added, and the reaction was allowed to warm to room temperature. The reaction mixture was then stirred at 50° C. overnight. After cooling to room temperature, the reaction mixture was extracted with EtOAc and washed with brine, then dried with $MgSO_4$ and concentrated. The crude residue was chromatographed twice on silica gel using 3:1 Hexanes/EtOAc then purified by preparative thin layer chromatography using 3:1 Hexanes/EtOAc to give TX63605 (4.5 mg) as a glass. $^1$H NMR (500 MHz, $CDCl_3$) δ 7.73-7.76 (m, 2H), 7.36-7.60 (m, 9H), 3.00-3.08 (m, 1H), 2.85-2.95 (m, 1H), 2.41-2.44 (m, 1H), 1.92-2.10 (m, 2H), 1.62 (s, 3H), 1.33 (s, 3H), 1.26 (s, 3H); m/z [M+H]+ 408.1.

Compound 208: Compound 207 (4.0 g, 19 mmol) was taken up in t-BuOH, and a solution of KOt-Bu in t-BuOH was added. The mixture was stirred at room temperature for 20 min and iodomethane was added. The reaction mixture was stirred for 45 min at room temperature, quenched with saturated $NH_4Cl$ (aq), and concentrated. The mixture was extracted with EtOAc and washed with brine, then dried with $MgSO_4$ and concentrated. The crude residue was purified by column chromatography (silica gel, 10% EtOAc in Hexanes) to give compound 208 (2.5 g, 55%) as a pale yellow liquid: m/z 177 (M-$CH_3OCH_2OH$).

Compound 209: Compound 208 (2.5 g, 10 mmol) was taken up in EtOAc under $N_2$ and 10% Pd/C added. The flask was rigorously purged with $H_2$ and stirred overnight at room temperature. The reaction mixture was filtered and concentrated to give compound 209 (2.5 g, 99%) as a solid. $^1$H NMR (500 MHz, $CDCl_3$) δ 4.70 (d, 1H, J=7 Hz), 4.61 (d, 1H, J=7 Hz), 3.65 (t, 1H, J=6 Hz), 3.38 (s, 3H), 2.58 (td, 1H, J=7, 17 Hz), 2.25 (td, 1H, J=7, 17 Hz), 1.91 (m, 3H), 1.77 (m, 2H), 1.53 (m, 1H), 1.23 (s, 6H), 1.10 (m, 1H), 1.01 (s, 3H).

Compound 210: A mixture of compound 209 (2.5 g, 10 mmol), ethylene glycol, and p-toluenesulfonic acid hydrate in toluene was heated to reflux for 3 h with azeotropic removal of water. The reaction mixture was cooled to room temperature, washed with saturated $NaHCO_3$ (aq) and brine, then dried with $MgSO_4$ and concentrated. The crude residue was taken up in $CH_2Cl_2$ and PDC (1.5 equiv.) was added. The reaction mixture was stirred at room temperature for 22 h. The reaction mixture was filtered through Celite (eluted with $CH_2Cl_2$) and concentrated. The crude residue was purified by column chromatography (silica gel, 10% EtOAc in Hexanes) to give compound 210 (1.8 g, 73%) as a colorless oil. $^1$H NMR (500 MHz, $CDCl_3$) δ 3.90 (m, 4H), 2.33 (m, 1H), 2.10 (m, 2H), 1.94 (m, 1H), 1.85 (m, 1H), 1.72 (m, 2H), 1.49 (m, 1H), 1.26 (m, 1H), 1.25 (s, 3H), 1.20 (s, 3H), 0.88 (s, 3H).

Compound 211: Compound 210 (0.81 g, 3.4 mmol) was taken up in ethyl formate (8.2 mL), cooled to 0° C., and 30% sodium methoxide (30 wt % solution in MeOH, 9.6 mL) was added. The mixture was warmed to room temperature and stirred for 1 h. The reaction mixture was diluted with t-BuOMe, cooled to 0° C., and quenched with concentrated HCl (4.25 mL). The mixture was diluted with water and extracted with EtOAc, then dried with $MgSO_4$ and concentrated to give compound 211 (0.92 g, quantitative) as a viscous oil. m/z 267 [M+H]+.

Compound 212: A mixture of 211 (0.90 g, 3.4 mmol) and methylhydrazine (0.20 g, 4.4 mmol) in ethanol (20 mL) was heated to 65° C. for 4 h. The reaction mixture was concentrated. The crude residue was purified by column chromatography (silica gel, 50 to 75% EtOAc in Hexanes) to give 212 (0.25 g, 27%) as a viscous oil. m/z 277 [M+H]+.

Compound 213: Compound 212 (0.25 g, 0.91 mmol) was taken up in THF, and 1 N HCl (aq) was added. The mixture was stirred for 24 h at room temperature. The reaction mixture was quenched with saturated $NaHCO_3$ (aq) and extracted with EtOAc, then washed with brine, dried with $MgSO_4$, and concentrated to give compound 213 (0.19 g, 90%) as a solid. m/z 233 [M+H]+.

Compound 214: A solution of compound 213 (0.27 g, 1.2 mmol) in THF was added to a −78° C. solution of LDA (2.5 equiv.) in THF. The reaction was stirred at −78° C. for 30 min, then a solution of TsCN (1.3 equiv.) in THF was added. The reaction was stirred at −78° C. for an additional 30 min, then quenched with saturated $NH_4Cl$ (aq) and warmed to room temperature. The reaction mixture was diluted with water and extracted with EtOAc, then washed with brine, dried with $MgSO_4$, and concentrated. The crude residue was purified by column chromatography (silica gel, 50% EtOAc in $CH_2Cl_2$) to give compound 214 (0.24 g, 80%) as a solid. m/z 258 [M+H]+.

Compound TX63436: Compound 214 (90 mg, 0.35 mmol) was dissolved in dry DMF, and the solution was cooled to 0° C. 1,3-Dibromo-5,5-dimethylhydantoin was added, and the reaction stirred at 0° C. for 1 h, then warmed to room temperature and stirred for 1 h. Then, pyridine was added, and the reaction was stirred at 60° C. overnight. After cooling to room temperature, the reaction mixture was extracted with ethyl acetate and washed with 1 N HCl (aq), saturated $NaHCO_3$ (aq), and brine, then dried with $MgSO_4$ and concentrated. The crude residue was recrystallized from EtOAc to give TX63436 (41 mg, 46%) as a crystalline solid. $^1$H NMR (500 MHz, $CDCl_3$) δ 7.24 (s, 1H), 7.15 (s, 1H), 3.91 (s, 3H), 2.95 (br t, 1H, J=10 Hz), 2.82 (dd, 1H, J=8, 15 Hz), 2.18 (dd, 1H, J=10, 15 Hz), 1.81 (s, 3H), 1.39 (s, 3H), 1.24 (s, 3H); m/z 256 [M+H]+.

Compound 216: Compound 215 (2.8 g, 9.5 mmol) was taken up in THF (75 mL) under $N_2$ and 10% Pd/C (0.25 g) added. The reaction was cooled to 0° C. and the flask was rigorously purged with $H_2$. The reaction was stirred at 0° C. for 8 h, then stirred overnight at room temperature. The flask was again cooled to 0° C. and an additional portion of 10% Pd/C (0.20 g) was added. The flask was rigorously purged with $H_2$ and the reaction was stirred at 0° C. for 8 h, then stirred 3 d at room temperature. The reaction mixture was filtered and concentrated. The residue was taken up in MeOH (50 mL) and 30% sodium methoxide (30 wt % solution in MeOH, 0.5 mL) was added. The reaction was stirred at room temperature overnight and then concentrated. The mixture was diluted with saturated $NH_4Cl$ (aq) and extracted with EtOAc, then dried with $MgSO_4$ and concentrated. The crude residue was purified by column chromatography (silica gel, 3 to 5% EtOAc in Hexanes) to give compound 216 (1.18 g, 42%) as an oil. m/z 297 $[M+H]^+$.

Compound 217: A mixture of compound 216 (0.95 g, 3.2 mmol), ethylene glycol, and p-toluenesulfonic acid hydrate in toluene was heated to reflux for 3 h with azeotropic removal of water. The reaction mixture was cooled to room temperature, diluted with saturated $NaHCO_3$ (aq), and extracted with EtOAc, then washed with brine, dried with $MgSO_4$, and concentrated to give compound 217 (1.09 g, quantitative) as an oil. m/z 342 $[M+H]^+$.

Compound 218: Compound 217 (1.33 g, 3.91 mmol) was taken up in THF, and TBAF hydrate (1.1 equiv.) was added. The reaction was stirred at room temperature for 3 d, with additional portions of TBAF hydrate (0.55 equiv.) being added after 8 and 24 h. The reaction mixture was diluted with saturated $NaHCO_3$ (aq) and extracted with EtOAc, then washed with brine, dried with $MgSO_4$, and concentrated. The crude residue was purified by column chromatography (silica gel, 40% EtOAc in Hexanes) to give compound 218 (0.83 g, 94%) as a solid. m/z 227 $[M+H]^+$.

Compound 219: Compound 218 (0.83 g, 3.67 mmol) was taken up in $CH_2Cl_2$ and PDC (1.5 equiv.) was added. The reaction mixture was stirred at room temperature for 12 h. The reaction mixture was filtered through Celite (eluted with $CH_2Cl_2$) and concentrated. The crude residue was purified by column chromatography (silica gel, 10% EtOAc in Hexanes) to give compound 219 (0.82 g, quantitative) as a solid. m/z 225 $[M+H]^+$.

Compound 220: Compound 219 (0.80 g, 3.6 mmol) was taken up in ethyl formate, cooled to 0° C., and 30% sodium methoxide (30 wt % solution in MeOH) was added. The mixture was warmed to room temperature and stirred for 2 h. The reaction mixture was quenched with saturated $NH_4Cl$ (aq) and extracted with EtOAc, then washed with brine, dried with $MgSO_4$, and concentrated to give compound 220 (0.90 g, quantitative) as a solid. m/z 253 $[M+H]^+$.

Compound 221: A mixture of 220 (0.70 g, 2.8 mmol) and methylhydrazine (0.32 g, 6.9 mmol) in ethanol (13 mL) was heated to 65° C. overnight. The reaction mixture was concentrated. The crude residue was purified by column chromatography (silica gel, 80 to 100% EtOAc in Hexanes) to give an off-white solid. The residue was taken up in THF, and 1 N HCl (aq) was added. The mixture was stirred for 3 d at room temperature. The reaction mixture was quenched with saturated $NaHCO_3$ (aq) and extracted with EtOAc, then washed with brine, dried with $MgSO_4$, and concentrated to give compound 221 (0.50 g, 83%) as a solid. m/z 219 $[M+H]^+$.

Compound 222: Compound 221 (225 mg, 1.03 mmol) was taken up in ethyl formate, cooled to 0° C., and 30% sodium methoxide (30 wt % solution in MeOH) was added. The mixture was warmed to room temperature and stirred for 2 h. The reaction mixture was quenched with saturated $KH_2PO_4$ (aq) and extracted with EtOAc, then washed with brine, dried with $MgSO_4$, and concentrated to give compound 222 (0.28 g, quantitative) as a solid. m/z 247 $[M+H]^+$.

Compound 223: Compound 222 (0.28 g, 1.03 mmol) was taken up in a 9/1 mixture of ethanol/water, and hydroxylamine hydrochloride was added. The reaction mixture was stirred overnight at 60° C. After cooling to room temperature, the reaction mixture was concentrated. The residue was diluted with saturated $NaHCO_3$ (aq) and extracted with EtOAc, then dried with $MgSO_4$ and concentrated to give compound 223 (0.26 g, quantitative) as a solid. m/z 244 $[M+H]^+$.

Compound 224: Compound 223 (0.25 g, 1.03 mmol) was dissolved in a 1/1 methanol/THF mixture, 30% sodium methoxide (30 wt % solution in MeOH) was added, and the reaction mixture was stirred at 50° C. for 6 h and then stirred at room temperature overnight. The reaction was quenched by addition of saturated $KH_2PO_4$ and extracted with EtOAc, then washed with brine, dried with $MgSO_4$, and concentrated to give compound 224 (0.15 g, 60%) as a solid. m/z 244 $[M+H]^+$.

Compound TX63533: Compound 224 (150 mg, 0.62 mmol) was dissolved in dry DMF, and the solution was cooled to 0° C. 1,3-Dibromo-5,5-dimethylhydantoin was added, and the reaction stirred at 0° C. for 1 h, then warmed to room temperature and stirred 1 h. Then, pyridine was added, and the reaction mixture was then stirred at 60° C. for 2 h. After cooling to room temperature, the reaction mixture was diluted with EtOAc and washed with 1 N HCl (aq), saturated $NaHCO_3$ (aq), and brine, then dried with $MgSO_4$ and concentrated. The combined aqueous fractions were extracted with $CHCl_3$, which was dried with $MgSO_4$ and concentrated. The combined crude product was purified by successive column chromatography, first (silica gel, 50% EtOAc in $CH_2Cl_2$), then (silica gel, 2% MeOH in $CH_2Cl_2$) to give TX63533 (30 mg, 20%) as a solid. $^1$H NMR (500 MHz, $CDCl_3$) δ 8.28 (s, 1H), 7.24 (s, 1H), 3.97 (s, 3H), 2.95 (ddd, 1H, J=6.2, 10.8, 13.9 Hz), 2.86 (qd, 1H, J=6.5, 13.7 Hz), 2.73 (dd, 1H, J=6.1, 13.9 Hz), 2.46 (dd, 1H, J=10.8, 13.9 Hz), 1.36 (s, 3H), 1.33 (d, 3H, J=6.6 Hz); m/z 242 $[M+H]^+$.

Compound 225: Compound 216 (0.61 g, 2.1 mmol) was taken up in MeCN, then hexamethyldisilazane (10 equiv) and NaI (5 equiv.) were added and the mixture stirred at room temperature for 5 minutes. The chlorotrimethylsilane (5 equiv.) was added and the solution was stirred at room temperature overnight. The reaction mixture was diluted with saturated $NH_4Cl$ (aq) and extracted with EtOAc, then washed with brine, dried with $MgSO_4$, and concentrated. The residue was taken up in EtOAc, filtered through a short pad of silica (eluted with EtOAc), and concentrated. The residue was taken up in MeCN, $Pd(OAc)_2$ (2 equiv.) was added, and the reaction mixture was stirred at room temperature overnight. The reaction mixture was filtered through a short pad of silica (eluted with EtOAc), washed with saturated $NaHCO_3$ (aq) and brine, dried with $MgSO_4$, and concentrated. The crude residue was purified by column chromatography (silica gel, 10% EtOAc in Hexanes) to give compound 225 (0.48 g, 79%) as a white solid. m/z 295 $[M+H]^+$.

Compound 226: A solution of compound 225 (0.47 g, 1.6 mmol) in THF was added to a 0° C. solution of KHMDS (2 equiv.) in THF. The solution was stirred at 0° C. for 30 min, then methyl iodide (4 equiv.) was added. The reaction mixture was stirred at 0° C. for 30 min, quenched with saturated $NH_4Cl$ (aq), and extracted with EtOAc, then washed with brine, dried with $MgSO_4$, and concentrated. The crude residue was purified by column chromatography (silica gel, 5 to 10% EtOAc in Hexanes) to give compound 226 (0.40 g, 81%) as a white solid. m/z 309 [M+H]$^+$.

Compound 227: Compound 226 (0.39 g, 1.3 mmol) was taken up in THF under $N_2$ and 10% Pd/C added. The flask was rigorously purged with $H_2$ and stirred at room temperature for 3 h. The reaction mixture was filtered and concentrated to give compound 227 (0.39 g, 99%) as an oil. m/z 311 [M+H]$^+$.

Compound 228: Compound 227 (0.39 g, 1.3 mmol) was taken up in $CH_2Cl_2$ (2 ml), then methylethyldioxolane (3 ml), ethylene glycol (1 drop), and p-toluenesulfonic acid (cat.) was added. The solution was stirred at room temperature for 2 d, quenched with saturated $NaHCO_3$ (aq), and extracted with EtOAc, then washed with brine, dried with $MgSO_4$, and concentrated to give compound 228 (0.44 g, 99%) as an oil. m/z 355 [M+H]$^+$.

Compound 229: Compound 228 (0.44 g, 1.3 mmol) was taken up in THF, and a solution of TBAF in THF (1.0 M, 2 ml) was added. The reaction was stirred at room temperature for 4 d, with portions of TBAF hydrate (0.65 equiv.) being added after 24 and 48 h. The reaction mixture was diluted with saturated $NaHCO_3$ (aq) and extracted with EtOAc, then washed with brine, dried with $MgSO_4$, and concentrated. The crude residue was purified by column chromatography (silica gel, 40% EtOAc in Hexanes) to give compound 229 (0.27 g, 89%) as a solid. m/z 241 [M+H]$^+$.

Compound 230: Compound 229 (0.27 g, 1.1 mmol) was taken up in $CH_2Cl_2$ and PDC (1.5 equiv.) was added. The reaction mixture was stirred at room temperature for 12 h. The reaction mixture was filtered through Celite (eluted with $CH_2Cl_2$) and concentrated. The crude residue was purified by column chromatography (silica gel, 20% EtOAc in Hexanes) to give compound 230 (0.24 g, 90%) as a solid. m/z 239 [M+H]$^+$.

Compound 231: Compound 230 (0.23 g, 0.97 mmol) was taken up in ethyl formate, cooled to 0° C., and 30% sodium methoxide (30 wt % solution in MeOH) was added. The mixture was warmed to room temperature and stirred for 2 h. The reaction mixture was quenched with saturated $NH_4Cl$ (aq) and extracted with EtOAc, then washed with brine, dried with $MgSO_4$, and concentrated to give compound 231 (0.29 g, quantitative) as a solid. m/z 267 [M+H]$^+$.

Compound 232: A mixture of 231 (0.29 g, 0.97 mmol) and methylhydrazine (90 mg, 2.0 mmol) in ethanol (0.5 mL) was heated to 65° C. overnight. The reaction mixture was concentrated. The crude residue was purified by column chromatography (silica gel, 75% EtOAc in Hexanes) to give a white solid. The residue was taken up in THF, and 1 N HCl (aq) was added. The mixture was stirred for 2 d at room temperature. The reaction mixture was quenched with saturated $NaHCO_3$ (aq) and extracted with EtOAc, then washed with brine, dried with $MgSO_4$, and concentrated to give compound 232 (0.17 g, 76%) as a solid. m/z 233 [M+H]$^+$.

Compound 233: Compound 232 (0.17 g, 0.73 mmol) was taken up in ethyl formate, cooled to 0° C., and 30% sodium methoxide (30 wt % solution in MeOH) was added. The mixture was warmed to room temperature and stirred for 2 h. The reaction mixture was quenched with saturated $KH_2PO_4$ (aq) and extracted with EtOAc, then washed with brine, dried with $MgSO_4$, and concentrated to give compound 233 (0.19 g, 96%) as a solid. m/z 261 [M+H]$^+$.

Compound 234: Compound 233 (0.19 g, 0.73 mmol) was taken up in a 8/1 mixture of ethanol/water, and hydroxylamine hydrochloride was added. The reaction mixture was stirred overnight at 60° C. After cooling to room temperature, the reaction mixture was concentrated. The residue was diluted with saturated $NaHCO_3$ (aq) and extracted with EtOAc, then washed with brine, dried with $MgSO_4$, and concentrated to give compound 234 (0.17 g, 91%) as a pale yellow solid. m/z 258 [M+H]$^+$.

Compound 235: Compound 234 (0.17 g, 0.66 mmol) was dissolved in a 1/1 methanol/THF mixture, 30% sodium methoxide (30 wt % solution in MeOH) was added, and the reaction mixture was stirred at 50° C. for 6 h and then stirred at room temperature overnight. The reaction was quenched by addition of saturated $KH_2PO_4$ and extracted with EtOAc, then washed with brine, dried with $MgSO_4$, and concentrated. The crude residue was purified by column chromatography (silica gel, 50% EtOAc in $CH_2Cl_2$) to give compound 235 (0.12 g, 71%) as a white solid. m/z 258 [M+H]$^+$.

Compound TX63559: Compound 235 (0.12 g, 0.47 mmol) was dissolved in dry DMF, and the solution was cooled to 0° C. 1,3-Dibromo-5,5-dimethylhydantoin was added, and the reaction stirred at 0° C. for 1 h, then warmed to room temperature and stirred 1 h. Then, pyridine was added, and the reaction mixture was then stirred at 60° C. for 5 h. After cooling to room temperature, the reaction mixture was concentrated. The crude residue was purified by column chromatography (silica gel, 50% EtOAc in $CH_2Cl_2$) to give TX63559 (85 mg, 71%) as a solid. $^1$H NMR (500 MHz, $CDCl_3$) δ 8.29 (s, 1H), 7.25 (s, 1H), 3.95 (s, 3H), 3.11 (dd, 1H, J=6.3, 11.3 Hz), 2.67 (dd, 1H, J=6.3, 13.8 Hz), 2.60 (dd, 1H, J=11.4, 13.6 Hz), 1.40 (s, 6H), 1.32 (s, 3H); m/z 256 [M+H]$^+$.

Compound 236: To a solution of 68 (260 mg, 0.70 mmol) in dioxane (4 mL) was added $Et_3N$ (0.5 mL) and CuI (6.7 mg, 0.035 mmol). Nitrogen was bubbled through the mixture for 15 min. TMS-acetylene (207 mg, 2.11 mmol) and $(Ph_3P)_2PdCl_2$ (14.8 mg, 0.021 mmol) were added, and the mixture was heated in a sealed vessel at 80° C. overnight. The mixture was cooled and concentrated. Flash chromatography (20% EtOAc/DCM) gave 9 mg (3%) of 236 as a white solid. MS (APCI): m/z 387.1 [M+H]$^+$.

Compound 237: Compound 236 (30 mg, 0.077 mmol) was taken up in THF (3 mL) and 1M HCl (0.5 mL) was added. The solution was stirred for 3 d, then diluted with sat. $NaHCO_3$ (20 mL) and extracted with EtOAc (2×25 mL). The combined organic extracts were dried over $MgSO_4$ and concentrated to give 26 mg (98%) of 237 as an oil. MS (APCI): m/z 343 [M+H]$^+$.

Compound 238: A solution of 237 (26 mg, 0.076 mmol) in ethyl formate (3 mL) was cooled in an ice bath. NaOMe (0.2 g, 30 wt % in MeOH) was added dropwise, and the solution was allowed to warm to RT and stirred overnight. The mixture was quenched by the addition of sat. aq. $KH_2PO_4$ (10 mL) and extracted with EtOAc (2×25 mL). The combined organic extracts were washed with brine, dried over $MgSO_4$, and concentrated to give 26 mg (>100%) of the 238 as an oil. MS (APCI): m/z 299 [M+H]$^+$.

Compound 239: Compound 238 (0.076 mmol) was taken up in EtOH (3 mL) and water (0.5 mL). Hydroxylamine hydrochloride (5.8 mg, 0.084 mmol) was added and the reaction was heated at 60° C. overnight. The solution was cooled and concentrated. The residue was diluted with sat. aq. $NaHCO_3$ (10 mL) and extracted with EtOAc (2×25 mL). The combined organic extracts were washed with brine (10 mL), dried over $MgSO_4$, and concentrated to give 27 mg (>100%) of 239 as a tan solid. MS (APCI): m/z 296 [M+H]$^+$.

Compound 240: Compound 239 (0.076 mmol) was taken up in THF (3 mL) and MeOH (1 mL) and NaOMe (0.1 g, 30 wt % in MeOH) was added. The solution was heated at 50° C. for 4 h, then allowed to cool to room temperature. Sat. aq. $KH_2PO_4$ (10 mL) was added, and the mixture was extracted with EtOAc (2×25 mL). The combined organic extracts were washed with brine, dried over $MgSO_4$, and concentrated.

Flash chromatography (1:4 EtOAc/DCM) gave 11 mg (50%) of 240 as a white solid. MS (APCI): m/z 296 [M+H]$^+$.

Compound TX63651: Compound 240 (11 mg, 0.0.037 mmol) was taken up in DMF (2 mL) and cooled in an ice bath. N,N'-Dibromodimethylhydantoin (6.4 mg, 0.022 mmol) was added and the solution was stirred 3 h at 0° C. Pyridine (0.05 mL) was added and the solution was heated at 60° C. overnight. After cooling, the solution was concentrated under vacuum to brown oil. Flash chromatography (25% EtOAc/Hexane) gave 6 mg (55%) of TX63651 as a white solid. $^1$H NMR (500 MHz, CDCl$_3$) δ 8.45 (s, 1H), 3.91 (s, 3H), 3.63 (s, 1H), 2.85-2.78 (dd, 1H, J=5.9, 11.5, 5.6 Hz), 2.61-2.52 (m, 1H), 2.18-2.13 (dd, 1H, J=1.9, 10.26, 1.9), 1.99-1.93 (m, 1H), 1.92-180 (m, 1H), 1.48 (s, 3H), 1.30 (s, 3H), 1.24 (s, 3H); MS (APCI): m/z 294 [M+H]$^+$.

Compound 241: Compound 68 (305 mg, 0.826 mmol) was dissolved in DMAc (5 mL). To this solution was added Zn(CN)$_2$ (65 mg, 0.56 mmol), dppf (95 mg, 0.17 mmol) and Na$_2$CO$_3$ (90 mg, 0.83 mmol). Nitrogen was bubbled through the mixture for 10 min. Pd(OAc)$_2$ (20 mg, 0.09 mmol) was added and nitrogen was bubbled for 10 min. The suspension was heated to 120° C. for 16 hours. The reaction mixture was quenched with 25 mL of water and extracted with ether (2×50 mL). The organic extracts were concentrated, purified on a silica gel column, eluted with 5-20% EtOAc/Hexanes to give 241 as an off-white solid (0.21 g, 80% yield). MS (APCI): [M+H]$^+$ 316.

Compound 242: A solution of 241 (145 mg, 0.46 mmol) in MeOH (5 mL) was treated with 3N HCl$_{(aq)}$ (1.5 mL), stirred at room temperature overnight. The reaction mixture was concentrated, extracted with EtOAc (2×25 mL) and sat'd NaHCO$_{3(aq)}$ (15 mL). The organic layer was dried with MgSO$_4$, concentrated to give 241 as a foam (120 mg, 96%). MS (APCI): [M+H]$^+$ 272.

Compound 243: To a solution of 242 (120 mg, 0.44 mmol) in 5 mL of HCOOEt at RT, 30% NaOMe in MeOH (0.5 g, 6 eq) was added dropwise. The reaction mixture was stirred at RT overnight, poured into water and acidified with sat. aq. KH$_2$PO$_4$. The mixture was extracted with EtOAc (2×25 mL). The combined organic extracts were washed with brine, dried with MgSO$_4$, and concentrated in vacuo to give 243 (130 mg, 100% yield). MS (APCI): [M+H]$^+$ 300.

Compound 244: To a solution of 243 (130 mg, 0.44 mmol) in 5 mL of EtOH, NH$_2$OH HCl salt (62 mg, 2 eq) was added, and the mixture was heated at 50° C. overnight. After concentration in vacuo, the residue was mixed with water and extracted with EtOAc (2×25 mL). The combined organic extracts were washed with brine, dried with MgSO$_4$, and concentrated in vacuo to give 244 (130 mg, 100%). MS (APCI): [M+H]$^+$ 297.

Compounds 245 and 246: To a solution of 244 (130 mg, 0.44 mmol) in 2 mL of THF and 1 mL of MeOH, 30% NaOMe (0.66 g, 8 eq) was added, and the solution was heated at 50° C. for 6 hours. After concentration in vacuo, the residue was mixed with KH$_2$PO$_4$ (sat., 15 mL) and extracted with EtOAc (2×25 mL). The combined organic extracts were washed with brine, dried with MgSO$_4$, and concentrated in vacuo to give a mixture of 245 and 246 (130 mg, 100% yield). MS (APCI): 297 [M+H]$^+$ and 315.

TX63613 and TX63619: To a mixture of 245 and 246 (130 mg, 0.44 mmol) in 2 mL of DMF at 0° C., DBDMH (72 mg, 0.55 eq) was added, and the solution was stirred for 2 hours. Pyridine (1 g, 30 eq) was added, and the solution was heated at 50° C. overnight. After concentration in vacuo, the residue was purified on a silica gel column, eluted with 10-100% EtOAc/Hexanes to collect the first less polar dicarbonitrile TX63613 as an off-white solid (50 mg, 39% yield). $^1$H NMR (500 MHz, CDCl$_3$) δ 8.36 (s, 1H), 3.98 (s, 3H), 2.90 (dd, 1H, J=15, 5 Hz), 2.64 (ddd, 1H, J=15, 10, 5 Hz), 2.12 (d, 1H, J=10 Hz), 1.98 (dd, 1H, J=15, 5 Hz), 1.86 (ddd, 1H, J=25, 15, 5 Hz), 1.45 (s, 3H), 1.28 (s, 3H), 1.22 (s, 3H); MS (APCI): [M+H]$^+$ 295; followed by the second more polar carboxamide TX63619 as an off-white solid (10 mg, 8% yield). $^1$H NMR (500 MHz, CDCl$_3$) δ 8.46 (s, 1H), 7.45 (s, 1H), 7.26 (s, 1H), 3.93 (s, 3H), 2.85 (dd, 1H, J=15, 5 Hz), 2.62-2.66 (m, 1H), 2.15 (d, 1H, J=10 Hz), 1.89-1.92 (m, 1H), 1.71-1.84 (m, 1H), 1.41 (s, 3H), 1.25 (s, 3H), 1.10 (s, 3H); MS (APCI): [M+H]$^+$ 313.

Compound 247: Compound 241 (110 mg, 0.34 mmol) was added to 10 mL MeOH saturated with HCl and the mixture was heated at 60° C. for 16 hours in a sealed bottle. The reaction mixture was concentrated, and quenched with K$_2$CO$_3$ (conc., 25 mL), and extracted with EtOAc (2×25 mL). The extracts were dried with MgSO$_4$ and concentrated to give 247 as a white solid (105 mg, 100% yield). MS (APCI): m/z [M+H]$^+$ 305.

Compound 248: To a solution of 247 (105 mg, 0.36 mmol) in 5 mL of HCOOEt at RT, 30% NaOMe in MeOH (0.2 g, 3 eq) was added dropwise. The reaction mixture was stirred at RT overnight, poured into water and acidified with sat. aq. KH$_2$PO$_4$. The mixture was extracted with EtOAc (2×25 mL). The combined organic extracts were washed with brine, dried with MgSO$_4$, and concentrated in vacuo to give 247 (110 mg, 88% yield). MS (APCI): m/z [M+H]$^+$ 347.

Compound 249: To a solution of 248 (110 mg, 0.32 mmol) in 5 mL of EtOH, NH$_2$OH HCl salt (50 mg, 2 eq) was added, and the solution was heated at 50° C. overnight. After concentration in vacuo, the residue was mixed with water and extracted with EtOAc (2×25 mL). The combined organic extracts were washed with brine, dried with MgSO$_4$, and concentrated in vacuo to give 249 (110 mg, 100%). MS (APCI): m/z [M+H]$^+$ 344.

Compound 250 and 251: To a solution of 248 (110 mg, 0.32 mmol) in 2 mL of THF and 1 mL of MeOH, NaOEt (40 mg of Na metal in 1 mL of EtOH, 5 eq) was added, and the solution was heated at 50° C. for 6 hours. After concentration in vacuo, the residue was mixed with KH$_2$PO$_4$ (sat., 15 mL) and extracted with EtOAc (2×25 mL). The combined organic extracts were washed with brine, dried with MgSO$_4$, and concentrated in vacuo to give a mixture of 250 and 251 (110 mg, 100% yield). MS (APCI): m/z [M+H]$^+$ 316 and 344.

Compound TX63630 and TX63631: To a mixture of 250 and 251 (110 mg, 0.32 mmol) in 2 mL of DMF at 0° C., DBDMH (51 mg, 0.55 eq) was added, and the solution was stirred for 2 hours. Pyridine (1 g, 40 eq) was added, and the solution was heated at 50° C. overnight. After concentration in vacuo, the residue was purified on a silica gel column, eluted with 10-100% EtOAc/Hexanes to give the less polar ethyl ester TX63630 as an off-white solid (40 mg, 37% yield). $^1$H NMR (500 MHz, CDCl$_3$) δ 8.48 (s, 1H), 4.40-4.34 (q, 2H, J=7.1, 7.2, 7.1 Hz), 4.15 (s, 3H), 3.10-3.00 (dd, 1H, J=5.3, 12.32, 5.3 Hz), 2.75-2.63 (m, 1H), 2.18-2.12 (dd, 1H, J=1.7, 10.49, 1.8), 2.01-1.93 (dd, 1H, J=6.91, 6.44, 1.93), 1.92-1.81 (m, 1H), 1.48 (s, 3H), 1.44-1.37 (t, 3H, J=7.13, 7.08), 1.31 (s, 3H), 1.25 (s, 3H); MS (APCI): m/z [M+H]$^+$ 342. And the more polar acid TX63631 was isolated as an off-white solid (13 mg, 13% yield). $^1$H NMR (500 MHz, DMSO) δ 13.40 (s, 1H), 8.47 (s, 1H), 4.05 (s, 3H), 2.92 (dd, 1H, J=5.6, 11.8, 5.6 Hz), 2.63-2.54 (m, 1H), 2.19-2.13 (m, 1H), 1.95-1.88 (m, 1H), 1.88-1.75 (m, 1H), 1.42 (s, 3H), 1.22 (s, 3H), 1.13 (s, 3H); MS (APCI): m/z [M+H]$^+$ 314.

Compound 252: To a solution of 241 (160 mg, 0.51 mmol) in toluene (5 mL) was added trimethylsilylazide (0.13 mL, 1.01 mmol) followed by dibutyltin oxide (13 mg, 0.051 mmol). The mixture was heated overnight in a 110° C. oil bath. The solution was cooled and transferred to a thick-walled vessel. Additional portions of trimethylsilylazide (0.13 mL) and dibutyltin oxide (13 mg) were added and the solution was heated overnight in a 130° C. oil bath. After cooling, MeOH (5 mL) was added and the solution was concentrated and dried under vacuum to give 0.26 g of crude 252 as an orange solid, MS (APCI): m/z 359.1 [M+H]$^+$.

Compound 253a: Compound 252 was taken up in DMF (5 mL), and potassium carbonate (0.35 g, 2.55 mmol) was added followed by methyl iodide (0.16 mL, 2.55 mmol). The mixture was stirred overnight, water (20 mL) was added and the mixture was extracted with EtOAc (2×50 mL). The combined organic extracts were washed with brine, dried over MgSO$_4$, concentrated, and dried under vacuum. Flash chromatography (50% EtOAc/Hexane) gave 112 mg (59%) of 253a as a white solid. MS (APCI): m/z 373.1 [M+H]$^+$.

Compound 254a: Compound 253a (108 mg, 0.29 mmol) was taken up in THF (4 mL) and 1M HCl (1 mL) was added. The solution was stirred for 3 d, diluted with sat. NaHCO$_3$ (20 mL) and extracted with EtOAc (2×50 mL). The combined organic extracts were washed with brine, dried over MgSO$_4$ and concentrated to give 95 mg (100%) of 254a as a white solid. MS (APCI): m/z 329.0 [M+H]$^+$.

Compound 255a: A solution of 254a (95 mg, 0.29 mmol) in ethyl formate (4 mL) was cooled in an ice bath. NaOMe (0.5 g, 30 wt % in MeOH) was added dropwise, and the solution was allowed to warm to RT and stirred overnight. The mixture was quenched by the addition of sat. aq. KH$_2$PO$_4$ (20 mL) and extracted with EtOAc (2×50 mL). The combined organic extracts were washed with brine, dried over MgSO$_4$, and concentrated to give 100 mg (97%) of the 254a as a white solid. MS (APCI): m/z 357.0 [M+H]$^+$.

Compound 256a: Compound 255a (100 mg, 0.28 mmol) was taken up in EtOH (2 mL), THF (2 mL), and water (0.5 mL). Hydroxylamine hydrochloride (21 mg, 0.31 mmol) was added and the reaction was stirred at room temperature for 30 min, then heated at 50° C. overnight. The solution was cooled and concentrated. The residue was diluted with sat. aq. NaHCO$_3$ (20 mL) and extracted with EtOAc (2×50 mL). The combined organic extracts were washed with brine (20 mL), dried over MgSO$_4$, concentrated, and dried under vacuum to give 97 mg (98%) of 256a as a white solid. MS (APCI): m/z 354.0 [M+H]$^+$.

Compound 257a: Compound 256a (97 mg, 0.27 mmol) was taken up in THF (3 mL) and MeOH (1 mL) and NaOMe (0.5 g, 30 wt % in MeOH) was added. The solution was heated at 50° C. for 4 h, then allowed to cool to room temperature and stirred overnight. Sat. aq. KH$_2$PO$_4$ (20 mL) was added, and the mixture was extracted with EtOAc (2×50 mL). The combined organic extracts were washed with brine, dried over MgSO$_4$, and concentrated. Flash chromatography (1:3 EtOAc/DCM) gave 86 mg (89%) of 257a as a white solid. MS (APCI): m/z 354.0 [M+H]$^+$.

Compound TX63665: Compound 256a (86 mg, 0.24 mmol) was taken up in DMF (2 mL) and cooled in an ice bath. N,N'-Dibromodimethylhydantoin (42 mg, 0.15 mmol) was added and the solution was stirred 2 h at 0° C. Pyridine (0.3 mL) was added and the solution was heated at 60° C. for 5 h. After cooling, the solution was concentrated and dried under vacuum to a light brown solid. Flash chromatography (15% EtOAc/DCM) gave 64 mg (74%) of TX63665 as a white solid. $^1$H NMR (500 MHz, CDCl$_3$) δ 8.53 (s, 1H), 4.46 (s, 3H), 4.24 (s, 3H), 3.15 (dd, 1H, J=6.1, 17.1 Hz), 2.78 (m, 1H), 2.24 (m, 1H), 1.87-2.05 (m, 2H), 1.55 (s, 3H), 1.32 (s, 3H), 1.27 (s, 3H); MS (APCI): m/z 352.0 [M+H]$^+$.

Compound 253b: Compound 252 (0.41 mmol) was taken up in DMF (3 mL), and K$_2$CO$_3$ (0.28 g, 2.06 mmol) was added followed by benzyl bromide (0.1 mL, 0.82 mmol). The mixture was stirred overnight, water (20 mL) was added and the mixture was extracted with EtOAc (2×50 mL). The combined organic extracts were washed with brine, dried over MgSO$_4$, concentrated, and dried under vacuum. Flash chromatography (30-50% EtOAc/Hexane) gave 47 mg (26%) of 253b as white foam. MS (APCI): m/z 449.3 [M+H]$^+$.

Compound 254b: Compound 253b (44 mg, 0.098 mmol) was taken up in THF (3 mL) and 1M HCl (0.5 mL) was added. The solution was stirred for 2 d, diluted with sat. NaHCO$_3$ (20 mL) and extracted with EtOAc (2×25 mL). The combined organic extracts were washed with brine, dried over MgSO$_4$ and concentrated to give 40 mg (100%) of 254b as a white solid. MS (APCI): m/z 405.3 [M+H]$^+$.

Compound 255b: A solution of 254b (95 mg, 0.23 mmol) in THF (3 mL) and ethyl formate (1 mL) was cooled in an ice bath. NaOMe (0.4 g, 30 wt % in MeOH) was added dropwise, and the solution was allowed to warm to RT and stirred overnight. The mixture was cooled in an ice bath and quenched by the addition of sat. aq. KH$_2$PO$_4$ (20 mL) and extracted with EtOAc (2×50 mL). The combined organic extracts were washed with brine, dried over MgSO$_4$, and concentrated to give 105 mg (>100%) of 255b as a white foam. MS (APCI): m/z 433.1 [M+H]$^+$.

Compound 256b: Compound 255b (0.23 mmol) was taken up in EtOH (1 mL), THF (3 mL), and water (0.5 mL). Hydroxylamine hydrochloride (19 mg, 0.28 mmol) was added and the reaction was heated at 50° C. for 4 h, then cooled and concentrated. The residue was diluted with sat. aq. NaHCO$_3$ (20 mL) and extracted with EtOAc (2×50 mL). The combined organic extracts were washed with brine (20 mL), dried over MgSO$_4$, concentrated, and dried under vacuum to give 100 mg (100%) of 256b as a white solid. MS (APCI): m/z 430.2 [M+H]$^+$.

Compound 257b: Compound 256b (100 mg, 0.23 mmol) was suspended in 3:1 THF/MeOH (4 mL) and NaOMe (0.4 g, 30 wt % in MeOH) was added. The solution was heated at 50° C. for 4 h, then cooled and concentrated. Sat. aq. KH$_2$PO$_4$ (20 mL) was added, and the mixture was extracted with EtOAc (2×50 mL). The combined organic extracts were washed with brine, dried over MgSO$_4$, concentrated, and dried under vacuum to give 70 mg (70%) of 257b as white foam. MS (APCI): m/z 430.2 [M+H]$^+$.

Compound TX63729: Compound 257b (70 mg, 0.16 mmol) was taken up in DMF (2 mL) and cooled in an ice bath. N,N'-Dibromodimethylhydantoin (28 mg, 0.098 mmol) was added and the solution was stirred 90 min at 0° C. Pyridine (0.3 mL) was added and the solution was heated at 60° C. for 3 h. After cooling, the solution was concentrated and dried under vacuum to a light brown solid. Flash chromatography (5% EtOAc/DCM) gave 55 mg (79%) of TX63729 as a light yellow solid. $^1$H NMR (400 MHz, CDCl$_3$) δ 8.47 (s, 1H), 7.38 (m, 5H), 5.81 (s, 2H), 4.18 (s, 3H), 3.08 (ddd, 1H, J=1.6, 6.0, 17.1 Hz), 2.73 (ddd, 1H, J=7.1, 11.7, 18.7, Hz), 2.18 (dd, 1H, J=2.1, 12.1 Hz), 1.81-1.99 (m, 2H), 1.48 (s, 3H), 1.27 (s, 3H), 1.22 (s, 3H); MS (APCI): m/z 428.2 [M+H]$^+$.

Compound 253c: Crude 252 (0.41 mmol) was taken up in DMF (3 mL), and K$_2$CO$_3$ (0.28 g, 2.05 mmol) was added followed by isopropyl iodide (0.2 mL, 2.05 mmol). The mixture was stirred overnight, water (20 mL) was added and the mixture was extracted with EtOAc (2×50 mL). The combined organic extracts were washed with brine, dried over MgSO$_4$, concentrated, and dried under vacuum to give 0.18 g of impure 253c as a brown oil. MS (APCI): m/z 401.2 [M+H]$^+$.

Compound 254c: Crude 253c (0.18 g) was taken up in THF (3 mL) and 1M HCl (0.5 mL) was added. The solution was stirred for 5 d, diluted with sat. NaHCO$_3$ (20 mL) and extracted with EtOAc (2×25 mL). The combined organic extracts were washed with brine, dried over MgSO$_4$ and concentrated to give 0.15 g of a crude oil. Flash chromatography (30% EtOAc/Hexane) gave 111 mg (76%) of 254c as a colorless oil. MS (APCI): m/z 357.2 [M+H]$^+$.

Compound 255c: A solution 254c (0.11 g, 0.31 mmol) in THF (3 mL) and ethyl formate (1 mL) was cooled in an ice bath. NaOMe (0.5 g, 30 wt % in MeOH) was added dropwise, and the solution was allowed to warm to RT and stirred overnight. The mixture was cooled in an ice bath and quenched by the addition of sat. aq. KH$_2$PO$_4$ (20 mL) and extracted with EtOAc (2×50 mL). The combined organic extracts were washed with brine, dried over MgSO$_4$, concentrated, and dried under vacuum to give 113 mg (95%) of 255c as a white foam. MS (APCI): m/z 385.1 [M+H]$^+$.

Compound 256c: Compound 255c (113 mg, 0.29 mmol) was taken up in EtOH (1 mL), THF (2 mL), and water (0.5 mL). Hydroxylamine hydrochloride (25 mg, 0.35 mmol) was added and the reaction was heated at 50° C. for 3 h, then cooled and concentrated. The residue was diluted with sat. aq. NaHCO$_3$ (20 mL) and extracted with EtOAc (2×50 mL). The combined organic extracts were washed with brine (20 mL), dried over MgSO$_4$, concentrated, and dried under vacuum to give 111 mg (99%) of 256c as a white solid. MS (APCI): 382.2 [M+H]$^+$.

Compound 257c: Compound 256c (111 mg, 0.29 mmol) was suspended in THF:MeOH (4 mL) and NaOMe (0.5 g, 30 wt % in MeOH) was added. The solution was heated at 50° C. for 4 h, then cooled and concentrated. Sat. aq. KH$_2$PO$_4$ (20 mL) was added, and the mixture was extracted with EtOAc (2×50 mL). The combined organic extracts were washed with brine, dried over MgSO$_4$, concentrated, and dried under vacuum to give 112 mg (100%) of 257c as a light yellow foam. MS (APCI): m/z 382.2 [M+H]$^+$.

Compound TX63734: Compound 257c (111 mg, 0.29 mmol) was taken up in DMF (3 mL) and cooled in an ice bath. N,N'-Dibromodimethylhydantoin (50 mg, 0.17 mmol) was added and the solution was stirred 90 min. at 0° C. Pyridine (0.5 mL) was added and the solution was heated at 60° C. for 4 h. After cooling, the solution was concentrated and dried under vacuum to give 0.18 g of a light brown solid. Flash chromatography (5% EtOAc/DCM) gave 75 mg (68%) of TX63734 as a light yellow solid. $^1$H NMR (400 MHz, CDCl$_3$) δ 8.50 (s, 1H), 5.16 (septet, 1H, J=6.7 Hz), 4.22 (s, 3H), 3.13 (ddd, 1H, J=1.3, 6.0, 17.1 Hz), 2.77 (ddd, 1H, J=7.1, 11.7, 17.1 Hz), 2.22 (dd, 1H, J=2.2, 12.1 Hz), 1.94 (m, 2H), 1.71 (d, 6H, J=6.7 Hz), 1.52 (s, 3H), 1.30 (s, 3H), 1.24 (s, 3H); MS (APCI): m/z 380.2 [M+H]$^+$.

Compound 258: Compound 241 (115 mg, 0.36 mmol) was suspended in EtOH (2 mL) and hydroxylamine (70 mg, 50% solution in water) was added. Heated at 50° C. overnight, then cooled and concentrated to a white solid to afford 258. MS (APCI): m/z 349.1 [M+H]$^+$.

Compound 259: Compound 258 (0.36 mmol) was suspended in dioxane (1 mL) and a solution of dimethylacetamide dimethylacetal (146 mg, 1.09 mmol) in dioxane (1 mL) was added. The mixture was heated at 60° C. for 2 h. The mixture was cooled and concentrated to a yellow solid. Flash chromatography (20% EtOAc/DCM) gave 130 mg (96%) of 259 as a white solid. MS (APCI) 373.1 [M+H]$^+$.

Compound 260: Compound 259 (125 mg, 0.34 mmol) was taken up in THF (4 mL) and 1M HCl (1 mL) was added. The solution was stirred for 2 d, diluted with sat. NaHCO$_3$ (20 mL) and extracted with EtOAc (2×50 mL). The combined organic extracts were washed with brine, dried over MgSO$_4$ and concentrated to give 110 mg (100%) of 260 as a white solid. MS (APCI): m/z 329.1 [M+H]$^+$.

Compound 261: A solution of 260 (110 mg, 0.33 mmol) in THF (2 mL) and ethyl formate (2 mL) was cooled in an ice bath. NaOMe (0.6 g, 30 wt % in MeOH) was added dropwise, and the solution was allowed to warm to RT and stirred overnight. The mixture was cooled in an ice bath and quenched by the addition of sat. aq. KH$_2$PO$_4$ (20 mL) and extracted with EtOAc (2×50 mL). The combined organic extracts were washed with brine, dried over MgSO$_4$, and concentrated to give 120 mg (100%) of 261 as a white solid. MS (APCI): m/z 357.1 [M+H]$^+$.

Compound 262: Compound 261 (119 mg, 0.33 mmol) was suspended in EtOH (2 mL), THF (2 mL), and water (0.5 mL). Hydroxylamine hydrochloride (28 mg, 0.40 mmol) was added and the reaction was stirred at room temperature for 30 min, and then heated at 50° C. overnight. The solution was cooled and concentrated. The residue was diluted with sat. aq. NaHCO$_3$ (20 mL) and extracted with EtOAc (2×50 mL). The combined organic extracts were washed with brine (20 mL), dried over MgSO$_4$, concentrated. Flash chromatography (15% EtOAc/DCM) gave 90 mg (77%) of 262 as a white solid. MS (APCI): m/z 354.1 [M+H]$^+$.

Compound 263: Compound 262 (90 mg, 0.25 mmol) was suspended in THF (3 mL) and MeOH (1 mL) and NaOMe (0.5 g, 30 wt % in MeOH) was added. The solution was heated at 50° C. for 3 h, then allowed to cool to room temperature and concentrated. Sat. aq. KH$_2$PO$_4$ (20 mL) was added, and the mixture was extracted with EtOAc (2×50 mL). The combined organic extracts were washed with brine, dried over MgSO$_4$, concentrated, and dried under vacuum to give 88 mg (98%) of 263 as a light yellow solid. MS (APCI): m/z 354.1 [M+H]$^+$.

Compound TX63723: Compound 263 (88 mg, 0.25 mmol) was taken up in DMF (2 mL) and cooled in an ice bath. N,N'-Dibromodimethylhydantoin (43 mg, 0.15 mmol) was added and the solution was stirred 90 min. at 0° C. Pyridine (0.4 mL) was added and the solution was heated at 60° C. for 4 h. After cooling, the solution was concentrated and dried under vacuum to a light brown solid. Flash chromatography (5% EtOAc/DCM) gave 68 mg (78%) of TX63723 as a light yellow solid. $^1$H NMR (400 MHz, CDCl$_3$) δ 8.41 (s, 1H), 4.10 (s, 3H), 3.02 (ddd, 1H, J=1.3, 6.0, 17.3 Hz), 2.64 (m, 1H), 2.59 (s, 3H), 2.12 (dd, 1H, J=2.1, 12.1 Hz), 1.75-1.94 (m, 2H), 1.43 (s, 3H), 1.22 (s, 3H), 1.16 (s, 3H); MS (APCI) m/z 352.1 [M+H]$^+$.

Compound 264: Crude 252 (0.41 mmol) was taken up in pyridine (3 mL), and acetic anhydride (0.42 mL, 4.44 mmol) was added. The solution was heated at 110° C. for 3 h, then cooled and concentrated. The residue was diluted with sat. NaHCO$_3$ (20 mL) and extracted with EtOAc (2×25 mL). The combined organic extracts were washed with brine, dried over MgSO$_4$, concentrated, and dried under vacuum to give 0.35 g of a dark brown oil. Flash chromatography (1:1 EtOAc/Hexane) gave 225 mg of impure 264 as a white foam. MS (APCI): m/z 373.1 [M+H]$^+$.

Compound 265: Impure 264 (0.22 g, 0.59 mmol) was taken up in THF (3 mL) and 1M HCl (0.5 mL) was added. The solution was stirred for 2 d, diluted with sat. NaHCO$_3$ (20 mL) and extracted with EtOAc (2×50 mL). The combined organic extracts were washed with brine, dried over MgSO$_4$ and concentrated to give 0.20 g of a crude foam. Flash chromatography (1:1 EtOAc/Hexane) gave 66 mg (34%) of 264 as a white solid. MS (APCI): m/z 329.1 [M+H]$^+$.

Compound 266: A solution of 265 (66 mg, 0.20 mmol) in THF (2 mL) and ethyl formate (2 mL) was cooled in an ice bath. NaOMe (0.36 g, 30 wt % in MeOH) was added dropwise, and the solution was allowed to warm to RT and stirred overnight. The mixture was cooled in an ice bath, quenched by the addition of sat. aq. $KH_2PO_4$ (20 mL), and extracted with EtOAc (2×50 mL). The combined organic extracts were washed with brine, dried over $MgSO_4$, concentrated, and dried under vacuum to give 71 mg (99%) of 266 as a white solid. MS (APCI): m/z 357.2 $[M+H]^+$.

Compound 267: Compound 266 (71 mg, 0.20 mmol) was taken up in EtOH (1 mL), THF (2 mL), and water (0.5 mL). Hydroxylamine hydrochloride (17 mg, 0.24 mmol) was added and the reaction was heated overnight at 50° C., then cooled and concentrated. The residue was diluted with sat. aq. $NaHCO_3$ (20 mL) and extracted with EtOAc (2×50 mL). The combined organic extracts were washed with brine (20 mL), dried over $MgSO_4$, concentrated, and dried under vacuum. Flash chromatography (1:1 EtOAc/DCM) gave 20 mg (28%) of 267 as a white solid. MS (APCI): m/z 354.2 $[M+H]^+$.

Compound 268: Compound 267 (20 mg, 0.057 mmol) was taken up in 1:1 THF/MeOH (2 mL) and NaOMe (0.1 g, 30 wt % in MeOH) was added. The solution was heated at 50° C. for 6 h, then cooled and concentrated. Sat. aq. $KH_2PO_4$ (10 mL) was added, and the mixture was extracted with EtOAc (2×25 mL). The combined organic extracts were washed with brine, dried over $MgSO_4$, concentrated, and dried under vacuum to give 20 mg (100%) of 268 as a beige foam. MS (APCI): m/z 354.1 $[M+H]^+$.

Compound TX63735: Compound 268 (20 mg, 0.057 mmol) was taken up in DMF (2 mL) and cooled in an ice bath. N,N'-Dibromodimethylhydantoin (9.7 mg, 0.034 mmol) was added and the solution was stirred 90 min. at 0° C. Pyridine (0.1 mL) was added and the solution was heated at 60° C. for 4 h. After cooling, the solution was concentrated and dried under vacuum. Flash chromatography (10% EtOAc/DCM) gave 12 mg (60%) of TX63735 as a white solid. $^1$H NMR (400 MHz, $CDCl_3$) δ 8.46 (s, 1H), 4.23 (s, 3H), 3.06 (ddd, 1H, J=1.0, 6.0, 11.2 Hz), 2.75 (ddd, 1H, J=7.2, 11.7, 17.1 Hz), 2.62 (s, 3H), 2.19 (dd, 1H, J=2.0, 12.1 Hz), 1.95 (m, 2H), 1.50 (s, 3H), 1.30 (s, 3H), 1.24 (s, 3H); MS (APCI): m/z 352.1 $[M+H]^+$.

Compound 269: To a solution of 241 (0.47 g, 1.49 mmol) in EtOH (6 mL) was added water (3 mL) followed by KOH (0.42 g, 7.45 mmol). The solution was stirred at room temperature for 3 d. Sat. $KH_2PO_4$ solution was added, and the mixture was extracted with EtOAc (2×50 mL). The combined organic extracts were washed with brine, dried over $MgSO_4$, concentrated, and dried under vacuum to give 0.50 g (100%) of 269 as a white foam. MS (APCI): m/z 334.2 $[M+H]^+$.

Compound 270: DMA-dimethylacetal (2 mL) was added to 269 (135 mg, 0.40 mmol) and the mixture was heated at 80° C. for 2 h. The solution was cooled and concentrated to give 270 as a white solid. MS (APCI): m/z 403.3 $[M+H]^+$.

Compound 271: Hydroxylamine hydrochloride (36 mg, 0.52 mmol) was suspended in dioxane (1 mL) and $Et_3N$ (0.073 mL, 0.52 mmol) was added. The mixture was sonicated for several minutes. A solution of 270 (0.40 mmol) in dioxane (2 mL) was added followed by acetic acid (50 mg, 0.83 mmol). The mixture was heated at 80° C. for 1 h, and then additional hydroxylamine hydrochloride (5 mg) was added followed by acetic acid (100 mg). The mixture was heated at 80° C. for 3 h, then allowed to cool to room temperature and stirred overnight. The mixture was diluted with sat. $NaHCO_3$ (20 mL) and extracted with EtOAc (2×50 mL). The combined organic extracts were washed with brine, dried over $MgSO_4$, concentrated, and dried under vacuum to give 150 mg of a sticky white foam. Flash chromatography (25% EtOAc/Hexane) gave 86 mg (58%) of 271 as a white foam. MS (APCI): m/z 373.2 $[M+H]^+$.

Compound 272: Compound 271 (83 mg, 0.22 mmol) was taken up in THF (2 mL) and 1M HCl (0.5 mL) was added. The solution was stirred 2 d, then diluted with sat. $NaHCO_3$ (10 mL) and extracted with EtOAc (2×25 mL). The combined organic extracts were washed with brine, dried over $MgSO_4$, concentrated, and dried under vacuum to give 75 mg (100%) of 272 as a white foam. MS (APCI): m/z 329.1 $[M+H]^+$.

Compound 273: Compound 272 (73 mg, 0.22 mmol) was taken up in THF (2 mL) and ethyl formate (1 mL) and cooled in an ice bath. NaOMe (0.4 g, 30 wt % in MeOH) was added dropwise, and the solution was allowed to warm to RT and stirred overnight. The mixture cooled in an ice bath, quenched by the addition of sat. aq. $KH_2PO_4$ (10 mL), and extracted with EtOAc (2×25 mL). The combined organic extracts were washed with brine, dried over $MgSO_4$, concentrated, and dried under vacuum to give 85 mg (>100%) of 273 as a light yellow solid. MS (APCI): m/z 357.1 $[M+H]^+$.

Compound 274: Compound 273 (0.22 mmol) was taken up in THF (2 mL), EtOH (1 mL) and water (0.5 mL). Hydroxylamine hydrochloride (23 mg, 0.33 mmol) was added and the reaction was heated at 50° C. for 3 h. The solution was cooled and concentrated. The residue was diluted with sat. aq. $NaHCO_3$ (10 mL) and extracted with EtOAc (2×25 mL). The combined organic extracts were washed with brine (10 mL), dried over $MgSO_4$, concentrated, and dried under vacuum to give 80 mg (>100%) of 274 as a light yellow foam. MS (APCI): m/z 354.1 $[M+H]^+$.

Compound 275: Compound 274 (Step 5) (0.22 mmol) was taken up in 2:1 THF/MeOH (3 mL) and NaOMe (0.4 g, 30 wt % in MeOH) was added. The solution was heated at 50° C. for 3 h, then allowed to cool to room temperature and concentrated. Sat. aq. $KH_2PO_4$ (10 mL) was added, and the mixture was extracted with EtOAc (2×25 mL). The combined organic extracts were washed with brine, dried over $MgSO_4$, and concentrated to give 78 mg of a light yellow foam. Flash chromatography (25% EtOAc/Hexane) gave 60 mg (77%) of 275 as a white foam. MS (APCI): m/z 354.2 $[M+H]^+$.

Compound TX63760: Compound 275 (59 mg, 0.17 mmol) was taken up in DMF (2 mL) and cooled in an ice bath. N,N'-Dibromodimethylhydantoin (29 mg, 0.10 mmol) was added and the solution was stirred 90 min at 0° C. Pyridine (0.3 mL) was added and the solution was heated at 60° C. for 4 h. After cooling, the solution was concentrated and dried under vacuum to a light brown solid. Flash chromatography (5% EtOAc/DCM) gave 49 mg (84%) of TX63760 as a white solid. $^1$H NMR (400 MHz, $CDCl_3$) δ 8.46 (s, 1H), 4.24 (s, 3H), 3.16 (dd, 1H, J=5.8, 17.7 Hz), 2.80 (ddd, 1H, J=7.1, 11.6, 17.5 Hz), 2.48 (s, 3H), 2.19 (dd, 1H, J=1.7, 12.1 Hz), 1.95 (m, 2H), 1.50 (s, 3H), 1.30 (s, 3H), 1.24 (s, 3H); MS (APCI): m/z 352.2 $[M+H]^+$.

Compound 276: Compound 269 (29 mg, 0.087 mmol) was slurried in DMF-DMA (2 mL) and heated at 80° C. overnight. The solution was cooled and concentrated to give 276 as a white solid. MS (APCI): m/z 389.1 $[M+H]^+$.

Compound 277: Compound 276 (0.087 mmol) was taken up in dioxane (1 mL) and HOAc (4 drops) was added followed by methyl hydrazine (1 drop). The solution was heated at 80° C. for 2 h, then cooled and concentrated to give the title compound 277 as an off-white solid. MS (APCI): m/z 372.1 $[M+H]^+$.

Compound 278: Compound 277 (0.087 mmol) was taken up in THF (3 mL) and 1M HCl (0.5 mL) was added. The solution was stirred overnight, diluted with sat. $NaHCO_3$ (10 mL) and extracted with EtOAc (2×25 mL). The combined organic extracts were washed with brine, dried over $MgSO_4$ and concentrated to give 28 mg (100%) of 278 as a light yellow oil. MS (APCI): m/z 328.1 $[M+H]^+$.

Compound 279: Compound 278 (28 mg, 0.087 mmol) in ethyl formate (2 mL) was cooled in an ice bath. NaOMe (0.15 g, 30 wt % in MeOH) was added dropwise, and the solution was allowed to warm to RT and stirred overnight. The mixture was quenched by the addition of sat. aq. $KH_2PO_4$ (10 mL) and extracted with EtOAc (2×25 mL). The combined organic extracts were washed with brine, dried over $MgSO_4$, and concentrated to give 30 mg (97%) of 279 as an oil. MS (APCI): m/z 356.0 $[M+H]^+$.

Compound 280: Compound 279 (30 mg, 0.084 mmol) was taken up in EtOH (3 mL) and water (0.5 mL). Hydroxylamine hydrochloride (9 mg, 0.13 mmol) was added and the reaction was heated at 60° C. overnight. The solution was cooled and concentrated. The residue was diluted with sat. aq. $NaHCO_3$ (10 mL) and extracted with EtOAc (2×25 mL). The combined organic extracts were washed with brine (10 mL), dried over $MgSO_4$, concentrated, and dried under vacuum to give 28 mg (94%) of 280 as a tan foam. MS (APCI): m/z 353.0 $[M+H]^+$.

Compound 281: Compound 280 (28 mg, 0.079 mmol) was taken up in 4:1 THF/MeOH (2 mL) and NaOMe (0.15 g, 30 wt % in MeOH) was added. The solution was heated at 50° C. for 4 h, then allowed to cool to room temperature and stirred overnight. Sat. aq. $KH_2PO_4$ (10 mL) was added, and the mixture was extracted with EtOAc (2×25 mL). The combined organic extracts were washed with brine, dried over $MgSO_4$, and concentrated. Flash chromatography (2-5% MeOH/$CHCl_3$) gave 22 mg (79%) of 280 as a clear glass. MS (APCI): m/z 353.0 $[M+H]^+$.

Compound TX63714: Compound 281 (21 mg, 0.060 mmol) was taken up in DMF (2 mL) and cooled in an ice bath. N,N'-Dibromodimethylhydantoin (10.2 mg, 0.15 mmol) was added and the solution was stirred 2 h at 0° C. Pyridine (0.1 mL) was added and the solution was heated at 60° C. for 6 h. After cooling, the solution was concentrated and dried under vacuum to a light brown solid. Flash chromatography (100% EtOAc) gave 15 mg (71%) of TX63714 as sticky white foam. $^1$H NMR (400 MHz, $CDCl_3$) δ 8.45 (s, 1H), 8.04 (s, 1H), 3.83 (s, 3H), 3.80 (s, 3H), 2.60 (m, 1H), 2.48 (ddd, 1H, J=6.6, 11.4, 16.1 Hz), 2.21 (dd, 1H, J=2.0, 12.0 Hz), 1.78-1.97 (m, 2H), 1.49 (s, 3H), 1.27 (s, 3H), 1.21 (s, 3H); MS (APCI): m/z 351.1 $[M+H]^+$.

Compound TX63587: Compound TX63445 (0.052 g, 0.14 mmol), $K_3PO_4$ (0.086 g, 0.40 mmol), 4-phenoxyphenylboronic acid (0.047 g, 0.22 mmol) and dimethoxyethane (6 mL) were mixed and the mixture was sparged with $N_2$ for 3-5 minutes. $Pd(PPh_3)_4$ (0.014 g, 0.012 mmol) was added and the reaction was sparged for another 3-5 minutes. The vial was tightly sealed and heated at 80° C. overnight with stirring. The reaction was cooled and concentrated to dryness. The residue was chromatographed on silica gel (230-400 mesh, 8 g) using 3:1 Hexanes/EtOAc to give TX63587 (25.3 mg) as a white solid. $^1$H NMR (500 MHz, $CDCl_3$) δ 8.58 (s, 1H), 7.38 (dd, 2H, J=7.6, 8.1 Hz), 7.25 (m, 2H), 7.17 (t, 1H, J=7.5 Hz), 7.07 (d, 4H, J=7.5 Hz), 3.83 (s, 3H), 2.65 (dd, 1H, J=6.0, 16.1 Hz), 2.52 (m, 1H), 2.21 (d, 1H, J=11.9 Hz), 1.92 (dd, 1H, J=6.6, 13.4 Hz), 1.83 (dddd, 1H, J=6.0, 12.5, 12.8, 12.8 Hz), 1.55 (s, 3H), 1.27 (s, 3H), 1.22 (s, 3H); m/z $[M+H]^+$ 438.0.

Compound TX63588: Compound TX63445 (0.054 g, 0.146 mmol), $K_3PO_4$ (0.090 g, 0.42 mmol), 1-methyl-1H-pyrazole-4-boronic acid pinacol ester (0.048 g, 0.23 mmol) and dimethoxyethane (6 mL) were mixed and the mixture was sparged with $N_2$ for 3-5 minutes. $Pd(PPh_3)_4$ (0.016 g, 0.014 mmol) was added and the reaction was sparged for another for 3-5 minutes. The vial was tightly sealed and heated at 80° C. overnight with stifling. The reaction was allowed to cool and was concentrated to dryness. The residue was chromatographed on silica gel (230-400 mesh, 10 g) using 50-100% EtOAc/Hexane to give TX63588 (11.6 mg) as a white solid. $^1$H NMR (500 MHz, $CDCl_3$) δ 8.47 (s, 1H), 7.57 (s, 1H), 7.45 (s, 1H), 3.97 (s, 3H), 3.83 (s, 3H), 2.68 (ddd, 1H, J=1.1, 6.0, 15.8 Hz), 2.52 (dddd, 1H, J=6.9, 7.9, 8.0, 11.6 Hz), 2.17 (dd, 1H, J=1.9, 12.0 Hz), 1.92 (dd, 1H, J=6.6, 13.5 Hz), 1.86 (m, 1H), 1.49 (s, 3H), 1.26 (s, 3H), 1.21 (s, 3H); m/z $[M+H]^+$ 350.0.

Compound TX63600: Compound TX63445 (0.049 g, 0.141 mmol), $K_3PO_4$ (0.091 g, 0.43 mmol), naphthalene-2-boronic acid (0.042 g, 0.28 mmol) and dimethoxyethane (7 mL) were mixed and the mixture was sparged with $N_2$ for 3-5 minutes. $Pd(PPh_3)_4$ (0.014 g, 0.012 mmol) was added and the reaction was sparged for another for 3-5 minutes. Then the vial was tightly sealed and heated at 80° C. overnight with stifling. The reaction was cooled and concentrated to dryness. The residue was chromatographed on silica gel (230-400 mesh, 10 g) using 3:1 Hexanes/EtOAc to give TX63600 (23.2 mg) as an off-white solid. $^1$H NMR (500 MHz, $CDCl_3$) δ 8.54 (s, 1H), 7.94 (d, 1H, J=5 Hz), 7.86-7.90 (m, 2H), 7.78 (br s, 1H), 7.54-7.56 (m, 1H), 7.42 (br d, 1H, J=10 Hz), 7.25 (s, 1H), 3.83 (s, 3H), 2.70 (dd, 1H, J=12.5, 5 Hz), 2.56-2.63 (m, 1H), 2.25 (dd, 1H, J=12.5, 2.5 Hz), 1.85-1.95 (m, 2H), 1.55 (s, 3H), 1.29 (s, 3H), 1.23 (s, 3H); m/z $[M+H]^+$ 396.1.

Compound TX63603: Compound TX63445 (0.051 g, 0.146 mmol), $K_3PO_4$ (0.093 g, 0.44 mmol), naphthalene-1-boronic acid (0.053 g, 0.35 mmol) and dimethoxyethane (7 mL) were mixed and the mixture was sparged with $N_2$ for 3-5 minutes. $Pd(PPh_3)_4$ (0.018 g, 0.016 mmol) was added and the reaction was sparged for another for 3-5 minutes. Then the vial was tightly sealed and heated at 80° C. overnight with stifling. The reaction was cooled and concentrated to dryness. The residue was chromatographed on silica gel (230-400 mesh, 10 g) using 3:1 Hexanes/EtOAc to give TX63603 (17 mg) as a mixture of interconverting atropisomers as a yellow glass. $^1$H NMR (500 MHz, $CDCl_3$) δ 8.58 (s, 1H), 7.93-7.96 (m, 2H), 7.35-7.56 (m, 5H), 3.59 (s, 1.5H), 3.58 (s, 1.5H), 2.25-2.48 (m, 3H), 1.85-1.88 (m, 2H), 1.61 (s, 1.5H), 1.58 (s, 1.5H), 1.28 (s, 1.5H), 1.27 (s, 1.5H), 1.23 (s, 3H); m/z $[M+H]^+$ 396.1.

Compound TX63625: Compound TX63445 (0.053 g, 0.152 mmol), $K_3PO_4$ (0.088 g, 0.42 mmol), 3,5-dimethylisoxazole-4-boronic acid (0.042 g, 0.30 mmol) and dimethoxyethane (6 mL) were mixed and nitrogen gas was bubbled through the stirred mixture for 3-5 minutes. $Pd(PPh_3)_4$ (0.014 g, 0.013 mmol) was added and nitrogen gas was bubbled through the stirred mixture for 3-5 minutes. The vial was tightly sealed and heated at 80° C. overnight with stirring. The reaction was cooled and concentrated to dryness. The residue was chromatographed on silica gel (230-400 mesh, 8 g) using 3:1 Hexanes/EtOAc followed by preparative thin layer chromatography using 3:1 Hexanes/EtOAc to give TX63625 (6.6 mg) as a solid. $^1$H NMR (500 MHz, $CDCl_3$) δ 8.51 (s, 1H), 3.63 (s, 3H), 2.49 (m, 1H), 2.43 (m, 1H), 2.36, 2.31 (s, s [1.5, 1.5] 3H), 2.25 (m, 1H), 2.20, 2.15 (s, s [1.5, 1.5] 3H), 2.1 (m, 2H), 1.58 (s, 3H), 1.31 (s, 3H), 1.26 (s, 3H); m/z: $[M+H]^+$ 365.0.

Compound TX63637: Compound TX63445 (0.049 g, 0.141 mmol), $K_2CO_3$ (0.061 g, 0.44 mmol), methylboronic acid (0.037 g, 0.64 mmol) and dioxane (8 mL) were mixed and the mixture was sparged with $N_2$ for 1-2 minutes. $Pd(dppf)Cl_2$ (0.0167 g, 0.023 mmol) was added and the reaction was sparged for another for 1-2 minutes. The vial was tightly sealed and heated at 90° C. overnight with stirring. The reaction was cooled and concentrated to dryness. The residue was chromatographed on silica gel (230-400 mesh, 9 g) using 50% Hexanes/EtOAc and rechromatographed on silica gel (230-400 mesh, 4 g) using dichloromethane/methyl-t-butyl ether/MeOH, 200/20/1 to give TX63637 (20 mg) as a white solid. $^1$H NMR (500 MHz, CDCl$_3$) δ 8.48 (s, 1H), 3.76 (s, 3H), 2.65 (dd, 1H, J=5.9, 15.6 Hz), 2.44 (m, 1H), 2.16 (s, 3H), 2.15 (m, 1H), 1.82-1.97 (m, 2H), 1.49 (s, 3H), 1.29 (s, 3H), 1.24 (s, 3H); m/z: [M+H]$^+$ 384.0.

Compound 282: A solution of 241 (175 mg, 0.55 mmol) in THF (5 mL) was cooled in an ice bath. PhMgBr (1.1 mL, 1.0 M in THF, 1.1 mmol) was added, and the solution was stirred at 0° C. for 1 h, then allowed to warm to room temperature and stirred overnight. Additional PhMgBr (1.1 mL) was added, and after 6 h another portion of PhMgBr (3.3 mL) was added. After stifling overnight, an additional portion of PhMgBr (3.3 mL) was added. After stirring overnight, the solution was cooled in an ice bath and quenched by the slow addition of 1M HCl (5 mL). The mixture was allowed to warm to room temperature and stirred 1 h. 6M HCl (2 mL) was added and the mixture was stirred overnight. Additional THF (5 mL) was added and the mixture was stirred for 3 d. The mixture was concentrated, neutralized with sat. NaHCO$_3$, and extracted with EtOAc (2×50 mL). The combined organic extracts were washed with brine, dried over MgSO$_4$, concentrated, and dried under vacuum to give 0.40 g of an oil. Flash chromatography (30% EtOAc/Hexane) gave 0.21 g of a white foam which was a mixture of 282 and 283 MS (APCI): m/z 395, 351 [M+H]$^+$.

Compound 283: The mixture of 282 and 283 (0.21 g) was taken up in THF (4 mL) and 1M HCl (1 mL) was added. The solution was stirred overnight, and then heated at 40° C. for 6 h. After cooling, the solution was neutralized with sat. NaHCO$_3$ (25 mL) and extracted with EtOAc (2×50 mL). The combined organic extracts were washed with brine, dried over MgSO$_4$, concentrated, and dried under vacuum to give 0.18 g (93%) of 283 as white foam. MS (APCI): m/z 351.0 [M+H]$^+$.

Compound 284: A solution of 283 (0.18 g, 0.51 mmol) in ethyl formate (3 mL) was cooled in an ice bath. NaOMe (0.9 g, 30 wt % in MeOH) was added dropwise, and the solution was allowed to warm to RT and stirred overnight. The mixture was cooled in an ice bath, quenched by the addition of sat. KH$_2$PO$_4$ (25 mL) and extracted with EtOAc (2×50 mL). The combined organic extracts were washed with brine, dried over MgSO$_4$, concentrated, and dried under vacuum to give 184 mg (97%) of 284 as a white solid. MS (APCI): m/z 379.0 [M+H]$^+$.

Compound 285: Compound 284 (184 mg, 0.49 mmol) was taken up in EtOH (2 mL), THF (5 mL), and water (0.5 mL). Hydroxylamine hydrochloride (37 mg, 0.53 mmol) was added and the reaction was stirred at room temperature for 30 min, and then heated at 50° C. for 4 h. Additional hydroxylamine hydrochloride (10 mg) was added, and heating was continued overnight. The solution was cooled and concentrated. The residue was diluted with sat. NaHCO$_3$ (20 mL) and extracted with EtOAc (2×50 mL). The combined organic extracts were washed with brine (20 mL), dried over MgSO$_4$, concentrated, and dried under vacuum to give 180 mg (98%) of 285 as white foam. MS (APCI): m/z 376.0 [M+H]$^+$.

Compound 286: Compound 285 (180 mg, 0.48 mmol) was taken up in 5:1 THF/MeOH (6 mL) and NaOMe (0.9 g, 30 wt % in MeOH) was added. The solution was heated at 50° C. for 4 h, then allowed to cool to room temperature and stirred overnight. The solution was concentrated, sat. aq. KH$_2$PO$_4$ (25 mL) was added, and the mixture was extracted with EtOAc (2×50 mL). The combined organic extracts were washed with brine, dried over MgSO$_4$, and concentrated to give 0.18 g of a light yellow foam. Flash chromatography (40% EtOAc/Hexane) gave 150 mg (83%) of 286 as a white solid. MS (APCI): m/z 376.0 [M+H]$^+$.

Compound TX63667: Compound 286 (150 mg, 0.40 mmol) was taken up in DMF (3 mL) and cooled in an ice bath. N,N'-Dibromodimethylhydantoin (69 mg, 0.24 mmol) was added and the solution was stirred 2 h at 0° C. Pyridine (0.5 mL) was added and the solution was heated at 55° C. for 5 h. After cooling, the solution was concentrated and dried under vacuum to a light brown solid. Flash chromatography (25% EtOAc/Hexane) gave 135 mg (90%) of TX63667 as white foam. $^1$H NMR (500 MHz, CDCl$_3$) δ 8.52 (s, 1H), 7.76 (m, 2H), 7.66 (m, 1H), 7.54 (m, 2H), 4.06 (s, 3H), 2.24-2.38 (m, 2H), 2.18 (m, 1H), 1.69-1.83 (m, 2H), 1.51 (s, 3H), 1.27 (s, 3H), 1.22 (s, 3H); MS (APCI): m/z 374.1 [M+H]$^+$.

Compound 287: N-Chlorosuccinimide (0.124 g. 0.93 mmol) was added to a stirred mixture of 27 (0.235 g, 0.81 mmol) in dichloromethane (10 mL) and the mixture was stirred for 4 days at room temperature. The reaction mixture was concentrated to dryness, and the residue taken up in EtOAc (80 mL), the solution was washed with aqueous NaHCO$_3$ solution (20 mL), the organic layer was dried MgSO$_4$, filtered and concentrated to afford 287 (347.8 mg) as a glass/solid. This material was used directly in the next step. m/z [M+H]$^+$ 325.0, 326.9.

Compound 288: Compound 287 (347.8 mg, 1.07 mmol) was taken up in MeOH, and 1 N HCl (aq) was added. The mixture was stirred overnight at room temperature. The reaction mixture was then concentrated. The residue was extracted with EtOAc (50 mL) and washed with saturated NaHCO$_3$ (aq), then dried with MgSO$_4$ and concentrated to give compound 288 (198 mg, 76%), m/z: [M+H]$^+$ 280.9, 282.8.

Compound 289: Compound 288 (192 mg, 0.68 mmol) was taken up in MeOH, and 1 N HCl (aq) was added. The mixture was stirred overnight at room temperature. The reaction mixture was then concentrated. The residue was extracted with EtOAc (50 mL) and washed with saturated NaHCO$_3$ (aq), then dried with MgSO$_4$ and concentrated to give compound 289 (189.8 mg, 91%). m/z [M+H]$^+$ 308.9.

Compound 290: Compound 289 (189.8 mg, 0.61 mmol) was taken up in ethyl formate, and sodium methoxide (30 wt % solution in MeOH) was added. The mixture was stirred overnight at room temperature. The reaction mixture was extracted with EtOAc and washed with KH$_2$PO$_4$ (aq), then dried with MgSO$_4$ and concentrated. The residue was chromatographed on silica gel (230-400 mesh, 12 g) using 3:1 Hexanes/EtOAc to give compound 290 (92.8 mg, 50%) as a white solid. m/z: [M+H]$^+$ 305.9.

Compound 291: Compound 290 (89 mg, 0.29 mmol) was dissolved in a 3/1 MeOH/THF mixture, and sodium methoxide (30 wt % solution in MeOH) was added, and the reaction mixture was stirred at 55° C. for 5 h and then stirred at room temperature overnight. The reaction was quenched by addition of saturated KH$_2$PO$_4$ (aq), and the reaction mixture was concentrated. The residue was extracted with EtOAc and washed with brine, then dried with MgSO$_4$ and concentrated. The crude residue was purified by column chromatography (silica gel, 25% EtOAc/Hexanes) to give compound 291 (88.6 mg) as a glass/foam. This material was used directly in the next step.

Compound TX63604: Compound 291 (88.6 mg, 0.29 mmol) was dissolved in dry DMF, and the solution was cooled to 0° C. Dibromodimethylhydantoin was added, and the reaction stirred at 0° C. until the starting material was consumed (approximately 30 min), as reported by thin layer chromatography. Then, pyridine was added, and the reaction was allowed to warm to room temperature. The reaction mixture was then stirred at 50° C. overnight. After cooling to room temperature, the reaction mixture was extracted with EtOAc and washed with brine, then dried with MgSO$_4$ and concentrated. The crude residue was purified by column chromatography (silica gel, 25% EtOAc/Hexanes) to give compound TX63604 (52.5 mg, 60%) as a light yellow solid. $^1$H NMR (500 MHz, CDCl$_3$) δ 8.39 (s, 1H), 3.77 (s, 3H), 2.65 (dd, 1H, J=17.5, 7.5 Hz), 2.39-2.46 (m, 1H), 2.11 (app d, 1H, J=10 Hz), 1.94 (dd, 1H, J=12.5, 7.5 Hz), 1.82 (ddd, 1H, J=25, 12.5, 5 Hz), 1.45 (s, 3H), 1.24 (s, 3H), 1.21 (s, 3H); m/z [M+H]$^+$ 303.9.

Compound 292: A solution of 106 (173 mg, 0.57 mmol) in MeOH was treated with 3N HCl solution, stirred at room temperature overnight. The reaction mixture was concentrated, extracted with EtOAc (2×25 mL) and sat. NaHCO$_3$ solution (15 mL). The organic layer was dried with MgSO$_4$, concentrated to give 292 which was used directly in the next step.

Compound 293: Compound 292 (assume 0.57 mmol from previous step) was taken up in dioxane (10 mL) and water (6 mL) and cooled to 0° C. Triethylamine (0.7 mL, 5 mmol), DMAP (0.013 g, 0.11 mmol), and Boc$_2$O (0.167 g, 0.78 mmol) were added and the reaction mixture was allowed to slowly warm to room temperature. After 3 hours more Boc$_2$O (0.48 g, 2.2 mmol) was added and the mixture was stirred at room temperature overnight. The reaction mixture was concentrated to dryness and taken up in MeCN. More catalytic DMAP and Boc$_2$O (0.21 g, 1.0 mmol) were added and the mixture was warmed to 50° C. The mixture was concentrated to dryness. EtOAc was added and the insoluble material was removed by filtration. The filtrate was concentrated and resuspended in THF (1 mL). More Boc$_2$O (0.71 g, 3.3 mmol) was added and the mixture was heated to 55° C. overnight, then heated at 65° C. overnight. The reaction mixture was concentrated to dryness and chromatographed on silica gel (230-400 mesh, 12 g) using 50% EtOAc/Hexane to give the product as a mixture of 293 and bis-Boc products, 0.0471 g. MS: m/z [M+H]$^+$ 362.1, 462.2.

Compound 294: To a solution of 293 (47.1 mg, ~0.11 mmol) in HCOOEt at RT, 30% NaOMe in MeOH (6 eq) was added dropwise. The reaction mixture was stirred at RT overnight, poured into water and acidified with sat. aq. KH$_2$PO$_4$. The mixture was extracted with EtOAc (2×25 mL). The combined organic extracts were washed with brine, dried with MgSO$_4$, and concentrated in vacuo to give 294 (49.8 mg). MS (APCI): [M+H]$^+$ 390.1.

Compound 295: To a solution of 294 (0.0498 g, 0.128 mmol) in EtOH, NH$_2$OH HCl salt (neutralized with TEA) and pyridinium para-toluenesulfonate solution in MeOH were added, and the mixture was heated at 50° C. for 4 hours. After concentration in vacuo, the residue was mixed with water and extracted with EtOAc (2×25 mL). The combined organic extracts were washed with brine, dried with MgSO$_4$, and concentrated in vacuo to give 295 (91 mg) as a foam (this total reflects combination with an earlier experiment). m/z [M+H]$^+$ 387.1.

Compound 296: To a solution of 295 (0.091 g, 0.23 mmol) in THF and MeOH, 30% NaOMe (8 eq) was added, and the solution was heated at 50° C. for 6 hours. After concentration in vacuo, the residue was mixed with KH$_2$PO$_4$ (sat., 15 mL) and extracted with EtOAc (2×25 mL). The combined organic extracts were washed with brine, dried with MgSO$_4$, and concentrated in vacuo to give 296 (71 mg, 78%) as an off-white foam. m/z [M+H]$^+$ 387.1

Compound TX63594: Compound 296 (0.071 g, 0.18 mmol) was dissolved in dry DMF, and the solution was cooled to 0° C. Dibromodimethylhydantoin was added, and the reaction stirred at 0° C. for 2 hours. Then, pyridine was added, and the reaction was allowed to warm to room temperature. The reaction mixture was then stirred at 50° C. overnight. After cooling to room temperature, the reaction mixture was extracted with EtOAc and washed with brine, then dried with MgSO$_4$ and concentrated. The crude residue was purified by column chromatography (silica gel, 50% EtOAc/Hexanes) to give compound TX63594 (8.7 mg, 12.5%). $^1$H NMR (500 MHz, d6-DMSO) δ 8.42 (s, 1H), 5.76 (s, 1H), 3.58 (s, 3H), 3.52-3.55 (m, 1H), 2.31-2.36 (m, 1H), 2.11-2.13 (m, 1H), 1.75-1.86 (m, 2H), 1.45 (s, 9H), 1.39 (s, 3H), 1.21 (s, 3H), 1.12 (s, 3H); m/z [M+H]$^+$ 385.1.

Compound TX63642: Compound TX63467 (0.021 g, 0.082 mmol) was taken up in a mixture of saturated aqueous NaHCO$_3$ (0.5 mL) and THF (2.0 mL) and was cooled in an ice bath. A solution of benzoyl chloride in THF was added and the reaction mixture was stirred at 0° C. for a few minutes, after which more benzoyl chloride solution was added and the reaction mixture was stirred for a few more minutes. The reaction mixture was partitioned between EtOAc (40 mL) and brine (2 mL), the layers were separated, the organic layer was dried over MgSO$_4$, filtered and concentrated to an oil. The oil was chromatographed on silica gel (230-400 mesh, 8 g) using 10:1 Hexanes/EtOAc. Compound TX63642 (14 mg) was obtained as a clear glass. $^1$H NMR (500 MHz, CDCl$_3$) δ 8.44 (s, 1H), 8.12-8.15 (m, 3H), 7.68 (m, 1H), 7.57 (m, 2H), 2.96 (dd, 1H, J=5.9, 16.7 Hz), 2.69 (m, 1H), 2.24 (dd, 1H, J=2.0, 12.0 Hz), 1.89-2.03 (m, 2H), 1.55 (s, 3H), 1.34 (s, 3H), 1.27 (s, 3H); m/z [M+H]$^+$ 360.0, 255.9 (M-PhCO).

Compound TX63611: TX63579 (17 mg, 0.051 mmol) was taken up in a mixture of saturated NaHCO$_3$ (aq, 0.5 mL) and THF (1.5 mL), and the mixture was cooled to 0° C. Acetyl chloride (1 drop, excess) was added, and the reaction mixture was stirred 40 min at 0° C. Then more acetyl chloride (2 drops, excess) was added, and the reaction mixture was stirred an additional 20 minutes. The reaction mixture was extracted with ethyl acetate (40 mL) and washed with NaCl (aq, 10 mL), then dried with MgSO$_4$ and concentrated. The crude residue was purified by column chromatography (silica gel, 25% EtOAc in Hexanes) to give TX63611 (2.9 mg, 15%) as a clear glass. $^1$H NMR (500 MHz, CDCl$_3$) δ 8.50 (s, 1H), 7.40-7.46 (m, 3H), 7.26-7.30 (m, 2H), 2.82 (s, 3H), 2.64-2.73 (m, 1H), 2.46-2.55 (m, 1H), 2.30-2.34 (m, 1H), 1.82-1.95 (m, 2H), 1.56 (s, 3H), 1.25 (s, 3H), 1.23 (s, 3H); m/z 298 [M+H]$^+$.

Compound 297: A solution of 25 (1.4 g, 5.5 mmol) in THF (10 mL) was added to a refluxing mixture of dimethyl carbonate (6 equiv.) and NaH (excess) in THF (10 mL). The reaction was stirred at reflux for 3 h. The reaction mixture was cooled to room temperature, quenched with KH$_2$PO$_4$ (aq) and extracted with EtOAc. The organic layer was washed with brine, dried with MgSO$_4$ and concentrated to give compound 297 (1.5 g, 87%) as a solid. m/z 311 [M+H]$^+$.

Compound 298: A mixture of 297 (1 g, 3.17 mmol), methyl hydrazine (300 mg, 6.5 mmol), and EtOH (15 mL) was heated at 60° C. for 16 h. The EtOH was removed, and the crude product was treated with 20 mL of diethyl ether. The precipitate was collected by filtration to give 298 as a white solid (450 mg, 46% yield). MS: m/z [M+H]$^+$ 307.

Compound 299: A solution of 298 (190 mg, 1.2 mmol) in MeOH (5 mL) was treated with 3N HCl$_{(aq)}$ (2 mL), and stirred at RT overnight. The reaction mixture was concentrated, extracted by EtOAc (2×25 mL) and washed with sat'd NaHCO$_{3(aq)}$ (20 mL). The organic layer was dried with MgSO$_4$, and concentrated to give 299 (165 mg, 100% yield). MS: m/z [M+H]$^+$ 263.

Compound 300: To a solution of 299 (165 mg, 0.62 mmol) in 5 mL of HCOOEt at RT was added 30% NaOMe in MeOH (1.3 g, 10 eq) dropwise. The reaction mixture was stirred at RT overnight, poured into water and acidified with KH$_2$PO$_4$.

The mixture was extracted with EtOAc (2×25 mL). The combined organic extracts were washed with brine, dried with MgSO$_4$, and concentrated in vacuo to give 300 (180 mg, 100% yield). MS: m/z [M+H]$^+$ 291.

Compound 301: To a solution of 300 (180 mg, 0.62 mmol) in 10 mL of EtOH was added NH$_2$OH—HCl (95 mg, 2 eq), and the mixture was heated at 50° C. overnight. After concentration in vacuo, the residue was mixed with water and extracted with EtOAc (2×25 mL). The combined organic extracts were washed with brine, dried with MgSO$_4$, and concentrated in vacuo to give 301 as a solid (178 mg, 100% yield). MS: m/z [M+H]$^+$ 288.

Compound 302: To a solution of 301 (178 mg, 0.62 mmol) in 2:1 THF/MeOH (3 mL) was added 30% NaOMe (1.2 g, 10 eq) dropwise, and the solution was heated at 50° C. for 9 hours. After concentration in vacuo, the residue was mixed with sat. KH$_2$PO$_4$ (25 mL) and extracted with EtOAc (2×25 mL). The combined organic extracts were washed with water and brine, dried with MgSO$_4$, concentrated to give 302 as an off-white solid product (175 mg, 99% yield). MS: m/z [M+H]$^+$ 288.

Compound TX63676: To a solution of 302 (175 mg, 0.61 mmol) in 2 mL of DMF at 0° C. was added dibromodimethylhydantoin (100 mg, 0.55 eq), and the solution was stirred for 2 hours. Pyridine (1 g) was added and the solution was heated at 50° C. overnight. After concentration in vacuo, the residue was purified on a silica gel column, eluted with 20-55% EtOAc/Hexanes to collect a mixture of starting cyanoketone and cyanoenone product (35 mg). This mixture (30 mg) was mixed with DDQ (30 mg, 0.13 mmol) in 1 mL of benzene, and heated to reflux for 16 h. The resulting mixture was dissolved in 10 mL of EtOAc and washed with sat. NaHCO$_3$ (2×15 mL). The organic layer was concentrated and the residue was purified on a silica gel column, eluted with 20-55% EtOAc/Hexanes to give TX63676 as an off-white solid (15 mg, 9% yield). $^1$H NMR (500 MHz, DMSO) δ 8.46 (s, 1H), 6.47 (s, 1H), 3.19 (s, 3H), 2.09 (m, 1H), 1.95 (m, 2H), 1.66 (m, 1H), 1.52 (s, 3H), 1.39 (m, 1H), 1.18 (s, 3H), 1.19 (s, 3H); MS: m/z [M+H]$^+$ 286.

Compound 303a-b: To a mixture 298 (670 mg, 2.18 mmol) and K$_2$CO$_3$ (910 mg, 6.55 mmol) in 15 mL of DMF at RT was added MeI (625 mg, 4.4 mmol). The mixture was stirred for 16 hours. The reaction mixture was quenched with 100 mL of water and extracted with EtOAc (2×50 mL). After concentration in vacuo, the residue was purified on a silica gel column, eluted with 10-35% EtOAc/Hexanes to give the mixture of 303a-b (450 mg). MS: m/z [M+H]$^+$ 321.

Compound 304a-b: A solution of 303a-b (450 mg, 1.4 mmol) in MeOH (10 mL) was treated with 3N HCl solution (4 mL), and stirred at RT overnight. The reaction mixture was concentrated, extracted by EtOAc (2×25 mL) and washed with sat'd NaHCO$_3$ solution (20 mL). The organic layer was dried with MgSO$_4$, and concentrated to give a mixture of 304a-b as an oil (390 mg, 100% yield). MS: m/z [M+H]$^+$ 277.

Compound 305a-b: To a solution of 304a-b (390 mg, 1.4 mmol) in 6 mL of HCOOEt at RT, was added 30% NaOMe in MeOH (1.5 g, 6 eq) dropwise. The reaction mixture was stirred at RT overnight, then poured into water and acidified with KH$_2$PO$_4$. The mixture was extracted with EtOAc (2×25 mL). The combined organic extracts were washed with brine, dried with MgSO$_4$, and concentrated in vacuo to give a mixture of 305a-b (425 mg, 100% yield). MS: m/z [M+H]$^+$ 305.

Compound 306a-b: To a solution of 305a-b (425 mg, 1.4 mmol) in 10 mL of EtOH, was added NH$_2$OH HCl salt (195 mg, 2 eq), and the mixture was heated at 50° C. overnight. After concentration in vacuo, the residue was mixed with water and extracted with EtOAc (2×25 mL). The combined organic extracts were washed with brine, dried with MgSO$_4$, and concentrated in vacuo to give a mixture of 306a-b as oil (425 mg, 100% yield). MS: m/z [M+H]$^+$ 302.

Compound 307a-b: To a solution of 306a-b (425 mg, 1.4 mmol) in 1:1 THF/MeOH (4 mL), was added 30% NaOMe (2 g, 8 eq). The solution was heated at 50° C. for 6 hours. After concentration in vacuo, the residue was mixed with sat. KH$_2$PO$_4$ (25 mL) and extracted with EtOAc (2×25 mL). The combined organic extracts were washed with water and brine, dried with MgSO$_4$, concentrated to give a mixture of the 307a-b as oil (425 mg, 100% yield). MS: m/z [M+H]$^+$ 302.

Compounds TX63691 and TX63692: To a solution of 307a-b (425 mg, 1.4 mmol) in 3 mL of DMF at 0° C. was added dibromodimethylhydantoin (222 mg, 0.55 eq), and the solution was stirred for 2 hours. Pyridine (2 g) was added, and the solution was heated at 50° C. overnight. After concentration in vacuo, the residue was purified on a silica gel column, eluted with 10-50% EtOAc/Hexanes to give TX63691 as an off-white solid. R$_f$=0.5 (Hexane/EtOAc 1:3) (25 mg, 6% yield); $^1$H NMR (400 MHz, CDCl$_3$) δ 8.42 (s, 1H), 3.94 (s, 3H), 3.58 (s, 3H), 2.84 (ddd, 1H, J=1.4, 5.9, 15.2 Hz), 2.59 (m, 1H), 2.11 (dd, 1H, J=2.4, 11.7 Hz), 1.75-1.91 (m, 2H), 1.45 (s, 3H), 1.25 (s, 3H), 1.19 (s, 3H); MS: m/z [M+H]$^+$ 300. Continued elution gave a yellow foam, R$_f$=0.25 (Hexane/EtOAc 1:3) (260 mg, 62% yield), MS: m/z [M+H]$^+$ 302. This material (260 mg) was mixed with DDQ (200 mg, 0.88 mmol) in 10 mL of benzene, and heated to reflux for 16 h. The resulting mixture was dissolved in 25 mL of EtOAc and washed with sat. NaHCO$_3$ (2×25 mL). The organic layer was concentrated, and the residue was purified on a silica gel column, eluted with 20-60% EtOAc/Hexanes to give TX63692 (60 mg, 15% yield) as an off-white solid. $^1$H NMR (400 MHz, CDCl$_3$) δ 8.34 (s, 1H), 3.30 (s, 3H), 2.09 (m, 1H), 1.73-1.92 (m, 3H), 1.48 (s, 3H), 1.42 (m, 1H), 1.42 (s, 3H), 1.21 (s, 6H); MS: m/z [M+H]$^+$ 300.

Compound 308 and TX63804: A mixture of 70 (0.48 g, 1.49 mmol) and IBX (1.67 g, 4 eq) in DMF (8 mL) was heated to 65° C. for 6 h. The reaction mixture was quenched with sat. NaHCO$_3$ solution (25 mL), and extracted with EtOAc (2×50 mL). The combined organic extracts were washed with brine, and dried with MgSO$_4$. After concentration in vacuo, the residue was purified on a silica gel column, eluted with 5-35% EtOAc/Hexanes to give the title compound as an off-white solid, 308, R$_f$=0.45 (Hexane/EtOAc 3:2) (286 mg, 60% yield), MS: m/z [M+H]$^+$ 321. TX63804 was also isolated as a yellow foam R$_f$=0.35 (Hexane/EtOAc 3:2) (15 mg, 3% yield). $^1$H NMR (400 MHz, CDCl$_3$) δ 7.73 (d, 1H, J=10.4 Hz), 7.39-7.51 (m, 5H), δ 6.08 (d, 1H, J=9.2 Hz), 3.75 (s, 3H), 2.63-2.75 (m, 2H), δ 2.54 (q, 1H, J=13.2 Hz), 1.53 (s, 3H), 1.20 (s, 6H); MS: m/z [M+H]$^+$ 335.

Compound 309: To a solution of 308 (286 mg, 0.89 mmol) in THF (5 mL) and pyridine (0.22 g, 3 eq) was added iodine (0.46 g, 2 eq), and the solution was heated at 60° C. for 16 h. The reaction mixture was quenched with sat. sodium thiosulfate solution (25 mL), and extracted with EtOAc (2×30 mL). The combined organic extracts were washed with brine and dried with MgSO$_4$. After concentration in vacuo, 309 was isolated as a light colored solid (395 mg, 100%), MS: m/z [M+H]$^+$ 447.

Compound TX63803: A mixture of 309 (0.2 g, 0.45 mmol) and CuI (0.22 g, 2.5 eq) in DMF (5 mL) was heated to 70° C. FSO$_2$CF$_2$CO$_2$Me (1.3 g, 15 eq) and HMPA (1.4 g, 17 eq) were added sequentially, and the mixture was heated at 70° C. for 6 h. The reaction mixture was quenched with sat. NH$_4$Cl (25 mL) and extracted with EtOAc (2×25 mL). The combined organic extracts were washed with brine and dried with MgSO$_4$. After concentration in vacuo, silica gel chromatography, eluted with 5-35% EtOAc/Hexanes, gave TX63803 as a white solid (110 mg, 63%). $^1$H NMR (400 MHz, CDCl$_3$) δ 8.31 (s, 1H), 7.47 (m, 2H), 7.41 (m, 1H), 7.32 (m, 2H), 3.80 (s, 3H), 2.66 (dd, 1H, J=5.9, 16.1 Hz), 2.54 (ddd, 1H, J=6.6, 11.2, 15.9 Hz), 2.21 (d, 1H, J=11.7 Hz), 1.86 (m, 2H), 1.51 (s, 3H), 1.25 (s, 3H), 1.24 (s, 3H); MS: m/z [M+H]$^+$ 389.

Compound 310a-b: Compound 26 (0.72 g, 2.57 mmol), 3-aminopyrazole (0.222 g, 2.67 mmol), p-toluenesulfonic acid hydrate (0.025 g, 0.12 mmol) and toluene (70 mL) were heated to reflux with removal of water employing a Dean-Stark trap. The reaction mixture was refluxed overnight and was cooled and concentrated to dryness. The residue was taken up in EtOAc (80 mL), washed with saturated aqueous NaHCO$_3$ solution (15 mL), and brine (15 mL), dried over MgSO$_4$, filtered and concentrated to a yellow solid. The solid was chromatographed on silica gel (230-400 mesh, 16 g) using 3:1 Hexanes/EtOAc. The product(s) was/were obtained as follows: 310a (410 mg, 49%)—pure nonpolar isomer as a white solid. m/z [M+H]$^+$ 328.0. 310b (56 mg, 6.7%)—pure polar isomer as a yellow glass, MS: m/z [M+H]$^+$ 328.0.

Compound 311a: Compound 311a (0.326 g, 1.15 mmol) was taken up in MeOH, and 1 N HCl (aq) was added. The mixture was stirred overnight at room temperature. The reaction mixture was then concentrated. The reaction mixture was extracted with EtOAc (50 mL) and washed with saturated NaHCO$_3$, then dried with MgSO$_4$ and concentrated. The crude residue was purified by column chromatography to give compound 311a (303.5 mg, 100%). m/z [M+H]$^+$ 283.9.

Compound 312a: Compound 311a (0.326 g, 1.15 mmol) was taken up in ethyl formate, and 30% sodium methoxide (30 wt % solution in MeOH) was added. The mixture was stirred overnight at room temperature. The reaction mixture was diluted with KH$_2$PO$_4$ (aq) and extracted with EtOAc, then dried with MgSO$_4$ and concentrated to give compound 311a (393 mg). m/z [M+H]$^+$ 312.0.

Compound 313a: A solution of 0.1 N hydroxylamine hydrochloride (aq) was added to Compound 312a (0.393 g, 1.26 mmol). A 9:1 mixture of EtOH/H$_2$O was added, and the reaction mixture was stirred overnight at 50° C. After cooling to room temperature, the reaction mixture was concentrated. The residue was taken up in EtOAc, then dried with MgSO$_4$ and concentrated to give compound 313a (352 mg) as a light yellow solid. m/z [M+H]$^+$ 309.0.

Compound 314a: Compound 313a (0.3518 g, 1.14 mmol) was dissolved in a 3:1 MeOH/THF mixture, and 30% sodium methoxide (30 wt % solution in MeOH) was added. The reaction mixture was stirred at 55° C. for 6 h and then stirred at room temperature overnight. The reaction was quenched by addition of saturated KH$_2$PO$_4$, and the reaction mixture was concentrated. The residue was extracted with EtOAc and washed with brine, then dried with MgSO$_4$ and concentrated. The crude residue was purified by column chromatography (silica gel, 50% EtOAc/Hexanes) to 313a (351 mg) as a yellow solid. This material was used directly in the next step.

Compound TX63627 and TX63615: Compound 314a (0.204 g, 0.66 mmol) was dissolved in dry DMF, and the solution was cooled to 0° C. 1,3-Dibromo-5,5-dimethylhydantoin was added, and the reaction stirred at 0° C. until the starting material was consumed (approximately 30 min), as reported by thin layer chromatography. Then, pyridine was added, and the reaction was allowed to warm to room temperature. The reaction mixture was then stirred at 50° C. overnight. After cooling to room temperature, the reaction mixture was extracted with EtOAc and washed with brine, then dried with MgSO$_4$ and concentrated. The crude residue was purified by column chromatography (230-400 mesh, 18 g) using 50% Hexanes/EtOAc to give TX63627 (34.1 mg, 17%) as a white solid. $^1$H NMR (500 MHz, CDCl$_3$) δ 9.62 (s, 1H), 8.42 (s, 1H), 8.15 (s, 1H), 7.28 (s, 1H) 3.06 (m, 1H), 2.99 (m, 1H), 2.38 (d, 1H, J=11.4 Hz), 2.12 (dd, 1H, 6.2, 5.9 Hz), 1.92 (m, 1H), 1.84 (s, 3H), 1.37 (s, 3H), 1.35 (s, 3H). m/z: [M+H]$^+$ 306.9. TX63615 (59.6 mg, 24%) was also isolated as a white solid. $^1$H NMR (500 MHz, CDCl$_3$) δ 9.58 (s, 1H), 8.38 (s, 1H), 8.11 (s, 1H), 3.04 (dd, 1H, J=20, 5 Hz), 2.90-2.97 (m, 1H), 2.33 (d, 1H, J=10 Hz), 2.08 (dd, 1H, J=15, 5 Hz), 1.83-1.92 (m, 1H), 1.80 (s, 3H), 1.33 (s, 3H), 1.32 (s, 3H); m/z [M+H]$^+$ 384.9, 386.8.

Compound TX63626: Compound TX63615 (0.0486 g, 0.126 mmol), K$_3$PO$_4$ (0.086 g, 0.41 mmol), phenylboronic acid (0.024 g, 0.20 mmol) and dimethoxyethane (6 mL) were mixed and nitrogen gas was bubbled through the stirred mixture for 1-2 minutes. Pd(PPh$_3$)$_4$ (0.015 g, 0.012 mmol) was added and nitrogen gas was bubbled through the stirred mixture for 1-2 minutes. The vial was tightly sealed and heated at 90° C. overnight with stirring. The reaction was cooled and concentrated to dryness. The residue was chromatographed on silica gel (230-400 mesh, 9.7 g) using 50% Hexanes/EtOAc, followed by a second purification on silica gel using 3:1 Hexanes/EtOAc to give TX63626 (12.8 mg, 26%) as a yellowish solid. $^1$H NMR (500 MHz, CDCl$_3$) δ 9.75 (s, 1H), 8.41 (d, 2H, J=13.3 HZ), 8.03 (d, 2H, J=7.5 Hz), 7.50 (t, 1H, J=7.6, 7.6 Hz), 7.33 (t, 1H, J=7.2, 7.6 Hz), 3.07 (m, 1H), 2.98 (m, 1H), 2.30 (d, 1H, J=12.4 Hz), 2.11 (m, 1H), 1.95 (m, 1H), 1.89 (s, 3H), 1.38 (s, 3H), 1.37 (s, 3H); m/z: [M+H]$^+$ 383.0.

Compound 311b: Compound 310b (0.0523 g, 0.16 mmol) was taken up in MeOH, and 1 N HCl (aq) was added. The mixture was stirred overnight at room temperature. The reaction mixture was then concentrated. The reaction mixture was extracted with EtOAc (50 mL) and washed with saturated NaHCO$_3$, then dried with MgSO$_4$ and concentrated. The crude residue was purified by column chromatography to give compound 311b (40.7 mg, 90%). m/z [M+H]$^+$ 283.9.

Compound 312b: Compound 311b (0.0407 g, 0.144 mmol) was taken up in ethyl formate, and 30% sodium methoxide (30 wt % solution in MeOH) was added. The mixture was stirred overnight at room temperature. The reaction mixture was diluted with KH$_2$PO$_4$ (aq) and extracted with EtOAc, then dried with MgSO$_4$ and concentrated to give compound 312b (42.2 mg). m/z [M+H]$^+$ 312.0.

Compound 313b: A solution of 0.1 N hydroxylamine hydrochloride (aq) was added to Compound 312b (0.0422 g, 0.136 mmol). A 9:1 mixture of EtOH/H$_2$O was added, and the reaction mixture was stirred overnight at 50° C. After cooling to room temperature, the reaction mixture was concentrated. The residue was taken up in EtOAc, then dried with MgSO$_4$ and concentrated to give compound 313b (43.7 mg) as a yellow glass. m/z [M+H]$^+$ 309.0.

Compound 314b: Compound 313b (0.0437 g, 0.14 mmol) was dissolved in a 3:1 MeOH/THF mixture, and 30% sodium methoxide (30 wt % solution in MeOH) was added. The reaction mixture was stirred at 55° C. for 6 h and then stirred at room temperature overnight. The reaction was quenched by addition of saturated KH$_2$PO$_4$, and the reaction mixture was concentrated. The residue was extracted with EtOAc and washed with brine, then dried with MgSO$_4$ and concentrated. The crude residue was purified by column chromatography (silica gel, 50% EtOAc/Hexanes) to give compound 314b (44.5 mg). This material was used directly in the next step.

Compound TX63617: Compound 314b (0.0445 g, 0.14 mmol) was dissolved in dry DMF, and the solution was cooled to 0° C. 1,3-Dibromo-5,5-dimethylhydantoin was added, and the reaction stirred at 0° C. until the starting material was consumed (approximately 30 min), as reported by thin layer chromatography. Then, pyridine was added, and the reaction was allowed to warm to room temperature. The reaction mixture was then stirred at 50° C. overnight. After cooling to room temperature, the reaction mixture was extracted with EtOAc and washed with brine, then dried with MgSO$_4$ and concentrated. The crude residue was purified by column chromatography (230-400 mesh, 10 g) using 50% Hexanes/EtOAc, followed by a second purification on silica gel (230-400 mesh, 8 g) using 1% methyl-t-butylether/DCM to give TX63617 (18 mg, 33%) as a white solid. $^1$H NMR (500 MHz, CDCl$_3$) δ 8.96 (s, 1H), 8.46 (s, 1H), 8.07 (s, 1H), 3.14 (dd, 1H, J=16.4, 6.0 Hz), 2.96-3.03 (m, 1H), 2.27 (dd, 1H, J=11.9, 3.4 Hz), 2.00-2.11 (m, 2H), 1.51 (s, 3H), 1.32 (s, 3H), 1.23 (s, 3H); m/z: [M+H]$^+$ 384.9, 386.9.

Compound 316a-b: A solution of a sl. impure mixture of 130, 315 and an impurity X (1.96 g, assume 5.21 mmol, with 130 as the majority fraction) and 3N HCl (20 mL, 60 mmol) in 20 mL of MeOH was stirred at room temperature under N$_2$ for 16 h. The sample was concentrated, cooled, basified with concentrated NH$_4$OH to a pH~10 then extracted with CHCl$_3$. The organic extract was washed with sat. NaCl solution, dried (MgSO$_4$), filtered and concentrated to give 1.47 g (91%) of an inseparable mixture of 316a-b and X as light yellow foamy solid, which was used without purification.

Compound 317a-b and X: To a stirring solution of a sl. impure mixture of 316a-b and X (1.47 g, assume 4.73 mmol) and ethyl formate (3.8 mL, 47.0 mmol) in 20 mL of benzene was added dropwise NaOMe, 30 wt. % solution in MeOH (4.4 mL, 23.4 mmol). The sample was stirred at room temperature under N$_2$ for 16 h, concentrated then partitioned between EtOAc and sat. KH$_2$PO$_4$ solution. The organic extract was washed with sat. NaCl solution, dried (MgSO$_4$), filtered and concentrated to give 1.51 g (94%) of an inseparable mixture of 317a-b and X as an orange solid, which was used without purification. MS (APCI): m/z 387 (78%) [M+H]$^+$ and 339/341 (91/100%) [M+H]$^+$.

Compound 318a-b and X: A solution of a sl. impure mixture of 317a-b and X (1.51 g, assume 4.46 mmol) and hydroxylamine hydrochloride (0.47 g, 6.76 mmol) in 20 mL of ethanol was heated at 50° C. under N$_2$ for 16 h. The sample was cooled, concentrated and partitioned between EtOAc and sat. NaHCO$_3$ solution. The organic extract was washed with sat. NaCl solution, dried (MgSO$_4$), filtered and concentrated to give 1.47 g (98%) of an inseparable mixture of 318a-b and X as dark brown foamy solid, which was used without purification. MS (APCI) m/z 384 (79%) [M+H]$^+$ and 336/338 (90/100%).

Compound 319a-b and X: To a stirring solution of a sl. impure mixture of 318a-b and X (1.47 g assume 4.37 mmol) at room temperature under N$_2$ in 50 mL of MeOH was added dropwise NaOMe, 30 wt. % solution in MeOH (4.1 mL, 21.8 mmol). The sample was stirred at room temperature for 16 h, concentrated then partitioned between EtOAc and sat. KH$_2$PO$_4$ solution. The organic extract was washed with sat. NaCl solution, dried (MgSO$_4$), filtered and concentrated. The sample was chromatographed (silica gel, 50% EtOAc/Hexanes) to give 0.81 g (55%) of an inseparable mixture of 319a-b and X as light yellow foamy solid. MS (APCI) m/z 336/338 (96/100%) [M+H]$^+$.

Compound TX63606 and TX63649: To a stirring solution at 0° C. under N$_2$ of a mixture of 319a-b and X (0.81 g, 2.40 mmol) in 10 mL of DMF was added in one portion 1,3-dibromo-5,5-dimethylhydantoin (0.38 g, 1.33 mmol). After stifling at 0° C. for 1 h, pyridine (1.90 mL, 23.49 mmol) was added. The ice bath was removed and the sample was heated at 50° C. for 16 h. The sample was concentrated (to remove most of the DMF and pyridine) then partitioned between EtOAc and sat. NaHCO$_3$ solution. The organic extract was washed with sat. KH$_2$PO$_4$ and sat. NaCl solutions, dried (MgSO$_4$), filtered and concentrated. The sample was chromatographed (silica gel, 50% EtOAc/Hexanes) to give 0.56 g (69%) of TX63606 as yellow solid. $^1$H NMR (500 MHz, CDCl$_3$) δ 8.36 (s, 1H), 3.82 (s, 3H), 2.49-2.60 (m, 2H), 2.38-2.45 (m, 1H), 2.00-2.06 (m, 2H), 1.66-1.75 (m, 1H), 1.39 (s, 3H), 1.28 (br d, 3H, J=5 Hz); MS (APCI) m/z 334/336 (95/100%) [M+H]$^+$. All impure fractions from the above chromatography were combined, concentrated and rechromatographed (silica gel, 25% EtOAc/Hexanes) to give 0.019 g (2%) of TX63649 as white solid. $^1$H NMR (400 MHz, CDCl$_3$) δ 8.21 (s, 1H), 4.00 (s, 3H), 2.51-2.63 (m, 2H), 2.38 (m, 1H), 2.14 (m, 1H), 2.05 (m, 1H), 1.62 (m, 1H), 1.47 (s, 3H), 1.32 (d, 3H, J=6.8 Hz); MS (APCI) m/z 334/336 (96/100%) [M+H]$^+$.

Compound TX63650 and TX63656: Compound TX63606 (0.102 g, 0.31 mmol), K$_3$PO$_4$ (0.190 g, 0.90 mmol), 3-methylphenylboronic acid (0.065 g, 0.48 mmol) and dimethoxyethane (7 mL) were mixed and the solution was sparged with N$_2$ for 3-5 min. Pd(PPh$_3$)$_4$ (0.022 g, 0.019 mmol) was added and the solution was sparged again for 3-5 minutes. The vial was tightly sealed and heated at 80° C. overnight with stifling. The reaction was allowed cooled and concentrated to dryness. The residue was chromatographed on silica gel (230-400 mesh, 10 g) using 3:1 Hexanes/EtOAc to give TX63650 (52 mg) as a light yellow solid. $^1$H NMR (400 MHz, CDCl$_3$) δ 8.48 (s, 1H), 7.34 (t, 1H, J=7.6, 7.3 Hz), 7.22 (d, 1H, 7.7 Hz), 7.11 (d, 2H, 7.8 Hz), 3.77 (s, 3H), 2.53 (m, 3H), 2.39 (s, 3H), 2.10 (m, 2H), 1.70 (m, 1H), 1.45 (s, 3H), 1.28 (d, 3H, J=6.8)); m/z: [M+H]$^+$ 346.1. TX63656 (2.9 mg) was also isolated as a yellow glass; m/z [M+H]$^+$ 344.0.

Compound TX63659 and TX63663: Compound TX63606 (0.141 g, 0.42 mmol), K$_3$PO$_4$ (0.27 g, 1.27 mmol), 3-fluorophenylboronic acid (0.091 g, 0.65 mmol) and dimethoxyethane (10 mL) were mixed and the solution was sparged with N$_2$ for 3-5 min. Pd(PPh$_3$)$_4$ (0.027 g, 0.023 mmol) was added and the solution was sparged again for 3-5 minutes. The vial was tightly sealed and heated at 80° C. overnight with stirring. The reaction was cooled, and the solvent was decanted from the solids. The liquid was concentrated to a residue that was chromatographed on silica gel (230-400 mesh, 14 g) using 3:1 Hexanes/EtOAc to give TX63659 (42 mg) as a yellow foam/glass. $^1$H NMR (500 MHz, CDCl$_3$) δ 8.51 (s, 1H), 7.47 (m, 1H), 7.14 (m, 2H), 7.06 (m, 1H), 3.83 (s, 3H), 2.58 (m, 3H), 2.15 (m, 1H), 2.07 (m, 1H), 1.75 (m, 1H), 1.50 (s, 3H), 1.33 (d, 3H); m/z: [M+H]$^+$ 350.0; and TX63663 (6.4 mg) as a yellow glass. $^1$H NMR (500 MHz, CDCl$_3$) δ 8.32 (s, 1H), 7.48 (dd, 1H, J=6.3, 7.79, 7.74), 7.15 (t, 1H, J=8.49, 8.49), 7.12 (d, 1H, J=7.67), 7.06-7.02 (m, 1H), 3.85 (s, 3H), 3.16-3.08 (m, 1H), 2.83-2.75 (m, 1H), 2.68-2.55 (m, 2H), 2.08 (s, 3H), 1.72 (s, 3H); m/z [M+H]$^+$ 348.0.

Compound TX63664: Compound TX63606 (0.1209 g, 0.36 mmol), K$_3$PO$_4$ (0.227 g, 1.07 mmol), 3-methoxyphenylboronic acid (0.083 g, 0.55 mmol) and dimethoxyethane (8 mL) were mixed and the solution was sparged with N$_2$ for 3-5 min. Pd(PPh$_3$)$_4$ (0.030 g, 0.026 mmol) was added and the solution was sparged again for 3-5 minutes. The vial was tightly sealed and heated at 80° C. overnight with stirring. The reaction cooled and concentrated to dryness. The residue was chromatographed on silica gel (230-400 mesh, 15 g) using 3:1 Hexanes/EtOAc to give TX63664 (34 mg) as a white solid. $^1$H NMR (500 MHz, CDCl$_3$) δ 8.52 (s, 1H), 7.42 (t, 1H, J=7.83, 8.06), 6.96 (d, 1H, J=8.38), 6.92 (d, 1H, J=7.58), 6.87 (s, 1H), 3.87 (s, 3H), 3.83 (s, 3H), 2.67 (dd, 1H, J=6.46, 9.77, 6.59 Hz), 2.62-2.54 (m, 2H), 2.16 (t, 1H, J=12.86, 12.75), 2.08-2.00 (m, 1H), 1.80-1.62 (m, 1H), 1.50 (s, 3H), 1.32 (d, 3H, J=6.74); m/z: [M+H]$^+$ 362.1.

Compound 320a: Compound 130 (0.450 g, 1.27 mmol), $K_3PO_4$ (0.86 g, 4.05 mmol), 1-methylpyrazole-4-boronic acid pinacol ester (0.554 g, 2.65 mmol) and dimethoxyethane (20 mL) were mixed and the mixture was sparged with $N_2$ for 3-5 min. $Pd(PPh_3)_4$ (0.122 g, 0.11 mmol) was added and the reaction was sparged again for 3-5 minutes. The vial was tightly sealed and heated at 95° C. overnight with stirring. The reaction was cooled and concentrated to dryness. The residue was partitioned between EtOAc (100 mL) and saturated aqueous NaCl solution (40 mL), and the organic layer dried over $MgSO_4$, filtered and concentrated. The resulting oil was chromatographed on silica gel (230-400 mesh, 18 g) using EtOAc as eluant to give 320a (374.5 mg) as a yellow foam/glass, m/z $[M+H]^+$ 357.1.

Compound 321a: Compound 320a (0.371 g, 1.04 mmol) was taken up in MeOH (15 mL) and 1N HCl (5 mL), and the mixture was stirred 3 days at room temperature. The reaction mixture was concentrated to remove MeOH and then partitioned between EtOAc (80 mL) and saturated aqueous $NaHCO_3$ (15 mL). The organic layer was dried over $MgSO_4$, filtered and concentrated to an off-white solid (321a, 285 mg). m/z: $[M+H]^+$ 313.1.

Compound 322a: Compound 321a (0.285 g, 0.91 mmol) was taken up in ethyl formate (30 mL) and 30% NaOMe in MeOH (1.1 mL, 5.9 mmol) was added and the mixture was stirred overnight at room temperature. The reaction mixture was partitioned between saturated aqueous $KH_2PO_4$ (20 mL) and EtOAc (100 mL). The organic layer was dried over $MgSO_4$, filtered and concentrated to a glass (322a, 323 mg). m/z: $[M+H]^+$ 341.0.

Compound 323a: A solution of hydroxylamine hydrochloride (0.105 g, 1.52 mmol) was added to 322a (0.323 g, 0.95 mmol) in 10:1 $EtOH/H_2O$ (22 mL). The mixture was heated briefly to 50° C. and was then stirred overnight at room temperature. The reaction mixture was concentrated to dryness, partitioned between EtOAc (100 mL) and brine (20 mL) and the organic solution was dried over $MgSO_4$, filtered and concentrated to a foam/solid (323a, 289 mg). m/z: $[M+H]^+$ 338.0.

Compound 324a: Compound 323a (0.289 g, 0.86 mmol) was taken up in 1:1 MeOH/THF, (20 mL) and 30% NaOMe in MeOH (1.0 mL, 5.4 mmol) was added and the mixture was stirred overnight at room temperature. The reaction was partitioned between saturated $KH_2PO_4$ (20 mL) and EtOAc (100 mL), the layers were separated and the aqueous layer was back-extracted with EtOAc. The combined organic layers were dried over $MgSO_4$, filtered and concentrated to give 324a (275 mg) as a glass/foam. m/z: $[M+H]^+$ 338.0.

Compound TX63690: Compound 324a (0.275 g, 0.82 mmol) was taken up in benzene (30 mL) and DDQ (0.220 g, 0.969 mmol) was added and the reaction mixture was briefly warmed to 45° C. and a dark precipitate formed. DCM (20 mL) was added and the mixture was stirred overnight at room temperature. The reaction mixture was concentrated and then diluted with EtOAc (80 mL) and washed with saturated aqueous $NaHCO_3$ solution (2×20 mL). The organic layer was dried over $MgSO_4$, filtered and concentrated. The residue was chromatographed two times on silica gel (230-400 mesh) using 50% EtOAc/DCM to give a glass. The glass was taken up in ethyl ether (5 mL) and upon standing at room temperature a solid formed and was collected by filtration, washed with ethyl ether (1 mL) and dried in a stream of air, to afford TX63690 (69 mg) as a yellow solid. $^1H$ NMR (500 MHz, $CDCl_3$) δ 8.46 (s, 1H), 7.58 (s, 1H), 7.46 (s, 1H), 3.97 (s, 3H), 3.85 (s, 3H), 2.65 (m, 1H), 2.48-2.58 (m, 2H), 1.99-2.12 (m, 2H), 1.72 (m, 1H), 1.43 (s, 3H), 1.28 (d, 3H, J=6.8 Hz); m/z: $[M+H]^+$ 336.0.

Compound 320b: Compound 130 (0.455 g, 1.28 mmol), $K_3PO_4$ (0.877 g, 4.14 mmol), 2-fluorophenylboronic acid (0.343 g, 2.48 mmol), dimethoxyethane (12 mL) and DMF (6 mL) were mixed and the mixture was sparged with $N_2$ for 3-5 min. $Pd(PPh_3)_4$ (0.126 g, 0.11 mmol) was added and the reaction was sparged again for 3-5 minutes. The vial was tightly sealed and heated at 95° C. for 2 days with stirring. The reaction was allowed to cool and was concentrated to dryness. The residue was partitioned between EtOAc (100 mL) and water (20 mL) and washed with saturated aqueous NaCl (20 mL), the layers were separated, the combined aqueous layers were washed with EtOAc (50 mL) and the combined organic layers dried over $MgSO_4$, filtered, concentrated and the residue was chromatographed on silica gel (230-400 mesh, 19.7 g) using 40% EtOAc/Hexanes as eluant to give 320b (134.6 mg) as a clear glass, m/z: $[M+H]^+$ 371.1.

Compound 321b: Compound 320b (0.1346 g, 0.36 mmol) was taken up in MeOH (20 mL) and 1N HCl (3 mL) and the mixture was stirred 3 days at room temperature. The reaction mixture was concentrated to remove MeOH and then partitioned between EtOAc (50 mL) and saturated aqueous $NaHCO_3$. The organic layer was dried over $MgSO_4$, filtered and concentrated to afford 321b (108 mg) as a foam/glass. m/z: $[M+H]^+$ 327.1.

Compound 322b: Compound 321b (0.108 g, 0.33 mmol) was taken up in ethyl formate (10 mL) and 30% NaOMe in MeOH (0.4 mL, 2.1 mmol) was added. The mixture was stirred overnight at room temperature, then partitioned between saturated aqueous $KH_2PO_4$ (10 mL) and EtOAc (80 mL). The organic layer was extracted with brine (10 mL) and dried over $MgSO_4$, filtered and concentrated to a glass (322b, 111 mg). m/z: $[M+H]^+$ 355.1.

Compound 323b: A solution of 0.1 M hydroxylamine hydrochloride in 9:1 $EtOH/H_2O$ (6 mL) was added to 322b (0.111 g, 0.31 mmol) and the mixture was stirred overnight at room temperature. The reaction mixture was concentrated to remove ethanol, partitioned between EtOAc (100 mL) and saturated aqueous NaCl solution (10 mL) and the organic solution was dried over $MgSO_4$, filtered and concentrated to a glass (323b, 113 mg). m/z: $[M+H]^+$ 352.1

Compound 324b: Compound 323b (0.113 g, 0.32 mmol) was taken up in 1:1 MeOH/THF (6 mL) and 30% NaOMe in MeOH (0.3 mL, 1.6 mmol) was added. The mixture was stirred 3 days at room temperature, then partitioned between saturated $KH_2PO_4$ (15 mL) and EtOAc (100 mL). The organic layer was dried over $MgSO_4$, filtered and concentrated to give 324b (110.5 mg) as a foam. m/z: $[M+H]^+$ 352.1.

Compound TX63721: Compound 324b (0.1105 g, 0.31 mmol) was taken up in DMF (2 mL) and the mixture was cooled to 0° C. N,N'-Dibromodimethylhydantoin (0.051 g, 0.18 mmol) was added and stirred until the starting material was consumed by thin layer chromatography. Pyridine (0.2 mL, 2.4 mmol) was added and the reaction mixture was warmed to room temperature, and was then heated at 60° C. for 2.5 hours. The reaction mixture was cooled and concentrated to dryness. The residue was chromatographed on silica gel (230-400 mesh, 16.6 g) using 3:1 Hexanes/EtOAc to give TX63721 (45.7 mg) as an off-white foam. $^1H$ NMR (400 MHz, $CDCl_3$) δ 8.48 (s, 1H), 7.26-7.43 (m, 4H), 3.72 (s, 3H), 2.47-2.57 (m, 3H), 2.14 (m, 1H), 1.95 (m, 1H), 1.70 (m, 1H), 1.45 (s, 3H), 1.22 (d, 3H, J=6.7 Hz); m/z: $[M+H]^+$ 350.1.

Compound 320c: Compound 130 (0.450 g, 1.27 mmol), $K_3PO_4$ (0.866 g, 4.08 mmol), 4-pyridineboronic acid (0.310 g, 2.58 mmol), dimethoxyethane (12 mL) and DMF (6 mL) were mixed and the mixture was sparged with $N_2$ for 3-5 min. $Pd(PPh_3)_4$ (0.120 g, 0.10 mmol) was added and the reaction was sparged again for 3-5 minutes. Then the vial was tightly sealed and heated at 95° C. overnight with stirring. The reaction was cooled and concentrated to dryness. The residue was partitioned between EtOAc (100 mL) and water (20 mL) and washed with saturated aqueous NaCl (20 mL), the layers were separated, and the combined aqueous layers were washed with EtOAc (50 mL). The combined organic layers were dried over MgSO$_4$, filtered and concentrated and the residue was chromatographed on silica gel (230-400 mesh, 20 g) using 3% MeOH/EtOAc as eluant to give 320c (404.4 mg) as a white foam/solid, m/z: [M+H]$^+$ 354.1.

Compound 321c: Compound 320c (0.402 g, 1.14 mmol) was taken up in MeOH (25 mL) and 1N HCl (6 mL) and the mixture was stirred 3 days at room temperature. The reaction mixture was concentrated to remove MeOH and was then partitioned between EtOAc (80 mL) and saturated aqueous NaHCO$_3$ (15 mL). The organic layer was dried over MgSO$_4$, filtered and concentrated to a foam/glass (321c, 342 mg). m/z: [M+H]$^+$ 310.0.

Compound 322c: Compound 321c (0.310 g, 1.0 mmol) was taken up in ethyl formate (30 mL), and 30% NaOMe in MeOH (1.2 mL, 6.5 mmol) was added and the mixture was stirred overnight at room temperature. The reaction mixture was partitioned between saturated aqueous KH$_2$PO$_4$ (40 mL) and EtOAc (100 mL). The aqueous layer was back-extracted with EtOAc (50 mL) and the combined organic layers were dried over MgSO$_4$, filtered and concentrated to a glass (322c, 330 mg). m/z: [M+H]$^+$ 338.0.

Compound 323c: A solution of 0.1 M hydroxylamine hydrochloride in 9:1 EtOH/H$_2$O (17.6 mL) was added to 322c (0.330 g, 0.98 mmol) and the mixture was stirred overnight at room temperature. The reaction mixture was concentrated to remove ethanol, partitioned between EtOAc (100 mL) and saturated aqueous NaHCO$_3$ solution (20 mL) and the organic solution was dried over MgSO$_4$, filtered and concentrated to a foam (323c, 321 mg). m/z: [M+H]$^+$ 335.1.

Compound 324c: Compound 323c (0.321 g, 0.96 mmol) was taken up in 1:1 MeOH/THF (20 mL) and 30% NaOMe in MeOH (1.0 mL, 5.4 mmol) was added. The mixture was stirred overnight at room temperature, and then partitioned between saturated KH$_2$PO$_4$ (20 mL) and EtOAc (150 mL). The organic layer was dried over MgSO$_4$, filtered and concentrated to give 324c (312 mg) as a foam. m/z: [M+H]$^+$ 335.1.

Compound TX63720: Compound 324c (0.312 g, 0.93 mmol) was taken up in DCM (40 mL). DDQ (0.252 g, 1.11 mmol) was added and the reaction mixture was stirred overnight at room temperature. The reaction mixture was concentrated to dryness, partitioned between EtOAc (150 mL), and the organic layer washed with saturated aqueous NaHCO$_3$ solution (50 mL). The aqueous layer was back-extracted with EtOAc (100 mL), and the combined organic layers were dried over MgSO$_4$, filtered and concentrated. The residue was chromatographed on silica gel (230-400 mesh, 20 g) using 2% MeOH/DCM as eluant to give a greenish oil. The oil was triturated with Hexanes/Et$_2$O to give TX63720 (38.5 mg) as an off-white solid. $^1$H NMR (400 MHz, CDCl$_3$) δ 8.73 (bs, 2H), 8.45 (s, 1H), 7.29 (m, 2H), 3.85 (s, 3H), 2.50-2.70 (m, 3H), 1.98-2.14 (m, 2H), 1.72 (m, 1H), 1.44 ppm (s, 3H), 1.29 (d, 3H, J=6.7 Hz); m/z: [M+H]$^+$ 333.1.

Compound 320d: Compound 130 (0.450 g, 1.27 mmol), K$_3$PO$_4$ (0.873 g, 4.12 mmol), 3-pyridineboronic acid (0.313 g, 2.61 mmol), dimethoxyethane (12 mL) and DMF (6 mL) were mixed and the mixture was sparged with N$_2$ for 3-5 min. Pd(PPh$_3$)$_4$ (0.124 g, 0.11 mmol) was added and the reaction was sparged again for 3-5 minutes. The vial was tightly sealed and heated at 95° C. overnight with stirring. The reaction was cooled and concentrated to dryness. The residue was partitioned between EtOAc (100 mL) and water (20 mL) and washed with saturated aqueous NaCl (20 mL). The combined aqueous layers were washed with EtOAc (50 mL) and the combined organic layers were dried over MgSO$_4$, filtered and concentrated. The residue was chromatographed on silica gel (230-400 mesh, 20 g) using 3% MeOH/EtOAc as eluant to give 320d (416 mg) as a white foam/glass, m/z: [M+H]$^+$ 354.1.

Compound 321d: Compound 320d (0.413 g, 1.17 mmol) was taken up in MeOH (25 mL) and 1N HCl (6 mL) and the mixture was stirred 3 days at room temperature. The reaction mixture was concentrated to remove MeOH and was then partitioned between EtOAc (80 mL) and saturated aqueous NaHCO$_3$ (15 mL). The organic layer was dried over MgSO$_4$, filtered and concentrated to a foam/glass (321d, 338 mg). m/z: [M+H]$^+$ 310.0.

Compound 322d: Compound 321d (0.303 g, 0.98 mmol) was taken up in ethyl formate (30 mL) and 30% NaOMe in MeOH (1.2 mL, 6.5 mmol) was added. The mixture was stirred overnight at room temperature, then partitioned between saturated aqueous KH$_2$PO$_4$ (40 mL) and EtOAc (100 mL). The aqueous layer was back-extracted with EtOAc (50 mL) and the combined organic layers were dried over KH$_2$PO$_4$ filtered and concentrated to a glass (322d, 346 mg). m/z: [M+H]$^+$ 338.0.

Compound 323d: A solution of 0.1 M hydroxylamine hydrochloride in 9:1 EtOH/H$_2$O (16 mL, 1.6 mmol) was added to 322d (0.346 g, 1.03 mmol) and the mixture was stirred overnight at room temperature. The reaction mixture was concentrated to remove ethanol, partitioned between EtOAc (100 mL) and saturated aqueous NaHCO$_3$ solution (20 mL) and the organic solution was dried over MgSO$_4$, filtered and concentrated to a foam/solid (323d, 299 mg). m/z: [M+H]$^+$ 335.1.

Compound 324d: Compound 323d (0.289 g, 0.86 mmol) was taken up in 1:1 MeOH/THF (20 mL) and 30% NaOMe in MeOH (1.0 mL, 5.4 mmol) was added. The mixture was stirred overnight at room temperature, and was then partitioned between saturated KH$_2$PO$_4$ (20 mL) and EtOAc (150 mL). The organic layer was dried over MgSO$_4$, filtered and concentrated to give 324d (307 mg) as a foam. m/z: [M+H]$^+$ 335.1.

Compound TX63722: Compound 324d (0.307 g, 0.92 mmol) was taken up in DCM (40 mL) and DDQ (0.228 g, 1.004 mmol) was added. The reaction mixture was stirred overnight at room temperature. The reaction mixture was filtered and the organic layer washed with saturated aqueous NaHCO$_3$ solution (50 mL), dried over MgSO$_4$, filtered and concentrated. The residue was chromatographed on silica gel (230-400 mesh, 18 g) using 1.5% MeOH/DCM as eluant to give a greenish oil. The oil was triturated with Hexanes/Et$_2$O to give TX63722 (40.3 mg) as an off-white solid. $^1$H NMR (400 MHz, CDCl$_3$) δ 8.67 (m, 1H), 8.61 (bs, 1H), 8.46 (s, 1H), 7.71 (m, 1H), 7.49 (m, 1H), 3.80 (s, 3H), 2.50-2.66 (m, 3H), 1.97-2.14 (m, 2H), 1.73 (m, 1H), 1.45 (s, 3H), 1.28 (d, 3H, J=6.8 Hz); m/z: [M+H]$^+$ 333.1.

Compound 320e: Compound 130 (0.453 g, 1.28 mmol), K$_3$PO$_4$ (0.882 g, 4.16 mmol), pyrimidine-5-boronic acid (0.315 g, 2.6 mmol), dimethoxyethane (12 mL) and DMF (6 mL) were mixed and the mixture was sparged with N$_2$ for 3-5 min. Pd(PPh$_3$)$_4$ (0.118 g, 0.10 mmol) was and the reaction was sparged again for 3-5 minutes. The vial was tightly sealed and heated at 95° C. overnight with stirring. The reaction was cooled and concentrated to dryness. The residue was partitioned between EtOAc (100 mL) and brine (20 mL). The organic layer was dried over MgSO$_4$, filtered and concentrated and the residue was chromatographed on silica gel (230-400 mesh, 18 g) using 3% MeOH/EtOAc as eluant to give 320e (333 mg) as an off-white solid, m/z: [M+H]⁺ 355.2.

Compound 321e: Compound 320e (0.333 g, 0.94 mmol) was taken up in MeOH (25 mL) and 1N HCl (6 mL) was added. The mixture was stirred overnight at room temperature, then concentrated to remove MeOH and partitioned between EtOAc (80 mL) and saturated aqueous NaHCO$_3$. The organic layer was dried over MgSO$_4$, filtered and concentrated to a solid (321e, 280.9 mg). m/z: [M+H]⁺ 311.2.

Compound 322e: Compound 321e (0.2809 g, 0.91 mmol) was taken up in ethyl formate (34 mL) and 30% NaOMe in MeOH (1.05 mL, 5.7 mmol) was added. The mixture was stirred 3 days at room temperature, then partitioned between saturated aqueous KH$_2$PO$_4$ (20 mL) and EtOAc (100 mL). The organic layer was extracted with brine (10 mL), then dried over MgSO$_4$, filtered and concentrated to a glass (322e, 280 mg). m/z: [M+H]⁺ 339.1.

Compound 323e: A solution of hydroxylamine hydrochloride (0.15 g, 2.2 mmol) in 10:1 EtOH/H$_2$O (22 mL) was added to 322e (0.280 g, 0.83 mmol) and the mixture was stirred 3 days at room temperature. The reaction mixture was concentrated to dryness, and partitioned between EtOAc (100 mL) and saturated aqueous NaHCO$_3$ solution (10 mL). The organic solution was dried over MgSO$_4$, filtered and concentrated to a glass that solidified on standing. The solid was chromatographed on silica gel (230-400 mesh, 11 g) using EtOAc as eluant to afford 323e (180 mg). m/z: [M+H]⁺ 336.1.

Compound 324e: Compound 323e (0.180 g, 0.54 mmol) was taken up in 1:1 MeOH/THF (10 mL) and 30% NaOMe in MeOH (0.6 mL, 3.2 mmol) was added. The mixture was stirred overnight at room temperature, then partitioned between saturated KH$_2$PO$_4$ (15 mL) and EtOAc (120 mL). The organic layer was washed with saturated aqueous NaCl solution, dried over MgSO$_4$, filtered and concentrated to give 324e (189 mg) as a foam. m/z: [M+H]⁺ 336.1.

Compound TX63748: Compound 324e (0.189 g, 0.56 mmol) was taken up in DMF (2 mL) and the mixture was cooled to 0° C. Bromine (0.092 g, 0.58 mmol) in DMF (0.5 mL) was added and stirred until the starting material was consumed by thin layer chromatography. Pyridine (0.45 mL, 5.6 mmol) was added and the reaction was warmed to room temperature, and then heated at 60° C. for 2 hours. The reaction mixture was cooled and concentrated to dryness. The residue was partitioned between EtOAc (100 mL) and saturated aqueous NaHCO$_3$ solution (50 mL), the layers separated, the organic layer dried over MgSO$_4$, filtered and concentrated to a yellow solid. The solid was triturated with ethyl ether and TX63748 (108 mg) was collected by filtration as a light yellow solid. ¹H NMR (400 MHz, CDCl$_3$) δ 9.25 (s, 1H), 8.74 (s, 2H), 8.44 (s, 1H), 3.83 (s, 3H), 2.59 (m, 3H), 2.08 (m, 2H), 1.75 (m, 1H), 1.45 (s, 3H), 1.29 (d, 3H, J=6.7 Hz); m/z: [M+H]⁺ 334.1.

Compound 325: A solution of 132 (431 mg, 1.4 mmol) and IBX (1.6 g, 5.6 mmol) in DMSO (7 mL) was heated at 65° C. for 7 h. The mixture was quenched with 50 mL of water and extracted with EtOAc (2×25 mL). The EtOAc extracts were concentrated, and purified by column chromatography (silica gel, 5-25% EtOAc/Hexanes) to give 325 as a white solid (189 mg, 43%). MS: m/z [M+H]⁺ 307.

Compound 326: A mixture of 325 (182 mg, 0.59 mmol), iodine (302 mg, 1.2 mmol) and pyridine (145 mg, 1.8 mmol) in THF (3 mL) was heated at 60° C. for 30 h. The reaction mixture was quenched with sodium thiosulfate (25 mL), extracted with EtOAc (2×25 mL), washed with water, dried with MgSO$_4$ and concentrated to give 326 as a light colored solid (258 mg, 100%). MS: m/z [M+H]⁺ 433.

Compound TX63829: A mixture of 326 (254 mg, 0.58 mmol) and CuI (0.28 g, 1.4 mmol) in 5 mL of DMF was heated to 70° C. FSO$_2$CF$_2$CO$_2$Me (1.7 g, 8.8 mmol) and HMPA (1.8 g, 10 mmol) were added sequentially, then kept at 70° C. for 6 h. The solvent was removed under vacuum and the crude product was purified by column chromatography (silica gel, 5-25% EtOAc/Hexanes) to give TX63829 as a light yellow solid (95 mg, 42%). ¹H NMR (400 MHz, CDCl$_3$) δ 8.27 (s, 1H), 7.35-7.48 (m, 3H), 7.28-7.32 (m, 2H), 3.79 (s, 3H), 2.49-2.65 (m, 3H), 2.10 (dt, 1H, J=2.0, 12.8 Hz), 1.95-2.02 (m, 1H), 1.64-1.77 (m, 1H), 1.44 (s, 3H), 1.26 (d, 3H, J=6.8 Hz); MS: m/z [M+H]⁺ 375.

Compound 327: Compound 130 (0.54 g, 1.52 mmol) was taken up in DMA (6 mL) and zinc cyanide (120 mg, 1.02 mmol), dppf (169 mg, 0.30 mmol), and sodium carbonate (161 mg, 1.52 mmol) were added. Nitrogen was bubbled through the mixture for 10 min, then Pd(OAc)$_2$ (34 mg, 0.15 mmol) was added and nitrogen bubbling was continued for another 10 min. The mixture was then heated at 120° C. in a sealed vessel overnight. After cooling, water (25 mL) was added, and the mixture was extracted with ether (3×50 mL). The combined organic extracts were washed with brine, dried over MgSO$_4$, concentrated, and dried under vacuum to give a brown semisolid. Flash chromatography (10% EtOAc/DCM) gave 0.41 g (90%) of 327 as a white solid. MS (APCI): m/z 302 [M+H]⁺.

Compound 328: Compound 327 (108 mg, 0.36 mmol) was taken up in THF (4 mL) and 1M HCl (1 mL) was added. The solution was stirred for 3 d, then diluted with sat. NaHCO$_3$ solution (20 mL) and extracted with EtOAc (2×50 mL). The combined organic extracts were washed with brine, dried over MgSO$_4$ and concentrated to give 91 mg (99%) of 328 as a white solid. MS (APCI): m/z 257.9 [M+H]⁺.

Compound 329: A solution of 328 (90 mg, 0.35 mmol) in THF (2 mL) and ethyl formate (2 mL) was cooled in an ice bath. NaOMe (0.6 g, 30 wt % in MeOH) was added dropwise, and the solution was allowed to warm to RT and stirred overnight. The mixture was cooled in an ice bath and quenched by the addition of sat. aq. KH$_2$PO$_4$ (20 mL) and extracted with EtOAc (2×50 mL). The combined organic extracts were washed with brine, dried over MgSO$_4$, and concentrated to give 105 mg (>100%) of 329 as a light yellow solid. MS (APCI): m/z 286 [M+H]⁺.

Compound 330: Compound 329 (0.35 mmol) was taken up in EtOH (2 mL), THF (2 mL), and water (0.5 mL). Hydroxylamine hydrochloride (27 mg, 0.38 mmol) was added and the reaction was stirred at room temperature for 30 min, and then heated at 50° C. overnight. An additional portion of hydroxylamine hydrochloride (5 mg) and heating was continued for an additional 4 h at 50° C. The solution was cooled and concentrated. The residue was diluted with sat. aq. NaHCO$_3$ (20 mL) and extracted with EtOAc (2×50 mL). The combined organic extracts were washed with brine (20 mL), dried over MgSO$_4$, concentrated, and dried under vacuum to give 100 mg (100%) of 330 as a light yellow solid. MS (APCI): m/z 283 [M+H]⁺.

Compound 331: Compound 330 (100 mg, 0.35 mmol) was suspended in 3:1 THF/MeOH (4 mL) and NaOMe (0.6 g, 30 wt % in MeOH) was added. The solution was heated at 50° C. for 4 h, then allowed to cool to room temperature and stirred overnight. The solution was concentrated and sat. aq. KH$_2$PO$_4$ (20 mL) was added. The mixture was extracted with EtOAc (2×50 mL) and the combined organic extracts were washed with brine, dried over MgSO$_4$, and concentrated. Flash chromatography (10% EtOAc/DCM) gave 71 mg (72%) of 331 as white solid. MS (APCI): m/z 283.1 [M+H]⁺.

Compound TX63725: Compound 331 (71 mg, 0.25 mmol) was taken up in DMF (2 mL) and cooled in an ice bath. N,N'-Dibromodimethylhydantoin (43 mg, 0.15 mmol) was added and the solution was stirred 90 min at 0° C. Pyridine (0.4 mL) was added and the solution was heated at 60° C. for 5 h. After cooling, the solution was concentrated and dried under vacuum to a light brown solid. Flash chromatography (5-10% EtOAc/DCM) gave 52 mg (74%) of TX63725 as a white solid. $^1$H NMR (400 MHz, CDCl$_3$) δ 8.28 (s, 1H), 3.93 (s, 3H), 2.81 (ddd, 1H, J=1.2, 6.4, 17.2 Hz), 2.60 (m, 1H), 2.48 (m, 1H), 1.92-2.06 (m, 2H), 1.67 (m, 1H), 1.34 (s, 3H), 1.24 (d, 3H, J=6.7 Hz); MS (APCI): m/z 281.1 [M+H]$^+$.

Compound 332: Compound 327 (0.29 g, 0.96 mmol) was taken up in toluene (5 mL) in a heavy-walled vessel. Trimethylsilylazide (0.25 mL, 1.92 mmol) was added followed by dibutyltin oxide (24 mg, 0.096 mmol). The vessel was sealed and heated overnight in a 130° C. oil bath. After cooling, MeOH (5 mL) was added and the solution was concentrated and dried under vacuum to give 0.45 g of a yellow glass. MS (APCI): m/z 345 [M+H]$^+$. This material was taken up in DMF (5 mL), and K$_2$CO$_3$ (0.66 g, 4.81 mmol) was added followed by methyl iodide (0.30 mL, 4.81 mmol). The mixture was stirred overnight, water (25 mL) was added and the mixture was extracted with EtOAc (2×50 mL). The combined organic extracts were washed with brine, dried over MgSO$_4$, concentrated, and dried under vacuum to give 0.40 g of a brown oil. Flash chromatography (50% EtOAc/Hexane) gave 147 mg (43%) of 332 as a white solid. MS (APCI): m/z 373.1 [M+H]$^+$.

Compound 333: Compound 332 (177 mg, 0.49 mmol) was taken up in THF (4 mL) and 1M HCl (1 mL) was added. The solution was stirred for 3 d, diluted with sat. NaHCO$_3$ (20 mL) and extracted with EtOAc (2×50 mL). The combined organic extracts were washed with brine, dried over MgSO$_4$ and concentrated to give 150 mg (97%) of 333 as a white solid. MS (APCI): m/z 315 [M+H]$^+$.

Compound 334: A solution of 333 (95 mg, 0.29 mmol) in THF (2 mL) and ethyl formate (2 mL) was cooled in an ice bath. NaOMe (0.85 g, 30 wt % in MeOH) was added dropwise, and the solution was allowed to warm to RT and stirred overnight. The mixture was cooled in an ice bath and quenched by the addition of sat. aq. KH$_2$PO$_4$ (20 mL) and extracted with EtOAc (2×50 mL). The combined organic extracts were washed with brine, dried over MgSO$_4$, and concentrated to give 165 mg (100%) of 334 as a white solid. MS (APCI): m/z 343.1 [M+H]$^+$.

Compound 335: Compound 334 (163 mg, 0.48 mmol) was suspended in EtOH (3 mL), THF (3 mL), and water (0.5 mL). Hydroxylamine hydrochloride (37 mg, 0.53 mmol) was added and the reaction was stirred at room temperature for 30 min, and then heated at 50° C. overnight. The solution was cooled and concentrated. The residue was diluted with sat. aq. NaHCO$_3$ (20 mL) and extracted with EtOAc (2×50 mL). The combined organic extracts were washed with brine (20 mL), dried over MgSO$_4$, concentrated, and dried under vacuum to give 145 mg (90%) of 335 as a white solid. MS (APCI): m/z 340.1 [M+H]$^+$.

Compound 336: Compound 335 (145 mg, 0.43 mmol) was suspended in THF (4 mL) and MeOH (1 mL) and NaOMe (0.8 g, 30 wt % in MeOH) was added. The solution was heated at 50° C. for 4 h, then allowed to cool to room temperature and concentrated. Sat. aq. KH$_2$PO$_4$ (20 mL) was added, and the mixture was extracted with EtOAc (2×50 mL). The combined organic extracts were washed with brine, dried over MgSO$_4$, concentrated, and dried under vacuum to give 148 mg of a tan foam. Flash chromatography (1:3 EtOAc/DCM) gave 125 mg (86%) of 336 as an off-white solid. MS (APCI): 340.1 [M+H]$^+$.

Compound TX63719: Compound 336 (125 mg, 0.37 mmol) was taken up in DMF (2 mL) and cooled in an ice bath. N,N'-Dibromodimethylhydantoin (63 mg, 0.22 mmol) was added and the solution was stirred 2 h at 0° C. Pyridine (0.5 mL) was added and the solution was heated at 60° C. for 3 h. After cooling, the solution was concentrated and dried under vacuum to a light brown solid. Flash chromatography (10% EtOAc/DCM) gave 87 mg (70%) of TX63719 as a light yellow solid. $^1$H NMR (400 MHz, CDCl$_3$) δ 8.46 (s, 1H), 4.41 (s, 3H), 4.20 (s, 3H), 3.06 (dd, 1H, J=6.3, 17.3 Hz), 2.75 (ddd, 1H, J=7.2, 11.6, 17.6 Hz), 2.55 (m, 1H), 2.01-2.13 (m, 2H), 1.76 (m, 1H), 1.44 (s, 3H), 1.30 (d, 3H, J=6.7 Hz); MS (APCI): 338.1 [M+H]$^+$.

Compound 337: Crude 332 (1.29 mmol) was taken up in pyridine (5 mL), and acetic anhydride (0.25 mL, 2.64 mmol) was added. The solution was heated at 110° C. for 3 h, then cooled and concentrated. The residue was diluted with sat. NaHCO$_3$ (20 mL) and extracted with EtOAc (2×50 mL). The combined organic extracts were washed with brine, dried over MgSO$_4$, concentrated, and dried under vacuum to give 0.40 g of 337 as a dark brown oil. MS (APCI): m/z 359.2 [M+H]$^+$.

Compound 338: Crude 337 (0.40 g, 1.12 mmol) was taken up in THF (5 mL) and 1M HCl (1 mL) was added. The solution was stirred for 3 d, diluted with sat. NaHCO$_3$ (20 mL) and extracted with EtOAc (2×50 mL). The combined organic extracts were washed with brine, dried over MgSO$_4$ and concentrated. Flash chromatography (75% EtOAc/Hexane) gave 70 mg (20%) of 338 as a white solid. MS (APCI): m/z 315.1 [M+H]$^+$.

Compound 339: A solution of 338 (69 mg, 0.22 mmol) in THF (2 mL) and ethyl formate (1 mL) was cooled in an ice bath. NaOMe (0.4 g, 30 wt % in MeOH) was added dropwise, and the solution was allowed to warm to RT and stirred overnight. The mixture was cooled in an ice bath, quenched by the addition of sat. aq. KH$_2$PO$_4$ (20 mL), and extracted with EtOAc (2×25 mL). The combined organic extracts were washed with brine, dried over MgSO$_4$, concentrated, and dried under vacuum to give 75 mg (100%) of 339 as a white solid. MS (APCI): m/z 343.1 [M+H]$^+$.

Compound 340: Compound 339 (75 mg, 0.22 mmol) was taken up in 3:1 THF/EtOH (4 mL). Hydroxylamine (34 mg, 50 wt % solution in water) was added and the reaction was stirred for 1 h. Another portion of hydroxylamine (34 mg) was added and the solution was stirred overnight at room temperature. The solution was heated at 50° C. for 4 h, then cooled and concentrated. The residue was diluted with sat. aq. NaHCO$_3$ (20 mL) and extracted with EtOAc (2×25 mL). The combined organic extracts were washed with brine (20 mL), dried over MgSO$_4$, concentrated, and dried under vacuum to give 70 mg of a tan foam. This material was suspended in benzene (3 mL) and p-TsOH (1 mg) was added. The mixture was heated at 70° C. for 8 h. After cooling, the solution was diluted with sat. aq. NaHCO$_3$ (20 mL) and extracted with EtOAc (2×25 mL). The combined organic extracts were washed with brine (20 mL), dried over MgSO$_4$, concentrated, and dried under vacuum to give 70 mg of a tan foam. Flash chromatography (1:2 EtOAc/DCM to 2:1 EtOAc/DCM)) gave 35 mg (47%) of 340 as a white solid. MS (APCI): m/z 340.1 [M+H]$^+$.

Compound 341: Compound 340 (35 mg, 0.10 mmol) was taken up in THF (2 mL) and MeOH (1 mL) and NaOMe (0.2 g, 30 wt % in MeOH) was added. The solution was heated at 50° C. for 5 h, then cooled and concentrated. Sat. aq. KH$_2$PO$_4$ (10 mL) was added, and the mixture was extracted with EtOAc (2×25 mL). The combined organic extracts were washed with brine, dried over $MgSO_4$, concentrated, and dried under vacuum to give 35 mg (100%) of 341 as a tan foam. MS (APCI): m/z 340.1 [M+H]$^+$.

Compound TX63857: Compound 341 (35 mg, 0.10 mmol) was taken up in DMF (2 mL) and cooled in an ice bath. N,N'-Dibromodimethylhydantoin (17.7 mg, 0.062 mmol) was added and the solution was stirred 1 h at 0° C. Pyridine (0.2 mL) was added and the solution was heated at 60° C. for 5 h. After cooling, the solution was concentrated and dried under vacuum. Flash chromatography (20% EtOAc/DCM) gave 16 mg (46%) of TX63857 as a white solid. $^1$H NMR (400 MHz, CDCl$_3$) δ 8.43 (s, 1H), 4.22 (s, 3H), 3.01 (dd, 1H, J=6.4, 17.2 Hz), 2.68-2.82 (m, 1H), 2.61 (s, 3H), 2.49-2.59 (m, 1H), 2.00-2.13 (m, 2H), 1.69-1.84 (m, 1H), 1.43 (s, 3H), 1.30 (d, 3H, J=6.8 Hz); MS (APCI): m/z 338.0 [M+H]$^+$.

Compound 342: Compound 327 (0.71 g, 2.36 mmol) was suspended in EtOH (10 mL), and water (5 mL) was added followed by KOH (0.66 g, 11.8 mmol). The mixture was stirred for 4 d, and then poured into sat. $KH_2PO_4$ (50 mL) and extracted with EtOAc (2×50 mL). The combined organic extracts were washed with brine (25 mL), dried over $MgSO_4$, concentrated, and dried under vacuum to give 0.75 g (100%) of 342 as a white solid. MS (APCI): m/z 320.1 [M+H]$^+$.

Compound 343: Compound 342 (380 mg, 1.19 mmol) was added to DMAc-DMA (3 mL) and the mixture was heated at 80° C. for 3 h. The solution was cooled, concentrated, and dried under vacuum to give 343 as a white solid. MS (APCI): m/z 389.1 [M+H]$^+$.

Compound 344: Hydroxylamine hydrochloride (124 mg, 1.78 mmol) was suspended in dioxane (4 mL) and Et$_3$N (0.25 mL, 1.78 mmol) was added. The mixture was sonicated for several minutes. A solution of 343 (1.19 mmol) in dioxane (4 mL) was added followed by acetic acid (0.36 g, 5.94 mmol). The mixture was heated at 80° C. for 2 h and allowed to cool to room temperature. The mixture was diluted with sat. NaHCO$_3$ (25 mL) and extracted with EtOAc (2×50 mL). The combined organic extracts were washed with brine (25 mL), dried over $MgSO_4$, concentrated, and dried under vacuum. Flash chromatography (5-20% EtOAc/DCM) gave 295 mg (69%) of 344 as a white solid. MS (APCI): m/z 359.1 [M+H]$^+$.

Compound 345: Compound 344 (290 mg, 0.81 mmol) was taken up in THF (12 mL) and 1M HCl (3 mL) was added. The solution was stirred 4 d, then diluted with sat. NaHCO$_3$ (25 mL) and extracted with EtOAc (2×50 mL). The combined organic extracts were washed with brine (25 mL), dried over $MgSO_4$, concentrated, and dried under vacuum to give 246 mg (97%) of 345 as a white foam. MS (APCI): m/z 315.0 [M+H]$^+$.

Compound 346: Compound 345 (230 mg, 0.73 mmol) was taken up in THF (6 mL) and ethyl formate (2 mL) and cooled in an ice bath. NaOMe (1.3 g, 30 wt % in MeOH) was added dropwise, and the solution was allowed to warm to RT and stirred overnight. The mixture cooled in an ice bath, quenched by the addition of sat. aq. $KH_2PO_4$ (30 mL), and extracted with EtOAc (2×50 mL). The combined organic extracts were washed with brine (25 mL), dried over $MgSO_4$, concentrated, and dried under vacuum to give 250 mg (100%) of 346 as a light yellow solid. MS (APCI): m/z 343.0 [M+H]$^+$.

Compound 347: Compound 346 (250 mg, 0.73 mmol) was suspended in THF (6 mL), EtOH (3 mL) and water (0.5 mL). Hydroxylamine hydrochloride (76 mg, 1.10 mmol) was added and the mixture was heated at 50° C. for 3 h. The solution was cooled and concentrated. The residue was diluted with sat. aq. NaHCO$_3$ (25 mL) and extracted with EtOAc (2×50 mL). The combined organic extracts were washed with brine (25 mL), dried over $MgSO_4$, concentrated, and dried under vacuum to give 250 mg (100%) of 347 as a light yellow foam. MS (APCI): m/z 340.1 [M+H]$^+$.

Compound 348: Compound 347 (0.73 mmol) was taken up in 3:1 THF/MeOH (8 mL) and NaOMe (1.3 g, 30 wt % in MeOH) was added. The solution was heated at 50° C. for 2 h, then allowed to cool to room temperature and concentrated. Sat. aq. $KH_2PO_4$ (40 mL) was added, and the mixture was extracted with EtOAc (2×50 mL). The combined organic extracts were washed with brine (25 mL), dried over $MgSO_4$, and concentrated to give 250 mg of a light yellow foam. Flash chromatography (10-15% EtOAc/DCM) gave 190 mg (77%) of 348 as a white foam. MS (APCI): m/z 340.1 [M+H]$^+$.

Compound TX63872: Compound 348 (190 mg, 0.56 mmol) was taken up in DMF (5 mL) and cooled in an ice bath. N,N'-Dibromodimethylhydantoin (96 mg, 0.34 mmol) was added and the solution was stirred 2 h at 0° C. Pyridine (1 mL) was added and the solution was heated at 60° C. for 3 h. After cooling, the solution was concentrated and dried under vacuum to a light brown solid. Flash chromatography (5% EtOAc/DCM) gave 150 mg (79%) of TX63872 as a light yellow solid. $^1$H NMR (400 MHz, CDCl$_3$) δ 8.42 (s, 1H), 4.23 (s, 3H), 3.10 (dd, 1H, J=6.0, 17.2 Hz), 2.75-2.86 (m, 1H), 2.48-2.60 (m, 1H), 2.46 (s, 3H), 2.00-2.15 (m, 2H), 1.69-1.83 (m, 1H), 1.43 (s, 3H), 1.30 (d, 3H, J=6.8 Hz); MS (APCI): m/z 338.0 [M+H]$^+$.

Compound 349: Diethyl oxalate (5 g, 10 eq) was added to a suspension of NaH (0.51 g, 60% in oil) in THF (10 mL). A solution of 127 (0.8 g, 3.35 mmol) in THF (10 mL) was added. After refluxing for 16 h, the mixture was cooled, neutralized with sat. $KH_2PO_4$, and extracted with EtOAc (2×25 mL). The EtOAc was washed with brine and dried with $MgSO_4$ to give 349 (1.1 g, 100%). MS: m/z [M+H]$^+$ 311.

Compound 350: A mixture of 349 (1.1 g, 3.35 mmol), methyl hydrazine (310 mg, 6.7 mmol), and EtOH (15 mL) was heated at 60° C. for 16 h. EtOH was removed, and the crude product was passed through a short packed silica gel column, eluted with 50% EtOAc/Hexanes, to give 350 as a white solid (220 mg, 19% yield). MS: m/z [M+H]$^+$ 349.

Compound 351: A solution of the 350 (0.22 g, 0.63 mmol) in MeOH (5 mL) was treated with 3N HCl$_{(aq)}$ (2 mL), stirred at RT overnight. The reaction mixture was concentrated, extracted with EtOAc (2×25 mL) and washed with sat'd NaHCO$_{3(aq)}$ (25 mL). The organic layer was dried with $MgSO_4$, and concentrated to give 351 as a solid. (0.14 g, 73% yield). MS: m/z [M+H]$^+$ 305.

Compound 352: To a solution of 351 (0.14 g, 0.46 mmol) in 5 mL of HCOOEt at RT was added 30% NaOMe in MeOH (0.4 g, 5 eq) dropwise. The reaction mixture was stirred at RT overnight, poured into water and acidified with sat. $KH_2PO_4$. The mixture was extracted with EtOAc (2×25 mL). The combined organic extracts were washed with brine, dried with $MgSO_4$, concentrated in vacuo to give 352 (155 mg, 100% yield). MS: m/z [M+H]$^+$ 333.

Compound 353: To a solution of 352 (155 mg, 0.46 mmol) in 10 mL of EtOH was added NH$_2$OH—HCl (75 mg, 2 eq), and the mixture was heated at 50° C. overnight. After concentration in vacuo, the residue was mixed with water and extracted with EtOAc (2×25 mL). The combined organic extracts were washed with brine, dried with $MgSO_4$, concentrated in vacuo to give 353 (155 mg, 100%). MS: m/z [M+H]$^+$ 330.

Compound 354: To a solution of 353 (155 mg, 0.46 mmol) in 2:1 THF/MeOH (3 mL) of was added MeOH, 30% NaOMe (0.95 g, 10 eq), and the solution was heated at 50° C. for 6 hours. After concentration in vacuo, the residue was mixed with sat. $KH_2PO_4$ (25 mL) and extracted with EtOAc (2×25 mL). The combined organic extracts were washed with brine, dried with MgSO$_4$, and concentrated in vacuo to give 354 (140 mg, 100% yield). MS: m/z [M+H]$^+$ 302.

Compound 355: To a solution of 354 (140 mg, 0.46 mmol) in 2 mL of DMF at 0° C. was added DBDMH (92 mg, 0.55 eq), and the solution was stirred for 2 hours. Pyridine (0.4 g, 10 eq) was added, and the solution was heated at 50° C. overnight. After concentration in vacuo, the residue was purified on a silica gel column, eluted with 25-100% EtOAc/Hexanes to give 355 as an off-white solid (110 mg, 80% yield). MS: m/z [M+H]$^+$ 300.

Compound TX63655: To a solution of 355 (110 mg, 0.36 mmol) in 5 mL of THF at 0° C., was added (COCl)$_2$ (350 mg, 6 eq) and 1 drop of DMF, and the solution was stirred for 3 hours at RT. After evaporation of the solvent, the residue was dissolved in pyridine (5 mL), dimethylamine hydrochloride (450 mg, 10 eq) was added, and mixture was stirred at RT for 16 h. After evaporation of the pyridine, the crude product was purified by silica column chromatography, eluted with 15-50% EtOAc/Hexanes to give TX63655 as an off-white solid (40 mg, 35% yield). $^1$H NMR (500 MHz, DMSO) δ 8.39 (s, 1H), 3.74 (s, 3H), 2.98 (s, 3H), 2.93 (s, 3H), 2.76-2.67 (m, 1H), 2.46-2.40 (m, 2H), 2.20-2.05 (t, 1H, J=2.37, 12.3, 12.5), 1.95-1.85 (m, 1H), 1.65-1.60 (m, 1H), 1.38 (s, 3H), 1.20-1.12 (d, 3H, J=6.61); MS: m/z [M+H]$^+$ 327.

Compound 356: n-BuLi (1.6 M in hexane, 0.6 mL, 0.96 mmol) was added to DIPA (110 mg, 1.1 mmol) in THF (2 mL) at 0° C., stirred for 30 min, and then the reaction was cooled to −78° C. Compound TX63570 (0.2 g, 0.68 mmol) in 1 mL of THF was added dropwise to the LDA solution. The reaction was stirred at −78° C. for 2 h and benzyl bromide (65 mg, 1.1 eq) in 1 mL of THF was added. After stifling for 2 h at 0° C., the mixture was stirred at RT overnight. 1N HCl (2 mL) was added, reaction mixture was extracted with EtOAc (2×25 mL). The combined organic layers were washed with water and brine. The crude product was purified by flash chromatography (silica gel, 5-30% EtOAc/Hexanes) to afford 356 as an oil (115 mg, 45%). MS (APCI): m/z [M+H]$^+$ 383.

Compound 357: Compound 356 (115 mg, 0.3 mmol) was dissolved in THF (15 mL) with 10% Pd/C (65 mg) at RT. The reaction mixture was treated with a hydrogen balloon and stirred for two days, filtered, and concentrated to give 357, 105 mg. MS (APCI): m/z [M+H]$^+$ 385.

Compound 358: To a solution of 357 (105 mg, 0.27 mmol) in 5 mL of HCOOEt at RT, 30% NaOMe in MeOH (0.5 g, 10 eq) was added dropwise. The reaction mixture was stirred at RT overnight, poured into water and acidified with sat. aq. KH$_2$PO$_4$. The mixture was extracted with EtOAc (2×25 mL). The combined organic extracts were washed with brine, dried with MgSO$_4$, and concentrated in vacuo to give 358 (110 g, 98% yield). MS (APCI): m/z [M+H]$^+$ 413.

Compound 359: To a solution of 358 (105 mg, 0.26 mmol) in 5 mL of EtOH, NH$_2$OH HCl salt (85 mg, 2 eq) was added, and the mixture was heated at 50° C. overnight. After concentration in vacuo, the residue was mixed with water and extracted with EtOAc (2×25 mL). The combined organic extracts were washed with brine, dried with MgSO$_4$, and concentrated in vacuo to give 359 (110 mg, 100%). MS (APCI): m/z [M+H]$^+$ 410.

Compound 360: To a solution 359 (110 mg, 0.26 mmol) in 2:1 THF/MeOH (3 mL), 30% NaOMe (0.5 g, 5 eq) was added, and the solution was heated at 50° C. for 9 hours. After concentration in vacuo, the residue was mixed with KH$_2$PO$_4$ (sat., 15 mL) and extracted with EtOAc (2×25 mL). The combined organic extracts were washed with brine, dried with MgSO$_4$, and concentrated in vacuo to give 360 (110 mg, 100% yield). MS (APCI): m/z [M+H]$^+$ 410.

Compound TX63607: To a solution of 360 (110 mg, 0.26 mmol) in 2 mL of DMF at 0° C., DBDMH (42 mg, 0.55 eq) was added, and the solution was stirred for 2 hours. Pyridine (1 g, 50 eq) was added, and the solution was heated at 50° C. overnight. After concentration in vacuo, the residue was purified on a silica gel column, eluted with 5-30% EtOAc/Hexanes to give TX63607 as an off-white solid (41 mg, 39% yield). $^1$H NMR (500 MHz, CDCl$_3$) δ 8.45 (s, 1H), 7.45-7.48 (m, 2H), 7.37-7.42 (m, 1H), 7.23-7.30 (m, 4H), 7.11-7.19 (m, 3H), 3.76 (s, 3H), 3.58 (br d, 1H, J=15 Hz), 3.07 (dd, 1H, J=15, 5 Hz), 2.84 (br d, 1H, J=10 Hz), 2.58 (dd, 1H, J=20, 5 Hz), 2.37-2.44 (m, 1H), 2.16-2.20 (m, 2H), 1.70-1.79 (m, 1H), 1.46 (s, 3H); MS (APCI): m/z [M+H]$^+$ 408.

Compound 361: A solution of KHMDS (658 mg, 3.30 mmol) in THF (6 mL) was cooled to −60° C. A solution of TX63570 (482 mg, 1.65 mmol) in THF (4 mL) was added dropwise. The solution was allowed to warm slowly to 0° C. and stirred 30 min. The solution was re-cooled to −60° C., and benzyl bromide (0.30 mL, 2.47 mmol) was added. The solution was allowed to warm to room temperature over 2 h. Sat. aq. NH$_4$Cl (20 mL) was added, and the mixture was extracted with EtOAc (2×50 mL). The combined organic extracts were washed with brine, dried over MgSO$_4$, and concentrated to give 0.67 g of a crude foam. Flash chromatography (10% EtOAc/DCM) gave 120 mg (15%) of 361 as a light yellow foam. MS (APCI): m/z 473.1 [M+H]$^+$.

Compound 362: Compound 361 (120 mg, 0.25 mmol) was dissolved in THF (15 mL) with 10% Pd/C (65 mg) at RT. The reaction mixture was treated with a hydrogen balloon and stirred for two days, filtered, and concentrated to give 362, 120 mg. MS (APCI): m/z [M+H]$^+$ 475.

Compound 363: To a solution of 362 (120 mg, 0.25 mmol) in 4 mL of HCOOEt at RT, 30% NaOMe in MeOH (0.3 g, 6 eq) was added dropwise. The reaction mixture was stirred at RT overnight, poured into water and acidified with sat. aq. KH$_2$PO$_4$. The mixture was extracted with EtOAc (2×25 mL). The combined organic extracts were washed with brine, dried with MgSO$_4$, concentrated in vacuo to give 363 (120 mg, 95% yield). MS (APCI): m/z [M+H]$^+$ 503.

Compound 364: To a solution of 363 (120 mg, 0.23 mmol) in 5 mL of EtOH, NH$_2$OH—HCl (85 mg, 2 eq) was added and heated at 50° C. overnight. After concentration in vacuo, the residue was mixed with water and extracted with EtOAc (2×25 mL). The combined organic extracts were washed with brine, dried with MgSO$_4$, concentrated in vacuo to give 364 (120 mg, 100%). MS (APCI): m/z [M+H]$^+$ 500.

Compound 365: To a solution of 364 (120 mg, 0.23 mmol) in 2:1 THF/MeOH (3 mL), 30% NaOMe (0.5 g, 5 eq) was added, and the mixture was heated at 50° C. for 12 hours. After concentration in vacuo, the residue was mixed with KH$_2$PO$_4$ (sat., 15 mL) and extracted with EtOAc (2×25 mL). The combined organic extracts were washed with brine, dried with MgSO$_4$, concentrated in vacuo to give 365 (115 mg, 98% yield). MS (APCI): m/z [M+H]$^+$ 500.

Compound TX63601: To a solution of 365 (115 mg, 0.23 mmol) in 2 mL of DMF at 0° C., DBDMH (38 mg, 0.55 eq) was added, and the solution was stirred for 2 hours. Pyridine (1 g, 55 eq) was added, and the solution was heated at 50° C. overnight. After concentration in vacuo, the residue was purified on a silica gel column (5-30% EtOAc/Hexanes) to give TX63601 as an off-white solid (31 mg, 28% yield). $^1$H NMR (500 MHz, CDCl$_3$) δ 8.35 (s, 1H), 7.40-7.48 (m, 3H), 7.25-7.31 (m, 5H), 7.09-7.18 (m, 5H), 6.91 (d, 2H, J=10 Hz), 3.74 (s, 3H), 3.28 (d, 1H, 15 Hz), 3.18 (d, 1H, J=15 Hz), 2.92 (d, 1H, J=15 Hz), 2.62-2.69 (m, 2H), 2.36-2.43 (m, 2H), 2.16 (dd, 1H, J=15, 5 Hz), 2.02-2.08 (m, 1H), 1.65 (s, 3H); MS (APCI): m/z [M+H]$^+$ 498.

Compound 366: A solution of diisopropylamine (0.30 mL, 2.15 mmol) in THF (2 mL) was cooled to −78° C., and BuLi (1.6 M in hexane, 1.35 mL, 2.15 mmol) was added dropwise. The solution was removed from the cooling bath and stirred 15 min. The solution was re-cooled to −78° C. and a solution of TX63570 (0.21 g, 0.72 mmol) in THF (3 mL) was added dropwise. The solution was stirred 15 min, then transferred to an ice bath and stirred 30 min. The solution was re-cooled to −78° C., and a suspension of diphenyliodonium chloride (0.227 g, 0.72 mmol) in DMF (8 mL) was added. The solution was stirred 1 h at −78° C., then allowed to warm to room temperature and stirred 3 h. The solution was quenched with sat. aq. $NH_4Cl$ (20 mL) and extracted with EtOAc (2×50 mL). The combined organic extracts were washed with brine (20 mL), dried over $MgSO_4$, and concentrated to give 0.33 g of a brown oil. Flash chromatography (25% EtOAc/DCM) gave 80 mg (31%) of 366 as white foam. MS (APCI): m/z 369 $[M+H]^+$.

Compound 367: Compound 366 (76 mg, 0.019 mmol) was taken up in THF (5 mL) and 10% Pd/C (20 mg) was added under nitrogen. The mixture was evacuated and purged with $H_2$ (3×), and stirred under a $H_2$ balloon overnight. The mixture was filtered through a fine frit, and the filtrate was concentrated to give 80 mg (>100%) of 367 as a white foam. MS (APCI): m/z 371.1 $[M+H]^+$.

Compound 368: A solution of 367 (75 mg, 0.20 mmol) in ethyl formate (5 mL) was cooled in an ice bath. NaOMe (0.55 g, 30 wt % in MeOH) was added dropwise, and the solution was allowed to warm to RT and stirred overnight. The mixture was quenched by the addition of sat. aq. $KH_2PO_4$ (10 mL) and extracted with EtOAc (2×25 mL). The combined organic extracts were washed with brine, dried over $MgSO_4$, and concentrated to give 90 mg (>100%) of 368 as a tan foam. MS (APCI): m/z 399 $[M+H]^+$.

Compound 369: Compound 368 (0.20 mmol) was taken up in EtOH (3 mL) and water (0.5 mL). Hydroxylamine hydrochloride (15 mg, 0.22 mmol) was added and the reaction was heated at 60° C. for 3 h. The solution was cooled and concentrated. The residue was diluted with sat. aq. $NaHCO_3$ (10 mL) and extracted with EtOAc (2×25 mL). The combined organic extracts were washed with brine (10 mL), dried over $MgSO_4$, and concentrated to give 90 mg (>100%) of 369 as a tan foam. MS (APCI): m/z 396 $[M+H]^+$.

Compound 370: Compound 369 (0.20 mmol) was taken up in 2:1 THF:MeOH (3 mL) and NaOMe (0.3 g, 30 wt % in MeOH) was added. The solution was heated at 50° C. for 4 h, and then allowed to cool to room temperature. Sat. aq. $KH_2PO_4$ (10 mL) was added, and the mixture was extracted with EtOAc (2×25 mL). The combined organic extracts were washed with brine, dried over $MgSO_4$, and concentrated. Flash chromatography (1:2 EtOAc/DCM) gave 72 mg (91%) of 370 as an off-white solid. MS (APCI): m/z 396.1 $[M+H]^+$ Compound TX63629: Compound 370 (71 mg, 0.18 mmol) was taken up in DMF (2 mL) and cooled in an ice bath. N,N'-Dibromodimethylhydantoin (31 mg, 0.11 mmol) was added and the solution was stirred 2 h at 0° C. Pyridine (0.2 mL) was added and the solution was heated at 60° C. for 4 h. After cooling, the solution was concentrated under vacuum to a brown solid. Flash chromatography (20% EtOAc/DCM) gave 56 mg (79%) of TX63629 as a pale yellow solid. MS (APCI): $^1H$ NMR (500 MHz, $CDCl_3$) δ 8.65 (s, 1H), 7.52-7.26 (m, 8H), 7.14 (m, 2H), 3.84 (s, 3H), 3.68 (d, 1H, J=13.6), 2.72 (m, 1H), 2.54-2.39 (m, 2H), 2.67 (m, 1H), 1.63 (s, 3H), 1.46 (m, 1H); m/z 394.1 $[M+H]^+$.

Compound 371: Dimethyl carbonate (3.1 g, 10 eq) was added to a suspension of NaH (0.51 g, 60% in oil) in THF (10 mL). A solution of 127 (0.8 g, 3.35 mmol) in THF (10 mL) was added. After refluxing for 16 h, the solution was cooled, neutralized with $KH_2PO_4$ (conc.), and extracted with EtOAc (2×25 mL). The EtOAc was washed with brine and dried with $MgSO_4$ to give crude compound 371 (1 g, 100%). MS: m/z $[M+H]^+$ 297.

Compound 372: A solution of acetimidamide hydrochloride (3.2 g, 10 eq) and piperidine (1.45 g, 5 eq) in 10 mL of i-PrOH was stirred at RT for 15 min. Crude 371 (1 g, 3.35 mmol) in 5 mL of 2-propanol was added slowly, and stirred at RT for 30 min. The reaction mixture was heated at reflux for two days, then concentrated. The reaction mixture was mixed with ether (50 mL). The product was precipitated, filtered and washed with water, to give 372 as an off-white solid (425 mg, 42% yield). MS: m/z $[M+H]^+$ 305.

Compound 373: To a suspension of 372 (0.4 g, 1.3 mmol) in phosphorus oxychloride (10 mL, 107 mmol) was added two drops of DMF at RT. The resulting mixture was stirred at 140° C. for 3 h. The mixture was then concentrated to dryness, diluted with EtOAc (50 mL) and washed with $NaHCO_3$ (50 mL) and water (50 mL). The organic layer was separated, dried ($MgSO_4$) and evaporated to dryness. Compound 373 was obtained as a crude yellow oil (385 mg, 100%) and was used without further purification.

Compound 374: 30% NaOMe (1.2 g, 5 eq) in MeOH was added dropwise to a stirred solution of 373 in dry MeOH (10 mL). The solution was heated at 50° C. for 3 h. The mixture was then concentrated to dryness, diluted with EtOAc (35 mL) and washed with sat. $KH_2PO_4$ (25 mL), followed by brine, dried ($MgSO_4$) and solvents removed. Purification by silica gel column chromatography using (5-40% EtOAc/Hexanes gradient) gave 374 as an oil (155 mg, 44% yield). MS: m/z $[M+H]^+$ 275.

Compound 375: To a solution of 374 (155 mg, 0.56 mmol) in 5 mL of HCOOEt was added 30% NaOMe in MeOH (1 g, 10 eq) dropwise. The reaction mixture was stirred at RT overnight, poured into water and acidified with sat. $KH_2PO_4$. The mixture was extracted with EtOAc (2×25 mL). The combined organic extracts were washed with brine, dried with $MgSO_4$, and concentrated in vacuo to give 375. (170 mg, 100% yield). MS: m/z $[M+H]^+$ 303.

Compound 376: To a solution of 375 (170 mg, 0.56 mmol) in 10 mL of EtOH was added $NH_2OH$ HCl salt (80 mg, 2 eq), and the mixture was heated at 50° C. overnight. After concentration in vacuo, the residue was mixed with water and extracted with EtOAc (2×25 mL). The combined organic extracts were washed with brine, dried with $MgSO_4$, concentrated in vacuo to give 376 (170 mg, 100% yield). MS: m/z $[M+H]^+$ 300.

Compound 377: To a solution of 376 (170 mg, 0.56 mmol) in 2 mL of THF and 1 mL of MeOH was added 30% NaOMe (1 g, 10 eq), and the solution was heated at 50° C. for 9 hours. After concentration in vacuo, the residue was mixed with sat. $KH_2PO_4$ (15 mL) and extracted with EtOAc (2×25 mL). The combined organic extracts were washed with brine, dried with $MgSO_4$, concentrated in vacuo to give 377 (170 mg, 100% yield). MS: m/z $[M+H]^+$ 300.

Compound TX63646: To a solution of 377 (170 mg, 0.56 mmol) in 2 mL of DMF at 0° C., was added DBDMH (90 mg, 0.55 eq), and the solution was stirred for 2 hours. Pyridine (1 g) was added, and the solution was heated at 50° C. overnight. After concentration in vacuo, the residue was purified on a silica gel column, eluted with 15-40% EtOAc/Hexanes to collect TX63646 as an off-white solid (50 mg, 30% yield). $^1H$ NMR (500 MHz, $CDCl_3$) δ 8.92 (s, 1H), 4.00 (s, 3H), 2.80 (dd, 1H, J=6.7, 18.3 Hz), 2.61 (s, 3H), 2.52-2.60 (m, 2H), 2.04-2.16 (m, 2H), 1.73 (m, 1H), 1.41 (s, 3H), 1.32 (d, 3H, J=6.7 Hz); MS: m/z $[M+H]^+$ 398.

Compound 378: In a sealable vial, a solution of sl. impure 371 (crude from previous step, assume 3.36 mmol) in 20 mL of i-PrOH was treated with solid cyclopropanecarboximidamide hydrochloride (4.05 g, 33.59 mmol) followed by piperidine (1.7 mL, 17.2 mmol). The sample was flushed with $N_2$, sealed and heated (via a block heater) at 90° C. for 72 h. The sample was cooled, concentrated then partitioned between EtOAc and sat. $KH_2PO_4$ solution. The organic extract was washed with sat. NaCl solution, dried ($MgSO_4$), filtered, concentrated and chromatographed (silica gel, 50% EtOAc/Hexanes) to give 0.85 g (77%) of 378 as an off-white solid. MS (APCI) m/z 331 (100%) $[M+H]^+$.

Compound 379: A solution of 378 (0.85 g, 2.58 mmol) in 10 mL of MeOH and 3N HCl (10 mL, 30 mmol) was stirred at room temperature under $N_2$ for 16 h. The sample was concentrated, cooled, basified with 10% aq. $NH_4OH$ solution to a pH~9-10 and extracted with $CHCl_3$. The organic extract was washed with sat. NaCl solution, dried ($MgSO_4$), filtered and concentrated to give 0.70 g (94%) of 379 as an off-white solid. MS (APCI) m/z 287 (100%) $[M+H]^+$.

Compound 380: To a stifling solution of 379 (0.70 g, 2.43 mmol) and N,N-diisopropylethylamine (0.47 mL, 2.70 mmol) in 24 mL of benzene was added dropwise (via syringe) phosphorus oxychloride (2.3 mL, 24.6 mmol). After addition, the sample was heated at 80° C. under $N_2$ for 16 h, cooled, concentrated then carefully partitioned between EtOAc and sat. $NaHCO_3$ solution. The organic extract was washed with sat. NaCl solution, dried ($MgSO_4$), filtered and concentrated to give 0.69 g (94%) of 380 as an off-white solid. MS (APCI) m/z 305/307 (100/47%) $[M+H]^+$.

Compound 381: A solution at room temperature under $N_2$ of 380 (0.32 g, 1.07 mmol) in 10 mL of THF:MeOH (1:1) was treated with NaOMe, 30 wt % solution in MeOH (2.0 mL, 10.7 mmol). The sample was heated at 50° C. for 2 h, cooled, concentrated then partitioned between EtOAc and sat. $KH_2PO_4$ solution. The organic extract was washed with sat. NaCl solution, dried ($MgSO_4$), filtered and concentrated to give 0.34 g (>100%) of sl. impure 381 as a yellow oil, which was used without purification.

Compound 382: To a stirring solution of sl. impure 381 (0.34 g, assume 1.07 mmol) and ethyl formate (9.0 mL, 111.0 mmol) in 10 mL of benzene was added dropwise (via syringe) NaOMe, 30 wt % solution in MeOH (2.0 mL, 10.7 mmol). The sample was stirred at room temperature under $N_2$ for 16 h, concentrated then partitioned between EtOAc and sat. $KH_2PO_4$ solution. The organic extract was washed with sat. NaCl solution, dried ($MgSO_4$), filtered and concentrated to give 0.35 g (>100%) of sl. impure 382 as a dark yellow oil, which was used without purification.

Compound 383: A solution of sl. impure 382 (0.35 g, assume 1.07 mmol) and hydroxylamine hydrochloride (0.11 g, 1.58 mmol) in 25 mL of EtOH was heated at 50° C. under $N_2$ for 2 h then room temperature overnight. The sample was concentrated and partitioned between EtOAc and sat. $NaHCO_3$ solution. The organic extract was washed with sat. NaCl solution, dried ($MgSO_4$), filtered and concentrated to give 0.31 g (90%) of sl. impure 383 as a tan foamy solid, which was used without purification. MS (ES) m/z 326 (100%) $[M+H]^+$.

Compound 384: To a stirring solution of sl. impure 383 (0.31 g, 0.96 mmol) at room temperature under $N_2$ in 20 mL of MeOH was added dropwise (via syringe) NaOMe, 30 wt % solution in MeOH (0.90 mL, 4.80 mmol). The sample was stirred at room temperature for 16 h, concentrated then partitioned between EtOAc and sat. $KH_2PO_4$ solution. The organic extract was washed with sat. NaCl solution, dried ($MgSO_4$), filtered, concentrated and chromatographed (silica gel, 30% EtOAc/Hexanes) to give 0.13 g (41%) 384 as an off-white foamy solid.

Compound TX63761: To a stirring solution at 0° C. under $N_2$ of 384 (0.13 g, 0.40 mmol) in 10 mL of DMF was added in one portion 1,3-dibromo-5,5-dimethylhydantoin (0.057 g, 0.20 mmol). After stirring at 0° C. for 1 h, pyridine (0.33 mL, 4.08 mmol) was added. The ice bath was removed and the sample was heated at 50° C. for 3 h. The sample was cooled, concentrated (to remove most of the DMF and pyridine) then partitioned between EtOAc and sat. $NaHCO_3$ solution. The organic extract was washed with sat. $KH_2PO_4$ and sat. NaCl solutions, dried ($MgSO_4$), filtered, concentrated and chromatographed (silica gel, 30% EtOAc/Hexanes) to give 0.030 g (23%) of TX63761 as an off-white solid. $^1$H NMR (400 MHz, $CDCl_3$) δ 8.88 (s, 1H), 3.94 (s, 3H), 2.75 (dd, 1H, J=7.0, 18.2 Hz), 2.52 (m, 2H), 2.16 (m, 1H), 2.06 (m, 2H), 1.68 (dq, 1H, J=6.5, 12.8 Hz), 1.38 (s, 3H), 1.29 (d, 3H, J=6.8 Hz), 1.10 (m, 2H), 1.02 (m, 2H); MS (APCI) m/z 324 (100%) $[M+H]^+$.

Compound 385: In a sealable vial, a solution of 371 (crude from previous step, assume 4.20 mmol) in 15 mL of n-BuOH was treated with solid 2,2-dimethylpropionamidine hydrochloride (5.0 g, 36.6 mmol) followed by piperidine (2.1 mL, 21.2 mmol). The sample was flushed with $N_2$, sealed and heated (via a block heater) at 100° C. for 72 h. The sample was cooled, concentrated then partitioned between EtOAc and sat. $NaHCO_3$ solution. The organic extract was washed with sat. NaCl solution, dried ($MgSO_4$), filtered, concentrated and chromatographed (silica gel, 50% EtOAc/Hexanes) to give 0.87 g (60%) of 385 as a tan gummy solid. MS (APCI) m/z 347 (100%) $[M+H]^+$.

Compound 386: A solution of 385 (0.87 g, 2.50 mmol) and N,N-diisopropylethylamine (0.48 mL, 2.76 mmol) in 10 mL of benzene was added dropwise (via syringe) phosphorus oxychloride (2.3 mL, 24.7 mmol). After addition, the sample was heated at 90° C. under $N_2$ for 2 h then room temperature overnight. The sample was concentrated then carefully partitioned between EtOAc and sat. $NaHCO_3$ solution. The organic extract was washed with sat. NaCl solution, dried ($MgSO_4$), filtered and concentrated to give 0.85 g (93%) of 386 as a light yellow oil, which was used without purification. MS (APCI) m/z 365/367 (100/38%) $[M+H]^+$.

Compound 387: A solution of 386 (0.42 g, 1.16 mmol) in 10 mL of MeOH was treated with NaOMe, 30 wt % solution in MeOH (1.1 mL, 5.9 mmol). The sample was flushed with $N_2$, sealed and heated at 80° C. for 48 h. The sample was cooled, concentrated then partitioned between EtOAc and sat. $KH_2PO_4$ solution. The organic extract was washed with sat. NaCl solution, dried ($MgSO_4$), filtered and concentrated to give 0.42 g (~100%) of 387 as a dark yellow oil, which was used without purification.

Compound 388: A solution of 387 (0.42 g, 1.16 mmol) and 3N HCl (10 mL, 30 mmol) in 10 mL of MeOH was stirred at room temperature under $N_2$ for 16 h. The sample was concentrated, cooled, basified with 10% aq. $NH_4OH$ solution to a pH~9-10 and extracted with EtOAc. The organic extract was washed with sat. NaCl solution, dried ($MgSO_4$), filtered and concentrated to give 0.34 g (92%) of 388 as a yellow solid, which was used without purification. MS (APCI) m/z 317 (100%) $[M+H]^+$.

Compound 389: To a stirring solution of 388 (0.34 g, 1.07 mmol) and ethyl formate (10 mL, 124 mmol) in 10 mL of benzene was added dropwise (via syringe) NaOMe, 30 wt % solution in MeOH (1.0 mL, 5.3 mmol). The sample was stirred at room temperature under $N_2$ for 16 h, concentrated then partitioned between EtOAc and sat. $KH_2PO_4$ solution. The organic extract was washed with sat. NaCl solution, dried (MgSO$_4$), filtered and concentrated to give 0.36 g (97%) of 389 as a dark yellow oil, which was used without purification. MS (APCI) m/z 345 (100%) [M+H]$^+$.

Compound 390: A solution of 389 (0.36 g, 1.04 mmol) and hydroxylamine hydrochloride (0.11 g, 1.58 mmol) in 10 mL of EtOH was heated at 50° C. under N$_2$ for 2 h then room temperature overnight. The sample was concentrated and partitioned between EtOAc and sat. NaHCO$_3$ solution. The organic extract was washed with sat. NaCl solution, dried (MgSO$_4$), filtered and concentrated to give 0.59 g (>100%) of 390 as a dark yellow oil, which was used without purification.

Compound 391: To a stifling solution of sl. impure 390 (crude from previous step, assume 1.04 mmol) at room temperature under N$_2$ in 10 mL of MeOH:THF (1:1) was added dropwise (via syringe) NaOMe, 30 wt % solution in MeOH (0.98 mL, 5.22 mmol). The sample was stirred at room temperature for 16 h, concentrated then partitioned between EtOAc and sat. KH$_2$PO$_4$ solution. The organic extract was washed with sat. NaCl solution, dried (MgSO$_4$), filtered, concentrated and chromatographed (silica gel, 20% EtOAc/Hexanes) to give 0.18 g (50%) 391 as a light yellow oil. MS (APCI) m/z 342 (100%) [M+H]$^+$.

Compound TX63853: To a stirring solution at 0° C. under N$_2$ of 391 (0.18 g, 0.52 mmol) in 10 mL of DMF was added in one portion 1,3-dibromo-5,5-dimethylhydantoin (0.075 g, 0.26 mmol). After stirring at 0° C. for 1 h, pyridine (0.42 mL, 5.20 mmol) was added. The ice bath was removed and the sample was heated at 50° C. for 2 h. The sample was cooled, concentrated (to remove most of the DMF and pyridine) then partitioned between EtOAc and sat. KH$_2$PO$_4$ solution. The organic extract was washed with sat. NaCl solution, dried (MgSO$_4$), filtered, concentrated and chromatographed (silica gel, 20% EtOAc/Hexanes) to give 0.068 g (38%) of TX63853 as a light yellow solid. $^1$H NMR (400 MHz, CDCl$_3$) δ 8.60 (s, 1H), 3.97 (s, 3H), 2.76 (dd, 1H, J=6.4, 18.0 Hz), 2.51-2.60 (m, 2H), 2.00-2.15 (m, 2H), 1.60-1.75 (m, 1H), 1.36 (s, 12H), 1.28 (d, 3H, J=6.8 Hz); MS (APCI) m/z 340 (100%) [M+H]$^+$.

Compound 392: KOt-Bu (250 mg, 1 eq) was dissolved in anhydrous EtOH (20 mL). Thiourea (1.7 g, 10 eq) and 371 (950 mg, 3.2 mmol) were added to the base solution. The reaction mixture was refluxed for 16 h. The solvent concentrated under vacuo to nearly dryness and the residue was redissolved in water (10 mL). The solution was neutralized with 3N HCl, the precipitate was collected, washed with water, and dried under vacuum to give 392 (900 mg, 87% yield). MS: m/z [M+H]$^+$ 323.

Compound 393: Compound 392 (900 mg, 2.79 mmol) was dissolved in DMF (10 mL), and K$_2$CO$_3$ (1.2 g, 3 eq) was added, and the mixture was stirred for 30 min. MeI (0.8 g, 2 eq) was added dropwise, and the mixture was stirred at RT for 2 h. The reaction mixture was quenched with water (100 mL) and extracted with EtOAc (2×50 mL). The organic layer was washed with water and brine, and concentrated to give 393 (975 mg, 100% yield). MS: m/z [M+H]$^+$ 351.

Compound 394: To a stirred mixture of 393 (975 mg, 2.79 mmol) and Pd (PPh$_3$)$_4$ (200 mg, 5 mol %) in THF (20 mL) under nitrogen, phenylboronic acid (1 g, 3 eq) and CuTC (1.8 g, 3.5 eq) were added. The reaction mixture was heated at reflux for 16 h. The solvent was removed in vacuo and the residue was purified by a silica gel column chromatography, eluted with 10-35% EtOAc/Hexanes to give 394 as a solid (415 mg, 40% yield). MS: m/z [M+H]$^+$ 381.

Compound 395: A solution of 394 (455 mg, 1.2 mmol) in MeOH (10 mL) was treated with 3N HCl$_{(aq)}$ (3 mL), and stirred at RT overnight. The reaction mixture was concentrated, extracted by EtOAc (2×25 mL) and washed with sat'd NaHCO$_{3(aq)}$ (25 mL). The organic layer was dried with MgSO$_4$, and concentrated to give 395 as an oil (405 mg, 100% yield). MS: m/z [M+H]$^+$ 337.

Compound 396: To a solution of 395 (405 mg, 1.2 mmol) in 5 mL of HCOOEt was added dropwise 30% NaOMe in MeOH (1.3 g, 6 eq). The reaction mixture was stirred at RT overnight, then poured into water and acidified with sat. KH$_2$PO$_4$. The mixture was extracted with EtOAc (2×25 mL). The combined organic extracts were washed with brine, dried with MgSO$_4$, concentrated in vacuo to give 396 (435 mg, 100% yield). MS: m/z [M+H]$^+$ 365.

Compound 397: To a solution of 396 (435 mg, 1.18 mmol) in 20 mL of EtOH was added NH$_2$OH HCl salt (170 mg, 2 eq), and the mixture was heated at 50° C. overnight. After concentration in vacuo, the residue was mixed with water and extracted with EtOAc (2×25 mL). The combined organic extracts were washed with brine, dried with MgSO$_4$, and concentrated in vacuo to give 397 (430 mg, 98% yield). MS: m/z [M+H]$^+$ 362.

Compound 398: To a solution of 397 (430 mg, 1.18 mmol) in 2 mL of THF and 2 mL of MeOH was added 30% NaOMe (1.7 g, 8 eq), and the solution was heated at 50° C. for 6 hours. After concentration in vacuo, the residue was mixed with sat. KH$_2$PO$_4$ (25 mL) and extracted with EtOAc (2×25 mL). The combined organic extracts were washed with water and brine, dried with MgSO$_4$, and purified on a silica gel column, eluted with 15-45% EtOAc/Hexanes to give 398 as an off-white solid (215 mg, 50% yield). MS: m/z [M+H]$^+$ 362.

Compound TX63666: To a solution of 398 (210 mg, 0.58 mmol) in 2 mL of DMF at 0° C. was added 1,3-dibromo-5,5-dimethylhydantoin (95 mg, 0.55 eq), and the solution was stirred for 2 hours. Pyridine (1 g) was added, and the solution was heated at 50° C. overnight. After concentration in vacuo, the residue was purified on a silica gel column, eluted with 15-45% EtOAc/Hexanes to give TX63666 as an off-white solid (130 mg, 62% yield). $^1$H NMR (500 MHz, CDCl$_3$) δ 8.76 (s, 1H), 7.58 (m, 5H), 3.50 (s, 3H), 2.90 (m, 1H), 2.52-2.61 (m, 2H), 2.05-2.20 (m, 2H), 1.72 (m, 1H), 1.45 (s, 3H), 1.34 (d, 3H, J=6.6 Hz); MS: m/z [M+H]$^+$ 360.

Compound 399: A mixture of 392 (2.6 g, 8.06 mmol) and 8.1 g of chloroacetic acid (10 eq) was heated at 100° C. for 1 h, then 10 mL of water was added and heating continued for another 5 h. Concentrated HCl (0.5 mL) was added and the mixture was heated at 100° C. for 16 h. The reaction was cooled and 50 mL of ice water was added. The precipitate was collected by filtration, and dried under vacuum to give 399 as an off-white solid (2.1 g, 93% yield). MS: m/z [M+H]$^+$ 263.

Compound 400: A mixture of 399 (2.03 g, 7.73 mmol) and diisopropylethylamine (1.01 g, 1 eq) in 10 mL of POCl$_3$ was heated at 90° C. for 16 h. The reaction was quenched with ice and the product was precipitated, filtered and dried under vacuum to give 400 as a brown solid (2.1 g, 90% yield). MS: m/z 299, 301 (3:2) [M+H]$^+$.

Compound 401a-b: A solution of 400 (2.05 g, 6.85 mmol), NaOMe (1.85 g, 1.5 eq, 30% in MeOH) and 25 mL of MeOH was heated at 50° C. for 1 h. The reaction mixture was concentrated, extracted with EtOAc (2×20 mL), washed with water, and purified on a silica gel column, with 10-15% EtOAc/Hexanes elution. The first compound obtained was 401a (1.3 g, 65% yield), MS: m/z 295, 297 (3:1) [M+H]$^+$. The second compound obtained was 401b (110 mg, 5.5% yield), MS: m/z 291 [M+H]$^+$.

Compound 402: To a solution of 401a (130 mg, 0.44 mmol) in 5 mL of HCOOEt was added dropwise 30% NaOMe in MeOH (0.5 g, 6 eq). The reaction mixture was stirred at RT overnight, then poured into water and acidified with KH$_2$PO$_4$. The mixture was extracted with EtOAc (2×25 mL). The combined organic extracts were washed with brine, dried with MgSO$_4$, and concentrated in vacuo to give 402 (140 mg, 100% yield). MS: m/z [M+H]$^+$ 319.

Compound 403: To a solution of 402 (140 mg, 0.44 mmol) in 10 mL of EtOH was added NH$_2$OH HCl salt (65 mg, 2 eq), and the mixture was heated at 50° C. overnight. After concentration in vacuo, the residue was mixed with water and extracted with EtOAc (2×25 mL). The combined organic extracts were washed with brine, dried with MgSO$_4$, concentrated in vacuo to give 403 (138 mg, 100% yield). MS: m/z [M+H]$^+$ 316.

Compound 404: To a solution of 403 (138 mg, 0.44 mmol) in 2 mL of THF and 1 mL of MeOH was added dropwise 30% NaOMe (0.63 g, 8 eq), and the solution was heated at 50° C. for 6 hours. After concentration in vacuo, the residue was mixed with sat. KH$_2$PO$_4$ (15 mL) and extracted with EtOAc (2×25 mL). The combined organic extracts were washed with brine, dried with MgSO$_4$, concentrated in vacuo to give 404 (136 mg, 100% yield). MS: m/z [M+H]$^+$ 316.

Compound TX63718: To a solution of 404 (136 mg, 0.44 mmol) in 2 mL of DMF at 0° C. was added 1,3-dibromo-5,5-dimethylhydantoin (70 mg, 0.55 eq), and the solution was stirred for 2 hours. Pyridine (1 g) was added, and the solution was heated at 50° C. overnight. After concentration in vacuo, the residue was purified on a silica gel column, eluted with 5-30% EtOAc/Hexanes to give TX63718 as an off-white solid (55 mg, 40% yield). $^1$H NMR (400 MHz, CDCl$_3$) δ 8.71 (s, 1H), 3.94 (s, 3H), 3.92 (s, 3H), 2.67 (dd, 1H, J=7.0, 17.5 Hz), 2.37-2.51 (m, 2H), 1.95-2.06 (m, 2H), 1.62 (m, 1H), 1.33 (s, 3H), 1.22 (d, 3H, J=6.5 Hz); MS: m/z [M+H]$^+$ 314.

Compounds TX63793 and TX63794: The enantiomers of compound TX63718 (32.7 mg) were separated using chiral HPLC(CHIRALPAK IA, 5μ, 30×250 mm, 2:50:50 EtOH/EtOAc/Hexane) to afford two well resolved two peaks. One is at 4.04 min, which gave TX63793 (17.6 mg, >99.9% ee). $^1$H NMR (400 MHz, CDCl$_3$) δ 8.79 (s, 1H), 4.02 (s, 3H), 4.00 (s, 3H), 2.75 (dd, 1H, J=6.4, 18.0 Hz), 2.52 (m, 2H), 2.09 (m, 2H), 1.70 (m, 1H), 1.41 (s, 3H), 1.30 (d, 3H, J=6.7 Hz). And another one is at 4.66 min, which gave TX63794 (15.1 mg, 98.8% ee). $^1$H NMR (400 MHz, CDCl$_3$) δ 8.79 (s, 1H), 4.02 (s, 3H), 4.00 (s, 3H), 2.75 (dd, 1H, J=6.4, 18.0 Hz), 2.52 (m, 2H), 2.09 (m, 2H), 1.70 (m, 1H), 1.41 (s, 3H), 1.30 (d, 3H, J=6.7 Hz).

Compound 405a: Compound 401b (0.25 g, 0.84 mmol) was dissolved in DME (6 mL) and DMF (3 mL). To this solution was added pyridin-3-ylboronic acid (125 mg, 1 mmol), Ph$_3$P (85 mg, 0.32 mmol) and K$_3$PO$_4$ (0.54 g, 2.54 mmol). Nitrogen was bubbled through the mixture for 10 min. Pd(OAc)$_2$ (35 mg, 0.16 mmol) was added and nitrogen bubbled for another 10 min. The suspension was heated to 90° C. for 16 hours. The reaction mixture was filtered, concentrated, and purified on a silica gel column, eluted with 5-35% EtOAc/Hexanes to give 405a as a solid (0.28 g, 98% yield). MS: m/z [M+H]$^+$ 338.

Compound 405b: Pyridin-4-ylboronic acid (125 mg, 1 mmol) was treated according to the procedure for compound 401b to give 405bb (270 mg, 95% yield). MS: m/z [M+H]$^+$ 338.

Compound 405c: 2-Methoxyphenylboronic acid (155 mg, 1 mmol) was treated according to the procedure for compound 401b to give 405c (150 mg, 49% yield). MS: m/z [M+H]$^+$ 367.

Compound 405d: Phenylboronic acid (155 mg, 1 mmol) was treated according to the procedure for compound 401b to give 405d (185 mg, 65% yield). MS: m/z [M+H]$^+$ 337.

Compound 405e: Pyrimidin-5-ylboronic acid (140 mg, 1.13 mmol) was treated according to the procedure for compound 401b to give 405e (185 mg, 58% yield). MS: m/z [M+H]$^+$ 339.

Compound 406a: To a solution of 405a (280 mg, 0.82 mmol) in 10 mL of HCOOEt was added dropwise 30% NaOMe in MeOH (6 eq). The reaction mixture was stirred at RT overnight, then poured into water and acidified with KH$_2$PO$_4$. The mixture was extracted with EtOAc. The combined organic extracts were washed with brine, dried with MgSO$_4$, and concentrated in vacuo to give 406a (300 mg). MS: m/z [M+H]$^+$ 366.

Compound 406b: Compound 405b (270 mg, 0.82 mmol) was treated according to the procedure for compound 406a to give the title compound 406b (290 mg). MS: m/z [M+H]$^+$ 366.

Compound 406c: Compound 405c (150 mg, 0.4 mmol) was treated according to the procedure for compound 406a to give the title compound 406c (120 mg). MS: m/z [M+H]$^+$ 395.

Compound 406d: Compound 405d (185 mg, 0.51 mmol) was treated according to the procedure for compound 406a to give the title compound 406d (185 mg). MS: m/z [M+H]$^+$ 365.

Compound 406e: Compound 405e (175 mg, 0.51 mmol) was treated according to the procedure for compound 406a to give the title compound 406e (185 mg). MS: m/z [M+H]$^+$ 367.

Compound 407a: To a solution of 406a (300 mg, 0.82 mmol) in 20 mL of EtOH was added NH$_2$OH HCl salt (2 eq), and the mixture was heated at 50° C. overnight. After concentration in vacuo, the residue was mixed with water and extracted with EtOAc. The combined organic extracts were washed with brine, dried with MgSO$_4$, concentrated in vacuo to give 407a (280 mg). MS: m/z [M+H]$^+$ 363.

Compound 407b: Compound 406b (290 mg, 0.79 mmol) was treated according to the procedure for compound 407a to give the title compound 407b (290 mg). MS: m/z [M+H]$^+$ 363.

Compound 407c: Compound 406c (120 mg, 0.3 mmol) was treated according to the procedure for compound 407a to give the title compound 407c (117 mg). MS: m/z [M+H]$^+$ 392.

Compound 407d: Compound 406d (130 mg, 0.34 mmol) was treated according to the procedure for compound 407a to give the title compound 407d (120 mg). MS: m/z [M+H]$^+$ 376.

Compound 407e: Compound 406e (185 mg, 0.5 mmol) was treated according to the procedure for compound 407a to give the title compound 407e (180 mg). MS: m/z [M+H]$^+$ 364.

Compound 408a: To a solution of compound 407a (280 mg, 0.78 mmol) in 4 mL of THF and 2 mL of MeOH was added dropwise 30% NaOMe (8 eq), and the solution was heated at 50° C. for 6 hours. After concentration in vacuo, the residue was mixed with sat. KH$_2$PO$_4$ solution (30 mL) and extracted with EtOAc. The combined organic extracts were washed with brine, dried with MgSO$_4$, concentrated in vacuo to give 408a (220 mg). MS: m/z [M+H]$^+$ 363.

Compound 408b: Compound 407b (290 mg, 0.79 mmol) was treated according to the procedure for compound 408a to give the title compound 408b (280 mg). MS: m/z [M+H]$^+$ 363.

Compound 408c: Compound 407c (117 mg, 0.3 mmol) was treated according to the procedure for compound 408a to give the title compound 408c (117 mg). MS: m/z [M+H]$^+$ 392.

Compound 408d: Compound 407d (120 mg, 0.32 mmol) was treated according to the procedure for compound 408a to give the title compound 408d (110 mg). MS: m/z [M+H]+ 376.

Compound 408e: Compound 407e (180 mg, 0.5 mmol) was treated according to the procedure for compound 408a to give the title compound 408e (180 mg). MS: m/z [M+H]+ 364.

Compound TX63724: Compound 408a (0.19 g, 0.52 mmol) was dissolved in 2 mL of DMF at 0° C. $Br_2$ (95 mg, 1.1 eq) was added, and the solution was stirred for 2 hours. Pyridine (2 mL) was added, and the solution was heated at 50° C. overnight. After concentration in vacuo, the residue was purified on a silica gel column, eluted with 5-45% EtOAc/Hexanes to give TX63724 as an off-white solid (45 mg, 24% yield). $^1$H NMR (400 MHz, $CDCl_3$) δ 9.60 (s, 1H), 8.86 (s, 1H), 8.77 (m, 1H), 8.67 (m, 1H), 7.48 (dd, 1H, J=4.9, 7.8 Hz), 4.06 (s, 3H), 2.82 (ddd, 1H, J=1.6, 6.8, 18.7 Hz), 2.47-2.64 (m, 2H), 2.03-2.13 (m, 2H), 1.69 (m, 1H), 1.40 (s, 3H), 1.25 (d, 3H, J=6.7 Hz); MS: m/z [M+H]+ 361.

Compound TX63728: Compound 408b (0.28 g, 0.77 mmol) was treated according to the procedure for compound TX63724 to give TX63728 (25 mg, 9%). $^1$H NMR (400 MHz, $CDCl_3$) δ 8.59 (s, 1H), 8.46 (bs, 2H), 3.80 (s, 3H), 2.56 (dd, 1H, J=5.9, 18.9 Hz), 2.22-2.35 (m, 2H), 1.75-1.87 (m, 2H), 1.44 (m, 1H), 1.13 (s, 3H), 0.99 (d, 3H, J=6.7 Hz); MS: m/z [M+H]+ 361.

Compound TX63727: To a solution of compound 408c (0.117 g, 0.3 mmol) in 2 mL of DMF at 0° C. was added 1,3-dibromo-5,5-dimethylhydantoin (0.55 eq), and the solution was stirred for 2 hours. Pyridine (1 g) was added, and the solution was heated at 50° C. overnight. After concentration in vacuo, the residue was purified on a silica gel column, eluted with 5-30% EtOAc/Hexanes to give 45 (80 mg). $^1$H NMR (400 MHz, $CDCl_3$) δ 8.97 (s, 1H), 7.81 (dd, 1H, J=1.8, 7.6 Hz), 7.42 (m, 1H), 7.04-7.09 (m, 2H), 4.03 (s, 3H), 3.89 (s, 3H), 2.85 (ddd, 1H, J=1.0, 6.7, 18.5 Hz), 2.51-2.66 (m, 2H), 2.07-2.17 (m, 2H), 1.75 (m, 1H), 1.43 (s, 3H), 1.30 (d, 3H, J=6.7 Hz); MS: m/z [M+H]+ 390.

Compound TX63769: Compound 408d (110 mg, 0.29 mmol) was treated according to the procedure for compound TX63727 to give TX63769 (75 mg, 69%). $^1$H NMR (400 MHz, $CDCl_3$) δ 9.00 (s, 1H), 8.46 (m, 2H), 7.49 (m, 2H), 4.10 (s, 3H), 2.86 (ddd, 1H, J=1.0, 6.8, 18.4 Hz), 2.59 (m, 2H), 2.13 (m, 2H), 1.74 (m, 2H), 1.45 (s, 3H), 1.31 (d, 3H, J=6.7 Hz); MS: m/z [M+H]+ 374.

Compound TX63757: Compound 408e (180 mg, 0.5 mmol) was treated according to the procedure for compound TX63724 to give TX63757 (100 mg). $^1$H NMR (400 MHz, $CDCl_3$) δ 9.70 (s, 2H), 9.33 (s, 1H), 8.89 (s, 1H), 4.13 (s, 3H), 2.90 (ddd, 1H, J=0.9, 6.6, 18.8 Hz), 2.63 (m, 2H), 2.16 (m, 2H), 1.77 (m, 1H), 3.49 (s, 3H), 1.33 (d, 3H, J=6.8 Hz); MS: m/z [M+H]+ 362.

Compound 409: Compound 401b (515 mg, 1.75 mmol) was dissolved in DMAc (10 mL). To this solution was added $Zn(CN)_2$ (135 mg, 1.15 mmol), dppf (200 mg, 0.36 mmol) and $Na_2CO_3$ (190 mg, 1.75 mmol). Nitrogen was bubbled through the mixture for 10 min. $Pd(OAc)_2$ (40 mg, 0.018 mmol) was added and nitrogen bubbled for another 10 min. The suspension was heated to 120° C. for 16 hours. The reaction mixture was quenched with 50 mL of water and extracted with ether (2×50 mL). The organic extracts were concentrated, and purified on a silica gel column, eluted with 5-20% EtOAc/Hexanes to give 409 as an off-white solid (0.2 g, 40% yield). MS (APCI): m/z [M+H]+ 286.

Compound 410: To a solution of 409 (0.2 g, 0.7 mmol) in 10 mL of HCOOEt was added dropwise 30% NaOMe in MeOH (6 eq). The reaction mixture was stirred at RT overnight, then poured into water and acidified with $KH_2PO_4$. The mixture was extracted with EtOAc. The combined organic extracts were washed with brine, dried with $MgSO_4$, and concentrated in vacuo to give 410 (220 mg). MS: m/z [M+H]+ 361.

Compound 411: To a solution of 410 (0.22 g, 0.7 mmol) in 20 mL of EtOH was added $NH_2OH$ HCl salt (2 eq), and the mixture was heated at 50° C. overnight. After concentration in vacuo, the residue was mixed with water and extracted with EtOAc. The combined organic extracts were washed with brine, dried with $MgSO_4$, concentrated in vacuo to give 411 (60 mg, 30% yield). MS: m/z [M+H]+ 358.

Compound 412: A solution of 411 (60 mg, 0.17 mmol) and 1 mL of triethylamine in 2 mL of acetonitrile was heated at 85° C. for 16 h. The reaction mixture was pumped under vacuo to dryness to give 412 (60 mg). MS: m/z [M+H]+ 358.

Compound TX63730: To a solution of compound 412 (60 mg, 0.17 mmol) in 1 mL of DMF at 0° C. was added 1,3-dibromo-5,5-dimethylhydantoin (0.55 eq), and the solution was stirred for 2 hours. Pyridine (1 g) was added, and the solution was heated at 50° C. overnight. After concentration in vacuo, the residue was purified on a silica gel column, eluted with 5-30% EtOAc/Hexanes to give TX63730 (25 mg, 41%). $^1$H NMR (400 MHz, $CDCl_3$) δ 8.83 (s, 1H), 4.42 (m, 2H), 4.03 (s, 3H), 2.82 (m, 1H), 2.45-2.63 (m, 2H), 2.10 (m, 1H), 2.02 (dd, 1H, J=2.7, 12.8 Hz), 1.70 (m, 1H), 1.39 (t, 3H, J=7.1 Hz), 1.37 (s, 3H), 1.25 (d, 3H, J=6.7 Hz); MS: m/z [M+H]+ 356.

Compound 413: A solution of sl. impure 372 (1.39 g, assume 4.20 mmol) and N,N-diisopropylethylamine (0.80 mL, 4.60 mmol) in 20 mL of benzene was added dropwise (via syringe) phosphorus oxychloride (4.0 mL, 42.9 mmol). After addition, the sample was heated at 90° C. under $N_2$ for 4 h, cooled, concentrated then carefully partitioned between EtOAc and sat. $NaHCO_3$ solution. The organic extract was washed with sat. NaCl solution, dried ($MgSO_4$), filtered, concentrated and chromatographed (silica gel, 30% EtOAc/Hexanes) to give 0.75 g (55%) of 413 as light yellow oil. MS (APCI) m/z 323/325 [M+H]+ (100/91%).

Compound 414a: A solution of 413 (0.44 g, 1.36 mmol), N,N-diisopropylethylamine (1.00 mL, 5.74 mmol) and morpholine (0.24 mL, 2.75 mmol) in 10 mL of i-PrOH was flushed with $N_2$, sealed and heated at 90° C. for 48 h. The sample was cooled, concentrated then partitioned between EtOAc and sat. $KH_2PO_4$ solution. The organic extract was washed with sat. NaCl solution, dried ($MgSO_4$), filtered and concentrated to give 0.50 g (98%) of 414a as a light tan foamy solid, which was used without purification. MS (APCI): m/z 374 [M+H]+ (100%).

Compound 415a: A solution of 414a (0.50 g, 1.34 mmol) and 3 N HCl (5 mL, 15 mmol) in 5 mL of MeOH was stirred at room temperature under $N_2$ for 16 h. The sample was concentrated, cooled, basified with 10% aq. $NH_4OH$ solution to a pH~9-10 and extracted with EtOAc. The organic extract was washed with sat. NaCl solution, dried ($MgSO_4$), filtered and concentrated to give 0.37 g (84%) of 415a as a tan solid, which was used without purification. MS (APCI) m/z 330 [M+H]+ (100%).

Compound 416a: To a stirring solution of sl. impure 415a (0.37 g, 1.12 mmol) and ethyl formate (9.0 mL, 111.0 mmol) in 10 mL of benzene was added dropwise (via syringe) NaOMe, 30 wt % solution in MeOH (1.0 mL, 5.3 mmol). The sample was stirred at room temperature under $N_2$ for 16 h, concentrated then partitioned between EtOAc and sat. $KH_2PO_4$ solution. The organic extract was washed with sat. NaCl solution, dried ($MgSO_4$), filtered and concentrated to give 0.45 g (>100%) of sl. impure 416a as a dark yellow oil, which was used without purification.

Compound 417a: A solution of sl. impure 416a (0.45 g, assume 1.12 mmol) and hydroxylamine hydrochloride (0.12 g, 1.73 mmol) in 20 mL of EtOH was heated at 50° C. under $N_2$ for 2 h, cooled, concentrated and partitioned between $CHCl_3$ and sat. $NaHCO_3$ solution. The organic extract was washed with sat. NaCl solution, dried ($MgSO_4$), filtered and concentrated to give 0.47 g (100%) of a dark yellow oil, which by TLC and MS was a mixture of desired 417a and undehydrated product. TLC (silica gel, 50% EtOAc/Hexanes) 2 components; $R_f$=0.47 and 0.12. MS (ES) m/z 355 (100%) $[M+H]^+$. A solution of the above mixture (entire amount) and a pinch of p-toluenesulfonic acid monohydrate in 50 mL of benzene were heated at 90° C. under $N_2$ for 2 h (TLC showed no lower component remaining). The sample was cooled and concentrated to give 0.77 g (>>100%) of 417a as a dark yellow oil, which was used without purification.

Compound 418a: To a stirring solution of sl. impure 417a (entire amount of crude mixture from previous step, assume 1.12 mmol) at room temperature under $N_2$ in 10 mL of MeOH was added dropwise (via syringe) NaOMe, 30 wt % solution in MeOH (1.1 mL, 5.9 mmol). The sample was stirred at room temperature for 16 h, concentrated then partitioned between EtOAc and sat. $KH_2PO_4$ solution. The organic extract was washed with sat. NaCl solution, dried ($MgSO_4$), filtered and concentrated to give 0.37 g (94%) of 418a as a yellow solid, which was used without purification.

Compound TX63758: To a stirring solution at 0° C. under $N_2$ of sl. impure 418a (0.37 g, 1.05 mmol) in 10 mL of DMF was added in one portion 1,3-dibromo-5,5-dimethylhydantoin (0.15 g, 0.52 mmol). After stifling at 0° C. for 1 h, pyridine (1.0 mL, 12 mmol) was added. The ice bath was removed and the sample was heated at 50° C. for 2 h. The sample was cooled, concentrated (to remove most of the DMF and pyridine) then partitioned between EtOAc and sat. $KH_2PO_4$ solution. The organic extract was washed with sat. NaCl solution, dried ($MgSO_4$), filtered, concentrated and chromatographed (silica gel, 40% EtOAc/Hexanes) to give 0.20 g (54%) of TX63758 as a light yellow solid. $^1H$ NMR (400 MHz, $CDCl_3$) δ 8.84 (s, 1H), 3.84 (ddd, 2H, J=2.9, 6.4, 11.3 Hz), 3.75 (ddd, 2H, J=2.8, 6.6, 11.2 Hz), 3.43 (ddd, 2H, J=2.4, 6.4, 13.1 Hz), 3.22 (ddd, 2H, J=2.4, 6.5, 13.1 Hz), 2.68 (m, 2H), 2.55 (m, 1H), 2.55 (s, 3H), 2.11 (m, 2H), 1.69 (m, 1H), 1.39 (s, 3H), 1.29 (d, 3H, J=6.7 Hz); MS (APCI) m/z 353 $[M+H]^+$ (100%).

Compound 414b: A mixture of 413 (0.38 g, 1.17 mmol), N,N-diisopropylethylamine (0.72 mL, 4.13 mmol) and dimethylamine hydrochloride (0.11 g, 1.35 mmol) in 10 mL of n-BuOH was flushed with $N_2$, sealed and heated at 90° C. for 16 h. The sample was cooled, concentrated then partitioned between EtOAc and sat. $KH_2PO_4$ solution. The organic extract was washed with sat. NaCl solution, dried ($MgSO_4$), filtered, concentrated and chromatographed (silica gel, 30% EtOAc/Hexanes) to give 0.25 g (64%) of 414b as a white waxy solid. MS (APCI) m/z 332 $[M+H]^+$ (100%).

Compound 415b: A solution of 414b (0.25 g, 0.75 mmol) and 3N HCl (6 mL, 18 mmol) in 10 mL of MeOH was stirred at room temperature under $N_2$ for 16 h. The sample was concentrated, cooled, basified with 10% aq. $NH_4OH$ solution to a pH~9-10 and extracted with EtOAc. The organic extract was washed with sat. NaCl solution, dried ($MgSO_4$), filtered and concentrated to give 0.22 g (>100%) of sl. impure 415b as a light yellow oil, which was used without purification.

Compound 416b: To a stifling solution of sl. impure 415b (entire amount from previous step, assume 0.75 mmol) and ethyl formate (6.1 mL, 75.5 mmol) in 10 mL of benzene was added dropwise (via syringe) NaOMe, 30 wt % solution in MeOH (1.42 mL, 7.57 mmol). The sample was stirred at room temperature under $N_2$ for 16 h, concentrated then partitioned between $CHCl_3$ and sat. $KH_2PO_4$ solution. The organic extract was washed with sat. NaCl solution, dried ($MgSO_4$), filtered and concentrated to give 0.25 g (>100%) of sl. impure 416b as a yellow oil, which was used without purification.

Compound 417b: A solution of sl. impure 416b (entire amount from previous step, assume 0.75 mmol) and hydroxylamine hydrochloride (0.080 g, 1.15 mmol) in 10 mL of EtOH was heated at 50° C. under $N_2$ for 2 h, then room temperature overnight. The sample was concentrated and partitioned between $CHCl_3$ and sat. $NaHCO_3$ solution. The organic extract was washed with sat. NaCl solution, dried ($MgSO_4$), filtered and concentrated to give 0.23 g (98%) of a yellow oil, which by TLC and MS was a mixture of desired 417b and undehydrated product. TLC (silica gel, 40% EtOAc/Hexanes) 2 components; $R_f$=0.38 and 0.06. MS (APCI) m/z 331 (M+19, 70%) and 313 (M+1, 100%). A solution of the above mixture (entire amount) and a pinch of p-toluenesulfonic acid monohydrate in 50 mL of benzene were heated at 90° C. under $N_2$ for 2 h (TLC showed no lower component remaining). The sample was cooled and concentrated and partitioned between $CHCl_3$ and sat. $NaHCO_3$ solution. The organic extract was washed with sat. NaCl solution, dried ($MgSO_4$), filtered and concentrated to give 0.20 g (83%) 417b as a light yellow foamy solid, which was used without purification.

Compound 418b: To a stirring solution of sl. impure 417b (0.20 g, 0.63 mmol) at room temperature under $N_2$ in 10 mL of MeOH was added dropwise (via syringe) NaOMe, 30 wt % solution in MeOH (1.2 mL, 6.4 mmol). The sample was stirred at room temperature for 16 h, concentrated then partitioned between $CHCl_3$ and sat. $KH_2PO_4$ solution. The organic extract was washed with sat. NaCl solution, dried ($MgSO_4$), filtered and concentrated to give 0.20 g (99%) of sl. impure 418b as a dark yellow oil, which was used without purification.

Compound TX63774: To a stirring solution at 0° C. under $N_2$ of sl. impure 418b (0.20 g, 0.62 mmol) in 10 mL of DMF was added in one portion 1,3-dibromo-5,5-dimethylhydantoin (0.088 g, 0.31 mmol). After stifling at 0° C. for 1 h, pyridine (0.50 mL, 6.18 mmol) was added. The ice bath was removed and the sample was heated at 50° C. for 2 h. The sample was cooled, concentrated (to remove most of the DMF and pyridine) then partitioned between $CHCl_3$ and sat. $KH_2PO_4$ solution. The organic extract was washed with sat. NaCl solution, dried ($MgSO_4$), filtered, concentrated and chromatographed (silica gel, 30% EtOAc/Hexanes) to give 0.046 g (24%) of TX63774 as a light yellow solid. $^1H$ NMR (400 MHz, $CDCl_3$) δ 8.85 (s, 1H), 3.00 (s, 6H), 2.75 (m, 2H), 2.54 (m, 1H), 2.52 (s, 3H), 2.10 (m, 2H), 1.67 (s, 1H), 1.39 (s, 3H), 1.29 (d, 3H, J=6.7 Hz); MS (APCI) m/z 311 $[M+H]^+$ (100%).

Compound 414c: A mixture of 413 (0.44 g, 1.37 mmol), N,N-diisopropylethylamine (0.26 mL, 1.49 mmol) and n-butylamine (0.70 mL, 7.08 mmol) in 5 mL of n-BuOH was flushed with $N_2$, sealed and heated at 90° C. for 48 h. The sample was cooled, concentrated then partitioned between EtOAc and sat. $KH_2PO_4$ solution. The organic extract was washed with sat. NaCl solution, dried ($MgSO_4$), filtered and concentrated to give 0.59 g (>100%) of sl. impure 414c as a yellow oil, which was used without purification. MS (APCI) m/z 360 $[M+H]^+$ (100%).

Compound 415c: A solution of sl. impure 414c (entire amount from previous step, assume 1.37 mmol) and 3N HCl (5 mL, 15 mmol) in 10 mL of MeOH was stirred at room temperature under $N_2$ for 16 h. The sample was concentrated, cooled, basified with 10% aq. NH$_4$OH solution to a pH~9-10 and extracted with CHCl$_3$. The organic extract was washed with sat. NaCl solution, dried (MgSO$_4$), filtered and concentrated to give 0.42 g (98%) of sl. impure 415c as a light yellow oil, which was used without purification. MS (APCI) m/z 316 [M+H]$^+$ (100%).

Compound 416c: To a stirring solution of sl. impure 415c (0.42 g, 1.34 mmol) and ethyl formate (10.8 mL, 133.7 mmol) in 20 mL of benzene was added dropwise (via syringe) NaOMe, 30 wt % solution in MeOH (1.25 mL, 6.66 mmol). The sample was stirred at room temperature under N$_2$ for 16 h, concentrated then partitioned between CHCl$_3$ and sat. KH$_2$PO$_4$ solution. The organic extract was washed with sat. NaCl solution, dried (MgSO$_4$), filtered and concentrated to give 0.60 g (>100%) of sl. impure 416c as a dark yellow oil, which was used without purification. MS (APCI) m/z 344 [M+H]$^+$ (100%).

Compound 417c: A solution of sl. impure 416c (entire amount from previous step, assume 1.34 mmol) and hydroxylamine hydrochloride (0.24 g, 3.45 mmol) in 10 mL of EtOH was heated at 50° C. under N$_2$ for 2 h, then room temperature overnight. The sample was concentrated and partitioned between CHCl$_3$ and sat. NaHCO$_3$ solution. The organic extract was washed with sat. NaCl solution, dried (MgSO$_4$), filtered and concentrated to give 0.58 g (>100%) of a dark yellow oil, which by TLC and MS was a mixture of desired 417c and undehydrated product. TLC (silica gel, 50% EtOAc/Hexanes) 2 components; R$_f$=0.42 and 0.06. MS (APCI) m/z 359 (M+19, 70%) and 341 (M+1, 100%). A solution of the above mixture (entire amount) and a pinch of p-toluenesulfonic acid monohydrate in 50 mL of benzene was heated at 90° C. under N$_2$ for 2 h (TLC showed no lower component remaining). The sample was cooled and concentrated and partitioned between CHCl$_3$ and sat. NaHCO$_3$ solution. The organic extract was washed with sat. NaCl solution, dried (MgSO$_4$), filtered and concentrated to give 0.46 g (~100%) of 417c as a dark yellow oil, which was used without purification. (APCI) m/z 341 [M+H]$^+$ (100%).

Compound 418c: To a stifling solution of sl. impure 417c (0.46 g, assume 1.34 mmol) at room temperature under N$_2$ in 10 mL of MeOH was added dropwise (via syringe) NaOMe, 30 wt % solution in MeOH (1.25 mL, 6.66 mmol). The sample was stirred at room temperature for 16 h, concentrated then partitioned between CHCl$_3$ and sat. KH$_2$PO$_4$ solution. The organic extract was washed with sat. NaCl solution, dried (MgSO$_4$), filtered, concentrated and chromatographed (silica gel, 50% EtOAc/Hexanes) to give 0.19 g (41%) of 418c as yellow oil.

Compound TX63827: To a stirring solution at 0° C. under N$_2$ of 418c (0.19 g, 0.55 mmol) in 10 mL of DMF was added in one portion 1,3-dibromo-5,5-dimethylhydantoin (0.078 g, 0.27 mmol). After stirring at 0° C. for 1 h, pyridine (0.44 mL, 5.44 mmol) was added. The ice bath was removed and the sample was heated at 50° C. for 2 h. The sample was cooled, concentrated (to remove most of the DMF and pyridine) then partitioned between EtOAc and sat. KH$_2$PO$_4$ solution. The organic extract was washed with sat. NaCl solution, dried (MgSO$_4$), filtered, concentrated and chromatographed (silica gel, 50% EtOAc/Hexanes) to give 0.079 g (43%) of TX63827 as a light yellow solid. $^1$H NMR (400 MHz, CDCl$_3$) δ 8.91 (s, 1H), 4.39 (s, br, 1H), 3.49 (q, 1H, J=7.2 Hz), 2.45-2.54 (m, 1H), 2.48 (s, 3H), 2.28-2.44 (m, 2H), 2.08-2.17 (m, 1H), 2.01 (dt, 1H, J=2.4, 12.8 Hz), 1.68-1.81 (m, 1H), 1.50-1.62 (m, 3H), 1.31-1.45 (m, 1H), 1.37 (s, 3H), 1.26 (d, 3H, J=6.8 Hz), 0.94 (t, 3H, J=7.6 Hz); MS (APCI) m/z 339 (100%) [M+H]$^+$.

Compound 414d: A mixture of 413 (0.40 g, 1.24 mmol) and methylamine, 2.0 M solution in THF (3.1 mL, 12.4 mmol) in 10 mL of i-PrOH was flushed with N$_2$, sealed and heated at 90° C. for 48 h. The sample was cooled, concentrated then partitioned between CHCl$_3$ and sat. NaHCO$_3$ solution. The organic extract was washed with sat. NaCl solution, dried (MgSO$_4$), filtered, concentrated and chromatographed (silica gel, 100% EtOAc) to give 0.34 g (87%) of 414d as a white solid. MS (APCI) m/z 318 [M+H]$^+$ (100%).

Compound 415d: A solution of 414d (0.34 g, 1.08 mmol) and 3N HCl (6 mL, 18 mmol) in 12 mL of MeOH:THF (2:1) was stirred at room temperature under N$_2$ for 16 h. The sample was concentrated, cooled, basified with 10% aq. NH$_4$OH solution to a pH~9-10 and extracted with CHCl$_3$. The organic extract was washed with sat. NaCl solution, dried (MgSO$_4$), filtered and concentrated to give 0.26 g (87%) of sl. impure 415d as a light yellow foamy solid, which was used without purification.

Compound 416d: To a stirring solution of sl. impure 415d (0.26 g, 0.94 mmol) and ethyl formate (7.6 mL, 94.1 mmol) in 10 mL of benzene was added dropwise (via syringe) NaOMe, 30 wt % solution in MeOH (0.88 mL, 4.69 mmol). The sample was stirred at room temperature under N$_2$ for 16 h, concentrated then partitioned between EtOAc and sat. KH$_2$PO$_4$ solution. The organic extract was washed with sat. NaCl solution, dried (MgSO$_4$), filtered and concentrated to give 0.20 g (70%) of sl. impure 416d as a light yellow solid, which was used without purification. MS (APCI) m/z 302 [M+H]$^+$ (100%).

Compound 417d: A solution of sl. impure 416d (0.20 g, 0.65 mmol) and hydroxylamine hydrochloride (0.069 g, 0.99 mmol) in 10 mL of EtOH was heated at 50° C. under N$_2$ for 2 h, then room temperature overnight. The sample was concentrated and partitioned between CHCl$_3$ and sat. NaHCO$_3$ solution. The organic extract was washed with sat. NaCl solution, dried (MgSO$_4$), filtered and concentrated to give 0.24 g (>100%) of a yellow foamy solid, which by TLC and MS was a mixture of desired 417d and undehydrated product. TLC (silica gel, 5% MeOH/CHCl$_3$) 2 components; R$_f$=0.44 and 0.13. MS (APCI) m/z 317 (M+19, 52%) and 299 (M+1, 100%). A solution of the above mixture (entire amount) and a pinch of p-toluenesulfonic acid monohydrate in 50 mL of benzene was heated at 90° C. under N$_2$ for 4 h (TLC showed no lower component remaining). The sample was cooled and concentrated and partitioned between CHCl$_3$ and 10% aq. NH$_4$OH solution. The organic extract was washed with sat. NaCl solution, dried (MgSO$_4$), filtered and concentrated to give 0.20 g (>100%) of sl. impure 417d as a yellow solid, which was used without purification. MS (APCI) m/z 299 [M+H]$^+$ (100%).

Compound 418d: To a stirring solution of sl. impure 417d (0.20 g, assume 0.65 mmol) at room temperature under N$_2$ in 10 mL of MeOH was added dropwise (via syringe) NaOMe, 30 wt % solution in MeOH (0.61 mL, 3.25 mmol). The sample was stirred at room temperature for 16 h, concentrated then partitioned between CHCl$_3$ and sat. KH$_2$PO$_4$ solution. The organic extract was washed with sat. NaCl solution, dried (MgSO$_4$), filtered and concentrated to give 0.17 g (89%) of 418d as a light yellow solid, which was used without purification.

Compound TX63852: To a stifling solution at 0° C. under N$_2$ of 418d (0.17 g, 0.58 mmol) in 10 mL of DMF was added in one portion 1,3-dibromo-5,5-dimethylhydantoin (0.083 g, 0.29 mmol). After stirring at 0° C. for 1 h, pyridine (0.47 mL, 5.81 mmol) was added. The ice bath was removed and the sample was heated at 50° C. for 2 h. The sample was cooled, concentrated (to remove most of the DMF and pyridine) then partitioned between EtOAc and sat. KH$_2$PO$_4$ solution. The organic extract was washed with sat. NaCl solution, dried (MgSO$_4$), filtered, concentrated and chromatographed (silica gel, 75% EtOAc/Hexanes) to give 0.044 g (25%) of TX63852 as a light yellow solid. $^1$H NMR (400 MHz, CDCl$_3$) δ 8.93 (s, 1H), 4.48 (s, br, 1H), 3.05 (d, 3H, J=4.4 Hz), 2.29-2.57 (m, 3H), 2.51 (s, 3H), 2.09-2.13 (m, 1H), 2.03 (t, 1H, J=13.2 Hz), 1.68-1.82 (m, 1H), 1.37 (s, 3H), 1.28 (d, 3H, J=6.8 Hz); MS (APCI) m/z 297 [M+H]$^+$ (100%).

Compound 419a-b: A solution of 400 (0.56 g, 1.87 mmol) and Na metal (200 mg, 8.7 mmol) in 15 mL of EtOH was heated at 50° C. for 3 h. The reaction mixture was concentrated, extracted with EtOAc (2×25 mL), washed with water, and purified on a silica gel column. Two compounds were isolated with 10-15% EtOAc/Hexanes elution. The first compound was 419a (160 mg, 28% yield), MS: m/z [M+H]$^+$ 309, 311 (3:1). The second compound was 419b (210 mg, 35% yield). MS: m/z [M+H]$^+$ 319.

Compound 420: To a solution of 419b (210 mg, 0.66 mmol) in 5 mL of HCOOEt at RT, a solution of Na metal (50 mg, 2.17 mmol) in EtOH (5 mL) was added dropwise. The reaction mixture was stirred at RT overnight, poured into water and acidified with KH$_2$PO$_4$. The mixture was extracted with EtOAc (2×25 mL). The combined organic extracts were washed with brine, dried with MgSO$_4$, concentrated in vacuo to give 420 (210 mg, 92% yield). MS: m/z [M+H]$^+$ 347.

Compound 421: To a solution of 420 (0.21 g, 0.6 mmol) in 13 mL of EtOH was added NH$_2$OH HCl salt (2 eq), and the mixture was heated at 50° C. overnight. After concentration in vacuo, the residue was mixed with water and extracted with EtOAc (2×25 mL). The combined organic extracts were washed with brine, dried with MgSO$_4$, concentrated in vacuo to give 421 (210 mg). MS: m/z [M+H]$^+$ 344.

Compound 422: To a solution of 421 (0.21 g, 0.6 mmol) in 3 mL of THF and 1.5 mL of MeOH was added dropwise 30% NaOMe (8 eq), and the solution was heated at 50° C. for 6 hours. After concentration in vacuo, the residue was mixed with sat. KH$_2$PO$_4$ (20 mL) and extracted with EtOAc. The combined organic extracts were washed with brine, dried with MgSO$_4$, concentrated in vacuo to give 422 (200 mg). MS: m/z [M+H]$^+$ 344.

Compound TX63736: To a solution of 422 (200 mg, 0.58 mmol) in 2 mL of DMF at 0° C. was added 1,3-dibromo-5,5-dimethylhydantoin (0.55 eq), and the solution was stirred for 2 hours. Pyridine (1 g) was added, and the solution was heated at 50° C. overnight. After concentration in vacuo, the residue was purified on a silica gel column, eluted with 5-30% EtOAc/Hexanes to give TX63736 as an off-white solid (23 mg, 12%). $^1$H NMR (400 MHz, CDCl$_3$) δ 8.78 (s, 1H), 4.44 (t, 2H, J=7.1), 4.42 (t, 2H, J=7.0), 2.74 (ddd, 1H, J=0.9, 6.7, 17.9 Hz), 2.51 (m, 2H), 2.08 (m, 2H), 1.69 (m, 1H), 1.45 (t, 3H, J=7.1 Hz), 1.40 (s, 3H), 1.39 (t, 3H, J=7.1 Hz), 1.30 (d, 3H, J=6.8 Hz); MS: m/z [M+H]$^+$ 342.

Compound 423: Compound 419a (0.16 g, 0.51 mmol) was dissolved in DME (6 mL) and DMF (3 mL). To this solution was added phenylboronic acid (80 mg, 0.65 mmol), Ph$_3$P (85 mg, 0.32 mmol) and K$_3$PO$_4$ (0.33 g, 1.56 mmol). Nitrogen was bubbled through the mixture for 10 min. Pd(OAc)$_2$ (35 mg, 0.16 mmol) was added and nitrogen bubbled for another 10 min. The suspension was heated to 90° C. for 16 hours. The reaction mixture was filtered, concentrated, and purified on a silica gel column, eluted with 5-25% EtOAc/Hexanes to give 423 as a solid (120 mg, 67% yield). MS: m/z [M+H]$^+$ 351.

Compound 424: To a solution of 423 (120 mg, 0.34 mmol) in 2.5 mL of HCOOEt was added dropwise 30% NaOMe in MeOH (6 eq). The reaction mixture was stirred at RT overnight, then poured into water and acidified with KH$_2$PO$_4$. The mixture was extracted with EtOAc. The combined organic extracts were washed with brine, dried with MgSO$_4$, and concentrated in vacuo to give 424 (130 mg). MS: m/z [M+H]$^+$ 379.

Compound 425: To a solution of 424 (130 mg, 0.34 mmol) in 6.5 mL of EtOH was added NH$_2$OH HCl salt (2 eq), and the mixture was heated at 50° C. overnight. After concentration in vacuo, the residue was mixed with water and extracted with EtOAc. The combined organic extracts were washed with brine, dried with MgSO$_4$, concentrated in vacuo to give 425 (120 mg). MS: m/z [M+H]$^+$ 376.

Compound 426: To a solution of 425 (120 mg, 0.32 mmol) in 1.5 mL of THF and 0.75 mL of MeOH was added dropwise 30% NaOMe (8 eq), and the solution was heated at 50° C. for 6 hours. After concentration in vacuo, the residue was mixed with sat. KH$_2$PO$_4$ (20 mL) and extracted with EtOAc. The combined organic extracts were washed with brine, dried with MgSO$_4$, concentrated in vacuo to give 426 (110 mg). MS: m/z [M+H]$^+$ 376.

Compound TX63731: To a solution of 426 (110 mg, 0.29 mmol) in 2 mL of DMF at 0° C. was added 1,3-dibromo-5,5-dimethylhydantoin (0.55 eq), and the solution was stirred for 2 hours. Pyridine (1 g) was added, and the solution was heated at 50° C. overnight. After concentration in vacuo, the residue was purified on a silica gel column, eluted with 5-30% EtOAc/Hexanes to give TX63731 (75 mg, 69%). $^1$H NMR (400 MHz, CDCl$_3$) δ 9.02 (s, 1H), 8.46 (m, 2H), 7.50 (m, 3H), 4.60 (q, 2H, J=7.1 Hz), 2.87 (ddd, 1H, J=1.1, 6.8, 18.6), 2.61 (m, 2H), 2.14 (m, 2H), 1.76 (m, 1H), 1.46 (s, 3H), 1.46 (t, 3H, J=7.1 Hz), 1.32 (d, 3H, J=6.8 Hz); MS: m/z [M+H]$^+$ 374.

Compound 427: A solution of 413 (0.38 g, 1.17 mmol) in 20 mL of EtOH was added (dropwise, via syringe) sodium ethoxide, 21 wt % solution in EtOH (4.4 mL, 11.8 mmol). The sample was stirred at room temperature under N$_2$ for 16 h (TLC, silica gel, 30% EtOAc/Hexanes still showed unreacted starting material) then heated at 70° C. for 8 h. The sample was concentrated then partitioned between EtOAc and sat. KH$_2$PO$_4$ solution. The organic extract was washed with sat. NaCl solution, dried (MgSO$_4$), filtered and concentrated to give 0.52 g (>100%) of sl. impure 427 as a dark yellow oil, which was used without purification.

Compound 428: A solution of sl. impure 427 (0.52 g, assume 1.17 mmol) and 3N HCl (4 mL, 12 mmol) in 10 mL of MeOH was stirred at room temperature under N$_2$ for 16 h. The sample was concentrated, cooled, basified with 10% aq. NH$_4$OH solution to a pH~9-10 and extracted with EtOAc. The organic extract was washed with sat. NaCl solution, dried (MgSO$_4$), filtered, concentrated and chromatographed (silica gel, 30% EtOAc/Hexanes) to give 0.28 g (84%) of 428 as a tan solid.

Compound 429: To a stirring solution of 428 (0.28 g, 0.98 mmol) and ethyl formate (9.0 mL, 111.0 mmol) in 10 mL of benzene was added dropwise (via syringe) sodium ethoxide, 21 wt % solution in EtOH (3.7 mL, 9.9 mmol). The sample was stirred at room temperature under N$_2$ for 16 h, concentrated then partitioned between EtOAc and sat. KH$_2$PO$_4$ solution. The organic extract was washed with sat. NaCl solution, dried (MgSO$_4$), filtered and concentrated to give 0.30 g (96%) of sl. impure 429 as a dark yellow oily solid, which was used without purification.

Compound 430: A solution of 429 (0.30 g, 0.94 mmol) and hydroxylamine hydrochloride (0.10 g, 1.44 mmol) in 10 mL of EtOH was heated at 50° C. under N$_2$ for 2 h, then room temperature overnight. The sample was concentrated and partitioned between EtOAc and sat. NaHCO$_3$ solution. The organic extract was washed with sat. NaCl solution, dried (MgSO$_4$), filtered and concentrated to give 0.30 g (>100%) of sl. impure 430 as a tan foamy solid, which was used without purification.

Compound 431: To a stirring solution of sl. impure 430 (entire amount from previous step, assume 0.94 mmol) at room temperature under N$_2$ in 10 mL of MeOH was added dropwise (via syringe) sodium ethoxide, 21 wt % solution in EtOH (3.5 mL, 9.4 mmol). The sample was stirred at room temperature for 16 h, concentrated then partitioned between EtOAc and sat. KH$_2$PO$_4$ solution. The organic extract was washed with sat. NaCl solution, dried (MgSO$_4$), filtered and concentrated to give 0.28 g (95%) of sl. impure 431 as a yellow-orange solid, which was used without purification.

Compound TX63773: To a stifling solution at 0° C. under N$_2$ of sl. impure 431 (0.28 g, 0.89 mmol) in 10 mL of DMF was added in one portion 1,3-dibromo-5,5-dimethylhydantoin (0.13 g, 0.45 mmol). After stifling at 0° C. for 1 h, pyridine (0.70 mL, 8.65 mmol) was added. The ice bath was removed and the sample was heated at 50° C. for 2 h. The sample was cooled, concentrated (to remove most of the DMF and pyridine) then partitioned between EtOAc and sat. KH$_2$PO$_4$ solution. The organic extract was washed with sat. NaCl solution, dried (MgSO$_4$), filtered, concentrated and chromatographed (silica gel, 30% EtOAc/Hexanes) to give 0.14 g (48%) of TX63773 as a light yellow solid. $^1$H NMR (400 MHz, CDCl$_3$) δ 8.87 (s, 1H), 4.40 (q, 2H, J=7.1 Hz), 2.75 (dd, 1H, J=7.0, 18.5 Hz), 2.54 (s, 3H), 2.52 (m, 2H), 2.03 (m, 2H), 1.65 (m, 1H), 1.38 (s, 3H), 1.37 (t, 3H, J=7.1 Hz), 1.27 (d, 3H, J=6.7 Hz); MS (APCI) m/z 312 [M+H]$^+$ (100%).

Compound 432: Compound 127 (0.964 g, 4.04 mmol) was taken up in DCM (100 mL) and MgBr$_2$-Et$_2$O (2.707 g, 10.5 mmol) and i-Pr$_2$NEt (1.39 mL, 8.0 mmol) were added. The reaction mixture was stirred at room temperature for about 30 min during which the reaction mixture gradually turned orange. Then, benzoyl chloride (1.17 g, 8.3 mmol) in DCM (3 mL) was added dropwise and the mixture was stirred overnight at room temperature. The reaction was warmed to reflux and the orange color gradually discharged. The reaction was quenched by adding saturated aqueous sodium bicarbonate solution (100 mL) which was stirred for 1 h at room temperature. The organic layer was separated and dried over MgSO$_4$, filtered and concentrated to an oil. The oil was chromatographed on silica gel (230-400 mesh, 42 g) 10% EtOAc/Hexanes as eluant to yield the product 432 as an almost clear oil (0.372 g, 27%). MS: m/z [M+H]$^+$ 343.1.

Compound 433: Compound 432 (0.372 g. 1.09 mmol) was taken up in EtOH (40 mL) and hydrazine monohydrate (0.244 g, 3.8 mmol) was added. The reaction mixture was heated to 65° C. for 1 h and then stirred at room temperature for 5 d. The reaction mixture was concentrated to dryness and the residual volatiles were removed under vacuum to give the product 433 as an oil/solid (0.41 g) that was used directly in the next step. MS: m/z [M+H]$^+$ 339.1.

Compound 434: Compound 433 (0.41 g, 1.2 mmol) was taken up in MeOH (35 mL) and 1N HCl (3 mL) and the mixture was stirred overnight at room temperature. The reaction mixture was stirred overnight at room temperature to remove MeOH and was then partitioned between EtOAc (60 mL) and saturated aqueous sodium bicarbonate. The organic layer was dried over MgSO$_4$, filtered, and concentrated to give 434 as an oil/glass (0.3266 g). m/z [M+H]$^+$ 295.1.

Compound 435: Compound 434 (0.3266 g, 1.11 mmol) was taken up in ethyl formate (50 mL) and 30% NaOMe in MeOH (1.8 mL, 9.7 mmol) was added. The mixture was stirred overnight at room temperature and was then poured into a separatory funnel containing saturated aqueous KH$_2$PO$_4$ (20 mL) and EtOAc (125 mL). The organic layer was separated and dried over MgSO$_4$, filtered and concentrated to an oil/glass that contained a large amount of starting material, and was resubjected to ethyl formate (30 mL) and 30% NaOMe in MeOH (1.2 mL, 6.48 mmol) overnight at room temperature. The reaction was worked up as before to give the product 435 as a yellow glass (0.247 g, 70% over three steps). MS: m/z [M+H]$^+$ 323.1.

Compound 436: A solution of 0.1 M hydroxylamine hydrochloride in 9:1 EtOH/water (12 mL, 1.2 mmol) was added to 435 (0.247 g, 0.77 mmol) and the mixture was stirred overnight at room temperature. The following morning the mixture was heated to 50° C. on the rotary evaporator and concentrated to dryness. The crude residue was partitioned between EtOAc (100 mL) and saturated aqueous sodium bicarbonate solution (15 mL) and the organic layer was dried over MgSO$_4$, filtered and concentrated to a glass. The glass was chromatographed on silica gel (230-400 mesh, 8 g) using 50% EtOAc/Hexanes as eluant to give the product 436 as a glass (0.0844 g, 34%). MS: m/z [M+H]$^+$ 320.1.

Compound 437: Isoxazole 436 (0.0844 g, 0.26 mmol) was taken up in 1:1 MeOH/THF, (10 mL) and 30% NaOMe in MeOH (0.2 mL, 1.08 mmol) was added. The mixture was stirred overnight at room temperature and was then partitioned between saturated KH$_2$PO$_4$ (15 mL) and EtOAc (100 mL). The organic layer was separated and dried over MgSO$_4$, filtered and concentrated to give the product 437 as a glass (0.085 g). MS: m/z [M+H]$^+$ 320.1.

Compound TX63836: Cyanoketone 437 (0.085 g, 0.26 mmol) was taken up in DMF (2.5 mL) and the mixture was cooled to 0° C. Dibromodimethylhydantoin (0.048 g, 0.17 mmol) was added and the reaction was stirred for 1.75 h. Anhydrous pyridine (0.25 mL, 3.1 mmol) was added and the reaction mixture was heated at 60° C. for 3 h. The reaction mixture was concentrated to dryness and chromatographed on silica gel (230-400 mesh, 6 g) using 3:1 Hexanes/EtOAc as eluant to give the product TX63836 as an off-white solid (0.0355 g, 43% over two steps). $^1$H NMR (400 MHz, CDCl$_3$) δ 8.47 (s, 1H), 7.42-7.50 (m, 5H), 7.33-7.41 (m, 1H), 2.91 (dd, 1H, J=6.4, 16.4 Hz), 2.70-2.82 (m, 1H), 2.51-2.62 (m, 1H), 2.05-2.18 (m, 2H), 1.69-1.85 (m, 1H), 1.46 (s, 3H), 1.31 (d, 3H, J=6.8 Hz); MS: m/z [M+H]$^+$ 318.0.

Compound TX63850: Compound TX63836 (0.015 g, 0.047 mmol) was mixed with Ac$_2$O (2 mL) and anhydrous NaOAc (0.013 g, 0.16 mmol). The mixture was stirred for 3 days at room temperature and was then concentrated to dryness and filtered through silica gel (230-400 mesh, 1 g) using 4:1 Hexanes/EtOAc to give the product TX63850 as a glass (0.0052 g, 31%). $^1$H NMR (400 MHz, CDCl$_3$) δ 8.42 (s, 1H), 7.28-7.41 (m, 3H), 7.15-7.27 (m, 2H), 2.63 (s, 3H), 2.38-2.62 (m, 4H), 1.90-2.10 (m, 2H), 1.43 (s, 3H), 1.23 (d, 3H, J=6.4 Hz); MS: m/z [M+H]$^+$ 360.1.

Compound TX63871: Compound TX63836 (0.015 g, 0.047 mmol) was mixed with ethylchloroformate (1 mL) and solid NaHCO$_3$ (0.056 g, 6.67 mmol) and the mixture was stirred overnight at room temperature. The reaction mixture was concentrated to dryness and chromatographed on silica gel (230-400 mesh, 4 g) using 3:1 Hexanes/EtOAc to give the product TX63871 as an off-white solid (0.014 g, 76%). $^1$H NMR (400 MHz, CDCl$_3$) δ 8.72 (s, 1H), 7.65-7.70 (m, 2H), 7.36-7.45 (m, 3H), 4.57 (q, 2H, J=7.2 Hz), 2.69-2.81 (m, 2H), 2.59-2.68 (m, 1H), 2.18 (dd, 1H, J=1.2, 12.4 Hz), 2.02-2.10 (m, 1H), 1.62-1.74 (m, 1H), 1.67 (s, 3H), 1.51 (t, 3H, J=6.8 Hz), 1.34 (d, 3H, J=6.8 Hz); MS: m/z [M+H]$^+$ 390.1.

Compound 438: Compound 127 (0.971 g, 4.1 mmol) was taken up in DCM (50 mL) and MgBr$_2$-Et$_2$O (2.90 g, 11.2 mmol) and i-Pr$_2$NEt (2.4 mL, 13.8 mmol) were added. The reaction mixture was stirred at room temperature for about 30 min, during which time the mixture gradually turned orange. Pyridine-2-carboxylic acid chloride hydrochloride (1.71 g, 9.6 mmol) was added and the mixture was stirred overnight at room temperature. The reaction was quenched by adding excess saturated aqueous sodium bicarbonate solution. The very dark reaction mixture was concentrated to remove DCM and EtOAc (250 mL) and excess saturated $KH_2PO_4$ were added. The organic layer was separated, dried over $MgSO_4$, and concentrated to give 438 as dark oil (1.09 g) that was used directly in the next step. MS: m/z $[M+H]^+$ 344.1.

Compound 439: Crude 438 (1.09 g. 3.2 mmol) was taken up in EtOH (100 mL) and methylhydrazine (1.306 g, 28.4 mmol) was added. The reaction mixture was stirred overnight at room temperature and then heated to 70° C., after which more EtOH was added and heating was continued at 70° C. The reaction mixture was concentrated to dryness and the dark oil was chromatographed on silica gel (230-400 mesh, 40 g) using 50% Hexanes/EtOAc and then EtOAc as eluant to give the product 439 as a yellow oil/glass (0.1453 g, 10% over two steps). MS: m/z $[M+H]^+$ 354.2.

Compound 440: Compound 439 (0.1453 g, 0.41 mmol) was taken up in MeOH (25 mL) and 1N HCl (4 mL) and the mixture was stirred overnight at room temperature. The reaction mixture was concentrated to remove MeOH and was then partitioned between EtOAc (100 mL) and saturated aqueous sodium bicarbonate. The organic layer was dried over $MgSO_4$, filtered and concentrated to give 440 as oil/glass (0.1197 g, 94%). m/z [M+H]E 310.1.

Compound 441: Compound 440 (0.1197 g, 0.39 mmol) was taken up in ethyl formate (20 mL) and 30% NaOMe in MeOH (0.6 mL, 3.24 mmol) was added. The mixture was stirred 3 d at room temperature and was then poured into a separatory funnel containing saturated aqueous $KH_2PO_4$ (20 mL) and EtOAc (100 mL). The organic layer was separated and dried over $MgSO_4$, filtered and concentrated to give 441 as an orange glass (0.1267 g, 96%). MS: m/z $[M+H]^+$ 338.1.

Compound 442: A solution of 0.1 M hydroxylamine hydrochloride in 9:1 EtOH/water (6 mL, 0.6 mmol) was added to 441 (0.1267 g, 0.37 mmol) and the mixture was stirred overnight at room temperature. Upon completion the mixture was concentrated to dryness (T=50° C.) and the residue was partitioned between EtOAc (100 mL) and saturated aqueous sodium bicarbonate solution (10 mL). The organic solution was dried over $MgSO_4$, filtered and concentrated to give 442 as a yellow glass (0.1053 g, 85%). MS: m/z [M+H]E 335.1.

Compound 443: Compound 442 (0.1053 g, 0.31 mmol) was taken up in 1:1 MeOH/THF (10 mL) and 30% NaOMe in MeOH (0.25 mL, 1.35 mmol) was added. The mixture was stirred overnight at room temperature and was then partitioned between saturated $KH_2PO_4$ (15 mL) and EtOAc (100 mL). The organic layer was separated, dried over $MgSO_4$, filtered and concentrated to give the product 443 as a glass (0.1022 g, 99%). MS: m/z $[M+H]^+$ 335.1.

Compound TX63851: Compound 443 (0.1022 g, 0.31 mmol) was taken up in DMF (2.5 mL) and the mixture was cooled to 0° C. $Br_2$ (0.055 g, 0.34 mmol) in DMF (0.3 mL) was added and the reaction was stirred for 1.75 h. Anhydrous pyridine (0.25 mL, 3.1 mmol) was added and the reaction mixture was heated at 60° C. for 3 h. The reaction mixture was concentrated to dryness and partitioned between EtOAc (80 mL) and saturated aqueous sodium bicarbonate solution (10 mL). The organic layer was washed with brine (10 mL), dried over $MgSO_4$, filtered and concentrated to a brown oil/glass. The oil was chromatographed on silica gel (230-400 mesh, 8 g) using 50% Hexanes/EtOAc as eluant and rechromatographed on silica gel (230-400 mesh, 6 g) using 50% Hexanes/EtOAc as eluant to give the product TX63851 (0.0163 g, 16%). $^1$H NMR (400 MHz, $CDCl_3$) δ 8.65 (d, 1H, J=4.4 Hz), 8.44 (s, 1H), 7.72 (t, 1H, J=7.6 Hz), 7.32 (d, 1H, J=7.6 Hz), 7.17-7.24 (m, 1H), 3.98 (s, 3H), 2.55-2.75 (m, 2H), 2.44-2.55 (m, 1H), 1.94-2.11 (m, 2H), 1.62-1.75 (m, 1H), 1.38 (s, 3H), 1.24 (d, 3H, J=6.8 Hz); MS: m/z $[M+H]^+$ 333.1.

Compound TX63849: Compound TX63690 (0.034 g, 0.10 mmol) was taken up in acetonitrile (1 mL) and Accufluor (0.042 g, 0.126 mmol (based on 3 mmol/g)) was added. The mixture was stirred 2 h at 80° C. and then 3 d at room temperature. More Accufluor (0.046 g, 0.138 mmol) was added and the mixture was heated overnight at 80° C. The reaction mixture was concentrated and chromatographed on silica gel (230-400 mesh, 6 g) using EtOAc and then 5% THF/EtOAc as eluant. The product-containing fractions were chromatographed again on silica gel (230-400 mesh, 2.8 g) using 1.2% MeOH/DCM as eluant to give the product TX63849 (0.005 g, 14%). $^1$H NMR (400 MHz, $CDCl_3$) δ 8.29 (s, 1H), 7.28 (s, 1H), 7.27 (s, 1H), 3.87 (s, 3H), 3.32 (s, 3H), 2.72 (d, 1H, J=14.0 Hz), 2.40-2.51 (m, 1H), 1.45-1.96 (m, 4H), 1.22 (d, 3H, J=6.8 Hz), 1.12 (s, 3H); MS: m/z $[M+H]^+$ 352.1.

Compound 444 and 445: A solution of 181 (1.663 g, 5.223 mmol) and $Et_3N$ (1.0 mL, 5.94 mmol) in $CHCl_3$ (50 mL) under $N_2$ was cooled to 0° C. and methyl trifluoromethanesulfonate (1.0 mL, 8.8 mmol) was added dropwise. The solution was allowed to warm to room temperature overnight then washed with sat. $NaHCO_3$ and sat. NaCl solutions, dried ($MgSO_4$), filtered and concentrated. Chromatography (silica gel, 70% EtOAc/Hexanes) afforded 444 (0.786 g, 33%) as an off-white solid; MS (APCI) m/z 333 (M+1, 100); and 445 (0.247 g, 10%) as a light yellow oil; MS (APCI) m/z 333 (100) $[M+H]^+$.

Compound 446: A solution of 444 (0.786 g, 2.365 mmol) and 3N HCl (4 mL, 12 mmol) in 20 mL of MeOH:THF (1:1) was stirred at room temperature under $N_2$ for 16 h. The solution was concentrated then partitioned between $CHCl_3$ and 10% aq. $NH_4OH$. The organic extract was washed with sat. NaCl solution, dried ($MgSO_4$), filtered and concentrated to give 446 (0.633 g, 93%) as foamy white solid. MS (APCI) m/z 289 (100%) $[M+H]^+$.

Compound 447: To a solution of 446 (1.8 mL, 22.3 mmol) in benzene (10 mL) was added dropwise (via syringe) NaOMe (30 wt % in MeOH, 2.0 mL, 10.7 mmol) under $N_2$. The sample was stirred at room temperature for 16 h, concentrated, and then partitioned between EtOAc and sat. $NaHCO_3$ solution. The organic extract was washed with sat. $KH_2PO_4$ and sat. NaCl solutions, dried ($MgSO_4$), filtered and concentrated to give 447 (0.502 g, 72%) as a light brown foamy solid. MS (APCI) m/z 317 (100%) $[M+H]^+$.

Compound 448: A solution of 447 (0.502 g, assume 1.585 mmol) in ethanol (10 mL) was treated with solid hydroxylamine hydrochloride (0.16 g, 2.30 mmol). The sample was heated at 50° C. under $N_2$ for 2 h and then room temperature overnight. The sample was concentrated then partitioned between $CHCl_3$ and sat. $NaHCO_3$ solution. The organic extract was washed with sat. NaCl solution, dried ($MgSO_4$), filtered and concentrated to give 448 (0.658 g, >100%) as a light brown foamy solid. MS (APCI) m/z 314 (100%) $[M+H]^+$.

Compound 449: A solution of slightly impure 448 (0.658 g, assume 1.585 mmol) in MeOH (10 mL) was treated with NaOMe (30 wt % in MeOH, 1.48 mL, 7.89 mmol). The sample was stirred at room temperature under $N_2$ for 16 h, concentrated then partitioned between EtOAc and sat. $KH_2PO_4$ solution. The organic extract was washed with sat. NaCl solutions, dried ($MgSO_4$), filtered and concentrated to give 449 (0.578 g, >100%) as a yellow foamy solid. MS (APCI) m/z 314 (100%) [M+H]$^+$.

Compound TX63584: Dibromodimethylhydantoin (0.272 g, 0.951 mmol) was added to a stirring solution of slightly impure 449 (0.578 g, assume 1.585 mmol) in DMF (10 mL) at 0° C. under N$_2$. After stifling at 0° C. for 1 h, pyridine (1.3 mL, 16.1 mmol) was added. The ice bath was removed and the sample was heated at 50° C. for 16 h. The sample was concentrated (to remove most of the DMF and pyridine) and then partitioned between EtOAc and sat. NaHCO$_3$ solution. The organic extract was washed with sat. KH$_2$PO$_4$ and sat. NaCl solution, dried (MgSO$_4$), filtered, and concentrated. Purification by chromatography (silica gel, 2% MeOH/CHCl$_3$) afforded TX63584 (0.151 g, 31%) as light yellow foamy solid. $^1$H NMR (500 MHz, CDCl$_3$) δ 8.75 (s, 1H), 3.51 (s, 3H), 2.79 (dd, 1H, J=6.1, 18.5 Hz), 2.57 (s, 3H), 2.46 (dddd, 1H, J=7.4, 9.4, 9.4, 11.4 Hz), 2.06 (dd, 1H, J=2.0, 12.8 Hz), 1.96 (dd, 1H, J=7.3, 13.3 Hz), 1.76 (m, 1H), 1.42 (s, 3H), 1.26 (s, 3H), 1.20 (s, 3H); MS (APCI) m/z 312 (100%) [M+H]$^+$.

Compound 450: A solution of 445 (0.247 g, 0.742 mmol) and 3 N HCl (4 mL, 12 mmol) in 20 mL of MeOH:THF (1:1) was stirred at room temperature under N$_2$ for 16 h. The solution was concentrated then partitioned between CHCl$_3$ and 10% aq. NH$_4$OH. The organic extract was washed with sat. NaCl solution, dried (MgSO$_4$), filtered and concentrated to give 450 (0.191 g, 89%) as a light yellow oil. MS (APCI) m/z 289 (100%) [M+H]$^+$.

Compound 451: To a stirring solution of 450 (0.191 g, 661 mmol) and ethyl formate (0.53 mL, 6.56 mmol) in benzene (10 mL) was added dropwise (via syringe) NaOMe (30 wt % in MeOH, 0.62 mL, 3.30 mmol). The sample was stirred at room temperature for 16 h, concentrated then partitioned between EtOAc and sat. KH$_2$PO$_4$ solution. The organic extract was washed with sat. NaCl solution, dried (MgSO$_4$), filtered and concentrated to give 451 (0.211 g, >100%) as a yellow oil. MS (APCI) m/z 317 (100%) [M+H]$^+$.

Compound 452: A solution of slightly impure 451 (0.211 g, assume 0.661 mmol) in ethanol (10 mL) was treated with solid hydroxylamine hydrochloride (0.069 g, 0.99 mmol). The sample was heated at 50° C. under N$_2$ for 16 h, cooled to room temperature, concentrated, and partitioned between EtOAc and sat. NaHCO$_3$. The organic extract was washed with sat. NaCl solution, dried (MgSO$_4$), filtered and concentrated to give 452 (0.176 g, 85%) as a yellow oil. MS (APCI) m/z 314 (100%) [M+H]$^+$.

Compound 453: A solution of 452 (0.176 g, 0.561 mmol) in MeOH (10 mL) was treated with NaOMe (30 wt % in MeOH, 0.53 mL, 2.82 mmol). The sample was stirred at room temperature under N$_2$ for 16 h, concentrated, and then partitioned between EtOAc and sat. KH$_2$PO$_4$. The organic extract was washed with sat. NaCl solutions, dried (MgSO$_4$), filtered and concentrated to give 453 (0.170 g, 96%) as a yellow gummy solid. MS (APCI) m/z 314 (100%) [M+H]$^+$.

Compound TX63595: Dibromodimethylhydantoin (0.093 g, 0.325 mmol) was added to stirring solution of 453 (0.170 g, 0.541 mmol) in DMF (10 mL) at 0° C. under N$_2$. After stirring at 0° C. for 1 h, pyridine (0.44 mL, 5.44 mmol) was added. The ice bath was removed and the sample was heated at 50° C. for 16 h. The sample was concentrated (to remove most of the DMF and pyridine) then partitioned between EtOAc and sat. NaHCO$_3$. The organic extract was washed with sat. KH$_2$PO$_4$ and sat. NaCl solution, dried (MgSO$_4$), filtered, and concentrated. Purification by chromatography (silica gel, 30% EtOAc/Hexanes) afforded TX63595 (0.066 g, 39%) as an off-white foamy solid. $^1$H NMR (500 MHz, d6-DMSO) δ 8.86 (s, 1H), 3.96 (s, 3H), 2.80 (dd, 1H, J=17.5, 7.5 Hz), 2.56 (s, 3H), 2.48-2.54 (m, 1H), 2.12 (dd, 1H, J=12.5, 2.5 Hz), 1.98 (app dd, 1H, J=12.5, 7.5 Hz), 1.78-1.87 (m, 1H), 1.43 (s, 3H), 1.27 (s, 3H), 1.21 (s, 3H); $^{13}$C NMR (125 MHz, CDCl$_3$) δ 197.6, 169.1, 167.9, 165.8, 165.0, 114.8, 114.6, 111.5, 53.9, 46.1, 44.8, 42.8, 27.1, 25.6, 25.4, 21.4, 17.9. MS (ES) m/z 312 (M+23, 100%) and 312 (67%) [M+H]$^+$.

Compound 454: To a stirring suspension at 0° C. under N$_2$ of 1 (4.67 g, 37.02 mmol) in 70 mL of acetonitrile was added dropwise 1-hexen-3-one (5 g, 46 mmol, 90+% stabilized with ~0.6% of 4-methoxyphenol) followed by dropwise addition of triethylamine (8.25 mL, 59.19 mmol). All solid was in solution towards the end of the triethylamine addition. The yellow solution was allowed to slowly warm to room temperature overnight. The sample was concentrated, dissolved into EtOAc, washed with sat. NaHCO$_3$ and sat. NaCl solutions, dried (MgSO$_4$), filtered and concentrated to give 8.85 g (>100%) of crude 454 as a yellow liquid. MS (APCI) m/z 225 (17%) [M+H]$^+$.

Compound 455: To a stifling solution at room temperature under N$_2$ of sl. crude 454 (entire amount from above, assume 37.02 mmol) in 150 mL of acetonitrile was added solid (R,S)-phenylalanine (6.11 g, 36.99 mmol) followed by addition of solid (1R)-(+)-10-camphorsulfonic acid (4.30 g, 18.51 mmol). The sample was heated under N$_2$ at 70° C. for 48 h, cooled to room temperature then filtered. The solid was washed with fresh acetonitrile, the combined filtrate was concentrated then carefully partitioned between sat. NaHCO$_3$ solution and diethyl ether. The organic extract was washed with sat. NaCl solution dried (MgSO$_4$), filtered, concentrated and chromatographed (silica gel, 50% CHCl$_3$-10% EtOAc-40% hexanes). Separation was poor, all fractions containing a UV visible component (TLC, SiO$_2$ [10% EtOAc-40% hexanes-50% CHCl$_3$], R$_f$~0.45) were combined and concentrated to give 5.38 g (70%) of impure 455 as a light yellow liquid. (APCI) m/z 207 (100%) [M+H]$^+$.

Compound 456: To a stifling solution at 0° C. under N$_2$ of Compound 455 (6.101 g, 29.575 mmol) in 100 mL of EtOH was added dropwise a slightly cloudy solution of sodium borohydride (0.31 g, 8.19 mmol) in 50 mL of EtOH. After ~15 min (no starting material remains by TLC), the cold sample was quenched by dropwise addition of acetic acid (3.4 mL, 59.4 mmol), stirred at room temperature for 1 h then concentrated. The resultant light yellow gummy solid was dissolved into 200 mL of EtOAc containing 5 mL of water, dried with excess solid NaHCO$_3$ and filtered to give 5.92 g (96%) of impure 456 as a light yellow oil. MS (APCI) m/z 209 (100%) [M+H]$^+$.

Compound 457: To a stirring solution at 0° C. under N$_2$ of sl. impure 456 (5.92 g, 28.42 mmol) and 3,4-dihydro-2H-pyran (3.6 mL, 39.6 mmol) in 100 mL of CH$_2$Cl$_2$ was added in one portion solid p-toluene-sulfonic acid monohydrate (0.50 g, 2.63 mmol). The sample immediately darkened (light yellow to brown) and was allowed to warm slowly to room temperature overnight. The dark sample was concentrated then partitioned between hexanes and sat. NaHCO$_3$ solution. The organic extract was washed with sat. KH$_2$PO$_4$ and sat. NaCl solutions, dried (MgSO$_4$), filtered, concentrated and chromatographed (silica gel, 20% EtOAc in hexanes) to give 3.868 g (46%) of 457 as light yellow oil. MS (APCI) m/z 293 (88%) [M+H]$^+$ and 191 (100%).

Compound 458: Liquid ammonia (~5 mL) was condensed in a two-necked flask at −78° C. Lithium wire (0.185 g, 26.66 mmol, 2 eq) was added in small portions. After 45 min, the lithium wire was dissolved then a solution of 457 (3.868 g, 13.227 mmol) in 15 mL of THF was added dropwise. The reaction mixture was stirred for 45 min at −78° C. then solid ammonium chloride (5 g, 93 mmol) was added and the ammonia was allowed to evaporate. The residue was dissolved into 100 mL of water and extracted with EtOAc (2×). The combined organic layer was concentrated and chromatographed (silica gel, 10% EtOAc in hexanes) to give 2.649 g (68%) of 458 as colorless oil. MS (APCI) m/z 175 (100%) [M+H]$^+$.

Compound 459: A solution of 458 (2.649 g, 8.997 mmol) and pyridinium p-toluenesulfonate (0.23 g, 0.92 mmol) in 50 mL of EtOH was heated at 70° C. under $N_2$ for 6 h then room temperature overnight. The sample was concentrated then partitioned between EtOAc and sat. NaHCO$_3$ solution. The organic extract was washed with sat. KH$_2$PO$_4$ and sat. NaCl solutions, dried (MgSO$_4$), filtered and concentrated to give 2.112 g (>100%) of sl. crude 459 as yellow oil. MS (APCI) m/z 211 (24%) [M+H]$^+$ and 175 (100%).

Compound 460: A solution under $N_2$ of sl. crude 459 (2.112 g, assume 8.997 mmol), ethylene glycol (5.0 mL, 89.6 mmol) and p-toluenesulfonic acid monohydrate (0.171 g, 0.899 mmol) in 100 mL of benzene was refluxed under Dean-Stark conditions for 16 h. The sample was concentrated then partitioned between EtOAc and sat. NaHCO$_3$ solution. The organic extract was washed with sat. KH$_2$PO$_4$ and sat. NaCl solutions, dried (MgSO$_4$), filtered and concentrated to give 2.388 g (>100%) of crude 460 as dark yellow oil. MS (APCI) m/z 255 (35%) [M+H]$^+$ and 175 (100%).

Compound 461: To a stifling solution at room temperature of sl. crude 460 (2.388 g, assume 8.997 mmol) in 100 mL of CH$_2$Cl$_2$ was added solid MgSO$_4$ (1.08 g, 8.97 mmol) followed by solid pyridinium dichromate (6.77 g, 17.99 mmol). The sample was stirred at room temperature for 24 h, concentrated, suspended in 100 mL of diethyl ether, stirred at room temperature for 30 min and filtered. The filtrate was concentrate and chromatographed (silica gel, 30% EtOAc in hexanes) to give 1.513 g (67%) of 461 as white solid. MS (APCI) m/z 253 (79%) [M+H]$^+$ and 173 (100%).

Compound 462: To a stifling solution at 0° C. under $N_2$ of 461 (1.513 g, 5.995 mmol) and ethyl formate (5 mL, 62 mmol) in 10 mL of benzene was added sodium methoxide, 30 wt. % solution in methanol (6 mL, 32 mmol). The sample was allowed to slowly warm to room temperature overnight. The sample was dissolved in EtOAc, washed with sat. KH$_2$PO$_4$ and sat. NaCl solutions, dried (MgSO$_4$), filtered and concentrated to give 1.624 g (97%) of 462 as yellow gummy solid. MS (APCI) m/z 295 (100%) [M+H]$^+$.

Compound 463: A solution of 462 (1.206 g, 4.303 mmol) in EtOH (20 mL) was treated with methylhydrazine (0.46 mL, 8.65 mmol). The sample was sealed, heated at 50° C. for 16 h, cooled, concentrated, and then partitioned between CHCl$_3$ and 10% aq. NH$_4$OH. The organic extract was washed with sat. NaCl solution, dried (MgSO$_4$), filtered, concentrated and chromatographed (silica gel, 50% EtOAc in hexanes) to afford 463 (0.989 g, 78%) as a gummy white solid. MS (APCI) m/z 291 (100) [M+H]$^+$.

Compound 464: A solution of 463 (0.320 g, 1.102 mmol) and 3 N HCl (4 mL, 12 mmol) MeOH/THF (1:1, 20 mL) was stirred at room temperature under $N_2$ for 16 h. The solution was concentrated and then partitioned between CHCl$_3$ and 10% aq. NH$_4$OH. The organic extract was washed with sat. NaCl solution, dried (MgSO$_4$), filtered and concentrated to give 464 (0.287 g, >100%) as a light yellow oil. MS (APCI) m/z 247 (100%) [M+H]$^+$.

Compound 465: To a stirring solution at room temperature under $N_2$ of slightly impure 464 (0.287 g, assume 1.102 mmol) and ethyl formate (0.89 mL, 11.02 mmol) in benzene (10 mL) was added dropwise (via syringe) NaOMe (30 wt % in MeOH, 1.0 mL, 5.5 mmol). The sample was stirred at room temperature for 16 h, concentrated then partitioned between EtOAc and sat. KH$_2$PO$_4$ solution. The organic extract was washed with sat. NaCl solution, dried (MgSO$_4$), filtered and concentrated to give 465 (0.296 g, 98%) as a yellow oil. MS (APCI) m/z 276 (100%) and 275 (90%) [M+H]$^+$.

Compound 466: A solution of 465 (0.296 g, assume 1.077 mmol) in EtOH (10 mL) was treated with solid hydroxylamine hydrochloride (0.12 g, 1.73 mmol). The sample was heated at 50° C. under $N_2$ for 16 h, cooled, concentrated then partitioned between CHCl$_3$ and 10% aq. NH$_4$OH. The organic extract was washed with sat. NaCl solution, dried (MgSO$_4$), filtered and concentrated to give 466 (0.273 g, 93%) as a dark yellow-brown oil. MS (APCI) m/z 273 (100%) and 272 (86%) [M+H]$^+$.

Compound 467: A solution of 466 (0.273 g, 1.006 mmol) in MeOH (10 mL) was treated with NaOMe (30 wt % in MeOH, 0.94 mL, 5.01 mmol). The sample was stirred at room temperature under $N_2$ for 16 h, concentrated then partitioned between EtOAc and sat. KH$_2$PO$_4$ solution. The organic extract was washed with sat. NaCl solution, dried (MgSO$_4$), filtered and concentrated to give 467 (0.226 g, 83%) as a dark yellow foamy solid. MS (APCI) m/z 273 (M+2, 100%) and 272 (85%) [M+H]$^+$.

Compound TX63589: To stifling solution at 0° C. under $N_2$ of 467 (0.226 g, 0.834 mmol) in DMF (10 mL) was added in one portion solid 1,3-dibromo-5,5-dimethylhydantoin (0.143 g, 0.500 mmol). After stifling at 0° C. for 1 h, pyridine (0.68 mL, 8.41 mmol) was added. The ice bath was removed and the sample was heated at 50° C. for 16 h. The sample was concentrated (to remove most of the DMF and pyridine) then partitioned between EtOAc and sat. NaHCO$_3$ solution. The organic extract was washed with sat. KH$_2$PO$_4$ and sat. NaCl solution, dried (MgSO$_4$), filtered, concentrated then chromatographed (silica gel, 50% EtOAc/Hexanes) to give TX63589 (0.068 g, 30%) as an off-white foamy solid. $^1$H NMR (500 MHz, CDCl$_3$) δ 8.36 (s, 1H), 7.06 (s, 1H), 3.83 (s, 3H), 2.74 (dd, 1H, J=15.0, 5.0 Hz), 2.50-2.55 (m, 2H), 2.19-2.31 (m, 2H), 1.95 (app dd, 1H, J=15.0, 5.0 Hz), 1.62-1.71 (m, 2H), 1.39 (s, 3H), 0.81 (t, 3H, J=7.5 Hz); MS (APCI) m/z 270 (100%) [M+H]$^+$.

Compound 468: A mixture of 462 (0.412 g, 1.471 mmol), benzamidine hydrochloride (2.3 g, 16.68 mmol) and piperidine (0.87 mL, 8.80 mmol) in 2-propanol (10 mL) was heated in a sealed vial at 85° C. for 96 h. The sample was cooled, concentrated then partitioned between CHCl$_3$ and 10% aq. NH$_4$OH. The organic extract was washed with sat. NaCl solution, dried (MgSO$_4$), filtered and concentrated to give 468 (0.910 g, >100%) as a brown-yellow solid, which was used without purification. MS (APCI) m/z 365 (100) [M+H]$^+$.

Compound 469: A solution of slightly impure 468 (0.910 g, assume 1.471 mmol) and 3 N HCl (10 mL, 30 mmol) in MeOH/THF (1:1, 20 mL) was stirred at room temperature under $N_2$ for 16 h. The solution was concentrated then partitioned between CHCl$_3$ and 10% aq. NH$_4$OH solution. The organic extract was washed with sat. NaCl solution, dried (MgSO$_4$), filtered and concentrated to give 469 (0.778 g, >100%) as a dark yellow gummy solid, which was used without purification. MS (APCI) m/z 321 (100%) [M+H]$^+$.

Compound 470: To a stirring solution at room temperature under $N_2$ of slightly crude 469 (0.778 g, assume 1.471 mmol) and ethyl formate (1.20 mL, 14.80 mmol) in benzene (10 mL) was added dropwise (via syringe) NaOMe (30 wt % in MeOH, 1.40 mL, 7.46 mmol). The sample was stirred at room temperature for 16 h, concentrated then partitioned between EtOAc and sat. KH$_2$PO$_4$ solution. The organic extract was washed with sat. NaCl solution, dried (MgSO$_4$), filtered and concentrated to give 470 (0.684 g, >100%) as a dark yellow oil, which was used without purification. MS (APCI) m/z 349 (100%) [M+H]⁺.

Compound 471: A solution of slightly impure 470 (0.684 g, assume 1.471 mmol) in EtOH (10 mL) was treated with solid hydroxylamine hydrochloride (0.15 g, 2.16 mmol). The sample was heated at 50° C. under $N_2$ for 16 h, cooled, concentrated then partitioned between EtOAc and sat. $NaHCO_3$ solution. The organic extract was washed with sat. NaCl solution, dried ($MgSO_4$), filtered and concentrated to give 471 (0.639 g, >100%) as a dark yellow oil, which was used without purification.

Compound 472: A solution of slightly impure 471 (0.639 g, assume 1.471 mmol) in MeOH (20 mL) was treated with NaOMe (30 wt % in MeOH solution (1.38 mL, 7.36 mmol). The sample was stirred at room temperature under $N_2$ for 16 h, concentrated then partitioned between EtOAc and sat. $KH_2PO_4$ solution. The organic extract was washed with sat. NaCl solutions, dried ($MgSO_4$), filtered, concentrated and chromatographed (silica gel, 30% EtOAc/Hexanes) to give 472 (0.267 g, 52%) as an off-white foamy solid. MS (APCI) m/z 368 (100%) [M+Na]⁺ and 346 (45%) [M+H]⁺.

Compound TX63598: To stirring solution at 0° C. under $N_2$ of 472 (0.267 g, 0.773 mmol) in DMF (10 mL) was added in one portion solid 1,3-dibromo-5,5-dimethylhydantoin (0.12 g, 0.42 mmol). After stirring at 0° C. for 1 h, pyridine (0.63 mL, 7.79 mmol) was added. The ice bath was removed and the sample was heated at 50° C. for 16 h. The sample was concentrated (to remove most of the DMF and pyridine) then partitioned between EtOAc and sat. $NaHCO_3$ solution. The organic extract was washed with sat. $KH_2PO_4$ and sat. NaCl solutions, dried ($MgSO_4$), filtered, concentrated and chromatographed (silica gel, 30% EtOAc/Hexanes) to afford TX63598 (0.209 g, 79%) as an off-white foamy solid. ¹H NMR (500 MHz, $CDCl_3$) δ 8.96 (s, 1H), 8.59 (s, 1H), 8.44-8.46 (m, 2H), 7.48-7.53 (m, 3H), 3.01 (dd, 1H, J=20.0, 5.0 Hz), 2.87-2.94 (m, 1H), 2.59 (app dt, 1H, J=12.5, 5.0 Hz), 2.41 (td, 1H, J=12.5, 3.3 Hz), 2.23-2.31 (m, 1H), 2.11-2.16 (m, 1H), 1.69-1.86 (m, 2H), 1.46 (s, 3H), 0.84 (t, 3H, J=7.5 Hz); MS (ES) m/z 366 (100%) [M+H]⁺ and 344 (37%) [M+H]⁺.

Compound 473: To a stifling solution of 463 (0.661 g, 2.275 mmol) in $CH_2Cl_2$ (10 L) was added in one portion solid 1,3-dibromo-5,5-dimethylhydantoin (0.36 g, 1.26 mmol). The solution immediately turned yellow-orange and all solid went into solution. The solution was stirred at room temperature for 30 min (TLC showed no starting material left), concentrated then partitioned between EtOAc and sat. $NaHCO_3$ solution. The organic extract was washed with sat. $KH_2PO_4$ and sat. NaCl solutions, dried ($MgSO_4$), filtered, concentrated and chromatographed (silica gel, 50% EtOAc/Hexanes) to give 473 (0.490 g, 58%) as colorless oil. MS (APCI) m/z 369/371 (100/64%) [M+H]⁺.

Compound 474: To a stifling degassed mixture of 473 (0.490 g, 1.327 mmol), potassium phosphate (0.85 g, 4.00 mmol) and phenylboronic acid (0.24 g, 1.97 mmol) in DME (10 mL) was added in one portion solid tetrakis(triphenylphosphine) palladium (0) (0.153 g, 0.132 mmol). The sample was degassed, heated at 80° C. under $N_2$ for 16 h, cooled and filtered through a pad of Celite. The filtrate was concentrated, dissolved into EtOAc, washed with 1N NaOH, sat. $KH_2PO_4$ and sat. NaCl solutions, dried ($MgSO_4$), filtered, concentrated and chromatographed (silica gel, 50% EtOAc/Hexanes) to give 474 (0.201 g, 41%) as an off-white solid. MS (APCI) m/z 367 (100%) [M+H]⁺.

Compound 475: A solution of 474 (0.201 g, 0.548 mmol) and 3N HCl (4 mL, 12 mmol) in MeOH (20 mL) was stirred at room temperature under $N_2$ for 16 h. The sample was concentrated then carefully partitioned between EtOAc and sat. $NaHCO_3$ solution. The organic extract was washed with sat. NaCl solution, dried ($MgSO_4$), filtered and concentrated to give 475 (0.163 g, 92%) as an off-white foamy solid. MS (APCI) m/z 323 (100%) [M+H]⁺.

Compound 476: To a stifling solution of 475 (0.163 g, 0.505 mmol) and ethyl formate (4.1 mL, 50.8 mmol) in benzene (10 mL) was added dropwise (via syringe) NaOMe (30 wt % solution in MeOH, 0.47 mL, 2.50 mmol). The sample was stirred at room temperature under $N_2$ for 16 h, concentrated then partitioned between EtOAc and sat. $KH_2PO_4$ solution. The organic extract was washed with sat. NaCl solution, dried ($MgSO_4$), filtered and concentrated to give 476 (0.187 g, >100%) as a yellow gummy solid, which was used without purification. MS (APCI) m/z 351 (100%) [M+H]⁺.

Compound 477: A solution of slightly impure 476 (0.187 g, assume 0.505 mmol) and hydroxylamine hydrochloride (0.53 g, 0.76 mmol) in EtOH (20 mL) was heated at 50° C. under $N_2$ for 16 h. The sample was cooled, concentrated and partitioned between EtOAc and sat. $NaHCO_3$ solution. The organic extract was washed with sat. NaCl solution, dried ($MgSO_4$), filtered and concentrated to give 477 (0.181 g, >100%) as a dark yellow-brown oil, which was used without purification. MS (APCI) m/z 348 (100%) [M+H]⁺.

Compound 478: To a stifling solution of slightly impure 477 (0.181 g, assume 0.505 mmol) at room temperature under $N_2$ in MeOH (20 mL) was added dropwise (via syringe) NaOMe (30 wt % solution in MeOH, 0.47 mL, 2.50 mmol). The sample was stirred at room temperature for 16 h, concentrated then partitioned between EtOAc and sat. $KH_2PO_4$ solution. The organic extract was washed with sat. NaCl solution, dried ($MgSO_4$), filtered and concentrated to give 478 (0.204 g, >100%) as a dark yellow oil, which was used without purification. MS (APCI) m/z 348 (100%) [M+H]⁺.

Compound TX63599: To a stifling solution at 0° C. under $N_2$ of slightly impure 478 (0.204 g, assume 0.505 mmol) in DMF (10 mL) was added in one portion 1,3-dibromo-5,5-dimethylhydantoin (0.072 g, 0.252 mmol). After stirring at 0° C. for 1 h, pyridine (0.63 mL, 7.79 mmol) was added. The ice bath was removed and the sample was heated at 50° C. for 16 h. The sample was concentrated (to remove most of the DMF and pyridine) then partitioned between EtOAc and sat. $NaHCO_3$ solution. The organic extract was washed with sat. $KH_2PO_4$ and sat. NaCl solutions, dried ($MgSO_4$), filtered, concentrated and chromatographed (silica gel, 50% EtOAc/Hexanes) to give TX63599 (0.052 g, 30% over 4 steps) as a yellow solid. ¹H NMR (500 MHz, $CDCl_3$) δ 8.48 (s, 1H), 7.45-7.48 (m, 2H), 7.39-7.42 (m, 1H), 7.31-7.33 (m, 2H), 3.79 (s, 3H), 2.53-2.65 (m, 3H), 2.35 (t, 1H, J=12.5 Hz), 2.22-2.25 (m, 1H), 1.95-1.99 (m, 1H), 1.66-1.70 (m, 2H), 1.45 (s, 3H), 0.82 (t, 3H, J=7.5 Hz); MS (APCI) m/z 346 (100%) [M+H]⁺.

Compound 479: Hydrazine hydrochloride (86 mg, 1.26 mmol) was suspended in dioxane (2 mL) and triethylamine (0.18 mL, 1.26 mmol) was added followed by acetic acid (0.19 g, 3.15 mmol). The mixture was sonicated for several minutes. A solution of 276 (0.24 g, 0.63 mmol) in dioxane (4 mL) was added, and the mixture was heated at 70° C. for 3 h. The mixture was cooled, diluted with sat. $NaHCO_3$ (20 mL), and extracted with EtOAc (2×50 mL). The combined organic extracts were washed with brine (20 mL), dried over $MgSO_4$, concentrated, and dried under vacuum to give 0.215 g (96%) of 479 as a white solid. APCI MS: m/z 358.1 [M+H]⁺.

Compound 480: Sodium hydride (72 mg, 1.80 mmol) was suspended in DMF (2 mL). Compound 479 (215 mg, 0.60 mmol) was added, and the mixture was stirred for 30 min.

Isopropyl iodide (0.30 mL, 3.01 mmol) was added and the mixture was stirred overnight. The reaction was quenched by the addition of sat. $NH_4Cl$ (20 mL), and extracted with EtOAc (2×50 mL). The combined organic extracts were washed with brine (20 mL), dried over $MgSO_4$, concentrated, and dried under vacuum to give a light yellow oil. Flash chromatography (EtOAc) gave 190 mg (79%) of 480 as a white foam. APCI MS: m/z 400.2 $[M+H]^+$.

Compound 481: Compound 480 (185 mg, 0.46 mmol) was taken up in THF (4 mL) and 1M HCl (1 mL) was added. The solution was stirred 2 d, then diluted with sat. $NaHCO_3$ (20 mL) and extracted with EtOAc (2×50 mL). The combined organic extracts were washed with brine (20 mL), dried over $MgSO_4$ and concentrated to give 160 mg (97%) of 481 as a white foam. APCI MS: m/z 356.0 $[M+H]^+$.

Compound 482: Compound 481 (160 mg, 0.45 mmol) was taken up in THF (4 mL) and ethyl formate (1 mL) and cooled in an ice bath. NaOMe (0.8 g, 30 wt. % in MeOH) was added dropwise, and the solution was allowed to warm to RT and stirred overnight. The mixture was quenched by the addition of sat. aq. $KH_2PO_4$ (20 mL) and extracted with EtOAc (2×50 mL). The combined organic extracts were washed with brine (20 mL), dried over $MgSO_4$, and concentrated to give 170 mg (98%) of 482 as a white solid. APCI MS: m/z 384.1 $[M+H]^+$.

Compound 483: Compound 482 (170 mg, 0.44 mmol) was taken up in THF (4 mL), EtOH (2 mL), and water (0.5 mL). Hydroxylamine hydrochloride (46 mg, 0.66 mmol) was added and the reaction was heated at 50° C. for 3 h, then allowed to cool to room temperature and stirred overnight. After concentration, the residue was diluted with sat. aq. $NaHCO_3$ (20 mL) and extracted with EtOAc (2×50 mL). The combined organic extracts were washed with brine (20 mL), dried over $MgSO_4$, concentrated, and dried under vacuum to give 170 mg (100%) of 483 as an off-white solid. APCI MS: m/z 381.1 $[M+H]^+$.

Compound 484: Compound 483 (170 mg, 0.44 mmol) was taken up in THF (4 mL) and MeOH (2 mL) and NaOMe (0.8 g, 30 wt. % in MeOH) was added. The solution was heated at 50° C. for 3 h, then cooled and concentrated. Sat. aq. $KH_2PO_4$ (20 mL) was added, and the mixture was extracted with EtOAc (2×50 mL). The combined organic extracts were washed with brine (20 mL), dried over $MgSO_4$, and concentrated. Flash chromatography (70% EtOAc/DCM) gave 121 mg (72%) of 484 as a white foam. APCI MS: m/z 381.1 $[M+H]^+$.

Compound TX63905: Compound 484 (120 mg, 0.32 mmol) was taken up in DMF (3 mL) and cooled in an ice bath. N,N'-Dibromodimethylhydantoin (54 mg, 0.19 mmol) was added and the solution was stirred 90 min. at 0° C. Pyridine (0.5 mL) was added and the solution was heated at 60° C. for 4 h. After cooling, the solution was concentrated and dried under vacuum to a light brown solid. Flash chromatography (3:1 EtOAc/DCM) gave 82 mg (69%) of TX63905 as a light yellow solid. $^1H$ NMR (400 MHz, $CDCl_3$) δ 8.50 (s, 1H), 8.10 (s, 1H), 4.52-4.63 (m, 1H), 4.17 (s, 3H), 3.08 (dd, 1H, J=5.2, 17.2 Hz), 2.66-2.77 (m, 1H), 2.20 (dd, 1H, J=2.0, 11.6 Hz), 1.80-1.99 (m, 2H), 1.58 (d, 6H, J=6.8 Hz), 1.49 (s, 3H), 1.27 (s, 3H), 1.22 (s, 3H); APCI MS m/z 379.1 $[M+H]^+$.

Compound TX63834: A solution of TX63465 (33 mg, 0.1 mmol) in MeCN (5 mL) was treated with 30% $H_2O_2$ (0.27 mL), and stirred at RT overnight. The reaction mixture was diluted with water (15 mL) and extracted with EtOAc (2×15 mL). The organic layer was dried with $MgSO_4$, and purified by column chromatography (silica gel, 5-25% EtOAc/Hexanes) to give TX63834 as white solid (30 mg, 85%). $^1H$ NMR (400 MHz, $CDCl_3$) δ 7.37-7.49 (m, 3H), 7.28-7.34 (m, 2H), 4.77 (s, 1H), 3.79 (s, 3H), 2.58 (dd, 1H, J=5.6, 15.6 Hz), 2.36-2.54 (m, 2H), 1.72-1.80 (m, 1H), 1.58-1.70 (m, 1H), 1.32 (s, 3H), 1.22 (s, 3H), 1.15 (s, 3H); MS: m/z $[M+H]^+$ 362.

Compound TX63848: A solution of TX64541 (80 mg, 0.24 mmol) in MeCN (7 mL) was treated with 30% $H_2O_2$ (0.63 mL), stirred at RT overnight. The reaction mixture was diluted with water (15 mL) and extracted with EtOAc (2×15 mL). The organic layer was dried with $MgSO_4$, and purified by column chromatography (silica gel, 5-35% EtOAc/Hexanes) to give TX63848 as a light yellow solid (8 mg, 10%). $^1H$ NMR (400 MHz, $CDCl_3$) δ 7.26-7.54 (m, 5H), 4.77 (s, 1H), 3.79 (s, 3H), 2.45-2.64 (m, 3H), 2.10-2.24 (m, 3H), 1.25-1.35 (m, 3H), 1.30 (s, 3H); MS: m/z $[M+H]^+$ 348.

Compounds 485 and 486: To a stirring solution at 0° C. of 152 (0.37 g, 1.59 mmol) in 20 mL of $CH_2Cl_2$ was added in one portion 1,3-dibromo-5,5-dimethylhydantoin (0.23 g, 0.80 mmol). The sample was stirred for 30 min. and while still cold, quenched with sat. $NaHCO_3$ solution (~100 mL). The sample was warmed to room temperature, concentrated then extracted with EtOAc. The organic extract was washed with sat. NaCl solution, dried ($MgSO_4$), filtered and concentrated. The sample was chromatographed (silica gel, 80% EtOAc/Hexanes) to give 485 (0.27 g, 55%) as a white solid (MS [APCI] m/z 311/313 (M+1, 91/100%) and 486 (0.080 g, 14%) as a white solid. MS (APCI) m/z 359 (100%) $[M+H]^+$.

Compound 487: To a stifling solution of 486 (0.080 g, 0.22 mmol) and ethyl formate (1.8 mL, 22.3 mmol) in 10 mL of benzene was added dropwise (via syringe) NaOMe (30 wt. % solution in methanol, 0.42 mL, 2.24 mmol). The sample was stirred at room temperature under $N_2$ for 16 h, concentrated then partitioned between $CHCl_3$ and sat. $KH_2PO_4$ solution. The organic extract was washed with sat. NaCl solution, dried ($MgSO_4$), filtered and concentrated to give 487 (0.067 g, 78%) as tan solid, which was used without purification. MS (APCI) m/z 387 (100%) $[M+H]^+$.

Compound 488: A solution of slightly impure 487 (0.067 g, 0.17 mmol) and hydroxylamine hydrochloride (0.018 g, 0.26 mmol) in 10 mL of ethanol was heated at 50° C. under $N_2$ for 2 h then room temperature overnight. The sample was concentrated and partitioned between $CHCl_3$ and sat. $NaHCO_3$ solution. The organic extract was washed with sat. NaCl solution, dried ($MgSO_4$), filtered and concentrated to give 488 (0.067 g, ~100%) as tan solid, which was used without purification.

Compound 489: To a stifling solution of slightly impure 488 (0.067 g, assume 0.17 mmol) at room temperature under $N_2$ in 10 mL of methanol:THF (1:1) was added dropwise (via syringe) NaOMe (30 wt. % solution in methanol, 0.32 mL, 1.71 mmol). The sample was stirred at room temperature for 16 h, concentrated then partitioned between $CHCl_3$ and sat. $KH_2PO_4$ solution. The organic extract was washed with sat. NaCl solution, dried ($MgSO_4$), filtered and concentrated to give 489 (0.054 g, 81%) as yellow oil, which was used without purification.

Compound TX63776: To a stifling solution at 0° C. under $N_2$ of slightly impure 489 (0.054 g, 0.14 mmol) in 5 mL of DMF was added in one portion 1,3-dibromo-5,5-dimethylhydantoin (0.020 g, 0.070 mmol). After stifling at 0° C. for 1 h, pyridine (0.12 mL, 1.48 mmol) was added. The ice bath was removed and the sample was heated at 50° C. for 2 h. The sample was cooled, concentrated (to remove most of the DMF and pyridine) then partitioned between $CHCl_3$ and sat. $KH_2PO_4$ solution. The organic extract was washed with sat. NaCl solution, dried ($MgSO_4$), filtered, concentrated and chromatographed (silica gel, 100% EtOAc) to give TX63776 (0.014 g, 27%) as yellow oil. $^1H$ NMR (400 MHz, $CDCl_3$) δ 8.36 (s, 1H), [5.70 (s), 5.65 (s), 1H], [3.63 (s), 3.63 (s), 3H], 2.41 (m, 3H), 2.05 (app.dt, 2.2, 12.8, 1H), 1.93 (m, 1H), 1.65

(m, 1H), [1.53 (s), 1.52 (s), 3H], [1.50 (s), 1.49 (s), 3H], 1.37 (s, 3H), 1.21 (d, 3H, J=6.8 Hz); MS (APCI) m/z 382 (100%) [M+H]$^+$.

Compound 490: A solution of 386 (0.42 g, 1.16 mmol) in 10 mL of ethanol was treated with sodium ethoxide, 21 wt. % solution in ethanol (2.2 mL, 5.9 mmol). The sample was flushed with N$_2$, sealed and heated at 80° C. for 48 h. The sample was cooled, concentrated then partitioned between EtOAc and sat. KH$_2$PO$_4$ solution. The organic extract was washed with sat. NaCl solution, dried (MgSO$_4$), filtered and concentrated to give 490 (0.40 g, ~92%) as dark yellow oil, which was used without purification.

Compound 491: A solution of 490 (0.40 g, 1.07 mmol) and 3 N HCl (10 mL, 30 mmol) in 10 mL of ethanol was stirred at room temperature under N$_2$ for 16 h. The sample was concentrated, cooled, basified with 10% aq. NH$_4$OH solution to a pH~9-10 and extracted with EtOAc. The organic extract was washed with sat. NaCl solution, dried (MgSO$_4$), filtered and concentrated to give 491 (0.35 g, 99%) as a yellow solid, which was used without purification. MS (APCI) m/z 331 (100%) [M+H]$^+$.

Compound 492: To a stirring solution of 491 (0.35 g, 1.06 mmol) and ethyl formate (10 mL, 124 mmol) in 10 mL of benzene was added dropwise (via syringe) sodium ethoxide, 21 wt. % solution in ethanol (2.0 mL, 5.4 mmol). The sample was stirred at room temperature under N$_2$ for 16 h, concentrated then partitioned between EtOAc and sat. KH$_2$PO$_4$ solution. The organic extract was washed with sat. NaCl solution, dried (MgSO$_4$), filtered and concentrated to give 492 (0.38 g, ~100%) as a dark yellow oil, which was used without purification. MS (APCI) m/z 359 (100%) [M+H]$^+$.

Compound 493: A solution of 492 (0.38 g, 1.06 mmol) and hydroxylamine hydrochloride (0.11 g, 1.58 mmol) in 10 mL of ethanol was heated at 50° C. under N$_2$ for 2 h then room temperature overnight. The sample was concentrated and partitioned between EtOAc and sat. NaHCO$_3$ solution. The organic extract was washed with sat. NaCl solution, dried (MgSO$_4$), filtered and concentrated to give 493 (0.33 g, 88%) as dark yellow oil, which was used without purification. MS (APCI) m/z 378 (100%) and 356 (88%) [M+H]$^+$.

Compound 494: To a stirring solution of slightly impure 493 (0.33 g, 0.93 mmol) at room temperature under N$_2$ in 20 mL of ethanol was added dropwise (via syringe) sodium ethoxide, 21 wt. % solution in ethanol (1.75 mL, 4.69 mmol). The sample was stirred at room temperature for 72 h, concentrated then partitioned between EtOAc and sat. KH$_2$PO$_4$ solution. The organic extract was washed with sat. NaCl solution, dried (MgSO$_4$), filtered, concentrated to give 494 (0.32 g, 96%) as a dark yellow foamy solid. MS (APCI) m/z 356 (100%) [M+H]$^+$.

Compound TX63900: To a stifling solution at 0° C. under N$_2$ of 494 (0.32 g, 0.89 mmol) in 10 mL of DMF was added in one portion 1,3-dibromo-5,5-dimethylhydantoin (0.125 g, 0.44 mmol). After stirring at 0° C. for 1 h, pyridine (0.72 mL, 8.90 mmol) was added. The ice bath was removed and the sample was heated at 50° C. for 2 h. The sample was cooled, concentrated (to remove most of the DMF and pyridine) then partitioned between EtOAc and sat. KH$_2$PO$_4$ solution. The organic extract was washed with sat. NaCl solution, dried (MgSO$_4$), filtered, concentrated, chromatographed (silica gel, 20% EtOAc/hexanes) then crystallized from cold hexanes to give TX63900 (0.097 g, 31%) as a light yellow solid. $^1$H NMR (400 MHz, CDCl$_3$) δ 8.85 (s, 1H), 4.42 (q, 2H, J=6.8 Hz), 2.53 (dd, 1H, J=6.4, 18.4 Hz), 2.45-2.55 (m, 2H), 1.98-2.10 (m, 2H), 1.60-1.73 (m, 1H), 1.35 (s, 3H), 1.35 (t, 3H, J=7.2 Hz), 1.33 (s, 9H), 1.26 (d, 3H, J=6.8 Hz); MS (APCI) m/z 354 (100%) [M+H]$^+$.

Compound 495: To a stirring solution at room temperature under N$_2$ of 127 (1.00 g, 4.20 mmol) and dimethyl carbonate (7.1 mL, 84.2 mmol) in 10 mL of THF was added portionwise sodium hydride, 60% dispersion in mineral oil (0.67 g, 16.75 mmol). The sample was stirred at room temperature for 1 h, and then 80° C. overnight. The sample was cooled to room temperature, concentrated then partitioned between Et$_2$O and sat. aq. KH$_2$PO$_4$. The organic extract was washed with sat. NaCl solution, dried (MgSO$_4$), filtered and concentrated to give the intermediate keto-ester (1.69 g, >100 as dark yellow oil. In a sealable vial, a solution of the intermediate (assume 4.20 mmol) in 10 mL of 2-propanol was treated with solid formamidine acetate (4.40 g, 42.26 mmol) followed by piperidine (2.1 mL, 21.2 mmol). The sample was flushed with N$_2$, sealed and heated (via a block heater) at 80° C. for 72 h. The sample was cooled, concentrated then partitioned between EtOAc and sat. KH$_2$PO$_4$ solution. The organic extract was washed with sat. NaCl solution, dried (MgSO$_4$), filtered, concentrated then chromatographed (silica gel, 30-50% EtOAc/hexanes) to give 495 (0.189 g, 16%) as a light yellow solid. MS (APCI) m/z 291 (100%) [M+H]$^+$.

Compound 496: A solution of 495 (0.189 g, 0.652 mmol) and N,N-diisopropylethylamine (0.125 mL, 0.718 mmol) in 10 mL of benzene was added dropwise (via syringe) phosphorus oxychloride (0.61 mL, 6.54 mmol). After addition, the sample was heated at 90° C. under N$_2$ for 2 h, cooled, concentrated then carefully partitioned between EtOAc and sat. NaHCO$_3$ solution. The organic extract was washed with sat. NaCl solution, dried (MgSO$_4$), filtered and concentrated to give 496 (0.172 g, 86%) as a tan solid. MS (APCI) m/z 309/311 (100/42%) [M+H]$^+$.

Compound 497: A solution of 496 (0.172 g, 0.558 mmol) in 10 mL of methanol was treated with sodium methoxide, 30 wt. % solution in methanol solution (0.52 mL, 2.77 mmol). The sample was flushed with N$_2$, sealed and heated at 60° C. for 16 h. The sample was cooled, concentrated then partitioned between EtOAc and sat. KH$_2$PO$_4$ solution. The organic extract was washed with sat. NaCl solution, dried (MgSO$_4$), filtered and concentrated to give 497 (0.151 g, 88%) as a yellow solid, which was used without purification. MS (APCI) m/z 305 (100%) [M+H]$^+$.

Compound 498: A solution of 497 (0.151 g, 0.496 mmol) and 3 N HCl (4 mL, 12 mmol) in 20 mL of methanol was stirred at room temperature under N$_2$ for 16 h. The sample was concentrated, cooled, basified with 10% aq. NH$_4$OH solution to a pH~9-10 and extracted with EtOAc. The organic extract was washed with sat. NaCl solution, dried (MgSO$_4$), filtered and concentrated to give 498 (0.128 g, 99%) as a dark yellow oil, which was used without purification. MS (APCI) m/z 261 (100%) [M+H]$^+$.

Compound 499: To a stifling solution of slightly impure 498 (0.128 g, 0.492 mmol) and ethyl formate (4.0 mL, 50 mmol) in 10 mL of benzene was added dropwise (via syringe) sodium methoxide, 30 wt. % solution in methanol (0.46 mL, 52.45 mmol). The sample was stirred at room temperature under N$_2$ for 48 h, concentrated then partitioned between EtOAc and sat. KH$_2$PO$_4$ solution. The organic extract was washed with sat. NaCl solution, dried (MgSO$_4$), filtered and concentrated to give 499 (0.115 g, 82%) as light yellow solid, which was used without purification. MS (APCI) m/z 289 (100%) [M+H]$^+$.

Compound 500: A solution of slightly impure 499 (0.115 g, assume 0.401 mmol) and hydroxylamine hydrochloride (0.042 g, 0.604 mmol) in 10 mL of ethanol was heated at 50° C. under N$_2$ for 16 h, cooled, concentrated and partitioned between CHCl$_3$ and sat. NaHCO$_3$ solution. The organic extract was washed with sat. NaCl solution, dried (MgSO$_4$), filtered and concentrated to give 500 (0.109 g, 95%) as a yellow oil, which was used without purification. MS (APCI) m/z 286 (100%) [M+H]$^+$.

Compound 501: To a stifling solution of slightly impure 500 (0.109 g, 0.381 mmol) at room temperature under $N_2$ in 10 mL of methanol was added dropwise (via syringe) sodium methoxide, 30 wt. % solution in methanol (0.36 mL, 1.92 mmol). The sample was stirred at room temperature for 16 h, concentrated then partitioned between EtOAc and sat. $KH_2PO_4$ solution. The organic extract was washed with sat. NaCl solution, dried ($MgSO_4$), filtered and concentrated to give 501 (0.096 g, 88%) as a yellow oil, which was used without purification. MS (APCI) m/z 286 (100%) [M+H]$^+$.

Compound TX63874: To a stifling solution at 0° C. under $N_2$ of slightly impure 501 (0.096 g, 0.338 mmol) in 10 mL of DMF was added in one portion 1,3-dibromo-5,5-dimethylhydantoin (0.048 g, 0.168 mmol). After stifling at 0° C. for 1 h, pyridine (0.27 mL, 3.34 mmol) was added. The ice bath was removed and the sample was heated at 50° C. for 2 h. The sample was cooled, concentrated (to remove most of the DMF and pyridine) then partitioned between EtOAc and sat. $KH_2PO_4$ solution. The organic extract was washed with sat. NaCl solution, dried ($MgSO_4$), filtered, concentrated and chromatographed (silica gel, 30% EtOAc/hexanes) to give TX63874 (0.028 g, 30%) as a tan solid. $^1$H NMR (400 MHz, $CDCl_3$) δ 8.81 (s, 1H), 8.61 (s, 1H), 3.99 (s, 3H), 2.81 (dd, 1H, J=6.4, 18.4 Hz), 2.49-2.64 (m, 2H), 2.00-2.15 (m, 2H), 1.64-1.77 (m, 1H), 1.39 (s, 3H), 1.29 (d, 3H, J=8.8 Hz); MS (APCI) m/z 284 (100%) [M+H]$^+$.

All of the methods disclosed and claimed herein can be made and executed without undue experimentation in light of the present disclosure. While the methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

Abraham and Kappas, *Free Radical Biol. Med.*, 39:1-25, 2005.
Ahmad et al., *Cancer Res.*, 68:2920-2926, 2008.
Ahmad et al., *J. Biol. Chem.*, 281:35764-9, 2006.
Araujo et al., *J. Immunol.*, 171(3):1572-1580, 2003.
Bach, *Hum. Immunol.*, 67(6):430-432, 2006.
Chauhan and Chauhan, *Pathophysiology*, 13(3):171-181 2006.
Dickerson et al., *Prog Neuropsychopharmacol Biol. Psychiatry*, Mar. 6, 2007.
Dinkova-Kostova et al., *Proc. Natl. Acad. Sci. USA*, 102(12): 4584-4589, 2005.
Dudhgaonkar et al., *Eur. J. Pain*, 10(7):573-9, 2006.
Forstermann, *Biol. Chem.*, 387:1521, 2006.
*Handbook of Pharmaceutical Salts: Properties, and Use*, Stahl and Wermuth Eds.), Verlag Helvetica Chimica Acta, 2002.
Hanson et al., *BMC Medical Genetics*, 6(7), 2005.
Honda et al. *Bioorg. Med. Chem. Lett.*, 12:1027-1030, 2002.
Honda et al., *J. Med. Chem.*, 43:4233-4246, 2000a.
Honda, et al., *J. Med. Chem.*, 43:1866-1877, 2000b.
Honda et al., *Bioorg. Med. Chem. Lett.*, 7:1623-1628, 1997.
Honda et al., *Bioorg. Med. Chem. Lett.*, 9(24):3429-3434, 1999.
Honda et al., *Bioorg. Med. Chem. Lett.*, 8(19):2711-2714, 1998.
Honda et al., *Bioorg. Med. Chem. Lett.*, 16(24):6306-6309, 2006.
Ishikawa et al., *Circulation*, 104(15):1831-1836, 2001.
Kawakami et al., *Brain Dev.*, 28(4):243-246, 2006.
Kendall-Tackett, *Trauma Violence Abuse*, 8(2):117-126, 2007.
Kruger et al., *J. Pharmacol. Exp. Ther.*, 319(3):1144-1152, 2006.
Lee et al., *Glia.*, 55(7):712-22, 2007.
Lencz et al., *Mol. Psychiatry*, 12(6):572-80, 2007.
Liby et al., *Cancer Res.*, 65(11):4789-4798, 2005.
Liby et al., *Nat. Rev. Cancer*, 7(5):357-356, 2007a.
Liby et al., *Mol. Cancer. Ther.*, 6(7):2113-9, 2007b.
Liby et al., 2007b
Liu et al., *FASEB J.*, 20(2):207-216, 2006.
Lu et al., *J. Clin. Invest.*, 121(10):4015-29, 2011.
*March's Advanced Organic Chemistry: Reactions*, Mechanisms, and Structure, 2007.
McIver et al., *Pain*, 120(1-2):161-9, 2005.
Morris et al., *J. Mol. Med.*, 80(2):96-104, 2002.
Morse and Choi, *Am. J. Respir. Crit. Care Med.*, 172(6):660-670, 2005.
Morse and Choi, *Am. J. Respir. Crit. Care Med.*, 27(1):8-16, 2002.
Pall, *Med. Hypoth.*, 69:821-825, 2007.
Place et al., *Clin. Cancer Res.*, 9(7):2798-806, 2003.
Rajakariar et al., *Proc. Natl. Acad. Sci. USA*, 104(52):20979-84, 2007.
Ross et al., *Am. J. Clin. Pathol.*, 120(Suppl):553-71, 2003.
Ross et al., *Expert Rev. Mol. Diagn.*, 3(5):573-585, 2003.
Ruster et al., *Scand. J. Rheumatol.*, 34(6):460-3, 2005.
Sacerdoti et al., *Curr Neurovasc Res.* 2(2):103-111, 2005.
Salvemini et al., *J. Clin. Invest.*, 93(5):1940-1947, 1994.
Sarchielli et al., *Cephalalgia*, 26(9):1071-1079, 2006.
Satoh et al., *Proc. Natl. Acad. Sci. USA*, 103(3):768-773, 2006.
Schulz et al., *Antioxid. Redox. Sig.*, 10:115, 2008.
Strejan et al., *J. Neuroimmunol.*, 7:27, 1984.
Suh et al., *Cancer Res.*, 58:717-723, 1998.
Suh et al., *Cancer Res.*, 59(2):336-341, 1999.
Szabo et al., *Nature Rev. Drug Disc.*, 6:662-680, 2007.
Takahashi et al., *Cancer Res.*, 57:1233-1237, 1997.
Tamir and Tannebaum, *Biochim. Biophys. Acta*, 1288:F31-F36, 1996.
Zhou et al., *Am. J. Pathol.*, 166(1):27-37, 2005.

What is claimed is:

1. A compound of the formula:

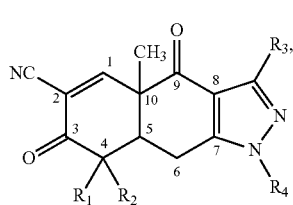

(VII)

wherein:
$R_1$ and $R_2$ are each methyl;
$R_3$ is hydrogen; and
$R_4$ is:
hydrogen; or
alkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, hetero-aryl$_{(C\leq 12)}$, acyl$_{(C\leq 12)}$ or a substituted version of any of these groups, wherein one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$;
or a pharmaceutically acceptable salt or tautomer thereof.

2. The compound of claim 1, wherein $R_4$ is aryl$_{(C\leq 8)}$.
3. The compound of claim 2, wherein $R_4$ is phenyl.
4. The compound of claim 1, wherein $R_4$ is alkyl$_{(C\leq 6)}$.
5. The compound of claim 4, wherein $R_4$ is t-butyl.
6. The compound of claim 1, further defined as:

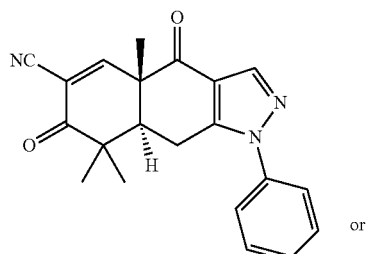

or

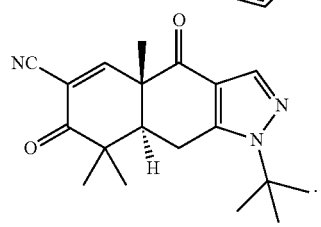

7. A pharmaceutical composition comprising:
a) the compound of claim 1;
b) an optical isomer of the compound, wherein the optical isomer is the enantiomer of the compound; and
c) an excipient.

* * * * *

UNITED STATES PATENT AND TRADEMARK OFFICE
CERTIFICATE OF CORRECTION

PATENT NO. : 9,174,941 B2  
APPLICATION NO. : 13/939818  
DATED : November 3, 2015  
INVENTOR(S) : Eric Anderson et al.

Page 1 of 1

It is certified that error appears in the above-identified patent and that said Letters Patent is hereby corrected as shown below:

In title page, item (56) References Cited - Foreign Patent Documents, delete the 24th reference on page 2 "WO    WO 2004/064723  3/2005" and replace with --WO    WO 2005/020932  3/2005-- therefor.

In title page, item (56) References Cited - Other Publications, delete the 41st reference on page 5 "Kind et al., "Pituitary gonadotropin inhibitory action of neutral steroids," *Acta. Endocrinologica*, 46: 300-306, 1964." and replace with --Kincl et al., "Pituitary gonadotropin inhibitory action of neutral steroids," *Acta. Endocrinologica*, 46: 300-306, 1964.-- therefor.

In title page, item (56) References Cited - Other Publications, delete the 30th reference on page 7 "On et al., "Steroids. CCLXV. Studies in cyano steroids. 3. Unsaturated 2-cyano steroids," *J. Org. Chem.*, 29(11): 3300-3303, 1964." and replace with --Orr et al., "Steroids. CCLXV. Studies in cyano steroids. 3. Unsaturated 2-cyano steroids," *J. Org. Chem.*, 29(11): 3300-3303, 1964.-- therefor.

Signed and Sealed this  
First Day of March, 2016

Michelle K. Lee  
*Director of the United States Patent and Trademark Office*